United States Patent
Lipkin et al.

(10) Patent No.: US 9,050,276 B2
(45) Date of Patent: Jun. 9, 2015

(54) AUTISM-ASSOCIATED BIOMARKERS AND USES THEREOF

(75) Inventors: W. Ian Lipkin, New York, NY (US); Mady Hornig, New York, NY (US); Brent L. Williams, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/328,982

(22) Filed: Dec. 16, 2011

(65) Prior Publication Data

US 2012/0207726 A1     Aug. 16, 2012

Related U.S. Application Data

(63) Continuation-in-part of application No. PCT/US2010/034254, filed on May 10, 2010.

(60) Provisional application No. 61/527,313, filed on Aug. 25, 2011.

(51) Int. Cl.
| | |
|---|---|
| C12Q 1/68 | (2006.01) |
| A61K 31/00 | (2006.01) |
| A61K 38/17 | (2006.01) |
| A61K 38/47 | (2006.01) |

(52) U.S. Cl.
CPC ............ A61K 31/00 (2013.01); A61K 38/1709 (2013.01); A61K 38/47 (2013.01); G01N 2333/62 (2013.01); G01N 2333/924 (2013.01); G01N 2800/28 (2013.01); C12Q 1/6883 (2013.01); C12Q 2600/106 (2013.01); C12Q 2600/156 (2013.01); C12Q 2600/158 (2013.01)

(58) Field of Classification Search
USPC ............................ 435/6.12; 424/93.41, 93.42
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,458,066 A | 7/1984 | Caruthers et al. |
| 4,683,195 A | 7/1987 | Mullis et al. |
| 4,683,202 A | 7/1987 | Mullis |
| 4,710,384 A | 12/1987 | Rotman |
| 4,861,719 A | 8/1989 | Miller |
| 5,059,595 A | 10/1991 | Le Grazie |
| 5,073,543 A | 12/1991 | Marshall et al. |
| 5,120,548 A | 6/1992 | McClelland et al. |
| 5,236,838 A | 8/1993 | Rasmussen et al. |
| 5,252,479 A | 10/1993 | Srivastava |
| 5,278,056 A | 1/1994 | Bank et al. |
| 5,328,470 A | 7/1994 | Nabel et al. |
| 5,354,556 A | 10/1994 | Sparks et al. |
| 5,391,377 A | 2/1995 | Barnwell |
| 5,580,757 A | 12/1996 | Desnick et al. |
| 5,591,767 A | 1/1997 | Mohr et al. |
| 5,639,476 A | 6/1997 | Oshlack et al. |
| 5,674,533 A | 10/1997 | Santus et al. |
| 5,721,118 A | 2/1998 | Scheffler |
| 5,733,566 A | 3/1998 | Lewis |
| 5,747,469 A | 5/1998 | Roth et al. |
| 5,879,680 A | 3/1999 | Ginns et al. |
| 5,882,877 A | 3/1999 | Gregory et al. |
| 6,013,516 A | 1/2000 | Verma et al. |
| 6,017,524 A | 1/2000 | Roth et al. |
| 6,025,155 A | 2/2000 | Hadlaczky et al. |
| 6,083,725 A | 7/2000 | Selden et al. |
| 6,143,290 A | 11/2000 | Zhang et al. |
| 6,188,045 B1 | 2/2001 | Hansen et al. |
| 6,210,666 B1 | 4/2001 | Miyamura |
| 6,395,884 B1 | 5/2002 | Selden et al. |
| 6,410,010 B1 | 6/2002 | Zhang et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,511,847 B1 | 1/2003 | Zhang et al. |
| 7,091,182 B2 | 8/2006 | Beck et al. |
| 2002/0077313 A1 | 6/2002 | Clayman |
| 2004/0170617 A1 | 9/2004 | Finegold |
| 2006/0115467 A1 | 6/2006 | Pangborn et al. |
| 2007/0065817 A1* | 3/2007 | Lee et al. .................... 435/6 |

(Continued)

FOREIGN PATENT DOCUMENTS

| | | |
|---|---|---|
| WO | WO-94/19478 A1 | 9/1994 |
| WO | WO-95/14785 A1 | 6/1995 |

(Continued)

OTHER PUBLICATIONS

Engberg, J., S. L. On, C. S. Harrington, and P. Gerner-Smidt. 2000. Prevalence of *Campylobacter, Arcobacter, Helicobacter*, and *Sutterella* spp. in human fecal samples as estimated by a reevaluation of isolation methods for *Campylobacters*. J Clin Microbiol 38:286-91.*
Sakon, H., F. Nagai, M. Morotomi, and R. Tanaka. 2008. *Sutterella parvirubra* sp. nov. and *Megamonas funiformis* sp. nov., isolated from human faeces. Int J Syst Evol Microbiol 58:970-5.*
Greetham, H. L., M. D. Collins, G. R. Gibson, C. Giffard, E. Falsen, and P. A. Lawson. 2004. *Sutterella stercoricanis* sp. nov., isolated from canine faeces. Int J Syst Evol Microbiol 54: 1581-4.*
Wexler, H. M., O. Reeves, P. H. Summanen, E. Molitoris, M. McTeague, J. Duncan, K. H. Wilson, and S. M. Finegold. 1996. *Sutterella wadsworthensis* gen. nov., sp. nov., bileresistant microaerophilic *Campylobacter gracilis*-like clinical isolates. Int J Syst Bacteriol 46:252-8.*

(Continued)

*Primary Examiner* — Angela M Bertagna
*Assistant Examiner* — Olayinka Oyeyemi
(74) *Attorney, Agent, or Firm* — Wilmer Cutler Pickering Hale and Dorr LLP

(57) ABSTRACT

The invention discloses biomarkers for human autism. The invention provides methods for treating, preventing, and diagnosing human autism and autism-related disorders.

9 Claims, 74 Drawing Sheets
(42 of 74 Drawing Sheet(s) Filed in Color)

(56) References Cited

U.S. PATENT DOCUMENTS

| | | |
|---|---|---|
| 2007/0180544 A1 | 8/2007 | Taylor et al. |
| 2009/0011414 A1 | 1/2009 | Philippi et al. |

FOREIGN PATENT DOCUMENTS

| | | |
|---|---|---|
| WO | WO-96/22378 A1 | 7/1996 |
| WO | WO-2006/060414 | 6/2006 |

OTHER PUBLICATIONS

Molitoris, E., H. M. Wexler, and S. M. Finegold. 1997. Sources and antimicrobial susceptibilities of *Campylobacter gracilis* and *Sutterella wadsworthensis*. Clin Infect Dis 25 Suppl 2:S264-5.*

Nagai F, Morotomi M, Sakon H, Tanaka R. *Parasutterella excrementihominis* gen. nov., sp. nov., a member of the family Alcaligenaceae isolated from human faeces. Int J Syst Evol Microbiol. Jul. 2009:59(Ft 7):1793-7 Epub Jun. 19, 2009.*

Nagashima et al. Phylogenetic Analysis of 16S Ribosomal RNA Gene Sequences from Human Fecal Microbiota and Improved Utility of Terminal Restriction Fragment Length Polymorphism Profiling. 2006. Bioscience Microflora vol. 25(3), 99-107.*

Victoria JG, Kapoor A, Li L, Blinkova O, Slikas B, Wang C, Naeem A, Zaidi S, Delwart E. Metagenomic analyses of viruses in stool samples from children with acute flaccid paralysis. J Virol. May 2009;83(9):4642-51. Epub. Feb. 11, 2009.*

Mukhopadhya I, Hansen R, Nicholl CE, Alhaidan YA, Thomson JM, Berry SH, Pattinson C, Stead DA, Russell RK, El-Omar EM, Hold GL. A comprehensive evaluation of colonic mucosal isolates of *Sutterella wadsworthensis* from inflammatory bowel disease. PLoS One. 2011;6(10):e27076. Epub Oct. 31, 2011.*

On, S. L. W., H. I. Atabay, J. E. L. Corry, C. S. Harrington, and P. Vandamme.1998. Emended description of *Campylobacter sputorum* and revision of its infrasubspecific (biovar) divisions, including *C. sputorum* bv. paraureolyticus, a urease-producing variant from cattle and humans. Int. J. Syst. Bacteriol. 48:195-206.*

Eckburg PB, Bik EM, Bernstein CN, Purdom E, Dethlefsen L, Sargent M, Gill SR, Nelson KE, Reiman DA. Diversity of the human intestinal microbial flora. Science. Jun. 10, 2005,308(5728):1635-8. Epub Apr. 14, 2005.*

Lowe T, Sharefkin J, Yang SQ, Dieffenbach CW. A computer program for selection of oligonucleotide primers for polymerase chain reactions. Nucleic Acids Res. Apr. 11, 1990;18(7):1757-61.*

Li M et al. Symbiotic gut microbes modulate human metabolic phenotypes. Proc Natl Acad Sci U S A. Feb. 12, 2008. 105(6):2117-22. Epub Feb. 5, 2008.*

De Hertogh G, Aerssens J, de Hoogt R, Peeters P, Verhasselt P, Van Eyken P, Ectors N, Vermeire S, Rutgeerts P, Coulie B, Geboes K. Validation of 16S Rdna sequencing in microdissected bowel biopsies from Crohn's disease patients to assess bacterial flora diversity. J Pathol. Aug. 2006; 209(4):532-9.*

GenBank L37785 submitted by Wexler et al. On Aug. 8, 2000 and <retrieved from http://www.ncbi.nlm.nih.gov/nuccore/L37785 on Apr. 17, 2013> (*Sutterella wadsworthensis* strain 7877 16S rRNA gene, complete sequence (GI:854703).*

GenBank EF401376.1 submitted by Li et al. on Jan. 26, 2007 and <retrieved from http://www.ncbi.nlm.nih.gov/nuccore/EF401376 on Apr. 17, 2013> (Uncultured bacterium clone SJTU_D_09_52 16S rRNA gene, partial sequence (GI:126111687)).*

GenBank AJ566849 submitted by Lawson et al. on Jun. 16, 2003 and <retrieved from http://www.ncbi.nlm.nih.gov/nuccore/AJ566849 on May 2, 2013> *Sutterella stercoricanis* 16S rRNA gene, type strain CCUG 47620 (GI:53127617)).*

GenBank AB370250 submitted by Nagai et al. on Dec. 4, 2007 and <retrieved from http://www.ncbi.nlm.nih.gov/nuccore/AB370250 on May 2, 2013> *Parasutterella excrementihominis* gene for 16S rRNA gene, partial sequence (GI: 215273584)).*

GenBank NR_041667.1 submitted by Nagai et al. on Dec. 4, 2007 and <retrieved from http://www.ncbi.nlm.nih.gov/nuccore/NR_041667.1 on Apr. 17, 2013> (*Parasutterella excrementihominis* strain YIT 11859 (JCM 15078, DSM 21040) 16S rRNA gene, partial sequence (GI:343200980).*

GenBank AY976224 submitted by Eckburg et al. on Mar. 28, 2005 and <retrieved from http://www.ncbi.nlm.nih.gov/nuccore/AY976224 on Apr. 17, 2013> (Uncultured bacterium clone LW53 16S rRNA gene, partial sequence (GI:62755714)).*

GenBank AB300989 submitted by Sakon et al. on Apr. 18, 2007 and <retrieved from http://www.ncbi.nlm.nih.gov/nuccore/AB300989 on May 2, 2013> (*Sutterella parvirubra* gene for 16S rRNA gene, partial sequence, strain YIT 11816 (GI:166244608).*

GenBank AB300990 submitted by Sakon et al. on Apr. 18, 2007 and <retrieved from http://www.ncbi.nlm.nih.gov/nuccore/AB300990 on Apr. 17, 2013> (*Sutterella parvirubra* gene for 16S rRNA gene, partial sequence, strain YIT 11817 (GI:166244609).*

GenBank EU530369 submitted by Shen et al. on Feb 29, 2008 and <retrieved from http://www.ncbi.nlm.nih.gov/nuccore/EU530369 on Apr. 17, 2013> (Uncultured *Sutterella* sp. clone M4-81 16S rRNA gene, partial sequence.*

GenBank AB491210.1 submitted by Watanabe et al. on Mar. 16, 2009 and <retrieved from http://www.ncbi.nlm.nih.gov/nuccore/AB491210.1 on Apr. 17, 2013> (*Sutterella* sp. YIT 12072 gene for 16S rRNA gene, partial sequence (GI:258612383).*

GenBank FJ503635 submitted by Walker et al. On Dec. 2, 2008 and <retrieved from http://www.ncbi.nlm.nih.gov/nuccore/FJ503635.1 on Apr. 17, 2013> (Uncultured bacterium clone 16sIp45-06h08.p1k 16S rRNA gene, partial sequence (GI:219526830)).*

Matsuki et al. (1999b). Distribution of bifidobacterial species in human intestinal microflora examined with 16S rRNA-genetargeted species-specific primers. Appl Environ Microbiol. Oct. 1999; 65(10):4506-12.*

Matsuki et al. (2004a). Quantitative PCR with 16S rRNA-gene-targeted species-specific primers for analysis of human intestinal bifidobacteria. Appl Environ Microbiol. Jan. 2004; 70(1):167-73.*

Blast-SEQ 17.pdf retrieved from http://blast.ncbi.nlm.nih.gov/Blast.cgi on Jan. 28, 2014.*

Blast-SEQ 18.pdf retrieved from http://blast.ncbi.nlm.nih.gov/Blast.cgi on Jan. 28, 2014.*

Horvath et al., "Gastrointestinal abnormalities in children with autistic disorder," The Journal of Pediatrics, vol. 135, pp. 559-563 (Nov. 1999).

Williams et al., "Impaired Carbohydrate digestion and transprt and mucosal dysbiosis in the intestines of Children with Autism and Gastrointestinal Disturbances," PLos One, vol. 6, issue 9, pp. 1-21 (Sep. 2011).

Extended European search report mailed on Sep. 11, 2012, for European Application No. 10789901.5 filed May 10, 2010.

International Search Report mailed on Oct. 15, 2010 for International Application No. PCT/US10/34254 filed May 10, 2010, 8 pages.

Written Opinion mailed on Oct. 15, 2010 for International Application No. PCT/US10/34254 filed May 10, 2010, 9 pages.

Abrams GD, et al., Influence of the normal flora on mucosal morphology and cellular renewal in the ileum. A comparison of germ-free and conventional mice. Lab Invest 1963;12:355-64.

Abt MC, et al., The intestinal microbiota in health and disease: the influence of microbial products on immune cell homeostasis. Curr Opin Gastroenterol 2009;25:496-502.

Adams, Hindered Dialkylamino Nucleoside Phosphite Reagents in the Synthesis of Two DNA 51-Mers, J. Am. Chem. Soc. 105:661-663, 1983, 6 pgs.

Adams, J. B., et al., 2011. Gastrointestinal flora and gastrointestinal status in children with autism—comparisons to typical children and correlation with autism severity. BMC Gastroenterol 11:22, 13 pgs.

Adams, R. J., et al., 2008. IgG antibodies against common gut bacteria are more diagnostic for Crohn's disease than IgG against mannan or flagellin. Am J Gastroenterol 103:386-96.

Agarwal S, et al., Gastrointestinal manifestations in primary immune disorders. Inflamm Bowel Dis 2010;16:703-11.

Agarwal S, et al., Pathogenesis and treatment of gastrointestinal disease in antibody deficiency syndromes. J Allergy Clin Immunol 2009;124:658-64.

Alberti A, et al., Sulphation deficit in "low-functioning" autistic children: a pilot study. Biol Psychiatry 1999;46:420-4.

(56) References Cited

OTHER PUBLICATIONS

Alper CM, et al., Recent advances in otitis media. 3. Middle ear physiology and pathophysiology. Ann Otol Rhinol Laryngol Suppl 2002;188:26-35.
Altaras et al., Production and formulation of adenovirus vectors, Adv Biochem Eng Biotechnol. 2005;99:193-260.
American Psychiatric Association, Diagnostic and Statistical Manual of Mental Disorders, Fourth Ed., APA, 2000, 5 pgs.
Anderson et al., Human gene therapy. Science 256:808-813 (1992).
Anderson, Human gene therapy, Nature, supplement to vol. 392, No. 6679, pp. 25-30 (1998).
Arumugam, M., et al., 2011. Enterotypes of the human gut microbiome. Nature 473:174-80.
Ashwood P, et al., The immune response in autism: a new frontier for autism research. J Leukoc Biol 2006;80:1-15.
Ausubel FM, ed., Current Protocols in Molecular Biology, John Wiley & Sons, Inc., New York, 1989; 17 pgs.
Backhed F, et al., Host-bacterial mutualism in the human intestine. Science 2005;307:1915-20.
Backhed F, et al., The gut microbiota as an environmental factor that regulates fat storage. Proc Natl Acad Sci U S A 2004;101:15718-23.
Bailey et al., Autism: towards an integration of clinical, genetic, neuropsychological, and neurobiological perspectives.(1996) J Child Psychol Psychiatry 37(1):89-126.
Bandini LG, Anderson SE, Curtin C, Cermak S, Evans EW, et al. (2010) Food selectivity in children with autism spectrum disorders and typically developing children. J Pediatr 157: 259-264.
Barringer et al., Blunt-end and single-strand ligations by *Escherichia coli* ligase: influence on an in vitro amplification scheme. Gene 89:117-122, 1990.
Barros R, Marcos N, Reis CA, De Luca A, David L, et al. (2009) CDX2 expression is induced by *Helicobacter pylori* in AGS cells. Scand J Gastroenterol 44: 124-125.
Beaucage, Deoxynucleoside Phosphoramidits—a new class of key intermediates for Deoxypolynucleotide synthesis. Tetra. Lett. 22:1859-1862, 1981.
Beck PL, et al., Paradoxical roles of different nitric oxide synthase isoforms in colonic injury. Am J Physiol Gastrointest Liver Physiol 2004;286:G137-47.
Belousov et al., Sequence-specific targeting and covalent modification of human genomic DNA. Nucleic Acids Res. 25:3440-3444, 1997.
Ben-Amor K, Heilig H, Smidt H, Vaughan EE, Abee T, et al. (2005) Genetic diversity of viable, injured, and dead fecal bacteria assessed by fluorescence-activated cell sorting and 16S rRNA gene analysis. Appl Environ Microbiol 71: 4679-4689.
Berger, Preparation of cDNA and the generation of cDNA libraries: overview. Methods Enzymol. 152:307-316, 1987.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry 33:7886-7896, 1994.
Born P. Carbohydrate malabsorption in patients with non-specific abdominal complaints. World J Gastroenterol 2007;13:5687-91.
Boyer LC, et al., A previously unrecognized protein-protein interaction between TWEAK and CD163: potential biological implications. J Immunol 2007;178:8183-94.
Brockmann K. The expanding phenotype of GLUT1-deficiency syndrome. Brain Dev 2009;31:545-52.
Brower, Naked DNA vaccines come of age. Nature Biotechnology, 16:1304-1305 (1998).
Brown AM, et al., Astrocyte glycogen and brain energy metabolism. Glia 2007;55:1263-1271.
Brown et al., Chemical synthesis and cloning of a tyrosine tRNA gene. Meth. Enzymol. 68:109-151, 1979.
Buchwald et al., Long-term, continuous intravenous heparin administration by an implantable infusion pump in ambulatory patients with recurrent venous thrombosis. Surgery 88(4):507-516 (1980).

Buie T, et al., Evaluation, diagnosis, and treatment of gastrointestinal disorders in individuals with ASDs: a consensus report. Pediatrics 2010;125 Suppl 1:S1-18.
Buning C, et al., The C/C(-13910) and G/G(-22018) genotypes for adult-type hypolactasia are not associated with inflammatory bowel disease. Scand J Gastroenterol 2003;38:538-42.
Burg et al., Single molecule detection of RNA reporter probes by amplification with Q beta replicase. Mol. Cell. Probes 10:257-271, 1996.
Burkly LC, et al., TWEAKing tissue remodeling by a multifunctional cytokine: role of TWEAK/Fn14 pathway in health and disease. Cytokine 2007;40:1-16.
Bushara KO, Neurologic presentation of celiac disease. Gastroenterology 2005;128:S92-S97.
Busse, H.J., et al., 2005. Family III. Alcaligenaceae in Bergey's Manual of Systematic Bacteriology vol. 2: The Proteobacteria, Part C. Springer-Verlag, New York. 39 pgs.
Chen et al., Gene therapy for brain tumors: regression of experimental gliomas by adenovirus-mediated gene transfer in vivo.1994. Proc. Natl. Acad. Sci. USA 91: 3054-3057.
Chun, J., et al., 2007. EzTaxon: a web-based tool for the identification of prokaryotes based on 6S ribosomal RNA gene sequences. Int J Syst Evol Microbiol 57:2259-61.
Collins SM, et al., The relationship between intestinal microbiota and the central nervous system in normal gastrointestinal function and disease. Gastroenterology 2009;136:2003-14.
Corbett BA, et al., A proteomic study of serum from children with autism showing differential expression of apolipoproteins and complement proteins. Mol Psychiatry 2007;12:292-306.
Curin JM, Terzic J, Petkovic ZB, Zekan L, Terzic IM, et al. (2003) Lower cortisol and higher ACTH levels in individuals with autism. J Autism Dev Disord 33: 443-448.
D'Eufemia P, et al., Abnormal intestinal permeability in children with autism. Acta Paediatr 1996;85:1076-9.
Dahlqvist A., Assay of intestinal disaccharidases. Scand J Clin Lab Invest. 1984;44:169-172.
Dahlqvist A., Specificity of the human intestinal disaccharidases and implications for hereditary disaccharide intolerance. J Clin Invest. 1962;41:463-470.
Dalmasso G et al., (2008) Butyrate transcriptionally enhances peptide transporter PepT1 expression and activity. PLoS One 3(6):e2476, 14 pgs. doi. 10.1371/journal.pone.0002476.
Dawson G. Recent advances in research on early detection, causes, biology, and treatment of autism spectrum disorders. Curr Opin Neurol 2010;23:95-6.
de Magistris, L., et al., 2010. Alterations of the intestinal barrier in patients with autism spectrum disorders and in their first-degree relatives. J Pediatr Gastroenterol Nutr 51:418-24.
Dohi T, et al., TWEAK/Fn14 pathway: a nonredundant role in intestinal damage in mice through a TWEAK/intestinal epithelial cell axis. Gastroenterology 2009;136:912-923.e8.
Duncan SH, et al., The role of pH in determining the species composition of the human colonic microbiota. Environ Microbiol 2009;11:2112-22.
During et al.,Controlled release of dopamine from a polymeric brain implant: in vivo characterization. Ann. Neurol. 25(4):351-356 (1989).
Durso, L. M., et al., 2010. Animal-to-animal variation in fecal microbial diversity among beef cattle. Appl Environ Microbiol 76:4858-62.
Dyer J, et al., Intestinal glucose sensing and regulation of intestinal glucose absorption. Biochem Soc Trans 2007;35:1191-4.
Dzau et al., Gene therapy for cardiovascular disease.Trends Biotechnol 11(5):205-210 (1993).
Eckburg PB, Bik EM, Bernstein CN, Purdom E, Dethlefsen L, et al. (2005) Diversity of the human intestinal microbial flora. Science 308: 1635-1638.
Eliyahu et al., Polymers for DNA delivery. Molecules, 2005 10(1):34-64.
Emond A, Emmett P, Steer C, Golding J (2010) Feeding symptoms, dietary patterns, and growth in young children with autism spectrum disorders. Pediatrics 126: e337-342.

(56) References Cited

OTHER PUBLICATIONS

Emvo EN, Raul F, Koch B, Neuville P, Foltzer-Jourdainne C (1996) Sucrase-isomaltase gene expression in suckling rat intestine: hormonal, dietary, and growth factor control. J Pediatr Gastroenterol Nutr 23: 262-269.

Enstrom AM, et al., Differential monocyte responses to TLR ligands in children with autism spectrum disorders. Brain Behav Immun 2010;24:64-71.

Fabriek BO, et al., The macrophage scavenger receptor CD163 functions as an innate immune sensor for bacteria. Blood 2009;113:887-92.

Fehm HL, et al., The selfish brain: competition for energy resources. Prog Brain Res 2006;153:129-40.

Filkova M, et al., The role of resistin as a regulator of inflammation: Implications for various human pathologies. Clin Immunol 2009;133:157-70.

Finegold SM, Dowd SE, Gontcharova V, Liu C, Henley Ke, et al. (2010) Pyrosequencing study of fecal microflora of autistic and control children. Anaerobe 16: 444-453.

Finegold SM, et al., Gastrointestinal microflora studies in late-onset autism. Clin Infect Dis 2002;35:S6-S16.

Fix JA, Oral controlled release technology for peptides: status and future prospects. Pharm Res. 13(12): 1760-1764, 1996.

Flint HJ, Duncan SH, Scott KP, Louis P (2007) Interactions and competition within the microbial community of the human colon: links between diet and health. Environ Microbiol 9: 1101-1111.

Flint HJ, et al., Polysaccharide utilization by gut bacteria: potential for new insights from genomic analysis. Nat Rev Microbiol 2008;6:121-31.

Fombonne, E. (2003). The prevalence of autism. JAMA 289(1): 87-89.

Frank DN, et al., 2007. Molecular-phylogenetic characterization of microbial community imbalances in human inflammatory bowel diseases. Proc Natl Acad Sci USA. 104: 13780-13785.

Fraser DA, et al., C1q differentially modulates phagocytosis and cytokine responses during ingestion of apoptotic cells by human monocytes, macrophages, and dendritic cells. J Immunol 2009;183:6175-85.

Frenkel K. et al., 7,12-dimethylbenz[a]anthracene induces oxidative DNA modification in vivo. Free Radic. Biol. Med. 19:373-380, 1995.

Freshney RI, Animal Cell Culture, A Practical Approach. IRL Press Limited, 1987, 10 pgs.

Friedmann T., Progress toward human gene therapy. Science, 244(4910):1275-1281 (1989).

Fullwood A, et al., The relationship of psychiatric illness with gastrointestinal disease. Annu Rev Med 1995;46:483-96.

Furlano RI, et al., Colonic CD8 and gamma delta T-cell infiltration with epithelial damage in children with autism. J Pediatr 2001;138:366-72.

Gait MJ, Oligonucleotide Synthesis, IRL Press Limited, Oxford, England (1984) 12 pgs.

Gennaro AR, Remmington's Pharmaceutical Sciences, Mack Publishing Co., Easton, PA (1985) 6 pgs.

Gillevet P, Sikaroodi M, Keshavarzian A, Mutlu EA (2010) Quantitative assessment of the human gut microbiome using multitag pyrosequencing. Chem Biodivers 7: 1065-1075.

Glover DN, ed., DNA Cloning, vols. I (1985) 8 pgs.

Goda et al., Characterization of degradation process of sucrase-isomaltase in rat jejunum with monoclonal-antibody-based enzyme-linked immunosorbent assay. Biochem J. 250(1): 41-46 (1988).

Goldstein EJ, et al., 2009. Activity of a novel carbapenem, doripenem, against anaerobic pathogens. Diagn Microbiol Infect Dis. 63: 447-454.

Goodson JM, In Medical Applications of Controlled Release, vol. 2, pp. 115-138 (1984).

Goodwin MS, et al., Malabsorption and cerebral dysfunction: a multivariate and comparative study of autistic children. J Autism Child Schizophr 1971;1:48-62.

Gophna U, et al., 2006. Differences between tissue-associated intestinal microfloras of patients with Crohn's disease and ulcerative colitis. J Clin Microbiol, 44(11): 4136-4141.

Greetham HL, et al., 2004. *Sutterella stercoricanis* sp. nov., isolated from canine faeces. Int J Syst Evol Microbiol. 54: 1581-1584.

Guatelli et al., Isothermal, in vitro amplification of nucleic acids by a multienzyme reaction modeled after retroviral replication. Proc. Natl. Acad. Sci. USA 87:1874-1878, 1990.

Guo X, et al., (2008) Development of a real-time PCR method for Firmicutes and Bacteroidetes in faeces and its application to quantify intestinal population of obese and lean pigs. Lett Appl Microbiol 47: 367-373.

Gupta G, et al., Increased risk for demyelinating diseases in patients with inflammatory bowel disease. Gastroenterology 2005;129:819-26.

Gupta S, et al., Pentoxifylline: brief review and rationale for its possible use in the treatment of autism. J Child Neurol 1996;11:501-4.

Hamady, M., et al., 2008. Error-correcting barcoded primers for pyrosequencing hundreds of samples in multiplex. Nat Methods 5:235-7.

Hames BD et al., Nucleic Acid Hybridization, IRL Press Limited, Oxford, England (1985) 11 pgs.

Hammer HF, Santa Ana CA, Schiller LR, Fordtran JS (1989) Studies of osmotic diarrhea induced in normal subjects by ingestion of polyethylene glycol and lactulose. J Clin Invest 84: 1056-1062.

Haznedar MM, et al., Anterior cingulate gyrus volume and glucose metabolism in autistic disorder. Am J Psychiatry 1997;154:1047-50.

Heijtz, R. D., et al., 2011. Normal gut microbiota modulates brain development and behavior. Proc Natl Acad Sci U S A 108:3047-52.

Herndon AC, DiGuiseppi C, Johnson SL, Leiferman J, Reynolds A (2009) Does nutritional intake differ between children with autism spectrum disorders and children with typical development? J Autism Dev Disord 39: 212-222.

Herweijer et al., Gene therapy progress and prospects: hydrodynamic gene delivery. Gene Ther. 14(2):99-107 (2007).

Hissin et al., Mechanism of insulin-resistant glucose transport activity in the enlarged adipose cell of the aged, obese rat. 1982, J. Clin. Invest. 70(4): 780-90.

Hodgson S, et al., Genetic testing in other GI diseases. Best Pract Res Clin Gastroenterol 2009;23:245-56.

Hodin RA, et al., Pattern of rat intestinal brush-border enzyme gene expression changes with epithelial growth state. Am J Physiol 1995;269:C385-91.

Hogan et al., Manipulating the Mouse Embryo: a laboratory manual, Cold Spring Harbor Laboratory Press, New York (1986) 6 pgs.

Hong et al., Pyrosequencing-based analysis of the mucosal microbiota in healthy individuals reveals ubiquitous bacterial groups and micro-heterogeneity. PLoS One 6(9):e25042, 10 pgs. doi: 10.1371/journal.pone.0025042 (2011).

Hooper LV, et al., Molecular analysis of commensal host-microbial relationships in the intestine. Science 2001;291:881-4.

Hornig, M., et al., 2008. Lack of association between measles virus vaccine and autism with enteropathy: a case-control study. PLoS One 3(9):e3140, 8 pgs. doi: 10.1371/journal.pone.0003140.

Howard et al., Intracerebral drug delivery in rats with lesion-induced memory deficits. J Neurosurg. 71:105-112 (1989).

Hruby et al., Conformational and topographical considerations in designing agonist peptidomimetics from peptide leads. Curr. Med. Chem. 7(9):945-970 (2000).

Hruby et al., Synthesis of oligopeptide and peptidomimetic libraries. Curr. Op. Chem. Biol. 1:114-119, 1997.

Huse et al., Accuracy and quality of massively parallel DNA pyrosequencing. Genome Biol 8(7):R143 (2007) 9 pgs.

Ikeda et al. (2007) Interaction of Toll-like receptors with bacterial components induces expression of CDX2 and MUC2 in rat biliary epithelium in vivo and in culture. Lab Invest 87: 559-571.

Innis et al., PCR Protocols, A Guide to Methods and Applications Academic Press Inc., N.Y. (1990) 16 pgs.

Innis et al., PCR Strategies, Academic Press Inc., N.Y. (1995) 13 pgs.

Iqbal CW, et al., Mechanisms of ileal adaptation for glucose absorption after proximal-based small bowel resection. J Gastrointest Surg 2008;12:1854-64; discussion 64-5.

(56) References Cited

OTHER PUBLICATIONS

Isaka et al., Electroporation-mediated gene therapy. Expert Opin Drug Deliv. 4(5):561-71 (2007).
Iseri et al., Increased Serum Levels of Epidermal Growth Factor in Children with Autism. J Autism Dev Disord. 41(2):237-41. (2010).
Ishigame H, et al., Differential roles of interleukin-17A and -17F in host defense against mucoepithelial bacterial infection and allergic responses. Immunity 2009;30:108-19.
Jacobs DM, et al., Non-digestible food ingredients, colonic microbiota and the impact on gut health and immunity: a role for metabolomics. Curr Drug Metab 2009;10:41-54.
Jager et al., Emerging adenoviral vectors for stable correction of genetic disorders. Curr Gene Ther. 7(4):272-83 (2007).
Jensen et al., Cutaneous gene therapy. Ann Med. 2007;39(2):108-15.
Johansson L, et al., Neutrophil-derived hyperresistinemia in severe acute streptococcal infections. J Immunol 2009;183:4047-54.
Jones et al., Application and evaluation of denaturing HPLC for molecular genetic analysis in tuberous sclerosis. Hum Genet., 106(6):663-8 (2000).
Jukes et al., Evolution of Protein Molecules in HN Mammalian protein metabolism. Academic Press, New York, 7 pgs. (1969).
Jyonouchi, H., et al., 2005. Dysregulated innate immune responses in young children with autism spectrum disorders: their relationship to gastrointestinal symptoms and dietary intervention. Neuropsychobiology 51:77-85.
Kalhan SC, et al., Carbohydrate as nutrient in the infant and child: range of acceptable intake. Eur J Clin Nutr 1999;53 Suppl 1:S94-100.
Kellett GL, et al., Sugar absorption in the intestine: the role of GLUT2. Annu Rev Nutr 2008;28:35-54, C-1-C-3.
Kern et al., Direct hybridization of large-insert genomic clones on high-density gridded cDNA filter arrays. Biotechniques 23:120-124, 1997.
Kikuchi et al., Cutaneous gene delivery. J Dermatol Sci. 50(2):87-98 (2008).
King A, et al., 1999. Antimicrobial susceptibility of non-Bacteroides fragilis group anaerobic Gram-negative bacilli in Europe. Clin Microbiol Infect. 5: 404-416.
Kishi et al., (1999) Sucrase-isomaltase and hexose transporter gene expressions are coordinately enhanced by dietary fructose in rat jejunum. J Nutr 129: 953-956.
Knivsberg AM, et al., A randomised, controlled study of dietary intervention in autistic syndromes. Nutr Neurosci 2002;5:251-61.
Kubes P, et al., Nitric oxide and intestinal inflammation. Am J Med 2000;109:150-8.
Kwoh et al., Transcription-based amplification system and detection of amplified human immunodeficiency virus type 1 with a bead-based sandwich hybridization format. Proc. Natl. Acad. Sci. USA 86(4):1173-1177 (1989).
Landegren et al., A ligase-mediated gene detection technique. Science 241(4869):1077-1080 (1988).
Langer et al., Chemical and Physical Structure of Polymers as Carriers for Controlled Release of Bioactive Agents: A Review. J. Macromol. Sci. 23:61-126 (1983).
Langer et al., Medical Applications of Controlled Release, vol. 2. Applications and Evaluation, CRC Press Inc., Boca Raton, Fla. (1974) 26 pgs.
Langer R, New methods of drug delivery. Science 249:1527-1533 (1990).
Lapointe TK, et al., The role of epithelial malfunction in the pathogenesis of enteropathogenic E. coli-induced diarrhea. Lab Invest 2009;89:964-70.
Le Gall M, et al., Sugar sensing by enterocytes combines polarity, membrane bound detectors and sugar metabolism. J Cell Physiol 2007;213:834-43.
Leturque A, et al., GLUT2 mutations, translocation, and receptor function in diet sugar managing. Am J Physiol Endocrinol Metab 2009;296:E985-92.
Levy et al. (2007) Relationship of dietary intake to gastrointestinal symptoms in children with autistic spectrum disorders. Biol Psychiatry 61: 492-497.
Levy et al., Inhibition of calcification of bioprosthetic heart valves by local controlled-release diphosphonate. Science 228(4696):190-192 (1985).
Ley et al. (2005) Obesity alters gut microbial ecology. Proc Natl Acad Sci U S A 102: 11070-11075.
Ley et al., (2006) Microbial ecology: human gut microbes associated with obesity. Nature 444: 1022-1023.
Lombardo L, et al., (2010) Increased incidence of small intestinal bacterial overgrowth during proton pump inhibitor therapy. Clin Gastroenterol Hepatol 8: 504-508.
Lossos A, et al., Neurologic aspects of inflammatory bowel disease. Neurology 1995;45:416-21.
Louis P, Young P, Holtrop G, Flint HJ (2010) Diversity of human colonic butyrate-producing bacteria revealed by analysis of the butyryl-CoA:acetate CoA-transferase gene. Environ Microbiol 12: 304-314.
Lu JH, et al., The classical and regulatory functions of C1q in immunity and autoimmunity. Cell Mol Immunol 2008;5:9-21.
Lupp C, et al., Host-mediated inflammation disrupts the intestinal microbiota and promotes the overgrowth of Enterobacteriaceae. Cell Host Microbe 2007;2:119-29.
Macpherson, A. J., et al., 2004. Interactions between commensal intestinal bacteria and the immune system. Nat Rev Immunol 4:478-85.
Maher KR, et al., Peculiarities in the endocrine response to insulin stress in early infantile autism. J Nerv Ment Dis 1975;161:180-4.
Mangin, I., et al., 2004. Molecular inventory of faecal microflora in patients with Crohn's disease. FEMS Microbiol Ecol 50:25-36.
Mariat et al., The Firmicutes/Bacteroidetes ratio of the human microbiota changes with age. BMC Microbiol 9:123, 6 pgs. doi: 10.1186/1471-2180-9-123 (2009).
Marteau et al. (2001) Comparative study of bacterial groups within the human cecal and fecal microbiota. Appl Environ Microbiol 67: 4939-4942.
Matosin-Matekalo M, Mesonero JE, Delezay O, Poiree JC, Ilundain AA, et al. (1998) Thyroid hormone regulation of the Na+/glucose cotransporter SGLT1 in Caco-2 cells. Biochem J 334 (Pt 3): 633-640.
Mavin, S., et al., 2011. Interpretation criteria in Western blot diagnosis of Lyme borreliosis. Br J Biomed Sci 68:5-10.
Mayer RJ et al., Immunochemical Methods in Cell and Molecular Biology, Academic Press, London (1987) 10 pgs.
Mazmanian SK, et al., A microbial symbiosis factor prevents intestinal inflammatory disease. Nature 2008;453:620-5.
McNay EC, et al., Fluctuations in brain glucose concentration during behavioral testing: dissociations between brain areas and between brain and blood. Neurobiol Learn Mem 2001;75:325-37.
McNay EC, et al., Food for thought: fluctuations in brain extracellular glucose provide insight into the mechanisms of memory modulation. Behav Cogn Neurosci Rev 2002;1:264-80.
Melis D, et al., Brain damage in glycogen storage disease type I, J Pediatr 2004, 144:637-42.
Miller AD, Human gene therapy comes of age. Nature, 357(6378): 455-460 (1992).
Miller JH et al., Gene Transfer Vectors for Mammalian Cells, 1987, Cold Spring Harbor Laboratory, 6 pgs.
Mochizuki et al., The regulation of jejunal induction of the maltase-glucoamylase gene by a high-starch/low-fat diet in mice. Mol Nutr Food Res 54: 1445-1451 (2010).
Molitoris, E., et al., 1997. Sources and antimicrobial susceptibilities of Campylobacter gracilis and Sutterella wadsworthensis. Clin Infect Dis 25 Suppl 2:S264-5.
Momozawa et al., Characterization of Bacteria in Biopsies of Colon and Stools by High Throughput Sequencing of the V2 Region of Bacterial 16S rRNA Gene in Human. PLoS One 6(2):e16952, 10 pgs. doi: 10.1371/journal.pone.0016952. (2011).
Montassir H, et al., Associated factors in neonatal hypoglycemic brain injury. Brain Dev 2009; 31:649-56.
Morgan et al., Chapter 26. Approaches to the Discovery of the Non-Peptide Ligands for Peptide Receptors and Peptidases. Ann. Rep. Med. Chem. 24:243-252 (1989).
Narang et al., Improved phosphotriester method for the synthesis of gene fragments. Meth. Enzymol. 68:90 (1979), 11 pgs.

(56) References Cited

OTHER PUBLICATIONS

Nehlig A, Cerebral energy metabolism, glucose transport and blood flow: changes with maturation and adaptation to hypoglycaemia. Diabetes Metab 23:18-29 (1997).

Nguyen et al., Pathogenic bacteria induce colonic PepT1 expression: an implication in host defense response. Gastroenterology 137: 1435-1447.e2 (2009).

Nichols BL, et al., Congenital maltase-glucoamylase deficiency associated with lactase and sucrase deficiencies. J Pediatr Gastroenterol Nutr 2002; 35:573-9.

Nichols BL, et al., Contribution of villous atrophy to reduced intestinal maltase in infants with malnutrition. J Pediatr Gastroenterol Nutr 2000; 30:494-502.

Nichols BL, et al., Mucosal maltase-glucoamylase plays a crucial role in starch digestion and prandial glucose homeostasis of mice. J Nutr 2009; 139:684-90.

O'Hara, A. M., et al., 2006. The gut flora as a forgotten organ. EMBO Rep 7:688-93.

O'Keefe SJ (2008) Nutrition and colonic health: the critical role of the microbiota. Curr Opin Gastroenterol 24: 51-58.

Onofre G, et al., Scavenger receptor CD163 and its biological functions. Acta Medica (Hradec Kralove) 2009; 52:57-61.

Parracho HM, et al., Differences between the gut microflora of children with autistic spectrum disorders and that of healthy children. J Med Microbiol 2005; 54:987-91.

Pascual JM, et al., Brain glucose supply and the syndrome of infantile neuroglycopenia. Arch Neurol 2007;64:507-13.

Pascual JM, et al., GLUT1 deficiency and other glucose transporter diseases. Eur J Endocrinol 2004;150:627-33.

Penders J, et al., Factors influencing the composition of the intestinal microbiota in early infancy. Pediatrics 2006;118:511-21.

Penders J, et al., The role of the intestinal microbiota in the development of atopic disorders. Allergy 2007;62:1223-36.

Perbal B., A Practical Guide to Molecular Cloning (1984); the treatise, Methods in Enzymology (Academic Press, Inc., N.Y.); 11 pgs.

Pfannkuche H, et al., Glucose, epithelium, and enteric nervous system: dialogue in the dark. J Anim Physiol Anim Nutr (Berl) 2009;93:277-86.

Quezada-Calvillo et al., Contribution of mucosal maltase-glucoamylase activities to mouse small intestinal starch alpha-glucogenesis. J. Nutr. 137:1725-1733 (2007).

Raiten et al., Perspectives on the nutritional ecology of autistic children. J Autism Dev Disord 16: 133-143 (1986).

Rautava S, et al., Commensal bacteria and epithelial cross talk in the developing intestine. Curr Gastroenterol Rep 2007;9, 12 pgs.

Reid et al., Microbiota restoration: natural and supplemented recovery of human microbial communities. Nat Rev Microbiol 9:27-38. (2011).

Ripka et al., Peptidomimetic design. Curr. Op. Chem. Biol. 22(4):441-452 (1998).

Robayo-Torres CC, Quezada-Calvillo R, Nichols BL (2006) Disaccharide digestion: clinical and molecular aspects. Clin Gastroenterol Hepatol 4: 276-287.

Rosenfeld MA, Human artificial chromosomes get real. Nat. Genet. 15:333-335 (1997).

Saitou, N., et al., 1987. The neighbor-joining method: a new method for reconstructing phylogenetic trees. Mol Biol Evol 4:406-25.

Samanen et al., Chemical approaches to improve the oral bioavailability of peptidergic molecules. J. Pharm. Pharmacol. 48: 119-135 (1996).

Sambrook et al., Molecular Cloning, a laboratory manual, Second Edition, vols. 1-3, Cold Spring Harbor Laboratory Press, USA (1989) 33 pgs.

Sandler RH, et al., Short-term benefit from oral vancomycin treatment of regressive-onset autism. J Child Neurol 2000;15:429-35.

Saudek et al., A preliminary trial of the programmable implantable medication system for insulin delivery. N. Engl. J. Med. 321(9):574-579 (1989).

Scheepers A, et al., The glucose transporter families SGLT and GLUT: molecular basis of normal and aberrant function. JPEN J Parenter Enteral Nutr 2004;28:364-71.

Schloss, P. D., et al., 2009. Introducing mothur: open-source, platform-independent, community-supported software for describing and comparing microbial communities. Appl Environ Microbiol 75:7537-41.

Schreck KA, Williams K, Smith AF (2004) A comparison of eating behaviors between children with and without autism. J Autism Dev Disord 34: 433-438.

Schulzke JD, et al., Disorders of intestinal secretion and absorption. Best Pract Res Clin Gastroenterol 2009;23:395-406.

Scupham JA et al., Comparison of the cecal microbiota of domestic and wild turkeys. Microb Ecol. 56(2):322-331. (2008).

Sefton MV, Implantable pumps. CRC Crit. Ref. Biomed. Eng. 14(3):201-240 (1987).

Seiderer J, et al., Role of the novel Th17 cytokine IL-17F in inflammatory bowel disease (IBD): upregulated colonic IL-17F expression in active Crohn's disease and analysis of the IL-17F p.His161Arg polymorphism in IBD. Inflamm Bowel Dis 2008;14:437-45.

Sekirov I, et al., The role of the intestinal microbiota in enteric infection. J Physiol 2009;587:4159-67.

Shearer TR, Larson K, Neuschwander J, Gedney B (1982) Minerals in the hair and nutrient intake of autistic children. J Autism Dev Disord 12: 25-34.

Smith et al., Detection of *Mycobacterium turberculosis* directly from sputum by using a prototype automated Q-beta replicase assay. J. Clin. Microbiol. 35:1477-1483 (1997).

Smolen et al., Controlled Drug Bioavailability, Drug Product Design and Performance, John Wiley & Sons, Inc., New York (1984) 3 pgs.

Song Y, et al., Real-time PCR quantitation of clostridia in feces of autistic children. Appl Environ Microbiol 2004;70:6459-65.

Sonnenburg ED, et al., A hybrid two-component system protein of a prominent human gut symbiont couples glycan sensing in vivo to carbohydrate metabolism. Proc Natl Acad Sci U S A 2006;103:8834-9.

Sonnenburg ED, Zheng H, Joglekar P, Higginbottom SK, Firbank SJ, et al. (2010) Specificity of polysaccharide use in intestinal *bacteroides* species determines diet-induced microbiota alterations. Cell 141: 1241-1252.

Sooknanan et al., A detection and amplification system uniquely suited for RNA. Biotechnology 13:563-564 (1995).

Stackebrandt, E., et al., 1994. A place for DNA-DNA reassociation and 16S ribosomal-RNA sequence analysis in the present species definition in bacteriology. Int J Syst Bacteriol 44:846-849.

Stecher B, et al., The role of microbiota in infectious disease. Trends Microbiol 2008;16:107-14.

Sudo N, Chida Y, Aiba Y, Sonoda J, Oyama N, et al. (2004) Postnatal microbial colonization programs the hypothalamic-pituitary-adrenal system for stress response in mice. J Physiol 558: 263-275.

Sudo N, Sawamura S, Tanaka K, Aiba Y, Kubo C, et al. (1997) The requirement of intestinal bacterial flora for the development of an IgE production system fully susceptible to oral tolerance induction. J Immunol 159: 1739-1745.

Suzuki K, Hashimoto K, Iwata Y, Nakamura K, Tsujii M, et al. (2007) Decreased serum levels of epidermal growth factor in adult subjects with high-functioning autism. Biol Psychiatry 62: 267-269.

Swallow DM. Genetic influences on carbohydrate digestion. Nutr Res Rev 2003;16:37-43.

Takahashi T. Pathophysiological significance of neuronal nitric oxide synthase in the gastrointestinal tract. J Gastroenterol 2003;38:421-30.

Tammali R, et al., Aldose reductase deficiency in mice prevents azoxymethane-induced colonic preneoplastic aberrant crypt foci formation. Carcinogenesis 2009;30:799-807.

Tamura, K., et al., 2007. MEGA4: Molecular Evolutionary Genetics Analysis (MEGA) software version 4.0. Mol Biol Evol 24:1596-9.

Tanaka T, Suzuki A, Kuranuki S, Mochizuki K, Suruga K, et al. (2008) Higher expression of jejunal LPH gene in rats fed the high-carbohydrate/low-fat diet compared with those fed the low-carbohydrate/high-fat diet is associated with in vitro binding of Cdx-2 in nuclear proteins to its promoter regions. Life Sci 83: 122-127.

(56) References Cited

OTHER PUBLICATIONS

Tijssen P, Laboratory Techniques in Biochemistry and Molecular Biology Hybridization with Nucleic Acid Probes, Part I. Theory and Nucleic Acid Preparation, Elsevier Science Publishers, New York (1993) 7 pgs.
Torrente F, et al., Focal-enhanced gastritis in regressive autism with features distinct from Crohn's and *Helicobacter pylori* gastritis. Am J Gastroenterol 2004;99:598-605.
Torrente F, et al., Small intestinal enteropathy with epithelial IgG and complement deposition in children with regressive autism. Mol Psychiatry 2002;7:8 pgs., 34.
Hames BD et al., Transcription and Translation, IRL Press Limited, Oxford, England (1984) 13 pgs.
Turnbaugh PJ, et al., An obesity-associated gut microbiome with increased capacity for energy harvest. Nature 2006;444:1027-31.
Ullner PM, et al., Murine Glut-1 transporter haploinsufficiency: postnatal deceleration of brain weight and reactive astrocytosis. Neurobiol Dis 2009;36:60-9.
Valicenti-McDermott MD, et al., Gastrointestinal symptoms in children with an autism spectrum disorder and language regression. Pediatr Neurol 2008;39:392-8.
Van Citters GW, et al., Ileal brake: neuropeptidergic control of intestinal transit. Curr Gastroenterol Rep 2006;8:367-73.
Verma IM, Gene Therapy, Treatment of disease by introducing healthy genes into the body is becoming feasible. But the therapy will not reach its full potential until the genes can be coaxed to work throughout life. Scientific American: 68-72, 81-82, 84 (1990).
Vollaard, E. J., et al., 1994. Colonization resistance. Antimicrob Agents Chemother 38:409-14.
Waehler et al., Engineering targeted viral vectors for gene therapy. Nat Rev Genet. 8(8):573-87 (2007).
Wakefield AJ, Anthony A, Murch SH, Thomson M, Montgomery SM, et al. (2000) Enterocolitis in children with developmental disorders. Am J Gastroenterol 95: 2285-2295.
Wakefield AJ, et al., Review article: the concept of entero-colonic encephalopathy, autism and opioid receptor ligands. Aliment Pharmacol Ther 2002;16:663-74.
Wakefield AJ, et al., The significance of ileo-colonic lymphoid nodular hyperplasia in children with autistic spectrum disorder. Eur J Gastroenterol Hepatol 2005;17:827-36.
Walker et al., High-throughput clone library analysis of the mucosa-associated microbiota reveals dysbiosis and differences between inflamed and non-inflamed regions of the intestine in inflammatory bowel disease. BMC Microbiol 11:711:7, 12 pgs. doi: 10.1186/1471-2180-11-7 (2011).
Wang, L., et al., 2011. Low Relative Abundances of the Mucolytic Bacterium *Akkermansia muciniphila* and *Bifidobacterium* spp. in Feces of Children with Autism. Appl Environ Microbiol 77:6718-21.
Warren RP, et al., Brief report: immunoglobulin a deficiency in a subset of autistic subjects. J Autism Dev Disord 1997;27:187-92.
Weir DM et al., Handbook of Experimental Immunology, vols. I-IV, Blackwell Scientific Publications Inc. (1986) 9 pgs.
Wells SM, et al., Elevated asymmetric dimethylarginine alters lung function and induces collagen deposition in mice. Am J Respir Cell Mol Biol 2009;40:179-88.
Wexler HM, et al., 1996. In vitro activities of trovafloxacin against 557 strains of anaerobic bacteria. Antimicrob Agents Chemother. 40: 2232-2235.
Wexler HM, et al., 2000. In vitro activities of MK-826 (L-749,345) against 363 strains of anaerobic bacteria. Antimicrob Agents Chemother. 44: 2222-2224.
Wexler HM, et al., 2002. In vitro activities of faropenem against 579 strains of anaerobic bacteria. Antimicrob Agents Chemother. 46: 3669-3675.
Wexler HM, Genus VIII. Sutterella in Bergey's Manual of Systematic Bacteriology vol. 2: The Proteobacteria, Part C. Springer-Verlag, New York (2005) 6 pgs.
Wexler HM et al., *Sutterella wadsworthensis* gen. nov., sp. nov., bile-resistant microaerophilic *Campylobacter gracilis*-like clinical isolates. Int J Syst Bacteriol 46:252-258 (1996).
White JF, Intestinal pathophysiology in autism. Exp Biol Med (Maywood) 228:639-649 (2003).
Williams et al., Endoplasmic reticulum stress and neurodegeneration in rats neonatally infected with borna disease virus. J Virol 80: 8613-8626 (2006).
Williams et al., Spatiotemporal analysis of purkinje cell degeneration relative to parasagittal expression domains in a model of neonatal viral infection. J Virol 81: 2675-2687 (2007).
Williams et al., Metallothioneins and zinc dysregulation contribute to neurodevelopmental damage in a model of perinatal viral infection. Brain Pathol 16: 1-14 (2006).
Williams et al., Impaired carbohydrate digestion and transport and mucosal dysbiosis in the intestines of children with autism and gastrointestinal disturbances. PLoS One 6(9):e24585, 21 pgs. doi: 10.1371/journal.pone.0024585 (2011).
Wong JM, et al., Carbohydrate digestibility and metabolic effects. J Nutr 2007;137:2539S-46S.
Wong JM, et al., Colonic health: fermentation and short chain fatty acids. J Clin Gastroenterol 2006;40:235-43.
Woodward J, Immobilized Cells and Enzymes, IRL Press Limited (1986) 8 pgs.
Woon et al., Construction and characterization of a 10-fold genome equivalent rat P1-derived artificial chromosome library. Genomics 50:306-316 (1998).
Wright EM, et al., Active sugar transport in health and disease. J Intern Med 2007;261:32-43.
Wu et al., Methods in Enzymology, vols. 154 and 155, Academic Press Inc., San Diego, CA. (1987) 11 pgs.
Wu et al., The ligation amplification reaction (LAR)—amplification of specific DNA sequences using sequential rounds of template-dependent ligation. Genomics 4(4):560-569 (1989).
Yap et al., Urinary metabolic phenotyping differentiates children with autism, from their unaffected siblings and age-matched controls. J. Proteome Res. 9(6):2996-3004 (2010).
Yu LC, et al., SGLT-1-mediated glucose uptake protects intestinal epithelial cells against LPS-induced apoptosis and barrier defects: a novel cellular rescue mechanism? FASEB J 2005;19:1822-35.
Zhao Y, et al., Neuronal glucose transporter isoform 3 deficient mice demonstrate features of autism spectrum disorders. Mol Psychiatry 2010;15:286-99.
Ziambaras T, Rubin DC, Perlmutter DH (1996) Regulation of sucrase-isomaltase gene expression in human intestinal epithelial cells by inflammatory cytokines. J Biol Chem 271: 1237-1242.
Zijlmans WC, et al., Glucose metabolism in children: influence of age, fasting, and infectious diseases. Metabolism 2009;58:1356-65.
Zilbauer M, et al., Intestinal alpha-defensin expression in pediatric inflammatory bowel disease. Inflamm Bowel Dis 2011; 17:2076-2086.

\* cited by examiner

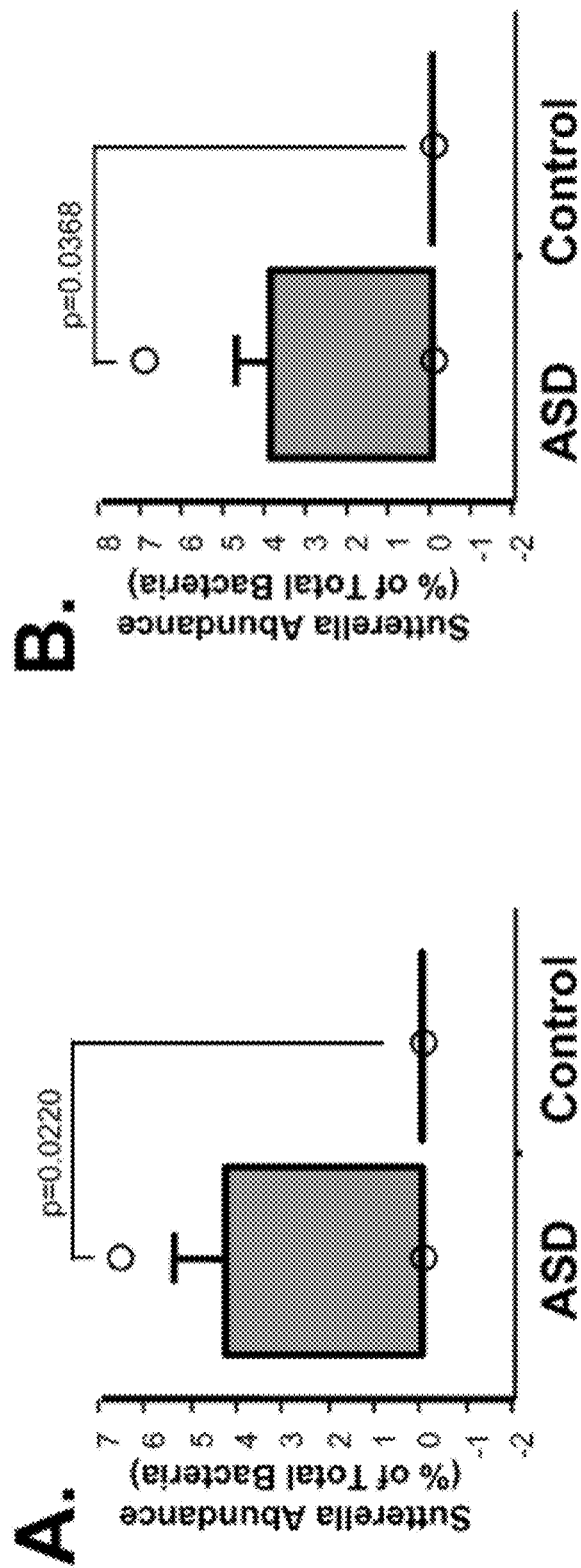
FIGS. 8A-B

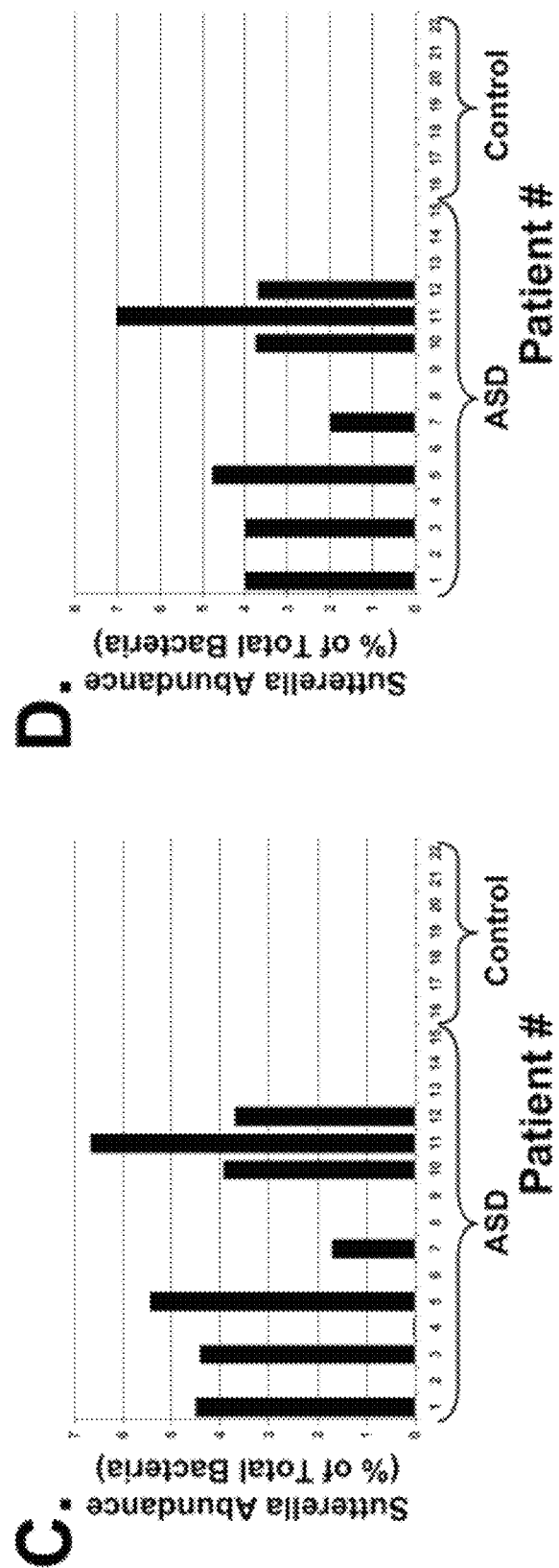
FIGS. 8C-D

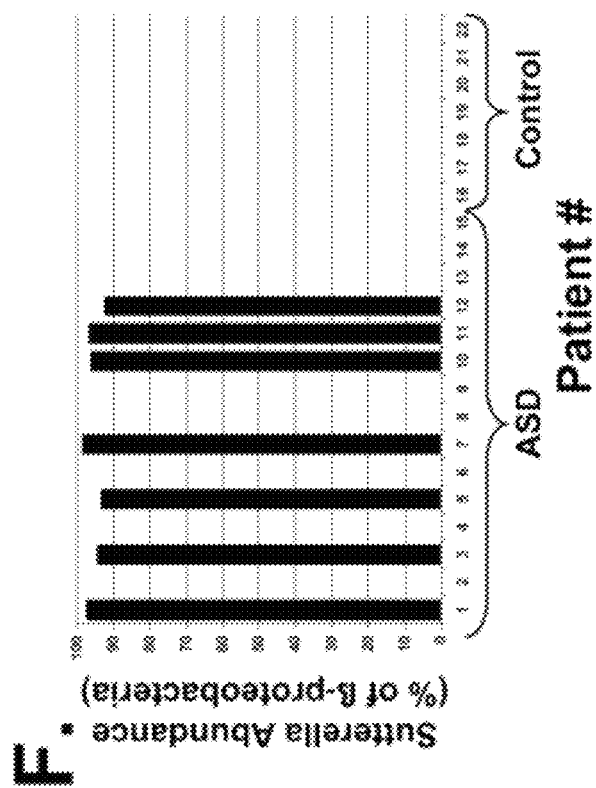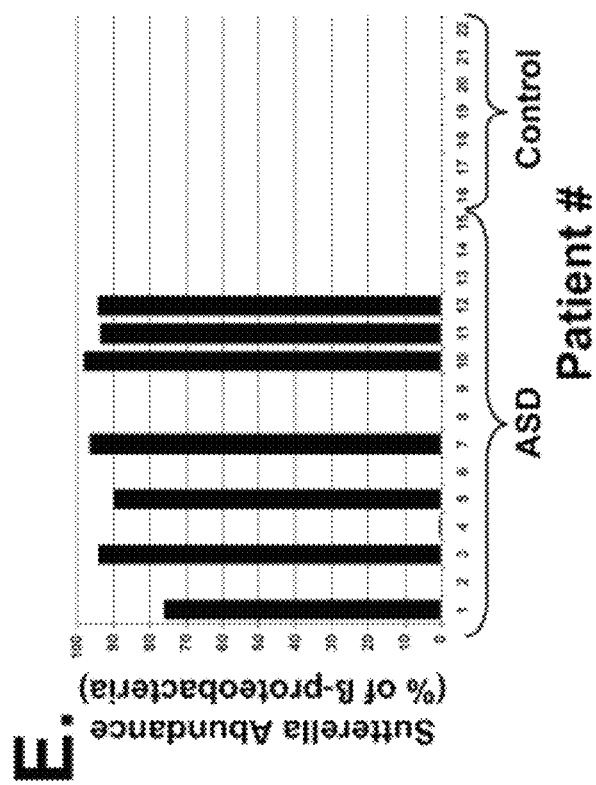
FIGS. 8E-F

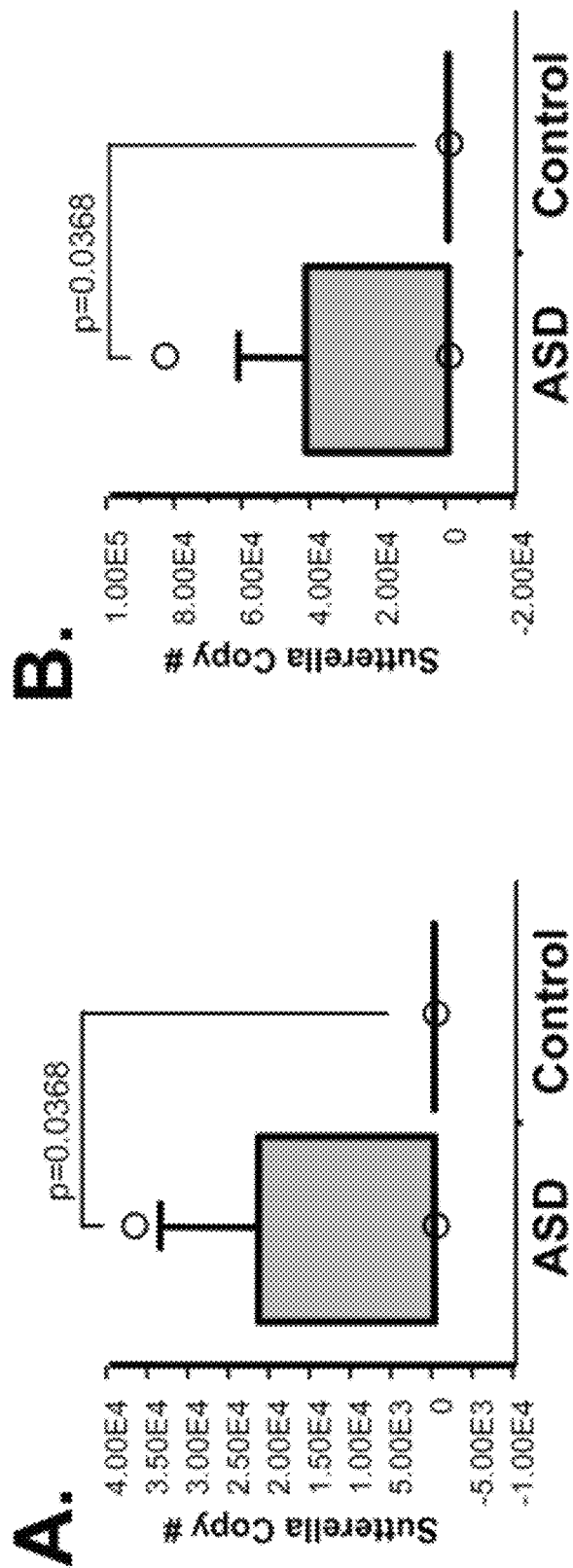
FIGS. 12A-B

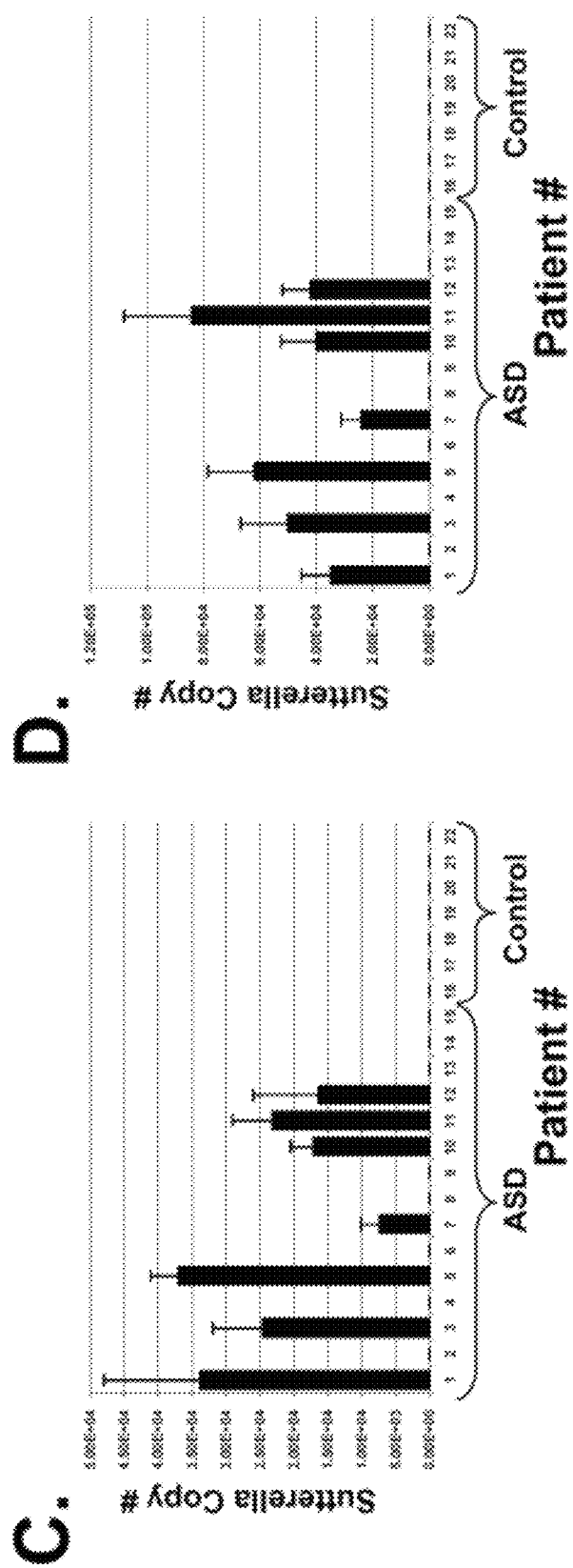
FIGS. 12C-D

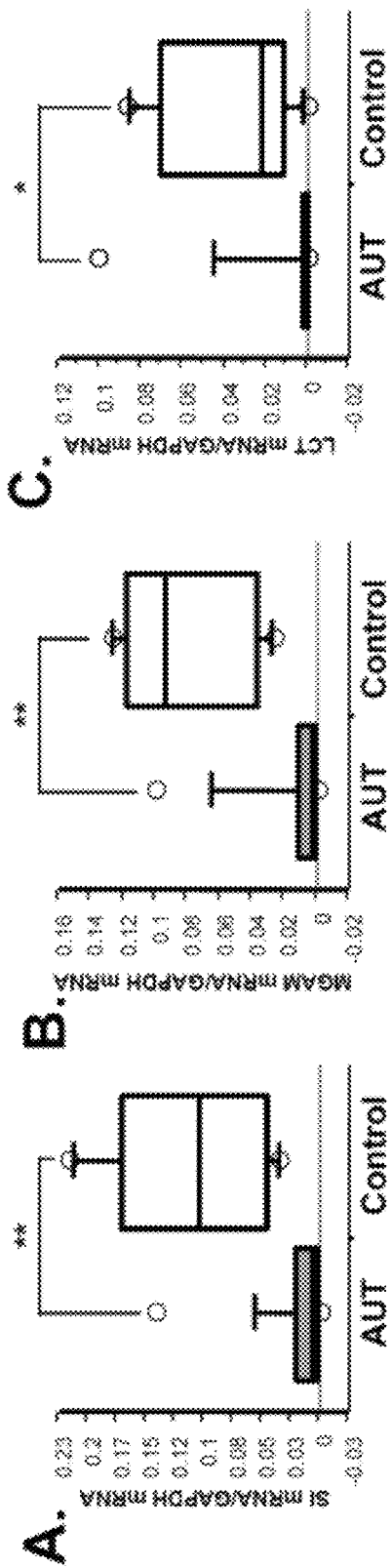
FIGS. 16A-C

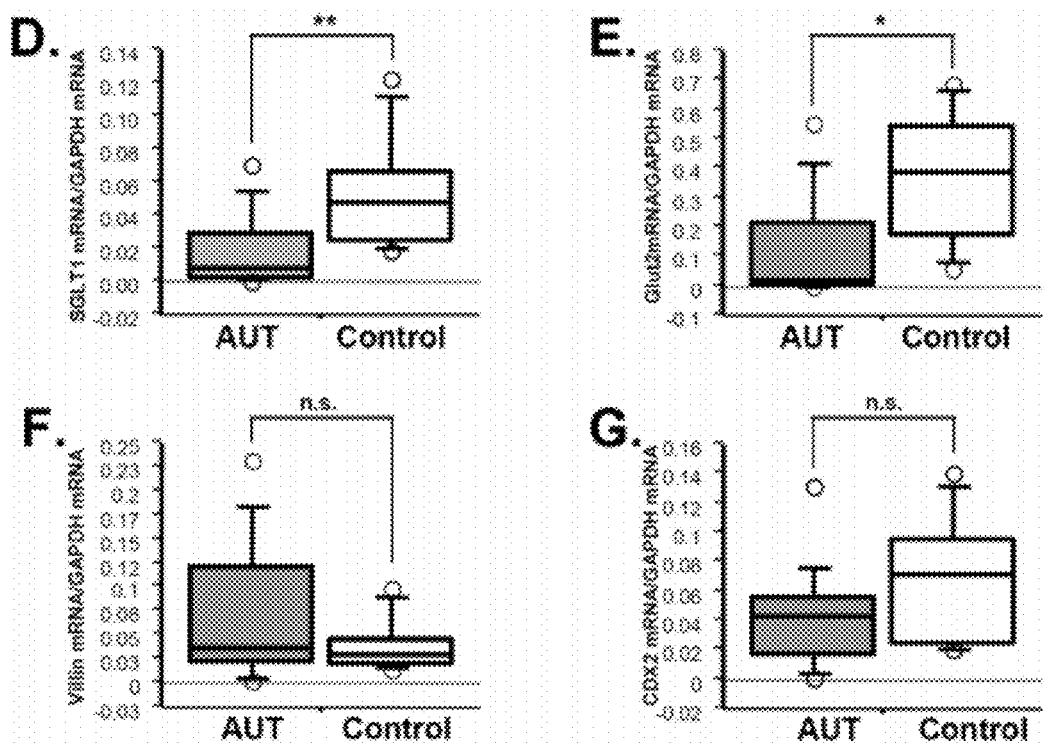
FIGS. 16D-G

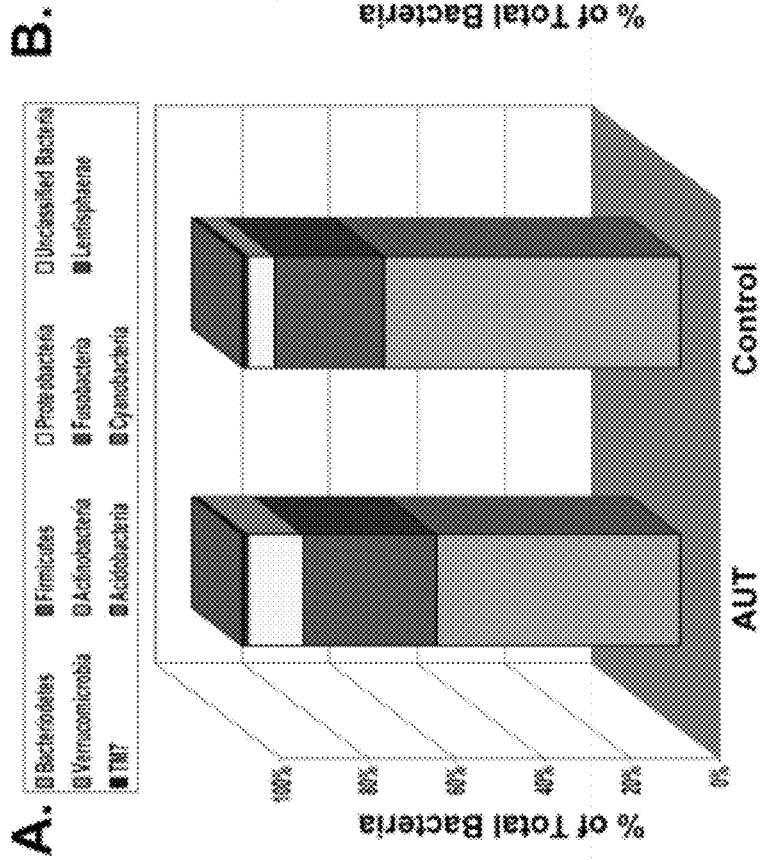
FIGS. 17A-B

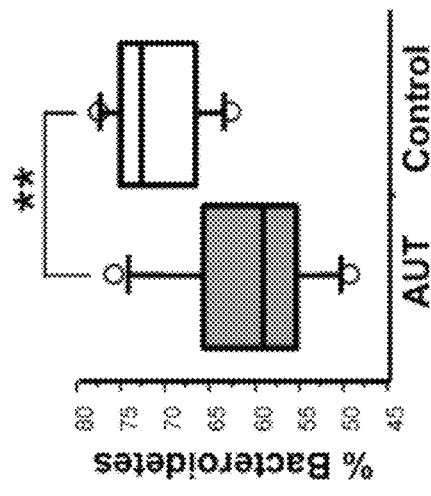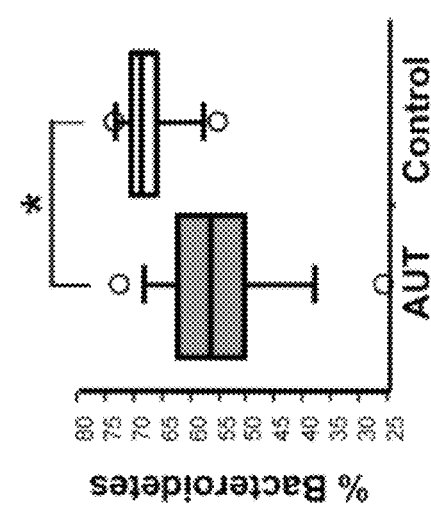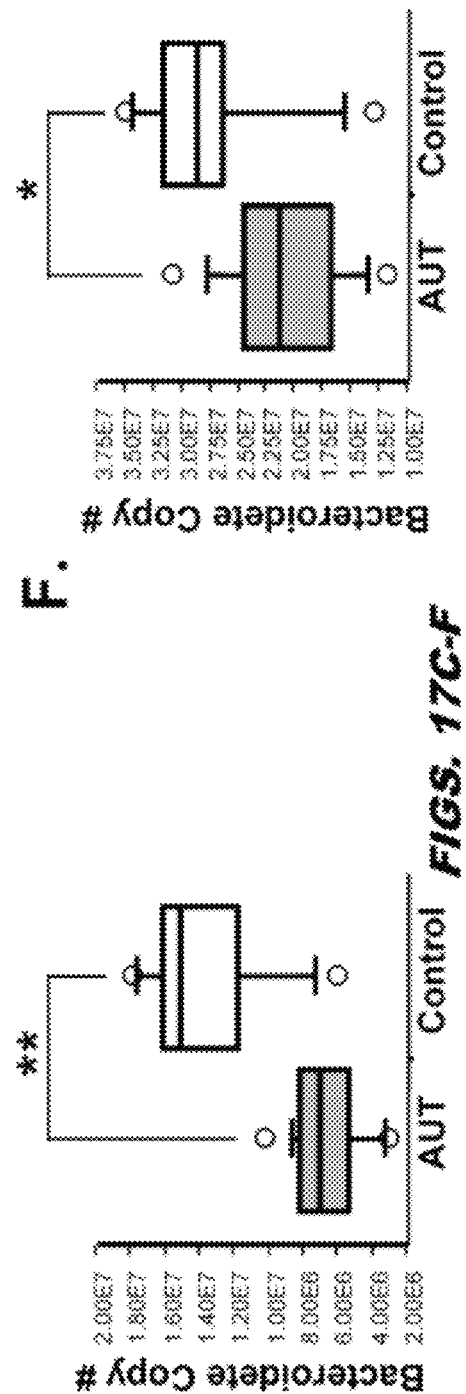
FIGS. 17C-F

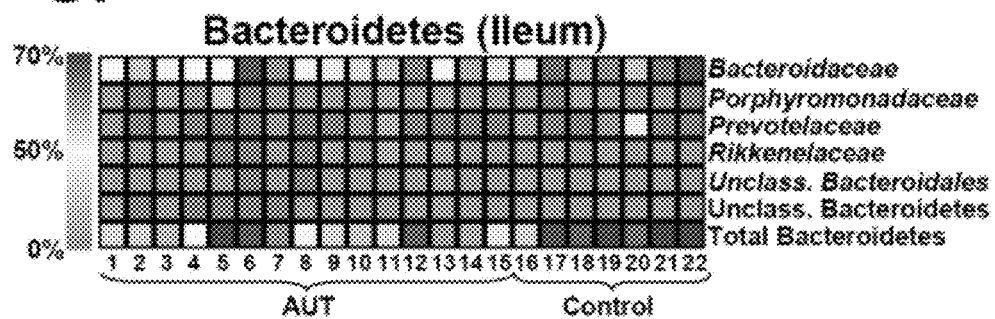
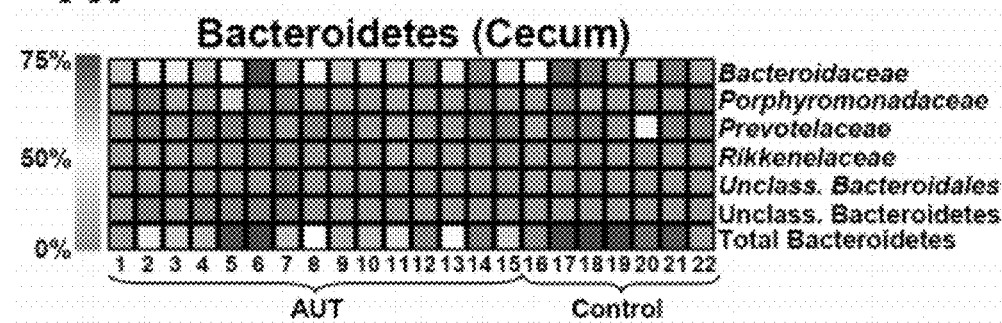
FIGS. 17G-H

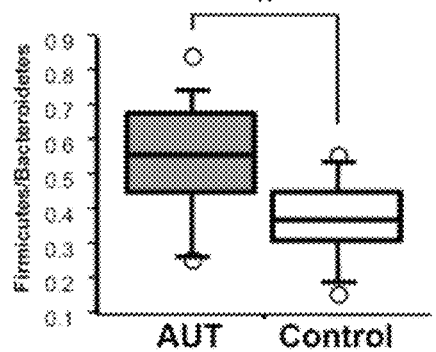
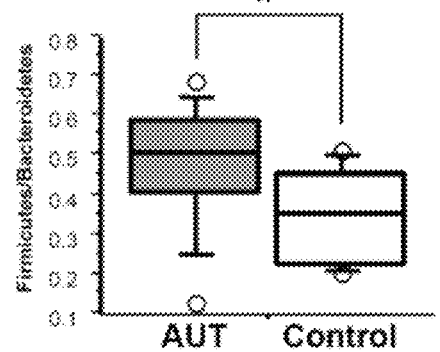
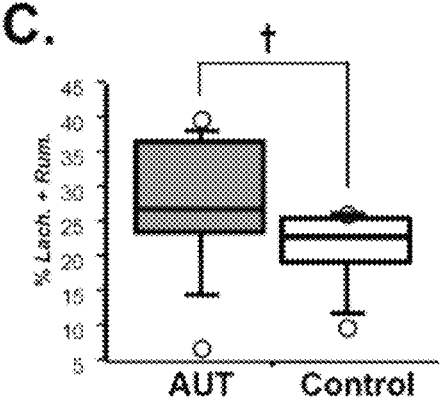
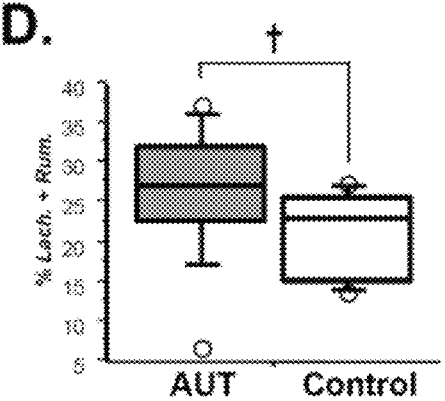
FIGS. 18A-D

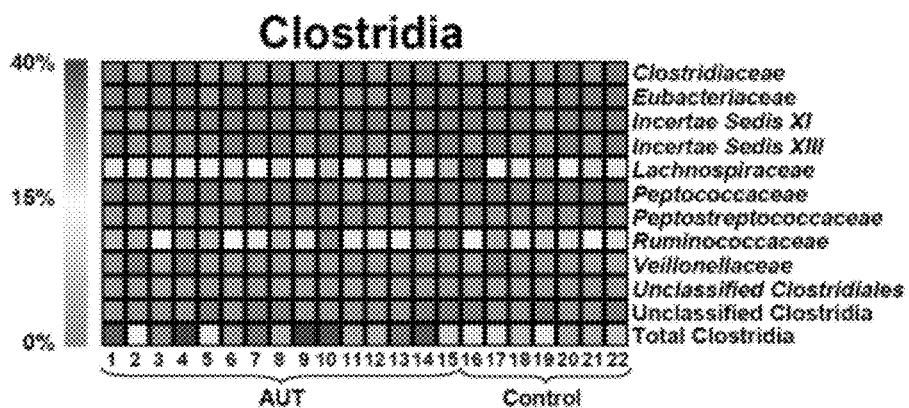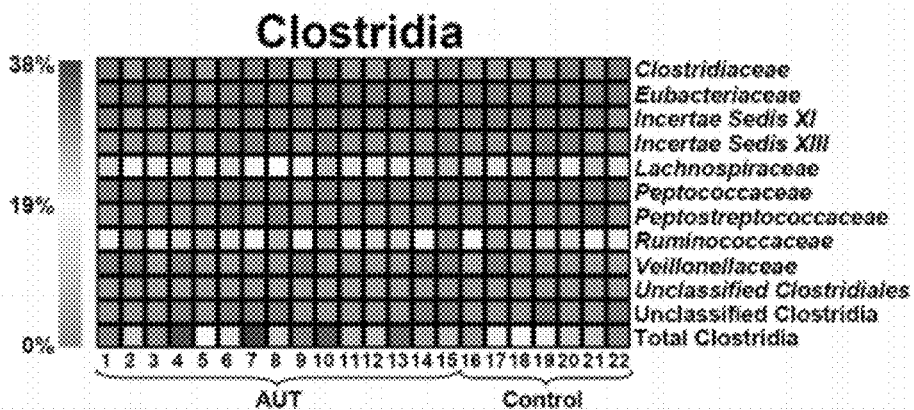
FIGS. 18E-F

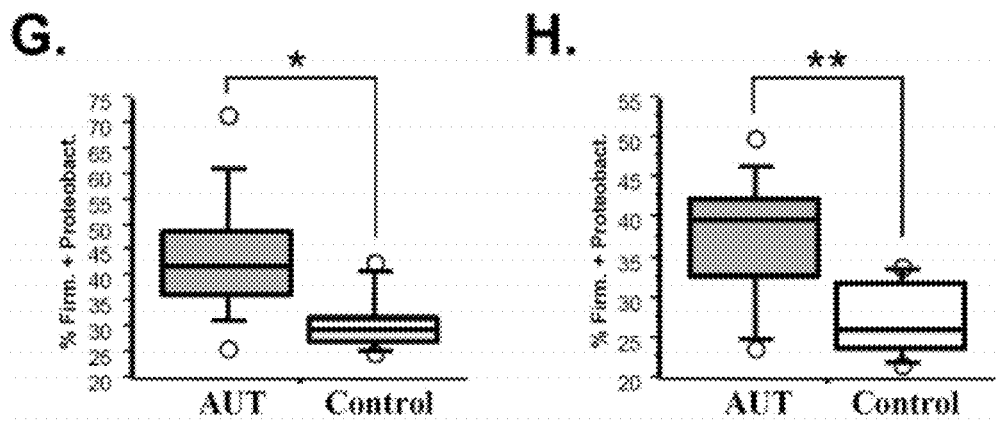
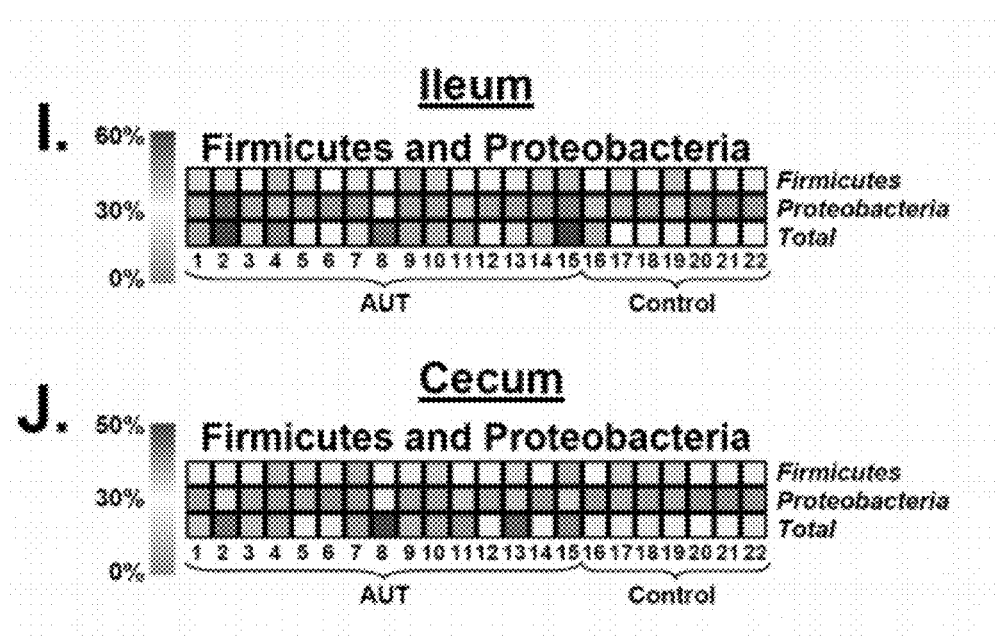
FIGS. 18G-J

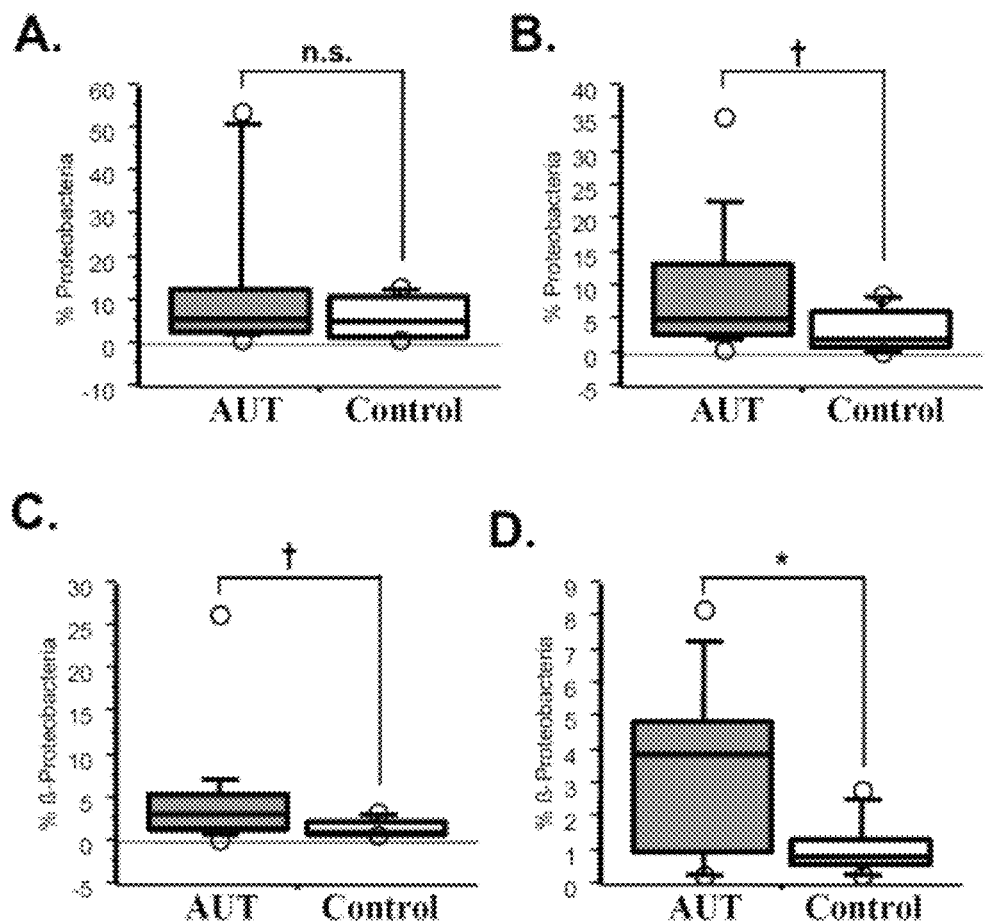
FIGS. 19A-D

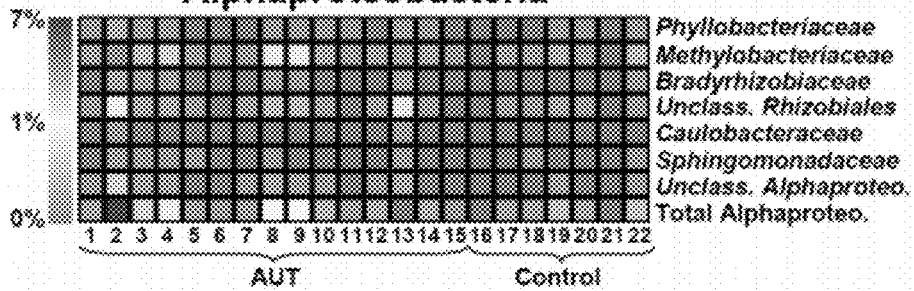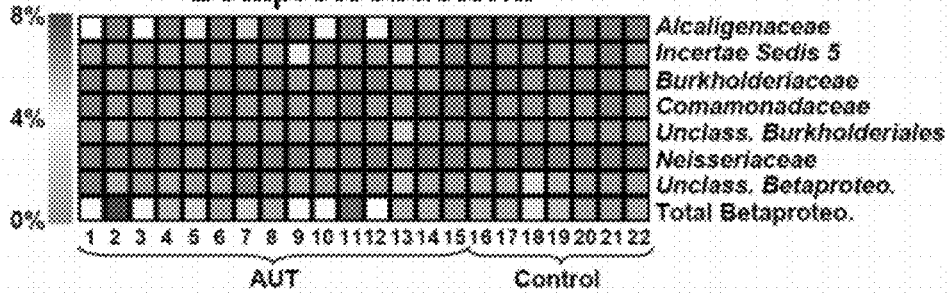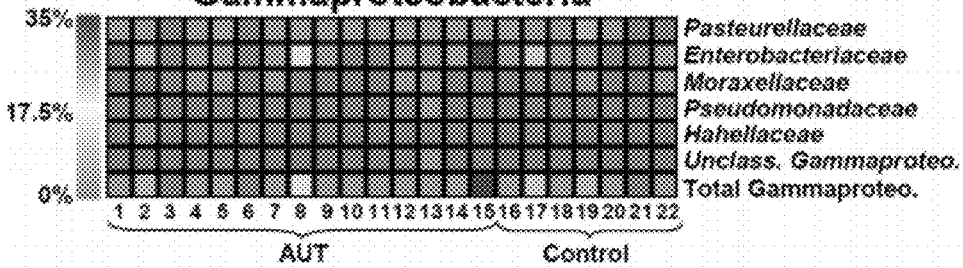
FIG. 19F

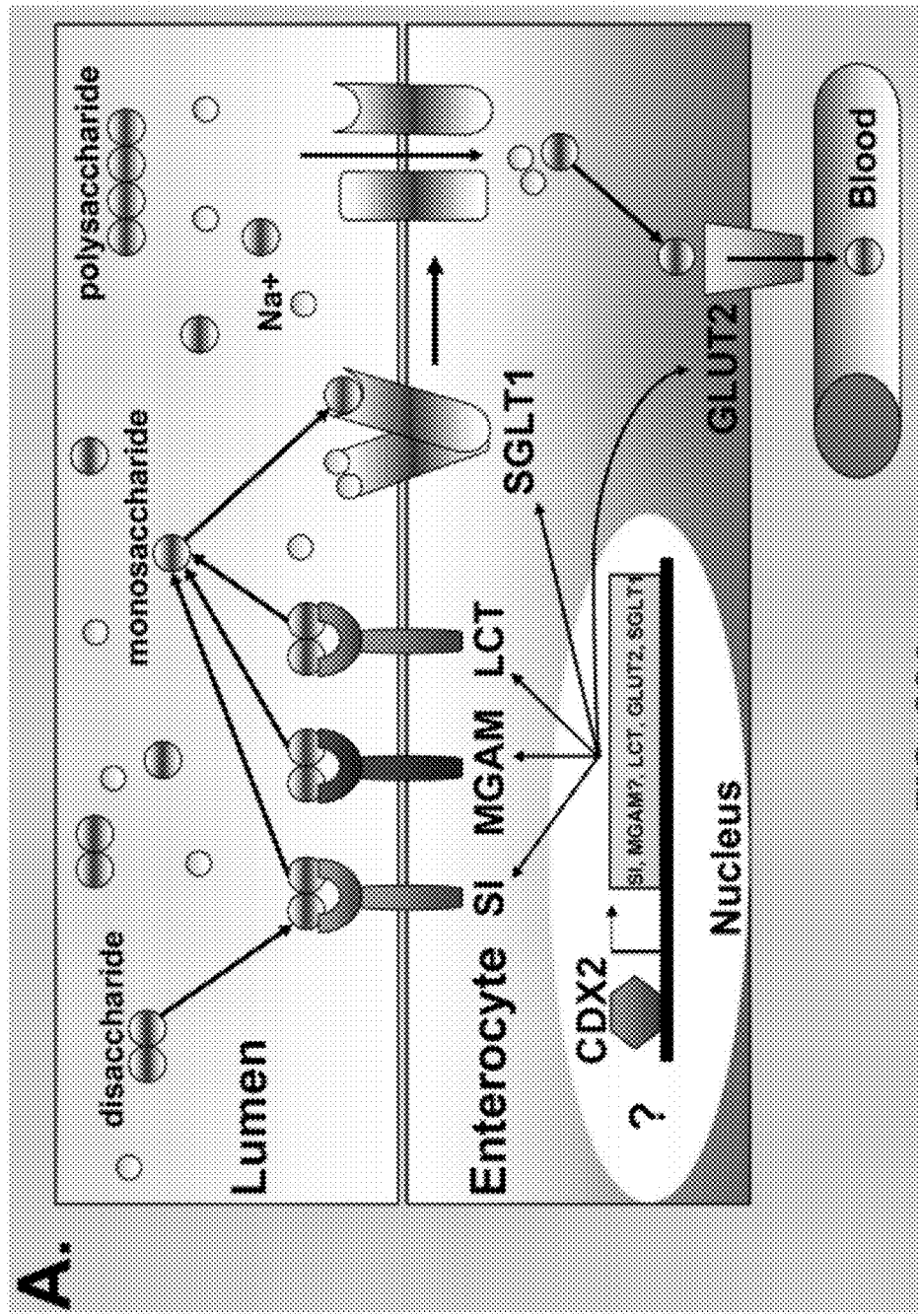

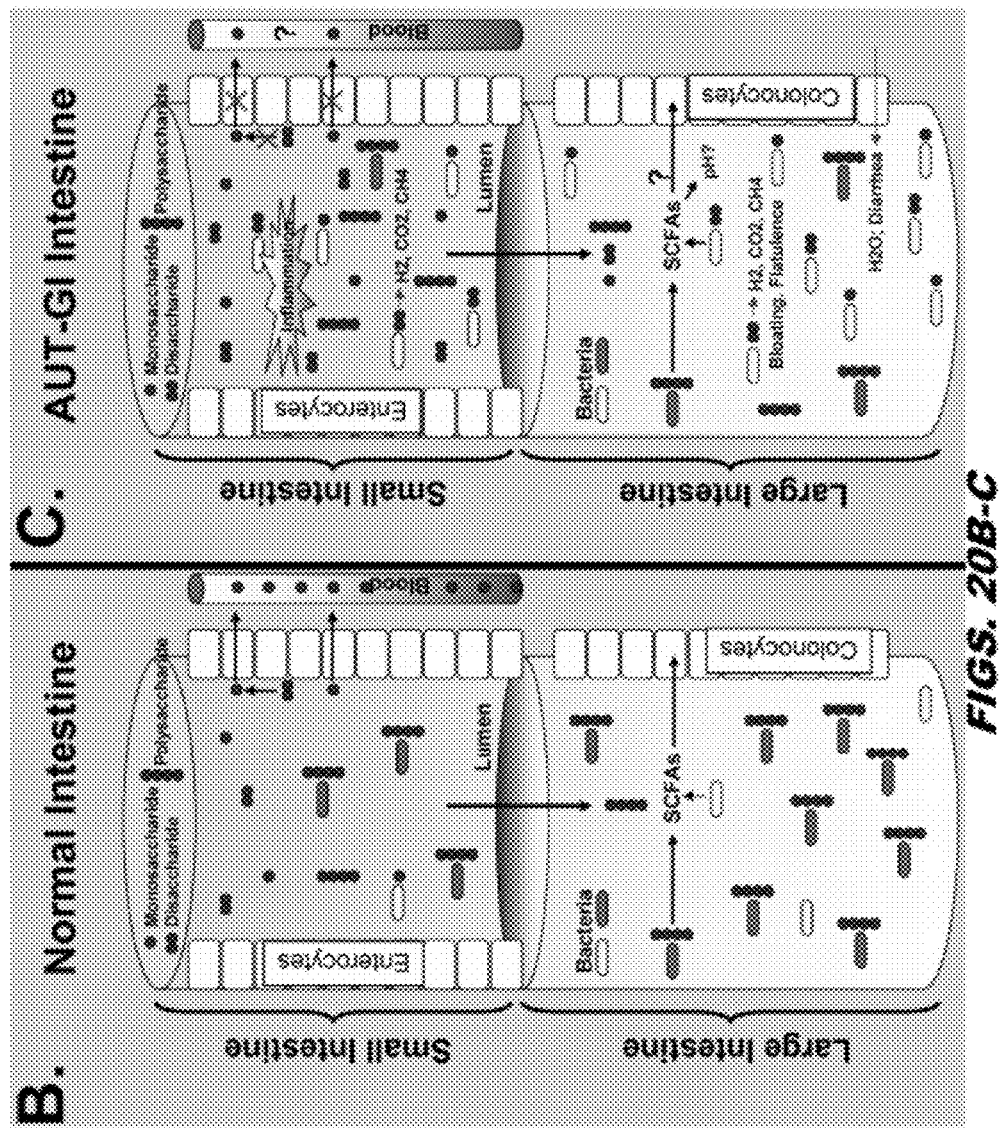
FIGS. 20B-C

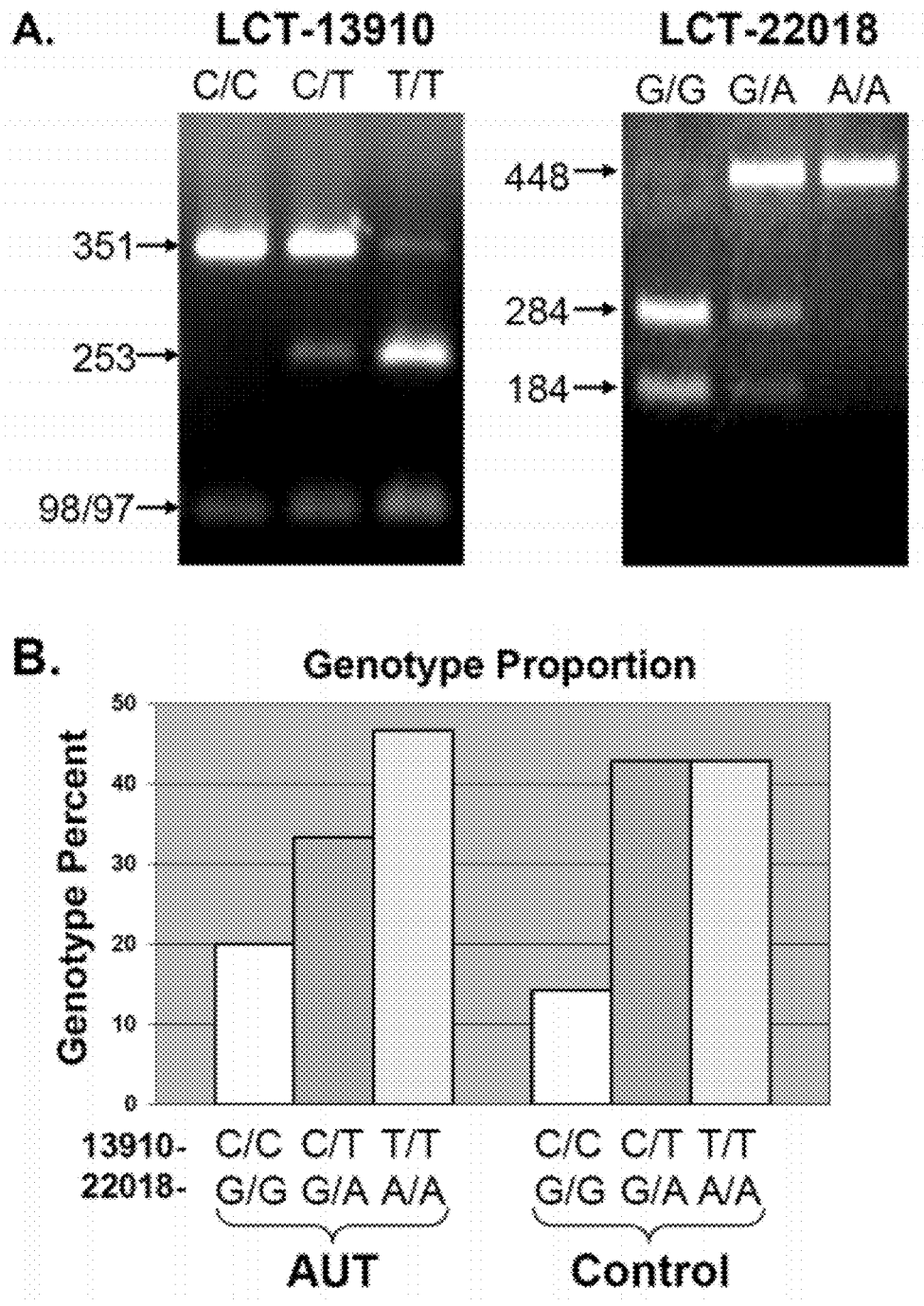
FIGS. 21A-B

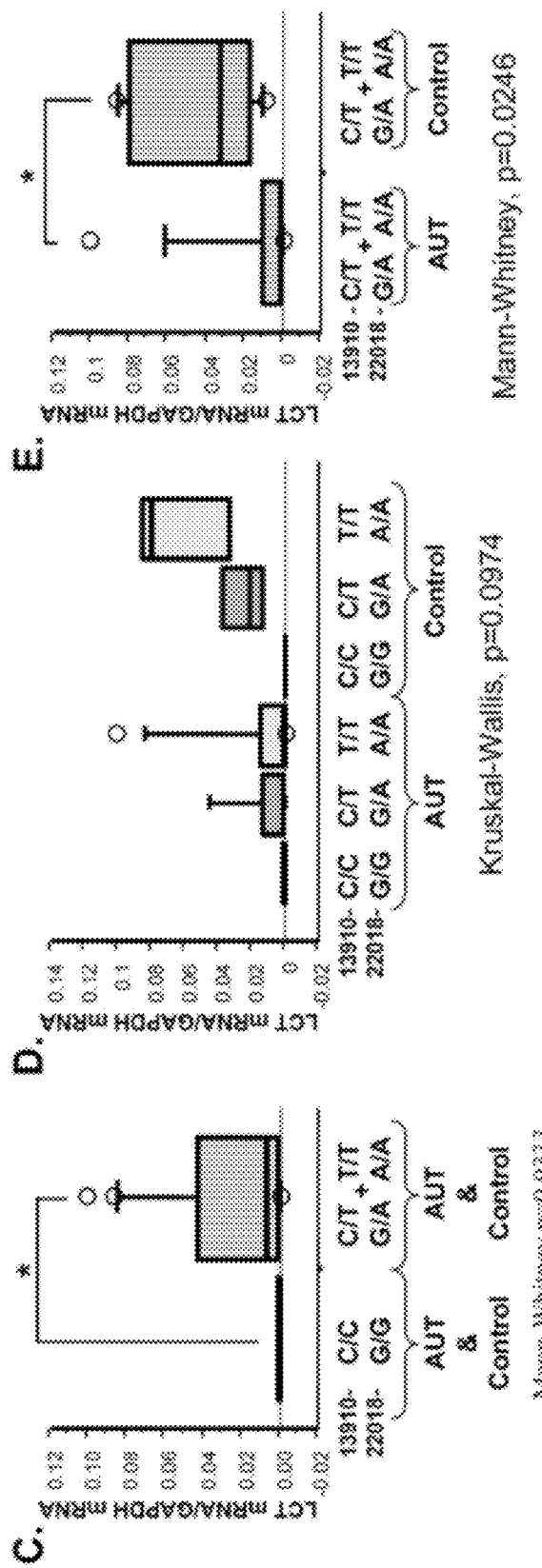
FIGS. 21C-E

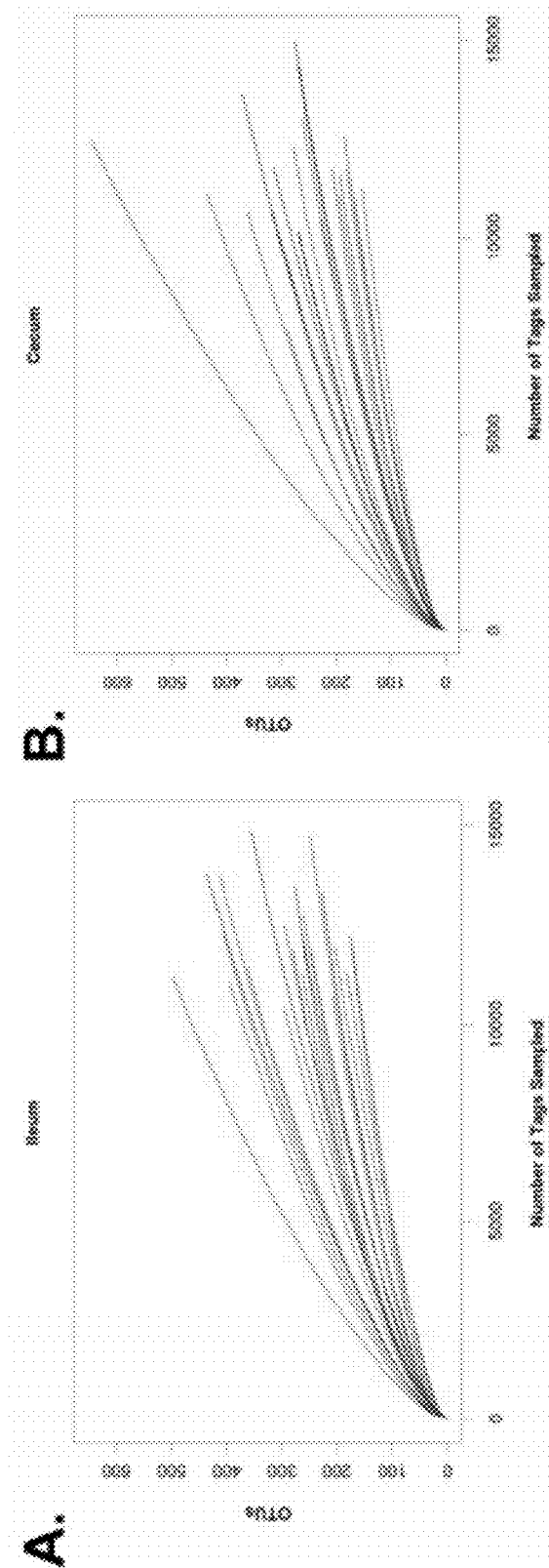
FIGS. 23A-B

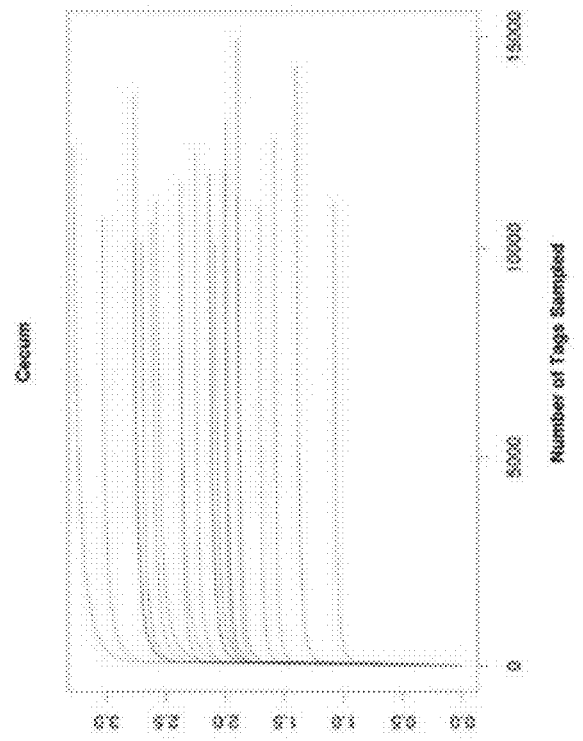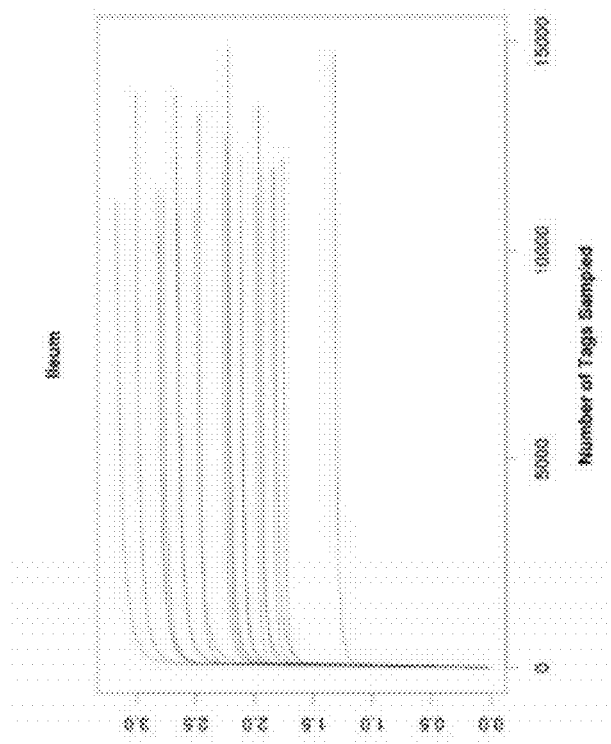
FIGS. 23C-D

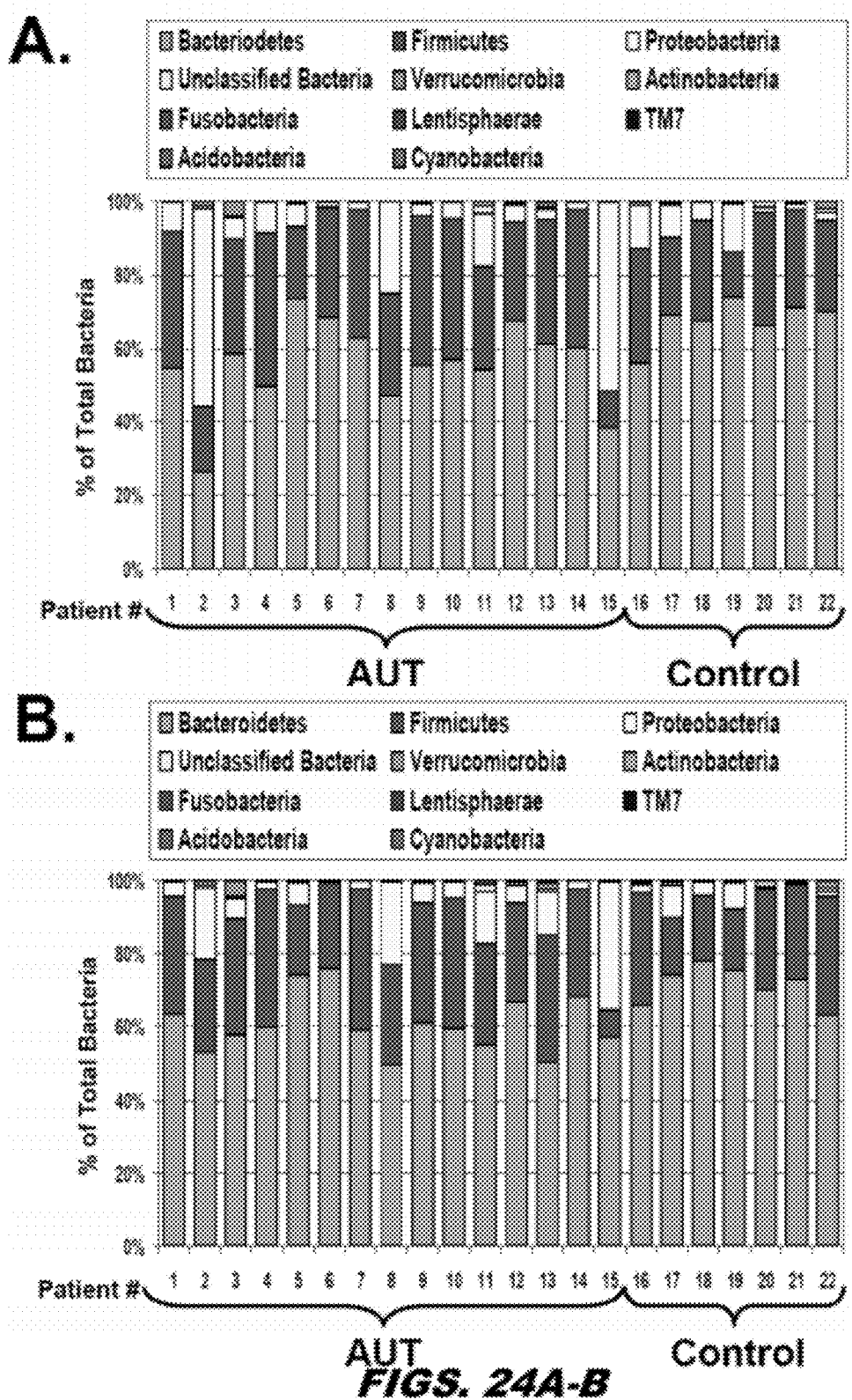
FIGS. 24A-B

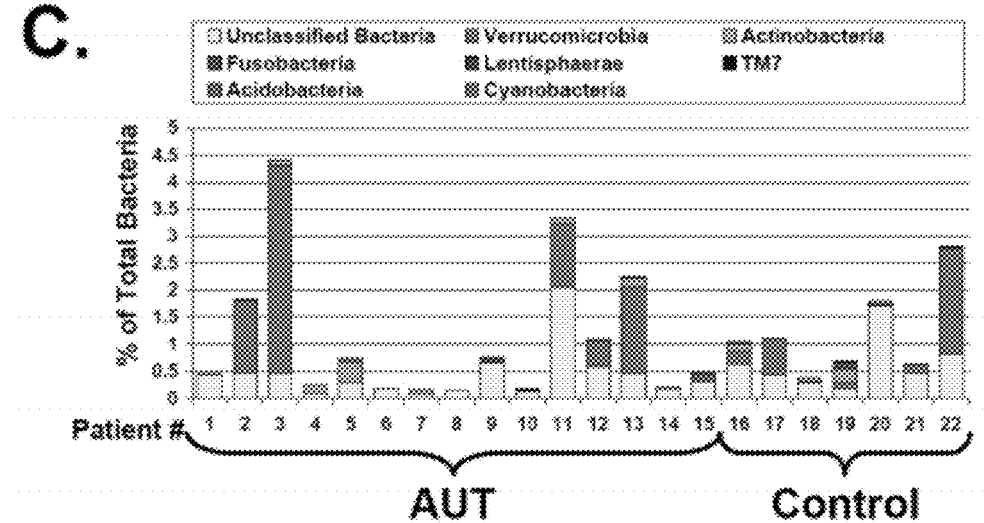
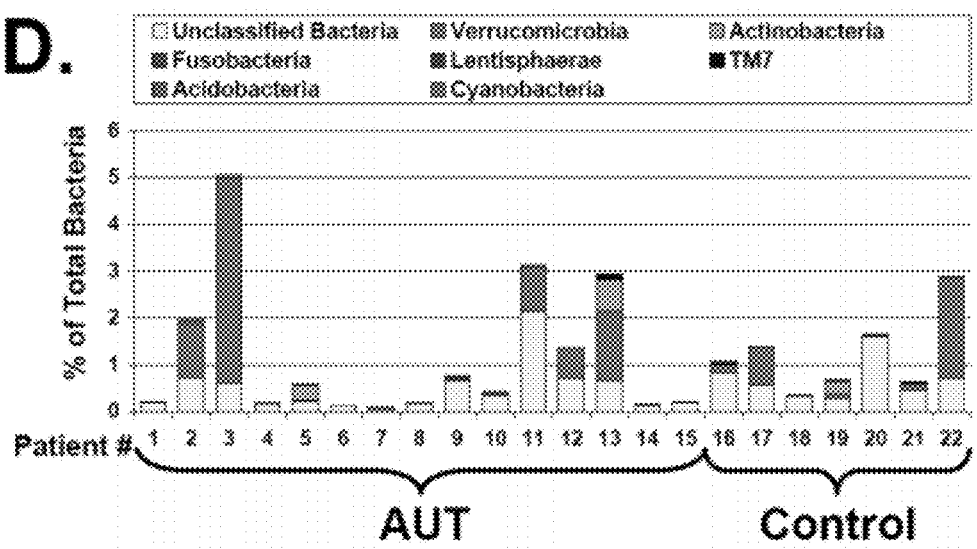
FIGS. 24C-D

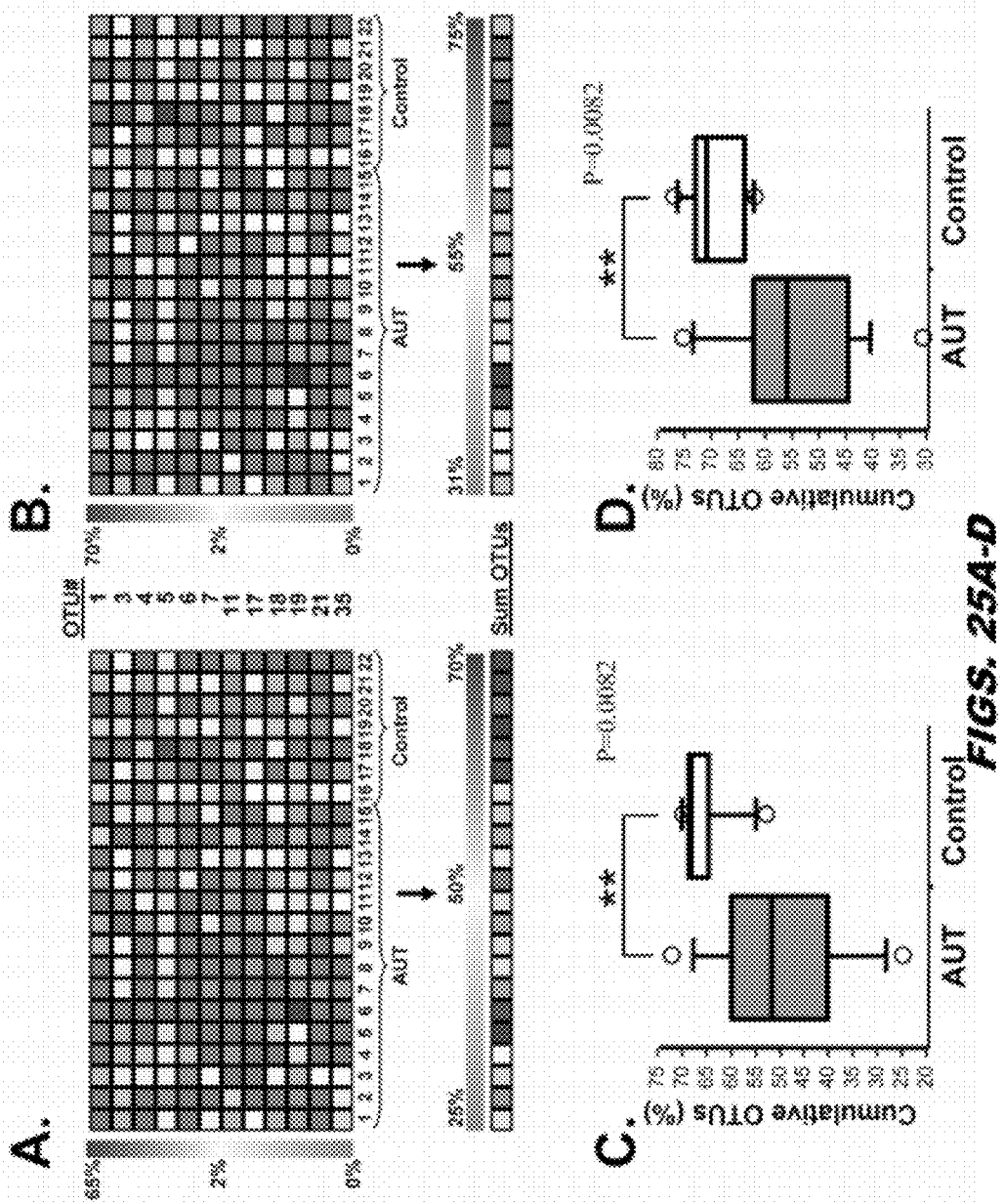
FIGS. 25A-D

E.

| OTU# | Sequence Match (Accession#) | %Identity | E-value |
|---|---|---|---|
| 1 | Human colon mucosal biopsy clone LW72 (AY976241.1) | 100.0 | e-103 |
| 3 | Bacteroides ovatus (AAXF02000043.1) | 100.0 | e-107 |
| 4 | Human fecal clone RL204_aaj58c11 (DQ824027.1) | 100.0 | e-103 |
| 5 | Bacteroides thetaiotaomicron (AY895203.1) | 98.4 | e-104 |
| 6 | Human fecal clone B2_414 (EU764955.1) | 100.0 | e-107 |
| 7 | Human fecal clone RL306aal92h04 (DQ805937.1) | 100.0 | e-105 |
| 11 | Alistipes Finegoldi (AY643083.1) | 99.2 | e-110 |
| 17 | Human colon mucosal biopsy clone Z468 (AY979269.1) | 100.0 | e-106 |
| 18 | Parabacteroides distasonis (EU722736.1) | 99.6 | 1e-96 |
| 19 | Bacteroides vulgatus (NC_009614) | 98.8 | 4e-117 |
| 21 | Prevotella copri (AB244773.1) | 100.0 | e-106 |
| 35* | Alistipes putredinis (NZ_ABFK02000016) | 99.6 | 3e-118 |

☐ = Bacteroidaceae  ☐ = Porphyromonadaceae
☐ = Rikenellaceae   ☐ = Prevotellaceae

*FIG. 25E*

B. Cecum
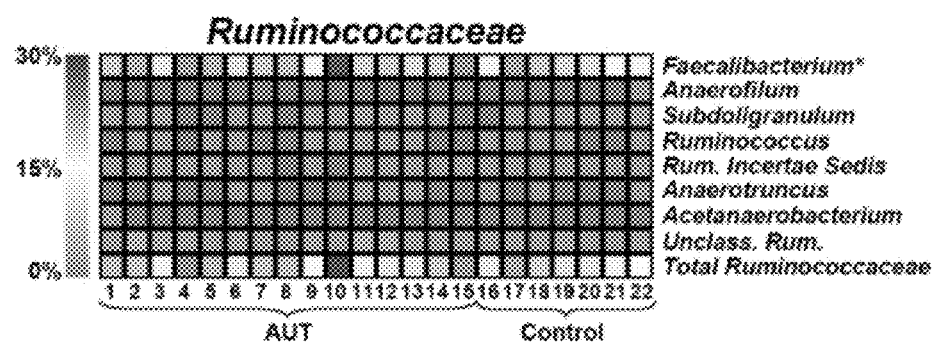
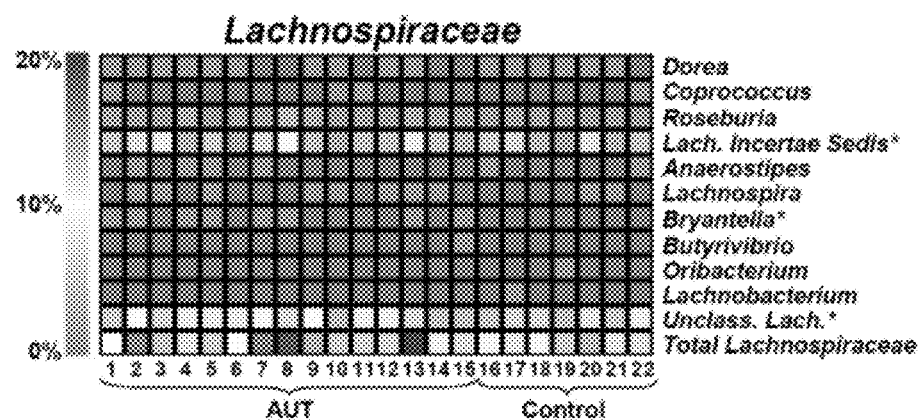
*FIG. 28B*

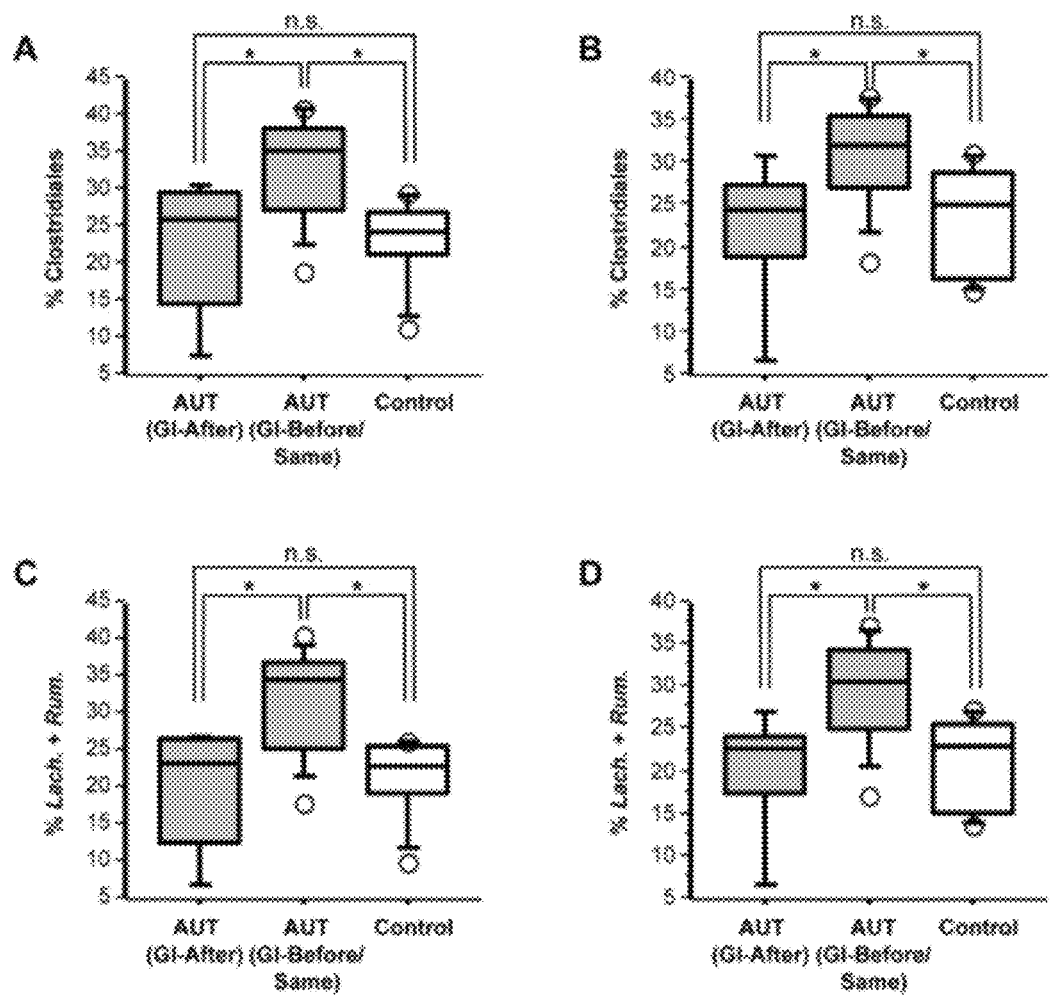
FIGS. 31A-D

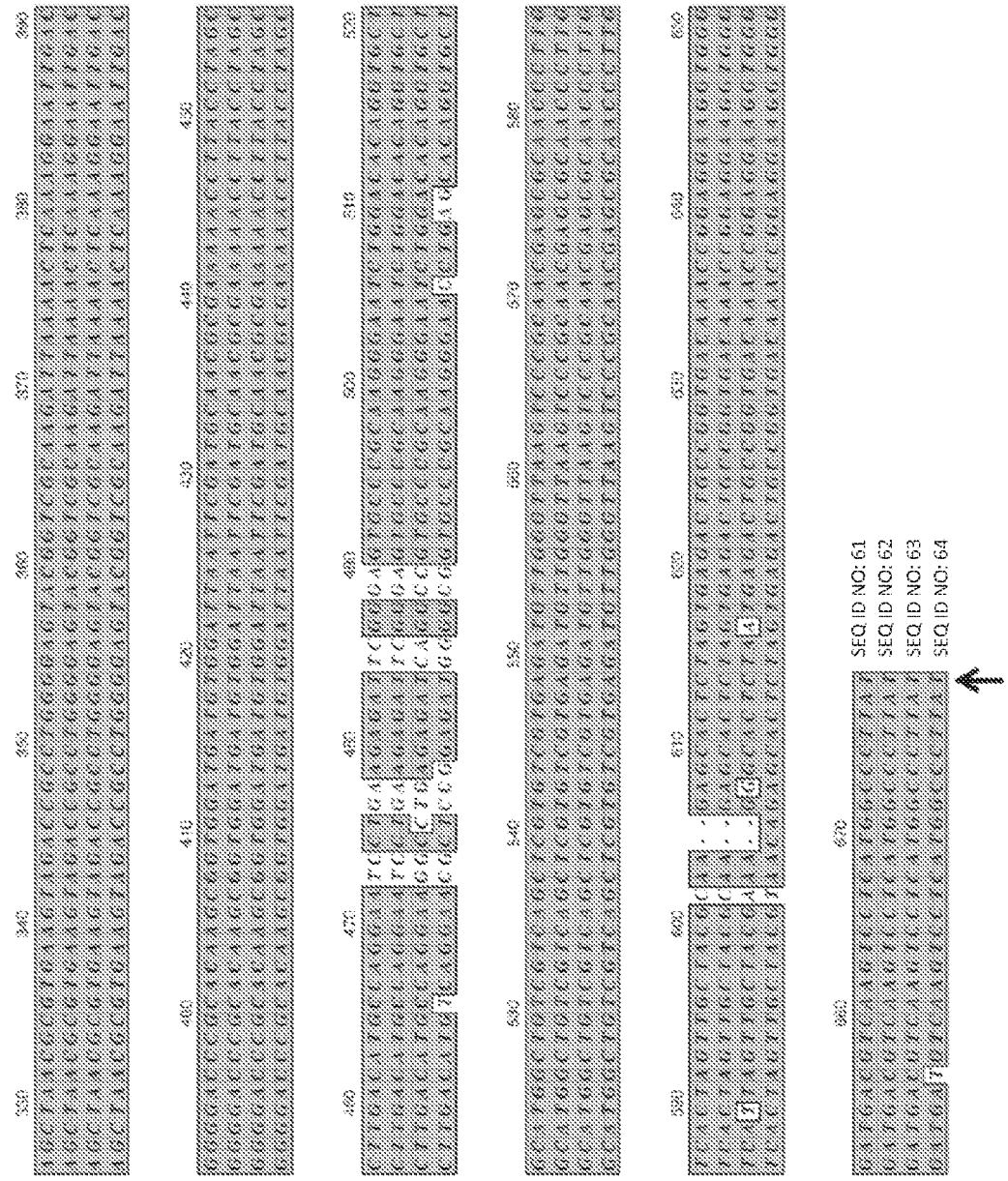

US 9,050,276 B2

AUTISM-ASSOCIATED BIOMARKERS AND USES THEREOF

This application is a continuation-in-part of International Application Number PCT/US2010/034254, filed on May 10, 2010, the contents of which are hereby incorporated by reference in its entirety. This application also claims priority to U.S. Provisional Application No. 61/527,313 filed on Aug. 25, 2011, the contents of which are hereby incorporated by reference in its entirety.

GOVERNMENT SUPPORT

This invention was made with government support under Grant No. U01 NS047537 and Grant No. AI57158 awarded by the National Institutes of Health. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted in ASCII format via EFS-Web and is hereby incorporated by reference in its entirety. Said ASCII copy, created on Mar. 14, 2012, is named 1924849U.txt and is 112,136 bytes in size.

BACKGROUND OF THE INVENTION

Autistic disorder is one of five pervasive developmental disorders defined in the Diagnostic and Statistical Manual of Mental Disorders, Fourth Edition, Text Revision DSM-IV-TR (2000). Autistic disorder is a developmental disorder of the human brain that manifests during infancy or childhood and is characterized by behavioral and social abnormalities that appear to be developmentally based (for example, impairments in social interaction and communication). In addition, autism interferes with imagination and the ability to reason. Autism is frequently associated with other disorders such as attention deficit/hyperactivity disorder (AD/HD) and can be associated with psychiatric symptoms such as anxiety and depression. In the last decade, autism diagnoses have increased by 300% to 500% in the United States and many other countries. A means of prevention and treatment is needed for this health crisis that addresses the underlying mechanisms leading to the development of autism versus those that merely address the symptoms.

Pervasive developmental disorders (PDDs) are also part of the Autism Spectrum Disorders (ASDs). PDD is used to categorize children who do not meet the strict criteria for Autistic Disorder but who come close, either by manifesting atypical autism or by nearly meeting the diagnostic criteria in two or three of the key areas. Some of these children meet criteria for the ASD known as Asperger's Disorder (ASP), wherein language capacities are relatively spared compared to children with Autistic Disorder. Others meet criteria for the PDDs known as Childhood Disintegrative Disorder, which begins at a slightly later age than the other ASDs, or Rett's Disorder, which is related to a mutation in a DNA methylation binding protein gene called MeCP2 and usually occurs in girls.

Many children with autism have gastrointestinal (GI) disturbances that affect their quality of life. Although some of these children have been investigated through GI immunopathology, molecular studies are lacking that characterize host gene expression or survey microflora using pyrosequencing methods.

SUMMARY OF THE INVENTION

The invention is based, at least in part, on the finding that decreased levels in sucrase isomaltase, maltase glucoamylase, lactase, GLUT2, and SGLT1 can serve as markers for human Autism Spectrum Disorders. Accordingly, in one aspect, the invention provides a method for detecting the presence of or a predisposition to autism or an autism spectrum disorder (ASD) in a human subject or a child of a human subject. The method comprises: (1) obtaining a biological sample from a human subject; and (2) detecting whether or not there is an alteration in the expression of a carbohydrate metabolic enzyme protein or a carbohydrate transporter protein in the subject as compared to a non-autistic subject. In one embodiment, the carbohydrate metabolic enzyme comprises sucrase isomaltase, maltase glucoamylase, lactase, or a combination thereof. In another embodiment, the carbohydrate transporter comprises GLUT2, SGLT1, or a combination thereof. In some embodiments, the method further comprises detecting a decrease in Bacteriodetes, an increase in the Firmicute/Bacteroidete ratios, an increase in cumulative levels of Firm icutes and Proteobacteria, an increase in Beta-proteobacteria, and an increase in Sutterella sp. in the small or large intestine of the subject. In one embodiment, the detecting comprises detecting whether there is an alteration in the gene locus that encodes the carbohydrate metabolic enzyme protein or the carbohydrate transporter protein. In a further embodiment, the detecting comprises detecting whether expression of the carbohydrate metabolic enzyme protein or the carbohydrate transporter protein is reduced. In some embodiments, the detecting comprises detecting in the sample whether there is a reduction in the mRNA expression of the carbohydrate metabolic enzyme protein or the carbohydrate transporter protein. In some embodiments of the invention, the subject is a human embryo, a human fetus, or an unborn human child. In other embodiments, the sample comprises blood, serum, sputum, lacrimal secretions, semen, vaginal secretions, fetal tissue, skin tissue, small intestine tissue (e.g., the ileum), large intestine tissue (e.g., the cecum), muscle tissue, amniotic fluid, or a combination thereof.

An aspect of the invention provides a method for treating or preventing autism or an autism spectrum disorder in a subject in need thereof. The method comprises administering to the subject a therapeutic amount of a pharmaceutical composition comprising a functional carbohydrate metabolic enzyme molecule or a carbohydrate transporter molecule, thereby treating or preventing autism or an autism spectrum disorder. In a further embodiment, the administering comprises a subcutaneous, intra-muscular, intra-peritoneal, or intravenous injection; an infusion; oral, nasal, or topical delivery; or a combination of the delivery modes described. In some embodiments, the administering comprises delivery of a carbohydrate metabolic enzyme molecule or a carbohydrate transporter molecule to the alimentary canal or intestine of the subject. In other embodiments, the administering comprises feeding the human subject or child thereof a therapeutically effective amount of the carbohydrate metabolic enzyme molecule or a carbohydrate transporter molecule. In further embodiments, the administering occurs daily, weekly, twice weekly, monthly, twice monthly, or yearly.

In other aspects, the invention provides for a pharmaceutical composition comprising: a carbohydrate metabolic enzyme molecule or a carbohydrate transporter molecule molecule; and a pharmaceutically acceptable carrier.

An aspect of the invention provides for an isolated nucleic acid composition. In one embodiment, the composition comprises a nucleic acid molecule having at least about 80% identity to SEQ ID NO: 11, 12, 13, or 14. In one embodiment, the composition comprises a nucleic acid molecule having at least about 85% identity to SEQ ID NO: 11, 12, 13, or 14. In one embodiment, the composition comprises a nucleic acid molecule having at least about 90% identity to SEQ ID NO: 11, 12, 13, or 14. In one embodiment, the composition comprises a nucleic acid molecule having at least about 95% identity to SEQ ID NO: 11, 12, 13, or 14. In one embodiment, the composition comprises a nucleic acid molecule having at least about 98% identity to SEQ ID NO: 11, 12, 13, or 14. In one embodiment, the composition comprises a nucleic acid molecule having at least about 99% identity to SEQ ID NO: 11, 12, 13, or 14. In one embodiment, the composition is SEQ ID NO: 11, 12, 13, or 14.

An aspect of the invention provides for a diagnostic kit for detecting the presence of *Sutterella* sp. in a sample. In one embodiment, the kit comprises a nucleic acid molecule that specifically hybridizes to or a primer combination that amplifies a *Sutterella* sp. 16S nucleic acid sequence. In one embodiment, the nucleic acid molecule comprises a nucleic acid primer or nucleic acid probe. In another embodiment, the 16S nucleic acid sequence comprises at least about 80% of SEQ ID NO: 59 or SEQ ID NO: 60. In some embodiments, the 16S nucleic acid sequence comprises at least about 85% of SEQ ID NO: 59 or SEQ ID NO: 60. In further embodiments, the 16S nucleic acid sequence comprises at least about 90% of SEQ ID NO: 59 or SEQ ID NO: 60. In other embodiments, the 16S nucleic acid sequence comprises at least about 95% of SEQ ID NO: 59 or SEQ ID NO: 60. In another embodiment, the 16S nucleic acid sequence comprises at least about 98% of SEQ ID NO: 59 or SEQ ID NO: 60. In some embodiments, the 16S nucleic acid sequence comprises at least about 99% of SEQ ID NO: 59 or SEQ ID NO: 60. In further embodiments, the 16S nucleic acid sequence is SEQ ID NO: 59 or SEQ ID NO: 60. In one embodiment, the probe comprises a nucleotide sequence having SEQ ID NOS: 13 or 14 in Table 1, or the italicized nucleotide of sequence SEQ ID NO: 19. In a further embodiment, the probe comprises at least 10 consecutive nucleotide bases comprising SEQ ID NO: 19, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide. In some embodiments, the probe comprises a reverse complement of SEQ ID NOS: 11, 12, 15, 16, 17, 18, or 19, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide. In other embodiments, the primer comprises a nucleotide sequence selected from the group consisting of SEQ ID NOS: 11, 12, 15, 16, 17, or 18, wherein, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide. In one embodiment, the sample is from a human or non-human animal. In other embodiments, the sample comprises intestinal tissue (e.g., the small intestine or large intestine), feces, blood, skin, or a combination of the mentioned tissues.

An aspect of the invention provides for a diagnostic kit for determining whether a sample from a subject exhibits a presence of or a predisposition to autism or an autism spectrum disorder (ASD). In one embodiment, the kit comprising a nucleic acid primer that specifically hybridizes to an autism biomarker, wherein the primer will prime a polymerase reaction only when an autism biomarker is present. In another embodiment, the primer comprises a nucleotide sequence selected from the group consisting of SEQ ID NOS: 11, 12, 15, 16, 17, or 18, wherein, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide. In some embodiments, the autism biomarker is a carbohydrate trasporter molecule, a carbohydrate metabolic enzyme molecule, or a gastrointestinal *Sutterella* sp. bacterium. In a further embodiment, the carbohydrate trasporter molecule is GLUT2 or SGLT1. In other embodiments, the carbohydrate metabolic enzyme molecule is SI, MGAM, or LCT. In one embodiment, the sample is from a human or non-human animal. In other embodiments, the sample comprises intestinal tissue (e.g., the small intestine or large intestine), feces, blood, skin, or a combination of the mentioned tissues.

An aspect of the invention provides for a method of treating or preventing a disease associated with elevated levels of Beta-proteobacteria. The method of the invention comprises administering to a subject in need thereof a therapeutic amount of an antimicrobial composition effective against Beta-proteobacteria for treating the disease. In one embodiment, the antimicrobial composition is an antibiotic, a probiotic agent, or a combination thereof. In another embodiment, the disease is ASD, autism, or a gastrointestinal disease. In a further embodiment, the gastrointestinal disease is diarrhea, inflammatory bowel disease, antimicrobial-associated colitis, or irritable bowel syndrome. In some embodiments, the diarrhea or inflammatory bowel diseases is ulcerative colitis or Crohn's disease. In one embodiment, the antibiotic comprises lincosamides, chloramphenicols, tetracyclines, aminoglycosides, beta-lactams, vancomycins, bacitracins, macrolides, amphotericins, sulfonamides, methenamin, nitrofurantoin, phenazopyridine, trimethoprim; rifampicins, metronidazoles, cefazol ins, lincomycin, spectinomycin, mupirocins, quinolones, novobiocins, polymixins, gramicidins, antipseudomonals, or a combination of the stated antibiotics. In another embodiment of the invention, the probiotic agent comprises Bacteroides, *Prevotella, Porphyromonas, Fusobacteriuni, Sutterella, Bilophila, Campylobacter, Wolinella, Butyrovibrio, Megamonas, Desulfomonas, Desulfovibrio, Bifidobacterium, Lactobacillus, Eubacterium, Actinomyces, Eggerthel la, Coriobacterium, Propionibacterium*, other genera of non-sporeforming anaerobic gram-positive bacilli, Bacillus, Peptostreptococcus, newly created genera originally classified as *Peptostreptococcus, Peptococcus, Acidaminococcus, Ruminococcus, Megasphaera, Gaffkya, Coprococcus, Veillonella, Sarcina, Clostridium, Aerococcus, Streptococcus, Enterococcus, Pediococcus, Micrococcus, Staphylococcus, Corynebacterium*, species of the genera comprising the Enterobacteriaceae and Pseudomonadaceae, or a combination of the listed probiotic agents.

An aspect of the invention provides for a method of detecting a *Sutterella* sp. in a sample. The method comprises: (a) selecting a *Sutterlla* sp.-specific primer pair, wherein the primer pair mediates amplification of a polynucleotide amplicon of a selected, known length from a nucleic acid of a *Sutterlla* sp.; contacting a nucleic acid from the sample with the *Sutterlla* sp.-specific primer pair in a reaction mixture under conditions that promote amplification of a polynucleotide amplicon, wherein the primer pair will prime a polymerase reaction only when the nucleic acid of a *Sutterlla* sp. is present; and detecting the amplicons, wherein the detection of an amplicon of a selected, known length is indicative of the sample containing the nucleic acid of a *Sutterlla* sp. In one embodiment, the sample comprises intestinal tissue (e.g., the small intestine or large intestine), feces, blood, skin, or a combination of the listed tissues. In one embodiment, the primer pair comprises a forward primer and a reverse primer. In some embodiments, the forward primer comprises SEQ ID NO: 11 or 17, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide. In other embodiments, the reverse primer comprises SEQ ID NO: 12 or 18, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide. In further embodiments, the forward primer comprises at least 10 consecutive nucleotide bases comprising SEQ ID NO: 17 or19, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or I nucleotide and/or C. In some embodiments, the reverse primer comprises at least 10 consecutive nucleotide bases comprising SEQ ID NO: 18 or19, wherein S is a G nucleotide and/or a C nucleotide, wherein Y is a C nucleotide and/or T nucleotide, wherein R is an A nucleotide and/or G nucleotide, wherein W is an A nucleotide and/or T nucleotide, and wherein H is an A nucleotide and/or T nucleotide and/or C nucleotide, wherein B is a T nucleotide, C nucleotide, or G nucleotide, wherein V is an A nucleotide, G nucleotide, or C nucleotide; wherein D is an A nucleotide, G nucleotide, or T nucleotide; and wherein K is a G nucleotide or T nucleotide.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 8A-B show the Presence of *Sutterella* sequences in a subset of AUT-GI patients: Detection by pyrosequencing of the V2-region of the 16S rRNA gene. FIGS. 8A-B are bar graphs showing the abundance of *Sutterella* sp. in the ileum (FIG. 8A) and cecum (FIG. 8B) of autism and control patients. Distribution of *Sutterella* sequences as a percentage of total bacterial 16S rRNA gene reads from ileal (FIG. 8A; Mann-Whitney, tied p=0.022) and cecal (FIG. 8B; Mann-Whitney, tied p =0.037) biopsies from AUT-GI and Control-GI patients.

FIGS. 8C-D show the presence of *Sutterella* sequences in a subset of AUT-GI patients: Detection by pyrosequencing of the V2-region of the 16S rRNA gene. FIGS. 8C-D are bar graphs showing the abundance of *Sutterella* sp. sequences in the ileum (FIG. 8C) and cecum (FIG. 8D) of autism and control patients. FIGS. 8C-D shows the distribution of *Sutterella* sequences by individual patient as a percentage of total bacteria 16S rRNA reads from ileal (FIG. 8C) and cecal (FIG. 8D) biopsies from AUT-GI (patients #1-15) and Control-GI (patients #16-22) patients. *, p<0.05.

FIGS. 8E-F show the presence of *Sutterella* sequences in a subset of AUT-GI patients: Detection by pyrosequencing of the V2-region of the 16S rRNA gene. FIGS. 8E-F are bar graphs showing the abundance of *Sutterella* sp. sequences comprising the Beta-proteobacteria sequences in the ileum (FIG. 8E) and cecum (FIG. 8F) of autism and control patients. FIGS. 8E-F show the distribution of *Sutterella* sequences by individual patient as a percentage of total Betaproteobacteria 16S rRNA reads from ileal (FIG. 8E) and cecal (FIG. 8F) biopsies from AUT-GI (patients #1-15) and Control-GI (patients #16-22) patients. *, p<0.05.

FIGS. 12A-B are bar graphs showing the copy number of *Sutterella* sp. in the ileum (FIG. 12A) and cecum (FIG. 12B) of autism and control patients using the V6-V8 *Sutterella* sp.-specific PCR.

FIGS. 12C-D are bar graphs showing the copy number of *Sutterella* sp. in the ileum (FIG. 12C) and cecum (FIG. 12D) of autism and control patients using the V6-V8 *Sutterella* sp.-specific PCR.

FIG. 16 shows graphs of quantitative real-time PCR analysis of disaccharidases, hexose transporters, villin and CDX2 transcripts. Box-and-whisker plots displaying (FIG. 16A) SI (Mann-Whitney; $p=0.001$), (FIG. 16B) MGAM (Mann-Whitney; $p=0.003$), (FIG. 16C) LCT (Mann-Whitney; $p=0.032$), (FIG. 16D) SGLT1 (Mann-Whitney; $p=0.008$), (FIG. 16E) GLUT2 (Mann-Whitney; $p=0.010$), (FIG. 16F) Villin (Mann-Whitney; $p=0.307$), and (FIG. 16G) CDX2 (Mann-Whitney; $p=0.192$) mRNA expression normalized to GAPDH mRNA in ileal biopsies from AUT-GI (AUT) and Control-GI (Control) patients. Box-and-whisker plots show the median and the interquartile (midspread) range (boxes containing 50% of all values), the whiskers (representing the $25^{th}$ and $75^{th}$ percentiles) and the extreme data points (open circles). *$p<0.05$; **, $p<0.01$; n.s., not significant.

FIG. 17 shows graphs depicting pyrosequencing analysis of intestinal microbiota in AUT-GI children. (FIGS. 17A-B) Phylum-level comparison of the average relative abundance of bacterial taxa in ileal (FIG. 17A) and cecal (FIG. 17B) biopsies from AUT-GI and Control-GI patients. (FIGS. 17C-D) Box-and-whisker plot displaying the distribution of Bacteroidetes as a percentage of total bacterial 16S rRNA V2 pyroseqeuncing reads from ileal (C; Mann-Whitney, $p=0.012$) and cecal (FIG. 17D; Mann-Whitney, $p=0.008$) biopsies from AUT-GI and Control-GI patients. (FIGS. 17E-F) Bacteroidete-specific quantitative real-time PCR analysis of ileal (FIG. 17E; Mann-Whitney, $p=0.003$) and cecal (FIG. 17F; Mann-Whitney, $p=0.022$) biopsies from AUT-GI and Control-GI patients. (FIGS. 17G-H) Heatmaps displaying abundance distributions (% of total sequence reads per patient) of Bacteroidetes classified at the family level in ileal (FIG. 17G) and cecal (FIG. 17H) biopsies from AUT-GI and Control-GI children (Bottom row displays cumulative levels of all family members by patient). copy number values are normalized relative to total bacteria copy numbers; *,$p<0.05$, **,$p<0.01$.

FIG. 18 shows graphs of Firmicute abundance in AUT-GI and Control-GI children. (FIGS. 18A-18B) Box-and-whisker plots displaying the Firmicute/Bacteroidete ratio from pyrosequencing reads obtained from ileal (FIG. 18A; Mann-Whitney, $p=0.026$) and cecal (FIG. 18B; Mann-Whitney, $p=0.032$) biopsies of AUT-GI and Control-GI patients. (FIGS. 18C-18D) Box-and-whisker plots displaying the cumulative levels of members of the families Lachnospiraceae and Ruminococcaceae in ileal (FIG. 18C; Mann-Whitney; $p=0.062$) and cecal (FIG. 18D; Mann-Whitney; $p=0.098$) biopsies from AUT-GI and Control-GI children. (FIGS. 18E-18F) Heatmaps displaying abundance distribution (% of total sequence reads per patient) of family members in the class Clostridia in ileum (FIG. 18E) and cecum (FIG. 18F) of AUT-GI and Control-Gi children (Bottom row displays cumulative levels of all family members by patient). (FIGS. 18G-18H) Box-and-whisker plots displaying the cumulative abundance of Firmicutes and Proteobacteria from ileal (FIG. 18G; Mann-Whitney, $p=0.015$) and cecal (FIG. 18H; Mann-Whitney, $p=0.007$) biopsies from AUT-GI and Control-GI patients. (FIGS. 18I-18J) Heatmaps displaying the abundance distribution (% of total sequence reads per patient) of Firmicutes and Proteobacteria by patient in ilea (FIG. 18I) and ceca (FIG. 18J) of AUT-GI and Control-GI children (Bottom row displays cumulative levels of Firmicutes and Proteobacteria by patient). *,$p<0.05$, **,$p<0.01$, †, $p<0.1$ (trend).

FIG. 19 shows graphs of the abundance of Proteobacteria in AUT-GI and Control-GI children. (FIGS. 19A-19B) Box-and-whisker plots displaying the phyla level abundance of Proteobacteria members in ilea (FIG. 19A; Mann-Whitney, $p=0.549$) and ceca (FIG. 19B; Mann-Whitney, $p=0.072$) of AUT-GI and Control-GI children biopsies obtained by pyrosequencing. (FIGS. 19C-19D) Box-and-whisker plots displaying the class level abundance of Betaproteobacteria members in ilea (FIG. 19C; Mann-Whitney, $p=0.072$) and ceca (FIG. 19D; $p=0.038$) of AUT-GI and Control-GI children. (FIGS. 19E-19F) Heatmaps displaying the abundance distribution (% of total sequence reads per patient) of family members within the classes Alpha-, Beta-, and Gammaproteobacteria in the ilea (FIG. 19E) and ceca (FIG. 19F) of AUT-GI and Control-GI children (Bottom row of each heatmap displays the cumulative levels of family members in each class by patient). *,$p<0.05$, †, $p<0.1$ (trend); n.s., not significant.

FIG. 20 shows schematics depicting factors that mediate GI disease in AUT-GI children. (FIG. 20A) Schematic representation of enterocyte-mediated digestion of disaccharides and absorption/transport of monosaccharides in the small intestine. Disaccharidase enzymes (SI, MGAM, and LCT) in the enterocyte brush border break down disaccharides into their component monosaccharides. The monosaccharides, glucose and galactose, are transported from the small intestinal lumen into the enterocyte by the sodium-dependent transporter SGLT1. On the basolateral enterocyte membrane, the facilitative transporter, GLUT2, transports glucose, galactose and fructose out of the enterocyte and into the circulation, thus regulating postprandial blood glucose levels. GLUT2 can also be transiently inserted into the apical enterocyte membrane, contributing a diffusive component to monosaccharide absorption in certain circumstances (Kellet et al., 2008). The expression levels of disaccharidases and hexose transporters can be controlled by the transcription factor CDX2. (FIG. 20B) In the normal small intestine, where expression of disaccharidases and hexose transporters are high, the majority, if not all, of disaccharides are efficiently digested and monosaccharides are absorbed from the lumen. Thus, only complex polysaccharides reach the large intestine and serve as growth substrates for colonic bacteria. Those bacteria best suited for growth on polysaccharides (i.e., Bacteroidetes) outcompete other bacteria and dominate the colonic space. In the normal intestine, colonic (i.e., cecal) microbial community structure can be kept within a normal homeostatic range by the level of expression of disaccharidases and hexose transporters upstream in the small intestine. The constraint on bacterial structure regulated by ileal gene expression would constrain bacterial byproducts of fermentation such as SCFAs, and limit the growth of potential pathogens. (FIG. 20C) In the AUT-GI intestine, where expression of disaccharidases and hexose transporters are deficient, mono- and disaccharides accumulate in the lumen of the distal small intestine (ileum) and proximal colon (cecum), and can exert extraintestinal effects by reducing postprandial blood glucose. The presence of additional carbohydrate substrates in the lumen abrogates the growth advantage of bacteria best suited for growth on polysaccharides (i.e., Bacteroidetes) and promotes the growth of other bacteria. In ASD-GI this specifically manifests as an increase in Firmicute/Bacteroidete ratios, cumulative levels of Firmicutes and Proteobacteria, and in levels of Betaproteobacteria in both the ileum and cecum. The level of dysbiosis in the ileum and cecum can thus be controlled by the degree and type of deficiency of carbohydrate metabolism and transport in the small intestine. Within the intestine, malabsorbed monosaccharides can lead to osmotic diarrhea; non-absorbed sugars can also serve as substrates for intestinal microflora, that produce fatty acids and gases (methane, hydrogen, and carbon dioxide) and promote additional GI symptoms of bloating and flatulence. Additional effects of dysbiosis can manifest in changes in SCFAs that can reduce colonic pH, further inhibiting the growth of Bacteroidetes. Disruption of symbiotic relationships between the host and the intestinal microbial ecosystem as a result of dysbiosis can also play a fundamental role in development, distribution, activation and differentiation of immune cells within the intestine (Abt and Artis, 2009; Mazmanian et al., 2008), thus providing a framework for understanding previous reports of inflammatory indices in the AUT-GI intestine.

FIG. 21 depicts lactase genotyping. (FIG. 21A) Representative agarose gel banding patterns observed for LCT-13910 and LCT-22018 polymorphisms. (FIG. 21B) Distribution of genotypes for 13910 and 22018 polymorphisms between AUT-GI (n=15) and Control-GI (n=7) patients (chi-squared test, p=0.896). (FIG. 21C) Box-and-whisker plot displaying the distribution of LCT mRNA expression in all individuals (AUT-GI and Control-GI) with the homozygous adult-type hypolactasia genotype (13910-C/C; 22018G/G) compared to all individuals (AUT-GI and Control-GI) possessing at least one copy of the normal allele (heterozygous: 13910-C/T; 22018-G/A and homozygous: 13910-T/T; 22018-A/A); Mann-Whitney, p=0.033. (FIG. 21D) Distribution of LCT mRNA expression levels split by genotype and group (AUT-GI and Control-GI); Kruskal-Wallis,p=0.097. (FIG. 21E) Distribution of LCT mRNA expression for all patients possessing at least one copy of the normal (lactase persistence) allele for AUT-GI (n=12) and Control-GI (n=6); Mann-Whitney, p=0.0246. Adult-type hypolactasia genotype is highlighted in red. *, p<0.05.

FIG. 23 shows graphs of the diversity of AUT-GI and Control-GI phylotypes. (FIGS. 23A-23B) Rarefaction curves assessing the completeness of sampling from pyrosequencing data obtained for individual AUT-GI (red) and Control-GI (blue) subjects' ileal (FIG. 23A) and cecal (FIG. 23B) biopsies. The y-axis indicates the number of OTUs detected (defined at 97% threshold for sequence similarity), the x-axis indicates the number of sequences sampled. (FIGS. 23C-23D) Rarefaction curves to estimate phylotype diversity, using the Shannon Diversity Index, from pyrosequencing data obtained for individual AUT-GI (red) and Control-GI (blue) subjects' ileal (FIG. 23C) and cecal (FIG. 23D) biopsies.

FIG. 24 shows graphs depicting the distribution of pyrosequencing reads by patient. (FIGS. 24A-24B) Phylum level distribution of bacteria by patient obtained from 16S rRNA gene barcoded pyrosequencing for ilea (FIG. 24A) and ceca (FIG. 24B). (FIGS. 24C-D) Distribution of low abundance bacterial phyla obtained by barcoded pyroseqeuncing. By-patient distribution of low abundance bacterial phyla in ilea (FIG. 24C) and ceca (FIG. 24D) from AUT-GI (patients 1-15) and Control-GI (patients 16-22).

FIG. 25 shows the OTU analysis of Bacteroidete phylotypes. (FIGS. 25A-25B) Heatmaps displaying abundance distributions (% of total sequence reads per patient) of the 12 most abundant Bacteroidete OTUs (defined at 97% threshold) in ileal (FIG. 25A) and cecal (FIG. 25B) biopsies from AUT-GI and Control-GI children (Bottom row displays cumulative levels of all 12 OTUs by patient). (FIGS. 25C-25D) Box-and-whisker plots displaying the cumulative abundance of the 12 OTUs in ilea (FIG. 25C; Mann-Whitney, p=0.008) and ceca (FIG. 25D; Mann-Whitney, p=0.008) of AUT-GI and Control-GI children. (FIG. 25E) Greengenes- or microbial blast (*)-derived classification of representative sequences obtained from each Bacteroidete OTU. Color code denotes the family-level, Ribosomal Database-derived taxonomic classification of each representative OTU sequence. **, p<0.01

(FIGS. 26A-26B) Box-and-whisker plot displaying the order-level distribution of the Clostridiales/Bacteroidales ratio from pyrosequencing reads obtained from ileal (FIG. 26A; Mann-Whitney, p=0.012) and cecal (FIG. 26B; Mann-Whitney, p=0.032) biopsies from AUT-GI and Control-GI patients. (FIGS. 26C-26D) Box-and-whisker plot displaying the Firmicute/Bacteroidete ratios obtained by real-time PCR for ilea (FIG. 26C; Mann-Whitney, p=0.0006) and ceca (FIG. 26D; Mann-Whitney, p=0.022) of AUT-GI and Control-GI children. *, p<0.05, ***, p<0.001.

(FIGS. 27A-27B) Box-and-whisker plots displaying the phyla level abundance of Firmicutes in the ilea (FIG. 27A; Mann-Whitney, p=0.098) and ceca (FIG. 27B; Mann-Whitney, p=0.148) of AUT-GI and Control-GI children obtained by pyrosequencing. (FIGS. 27C-27D) Box-and-whisker plots displaying the phyla level abundance of Firmicutes in the ilea (FIG. 27C; Mann-Whitney, p=0.245) and ceca (FIG. 27D; Mann-Whitney, p=0.053) of AUT-GI and Control-GI children obtained by real-time PCR. Copy number values for Firmicutes are normalized relative to total bacteria copy numbers. (FIGS. 27E-27F) Box-and-whisker plots displaying the abundance of Clostridiales from ileal (FIG. 27E; Mann-Whitney, p=0.072) and cecal (FIG. 27F; Mann-Whitney, p=0.098) biopsies from AUT-GI and Control-GI patients obtained by pyrosequencing. *, p<0.05; †, p<0.1 (trend); n.s., not significant.

FIG. 28 shows genus-level distribution of members of the families Ruminococcaceae and Lachnospiraceae. (FIGS. 28A-28B) Heatmap representation of the individual patient distributions (by patient) of Ruminococcaceae and Lachnospiraceae genus members in ileal (FIG. 28A) and cecal (FIG.

28B) biopsies from AUT-GI (Patients 1-15) and Control-GI (Patients 16-22) patients. *, genus members contributing to the trend toward increased Firmicutes in AUT-GI children.

Figure 29:
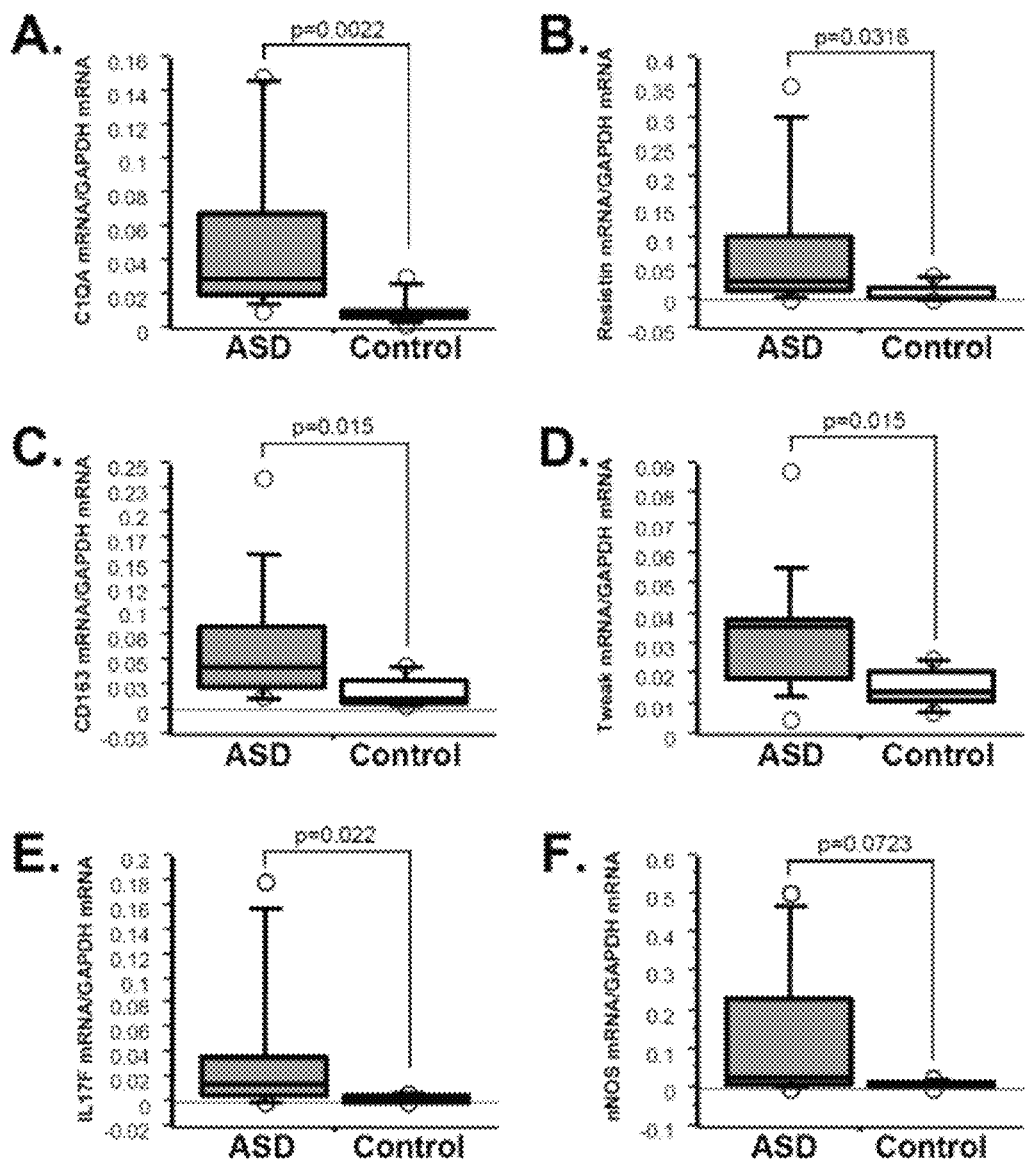

FIG. 29 shows graphs depicting increases in inflammatory markers, such as CIQ, Resistin, CD163, Tweak, IL17F, and nNOS. These inflammatory markers can also serve as biomarkers for diagnosis of human Autism Spectrum Disorders, as well as for detecting the presence of or a predisposition to autism or an autism spectrum disorder.

Figure 30:
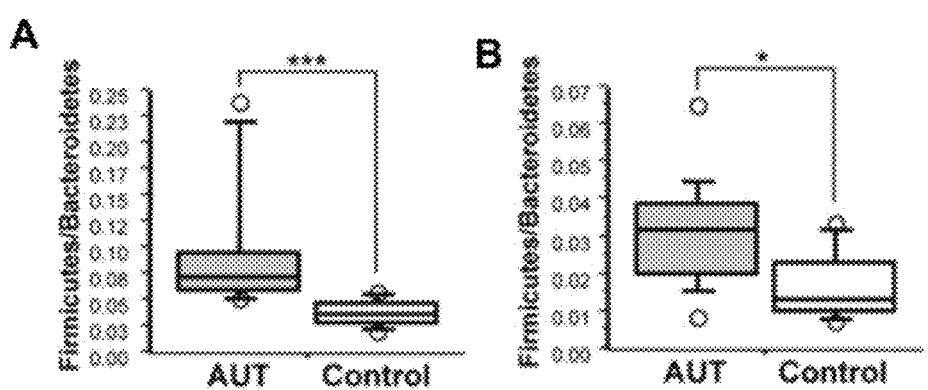

FIG. 30 depicts graphs of Firmicute/Bacteroidete ratios obtained by real-time PCR for ilea (FIG. 30A; Mann-Whitney, p=0.0006) and ceca (FIG. 30B; Mann-Whitney, p=0.022).

FIG. 31 shows levels of Clostridiales members in AUT-GI patients stratified by timing of GI onset. FIGS. 31A-B show the abundance of Clostridiales from ileal (FIG. 31A) and cecal (FIG. 31B) biopsies from AUT-GI and Control-GI patients (n=7), with AUT-GI stratified by whether the onset of GI symptoms occurred after (n=5) the onset of autism symptoms (GI-After) or before and at the same time (n=10) as autism symptoms (GI-Before/Same). [FIG. 31A: AUT (GI-After) vs. AUT (GI-Before/Same), Mann-Whitney, p=0.028; AUT (GI-Before/Same) vs. Control-GI, Mann-Whitney, p=0.015; AUT (GI-After) vs. Control-GI, Mann-Whitney, p=0.935] [FIG. 31B: AUT (GI-After) vs. AUT (GI-Before/Same), Mann-Whitney, p=0.037; AUT (GI-Before/Same) vs. Control-GI, Mann-Whitney, p=0.019; AUT (GI-After) vs. Control-GI, Mann-Whitney, p=0.935]. FIGS. 31C-D show the cumulative abundance of Lachnospiraceae and Ruminococcaceae from ileal (FIG. 31C) and cecal (FIG. 31D) biopsies from AUT-GI and Control-GI patients (n=7), with AUT-GI stratified by whether the onset of GI symptoms occurred after (n=5) the onset of autism symptoms or before and at the same time (n=10) as autism symptoms [FIG. 31C: AUT (GI-After) vs. AUT (GI-Before/Same), Mann-Whitney, p=0.028; AUT (GI-Before/Same) vs. Control-GI, Mann-Whitney, p=0.015; AUT (GI-After) vs. Control-GI, Mann-Whitney, p=0.808] [FIG. 31D: AUT (GI-After) vs. AUT (GI-Before/Same), Mann-Whitney, p=0.020; AUT (GI-Before/Same) vs. Control-GI, Mann-Whitney, p=0.011; AUT (GI-After) vs. Control-GI, Mann-Whitney, p=0.685]. *, p<0.05; **, p<0.01; n.s., not significant.

Figure 31E:
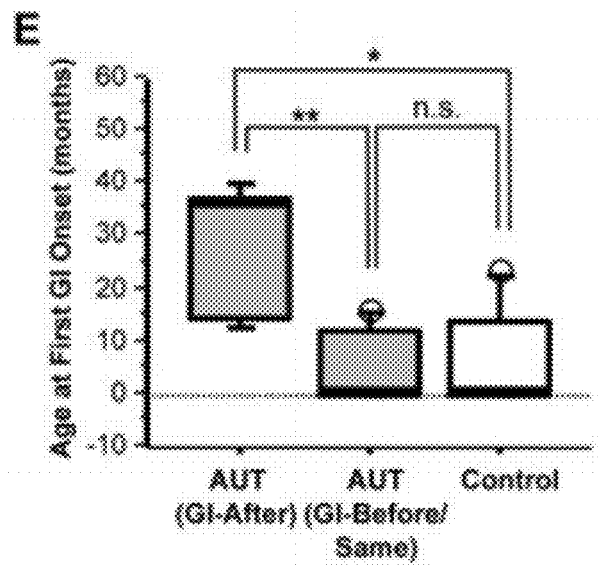

FIG. 31E shows the age at GI onset (in months) for AUT-GI and Control-GI patients, with AUT-GI stratified by whether GI onset occurred after (n=5) the onset of autism symptoms or before and at the same time (n=10) as autism symptoms [FIG. 31E: AUT (GI-After) vs. AUT (GI-Before/Same), Mann-Whitney, tied p=0.007; AUT (GI-Before/Same) vs. Control-GI, Mann-Whitney, tied p=0.757; AUT (GI-After) vs. Control-GI, Mann-Whitney, tied p=0.027]. *, p<0.05; **, p<0.01; n.s., not significant.

Figure 32:
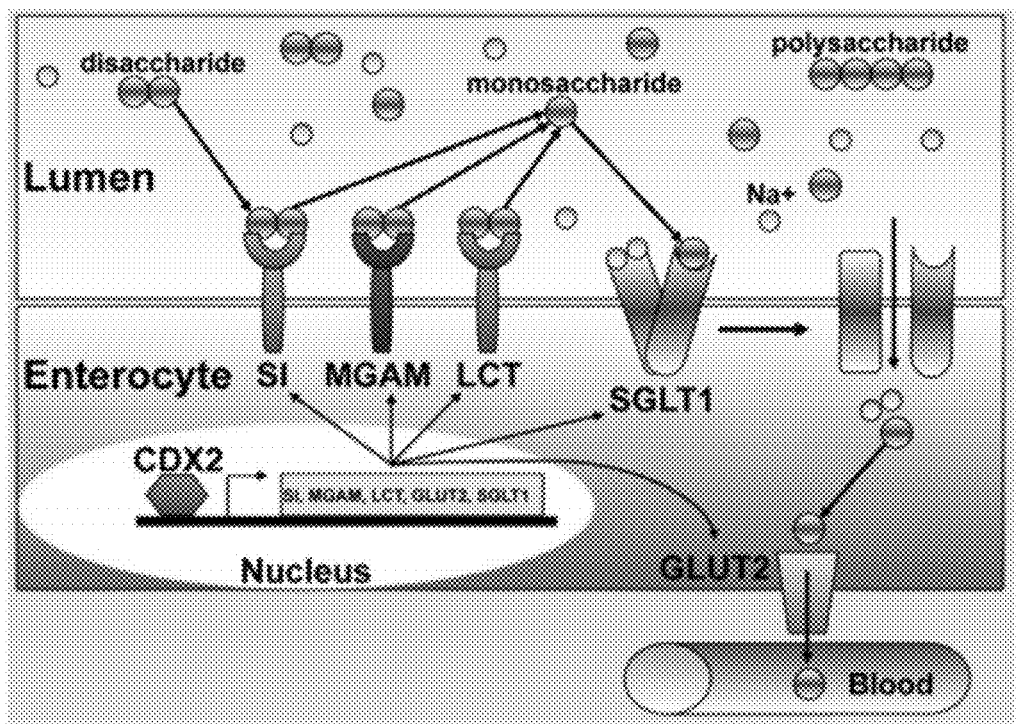

FIG. 32 is a schematic representation of enterocyte-mediated digestion of disaccharides and transport of monosaccharides in the small intestine. Disaccharidases (SI, MGAM, and LCT) in the enterocyte brush border break down disaccharides into their component monosaccharides. The monosaccharides, glucose and galactose, are transported from the small intestinal lumen into enterocytes by the sodium-dependent transporter SGLT1. On the basolateral enterocyte membrane, GLUT2, transports glucose, galactose and fructose out of enterocytes and into the circulation. The expression levels of disaccharidases and hexose transporters can be controlled, in part, by the transcription factor CDX2.

Figure 33:
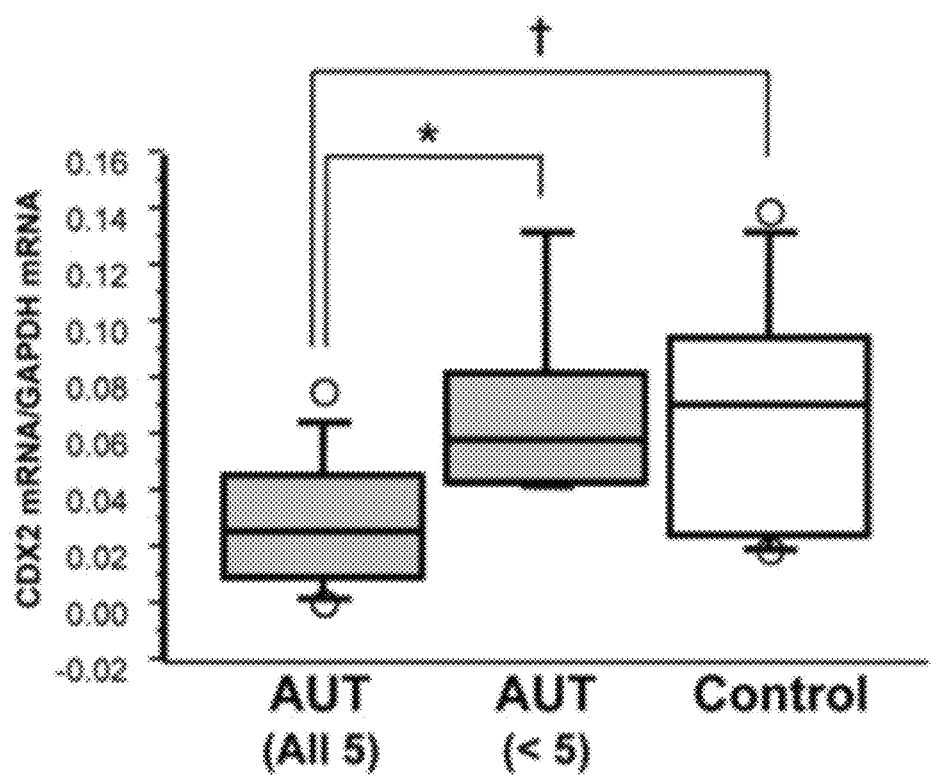

FIG. 33 is a bar grah showing CDX2 mRNA expression in AUT-GI children stratified by number of total disaccharidase and transporter deficiencies [All 5 deficient (n=10) or fewer than 5 deficient (n=5)] compared to all Control-GI children (n=7). AUT (All 5) vs AUT (<5); Mann-Whitney, p =0.037. AUT (All 5) vs Control; Mann-Whitney, p=0.064. *, p<0.05; ,p<0.01; *, p<0.001; †, p<0.1 (trend).

Figure 34:
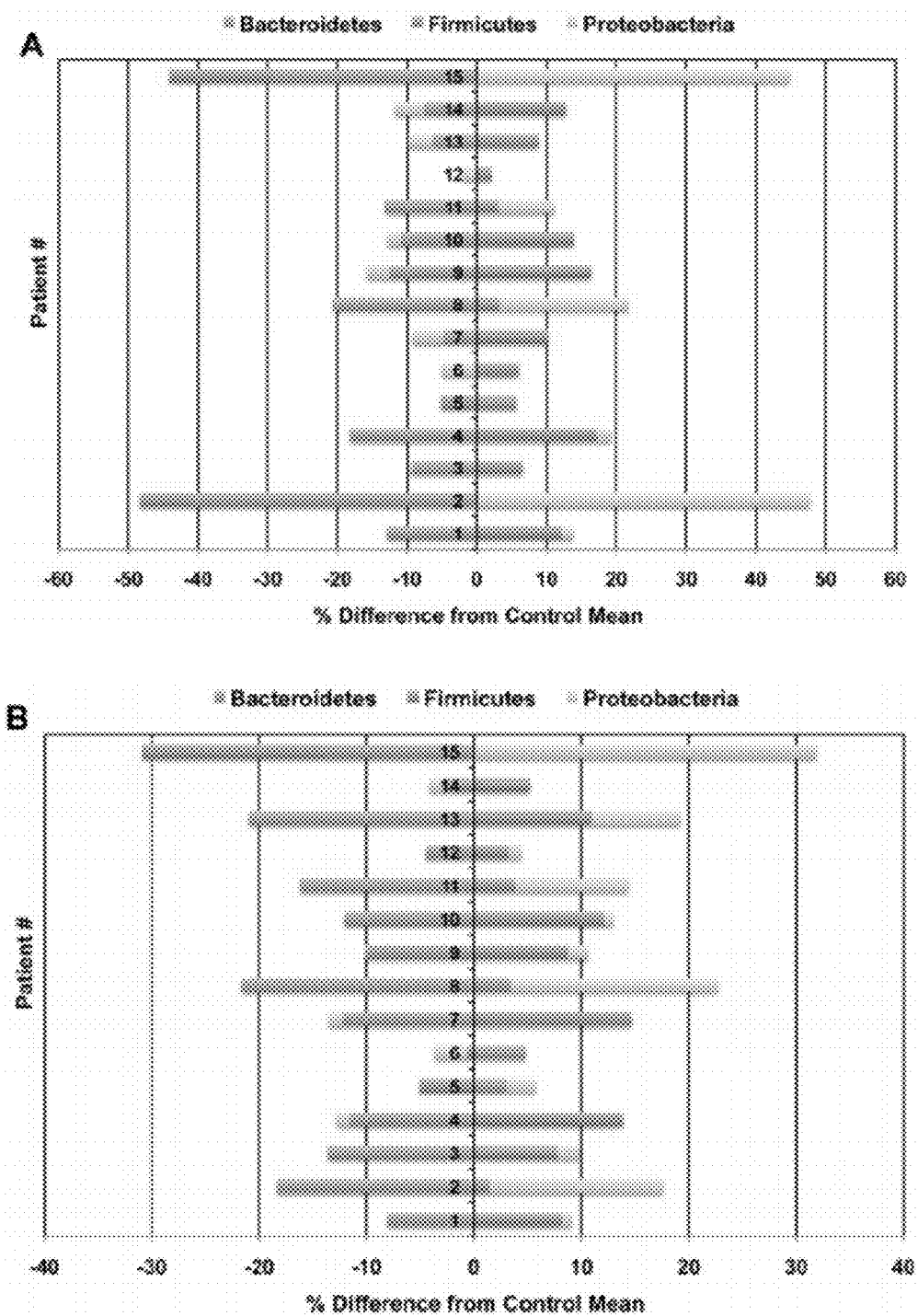

FIG. 34 shows the percent difference in abundance of Bacteroidetes, Firmicutes, and Proteobacteria in individual AUT-GI patients. (FIGS. 34A-B show bar graphs indicating the percent difference in phylotype abundance for Bacteroidetes, Firmicutes and Proteobacteria in AUT-GI patients (#1-15) relative to the Control-GI mean abundance for each of the three phylotypes obtained by pyrosequencing of ieal (FIG. 34A) and cecal (FIG. 34B) biopsies.

Figure 35:
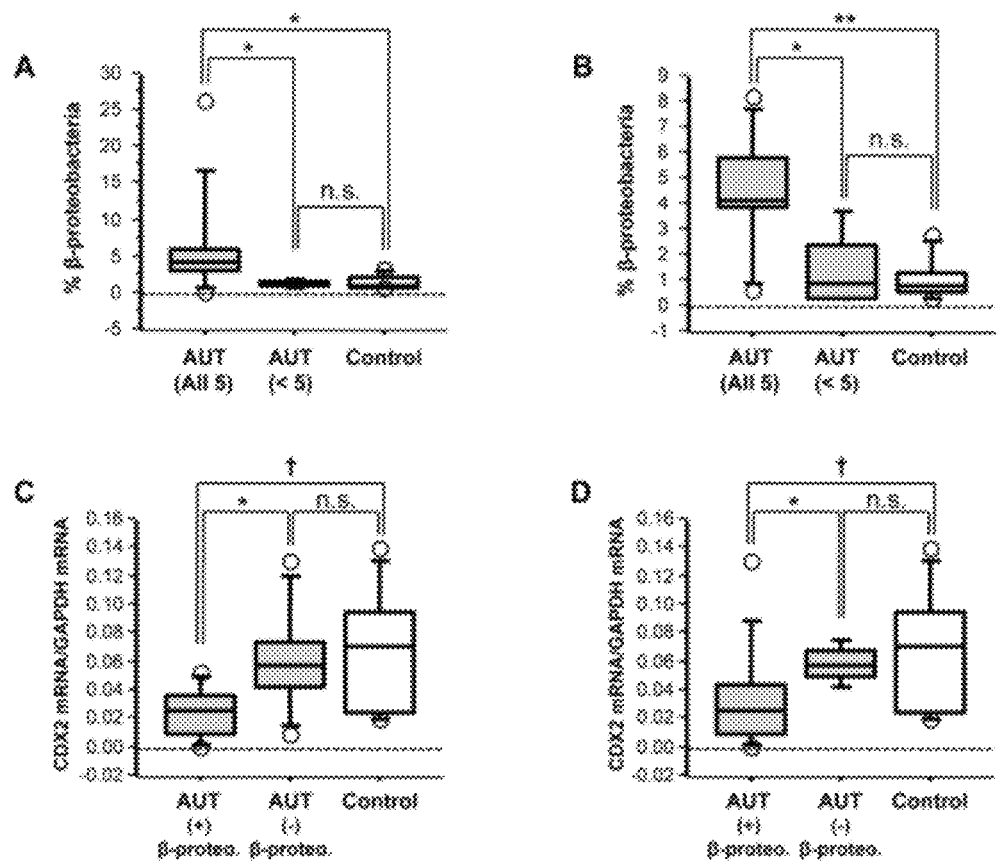

FIG. 35 shows graphs of increased Betaproteobacteria in AUT-GI children is associated with total deficiencies in disaccharidases and hexose transporters and CDX2 mRNA expression. FIGS. 35A-B show the abundance of Betaproteobacteria in AUT-GI children with deficiency in all 5 disaccharidases and transporters (All 5; n=10), AUT-GI children with deficiency in fewer than 5 disaccharidases and transporters (<5; n=5), and Control-GI children (n=7) in ileum (FIG. 35A) and cecum (FIG. 35B). (FIG. 35A) Ileum: AUT-GI (All 5) vs. AUT-GI (<5), Mann-Whitney, p=0.028; AUT-GI (All 5) vs. Control-GI, Mann-Whitney, p=0.015; AUT-GI (<5) vs. Con-trol-Gr, Mann-Whitney, p=0.935. (FIG. 35B) Cecum: AUT-GI (All 5) vs. AUT-GI (<5), Mann-Whitney, p=0.014; AUT-GI (All 5) vs. Control-GI, Mann-Whitney, p=0.006; AUT-GI (<5) vs. Control-GI, Mann-Whitney, p=0.808. FIGS. 35C-D show Ileal CDX2 mRNA expression in AUT-GI children with Betaproteobacteria above the $75^{th}$ percentile of Control-GI children [AUT (+) β-proteol.], AUT-GI children with Betaproteobacteria levels below the $75^{th}$ percentile of Control-GI children [AUT (−) β-proteol.], and Control-GI children in ileum (FIG. 35C) and cecum (FIG. 35D). (FIG. 35C) Ileum: AUT (+) β-proteo. (n=8) vs. AUT (−) β-proteo. (n=7), Mann-Whitney, p=0.037; AUT (+) β-proteo. vs. Control-GI (n=7), Mann-Whitney, p=0.064; AUT (−) β-proteo. vs. Control-GI, Mann-Whitney, p=0.749. (FIG. 35D) Cecum: AUT (+) β-proteo. (n=10) vs. AUT (−) β-proteo. (n=5), Mann-Whitney, p=0.028; AUT (+) β-proteo. vs. Control-GI (n=7), Mann-Whitney, p=0.097; AUT (−) β-proteo. vs. Control-GI, Mann-Whitney, p=0.808. *, p<0.05; **,p<0.01; †, p<0.1 (trend); n.s., not significant.

Figure 36:
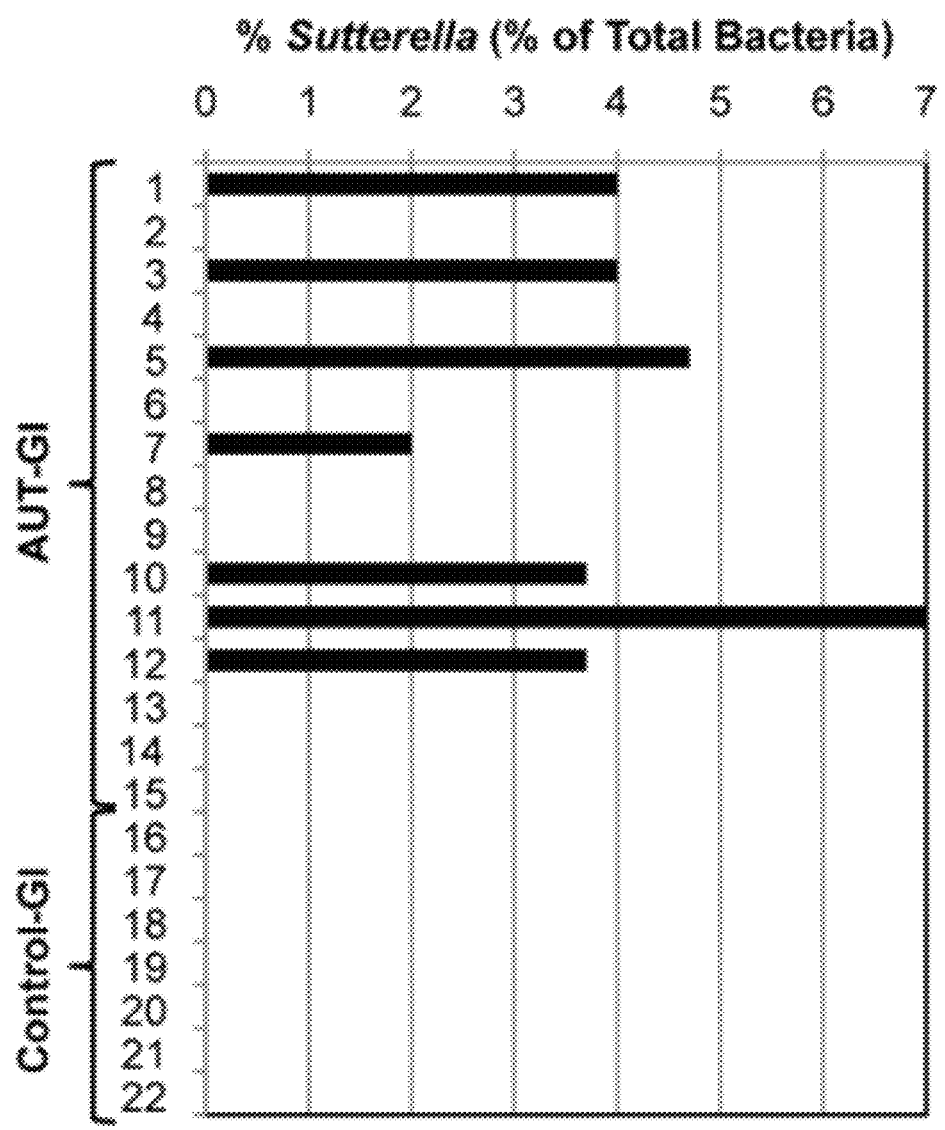

FIG. 36 shows the distribution of Sutterella sequences by individual patient as a percentage of total bacteria 16S rRNA reads from cecal biopsies from AUT-GI (patients #1-15) and Control-GI (patients #16-22) patients. *, p<0.05.

Figure 37:
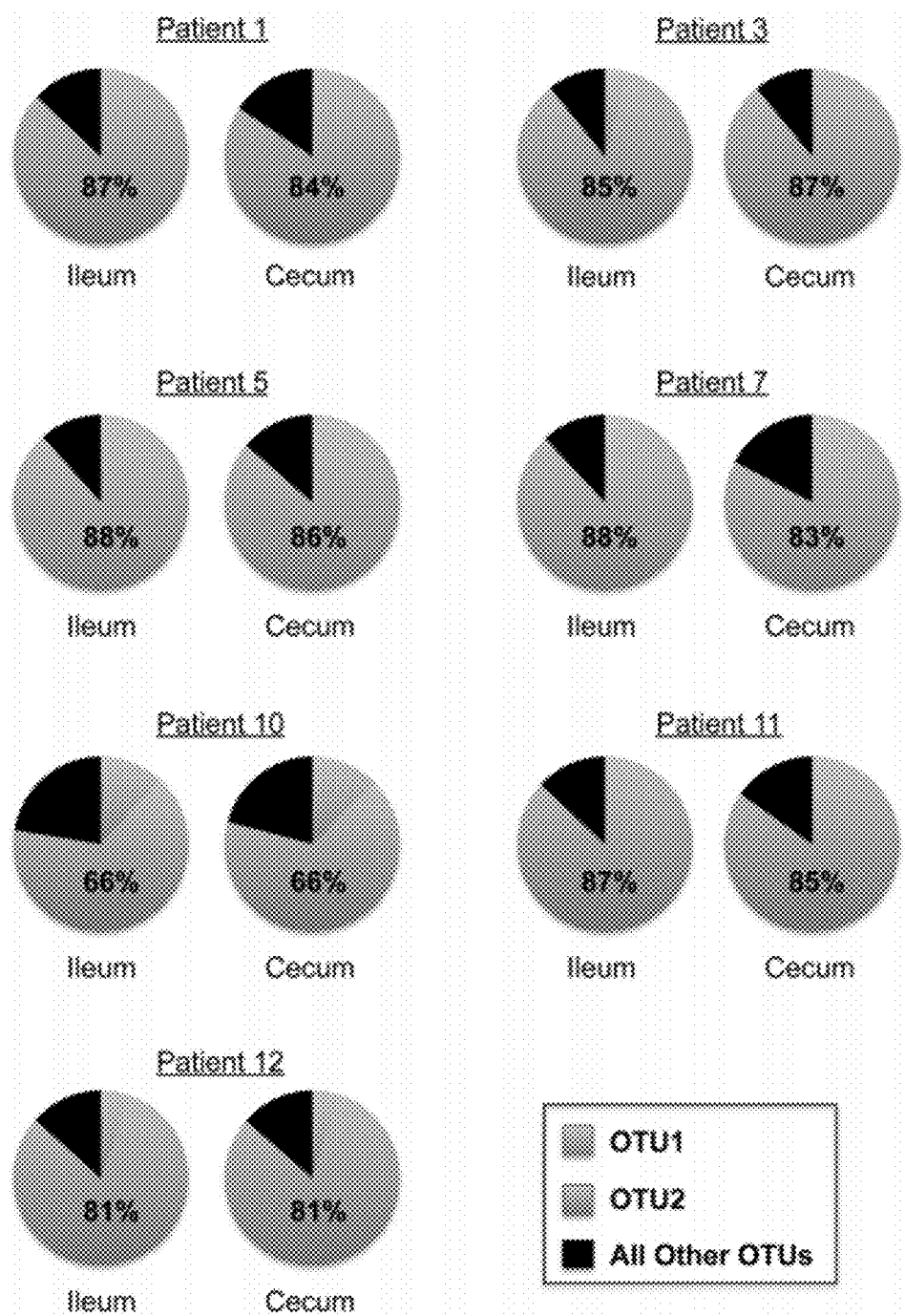

FIG. 37 is a pie chart indicating the percentage of Sutterella sequences in the dominant OTU (either OTU 1 or OTU 2) relative to sequences from subdominant Sutterella OTUs in ileum and cecum of the seven Sutterella-positive patients. The percentage of the dominant OTU is shown per individual patient.

Figure 38:
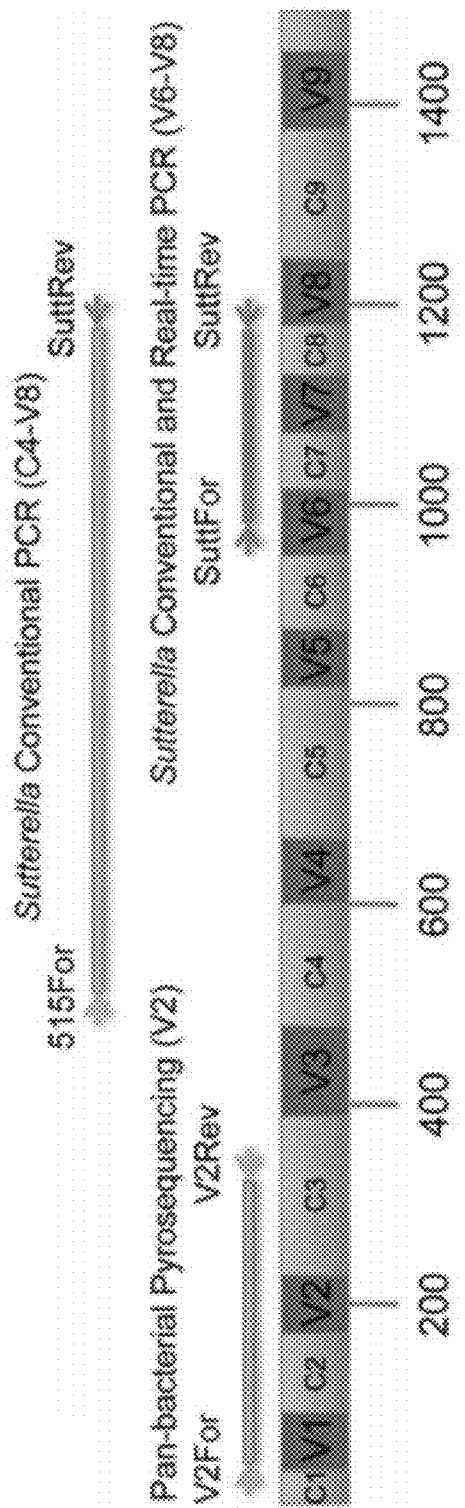

FIG. 38 is a schematic representation showing the location of PCR primers and products evaluated in Sutterella-specific PCR assays.

Figure 39:
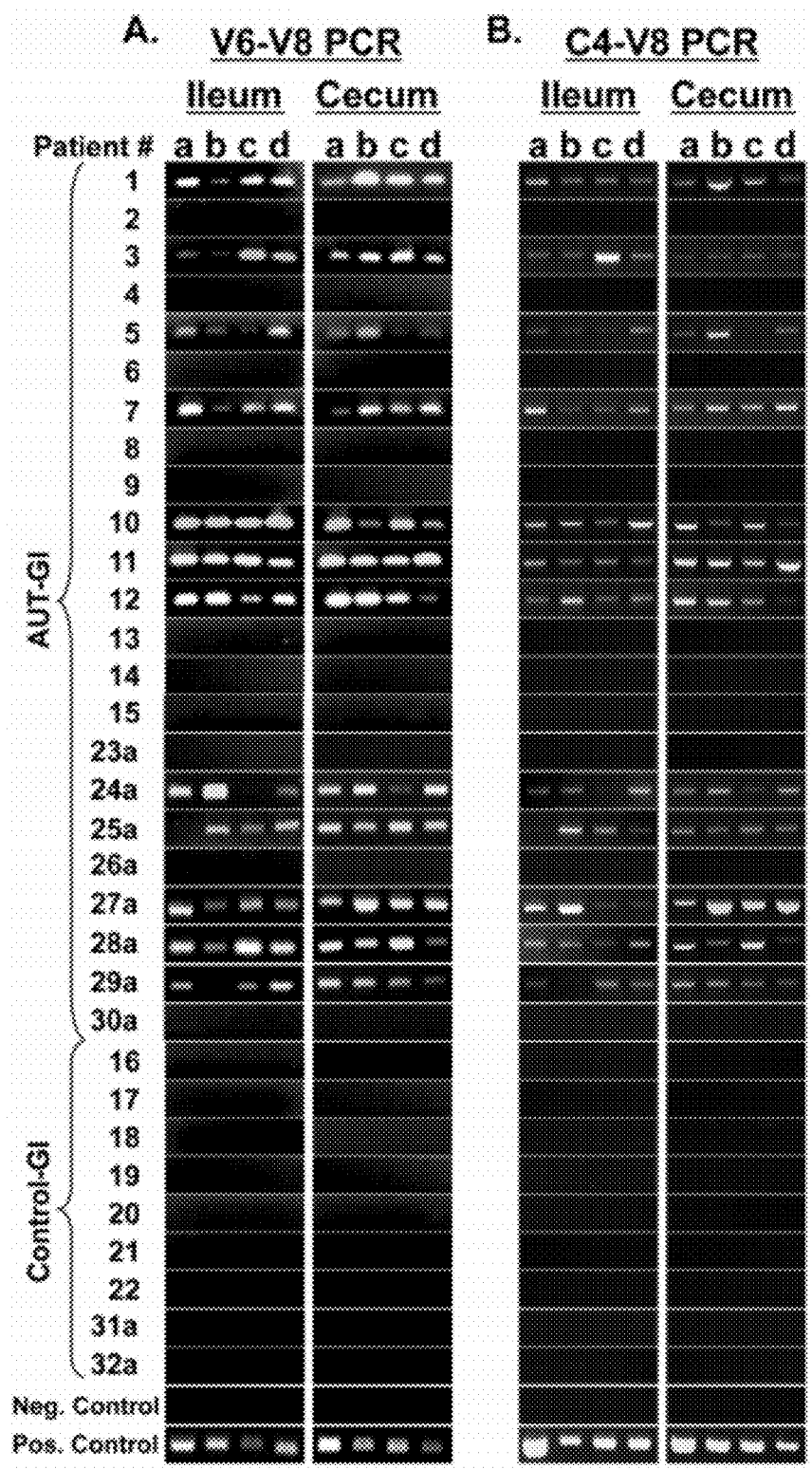

FIG. 39 are photographic images of gels showing PCR-based detection of Sutterella 16S rRNA gene sequences (V6-V8 region and C4-V8 region) in biopsies from AUT-GI and Control-GI patients. FIG. 39A shows agarose gel detection of 260 by Sutterella products in ileal (4 biopsies/patient) and cecal (4 biopsies/patient) biopsy DNA using SuttFor and SuttRev primers (V6-V8 region) in conventional PCR assays. FIG. 39B shows agarose gel detection of 715 by Sutterella products in ileal and cecal biopsy DNA using pan-bacterial primer 515For and SuttRev primer (C4-V8) in conventional PCR assays. Negative control is PCR reagents with water substituted for DNA. Positive control is DNA isolated from cultured S. wadsworthensis (ATCC, #51579).

Figure 40:
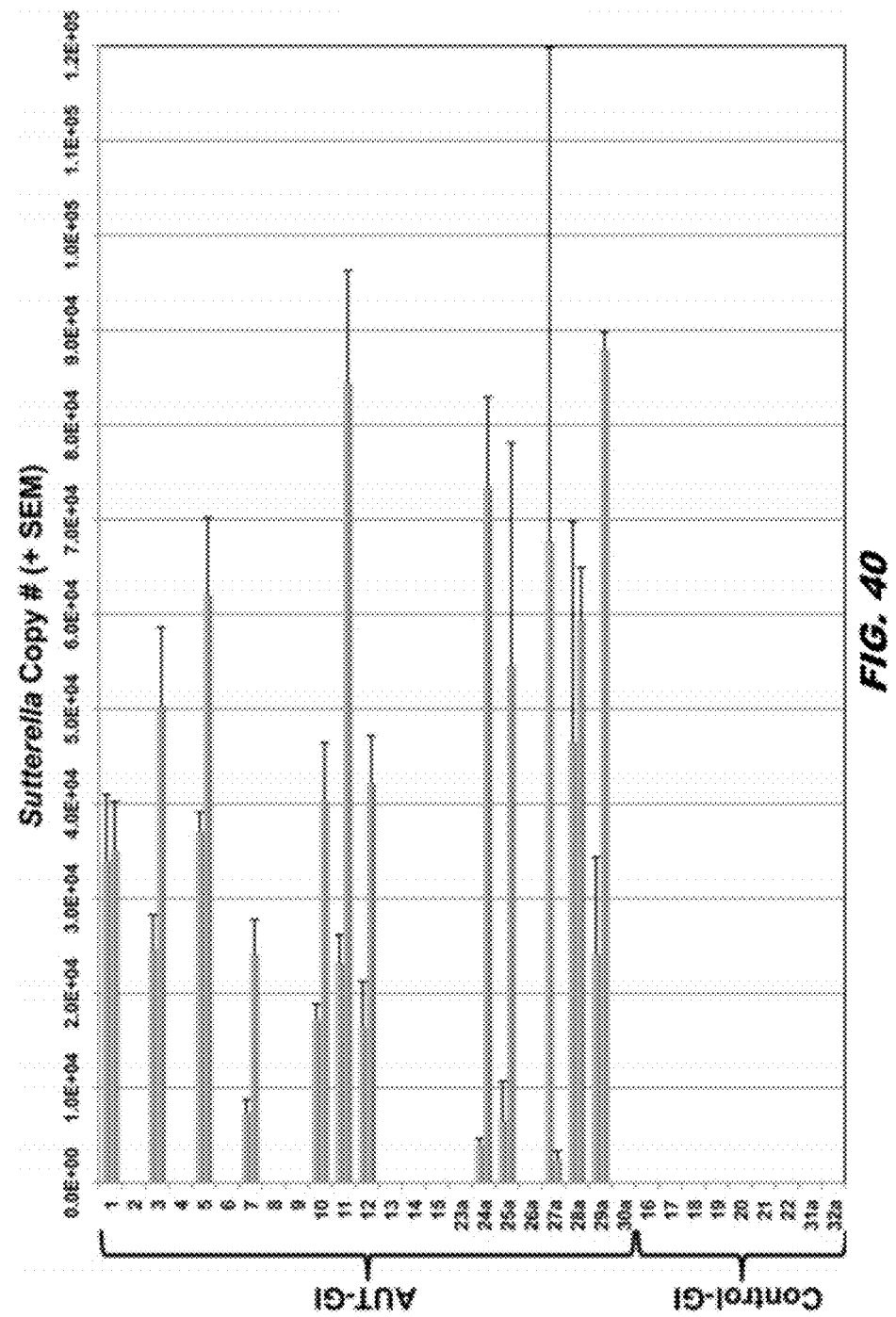

FIG. 40 is a graph that shows quantitation of *Sutterella* sequences in ileal and cecal biopsies from AUT-GI and Control-GI patients using a novel *Sutterella*-specific real-time PCR assay. Bars in graph show mean copy number in 4 biopsies from ileum (blue) and 4 biopsies from cecum (red)+ the standard error mean for each individual patient.

Figure 41:
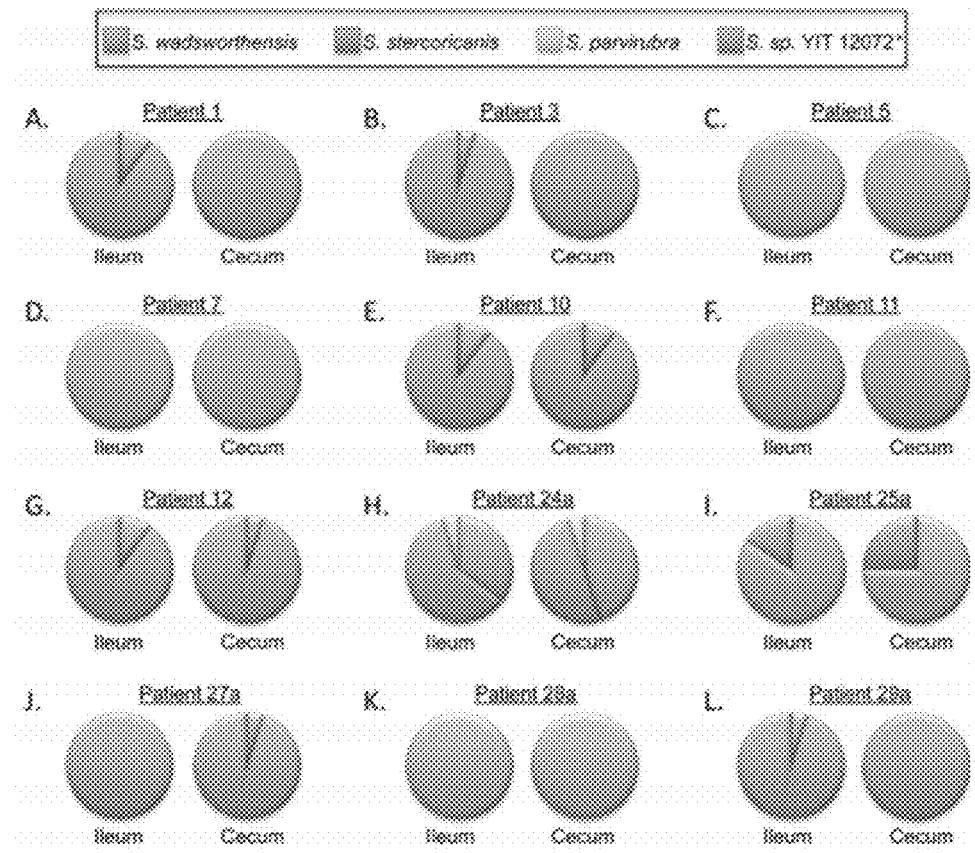

FIG. 41 shows pie charts of the distribution of *Sutterella* species in ileal and cecal biopsies of AUT-GI patients based on C4-V8 products. The closest sequence match to known *Sutterella* isolates was determined using the RDP seqmatch tool. The frequency of *Sutterella* species matches in ileal and cecal clone libraries are shown as pie charts for patient #1 (FIG. 41A), patient #3 (FIG. 41B), patient #5 (FIG. 41C), patient #7 (FIG. 41D), patient #10 (FIG. 41E), patient #11 (FIG. 41F), patient #12 (FIG. 41G), patient #24a (FIG. 41H), patient #25a (FIG. 41I), patient #27a (FIG. 41J), patient #28a (FIG. 41K), patient #29a (FIG. 41L). *, Note: *Sutterella* 16S sequences obtained from patient #28a were less than 97% similar to the 16S sequence of all known isolates of *Sutterella* species.

Figure 42:
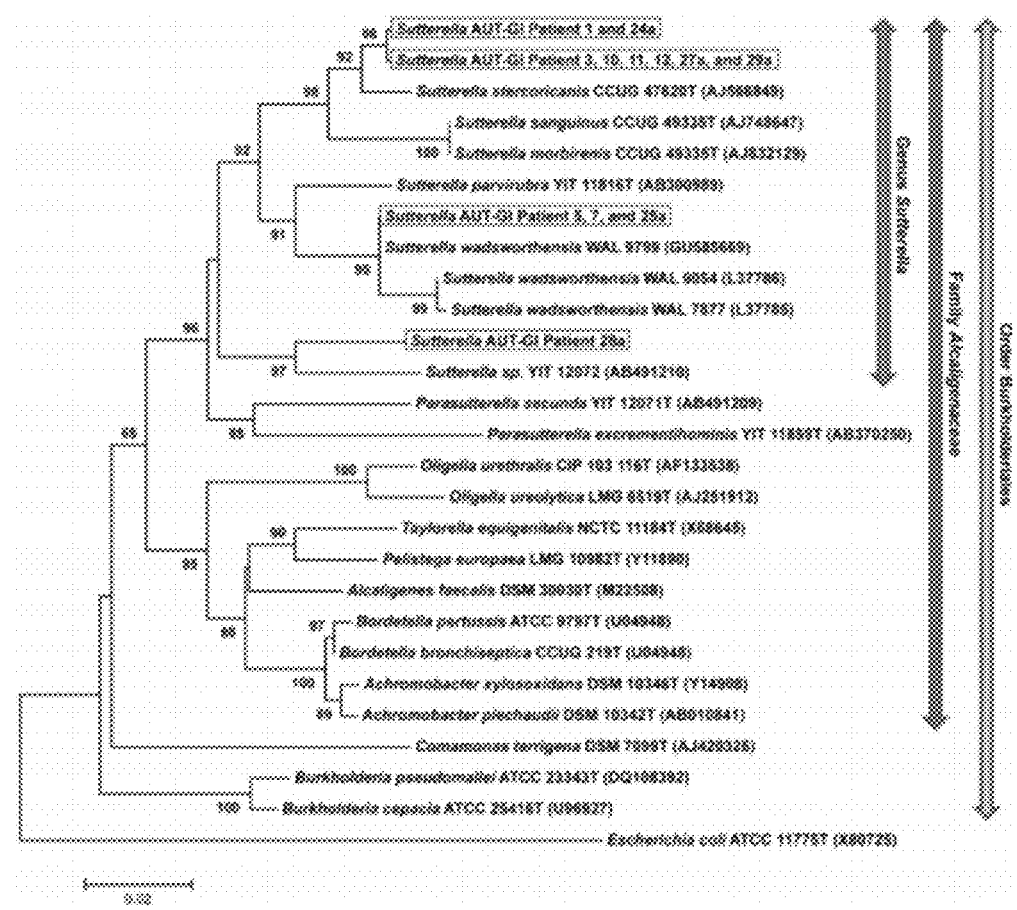

FIG. 42 is a schematic of a phylogenetic tree based on predominant 16S rRNA gene sequences obtained by C4-V8 *Sutterella* PCR from AUT-GI patients, *Sutterella* species isolates, and related species. The tree was constructed using the Neighbor-joining method. Bootstrap values (>60%) based on 1000 replicates are shown next to the branches. There were a total of 653 positions in the final dataset. The evolutionary distances were computed using the Jukes-Cantor method and are in the units of the number of base substitutions per site. The optimal tree with sum of branch length=0.66371685 is shown. The tree is rooted to the outgroup *Escherichia coli*. Accession numbers are shown in parentheses. AUT-GI patient sequences are boxed in red.

Figure 43A:
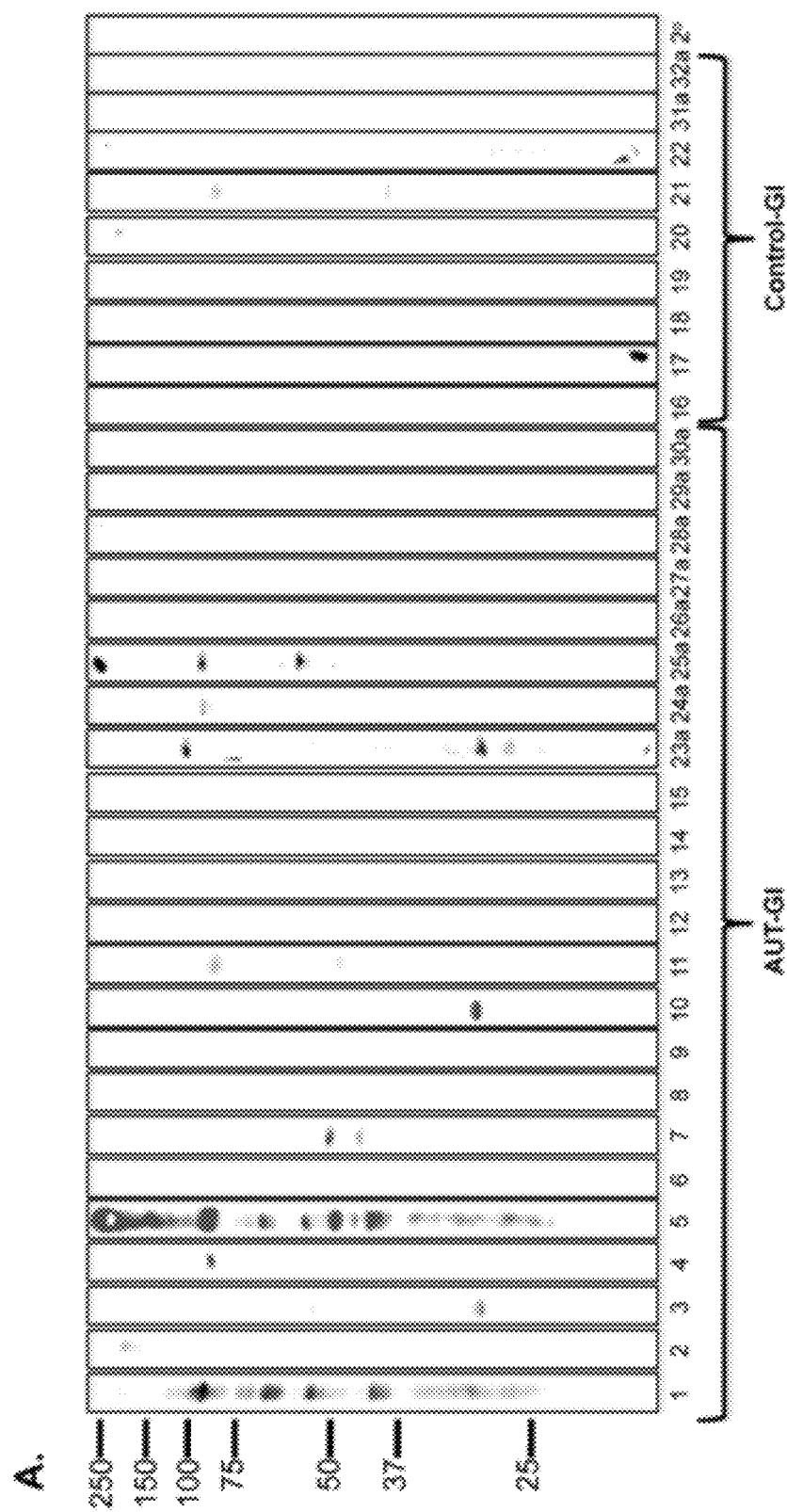
Figure 43B:
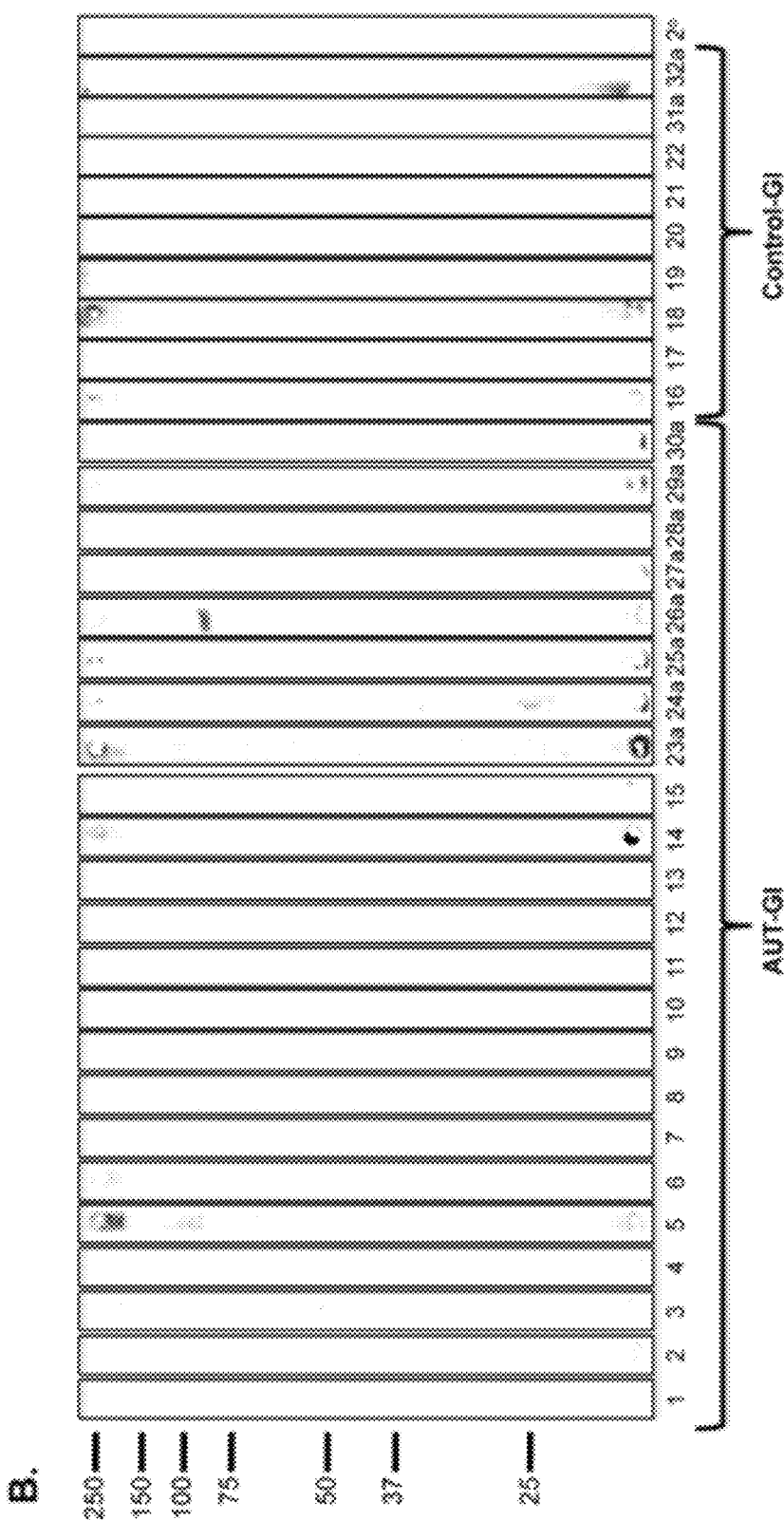
Figure 44A:
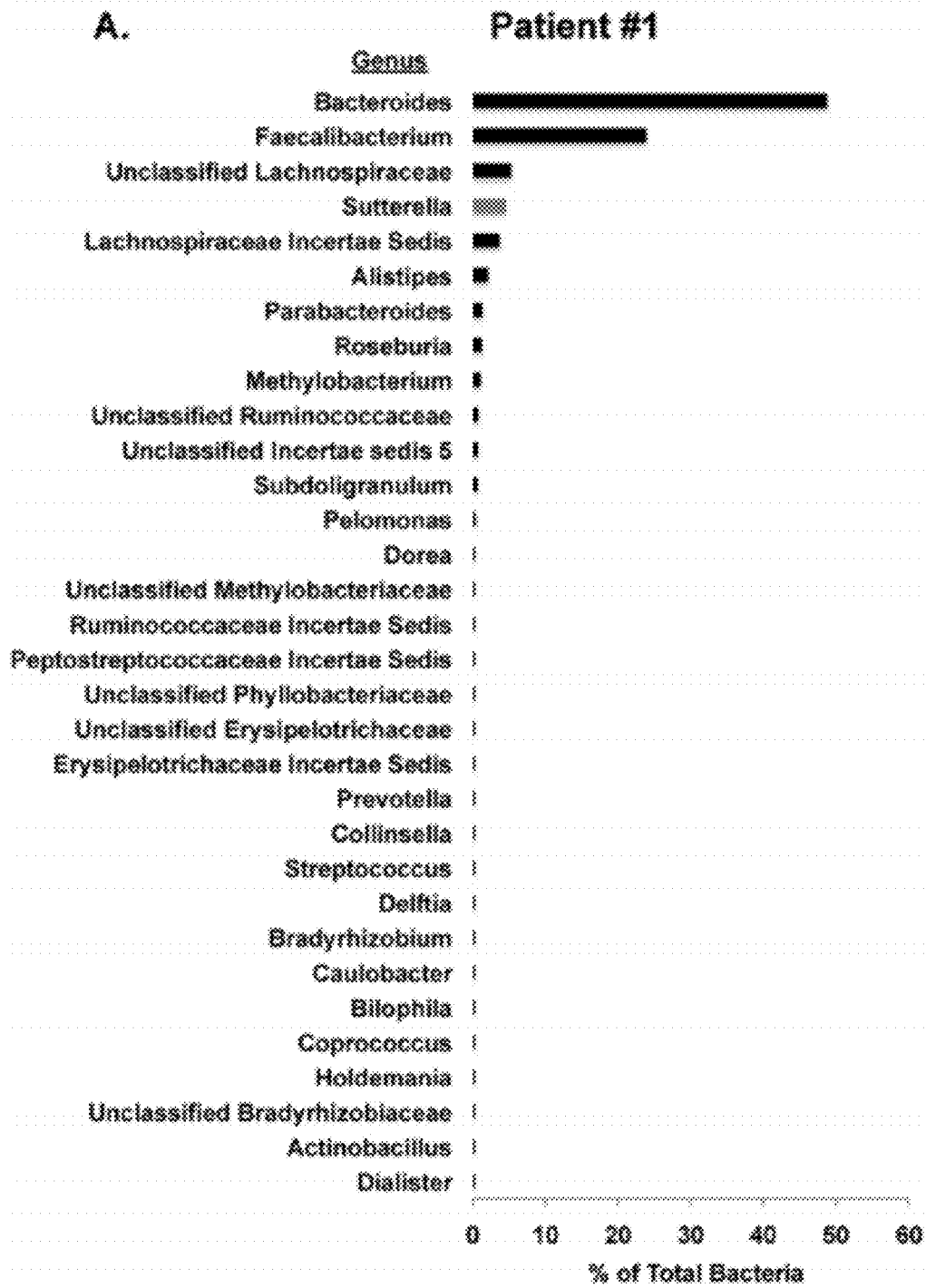
Figure 44B:
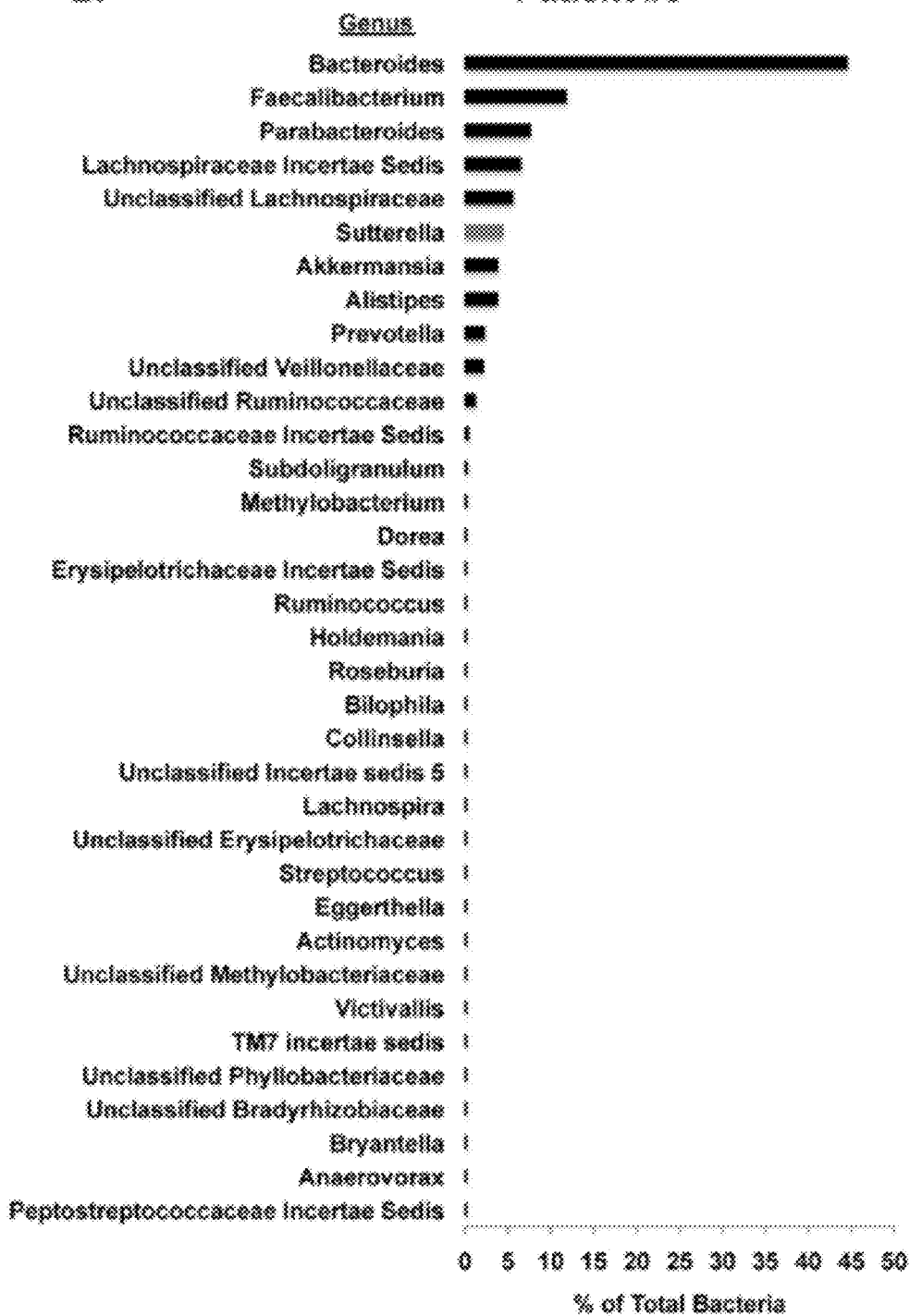
Figure 44C:
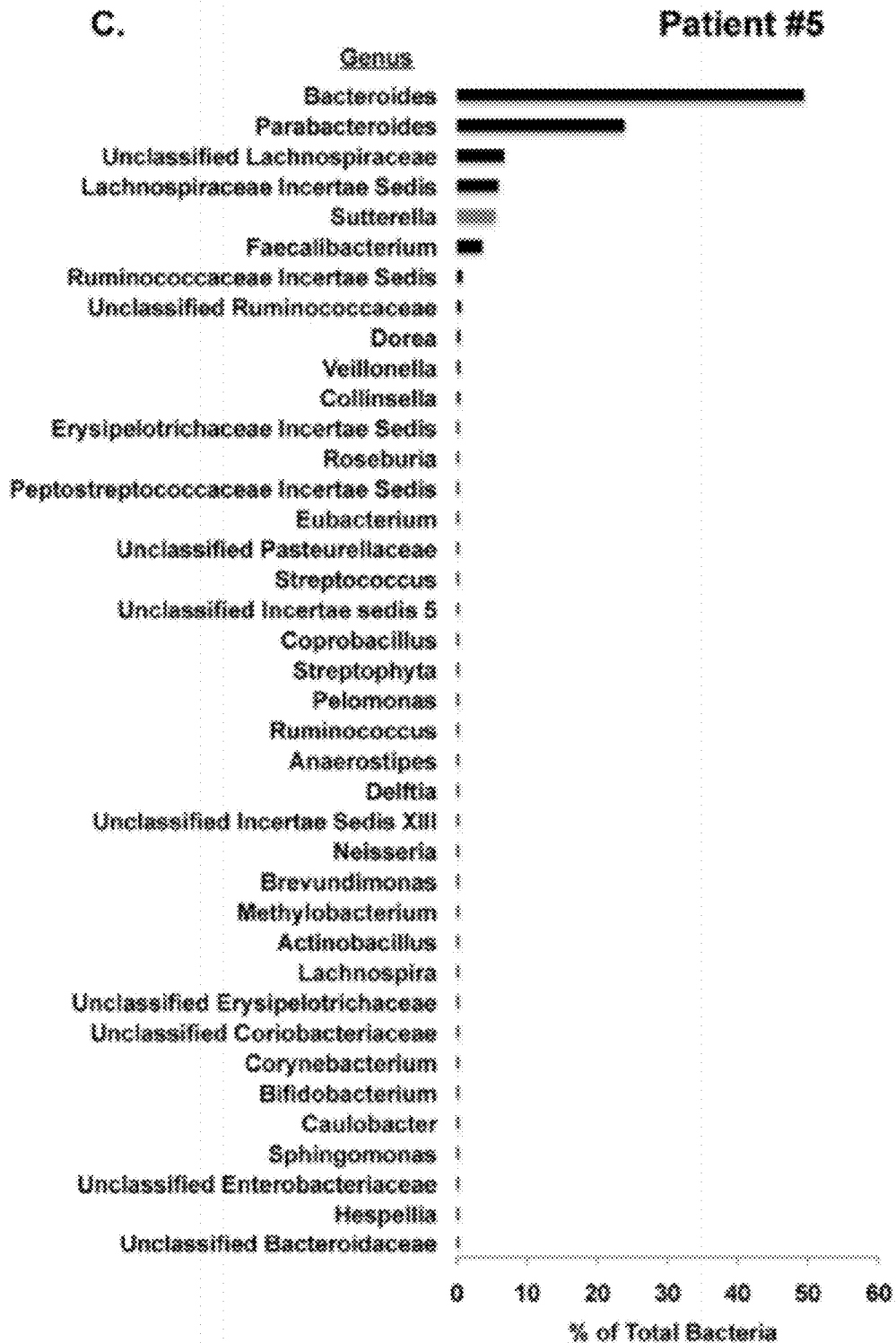
Figure 44D:
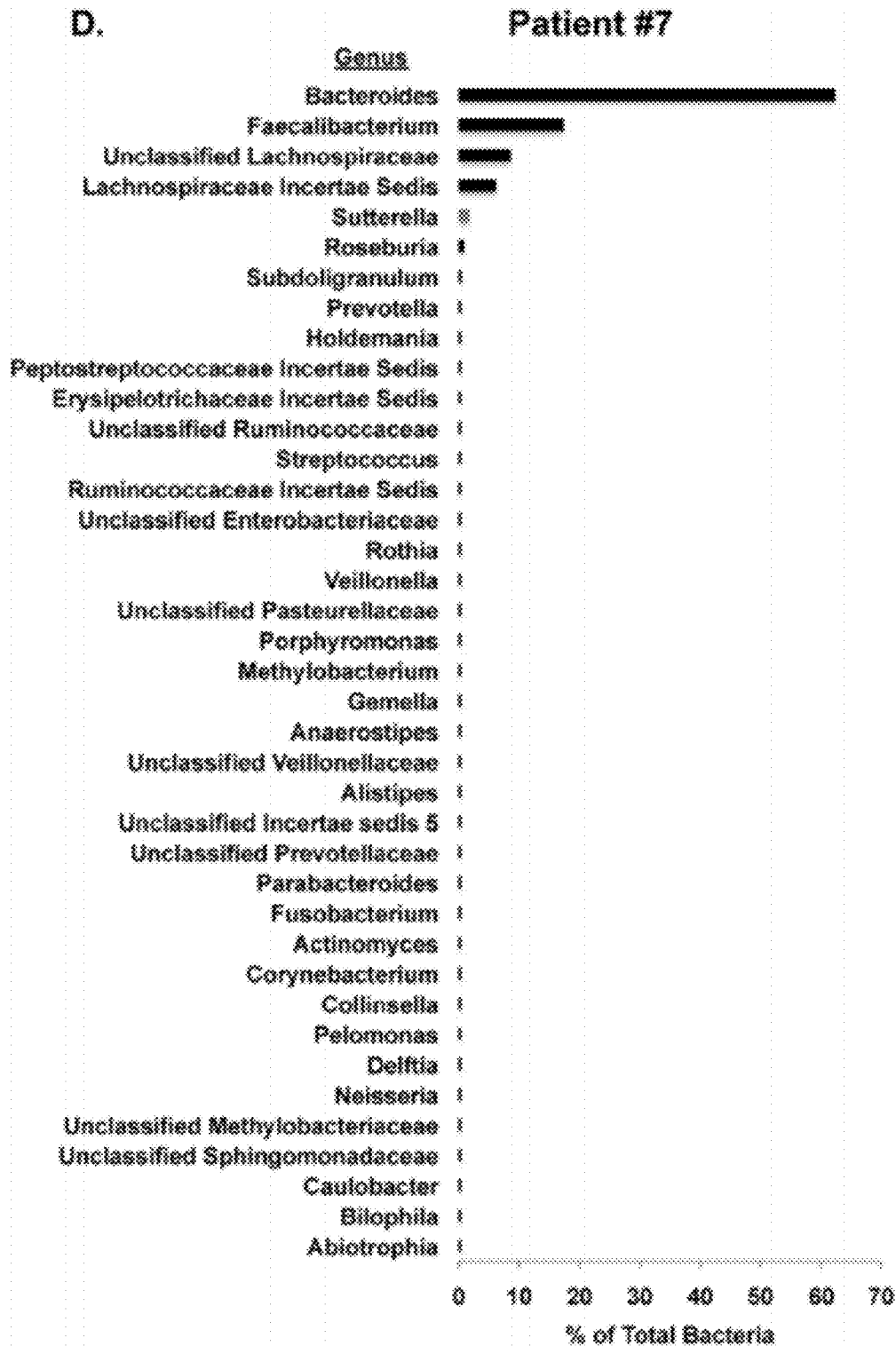

FIG. 43 shows western immunoblot analysis of AUT-GI and Control-GI patients' plasma antibody immunoreactivity against S. wadsworthensis antigens. FIG. 43A depicts patients' plasma IgG antibody immunoreactivity against S. wadsworthensis antigens: FIG. 43B depicts patients' IgM antibody immunoreactivity against S. wadsworthensis antigens. 2°=Secondary antibody control.

FIG. 44 shows graphs of the abundance distribution of all genus level classifications of sequences from pyrosequencing for patients #1, 3, 5 and 7. Bar graph showing all ileal genera, in order of highest abundance (top) to lowest abundance (bottom), from (FIG. 44A) patient #1 (32 total genera), (FIG. 44B) patient #3 (35 total genera), (FIG. 44C) patient #5 (39 total genera), and (FIG. 44D) patient #7 (39 total genera). The abundances of *Sutterella* sequences are indicated in red. Note unclassified family members can represent more than one genus (i.e. Unclassified Lachnospiraceae).

Figure 45A:
Figure 45B:
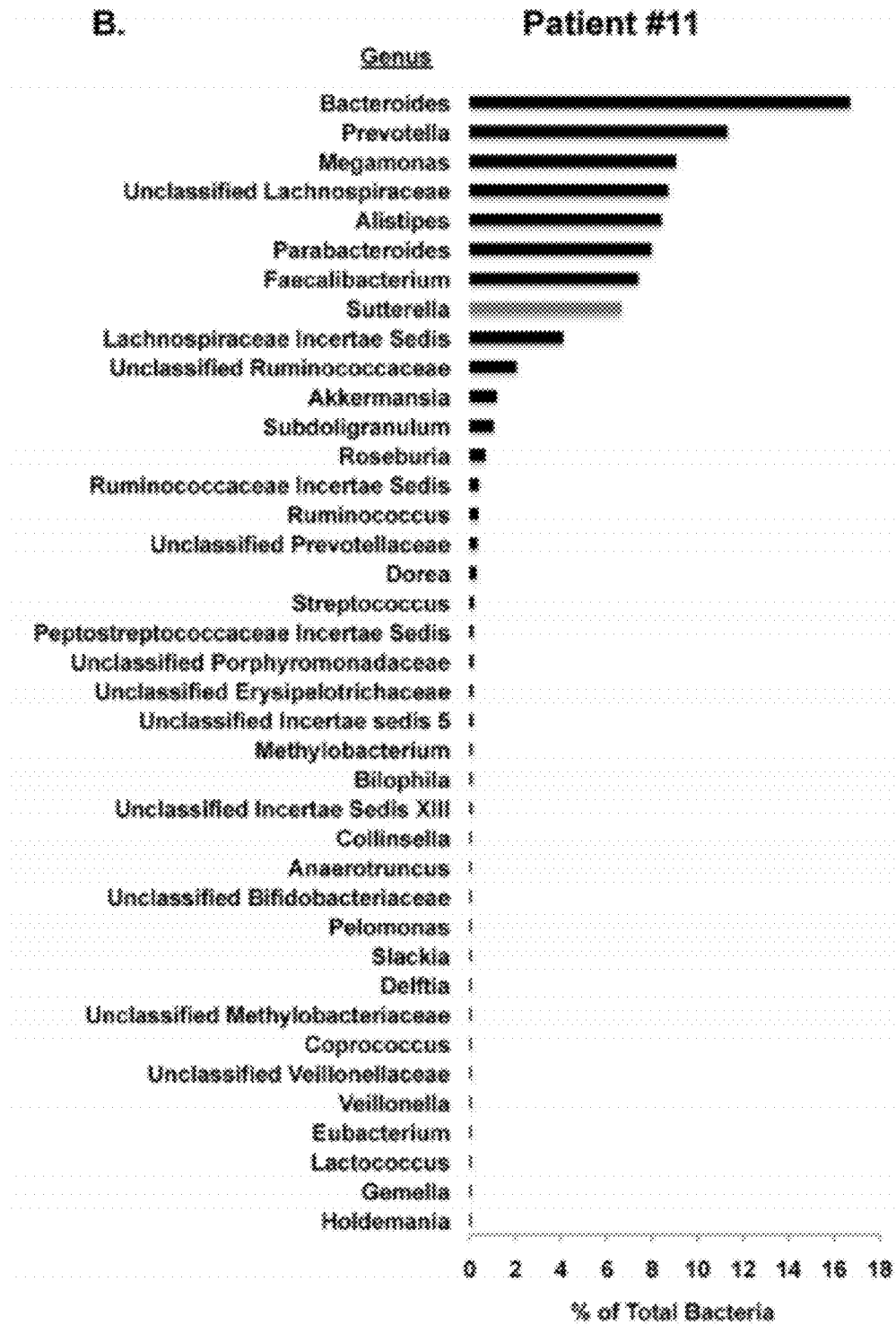
Figure 45C:

FIG. 45 shows graphs of the abundance distribution of all genus level classifications of sequences from pyrosequencing for patients #10, 11, and 12. Bar graph showing all ileal genera, in order of highest abundance (top) to lowest abundance (bottom) from (FIG. 45A) patient #10 (32 total genera), (FIG. 45B) patient #11 (39 total genera), and (FIG. 45C) patient #12 (44 total genera). The abundances of *Sutterella* sequences are indicated in red. Note unclassified family members can represent more than one genus (i.e. Unclassified Lachnospiraceae).

Figure 46A:
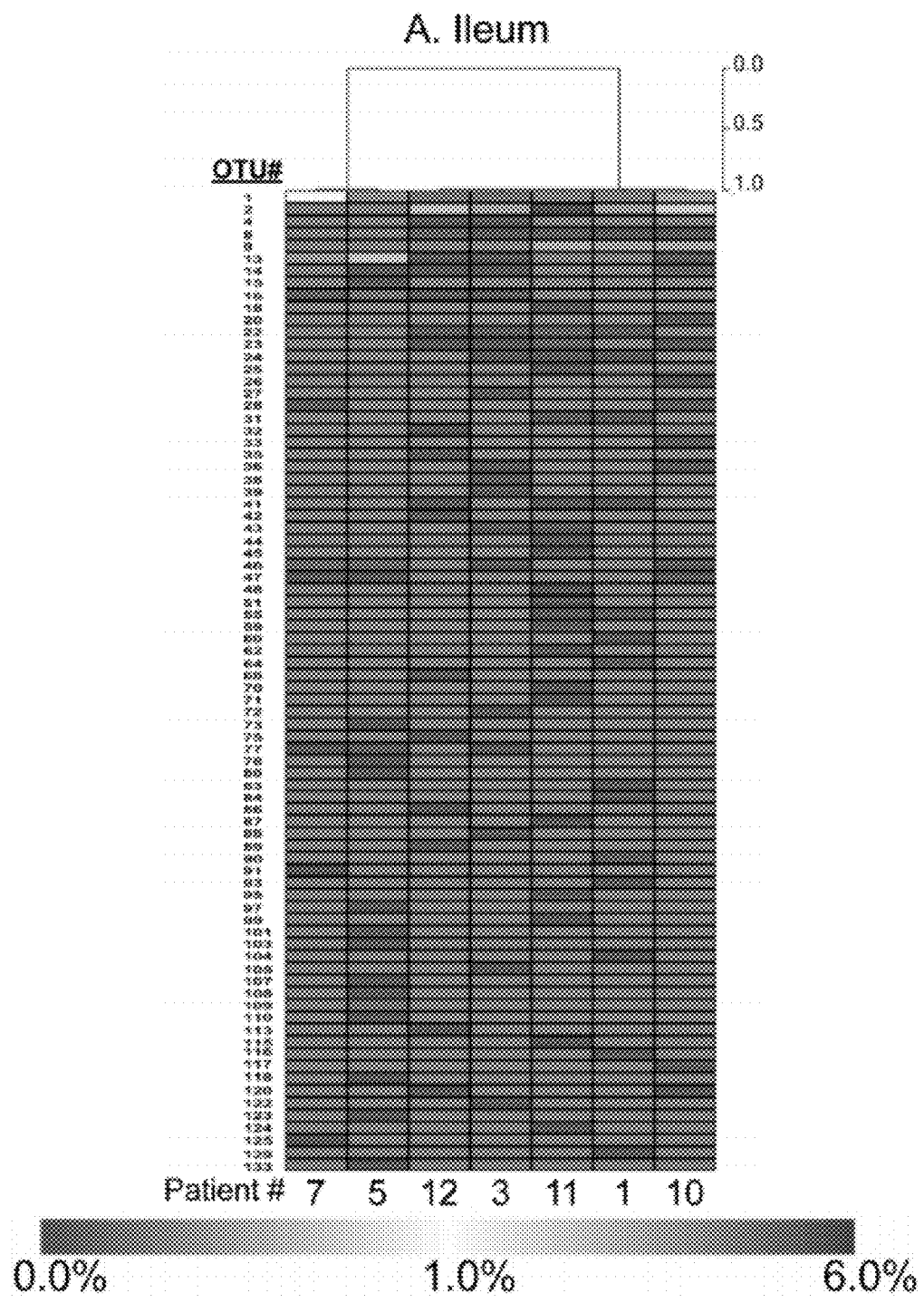
Figure 46B:
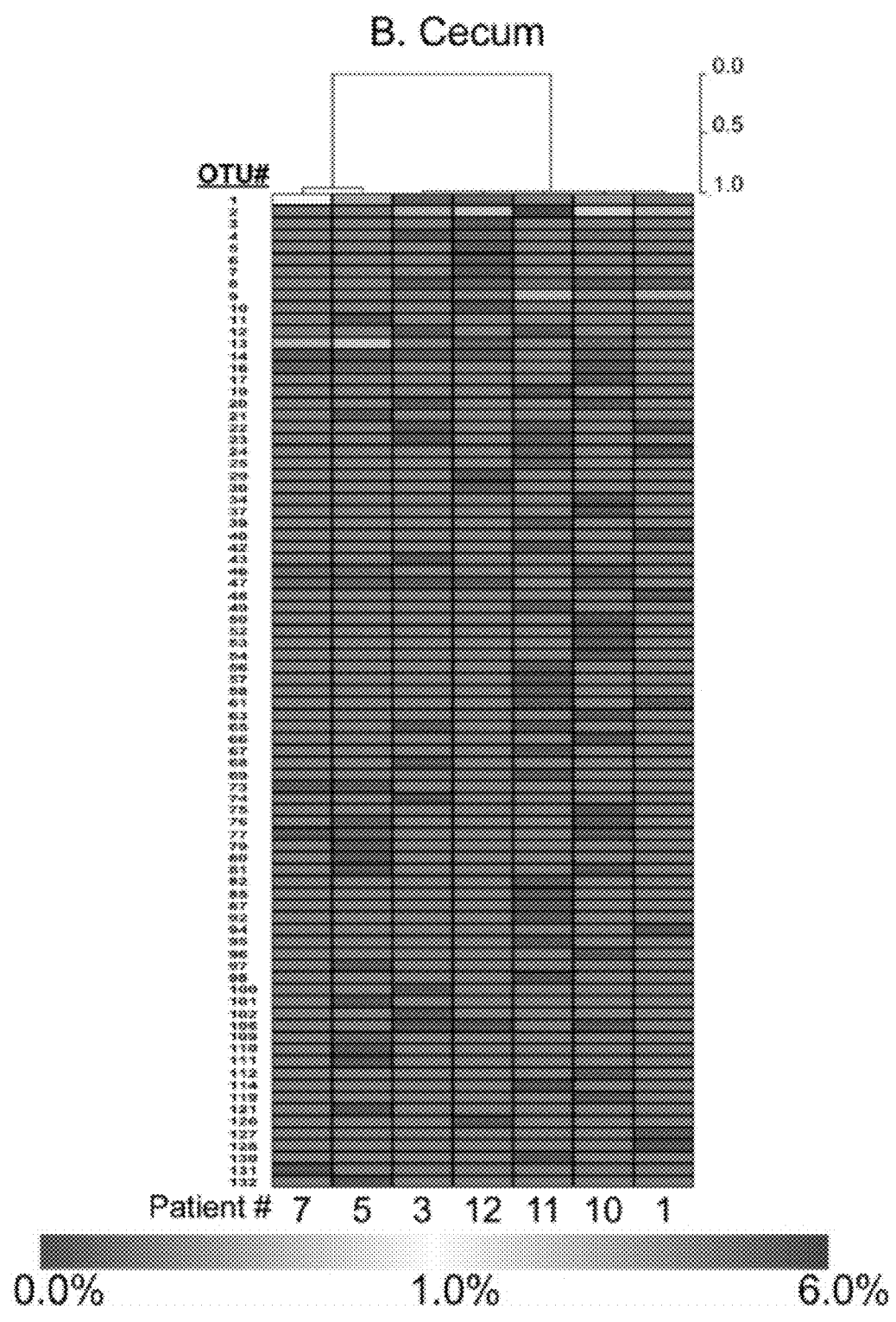

FIG. 46 depicts *Sutterella* OTU analysis. Heatmap generated from OTU analysis of all *Sutterella* sequences by patient. Note patients #1, 3, 10, 11, and 12 cluster together and the majority of *Sutterella* sequences are present in OTU 2. Patients #5 and 7 cluster together and the majority of *Sutterella* sequences are present in OTU 1. Heatmap scale represents OTU abundance (expressed as % of total bacterial pyrosequencing reads per patient).

Figure 47:
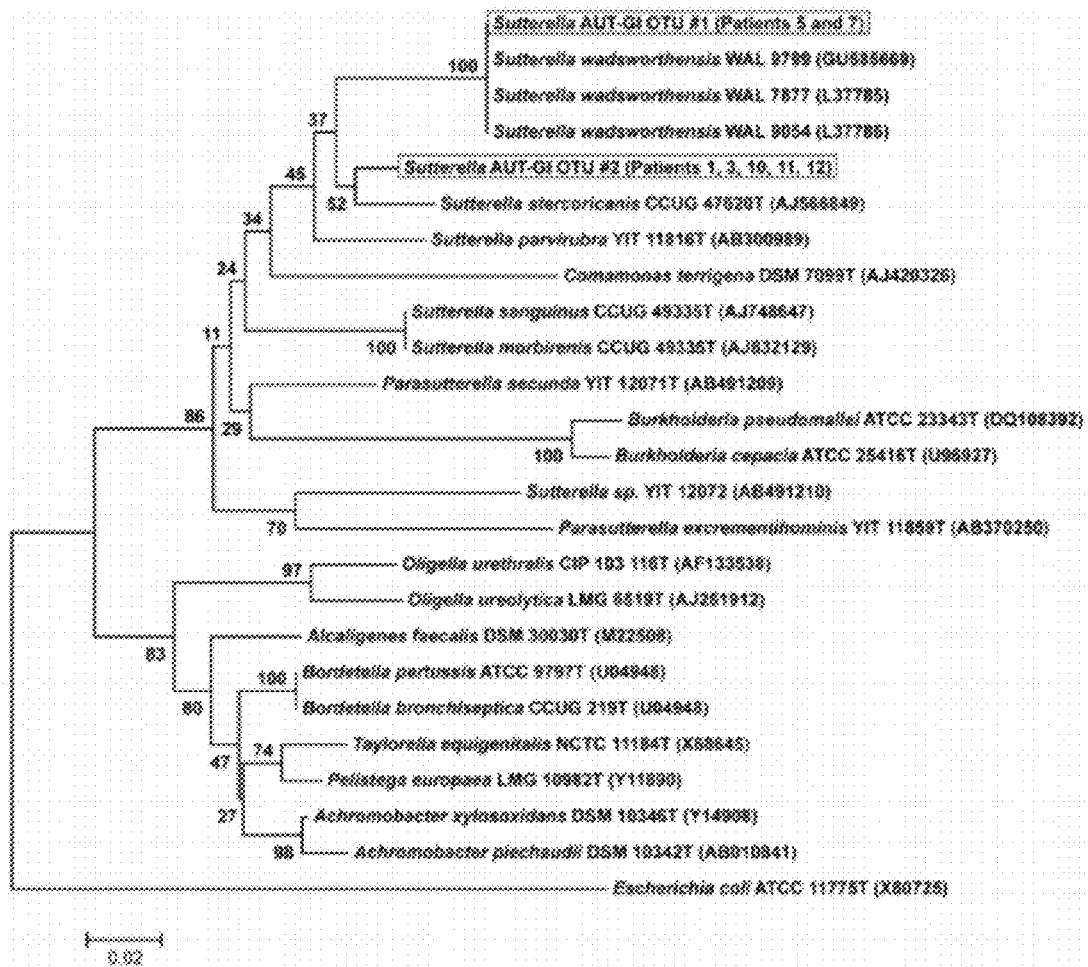

FIG. 47 is a schematic of a phylogenetic tree based on the representative 16S rRNA gene sequences obtained by V2 region pyrosequencing (OTU 1 and OTU 2) from AUT-GI patients, *Sutterella* species isolates, and related species. The tree was constructed using the Neighbor-joining method. Bootstrap values based on 1000 replicates are shown next to the branches (% bootstrap support). There were a total of 218 positions in the final dataset. The evolutionary distances were computed using the Jukes-Cantor method and are in the units of the number of base substitutions per site. The optimal tree with sum of branch length=1.01142743 is shown. The tree is rooted to the outgroup *Escherichia coli*. Accession numbers are shown in parentheses. The location of AUT-GI patients' representative OTU 1 and OTU 2 sequences are boxed in red.

Figure 48:
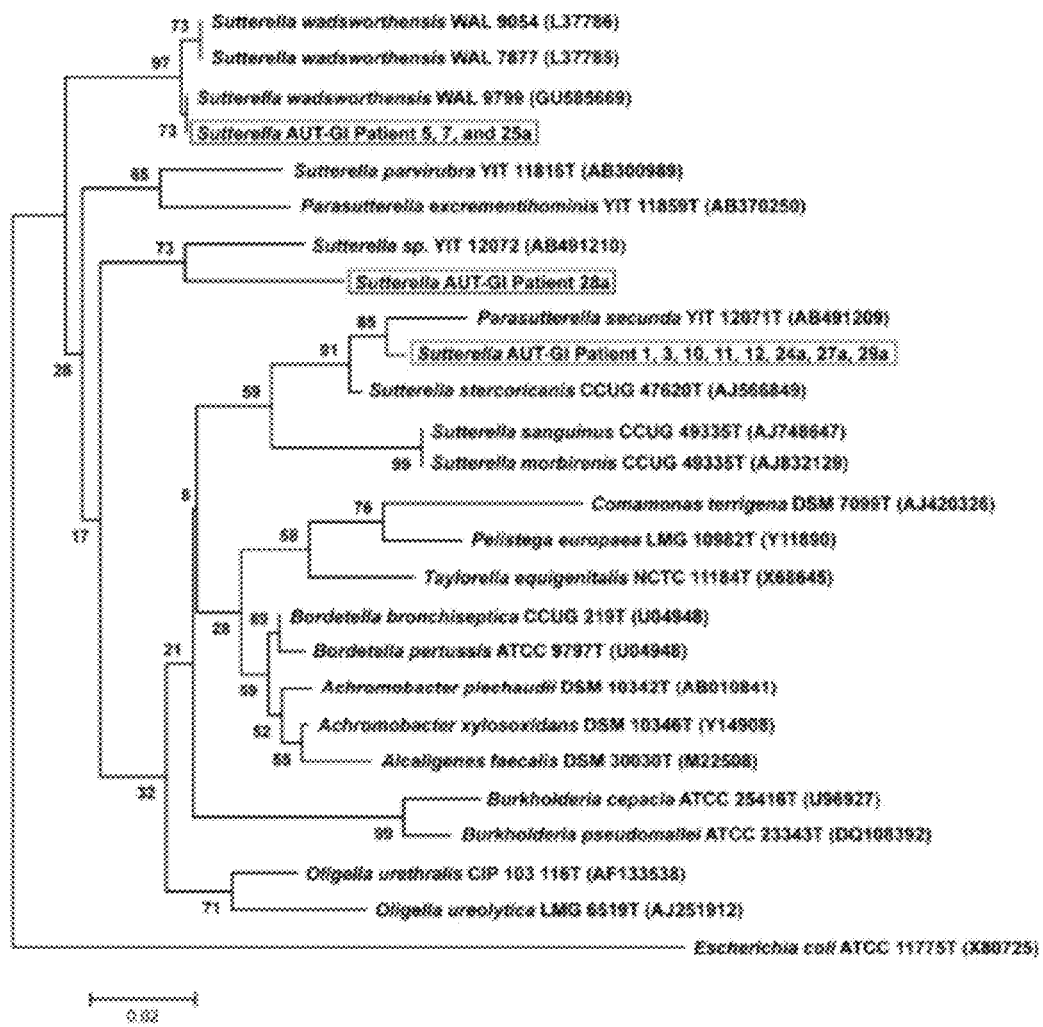

FIG. 48 is a schematic of a phylogenetic tree based on predominant 16S rRNA gene sequences obtained by V6-V8 *Sutterella* PCR from AUT-GI patients, *Sutterella* species isolates, and related species. The tree was constructed using the Neighbor-joining method. Bootstrap values based on 1000 replicates are shown next to the branches (% bootstrap support). There were a total of 215 positions in the final dataset. The evolutionary distances were computed using the Jukes-Cantor method and are in the units of the number of base substitutions per site. The optimal tree with sum of branch length=0.67013793 is shown. The tree is rooted to the outgroup *Escherichia coli*. Accession numbers are shown in parentheses. The location of AUT-GI patients' sequences are boxed in red.

Figure 49:
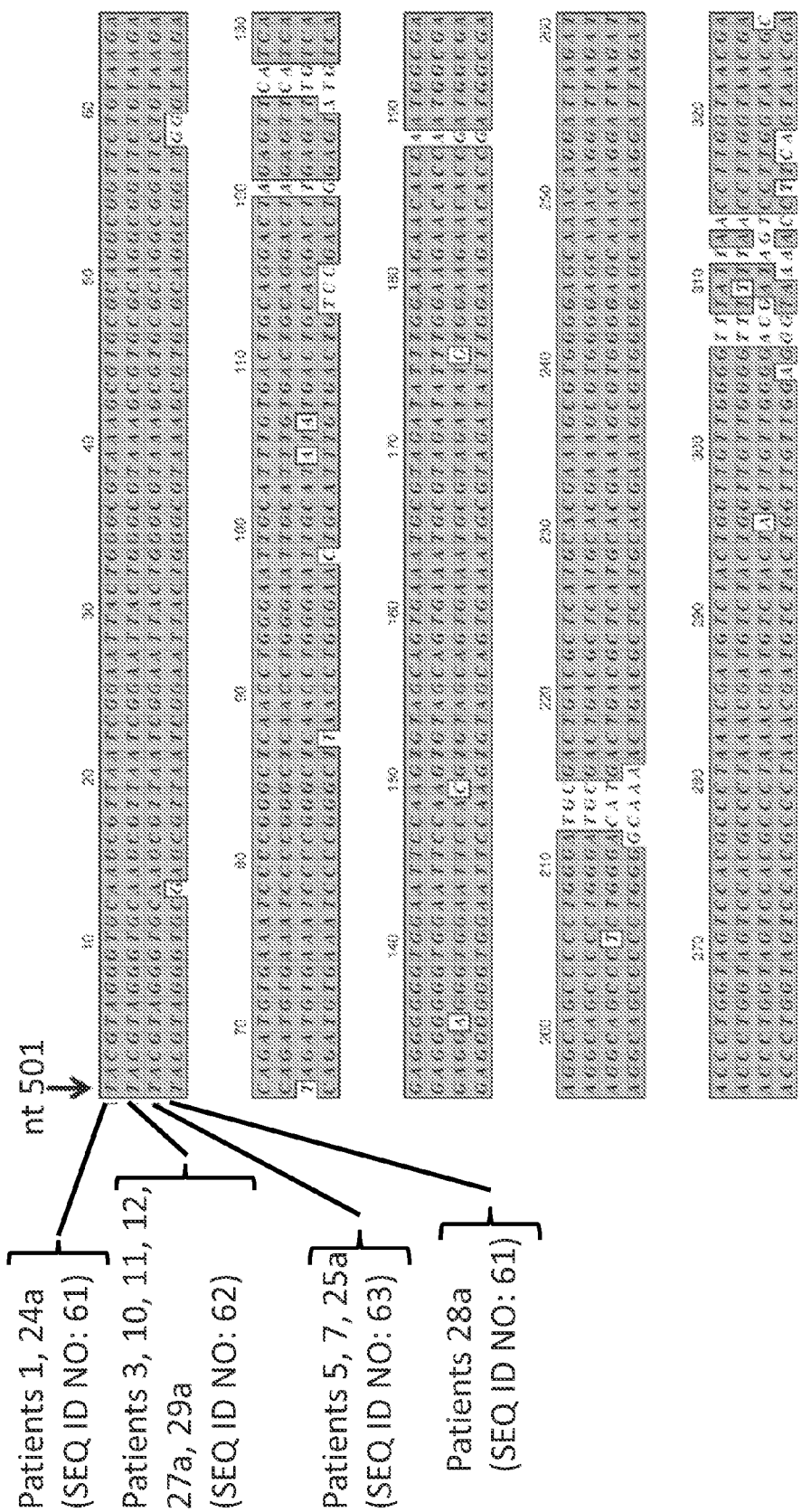

FIG. 49 shows a *Sutterella* sequence alignment. Clustal W alignment of the most abundant *Sutterella* 16S rRNA gene (C4-V8 region) sequences in the 12 *Sutterella*-positive patients. Sequences have had the 515For and SuttRev primer sequences removed. The positions of the beginning (nucleotide position 501) and end (nucleotide position 1176) of the sequences are relative to the 16S rRNA gene of S. wadsworthensis (Accession L37785). Patients 1, 24a (SEQ ID NO: 61); Patients 3, 10, 11, 12, 27a, 29a (SEQ ID NO: 62); Patients 5, 7, 25a (SEQ ID NO: 63); Patient 28a (SEQ ID NO: 64).

ABBREVIATIONS used herein: ASD, autism spectrum disorders; GI, gastrointestinal; AUT-GI, children with autistic disorder and GI disease; Control-GI, normally developing children with GI disease; FA, food allergy; MA, milk-related allergy; WA, wheat-related allergy; AD, atopic disease; SI, sucrase isomaltase; MGAM, maltase glucoamylase; LCT, lactase; SGLT1, sodium-dependent glucose cotransporter; GLUT2, glucose transporter 2; CDX2, caudal type homeobox 2; OTU, operational taxonomic unit.

DETAILED DESCRIPTION OF THE INVENTION

Autism, one of the ASDs, is mostly diagnosed clinically using behavioral criteria because few specific biological markers are known for diagnosing the disease. Autism is a neuropsychiatric developmental disorder characterized by impaired verbal communication, non-verbal communication, and reciprocal social interaction. It is also characterized by restricted and stereotyped patterns of interests and activities, as well as the presence of developmental abnormalities by 3 years of age (Bailey et al., (1996) J Child Psychol Psychiatry 37(1):89-126). Autism-associated disorders, diseases or pathologies can comprise any metabolic, immune or systemic disorders; epilepsy; gastrointestinal disorders; congenital malformations or genetic syndromes; anxiety, depression, or AD/HD; or speech delay and motor in-coordination.

Autism spectrum disorders (ASD) are defined by impairments in verbal and non-verbal communication, social interactions, and repetitive and stereotyped behaviors (DSM-IV-TR criteria, American Psychiatric Association, 2000). In addition to these core deficits, previous reports indicate that the prevalence of gastrointestinal symptoms ranges widely in individuals with ASD, from 9 to 91% (Buie et al., 2010). Macroscopic and histological observations in ASD include findings of ileo-colonic lymphoid nodular hyperplasia (LNH), enterocolitis, gastritis and esophagitis (Wakefield et al., 2000; Wakefield et al., 2005; Furlano et al., 2001; Torrente et al., 2002; Horvath et al., 1999). Associated changes in intestinal inflammatory parameters include higher densities of lymphocyte populations, aberrant cytokine profiles, and deposition of immunoglobulin (IgG) and complement Clq on the basolateral enterocyte membrane (Furlano et al., 2001; Ashwood and Wakefield, 2006). Functional disturbances include increased intestinal permeability (D'Eufemia et al., 1996), compromised sulphoconjugation of phenolic compounds (O'Reilly and Waring, 1993; Alberti et al., 1999), deficient enzymatic activity of disaccharidases (Horvath et al., 1999), increased secretin-induced pancreatico-biliary secretion (Horvath et al., 1999), and abnormal Clostridia taxa (Finegold et al., 2002; Song et al., 2004; Parracho et al., 2005). Some children placed on exclusion diets or treated with the antibiotic vancomycin are reported to improve in cognitive and social function (Knivsberg et al., 2002; Sandler et al., 2000).

The gastrointestinal tract is exposed to an onslaught of foreign material in the form of food, xenobiotics, and microbes. The intestinal muco-epithelial layer must maximize nutritional uptake of dietary components while maintaining a barrier to toxins and infectious agents. Although some aspects of these functions are host-encoded, others are acquired through symbiotic relationships with microbial flora. Dietary carbohydrates enter the intestine as monosaccharides (glucose, fructose, and galactose), disaccharides (lactose, sucrose, maltose), or complex polysaccharides. Following digestion with salivary and pancreatic amylases, carbohydrates are further digested by disaccharidases expressed by absorptive enterocytes in the brush border of the small intestine and transported as monosaccharides across the intestinal epithelium. However, humans lack the glycoside hydrolases and polysaccharide lyases necessary for cleavage of glycosidic linkages present in plant cell wall polysaccharides, oligosaccharides, storage polysaccharides, and resistant starches. Intestinal bacteria encoding these enzymes expand the capacity to extract energy from dietary polysaccharides (Sonnenburg et al., 2008; Flint et al., 2008). As an end product of polysaccharide fermentation, bacteria produce short-chain fatty acids (butyrate, acetate, and propionate) that serve as energy substrates for colonocytes, modulate colonic pH, regulate colonic cell proliferation and differentiation, and contribute to hepatic gluconeogenesis and cholesterol synthesis (Wong et al., 2006; Jacobs et al., 2009). Indigenous microflora also mediate postnatal development of the muco-epithelial layer, provide resistance to potential pathogens, regulate development of intraepithelial lymphocytes and Peyer's patches, influence cytokine production and serum immunoglobulin levels, and promote systemic lymphoid organogenesis (O'Hara and Shanahan, 2006; Macpherson and Harris, 2004).

The prevalence of autism in the US is about 1 in 91 births and, largely due to changes in diagnostic practices, services, and public awareness. Autism is growing at the fastest pace of any developmental disability (10-17%) (Fombonne, E. (2003). The prevalence of autism. JAMA 289(1): 87-9). Care and treatment of autism costs the U.S. healthcare system $90B annually. Early detection and intervention can result in reducing life-long costs. In the last 5 years, federal funding for autism research rose by 16.1%. The Autism Society is currently lobbying Congress for $37 million for autism monitoring and studies, another $16.5 million for autism screening and academic research. At present, few tools outside psychiatric evaluation are available for diagnosing autism. While a causative link between GI abnormalities and pathology of autism has yet to be established, a correlation between the two disorders is relatively well established. Thus, technologies facilitating detection and treatment of abnormal gut flora in autistic patients has great potential utility for diagnosis and treatment.

The present invention provides the discovery and the identification of GLUT2 as well SGLT1 as biomarkers for human Autism Spectrum Disorders. The present invention provides for methods to use genes encoding carbohydrate metabolic enzyme molecules (such as sucrase isomaltase, maltase glucoamylase, and lactase) or carbohydrate transporter molecules, or a combination of the two, and corresponding expression products for the diagnosis, prevention and treatment of autism and autism spectrum disorders.

The methods of the invention are useful in various subjects, such as humans, including adults, children, and developing human fetuses at the prenatal stage.

The GLUT2 gene locus can comprise all GLUT2 sequences or products in a cell or organism, including GLUT2 coding sequences, GLUT2 non-coding sequences (e.g., introns), GLUT2 regulatory sequences controlling transcription and/or translation (e.g., promoter, enhancer, terminator).

A GLUT2 gene, also known as SLC2A2, encodes the glucose transporter 2 isoform. It is an integral plasma membrane glycoprotein of the liver, pancreatic islet beta cells, intestine, and kidney epithelium. GLUT2 mediates the bidirectional transport of glucose. In the context of the invention, the GLUT2 gene also encompasses its variants, analogs and fragments thereof, including alleles thereof (e.g., germline mutations) which are related to susceptibility to autism and/or autism spectrum disorders.

The SGLT1 gene locus can comprise all SGLT1 sequences or products in a cell or organism, including SGLT1 coding sequences, SGLT1 non-coding sequences (e.g., introns), SGLT1 regulatory sequences controlling transcription and/or translation (e.g., promoter, enhancer, terminator).

A SGLT1 gene, also known as SLC5A1, encodes the sodium/glucose co-transporter 1. The sodium dependent glucose transporter is an integral plasma membrane glycoprotein of the intestine. SGLT1 mediates glucose and galactose uptake from the intestinal lumen. Mutations in this gene have been associated with glucose-galactose malabsorption. In the context of the invention, the SGLT1 gene also encompasses its variants, analogs and fragments thereof, including alleles thereof (e.g., germline mutations) which are related to susceptibility to autism and/or autism spectrum disorders.

As used herein, "carbohydrate transport activity" means the ability of a polypeptide to bind a carbohydrate, such as glucose, to a transporter protein, and subsequently facilitate uptake of the carbohydrate from the serum or extracellular millieu into a cell (e.g., a liver cell, or pancreatic n-cell). Glucose transport activity can be measured as described by Hissin et al., 1982, *J Clin. Invest.* 70(4): 780-90. In one embodiment, the carbohydrate transport activity is glucose transport activity, and the activity can be measured by determining glucose transport activity as described in Hissin as well as the ability to decrease extracellular or serum glucose levels. Non-limiting examples of a carbohydrate transporter include GLUT 1, GLUT2, GLUT3, GLUT4, GLUT5, GLUT6, GLUT7, GLUT8, GLUT9, GLUT10, GLUT11, GLUT12, and HMIT (see Scheepers et al., JPEN J Parenter Enteral Nutr. 2004 September-Octtober; 28(5):364-71).

A sucrase isomaltase (SI) gene encodes a sucrase-isomaltase protein, which is a glucosidase enzyme, that is expressed in the intestinal brush border. The encoded protein is synthesized as a precursor protein that is cleaved by pancreatic proteases into two enzymatic subunits, sucrase and isomaltase. The two subunits heterodimerize to form the sucrose-isomaltase complex, which is essential for the digestion of dietary carbohydrates including starch, sucrose and isomaltose. Mutations in this gene are the cause of congenital sucrase-isomaltase deficiency. In the context of the invention, the SI gene also encompasses its variants, analogs and fragments thereof, including alleles thereof (e.g., germline mutations) which are related to susceptibility to autism and/or autism spectrum disorders.

A maltase glucoamylase (MGAM) gene encodes a maltase-glucoamylase enzyme. It is localized to the brush border membrane and plays a role in the final steps of digestion of starch. The protein has two catalytic sites identical to those of sucrase-isomaltase, but the proteins are only 59% homologous. Both are members of glycosyl hydrolase family 31, which has a variety of substrate specificities. In the context of the invention, the MGAM gene also encompasses its variants, analogs and fragments thereof, including alleles thereof (e.g., germline mutations) which are related to susceptibility to autism and/or autism spectrum disorders.

A lactase (LCT) gene encodes a glycosyl hydrolase of family 1. The protein is integral to plasma membrane and has both phlorizin hydrolase activity and lactase activity.

As used herein, "carbohydrate metabolic enzyme activity" includes "sucrase isomaltase activity", "maltase glucoamylase activity", "lactase activity", "sucrase activity", "maltase activity", "trehalase activity", "amylase activity", "cellulase activity", "glucosidase activity", "pullulanase activity", "galactosidase activity", "alpha-Mannosidase acivity", "glucuronidase activity", "hyaluronidase activity", "glycosylase activity", "fucosidase activity", "hexosaminidase activity", "iduronidase activity", or "maltase-glucoamylase activity". "Sucrase isomaltase activity" means the ability of a polypeptide to catalyze the hydrolysis of sucrose to fructose and glucose and to enzymatically digest polysaccharides at the alpha 1-6 linkages. Sucrase and isomaltase activities can be measured as described by Dahlqvist, A. (1964) Anal. Biochem. 7,18-25 and and the enzyme assays described by Goda et al., Biochem J. 1988 Feb. 15; 250(1): 41-46. "Maltase glucoamylase activity" means the ability of a polypeptide to enzymatically digest starch, releasing malstose and free glucose, as well as to catalyze the hydrolysis of the disaccharide maltose. Maltase and glucoamylase activities can be measured as described by Dahlqvist A. Specificity of the human intestinal disaccharidases and implications for hereditary disaccharide intolerance. J Clin Invest. 1962;41:463-9; Dahlqvist A. Assay of intestinal disaccharidases. Scand J Clin Lab Invest. 1984;44:169-72; and Quezada-Calvillo et al., J. Nutr. 137:1725-1733, July 2007. "Lactase activity" means the ability of a polypeptide to hydrolyze lactose to galactose and glucose. Lactase activity can be measured as described by Dahlqvist A. Specificity of the human intestinal disaccharidases and implications for hereditary disaccharide intolerance. J Clin Invest. 1962;41:463-9; Dahlqvist A. Assay of intestinal disaccharidases. Scand J Clin Lab Invest. 1984;44: 169-72; and Quezada-Calvillo et al., J. Nutr. 137:1725-1733, July 2007. "Trehalase activity" means the ability of a polypeptide to catalyze the conversion of the dissacharide trehalose (a-D-glucopyranosyl-1,1-α-D-glucopyranoside) to glucose.

```
SEQ ID NO: 1 is the human wild type amino acid sequence corresponding
to the GLUT2 enzyme (residues 1-524) having GenBank Accession No.
NP_000331:
    1 MTEDKVTGTL VFTVITAVLG SFQFGYDIGV INAPQQVIIS HYRHVLGVPL DDRKAINNYV
   61 INSTDELPTI SYSMNPKPTP WAEEETVAAA QLITMLWSLS VSSFAVGGMT ASFFGGWLGD
  121 TLGRIKAMLV ANILSLVGAL LMGFSKLGPS HILIIAGRSI SGLYCGLISG LVPMYIGEIA
  181 PTALRGALGT FHQLAIVTGI LISQIIGLEF ILGNYDLWHI LLGLSGVRAI LQSLLLFFCP
  241 ESPRYLYIKL DEEVKAKQSL KRLRGYDDVT KDINEMRKER EEASSEQKVS IIQLFTNSSY
  301 RQPILVALML HVAQQFSGIN GIFYYSTSIF QTAGISKPVY ATIGVGAVNM VFTAVSVFLV
  361 EKAGRRSLFL IGMSGMFVCA IFMSVGLVLL NKFSWMSYVS MIAIPLFVSF FEIGPGPIPW
  421 FMVAEFFSQG PRPAALAIAA FSNWTCNFIV ALCFQYIADF CGPYVFFLFA GVLLAFTLFT
  481 FFKVPETKGK SFEEIAAEFQ KKSGSAHRPK AAVEMKFLGA TETV SEQ ID NO: 2 is the human wild type nucleic acid sequence corresponding
to the GLUT2 enzyme (bps 1-3439) having GenBank Accession No. NM_000340:
    1 tctggtttgt aacttatgcc taagggacct gctcccattt tctttcctag tggaacaaag
   61 gtattgaagc cacaggttgc tgaggcaaag cacttattga ttagattccc atcaatattc
  121 agctgccgct gagaagatta gacttggact ctcaggtctg ggtagcccaa ctcctccctc
  181 tccttgctcc tcctcctgca atgcataact aggcctaggc agagctgcga ataaacaggc
  241 aggagctagt caggtgcatg tgccacactc acacaagacc tggaattgac aggactccca
  301 actagtacaa tgacagaaga taaggtcact gggaccctgg ttttcactgt catcactgct
  361 gtgctgggtt ccttccagtt tggatatgac attggtgtga tcaatgcacc tcaacaggta
  421 ataatatctc actatagaca tgtttgggt gttccactgg atgaccgaaa agctatcaac
  481 aactatgtta tcaacagtac agatgaactg cccacaatct catactcaat gaacccaaaa
  541 ccaaccccctt gggctgagga agagactgtg gcagctgctc aactaatcac catgctctgg
  601 tccctgtctg tatccagctt tgcagttggt ggaatgactg catcattctt tggtgggtgg
  661 cttggggaca cacttggaag aatcaaagcc atgttagtag caaacattct gtcattagtt
  721 ggagctctct tgatggggtt ttcaaaattg ggaccatctc atatacttat aattgctgga
  781 agaagcatat caggactata ttgtgggcta atttcaggcc tggttcctat gtatatcggt
  841 gaaattgctc caaccgctct caggggagca cttggcactt ttcatcagct ggccatcgtc
  901 acgggcattc ttattagtca gattattggt cttgaattta tcttgggcaa ttatgatctg
  961 tggcacatcc tgcttggcct gtctggtgtg cgagccatcc ttcagtctct gctactcttt
 1021 ttctgtccag aaagccccag atacctttac atcaagttag atgaggaagt caaagcaaaa
 1081 caaagcttga aaagactcag aggatatgat gatgtcacca aagatattaa tgaaatgaga
 1141 aagaaagag aagaagcatc gagtgagcag aaagtctcta taattcagct cttcaccaat
 1201 tccagctacc gacagcctat tctagtggca ctgatgctgc atgtggctca gcaatttttcc
```

-continued

```
1261 ggaatcaatg gcattttta ctactcaacc agcattttc agacggctgg tatcagcaaa
1321 cctgtttatg caaccattgg agttggcgct gtaaacatgg ttttcactgc tgtctctgta
1381 ttccttgtgg agaaggcagg gcgacgttct ctctttctaa ttggaatgag tgggatgttt
1441 gtttgtgcca tcttcatgtc agtgggactt gtgctgctga ataagttctc ttggatgagt
1501 tatgtgagca tgatagccat cttcctcttt gtcagcttct ttgaaattgg gccaggcccg
1561 atcccctggt tcatggtggc tgagtttttc agtcaaggac cacgtcctgc tgctttagca
1621 atagctgcat tcagcaattg gacctgcaat tcattgtag ctctgtgttt ccagtacatt
1681 gcggacttct gtggaccta tgtgtttttc ctctttgctg gagtgctcct ggcctttacc
1741 ctgttcacat tttttaaagt tccagaaacc aaaggaaagt cttttgagga aattgctgca
1801 gaattccaaa agaagagtgg ctcagcccac aggccaaaag ctgctgtaga aatgaaattc
1861 ctaggagcta cagagactgt gtaaaaaaaa aaccctgctt tttgacatga acagaaacaa
1921 taagggaacc gtctgttttt aaatgatgat tccttgagca ttttatatcc acatctttaa
1981 gtattgtttt atttttatgt gctctcatca gaaatgtcat caaatattac caaaaaagta
2041 tttttttaag ttagagaata tatttttgat ggtaagactg taattaagta aaccaaaaag
2101 gctagtttat tttgttacac taaagggcag gtggttctaa tattttttagc tctgttcttt
2161 ataacaaggt tcttctaaaa ttgaagagat tcaacatat cattttttta acacataact
2221 agaaacctga ggatgcaaca aatatttata tatttgaata tcattaaatt ggaattttct
2281 tacccatata tctttatgtta aaggagatat ggctagtgta aataagttcc atgttaaaat
2341 agacaactct tccatttatt gcactcagct tttttctga gtactagaat ttgtatttg
2401 cttaaatttt tacttttgtt ctgtatttc atgtggaatg gattagag tatactaaaa
2461 aatgtctata gagaaaact ttcattttg gtaggcttat caaatcttt cagcactcag
2521 aaaagaaaac cattttagtt ccttttattta atggccaaat ggttttttgca agatttaaca
2581 ctaaaaaggt ttccctgat catatagcgt gggttatcag ttaacattaa catctattat
2641 aaaaccatgt tgattccctt ctggtacaat cctttgagtt atagtttgct ttgcttttta
2701 attgaggaca gcctggtttt cacatacact caaacaatca tgagtcagac atttggtata
2761 ttacctcaaa ttcctaataa gtttgatcaa atctaatgta agaaatttg aagtaaagga
2821 ttgatcactt tgttaaaaat attttctgaa ttattatgtc tcaaaataag ttgaaaaggt
2881 agggtttgag gattcctgag tgtgggcttc tgadacttca taaatgttca gcttcagact
2941 tttatcaaaa tccctattta attttcctgg aaagactgat tgttttatgt gtgttccta
3001 acataaaata atcgtctcct ttgacatttc cttctttgtc ttagctgtat acagattcta
3061 gccaaactat tctatggcca ttactaacac gcattgtaca ctatctatct gcctttacct
3121 acataggcaa attggaaata cacagatgat taaacagact ttagcttaca gtcaattta
3181 caattatgga aatatagttc tgatgggtcc caaaagctta gcagggtgct aacgtatctc
3241 taggctgttt tctccaccaa ctggagcact gatcaatcct tcttatgttt gctttaatgt
3301 gtattgaaga aaagcacttt ttaaaaagta ctctttaaga gtgaaataat taaaaaccac
3361 tgaacatttg ctttgttttc taaagttgtt cacatatatg taatttagca gtccaaagaa
3421 caagaaattg tttctttc
```

SEQ ID NO: 3 is the human wild type amino acid sequence corresponding to the SGLT1 enzyme (residues 1-664) having GenBank Accession No. NP_000334:

```
  1 MDSSTWSPKT TAVTRPVETH ELIRNAADIS IIVIYFVVVM AVGLWAMFST NRGTVGGFFL
 61 AGRSMVWWPI GASLFASNIG SGHFVGLAGT GAASGIAIGG FEWNALVLVV VLGWLFVPIY
121 IKAGVVTMPE YLRKRFGGQR IQVYLSLLSL LLYIFTKISA DIFSGAIFIN LALGLNLYLA
181 IFLLLAITAL YTITGGLAAV IYTDTLQTVI MLVGSLILTG FAFHEVGGYD AFMEKYMKAI
241 PTIVSDGNTT FQEKCYTPRA DSFHIFRDPL TGDLPWPGFI FGMSILTLWY WCTDQVIVQR
301 CLSAKNMSHV KGGCILCGYL KLMPMFIMVM PGMISRILYT EKIACVVPSE CEKYCGTKVG
361 CTNIAYPTLV VELMPNGLRG LMLSVMLASL MSSLTSIFNS ASTLFTMDIY AKVRKRASEK
421 ELMIAGRLFI LVLIGISIAW VPIVQSAQSG QLFDYIQSIT SYLGPPIAAV FLLAIFWKRV
481 NEPGAFWGLI LGLLIGISRM ITEFAYGTGS CMEPSNCPTI ICGVHYLYFA IILFAISFIT
541 IVVISLLTKP IPDVHLYRLC WSLRNSKEER IDLDAEEENI QEGPKETIEI ETQVPEKKKG
601 IFRRAYDLFC GLEQHGAPKM TEEEEKAMKM KMTDTSEKPL WRTVLNVNGI ILVTVAVFCH
661 AYFA
```

SEQ ID NO: 4 is the human wild type nucleic acid sequence corresponding to the SGLT1 enzyme (bps 1-5061) having GenBank Accession No. NM_000343:

```
   1 ccccattcgc aggacagctc ttacctgccg ggccgccgcc ccagccaaca gctcagccgg
  61 gtgctccttc ctgggctcca cgcccgagc tgcttcctga cggtgcagcc gcaaggcatc
 121 gcaggggccc cgcgctactg ccctgctccc tcaaagtccc aggtcccctc ccctggtgct
 181 gatcattaac caggaggccg tataaggagg tagcggccgc ggcgagaggg aaggacgcaa
 241 cgctgccacc atggacagta gcacctggag ccccaagacc accgcggtca cccggcctgt
 301 tgagacccac gagctcatc gcaatgcagc cgatatctcc atcatcgtta tctacttcgt
 361 ggtagtgatg gccgtcggac tgtgggctat gttttccacc aatcgtggga ctgttggagg
 421 cttcttcctg gcaggccgaa gtatggtgtg gtggccgatt ggagcctccc tcttttgctag
 481 taacattgga agtggccact ttgtggggct ggccgggact ggggcagctt caggcatcgc
 541 cattggaggc tttgaatgga tgcccgtggt tttggtggtt gtgctgggct ggctgtttgt
 601 ccccatctat attaaggctg ggtggtgac aatgccagag tacctgagga agcggtttgg
 661 aggccagcgg attccaggtc acctttccct tctgtcctg ctgctctaca ttttcaccaa
 721 gatctcggca gacatcttct cgggggccat attcatcaat ctggcctag gcctgaatct
 781 gtatttagcc atctttctct tattggcaat cactgccctt tacacaatta caggggggcct
 841 ggcggcggtg atttacacgg acaccttgca gacggtgatc atgctggtgg ggtctttaat
 901 cctgactggg tttgcttttc acgaagtggg aggctatgac gccttcatgg aaaagtacat
 961 gaaagccatt ccaaccatag tgtctgatgg caacaccacc ttcaggaaa aatgctacac
1021 tccaagggcc gactccttcc acatcttccg agatccctc acgggagacc tcccatggcc
1081 tgggttcatc tttgggatgt ccatccttac cttgtggtac tggtgcacag atcaggtcat
1141 tgtgcagcgc tgcctctcag ccaagaatat gtctcacgtg aagggtggct gcatcctgtg
1201 tgggtatcta aagctgatgc ccatgttcat catggtgatg ccaggaatga tcagccgcat
1261 tctgtacaca gaaaaaattg cctgtgtcgt cccttcagaa tgtgagaaat attgcggtac
1321 caaggttggc tgtaccaaca tcgcctatcc aaccttagtg gtggagctca tgcccaatgg
1381 actgcgaggc ctgatgctat cagtcatgct ggcctcctc atgagctccc tgacctccat
1441 cttcaacagc gccagcaccc tcttcaccat ggacatctac gccaaggtcc gcaagagagc
```

-continued

```
1501 atctgagaaa gagctcatga ttgccggaag gttgtttatc ctggtgctga ttggcatcag
1561 catcgcctgg gtgcccattg tgcagtcagc acaaagtggg caactcttcg attacatcca
1621 gtccatcacc agttacttgg gaccacccat tgcggctgtc ttcctgcttg ctatttttctg
1681 gaagagagtc aatgagccag gagcctttttg gggactgatc ctaggacttc tgattgggat
1741 ttcacgtatg attactgagt ttgcttatgg aaccgggagC tgcatggagc ccagcaactg
1801 tcccacgatt atctgtgggg tgcactactt gtactttgcc attatcctct tcgccatttc
1861 tttcatcacc atcgtggtca tctccctcct caccaaaccc attccggatg tgcatctcta
1921 ccgtctgtgt tggagcctgc gcaacagcaa agaggagcgt attgacctgg atgcggaaga
1981 ggagaacatc caagaaggcc taaggagac cattgaaata gaaacacaag ttcctgagaa
2041 gaaaaaagga atcttcagga gagcctatga cctatttttgt gggctagagc agcacggtgc
2101 acccaagatg actgaggaag aggagaaagc catgaagatg aagtgacgg acacctctga
2161 gaagcctttg tggaggacag tgttgaacgt caatggcatc atcctggtga ccgtggctgt
2221 cttttgccat gcatattttg cctgagtcct accttttgct gtagatttac catggctgga
2281 ctcttactca ccttcctta gtctcgtcct gtggtgttga agggaaatca gccagttgta
2341 aattttgccc aggtggataa atgtgtacat gtgtaattat aggctagctg gaagaaaacc
2401 attagtttgc tgttaattta tgcatttgaa gccagtgtga tacagccatc tgtacctact
2461 ggagctgcag aagggaagtc cactcagtca catccagaaa aaggcagact aagaatcaga
2521 agccatgtga ttgatgtctg acgtgagtct gtctcaggta gattccggag gtcagtgtga
2581 tttataatcc ttgaatattg tttagaaac tttggtctcc ctggttcctg ccacttttcc
2641 tgtccgtcct cctcccattt tttttttaa aagaaagctg tttttcccct atcatatccc
2701 tcttgagttt tgcctggact ttccctctca agtgtgtcaa tcaggtaaac tgaggaatgc
2761 atggaagctg aggatggagc ttgatgggct ccctgtcctg ggtgtttgct ctctgaagtg
2821 gaggcctgag gaaggtagta cttccacaaa agggagggac ccgggcccca gcctcaagct
2881 agtgggggag gcagatagcc tgaatccagg ggattttctg ggcttcttaa aatgtccatt
2941 gtgagttccc cgtgtttggg attccactca ttttggcatt cacagtgcct ggaatgtctt
3001 agattttcag caatgcgtgt tgaataaatg aatgacatag gcattttttt ttaaatcttt
3061 gcttgctttt tacatgagcc tggcccttag ttaacctttt cttgtgcta cacaaagtat
3121 gctcactggt tactaatgac ttgggatgca tttgtcaaac tgattatatt agttttctag
3181 ggatgccata acaaagtagc acagaccaga tggctcaagc agcagacatt tatttttctca
3241 cagttctaga ggctagaagt tggaggccaa gatgtcagca gggttggttt cttctgaggc
3301 ctctctcctt ggttgcagat ggtcatatct cactctgtct tccgtggcct tccttttgtc
3361 tgtgtcctaa atctactctt ctgataagga catcagtcat attggaatag gacccaccct
3421 aatgtcttca ttttaatcac ctctttaaag cccctacctc caaatacagt cacactgtga
3481 gaaactgagg gttaggaagt cagcaagtga gtcttgaaga gatactaaac aaacccacaa
3541 cacagataaa gtatgcattt tggagatttc caagccagag tctcccgtga aaaaggtaaa
3601 cggaagcagt tattgtgcag caaaaggaaa aagaattaca aactgaacgt atgtaggtga
3661 ggcaaggcag ggtagggcag ggcctttggg taggctgatc agaggggtttt tcaacaataa
3721 atcaatggga atgcatttgt tgctcccagg accctggcac cttgactctg gtactatagc
3781 atgtcagcaa ataaagcaa agcccaacac tctgatttgc atttatgcca atctaaacta
3841 tccggtgttt agtttgattt tttgagtgca ggttcattca aggaccaggt tcccttgtgc
3901 tcagggtgaa gtagaaccag aaaacatcgt tatccattcc cagaagtttt ggaagagcct
3961 tggtagaaaa gcagaagctg ctttgaccgt gaaaatattt gactcctatc agttttttggt
4021 caggagaaga tatcccacta gaccaacctg aggagaaggc tcagagtaca gatatacccc
4081 gagcaacgtg atcaatgtcc ttgaaccttc atttttcatc tgaaaacaga gacataaatg
4141 cctggctcac agatttaaat gttatacatt gacagcattt atcagtataa catttattta
4201 aataagtagg tgctcaatag gtgttggtct tctaacttgt ctacatccca tccccattcc
4261 agggtcttca gaattgaagg agagatgttg tatcactgtt agaaggctgc tttgggacat
4321 tctgcagcag ggaggaggga ctgtcaaccc ctacaccatg accaccaagt tcctcacctt
4381 ggctgagtcc ctaaaactct ctgaacctca ggttcctcca agcataatgc agacttcaca
4441 gagctgttgt aaagattagg tgaggtcaat tgatactgct taaaaggccc ggtccgtaga
4501 aaatgcccaa taaacattac tgctttcccc ctcaccctac tgcctgaaaa aatattacac
4561 ctgtgagact gactttgaga accagtgtgg gtggggagtt gtgcatataa actatttaat
4621 gagtaccaaa cacaaaagtc aagcttgtaa aatatcaggc cttgccccag aaagacaaat
4681 accacatgat ctcactgata tgtagaatct taaaaagtca aactcagaag cagagagtag
4741 aatgatggtt atcaagggct ggggagggga gggactgggg agatgttggt caaatgatac
4801 aaaggtttag ttaggtggaa taagttcaga aaatcaattg tacaatgtat caattatagt
4861 taatagcaat ataacatata cttgaaaatt gctgagagta gtgtgagtgt tctaccacaa
4921 aaaaatatgt gcagtaatag atgttaatta ccttaattta gtcatttcac aatatgtaca
4981 tatataaaaa tatgttgtat gccatgagta tatataatta ttatttgtga atttaaaaaa
5041 taaaaataat ttccaaaaaa a
```

SEQ ID NO: 5 is the human wild type amino acid sequence corresponding to the sucrase isomaltase (SI) enzyme (residues 1-1827) having GenBank Accession No. NP_001032:

```
  1 MARKKFSGLE ISLIVLFVIV TIIAIALIVV LATKTPAVDE ISDSTSTPAT TRVTTNPSDS
 61 GKCPNVLNDP VNVRINCIPE QFPTEGICAQ RGCCWRPWND SLIPWCFFVD NHGYNVQDMT
121 TTSIGVEAKL NRIPSPTLFG NDINSVLFTT QNQTPNRFRF KITDPNNRRY EVPHQYVKEF
181 TGPTVSDTLY DVKVAQNPFS IQVIRKSNGK TLFDTSIGPL VYSDQYLQIS TRLPSDYIYG
241 IGEQVHKRFR HDLSWKTWPI FTRDQLPGDN NNLYGHQTF FMCIEDTSGK SFGVFLMNSN
301 AMEIFIQPTP IVTYRVTGGI LDFYILLGDT PEQVVQQYQQ LVGLPAMPAY WNLGFQLSRW
361 NYKSLDVVKE VVRRNREAGI PFDTQVTDID YMEDKKDFTY DQVAFNGLPQ FVQDLHDHGQ
421 KYVIILDPAI SIGRRANGTT YATYERGNTQ HVWINESDGS TPIIGEVWPG LTVYPDFTNP
481 NCIDWWANEC SIFHQEVQYD GLWIDMNEVS SFIQGSTKGC NVNKLNYPPF TPDILDKLMY
541 SKTICMDAVQ NWGKQYDVHS LYGYSMAIAT EQAVQKVFPN KRSFILTRST FAGSGRHAAH
601 WLGDNTASWE QMEWSITGML EFSLFGIPLV GADICGFVAE TTEELCRRWM QLGAFYPFSR
661 NHNSDGYEHQ DPAFFGQNSL LVKSSRQYLT IRYTLLPFLY TLFYKAHVFG ETVARPVLHE
721 FYEDTNSWIE DTEFLWGPAL LITPVLKQGA DTVSAYIPDA IWYDYESGAK RPWRKQRVDM
781 YLPADKIGLH LRGGYIIPIQ EPDVTTTASR KNPLGLIVAL GENNTAKGDF FWDDGETKDT
841 IQNGNYILYT FSVSNNTLDI VCTHSSYQEG TTLAFQTVKI LGLTDSVTEV RVAENNQPMN
901 AHSNFTYDAS NQVLLIADLK LNLGRNFSVQ WNQIFSENER FNCYPDADLA TEQKCTQRGC
961 VWRTGSSLSK APECYFPRQD NSYSVNSARY SSMGITADLQ LNTANARIKL PSDPISTLRV
```

-continued

```
1021 EVKYHKNDML QFKIYDPQKK RYEVPVPLNI PTTPISTYED RLYDVEIKEN PFGIQIRRRS
1081 SGRVIWDSWL PGFAFNDQFI QISTRLPSEY IYGFGEVEHT AFKRDLNWNT WGMFTRDQPP
1141 GYKLNSYGFH PYYMALEEEG NAHGVFLLNS NAMDVTFQPT PALTYRTVGG ILDFYMFLGP
1201 TPEVATKQYH EVIGHPVMPA YWALGFQLCR YGYANTSEVR ELYDAMVAAN IPYDVQYTDI
1261 DYMERQLDFT IGEAFQDLPQ FVDKIRGEGM RYIIILDPAI SGNETKYPA FERGQQNDVF
1321 VKWPNTNDIC WAKVWPDLPN ITIDKTLTED EAVNASRAHV AFPDFFRTST AEWWAREIVD
1381 FYNEKMKFDG LWIDMNEPSS FVNGTTTNQC RNDELNYPPY FPELTKRTDG LHFRTICMEA
1441 EQILSDGTSV LHYDVHNLYG WSQMKPTHDA LQKTTGKRGI VISRSTYPTS GRWGGHWLGD
1501 NYARWDNMDK SIIGMMEFSL FGMSYTGADI CGFFNNSEYH LCTRWMQLGA FYPYSRNHNI
1561 ANTRRQDPAS WNETFAEMSR NILNIRYTLL PYFYTQMHEI HANGGTVIRP LLHEFFDEKP
1621 TWDIFKQFLW GPAFMVTPVL EPYVQTVNAY VPNARWFDYH TGKDIGVRGQ FQTFNASYDT
1681 INLHVRGGHI LPCQEPAQNT FYSRQKHMKL IVAADDNQMA QGSLFWDDGE SIDTYERDLY
1741 LSVQFNLNQT TLTSTILKRG YINKSETRLG SLHVWGKGTT PVNAVTLTYN GNKNSLPFNE
1801 DTTNMILRID LTTHNVTLEE PIEINWS
```

SEQ ID NO: 6 is the human wild type nucleic acid sequence corresponding to the sucrase isomaltase (SI) enzyme (bps 1-6023) having GenBank Accession No. NM_001041:

```
   1 ttattttggc agccttatcc aagtctggta caacatagca aagagaacag gctatgaaat
  61 aagatggcaa gaaagaaatt tagtggattg gaaatctctc tgattgtcct ttttgtcata
 121 gttactataa tagctattgc cttaattgtt gttttagcaa ctaagacacc tgctgttgat
 181 gaaattagtg attctacttc aactccagct actactcgta tactacaaa tccttctgat
 241 tcaggaaaat gtccaaatgt gttaaatgat cctgtcaatg tgagaataaa ctgcattcca
 301 gaacaattcc aacagaggg aatttgtgca cagagaggct gctgctggag gccgtggaat
 361 gactctctta ttccttggtg cttcttcgtt gataatcatg ttataacgt tcaagacatg
 421 acaacaacaa gtattggagt tgaagccaaa ttaaacagga taccttcacc tacactattt
 481 ggaaatgaca tcaacagtgt tctcttcaca actcaaaatc agacacccaa tcgtttccgg
 541 ttcaagatta ctgatccaaa taatagaaga tatgaagttc ctcatcagta tgtaaaagag
 601 tttactggac ccacagtttc tgatacgttg tatgatgtga aggttgccca aaacccattt
 661 agcatccaag ttattaggaa aagcaacggt aaaactttgt ttgacaccag cattggtccc
 721 ttagtgtact ctgaccagta cttacagatc tcaaccgtc ttccaagtga ttatattat
 781 ggtattggag aacaagttca taagagattt cgtcatgatt tatccctgaa aacatggcca
 841 attttactc gagaccaact tcctggtgat aataataata atttatacgg ccatcaaaca
 901 ttcttttatgt gtattgaaga tacatctgga aagtcattcg gtgtttttt aatgaatagc
 961 aatgcaatgg agatttttat ccagcctact ccaatagtaa catatagagt taccggtggc
1021 attctggatt tttacatcct tctaggagat acaccagaac aagtagttca acagtatcaa
1081 cagcttgttg gactaccagc aatgccagca tattggaatc ttggattcca actaagtcgc
1141 tggaattata agtcactaga tgtagtgaaa gaagtggtaa ggagaaaccg ggaagctggc
1201 ataccatttg atacacaggt cactgatatt gactacatgg aagacaagaa agactttact
1261 tatgatcaag ttgcgtttaa cggactccct caatttgtgc aagatttgca tgaccatgga
1321 cagaaaatatg tcatcatctt ggaccctgca atttccatag tcgacgtgc caatggaaca
1381 acatatgcaa cctatgagag gggaaacaca caacatgtgt ggataaatga gtcagatgga
1441 agtacaccaa ttattggaga ggtatggcca ggattaacta taccctga tttcactaac
1501 ccaaactgca ttgattggtg ggcaaatgaa tgcagtattt tccatcaaga agtgcaatat
1561 gatggacttt ggattgacat gaatgaagtt tccagcttta ttcaaggttc aacaaaagga
1621 tgtaatgtaa acaaattgaa ttatccaccg tttactcctg atattcttga caaactcatg
1681 tattccaaaa caatttgcat ggatgctgtg cagaactggg gtaaacagta tgatgttcat
1741 agcctctatg gatacagcat ggctatagcc acagagcaag ctgtacaaaa agttttttcct
1801 aataagagaa gcttcattct taccgctca acatttgctg gatctggaag acatgctgcg
1861 cattggttag agacaatac tgcttcatgg gaacaaatgg aatggtctat aactggaatg
1921 ctggagttca gtttgttttgg aataccttttg gttggagcag acatctgtgg atttgtggct
1981 gaaccacag aagaaccttttg cagaagatgg atgcaactg gggcatttta tccattttcc
2041 agaaaccata attctgacgg atatgaacat caggatcctg catttttttgg gcagaattca
2101 cttttggtta aatcatcaag gcagtattta actattcgct acaccttatt acccttcctc
2161 tacactctgt tttataaagc ccatgtgttt ggagaaacag tagcaagacc agttcttcat
2221 gagttttatg aggatacgaa cagctggatt gaggacactg agtttttgtg gggccctgca
2281 ttacttatta ctcctgttct aaaacaggga gcagatactg tgagtgccta catccctgat
2341 gctatttggt atgattatga atctggtgca aaaaggccat ggaggaaaca acgggttgat
2401 atgtatcttc cagcagacaa aataggatta catcttagag gaggtttat catccccatt
2461 caagaaccag atgtaacaac aacagcaagc cgtaagaatc ctctaggact tatagtcgca
2521 ttaggtgaaa acaacacagc caaaggagac tttttctggg atgatggaga aactaaagat
2581 acaatacaaa atggcaacta catattatat acattttcag tttctaataa cacattagat
2641 attgtgtgca cacattcatc atatcaggaa ggaactacct tagcatttca gactgtaaaa
2701 atccttgggt tgacagacag tgttacagaa gttagagtgg cggaaaataa tcaaccaatg
2761 aacgctcatt ccaatttcac ttatgatgct tctaaccagg ttctcctaat tgcagatctc
2821 aaacttaatc ttggaagaaa ctttagtgtt caatgaaatc aaattttctc agaaaatgaa
2881 agatttaatt gttatccaga tgcagatttg gcaactgaac aaaagtgcac acaacgtggc
2941 tgtgtatgga aacgggttc ttctctatcc aaagcacctg agtgttactt tcccagacaa
3001 gataactctt attcagtcaa ctcagctcgc tattcatcca tgggtataac agctgacctc
3061 caactaaaata ctgcaaatgc cagaataaag ttaccttctg accccatctc aactcttcgt
3121 gtggaggtga atatcacaa aaatgatatg ttgcagtttaa agattatga tccccaaaag
3181 aagagatatg aagtaccagt accgttaaac attccaacca ccccaataag tacttatgaa
3241 gacagactttt atgatgtgga aatcaaggaa aatccttttg gcatccagat tcgacgagga
3301 agcagtggaa gagtcattttg ggattcttgg ctgcctggat ttgcttttaa tgaccagttc
3361 attcaaatat cgactcgcct gccatcagaa tatatatatg gtttggggga agtggaacat
3421 acagcatttta agcgagatct gaactggaat gttgggggaa tgttcacaag agaccaaccc
3481 cctggttaca aacttaattc ctatgcattt catccccatt acatgactct ggaagaggag
3541 ggcaatgctc atggtgtttt cttactcaac agcaatgcaa tggatgttac attccagcca
3601 actcctgctc taacttaccg tacagttgga gggatcttgg atttttat gtttttgggc
3661 ccaactccag aagttgcaac aaagcaatac catgaagtaa ttggccatcc agtcatgcca
3721 gcttattggg ctttgggatt ccaattgtgt cgttatggat atgcaaaatac ttcagaggtt
```

-continued

```
3781 cgggaattat atgacgctat ggtggctgct aacatcccct atgatgttca gtacacagac
3841 attgactaca tggaaaggca gctagacttt acaattggtg aagcattcca ggaccttcct
3901 cagtttgttg acaaaataag aggagaagga atgagataca ttattatcct ggatccagca
3961 atttcaggaa atgaaacaaa gacttaccct gcatttgaaa gaggacagca gaatgatgtc
4021 tttgtcaaat ggccaaacac caatgacatt tgttgggcaa aggtttggcc agatttgccc
4081 aacataacaa tagataaaac tctaacggaa gatgaagctg ttaatgcttc cagagctcat
4141 gtagctttcc cagatttctt caggacttcc acagcagagt ggtgggccag agaaattgtg
4201 gacttttaca tgaaaagat gaagtttgat ggtttgtgga ttgatatgaa tgagccatca
4261 agttttgtaa atggaacaac tactaatcaa tgcagaaatg acgaactaaa ttatccacct
4321 tatttcccag aactcacaaa aagaactgat ggattacatt tcagaacaat ttgcatggaa
4381 gctgagcaga ttcttagtga tggaacatca gttttgcatt acgatgttca caatctctat
4441 ggatggtcac agatgaaacc tactcatgat gcattgcaga agacaactgg aaaaagaggg
4501 attgtaattt ctcgttccac gtatcctact agtggacgat ggggaggaca ctggcttgga
4561 gacaactatg cacgatggga caacatggac aaatcaatca ttggtatgat ggaatttagt
4621 ctgtttggaa tgtcatatac tggagcagca atctgtggtt ttttcaacaa ctcagaatat
4681 catctctgta cccgctggat gcaacttgga gcattttatc catactcaag gaatcacaac
4741 attgcaaata ctagaagaca agatcccgct tcctgaatg aaacttttgc tgaaatgtca
4801 aggaatattc taaatattag atacacctta ttgccctatt tttacacaca aatgcatgaa
4861 attcatgcta atggtggcac tgttatccga ccccttttgc atgagttctt tgatgaaaaa
4921 ccaacctggg atatattcaa gcagttctta tggggtccag catttatggt taccccagta
4981 ctggaacctt atgttcaaac tgtaaatgcc tacgtcccca atgctcggtg gtttgactac
5041 catacaggca aagatattgg cgtcagagga caatttcaaa catttaatgc ttcttatgac
5101 acaataaacc tacatgtccg tggtggtcac atcctaccat gtcaagagc agctcaaaac
5161 acattttaca gtcgacaaaa acacatgaag ctcattgttg ctgcagatga taatcagatg
5221 gcacagggtt ctctgttttg ggatgatgga gagagtatag acacctatga agagaccta
5281 tatttatctg tacaatttaa tttaaaccag accaccttaa caagcactat attgaagaga
5341 ggttacataa ataaaagtga aacgaggctt ggatccttc atgtatgggg gaaaggaact
5401 actcctgtca atgcagttac tctaacgtat aacggaaata aaaattcgct tccttttaat
5461 gaagacacta ccaacatgat attacgtatt gatctgacca cacacaatgt tactctagaa
5521 gaaccaatag aaatcaactg gtcatgaaga tcaccatcaa ttttagttgt caatgggaaa
5581 aaacaccagg atttaagttt cacagcactt acaattttcc ctcttcactt ggttcttgta
5641 ctctacaaaa tatagctttc ataacatcga aaagttattt tgtagcgtac atcaatgata
5701 atgctaattt tattatagta atgtgacttg gattcaattt taaggcatat ttaacaaaat
5761 ttgaatagcc ctatttatcc ttgttaagta tcagctacaa ttgtaaacta gttactaaac
5821 atgtatgtaa atagctaaga tataatttaa acgtgatttt taaattaaat aaaatttta
5881 tgtaattata tatactatat ttttctcaat gtttagcaga tttaagatat gtaacaacaa
5941 ttatttgaag atttaattac ttccttagtat gtgcatttaa ttagaaaaag agaataaaaa
6001 atgtaagtgt aaaaaaaaaa aaa
```

SEQ ID NO: 7 is the human wild type amino acid sequence corresponding to
the maltase glucoamylase (MGAM) enzyme (residues 1-1857) having GenBank
Accession No. NP_004659:

```
    1 MARKKLKKFT TLEIVLSVLL LVLFIISIVL IVLLAKESLK STAPDPGTTG TPDPGTTGTP
   61 DPGTTGTTHA RTTGPPDPGT TGTTPVSAEC PVVNELERIN CIPDQPPTKA TCDQRGCCWN
  121 PQGAVSVPWC YYSKNHSYHV EGNLVNTNAG FTARLKNLPS SPVFGSNVDN VLLTAEYQTS
  181 NRFHFKLTDQ TNNRFEVPHE HVQSFSGNAA ASLTYQVEIS RQPFSIKVTR RSNNRVLFDS
  241 SIGPLLFADQ FLQLSTRLPS TNVYGLGEHV HQQYRHDMNW KTWPIFNRDT TPNGNGTNLY
  301 GAQTFFLCLE DASGLSFGVF LMNSNAMEVV LQPAPAITYR TIGGILDFYV FLGNTPEQVV
  361 QEYLELIGRP ALPSYWALGF HLSRYEYGTL DNMREVVERN RAAQLPYDVQ HADIDYMDER
  421 RDFTYDSVDF KGFPEFVNEL HNNGQKLVII VDPAISNNSS SSKPYGPYDR GSDMKIWVNS
  481 SDGVTPLIGE VWPGQTVFPD YTNPNCAVWW TKEFELPHNQ VEFDGIWIDM NEVSNFVDGS
  541 VSGCSTNNLN NPPFTPRILD GYLFCKTLCM DAVQHWGKQY DIHNLYGYSM AVATAEAAKT
  601 VFPNKRSFIL TRSTFAGSGK FAAHWLGDNT ATWDDLRWSI PGVLEFNLFG IPMVGPDICG
  661 FALDTPEELC RRWMQLGAFY PFSRNHNGQG YKDQDPASFG ADSLLLNSSR HYLNIRYTLL
  721 PYLYTLFFRA HSRGDTVARP LLHEFYEDNS TWDVHQQFLW GPGLLITPVL DEGAEKVMAY
  781 VPDAVWYDYE TGSQVRWRKQ KVEMELPGDK IGLHLRGGYI FPTQQPNTTT LASRKNPLGL
  841 IIALDENKEA KGELFWDNGE TKDTVANKVY LLCEFSVTQN RLEVNISQST YKDPNNLAFN
  901 EIKILGTEEP SNVTVKHNGV PSQTSPTVTY DSNLKVAIIT DIDLLLGEAY TVEWSIKIRD
  961 EEKIDCYPDE NGASAENCTA RGCIWEASNS SGVPFCYFVN DLYSVSDVQY NSHGATADIS
 1021 LKSSVYANAF PSTPVNPLRL DVTYHKNEML QFKIYDPNKN RYEVPVPLNI PSMPSSTPEG
 1081 QLYDVLIKKN PFGIEIRRKS TGTIIWDSQL LGFTFSDMFI RISTRLPSKY LYGFGETEHR
 1141 SYRRDLEWHT WGMFSRDQPP GYKKNSYGVH PYYMGLEEDG SAHGVLLLNS NAMDVTFQPL
 1201 PALTYRTTGG VLDFYVFLGP TPELVTQQYT ELIGRPVMVP YWSLGFQLCR YGYQNDSEIA
 1261 SLYDEMVAAQ IPYDVQYSDI DYMERQLDFT LSPKFAGFPA LINRMKADGM RVILILDPAI
 1321 SGNETQPYPA FTRGVEDDVF IKYPNDGDIV WGKVWPDFPD VVVNGSLDWD SQVELYRAYV
 1381 AFPDFFRNST AKWWKREIEE LYNNPQNPER SLKFDGMWID MNEPSSFVNG AVSPGCRDAS
 1441 LNHPPYMPHL ESRDRGLSSK TLCMESQQIL PDGSLVQHYN VHNLYGWSQT RPTYEAVQEV
 1501 TGQRGVVITR STFPSSGRWA GHWLGDNTAA WDQLKKSIIG MMEFSLFGIS YTGADICGFF
 1561 QDAEYEMCVR WMQLGAFYPF SRNHNTJGTR RQDPVSWDVA FVNISRTVLQ TRYTLLPYLY
 1621 TLMHKAHTEG VTVVRPLLHE FVSDQVTWDI DSQFLLGPAF LVSPVLERNA RNVTAYFPRA
 1681 RWYDYYTGVD INARGEWKTL PAPLDHINLH VRGGYILPWQ EPALNTHLSR QKFMGFKIAL
 1741 DDEGTAGGWL FWDDQSIDT YGKGLYYLAS FSASQNTMQS HIIFNNYITG TNPLKLGYIE
 1801 IWGVGSVPVT SVSISVSGMV ITPSFNNDPT TQVLSIDVTD RNISLHNFTS LTWISTL
```

SEQ ID NO: 8 is the human wild type nucleic acid sequence corresponding
to the maltase glucoamylase (MGAM) enzyme (bps 1-6513) having GenBank
Accession No. NM_004668:

```
    1 attgctaagc catccttcag acagagaggg agcggctgca agaggtaatg agagatggca
   61 agaaagaagc tgaaaaaatt tactactttg gagattgtgc tcagtgttct tctgcttgtg
  121 ttgtttatca tcagtattgt tctaattgtg cttttagcca aagagtcact gaaatcaaca
  181 gccccagatc ctgggacaac tgggaccccca gatcctggga caactggtac cccagatcct
```

-continued

```
 241 ggaacaactg gtaccacaca tgctaggaca acgggtcccc cagatcctgg aacaactggt
 301 accactcctg tttctgctga atgtccagtg gtaaatgaat tggaacgaat taattgcatc
 361 cctgaccagc cgccaacaaa ggccacatgt gaccaacgtg gctgttgctg aatccccag
 421 ggagctgtaa gtgttcctg gtgctactat tccaagaatc atagctacca tgtagagggc
 481 aaccttgtca acacaaatgc aggattcaca gcccggttga aaaatctgcc ttcttcacca
 541 gtgtttggaa gcaatgttga caatgttctt ctcacagcag aatatcagac atctaatcgt
 601 ttccacttta agttgactga ccaaaccaat aacaggtttg aagtgcccca cgaacacgtg
 661 cagtccttca gtggaaatgc tgctgcttct ttgacctacc aagttgaaat ctccagacag
 721 ccatttagca tcaaagtgac cagaagaagc aacaatcgtg ttttgtttga ctcgagcatt
 781 gggcccctac tgtttgctga ccagttcttg cagctctcca ctcgactgcc tagcactaac
 841 gtgtatggcc tgggagagca tgtgcaccag cagtatcggc atgatatgaa ttggaagacc
 901 tggcccatat taacagaga cacaactccc aatggaaacg gaactaattt gtatggtgcg
 961 cagacattct tcttgtgcct tgaagatgct agtggattgt cctttggggt gtttctgatg
1021 aacagcaatg ccatggaggt tgtccttcag cctgcgccag ccatcactta ccgcaccatt
1081 gggggcattc tcgacttcta tgtgttcttg ggaaacactc cagagcaagt tgttcaagaa
1141 tatctagagc tcattgggcg gccagccctt ccctcctact gggcgcttgg atttcacctc
1201 agtcgttacg aatatggaac cttagacaac atgagggaag tcgtggagag aaatcgcgca
1261 gcacagctcc cttatgatgt tcagcatgct gatattgatt atatgatga gagaagggac
1321 ttcacttatg attcagtgga ttttaaaggc ttccctgaat tgtcaacga gttacacaat
1381 aatggacaga agcttgtcat cattgtggat ccagccatct ccaacaactc ttcctcaagt
1441 aaaccctatg cccatatga caggggttca gatatgaaga tatggtgaa tagttcagat
1501 ggagtgactc cactcattgg ggaggtctgg cctggacaaa ctgtgttcc tgattatacc
1561 aatcccaact gtgctgtttg gtggacaaag gaatttgagc ttttcacaa tcaagtagag
1621 tttgatggaa tctgattga tatgaatgaa gtctccaact ttgttgatgg ttcggtctca
1681 ggatgttcca caaacaacct aaataatccc ccattcactc ccagaatcct ggatgggtac
1741 ctgttctgca agactctctg tatggatgca gtgcagcact gggggcaagca gtatgacatt
1801 cacaatctgt atggctactc catggcggtc gccacagcag aagctgccaa gactgtgttc
1861 cctaataaga gaagcttcat tctgacccgt tctacccttg cgggctctgg caagtttgca
1921 gcacattggt taggagacaa cactgccacc tgggatgacc tgagatggtc catccctggc
1981 gtgcttgagt tcaacctttt tggcatccca atggtgggtc ctgacatatg tggctttgct
2041 ttggacaccc ctgaggagct ctgtaggcgg tggatgcagt tgggtgcatt ttatccgttt
2101 tctagaaatc acaatggcca aggctacaag gaccaggatc ctgcctcctt tggagctgac
2161 tccctgctgt tgaattcctc caggcactac cttaacatcc gctatactct attgccctac
2221 ctatacaccc tcttcttccg tgctcacagc cgaggggaca cggtggccag gccccttttg
2281 catgagttct acgaggacaa cagcacttgg gatgtgccac aacagttctt atggggggcc
2341 ggcctcctca tcactccagt tctggatgaa ggtgcagaga agtgatggc atatgtgcct
2401 gatgctgtct ggtatgacta cgagactggg agccaagtga gatggaggaa gcaaaaagtc
2461 gagatggaac ttcctggaga caaaattgga cttcaccttc gaggaggcta catcttcccc
2521 acacagcagc caaatacaac cactctggcc agtcgaaaga accctcttgg tcttatcatt
2581 gccctagatg agaacaaaga agcaaaagga gaacttttct gggataatgg ggaaacgaag
2641 gatactgtgg ccaataaagt gtatcttta tgtgagtttt ctgtcactca aaaccgcttg
2701 gaggtgaata tttcacaatc aacctacaag gaccccaata atttagcatt taatgagatt
2761 aaaattcttg ggacggagga acctagcaat gttacagtga aacacaatgg tgtcccaagt
2821 cagacttctc ctacagtcac ttatgattct aacctgaagg ttgccattat cacagatatt
2881 gatcttctcc tgggagaagc atacacagtg gaatgagca taagataag ggatgaagaa
2941 aaaatagact gttaccctga tgagaatggt gcttctgccg aaaactgcac tgcccgtggc
3001 tgtatctggg aggcatccaa ttccttctgga gtcccttttt gctattttgt caacgaccta
3061 tactctgtca gtgatgttca gtataattcc catggggcca cagctgacat ctccttaaag
3121 tcttccgttt atgccaatgc cttcccctcc acacccgtga accccttcg cctggatgtc
3181 acttaccata agaatgaaat gctgcagttc aagatttatg atcccaacaa gaatcggtat
3241 gaagttccag tccctctgaa cataccccagc atgccatcca gcaccccctga gggtcaactc
3301 tatgatgtgc tcattaagaa gaatccattt gggattgaaa ttcgccggaa gagtacaggc
3361 actataattt gggactctca gctccttggc tttaccttca gtgacatgtt tatccgcatc
3421 tccacccgcc ttccctccaa gtacctctat ggctttgggg aaactgagca caggtcctat
3481 aggagagact tggagtggca cacttggggg atgttctccc gagaccagcc ccagggtac
3541 aagaagaatt cctatggtgt ccacccctac tacatgggc tggaggagga cggcagtgcc
3601 catggagtgc tcctgctgaa cagcaatgcc atggatgtga cgttccagcc cctgcctgcc
3661 ttgacatacc gcaccacagg gggagttctg gacttttatg tgttcttggg gccgactcca
3721 gagcttgtca cccagcgtga cactgagttg attggccggc ctgtgatggt accttactgg
3781 tcttttgggt tccagctgta tcgctatgcc taccagaatg actctgagat cgccagcttg
3841 tatgatgaga tggtggctgc ccagatccct tatgatgtgc agtactcaga catcgactac
3901 atggagcggc agctggactt caccctcagc cccaagtttg ctgggttttcc agctctgatc
3961 aatcgcatga aggctgatgg gatgcgggtc atcctcattc tggatccagc catttctggc
4021 aatgagacac agccttatcc tgccttcact cggggcgttgg aggatgacgt cttcatcaaa
4081 tacccaaatg atggagacat tgtctgggga aaggtctggc ctgattttcc tgatgttgtt
4141 gtgaatgggt ctctagactg gacagccaa gtggagcat atcgagctta tgtggccttc
4201 ccagactttt tccgtaattc aactgccaag tggtggaaga gggaaatagaa gaactatac
4261 aacaatccac agaatccaga gaggagcttg aagtttgatg gcatgtgaat tgatatgaat
4321 gaaccatcaa gcttcgtgaa tggggcagtt tctccaggct gcagggacgc ctctctgaac
4381 caccctccct acatgccaca tttggagtcc agggacaggg gcctgagcag caagaccctt
4441 tgtatggaga gtcagcagat cctcccagac ggctcctggt gcagcacta caacgtgcac
4501 aacctgtatg gtggtccca gaccagaccc acatacgaag ccgtgcagga ggtgacggga
4561 cagcgagggg tcgtcatcac ccgctccaca tttccctctt ctggccgctg ggcaggacat
4621 tggctgggag acaacacggc cgcatgggat cagctgaaga agtctatcat tggcatgatg
4681 gagttcagcc tcttcggcat atcctatacg ggagcagata tctgtgggtt ctttcaagat
4741 gctgaatatg agatgtgtgt tcgctggatg ctggggggg cctttttaccc ctttctcaaga
4801 aaccacaaca ccattgggac caggagacaa gaccccgtgt cctgggatgt tgcttttgtg
4861 aatatttcca gaactgtcct gcagaccaga tacaccctgt tgccatatct gtatcccttg
4921 atgcataagg cccacacgga gggcgtcact gttgtgcggc ctctgctcca tgagtttgtg
4981 tcagaccagg tgacatggga catagacagt cagttcctgc tgggccacgc cttcctggtc
5041 agccctgtcc tggagcgtaa tgccagaaat gtcactgcat atttccctag agcccgctgg
```

```
5101 tatgattact acacgggtgt ggatattaat gcaagaggag agtggaagac cttgccagcc
5161 cctcttgacc acattaatct tcatgtccgt gggggctaca tcctgccctg gcaagagcct
5221 gcactgaaca cccacttaag ccgccagaaa ttcatgggct tcaaaattgc cttggatgat
5281 gaaggaactg ctgggggctg gctcttctgg gatgatgggc aaagcattga tacctatggg
5341 aaaggactct attacttggc cagcttttct gccagccaga atacgatgca aagccatata
5401 attttcaaca attacatcac tggtacaaat cctttgaaac tgggctacat tgaaatctgg
5461 ggagtgggca gtgtccccgt taccagtgtc agcatctctg tgagtggcat ggtcataaca
5521 ccctccttca acaatgaccc cacgacacag gtattaagca tcgatgtgac tgacagaaac
5581 atcagcctac ataatttac ttcattgacg tggataagca ctctgtgaat ttttacagca
5641 agattctaac taactatgaa tgactttgaa actacttata cttcatactc ataaaaatta
5701 ttgtgtgttg ctaatttgtt cataccact attggtgaaa tatttctgtt aattttgtta
5761 tatgttttt gtgtgaaccc taaaggttaa accttagccc tgtgggatag gcagttaggg
5821 aggtgtggaa aatctatgca ttaccttaat gtctctgtgt ggttagtatg gtagtgactg
5881 ttcatcatat gacatttact gaagatgaac tgggtccatg atgaagtgtg tgtatgtcca
5941 cgtttgtaat catagaatgg acccccattct tttgttaaat acacaagaga aagctttctg
6001 tgacagttcc aggtcttgaa gctaatcagc atctcaagaa agtatcccaga aagaacatct
6061 gctagttggt tataggcggt gggaggaata atatacctaa ttggttatag gtgggggggag
6121 catgataagc aaagaaaagg caaacacaag gaaagatcag atgaaacaga agatgatagt
6181 aaaagtgatc ctaagtaaga acataatgta aaattgtcag cagcctcatg ggaggaaaa
6241 aggaagagtc aactcacttg aagaagaggg tcttgagaaa tccttagcat aaagggctac
6301 tggtgagatt gagatctgag caggcaaagc tcaaaagaga gttttggaggt taaaaataat
6361 ttattttgc agtagtgtgc tttgaaatgt gtaaatctta tttctaatgt atacaaccac
6421 atttcacata aaaatatgca atttatatgc cagataaaaa taaaacaagt gaatttgcaa
6481 gtgaaaaaaa aaaaaaaaaa aaaaaaaaaa aaa
```

SEQ ID NO: 9 is the human wild type amino acid sequence corresponding to the lactase (LCT) enzyme (residues 1-1927) having GenBank Accession No. NP_002290:

```
   1 MELSWHVVFI ALLSFSCWGS DWESDRNFIS TAGPLTNDLL HNLSGLLGDQ SSNFVAGDKD
  61 MYVCHQPLPT FLPEYFSSLH ASQITHYKVF LSWAQLLPAG STQNPDEKTV QCYRLLKAL
 121 KTARLQPMVI LHHQTLPAST LRRTEAFADL FADYATFAFH SFGDLVGIWF TFSDLEEVIK
 181 ELPHQESRAS QLQTLSDAHR KAYEIYHESY AFQGGKLSVV LRAEDIPELL LEPPISALAQ
 241 DTVDFLSLDL SYECQNEASL RQKLSKLQTI EPKVKVFIFN LKLPDCPSTM KNPASLLFSL
 301 FEAINKDQVL TIGFDINEFL SCSSSSKKSM SCSLTGSLAL QPDQQQDHET TDSSPASAYQ
 361 RIWEAFANQS RAERDAFLQD TFPEGFLWGA STGAFNVEGG WAEGGRGVSI WDPRRPLNTT
 421 EGQATLEVAS DSYHKVASDV ALLCGLRAQV YKFSISWSRI FPMGHGSSPS LPGVAYYNKL
 481 IDRLQDAGIE PMATLFHWDL PQALQDHGGW QNESVVDAFL DYAAFCFSTF GDRVKLWVTF
 541 HEPWVMSYAG YGTGQHPPGI SDPGVASFKV AHLVLKAHAR TWHHYNSHHR PQQQGHVGIV
 601 LNSDWAEPLS PERPEDLRAS ERFLHFMLGW FAHPVFVDGD YPATLRTQIQ QMNRQCSHPV
 661 AQLPEFTEAE KQLLKGSADF LGLSHYTSRL ISNAPQNTCI PSYDTIGGFS QHVNHVWPQT
 721 SSSWIRVVPW GIRRLLQFVS LEYTRGKVPI YLAGNGMPIG ESENLFDDSL RVDYFNQYIN
 781 EVLKAIKEDS VDVRSYIARS LIDGFEGPSG YSQRFGLHHV NFSDSSKSRT PRKSAYFFTS
 841 IIEKNGFLTK GAKRLLPPNT VNLPSKVRAF TFPSEVPSKA KVVWEKFSSQ PKFERDLFYH
 901 GTFRDDFLWG VSSSAYQIEG AWDADGKGPS IWDNFTHPG SNVKDNATGD IACDSYHQLD
 961 ADLNMLRALK VKAYRFSISW SRIFPTGRNS SINSHGVDYY NRLINGLVAS NIFPMVTLFH
1021 WDLPQALQDI GGWENPALID LFDSYADFCF QTFGDRVKFW MTFNEPMYLA WLGYGSGEFP
1081 PGVKDPGWAP YRIAHAVIKA HARVYHTYDE KYRQEQKGVI SLSLSTHWAE PKSPGVPRDV
1141 EAADRMLQFS LGWFAHPIFR NGDYPDTMKW KVGNRSELQH LATSRLPSFT EEEKRFIRAT
1201 ADVFCLNTYY SRIVQHKTPR LNPPSYEDDQ EMAEEEDPSW PSTAMNRAAP WGTRRLLNWI
1261 KEEYGDIPIY ITENGVGLTN PNTEDTDRIF YHKTYINEAL KAYRLDGIDL RGYVAWSLMD
1321 NFEWLNGYTV KFGLYHVDFN NTNRPRTARA SARYYTEVIT NNGMPLARED EFLYGRFPEG
1381 FIWSAASAAY QIEGAWRADG KGLSIWDTFS HTPLRVENDA IGDVACDSYH KIAEDLVTLQ
1441 NLGVSHYRFS ISWSRILPDG TTRYINEAGL NYYVRLIDTL LAASIQPQVT IYHWDLPQTL
1501 QDVGGWENET IVQRFKEYAD VLFQRLGDKV KFWITLNEPF VIAYQGYGYG TAAPGVSNRP
1561 GTAPYIVGHN LIKAHAEAWH LYNDVYRASQ GGVISITISS DWAEPRDPSN QEDVEAARRY
1621 VQFMGGWFAH PIPFKNGDYNE VMKTRIRDRS LAAGLNKSRL PEFTESEKRR INGTYDFFGF
1681 NHYTTVLAYN LNYATAISSF DADRGVASIA DRSWPDSGSF WLKMTPGFR RILNWLKEEY
1741 NDPPIYVTEN GVSQREETDL NDTARIYYLR TYINEALKAV QDKVDLRGYT VWSAMDNFEW
1801 ATGFSERFGL HFVNYSDPSL PRIPKASAKF YASVVRCNGF PDPATGPHAC LHQPDAGPTI
1861 SPVRQEEVQF LGLMLGTTEA QTALYVLFSL VLLGVCGLAF LSYKYCKRSK QGKTQRSQQE
1921 LSPVSSF
```

SEQ ID NO: 10 is the human wild type nucleic acid sequence corresponding to the lactase (LCT) enzyme (bps 1-6274) having GenBank Accession No. NM_002299:

```
   1 gttcctagaa aatggagctg tcttggcatg tagtctttat tgccctgcta agttttcat
  61 gctggggtc agactgggag tctgatagaa atttcatttc caccgctggt cctctaacca
 121 atgacttgct gcacaacctg agtggtctcc tgggagacca gagttctaac tttgtagcag
 181 gggacaaaga catgtatgtt tgtcaccagc cactgccac tttcctgcca gaatacttca
 241 gcagtctcca tgccagtcag atcacccatt ataaggtatt tctgtcatgg cacagctcc
 301 tcccagcagg aagcacccag aatccagacg agaaaacagt gcagtgctac cggcgactcc
 361 tcaaggccct caagactgca cggcttcagc ccatggtcat cctgcaccac cagacctcc
 421 ctgccagcac cctcggagaa accgaagcct ttgctgacct cttcgccgac tatgccacat
 481 tcgccttcca ctccttcggg gacctagttg gatctggtt cacctttcagt gacttggagg
 541 aagtgatcaa ggagcttccc caccaggaat caagagcgtc acaactccag accctcagtg
 601 atgcccacag aaaagcctat gagatttacc acgaaagcta tgcttttcag ggcgggaaac
 661 tctctgttgt cctgcgagct gaagatatcc cggagctcct gctagaacca cccatatctg
 721 cgcttgccca ggacacggtc gatttcctct ctcttgattt gtcttatgaa tgccaaaatg
 781 aggcaagtct gcggcagaag ctgagtaaat tgcagaccat tgagccaaaa gtgaaagttt
 841 tcatcttcaa cctaaaactc ccagactgcc cctccaccat gaagaaccca gccagtctgc
 901 tcttcagcct ttttgaagcc ataaataaag accaagtgct caccattggg tttgatatta
```

-continued

```
 961 atgagtttct gagttgttca tcaagttcca agaaaagcat gtcttgttct ctgactggca
1021 gcctggccct tcagcctgac cagcagcagg accacgagac cacggactcc tctcctgcct
1081 ctgcctatca gagaatctgg gaagcatttg ccaatcagtc cagggcggaa agggatgcct
1141 tcctgcagga tactttccct gaaggcttcc tctggggtgc ctccacagga gcctttaacg
1201 tggaaggagg ctgggccgag ggtgggagag gggtgagcag ctgggatcca cgcaggcccc
1261 tgaacaccac tgagggccaa gcgacgctgg aggtggccag cgacagttac cacaaggtag
1321 cctctgacgt cgccctgctt tgcggcctcc gggctcaggt gtacaagttc tccatctcct
1381 ggtcccggat cttccccatg gggcacggga gcagcccag cctcccaggc gttgcctact
1441 acaacaagct gattgacagg ctacaggatg cgggcatcga gcccatggcc acgctgttcc
1501 actgggacct gcctcaggcc ctgcaggatc atggtggatg gcagaatgag agcgtggtgg
1561 atgccttcct ggactatgcg gccttctgct tctccacatt tggggaccgt gtgaagctgt
1621 gggtgacctt ccatgagccg tgggtgatga gctacgcagg ctatggcacc ggccagcacc
1681 ctcccggcat ctctgaccca ggagtggcct cttttaaggt ggctcacttg gtcctcaagg
1741 ctcatgccag aacttggcac cactacaaca gccatcatcg cccacagcag cagggggcacg
1801 tgggcattgt gctgaactca gactgggcag aaccectgtc tccagagagg cctgaggacc
1861 tgagagcctc tgagcgcttc ttgcacttca tgctgggctg gtttgcacac ccgtctttg
1921 tggatggaga ctacccagcc accctgagga cccagatcca acagatgaac agacagtgct
1981 cccatcctgt ggctcaactc cccgagttca cagaggcagg aagcagctc ctgaaaggct
2041 ctgctgattt tctgggtctg tcgcattaca cctcccgcct catcagcaac gccccacaaa
2101 acacctgcat ccctagctat gataccattg gaggcttctc ccaacacgtg aaccatgtgt
2161 ggccccagac ctcatcctct tggattcgtg tggtgccctg ggggataagg aggctgttgc
2221 agtttgtatc cctggaatac acaagaggaa aagttccaat ataccttgcc gggaatggca
2281 tgcccatagg ggaaagtgaa aatctctttg atgattcctt aagagtagac tacttcaatc
2341 aatatatcaa tgaggtgctc aaggctatca aggaagactc tgtggatgtt cgttcctaca
2401 ttgctcgttc cctcattgat ggcttcgaag gcccttctgg ttacagccag cggtttggcc
2461 tgcaccacgt caacttcagc gacagcagca agtcaaggac tcccaggaaa tctgcctact
2521 ttttcactag catcatagaa aagaacggtt tcctcaccaa gggggcaaaa agactgctac
2581 cacctaatac agtaaacctc ccctccaaag tcagagcctt cacttttcca tctgaggtgc
2641 cctccaaggc taaagtcgtt tgggaaaagt tctccagcca acccaagttc gaaagagatt
2701 tgttctacca cgggacgttt cgggatgact ttctgtgggg cgtgtcctct tccgcttatc
2761 agattgaagg cgcgtgggat gccgatggca aaggccccag catctgggat aactttaccc
2821 acacaccagg gagcaatgtg aaagacaatg ccactggaga catcgcctgt gacagctatc
2881 accagctgga tgccgatctg aatatgctcc gagcttttgaa ggtgaaggcc taccgcttct
2941 ctatctcctg gtctcggatt ttcccaactg ggagaaacag ctctatcaac agtcatgggg
3001 ttgattatta caacaggctg atcaatggct tggtggcaag caacatcttt cccatggtga
3061 cattgttcca ttgggacctg ccccaggccc tccaggatat cggaggctgg gagaatcctg
3121 ccttgattga cttgtttgac agctacgcag acttttgttt ccagacctt ggtgatagag
3181 tcaagttttg gatgactttt aatgagccca tgtacctggc atggctaggt tatggctcag
3241 gggaatttcc cccagggtg aaggacccag gctgggcacc atataggata gcccacgccg
3301 tcatcaaagc ccatgccaga gtctatcaca cgtacgatga gaaatacagg caggagcaga
3361 agggggtcat ctcgctgagc ctcagtacac actgggcaga gcccaagtca ccaggggtcc
3421 ccagagatgt ggaagccgct gaccgaatgc tgcagttctc cctgggctgg tttgctcacc
3481 ccattttag aaacggagac tatcctgaca ccatgaagtg gaaagtgggg aacaggagtg
3541 aactgcagca cttagccacc tcccgcctgc caagcttcac tgaggaagag aagaggttca
3601 tcagggcgac ggccgacgtc ttctgcctca acacgtacta ctccagaatc gtgcagcaca
3661 aaacacccag gctaaaccca ccctcctacg aagacgacca ggagatggct gaggaggagg
3721 acccttcgtg gccttccacg gcaatgaaca gagctgcgcc ctgggggacg cgaaggctgc
3781 tgaactggat caaggaagag tatggtgaca tccccattta catcaccgaa aacggagtgg
3841 ggctgaccaa tccgaacacg gaggatactg ataggatatt ttaccacaaa acctacatca
3901 atgaggcttt gaaagcctac aggctcgatg gtatagacct tcgagggtat gtcgcctggt
3961 ctctgatgga caactttgag tggctaaatg gctacacggt caagtttgga ctgtaccatg
4021 ttgatttcaa caacacgaac aggcctcgca cagcaagagc ctccgccagg tactacacag
4081 aggtcattac caacaacggc atgccactgg ccaggaggga tgagtttctg tacggacggt
4141 ttcctgaggg cttcatctgg agtgcagctt ctgctgcata tcagattgaa ggtgcgtgga
4201 gagcagatgg caaaggactc agcatttggg acacgttttc tcacacacca ctgaggggttg
4261 agaacgatgc cattgagac gtgccctgtg acagttatca caagattgct gaggatctgg
4321 tcaccctgca gaacctgggc gtgtcccact accgttttttc catctcctgg tctcgcatcc
4381 tccctgatgg aaccaccagg tacatcaatg aagcgggcct gaactactac gtgaggctca
4441 tcgatacact gctggccgcc agcatccagc cccaggtgac catttaccac tgggacctac
4501 cacagacgct ccaagatgta ggaggctggg agaatgacag catcgtgcag cggtttaagg
4561 agtatgcaga tgtgctcttc cagaggctgg gagacaaggt gaagtttttgg atcacgctga
4621 atgagccctt tgtcattgct taccagggct atggctacgg aacagcagct ccaggagtct
4681 ccaataggcc tggcactgcc ccctacattg ttggccacaa tctaataaag gctcatgctg
4741 aggcctggca tctgtacaac gatgtgtacc gcgccagtca agtggcgtg attttccatca
4801 ccatcagcag tgactgggct gaacccagag atccctctaa ccaggaggat gtggaggcag
4861 ccaggagata tgttcagttc atgggaggct ggtttgcaca tcctatttc aagaatggag
4921 attacaatga ggtgatgaag acgcggatcc gtgacaggag cttggctgca ggcctcaaca
4981 agtctcggct gccagaattt acagagagtg agaagaggac acctgagc acctatgact
5041 ttttttgggtt caatcactac accactgtcc tcgcctacaa cctcaactat gccactgcca
5101 tctcttcttt tgatgcagac agaggagttg cttccatcgc agatcgctcg tggccagact
5161 ctggctcctt ctggctgaag atgacgcctt ttggcttcag gaggatcctg aactggttaa
5221 aggaggaata caatgaccct ccaatttatg tcacagagaa tggagtgtcc cagcgggaag
5281 aaacagacct caatgacact gcaaggatct actaccttcg gacttacatc aatgaggccc
5341 tcaaagctgt gcaggacaag gtggaccttc gaggatacac agtttgagt gcgatggaca
5401 attttgagtg ggccacaggc ttttcagaga gatttggtct gcattttgtg aactacagtg
5461 acccttctct gccaaggatc cccaaagcat cagcgaagtt ctacgctctct gtggtccgat
5521 gcaatggctt ccctgacccc gctacagggc ctcacgcttg tctccaccag ccagatgctg
5581 gacccaccat cagcccgtg agacaggagg aggtgcagtt cctgggggcta atgctcggca
5641 ccacagaagc acagacagct ttgtacgttc tcttttctct tgtgcttctt ggagtctgtg
5701 gcttggcatt tctgtcatac aagtactgca agcgctctaa gcaagggaaa acacaacgaa
5761 gccaacagga attgagcccg gtgtcttcat tctgatgagt taccacctca agttctatga
```

```
                            -continued
5821 agcaggccta gtttcttcat ctatgtttac cggccaccaa acaccttagg gtcttagact
5881 ctgctgatac tggacttctc cataaagtcc tgctgcaccg ttagagatga ctttaatctt
5941 gaatgatttc gacttgctga gtaaaatgga aatatctcca tcttgctcca gtatcagagt
6001 tcatttgggc atttgagaag caagtagctc ttgcggaaac gtgtagatac tggtctagtg
6061 ggtctgtgaa ccacttaatt gaacttaaca gggctgtttt aagtttcaga gttgttaagg
6121 gttgttaagg gagcaaaaac cgtaaaaatc cttcctataa gaagaaatca actccattgc
6181 atagactgca atatcatctc ctgcccttct gcaagctctc cctagcttca catcttgtgt
6241 tttccagaaa ataaaaacag cagactgtcc tttc
```

As used herein, a "carbohydrate transporter molecule" means a nucleic acid which encodes a polypeptide that exhibits carbohydrate transporter activity, or a polypeptide or peptidomimetic that exhibits carbohydrate transporter activity. For example, a carbohydrate transporter molecule can include the human GLUT2 protein (e.g., having the amino acid sequence shown in SEQ ID NO: 1), or a variant thereof, such as a fragment thereof, that exhibits carbohydrate transporter activity. For example, a carbohydrate transporter molecule can include the human SGLT1 protein (e.g., having the amino acid sequence shown in SEQ ID NO: 3), or a variant thereof, such as a fragment thereof, that exhibits carbohydrate transporter activity. The nucleic acid can be any type of nucleic acid, including genomic DNA, complementary DNA (cDNA), synthetic or semi-synthetic DNA, as well as any form of corresponding RNA. For example, a carbohydrate transporter molecule can comprise a recombinant nucleic acid encoding human GLUT2 protein or human SGLT1 protein. In one embodiment, a carbohydrate transporter molecule can comprise a non-naturally occurring nucleic acid created artificially (such as by assembling, cutting, ligating or amplifying sequences). A carbohydrate transporter molecule can be double-stranded. A carbohydrate transporter molecule can be single-stranded. The carbohydrate transporter molecules of the invention can be obtained from various sources and can be produced according to various techniques known in the art. For example, a nucleic acid that is a carbohydrate transporter molecule can be obtained by screening DNA libraries, or by amplification from a natural source. The carbohydrate transporter molecules of the invention can be produced via recombinant DNA technology and such recombinant nucleic acids can be prepared by conventional techniques, including chemical synthesis, genetic engineering, enzymatic techniques, or a combination thereof. Non-limiting examples of a carbohydrate transporter molecule, that is a nucleic acid, is the nucleic acid having the nucleotide sequence shown in SEQ ID NO: 2 or SEQ ID NO: 4. Another example of a carbohydrate transporter molecule is a fragment of a nucleic acid having the sequence shown in SEQ ID NO: 2 or SEQ ID NO:4, wherein the fragment is exhibits carbohydrate transporter activity.

As used herein, a "carbohydrate metabolic enzyme molecule" means a nucleic acid which encodes a polypeptide that exhibits carbohydrate metabolic enzyme activity, or a polypeptide or peptidomimetic that exhibits carbohydrate metabolic enzyme activity. For example, a carbohydrate metabolic enzyme molecule can include the human sucrase-isomaltase (SI) protein (e.g., having the amino acid sequence shown in SEQ ID NO: 5), or a variant thereof, such as a fragment thereof, that exhibits carbohydrate metabolic enzyme activity. For example, a carbohydrate metabolic enzyme molecule can include the human maltase-glucoamylase protein (e.g., having the amino acid sequence shown in SEQ ID NO: 7), or a variant thereof, such as a fragment thereof, that exhibits carbohydrate metabolic enzyme activity. For example, a carbohydrate metabolic enzyme molecule can include the human lactase protein (e.g., having the amino acid sequence shown in SEQ ID NO: 9), or a variant thereof, such as a fragment thereof, that exhibits carbohydrate metabolic enzyme activity. The nucleic acid can be any type of nucleic acid, including genomic DNA, complementary DNA (cDNA), synthetic or semi-synthetic DNA, as well as any form of corresponding RNA. For example, a carbohydrate metabolic enzyme molecule can comprise a recombinant nucleic acid encoding human sucrase-isomaltase (SI) protein, human maltase-glucoamylase protein, or human lactase protein. In one embodiment, a carbohydrate metabolic enzyme molecule can comprise a non-naturally occurring, nucleic acid created artificially (such as by assembling, cutting, ligating or amplifying sequences). A carbohydrate metabolic enzyme molecule can be double-stranded. A carbohydrate metabolic enzyme molecule can be single-stranded. The carbohydrate metabolic enzyme molecules of the invention can be obtained from various sources and can be produced according to various techniques known in the art. For example, a nucleic acid that is a carbohydrate metabolic enzyme molecule can be obtained by screening DNA libraries, or by amplification from a natural source. The carbohydrate metabolic enzyme molecules of the invention can be produced via recombinant DNA technology and such recombinant nucleic acids can be prepared by conventional techniques, including chemical synthesis, genetic engineering, enzymatic techniques, or a combination thereof. A non-limiting example of a carbohydrate metabolic enzyme, that is a nucleic acid, is the nucleic acid having the nucleotide sequence shown in SEQ ID NO: 6, 8, or 10. Another example of a carbohydrate metabolic enzyme molecule is a fragment of a nucleic acid having the sequence shown in SEQ ID NO: 6, 8, or 10, wherein the fragment is exhibits carbohydrate metabolic enzyme activity.

According to this invention, a carbohydrate transporter molecule encompass es orthologs of human GLUT2 and SGLT1. According to this invention, a carbohydrate metabolic enzyme molecule encompass orthologs of human sucrase-isomaltase (SI), human maltase-glucoamylase, and human lactase. For example, a carbohydrate transporter molecule or a carbohydrate metabolic enzyme molecule encompass the orthologs in mouse, rat, non-human primates, canines, goat, rabbit, porcine, feline, and horses. In other words, a carbohydrate transporter molecule or a carbohydrate metabolic enzyme molecule can comprise a nucleic acid sequence homologous to the human nucleic acid that encodes a human GLUT2 and SGLT1 protein, or human sucrase-isomaltase (SI), human maltase-glucoamylase, and human lactase protein, respectively, wherein the nucleic acid is found in a different species and wherein that homolog encodes a protein with a glucose transporter function similar to a carbohydrate transporter molecule or an enzymatic function similar to a carbohydrate metabolic enzyme molecule.

A carbohydrate transporter molecule of this invention also encompasses variants of the human nucleic acid encoding the GLUT2 or SGLT1 proteins that exhibit carbohydrate transporter activity, or variants of the human GLUT2 or SGLT1 proteins that exhibit carbohydrate transporter activity. A carbohydrate transporter molecule of this invention also includes a fragment of the human GLUT2 or SGLT1 nucleic acid which encodes a polypeptide that exhibits carbohydrate transporter activity. A carbohydrate transporter molecule of this invention encompasses a fragment of the human GLUT2 or SGLT1 protein that exhibits carbohydrate transporter activity.

A carbohydrate metabolic enzyme molecule of this invention also encompasses variants of the human nucleic acid encoding the sucrase-isomaltase (SI), human maltase-glucoamylase, and human lactase proteins that exhibit carbohydrate metabolic enzyme activity, or variants of the human sucrase-isomaltase (SI), human maltase-glucoamylase, and human lactase proteins that exhibit carbohydrate metabolic enzyme activity. A carbohydrate metabolic enzyme molecule of this invention also includes a fragment of the human sucrase-isomaltase (SI), human maltase-glucoamylase, and human lactase nucleic acid which encodes a polypeptide that exhibits carbohydrate metabolic enzyme activity. A carbohydrate metabolic enzyme molecule of this invention encompasses a fragment of the human sucrase-isomaltase (SI), human maltase-glucoamylase, and human lactase protein that exhibits carbohydrate metabolic enzyme activity.

The variants can comprise, for instance, naturally-occurring variants due to allelic variations between individuals (e.g., polymorphisms), mutated alleles related to autism, or alternative splicing forms. In one embodiment, a carbohydrate transporter molecule is a nucleic acid variant of the nucleic acid having the sequence shown in SEQ ID NO: 2, wherein the variant has a nucleotide sequence identity to SEQ ID NO: 2 of at least about 65%, at least about 75%, at least about 85%, at least about 90%, at least about 91%, at least about 92%, at least about 93%, at least about 94%, at least about 95%, at least about 96%, at least about 97%, at least about 98%, or at least about 99% with SEQ ID NO: 2. In another embodiment, a carbohydrate transporter molecule is a nucleic acid variant of the nucleic acid having the sequence shown in SEQ ID NO: 4, wherein the variant has a nucleotide sequence identity to SEQ ID NO: 4 of at least about 65%, at least about 75%, at least about 85%, at least about 90%, at least about 91%, at least about 92%, at least about 93%, at least about 94%, at least about 95%, at least about 96%, at least about 97%, at least about 98%, or at least about 99% with SEQ ID NO: 4. In one embodiment, a carbohydrate metabolic enzyme molecule is a nucleic acid variant of the nucleic acid having the sequence shown in SEQ ID NO: 6, wherein the variant has a nucleotide sequence identity to SEQ ID NO: 6 of at least about 65%, at least about 75%, at least about 85%, at least about 90%, at least about 91%, at least about 92%, at least about 93%, at least about 94%, at least about 95%, at least about 96%, at least about 97%, at least about 98%, or at least about 99% with SEQ ID NO: 6. In another embodiment, a carbohydrate metabolic enzyme molecule is a nucleic acid variant of the nucleic acid having the sequence shown in SEQ ID NO: 8, wherein the variant has a nucleotide sequence identity to SEQ ID NO: 8 of at least about 65%, at least about 75%, at least about 85%, at least about 90%, at least about 91%, at least about 92%, at least about 93%, at least about 94%, at least about 95%, at least about 96%, at least about 97%, at least about 98%, or at least about 99% with SEQ ID NO: 8. In a further embodiment, a carbohydrate metabolic enzyme molecule is a nucleic acid variant of the nucleic acid having the sequence shown in SEQ ID NO: 10, wherein the variant has a nucleotide sequence identity to SEQ ID NO: 10 of at least about 65%, at least about 75%, at least about 85%, at least about 90%, at least about 91%, at least about 92%, at least about 93%, at least about 94%, at least about 95%, at least about 96%, at least about 97%, at least about 98%, or at least about 99% with SEQ ID NO: 10.

In one embodiment, a carbohydrate transporter molecule encompasses any portion of at least about 8 consecutive nucleotides of SEQ ID NO: 2 or 4. In one embodiment, the fragment can comprise at least about 15 nucleotides, at least about 20 nucleotides, or at least about 30 nucleotides of SEQ ID NO: 2 or 4. Fragments include all possible nucleotide lengths between about 8 and 100 nucleotides, for example, lengths between about 15 and 100, or between about 20 and 100. In one embodiment, a carbohydrate metabolic enzyme molecule encompasses any portion of at least about 8 consecutive nucleotides of SEQ ID NO: 6, 8, or 10. In one embodiment, the fragment can comprise at least about 15 nucleotides, at least about 20 nucleotides, or at least about 30 nucleotides of SEQ ID NO: 6, 8, or 10. Fragments include all possible nucleotide lengths between about 8 and 100 nucleotides, for example, lengths between about 15 and 100, or between about 20 and 100.

The invention further provides for nucleic acids that are complementary to a nucleic acid encoding GLUT2, SGLT1, sucrase-isomaltase (SI), human maltase-glucoamylase, or human lactase proteins. Such complementary nucleic acids can comprise nucleic acid sequences, which hybridize to a nucleic acid sequence encoding a GLUT2, SGLT1, sucrase-isomaltase (SI), maltase-glucoamylase, or lactase protein under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

In one embodiment, a carbohydrate transporter molecule comprises a protein or polypeptide encoded by a carbohydrate transporter nucleic acid sequence, such as the sequence shown in SEQ ID NO: 2 or 4. In another embodiment, the polypeptide can be modified, such as by glycosylations and/or acetylations and/or chemical reaction or coupling, and can contain one or several non-natural or synthetic amino acids. An example of a carbohydrate transporter molecule is the polypeptide having the amino acid sequence shown in SEQ ID NO: 1 or 3. In one embodiment, a carbohydrate metabolic enzyme molecule comprises a protein or polypeptide encoded by a carbohydrate metabolic enzyme nucleic acid sequence, such as the sequence shown in SEQ ID NO: 6, 8, or 10. In another embodiment, the polypeptide can be modified, such as by glycosylations and/or acetylations and/or chemical reaction or coupling, and can contain one or several non-natural or synthetic amino acids. An example of a carbohydrate transporter molecule is the polypeptide having the amino acid sequence shown in SEQ ID NO: 5, 7, or 9.

In another embodiment, a carbohydrate transporter molecule can be a fragment of a carbohydrate transporter protein, such as GLUT2 or SGLT1. For example, the carbohydrate transporter molecule can encompass any portion of at least about 8 consecutive amino acids of SEQ ID NO: 1 or 3. The fragment can comprise at least about 10 amino acids, a least about 20 amino acids, at least about 30 amino acids, at least about 40 amino acids, a least about 50 amino acids, at least about 60 amino acids, or at least about 75 amino acids of SEQ ID NO: 1 or 3. In another embodiment, a carbohydrate metabolic enzyme molecule can be a fragment of a carbohydrate metabolic enzyme protein, such as sucrase-isomaltase (SI), maltase-glucoamylase, or lactase. For example, the carbohydrate metabolic enzyme molecule can encompass any portion of at least about 8 consecutive amino acids of SEQ ID NO: 5, 7, or 9. The fragment can comprise at least about 10 amino acids, a least about 20 amino acids, at least about 30 amino acids, at least about 40 amino acids, a least about 50 amino acids, at least about 60 amino acids, or at least about 75 amino acids of SEQ ID NO: 5, 7, or 9. Fragments include all possible amino acid lengths between about 8 and 100 about amino acids, for example, lengths between about 10 and 100 amino acids, between about 15 and 100 amino acids, between about 20 and 100 amino acids, between about 35 and 100 amino acids, between about 40 and 100 amino acids, between about 50 and 100 amino acids, between about 70 and 100 amino acids, between about 75 and ,100 amino acids, or between about 80 and 100 amino acids.

In certain embodiments, the carbohydrate transporter molecule of the invention includes variants of the human GLUT2 or SGLT1 protein (having the amino acid sequence shown in SEQ ID NO: 1 and 3, respectively). Such variants can include those having at least from about 46% to about 50% identity to SEQ ID NO: 1 or 3, or having at least from about 50.1% to about 55% identity to SEQ ID NO: 1 or 3, or having at least from about 55.1% to about 60% identity to SEQ ID NO: 1 or 3, or having at least from about 60.1% to about 65% identity to SEQ ID NO: 1 or 3, or having from about 65.1% to about 70% identity to SEQ ID NO: 1 or 3, or having at least from about 70.1% to about 75% identity to SEQ ID NO: 1 or 3, or having at least from about 75.1% to about 80% identity to SEQ ID NO: 1 or 3, or having at least from about 80.1% to about 85% identity to SEQ ID NO: 1 or 3, or having at least from about 85.1% to about 90% identity to SEQ ID NO: 1 or 3, or having at least from about 90.1% to about 95% identity to SEQ ID NO: 1 or 3, or having at least from about 95.1% to about 97% identity to SEQ ID NO: 1 or 3, or having at least from about 97.1% to about 99% identity to SEQ ID NO: 1 or 3.

In certain embodiments, the carbohydrate metabolic enzyme molecule of the invention includes variants of the human sucrase-isomaltase (SI), maltase-glucoamylase, or lactase protein (having the amino acid sequence shown in SEQ ID NO: 5, 7, and 9, respectively). Such variants can include those having at least from about 46% to about 50% identity to SEQ ID NO: 5, 7, or 9, or having at least from about 50.1% to about 55% identity to SEQ ID NO: 5, 7, or 9, or having at least from about 55.1% to about 60% identity to SEQ ID NO: 5, 7, or 9, or having from at least about 60.1% to about 65% identity to SEQ ID NO: 5, 7, or 9, or having from about 65.1% to about 70% identity to SEQ ID NO: 5, 7, or 9, or having at least from about 70.1% to about 75% identity to SEQ ID NO: 5, 7, or 9, or having at least from about 75.1% to about 80% identity to SEQ ID NO: 5, 7, or 9, or having at least from about 80.1% to about 85% identity to SEQ ID NO: 5, 7, or 9, or having at least from about 85.1% to about 90% identity to SEQ ID NO: 5, 7, or 9, or having at least from about 90.1% to about 95% identity to SEQ ID NO: 5, 7, or 9, or having at least from about 95.1% to about 97% identity to SEQ ID NO: 5, 7, or 9, or having at least from about 97.1% to about 99% identity to SEQ ID NO: 5, 7, or 9.

In another embodiment, the carbohydrate transporter molecule of the invention encompasses a peptidomimetic which exhibits carbohydrate transporter activity. In another embodiment, the carbohydrate transporter molecule of the invention encompasses a peptidomimetic which exhibits carbohydrate transporter activity. In another embodiment, the carbohydrate metabolic enzyme molecule of the invention encompasses a peptidomimetic which exhibits carbohydrate metabolic enzyme activity. In another embodiment, the carbohydrate metabolic enzyme molecule of the invention encompasses a peptidomimetic which exhibits carbohydrate metabolic enzyme activity. A peptidomimetic is a small protein-like chain designed to mimic a peptide that can arise from modification of an existing peptide in order to protect that molecule from enzyme degradation and increase its stability, and/or alter the molecule's properties (for example modifications that change the molecule's stability or biological activity). These modifications involve changes to the peptide that can not occur naturally (such as altered backbones and the incorporation of non-natural amino acids). Drug-like compounds can be able to be developed from existing peptides. A peptidomimetic can be a peptide, partial peptide or non-peptide molecule that mimics the tertiary binding structure or activity of a selected native peptide or protein functional domain (e.g., binding motif or active site). These peptide mimetics include recombinantly or chemically modified peptides.

In one embodiment, a carbohydrate transporter molecule comprising SEQ ID NO: 1, SEQ ID NO: 3, variants of each, or fragments thereof, can be modified to produce peptide mimetics by replacement of one or more naturally occurring side chains of the 20 genetically encoded amino acids (or D amino acids) with other side chains. In one embodiment, a carbohydrate metabolic enzyme molecule comprising SEQ ID NO: 5, SEQ ID NO: 7, SEQ ID NO: 9, variants of, or fragments thereof, can be modified to produce peptide mimetics by replacement of one or more naturally occurring side chains of the 20 genetically encoded amino acids (or D amino acids) with other side chains. This can occur, for instance, with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4, 5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, ifuryl, imidazolidinyl imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics can also have amino acid residues that have, been chemically modified by phosphorylation, sulfonation, biotinylation, or the addition or removal of other moieties. For example, peptidomimetics can be designed and directed to amino acid sequences encoded by a carbohydrate transporter molecule comprising SEQ ID NO: 1 or 3. For example, peptidomimetics can be designed and directed to amino acid sequences encoded by a carbohydrate metabolic enzyme molecule comprising SEQ ID NO: 5, 7, or 9.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24,243-252, 1989). Certain peptidomimetic compounds are based upon the amino acid sequence of the peptides of the invention. Peptidomimetic compounds can be synthetic compounds having a three-dimensional structure (i.e. a peptide motif) based upon the three-dimensional structure of a selected peptide. The peptide motif provides the peptidomimetic compound with the desired biological activity, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life. Peptidomimetic design strategies are readily available in the art (see, e.g., Ripka & Rich, Curr. Op. Chem. Biol. 2, 441452, 1998; Hrubyet al., Curr. Op. Chem. Biol. 1, 114119, 1997; Hruby & Balse, Curr. Med. Chem. 9, 945-970,-2000).

Diagnosis

The invention provides diagnosis methods based on monitoring a gene encoding a carbohydrate metabolic enzyme molecule (such as sucrase isomaltase, maltase glucoamylase, or lactase) or a carbohydrate transporter molecule (such as GLUT2 or SGLT1). As used herein, the term "diagnosis" includes the detection, typing, monitoring, dosing, comparison, at various stages, including early, pre-symptomatic stages, and late stages, in adults, children, and unborn human children. Diagnosis can include the assessment of a predisposition or risk of development, the prognosis, or the characterization of a subject to define most appropriate treatment (pharmacogenetics).

The invention provides diagnostic methods to determine whether an individual is at risk of developing autism or an autism spectrum disorder (ASD), or suffers from autism or an ASD, wherein the disease reflects an alteration in the expression of a gene encoding a carbohydrate metabolic enzyme molecule (such as sucrase isomaltase, maltase glucoamylase, or lactase) or a carbohydrate transporter molecule (such as GLUT2 or SGLT1). Subjects diagnosed with autism, as well as ASD, can display some core symptoms in the areas of a) social interactions and relationships, b) verbal and non-verbal communication, and c) physical activity, play, physical behavior. For example, symptoms related to social interactions and relationships can include but are not limited to the inability to establish friendships with children the same age, lack of empathy, and the inability to develop nonverbal communicative skills (for example, eye-to-eye gazing, facial expressions, and body posture). For example, symptoms related to verbal and nonverbal communication comprises delay in learning to talk, inability to learn to talk, failure to initiate or maintain a conversation, failure to interpret or understand implied meaning of words, and repetitive use of language. For example, symptoms related to physical activity, play, physical behavior include, but are not limited to unusual focus on pieces or parts of an object, such as a toy, a preoccupation with certain topics, a need for routines and rituals, and stereotyped behaviors (for example, body rocking and hand flapping).

In one embodiment, a method of detecting the presence of or a predisposition to autism or an autism spectrum disorder in a subject is provided. The subject can be a human or a child thereof. The subject can also be a human embryo, a human fetus, or an unborn human child. The method can comprise detecting in a sample from the subject the presence of an alteration in the expression of a gene of a carbohydrate metabolic enzyme molecule (such as sucrase isomaltase, maltase glucoamylase, or lactase) or a carbohydrate transporter molecule (such as GLUT2 or SGLT1). In one embodiment, the detecting comprises detecting whether there is an alteration in the gene locus encoding a carbohydrate metabolic enzyme molecule (such as sucrase isomaltase, maltase glucoamylase, or lactase) or a carbohydrate transporter molecule (such as GLUT2 or SGLT1). In a further embodiment, the detecting comprises detecting whether expression of a carbohydrate metabolic enzyme molecule (such as sucrase isomaltase, maltase glucoamylase, or lactase) or a carbohydrate transporter molecule (such as GLUT2 or SGLT1) is reduced. In some embodiments, the detecting comprises detecting in the sample whether there is a reduction in an mRNA encoding a carbohydrate metabolic enzyme molecule or a carbohydrate transporter molecule, or a reduction in either the carbohydrate metabolic enzyme protein or a carbohydrate transporter protein, or a combination thereof. The presence of such an alteration is indicative of the presence or predisposition to autism or an autism spectrum disorder. The presence of an alteration in a gene encoding a carbohydrate metabolic enzyme molecule or a carbohydrate transporter molecule in the sample is detected through the genotyping of a sample, for example via gene sequencing, selective hybridization, amplification, gene expression analysis, or a combination thereof. In one embodiment, the sample can comprise blood, serum, sputum, lacrimal secretions, semen, vaginal secretions, fetal tissue, skin tissue, ileum tissue, cecum tissue, muscle tissue, amniotic fluid, or a combination thereof.

The invention also provides a method for treating or preventing autism or an autism spectrum disorder in a subject. In one embodiment, the method comprises (1) detecting the presence of an alteration in a carbohydrate transporter gene or a carbohydrate metabolic enzyme in a sample from the subject, where the presence of the alteration is indicative of autism or an ASD, or the predisposition to autism or ASD, and, (2) administering to the subject in need a therapeutic treatment against autism or an autism spectrum disorder. In one embodiment, the carbohydrate transporter gene can be a GLUT2 gene or a SGLT1 gene. In another embodiment, the carbohydrate metabolic enzyme gene can be a sucrase isomaltase gene, a maltase glucoamylase gene, or a lactase gene. The therapeutic treatment can be a drug administration (for example, a pharmaceutical composition comprising a functional carbohydrate transporter molecule or a functional carbohydrate metabolic enzyme molecule). In one embodiment, the molecule comprises a carbohydrate transporter polypeptide comprising at least about 75%, at least about 80%, at least about 85%, at least about 90%, at least about 93%, at least about 95%, at least about 97%, at least about 98%, at least about 99%, or 100% of the amino acid sequence of SEQ ID NO: 1 or SEQ ID NO: 3, and exhibits the function of restoring functional carbohydrate transporter expression in deficient individuals, thus restoring the capacity for carbohydrate transport. In another embodiment, the molecule comprises a carbohydrate metabolic enzyme polypeptide comprising at least about 75%, at least about 80%, at least about 85%, at least about 90%, at least about 93%, at least about 95%, at least about 97%, at least about 98%, at least about 99%, or 100% of the amino acid sequence of SEQ ID NO: 5, 7, or 9, and exhibits the function of restoring functional carbohydrate metabolic enzyme expression in deficient individuals, thus restoring the capacity for carbohydrate metabolism.

In some embodiments, the molecule comprises a nucleic acid encoding a carbohydrate transporter polypeptide comprising at least about 75%, at least about 80%, at least about 85%, at least about 90%, at least about 93%, at least about 95%, at least about 97%, at least about 98%, at least about 99%, or 100% of the nucleic acid sequence of SEQ ID NO: 2 or 4 and encodes a polypeptide with the function of restoring functional carbohydrate transporter expression in deficient individuals, thus restoring the capacity for carbohydrate transport. In further embodiments, the molecule comprises a nucleic acid encoding a carbohydrate metabolic enzyme polypeptide comprising at least about 75%, at least about 80%, at least about 85%, at least about 90%, at least about 93%, at least about 95%, at least about 97%, at least about 98%, at least about 99%, or 100% of the nucleic acid sequence of SEQ ID NO: 6, 8, or 10, and encodes a polypeptide with the function of restoring functional carbohydrate metabolic enzyme expression in deficient individuals, thus restoring the capacity for carbohydrate metabolism.

The alteration can be determined at the DNA, RNA or polypeptide level of the carbohydrate transporter or carbohydrate metabolic enzyme. The detection can also be determined by performing an oligonucleotide ligation assay, a confirmation based assay, a hybridization assay, a sequencing assay, an allele-specific amplification assay, a microsequencing assay, a melting curve analysis, a denaturing high performance liquid chromatography (DHPLC) assay (for example, see Jones et al, (2000) Hum Genet., 106(6):663-8), or a combination thereof. In some embodiments, the detection is performed by sequencing all or part of a carbohydrate transporter or carbohydrate metabolic enzyme gene or by selective hybridization or amplification of all or part of a carbohydrate transporter or carbohydrate metabolic enzyme gene. A carbohydrate transporter or carbohydrate metabolic enzyme gene specific amplification can be carried out before the alteration identification step.

An alteration in a carbohydrate transporter gene locus (e.g., where GLUT2 or SGLT1 are located) or a carbohydrate metabolic enzyme gene locus (e.g., where SI, MGAM, or LCT are located) can be any form of mutation(s), deletion(s), rearrangement(s) and/or insertions in the coding and/or non-coding region of the locus, alone or in various combination(s). Mutations can include point mutations. Insertions can encompass the addition of one or several residues in a coding or non-coding portion of the gene locus. Insertions can comprise an addition of between 1 and 50 base pairs in the gene locus. Deletions can encompass any region of one, two or more residues in a coding or non-coding portion of the gene locus, such as from two residues up to the entire gene or locus. Deletions can affect smaller regions, such as domains (introns) or repeated sequences or fragments of less than about 50 consecutive base pairs, although larger deletions can occur as well. Rearrangement includes inversion of sequences. The carbohydrate transporter gene locus alteration or carbohydrate metabolic enzyme gene locus alteration can result in amino acid substitutions, RNA splicing or processing, product instability, the creation of stop codons, frame-shift mutations, and/or truncated polypeptide production. The alteration can result in the production of a carbohydrate transporter polypeptide or a carbohydrate metabolic enzyme with altered function, stability, targeting or structure. The alteration can also cause a reduction in protein expression. In one embodiment, the alteration in a carbohydrate transporter gene locus can comprise a point mutation, a deletion, or an insertion in the carbohydrate transporter gene or corresponding expression product. In another embodiment, the alteration in a carbohydrate metabolic enzyme gene locus can comprise a point mutation, a deletion, or an insertion in the carbohydrate metabolic enzyme gene or corresponding expression product. In one embodiment, the alteration can be a deletion or partial deletion of a carbohydrate transporter gene or a carbohydrate metabolic enzyme gene. The alteration can be determined at the level of the DNA, RNA, or polypeptide of a carbohydrate transporter or a carbohydrate metabolic enzyme.

In another embodiment, the method can comprise detecting the presence of an altered RNA expression of a carbohydrate transporter or a carbohydrate metabolic enzyme. Altered RNA expression includes the presence of an altered RNA sequence, the presence of an altered RNA splicing or processing, or the presence of an altered quantity of RNA. These can be detected by various techniques known in the art, including by sequencing all or part of the RNA of a carbohydrate transporter or a carbohydrate metabolic enzyme, or by selective hybridization or selective amplification of all or part of the RNA. In a further embodiment, the method can comprise detecting the presence of an altered polypeptide expression of a carbohydrate transporter or a carbohydrate metabolic enzyme. Altered polypeptide expression includes the presence of an altered polypeptide sequence, the presence of an altered quantity of carbohydrate transporter polypeptide or carbohydrate metabolic enzyme polypeptide, or the presence of an altered tissue distribution. These can be detected by various techniques known in the art, including by sequencing and/or binding to specific ligands (such as antibodies).

Various techniques known in the art can be used to detect or quantify altered gene expression, RNA expression, or sequence, which include, but are not limited to, hybridization, sequencing, amplification, and/or binding to specific ligands (such as antibodies). Other suitable methods include allele-specific oligonucleotide (ASO), oligonucleotide ligation, allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, denaturing HLPC, melting curve analysis, heteroduplex analysis, RNase protection, chemical or enzymatic mismatch cleavage, ELISA, radio-immunoassays (RIA) and immunoenzymatic assays (IEMA). Some of these approaches (such as SSCA and CGGE) are based on a change in electrophoretic mobility of the nucleic acids, as a result of the presence of an altered sequence. According to these techniques, the altered sequence is visualized by a shift in mobility on gels. The fragments can then be sequenced to confirm the alteration. Some other approaches are based on specific hybridization between nucleic acids from the subject and a probe specific for wild type or altered gene or RNA. The probe can be in suspension or immobilized on a substrate. The probe can be labeled to facilitate detection of hybrids. Some of these approaches are suited for assessing a polypeptide sequence or expression level, such as Northern blot, ELISA and RIA. These latter require the use of a ligand specific for the polypeptide, for example, the use of a specific antibody.

Sequencing. Sequencing can be carried out using techniques well known in the art, using automatic sequencers. The sequencing can be performed on the complete gene or on specific domains thereof, such as those known or suspected to carry deleterious mutations or other alterations.

Amplification. Amplification is based on the formation of specific hybrids between complementary nucleic acid sequences that serve to initiate nucleic acid reproduction. Amplification can be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Useful techniques in the art encompass real-time PCR, allele-specific PCR, or PCR-SSCP. Amplification usually requires the use of specific nucleic acid primers, to initiate the reaction. For example, nucleic acid primers useful for amplifying sequences from the gene or locus of a carbohydrate transporter (such as GLUT2 or SGLT1) or a carbohydrate metabolic enzyme (such as SI, MGAM, or LCT) are able to specifically hybridize with a portion of the gene locus that flanks a target region of the locus, wherein the target region is altered in certain subjects having autism or an autism spectrum disorder. In one embodiment, amplification comprises using forward and reverse RT-PCR primers comprising nucleotide sequences of SEQ ID NOS: 26, 27, 29, 30, 32, 33, 35, 36, 38, or 39.

The invention provides for a nucleic acid primer, wherein the primer can be complementary to and hybridize specifically to a portion of a coding sequence (e.g., gene or RNA) of a carbohydrate transporter (such as GLUT2 or SGLT1) or a carbohydrate metabolic enzyme (such as SI, MGAM, or LCT) that is altered in certain subjects having autism or an autism spectrum disorder. Primers of the invention can thus be specific for altered sequences in a gene or RNA of a carbohydrate transporter or a carbohydrate metabolic enzyme. By using such primers, the detection of an amplification product indicates the presence of an alteration in the gene or the absence of such gene. Examples of primers of this invention can be single-stranded nucleic acid molecules of about 5 to 60 nucleotides in length, or about 8 to about 25 nucleotides in length. The sequence can be derived directly from the sequence of the carbohydrate transporter or the carbohydrate metabolic enzyme gene (e.g., GLUT2 or SGLT1, and SI, MGAM, or LCT, respectively). Perfect complementarity is useful, to ensure high specificity. However, certain mismatch can be tolerated. In one embodiment, the primer can be an isolated nucleic acid comprising a nucleotide sequence of SEQ ID NOS: 26, 27, 29, 30, 32, 33, 35, 36, 38, or 39. For example, a nucleic acid primer or a pair of nucleic acid primers as described above can be used in a method for detecting the presence of or a predisposition to autism or an autism spectrum disorder in a subject.

Amplification methods include, e.g., polymerase chain reaction, PCR (PCR PROTOCOLS, A GUIDE TO METHODS AND APPLICATIONS, ed. Innis, Academic Press, N.Y., 1990 and PCR STRATEGIES, 1995, ed. Innis, Academic Press, Inc., N.Y., ligase chain reaction (LCR) (see, e.g., Wu, Genomics 4:560, 1989; Landegren, Science 241:1077, 1988; Barringer, Gene 89:117, 1990); transcription amplification (see, e.g., Kwoh, Proc. Natl. Acad. Sci. USA 86:1173, 1989); and, self-sustained sequence replication (see, e.g., Guatelli, Proc. Natl. Acad. Sci. USA 87:1874, 1990); Q Beta replicase amplification (see, e.g., Smith, J. Clin. Microbiol. 35:1477-1491, 1997), automated Q-beta replicase amplification assay (see, e.g., Burg, Mol. Cell. Probes 10:257-271, 1996) and other RNA polymerase mediated techniques (e.g., NASBA, Cangene, Mississauga, Ontario); see also Berger, Methods Enzymol. 152:307-316, 1987; Sambrook; Ausubel; U.S. Pat. Nos. 4,683,195 and 4,683,202; Sooknanan, Biotechnology 13:563-564, 1995. All the references stated above are incorporated by reference in their entireties.

Selective Hybridization. Hybridization detection methods are based on the formation of specific hybrids between complementary nucleic acid sequences that serve to detect nucleic acid sequence alteration(s). A detection technique involves the use of a nucleic acid probe specific for wild type or altered gene or RNA, followed by the detection of the presence of a hybrid. The probe can be in suspension or immobilized on a substrate or support (for example, as in nucleic acid array or chips technologies). The probe can be labeled to facilitate detection of hybrids. In one embodiment, the probe according to the invention can comprise a nucleic acid having SEQ ID NOS: 28, 31, 34, 37, or 40. For example, a sample from the subject can be contacted with a nucleic acid probe specific for a wild type carbohydrate transporter or carbohydrate metabolic enzyme gene or an altered carbohydrate transporter or carbohydrate metabolic enzyme gene, and the formation of a hybrid can be subsequently assessed. In one embodiment, the method comprises contacting simultaneously the sample with a set of probes that are specific, respectively, for the wild type carbohydrate transporter or carbohydrate metabolic enzyme gene and for various altered forms thereof. Thus, it is possible to detect directly the presence of various forms of alterations in the carbohydrate transporter gene (e.g., GLUT2 or SGLT1) or carbohydrate metabolic enzyme gene (e.g., SI, MGAM, or LCT) in the sample. Also, various samples from various subjects can be treated in parallel.

According to the invention, a probe can be a polynucleotide sequence which is complementary to and specifically hybridizes with a, or a target portion of a, carbohydrate transporter or carbohydrate metabolic enzyme gene or RNA, and that is suitable for detecting polynucleotide polymorphisms associated with alleles of such, which predispose to or are associated with autism or an autism spectrum disorder. Useful probes are those that are complementary to the carbohydrate transporter or carbohydrate metabolic enzyme gene, RNA, or target portion thereof. Probes can comprise single-stranded nucleic acids of between 8 to 1000 nucleotides in length, for instance between 10 and 800, between. 15 and 700, or between 20 and 500. Longer probes can be used as well. A useful probe of the invention is a single stranded nucleic acid molecule of between 8 to 500 nucleotides in length, which can specifically hybridize to a region of a gene or RNA that carries an alteration.

The sequence of the probes can be derived from the sequences of the carbohydrate transporter or carbohydrate metabolic enzyme genes provided herein. Nucleotide substitutions can be performed, as well as chemical modifications of the probe. Such chemical modifications can be accomplished to increase the stability of hybrids (e.g., intercalating groups) or to label the probe. Some examples of labels include, without limitation, radioactivity, fluorescence, luminescence, and enzymatic labeling.

A guide to the hybridization of nucleic acids is found in e.g., Sambrook, ed., MOLECULAR CLONING: A LABORATORY MANUAL ($2^{ND}$ ED.), Vols. 1-3, Cold Spring Harbor Laboratory, 1989; CURRENT PROTOCOLS IN MOLECULAR BIOLOGY, Ausubel, ed. John Wiley & Sons, Inc., New York, 1997; LABORATORY TECHNIQUES IN BIOCHEMISTRY AND MOLECULAR BIOLOGY: HYBRIDIZATION WITH NUCLEIC ACID PROBES, PART I. Theory and Nucleic Acid Preparation, Tijssen, ed. Elsevier, N.Y., 1993.

Specific Ligand Binding. As indicated herein, alteration in a carbohydrate transporter or carbohydrate metabolic enzyme gene locus or in carbohydrate transporter or carbohydrate metabolic enzyme expression can also be detected by screening for alteration(s) in corresponding polypeptide sequence or expression levels. Different types of ligands can be used, such as specific antibodies. In one embodiment, the sample is contacted with an antibody specific for a carbohydrate transporter or carbohydrate metabolic enzyme polypeptide and the formation of an immune complex is subsequently determined. Various methods for detecting an immune complex can be used, such as ELISA, radioimmunoassays (RIA) and immuno-enzymatic assays (IEMA).

For example, an antibody can be a polyclonal antibody, a monoclonal antibody, as well as fragments or derivatives thereof having substantially the same antigen specificity. Fragments include Fab, Fab'2, or CDR regions. Derivatives include single-chain antibodies, humanized antibodies, or poly-functional antibodies. An antibody specific for a carbohydrate transporter or a carbohydrate metabolic enzyme polypeptide can be an antibody that selectively binds a carbohydrate transporter or carbohydrate metabolic enzyme polypeptide, respectively, namely, an antibody raised against a carbohydrate transporter or carbohydrate metabolic enzyme polypeptide or an epitope-containing fragment thereof. Although non-specific binding towards other antigens can occur, binding to the target polypeptide occurs with a higher affinity and can be reliably discriminated from non-specific binding. In one embodiment, the method comprises contacting a sample from the subject with an antibody specific for a wild type or an altered form of a carbohydrate transporter or carbohydrate metabolic enzyme polypeptide, and determining the presence of an immune complex. Optionally, the sample can be contacted to a support coated with antibody specific for the wild type or altered form of a carbohydrate transporter or carbohydrate metabolic enzyme polypeptide. In one embodiment, the sample can be contacted simultaneously, or in parallel, or sequentially, with various antibodies specific for different forms of a carbohydrate transporter or carbohydrate metabolic enzyme polypeptide, such as a wild type and various altered forms thereof.

The invention also provides for a diagnostic kit comprising products and reagents for detecting in a sample from a subject the presence of an alteration in a carbohydrate transporter gene (e.g., GLUT2 or SGLT1) or a carbohydrate metabolic enzyme gene (e.g., SI, MGAM, or LCT), or a carbohydrate transporter polypeptide or carbohydrate metabolic enzyme polypeptide; alteration in the expression of a carbohydrate transporter gene (e.g., GLUT2 or SGLT1) or carbohydrate metabolic enzyme gene (e.g., SI, MGAM, or LCT), or a carbohydrate transporter or carbohydrate metabolic enzyme polypeptide; and/or an alteration in carbohydrate transporter or carbohydrate metabolic enzyme activity. The kit can be useful for determining whether a sample from a subject exhibits reduced carbohydrate transporter or carbohydrate metabolic enzyme expression or exhibits a gene deletion of a carbohydrate transporter (e.g., GLUT2 or SGLT1) or carbohydrate metabolic enzyme (e.g., SI, MGAM, or LCT). For example, the diagnostic kit according to the present invention comprises any primer, any pair of primers, any nucleic acid probe and/or any ligand, (for example, an antibody directed to a carbohydrate transporter or carbohydrate metabolic enzyme). The diagnostic kit according to the present invention can further comprise reagents and/or protocols for performing a hybridization, amplification or antigen-antibody immune reaction. In one embodiment, the kit can comprise nucleic acid primers that specifically hybridize to and can prime a polymerase reaction from a carbohydrate transporter (e.g., GLUT2 or SGLT1) or carbohydrate metabolic enzyme (e.g., SI, MGAM, or LCT). In another embodiment, the primer can comprise a nucleotide sequence of SEQ ID NOS: 26, 27, 29, 30, 32, 33, 35, 36, 38, or 39.

The diagnosis methods can be performed in vitro, ex vivo, or in vivo. These methods utilize a sample from the subject in order to assess the status of a carbohydrate transporter gene locus or a carbohydrate metabolic enzyme gene locus. The sample can be any biological sample derived from a subject, which contains nucleic acids or polypeptides. Examples of such samples include, but are not limited to, fluids, tissues, cell samples, organs, or tissue biopsies. Non-limiting examples of samples include blood, plasma, saliva, urine, or seminal fluid. Pre-natal diagnosis can also be performed by testing fetal cells or placental cells, for instance. Screening of parental samples can also be used to determine risk/likelihood of offspring possessing the germline mutation. The sample can be collected according to conventional techniques and used directly for diagnosis or stored. The sample can be treated prior to performing the method, in order to render or improve availability of nucleic acids or polypeptides for testing. Treatments include, for instance, lysis (e.g., mechanical, physical, or chemical), centrifugation. Also, the nucleic acids and/or polypeptides can be pre-purified or enriched by conventional techniques, and/or reduced in complexity. Nucleic acids and polypeptides can also be treated with enzymes or other chemical or physical treatments to produce fragments thereof. In one embodiment, the sample is contacted with reagents, such as probes, primers, or ligands, in order to assess the presence of an altered carbohydrate transporter gene locus or carbohydrate metabolic enzyme gene locus. Contacting can be performed in any suitable device, such as a plate, tube, well, or glass. In specific embodiments, the contacting is performed on a substrate coated with the reagent, such as a nucleic acid array or a specific ligand array. The substrate can be a solid or semi-solid substrate such as any support comprising glass, plastic, nylon, paper, metal, or polymers. The substrate can be of various forms and sizes, such as a slide, a membrane, a bead, a column, or a gel. The contacting can be made under any condition suitable for a complex to be formed between the reagent and the nucleic acids or polypeptides of the sample.

Identifying an altered polypeptide, RNA or DNA of a carbohydrate transporter (e.g., GLUT2 or SGLT1) or a carbohydrate metabolic enzyme (e.g., SI, MGAM, or LCT) in the sample is indicative of the presence of an altered carbohydrate transporter or carbohydrate metabolic enzyme gene in the subject, which can be correlated to the presence, predisposition or stage of progression of autism or an autism spectrum disorder. For example, an individual having a germ line mutation in a carbohydrate transporter gene (e.g., GLUT 2 or SGLT1) or a carbohydrate metabolic enzyme gene (e.g., SI, MGAM, or LCT) has an increased risk of developing autism or an autism spectrum disorder. The determination of the presence of an altered gene locus in a subject also allows the design of appropriate therapeutic intervention, which is more effective and customized. Also, this determination at the pre-symptomatic level allows a preventive regimen to be applied.

GI Bacterial Colonization in ASD Subjects

An aspect of the invention provides for a new PCR strategy for the identification, quantitation, and taxonomic classification of *Sutterella* bacterial colonization from biological samples. As shown in Example 2 herein, intestinal biopsies of children with autism accompanied by gastrointestinal (GI) complaints showed highly significant elevation of intestinal levels of *Sutterella* bacteria. These findings can provide insights into pathogenesis of autism associated with GI disorder, enabling new strategies for therapeutic intervention.

Bacterial members of the genus *Sutterella*, a class of Betaproteobacteria in the order Burkholderiales and the family Alcaligenaceae have been associated with human infections below the diaphragm (A1). Furthermore, *Sutterella* sp. sequences have been identified in intestinal biopsies and fecal samples from individuals with Crohn's disease and ulcerative colitis (A2, A3). *Sutterella* sp. have also been found in canine faeces and the cecal microbiota of domestic and wild turkeys (A4, A5). However, little is known about the pathogenic potential of *Sutterella* sp. According to the *Sutterella* sp.-specific PCR methods described herein, *Sutterella* detection can be achieved in a mammal, such as a dog, a cat, a cow, a horse, a rabbit, a monkey, a pig, a sheep, a goat, a turkey, or a human.

*Sutterella* bacterial infections have been associated with ASD in addition to Crohn's disease and ulcerative colitis. Bacterial infections are also associated with various intestinal diseases, such as irritable bowel syndrome (IBS). Over 40 million people in the U.S. suffer from irritable bowel syndrome (IBS), a type of inflammatory bowel disease. IBS, though not fatal, has a huge impact on quality-of-life. After the common cold, IBS is the second most common reason for missed work and is estimated to generate $30B in healthcare costs. Few simple molecular diagnostic tests for IBS/IBD are presently available. Diagnosis usually relies upon symptom analysis and/or invasive colonoscopy procedures. The IBD/IBS diagnostics market has significant growth potential.

Little is known of the epidemiology and pathogenesis of *Sutterella* infection and their role in Crohn's disease, ASD, and ulcerative colitis. Current methods for *Sutterella* biopsies are costly, laborious and non-specific. There are no known rapid, specific, or cost-effective technologies to identify *Sutterella* sp. in biological samples.

An aspect of the invention provides for a PCR assay that allows for rapid identification, quantification, classification, and diagnosis of *Sutterella* sp. in biological or industrial samples. This would allow for specific therapies to be implemented in subjects in need (e.g., ASD patients, IB patients, intestinal disease patients, etc.) following identification of *Sutterella* in infections. Directed administration of antimicrobial agents (e.g., antibiotics) that limit the growth of *Sutterella* could be fascilitated rapidly following identification of *Sutterella* species. An antibiotic refers to any compound known to one of ordinary skill in the art that will inhibit the growth of, or kill, bacteria. Useful, non-limiting examples of an antibiotic include lincosamides (clindomycin); chloramphenicols; tetracyclines (such as Tetracycline, Chlortetracycline, Demeclocycline, Methacycline, Doxycycline, Minocycline); aminoglycosides (such as Gentamicin, Tobramycin, Netilmicin, Amikacin, Kanamycin, Streptomycin, Neomycin); beta-lactams (such as penicillins, cephalosporins, Imipenem, Aztreonam); vancomycins; bacitracins; macrolides (erythromycins), amphotericins; sulfonamides (such as Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole); Methenamin; Nitrofurantoin; Phenazopyridine; trimethoprim; rifampicins; metronidazoles; cefazolins; Lincomycin; Spectinomycin; mupirocins; quinolones (such as Nalidixic Acid, Cinoxacin, Norfloxacin, Ciprofloxacin, Perfloxacin, Ofloxacin, Enoxacin, Fleroxacin, Levofloxacin); novobiocins; polymixins; gramicidins; and antipseudomonals (such as Carbenicillin, Carbenicillin Indanyl, Ticarcillin, Azlocillin, Mezlocillin, Piperacillin) or any salts or variants thereof. Such antibiotics can be obtained commercially, e.g., from Daiichi Sankyo, Inc. (Parsipanny, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of bacterial infection.

In one embodiment, the invention provides for a method of detecting *Sutterella* sp. DNA from biological or industrial sources, e.g. intestinal tissue, feces, blood, or skin. In another embodiment, the invention provides for *Sutterella* diagnostics to detect *Sutterella* sp. in samples from children with autism as well as patients with intestinal disease, e.g. irritable bowel syndrome (IBS). In some embodiments, the invention provides for PCR-based methods of assessing a subject's response to exposure to therapeutic treatments directed at bacterial infections, for example, *Sutterella* sp. infections, or exposure to other pathogens.

For example, primers having SEQ ID NOS: 11, 12, 15, or 16 can be used for detecting *Sutterella* sp. DNA. SEQ ID NOS: 17 and 18 can also be used for detecting *Sutterella* sp. DNA.

Sutt For Primer (SEQ ID NO: 17)-

5'-CGGTGGATGATGTGGATTAATTCGA*Y*GCAA*CGCGAAAAACCTTACSYAGCC*

TTGACCATG*YCRR*GAA*BBY*BB*VDKRR*-3'

Sutt Rev Primer (SEQ ID NO: 18)-

5'-CCCTCTGTTCCGACCATTGTAT*GACGTGTGARGCCCYAGCQR*TAAGGGCCA
TGAGGACT-3'

Sutt Probe 3 (SEQ ID NO: 19)-

5'-GT*RCCCGHAAGRGARYYYGRRCACAGGTGCTGCATGGCTGTCGTCAG*CTCG

TGTCGTG*RGATRTYRRG*TTA*R*GTCCCGCA*RCR*AGCGCAACCCTY*GW*CA*Y*-3'

In addition to the primers having SEQ ID NOS: 11, 12, and 15-18, additional primers containing any part of SEQ ID NOS: 17, 18, or 19 and containing any portion of the italicized DNA sequence regions can be used to assess the presence or absence of *Sutterella* species. Further, inclusion of degenerate bases (bolded and underlined) can be used to increase coverage of *Sutterella* species (for example, where S can be a G nucleotide and/or a C nucleotide; where Y can be a C nucleotide and/or T nucleotide; where R can be an A nucleotide and/or G nucleotide; where W can be an A nucleotide and/or T nucleotide; where H can be an A nucleotide and/or T nucleotide and/or C nucleotide; where B can be a T nucleotide, C nucleotide, or G nucleotide; where V can be an A nucleotide, G nucleotide, or C nucleotide; where D can be an A nucleotide, G nucleotide, or T nucleotide; where K can be a G nucleotide or T nucleotide).

In addition to the highlighted probe sequence of SEQ ID NO:19 as well as SEQ ID NOS: 13 and 14, any portion of SEQ ID NO: 19 shown above can be used for *Sutterella* species detection and quantitation. The reverse complement of SEQ ID NOS: 11, 12, or 15-19 can also be used to detect the opposite DNA strand of *Sutterella* species 16S rRNA genes.

The invention can be used to detect *Sutterella* sp. 16S rRNA sequences in small amounts of DNA from any biological or industrial source. These sources include, but are not limited to human or animal intestinal tissue, feces, blood, or skin (swabs or tissue). Based on these findings, the invention can be used to detect, quantitate, and classify *Sutterella* sp. in biological samples from children with Autism. In one embodiment, the invention can be used to detect *Sutterella* sp. in biological samples from individuals with various forms of intestinal disease. Intestinal diseases include, but are not limited to, Crohn's disease and Ulcerative colitis. In one embodiment, detection of *Sutterella* sp. can occur in biological samples from any undiagnosed infection below or above the diaphragm. The invention will allow for large cohort investigations of *Sutterella* sp. in the aforementioned, and as yet to be determined, diseases in order to establish an association between *Sutterella* sp. and disease manifestation. In one embodiment, the presence and quantity of *Sutterella* sp. in intestinal tissues can be investigated following any number of experimental manipulations. Experimental manipulations include, but are not limited to, responses to chemicals (i.e. antibiotics), changes in diet, pathogen exposure (i.e. pathogenic viruses, bacteria, fungi), or probiotic usage. The rapid identification of *Sutterella* sp. in human and animal samples facilitated by this invention can lead to rapid diagnosis and directed antimicrobial treatment of infections caused by *Sutterella* sp.

Gene. Vectors, Recombinant Cells, and Polypeptides

The invention encompasses an altered or mutated genes of a carbohydrate transporter or carbohydrate metabolic enzyme, or a fragment thereof. The invention also encompasses nucleic acid molecules encoding an altered or mutated polypeptide of s carbohydrate transporter or carbohydrate metabolic enzyme, or a fragment thereof. The alteration or mutation of the nucleotide or amino acid sequence modifies the carbohydrate transporter or carbohydrate metabolic enzyme activity, respectively. The invention provides for a vector that comprises a nucleic acid encoding a carbohydrate transporter or carbohydrate metabolic enzyme polypeptide (for example, a nucleic acid comprising SEQ ID NO: 2 or 4, and a nucleic acid comprising SEQ ID NO: 6, 8, or 10, respectively) or mutant thereof. The vector can be a cloning vector or an expression vector, i.e., a vector comprising regulatory sequences causing resulting in the expression of carbohydrate transporter or carbohydrate metabolic enzyme polypeptides from the vector in a competent host cell. These vectors can be used to express polypeptides, or mutants thereof, of carbohydrate transporters or carbohydrate metabolic enzymes in vitro, ex vivo, or in vivo, to create transgenic or Knock-Out non-human animals, to amplify the nucleic acids, or to express antisense RNAs.

The nucleic acids used to practice the invention, whether RNA, RNAi, antisense nucleic acid, cDNA, genomic DNA, vectors, viruses or hybrids thereof, can be produced or isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems. Alternatively, these nucleic acids can be synthesized in vitro by well-known chemical synthesis techniques, as described in, e.g., Adams, J. Am. Chem. Soc. 105:661, 1983; Belousov, Nucleic Acids Res. 25:3440-3444, 1997; Frenkel, Free Radic. Biol. Med. 19:373-380, 1995; Blommers, Biochemistry 33:7886-7896, 1994; Narang, Meth. Enzymol. 68:90, 1979; Brown Meth. Enzymol. 68:109, 1979; Beaucage, Tetra. Lett. 22:1859, 1981; U.S. Pat. No. 4,458,066, all of which are incorporated by reference in their entireties.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which can be chemically synthesized.

Techniques for the manipulation of nucleic acids, such as, subcloning, labeling probes (for example, random-primer labeling using Klenow polymerase, nick translation, amplification), sequencing, and hybridization are well described in the scientific and patent literature, see, e.g., Sambrook, ed., MOLECULAR CLONING: A LABORATORY MANUAL ($2^{ND}$ ED.), Vols. 1-3, Cold Spring Harbor Laboratory, 1989; CURRENT PROTOCOLS IN MOLECULAR BIOLOGY, Ausubel, ed. John Wiley & Sons, Inc., New York, 1997; LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y., 1993.

Nucleic acids, vectors, or polypeptides can be analyzed and quantified by any of a number of general means well known to those of skill in the art. These include, for example, analytical biochemical methods such as radiography, electrophoresis, NMR, spectrophotometry, capillary electrophoresis, thin layer chromatography (TLC), high performance liquid chromatography (HPLC), and hyperdiffusion chromatography; various immunological methods, such as immuno-electrophoresis, Southern analysis, Northern analysis, dot-blot analysis, fluid or gel precipitation reactions, immunodiffusion, quadrature radioimmunoassay (RIAs), enzyme-linked immunosorbent assays (ELISAs), immunofluorescent assays, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld, Nat. Genet. 15:333-335, 1997; yeast artificial chromosomes (YAC); bacterial artificial chromosomes (BAC); P1 artificial chromosomes, see, e.g., Woon, Genomics 50:306-316, 1998; P1-derived vectors (PACs), see, e.g., Kern, Biotechniques 23:120-124, 1997; cosmids, recombinant viruses, phages or plasmids The vectors of this invention can comprise a coding sequence for a carbohydrate transporter molecule or a carbohydrate metabolic enzyme molecule that is operably linked to regulatory sequences, e.g., a promoter, or a polyA tail. Operably linked indicates that the coding and regulatory sequences are functionally associated so that the regulatory sequences cause expression (e.g., transcription) of the coding sequences. The vectors can further comprise one or several origins of replication and/or selectable markers. The promoter region can be homologous or heterologous with respect to the coding sequence, and can provide for ubiquitous, constitutive, regulated and/or tissue specific expression, in any appropriate host cell, including for in vivo use. Examples of promoters include bacterial promoters (T7, pTAC, Trp promoter), viral promoters (LTR, TK, CMV-IE), mammalian gene promoters (albumin, PGK), etc.

The vector can be a plasmid, a virus, a cosmid, a phage, a BAC, a YAC. Plasmid vectors can be prepared from commercially available vectors such as pBluescript, pUC, or pBR.

Viral vectors can be produced from baculoviruses, retroviruses, adenoviruses, or AAVs, according to recombinant DNA techniques known in the art. In one embodiment, a recombinant virus can encode a polypeptide of a carbohydrate transporter or carbohydrate metabolic enzyme of the invention. The recombinant virus is useful if replication-defective, for example, if selected from E1- and/or E4-defective adenoviruses, Gag-, pol- and/or env-defective retroviruses and Rep- and/or Cap-defective AAVs. Such recombinant viruses can be produced by techniques known in the art, such as by transfecting packaging cells or by transient transfection with helper plasmids or viruses. Examples of virus packaging cells include PA317 cells, PsiCRIP cells, GPenv+ cells, or 293 cells. Detailed protocols for producing such replication-defective recombinant viruses can be found for instance in WO95/14785, WO96/22378, U.S. Pat. Nos. 5,882,877, 6,013,516, 4,861,719, 5,278,056 and WO94/19478, which are all hereby incorporated by reference.

In another embodiment, the invention provides for a recombinant host cell comprising a recombinant carbohydrate transporter gene (e.g., GLUT2 or SGLT1) or a carbohydrate metabolic enzyme gene (e.g., SI, MGAM, or LCT), or a recombinant vector as described herein. Suitable host cells include, without limitation, prokaryotic cells (such as bacteria) and eukaryotic cells (such as yeast cells, mammalian cells, insect cells, or plant cells). Specific examples include *E. coli*, the yeasts *Kluyveromyces* or *Saccharomyces*, mammalian cell lines (e.g., Vero cells, CHO cells, 3T3 cells, or COS cells) as well as primary or established mammalian cell cultures (e.g., produced from fibroblasts, embryonic cells, epithelial cells, nervous cells, or adipocytes). In a further embodiment, the invention provides a method for producing a recombinant host cell expressing a polypeptide of a carbohydrate transporter or carbohydrate metabolic enzyme. The method can entail (a) introducing in vitro or ex vivo into a competent host cell a recombinant nucleic acid or a vector as described herein, (b) culturing in vitro or ex vivo the recombinant host cells obtained, and (c) optionally, selecting the cells which express the polypeptide of a carbohydrate transporter or carbohydrate metabolic enzyme. Such recombinant host cells can be used for the production of carbohydrate transporter or carbohydrate metabolic enzyme polypeptides, as well as for screening of active molecules, as described below. Such cells can also be used as a model system to study autism. These cells can be maintained in suitable culture media, such as HAM, DMEM, or RPMI, in any appropriate culture device (plate, flask, dish, tube, or pouch).

The practice of aspects of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Caner and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986). All patents, patent applications and references cited herein are incorporated in their entirety by reference.

Administration and Dosing

A carbohydrate transporter molecule (e.g., GLUT2 or SGLT1) or carbohydrate metabolic enzyme molecule (e.g., SI, MGAM, or LCT) can be administered to the subject once (e.g., as a single injection or deposition). Alternatively, a carbohydrate transporter or carbohydrate metabolic enzyme molecule of the invention can be administered once or twice daily to a subject in need thereof for a period of from about two to about twenty-eight days, or from about seven to about ten days. It can also be administered once or twice daily to a subject for a period of 1, 2, 3, 4, 5, 6, 7, 8, 9, 10, 11, 12 times per year, or a combination thereof. Furthermore, the carbohydrate transporter or carbohydrate metabolic enzyme molecule of the invention can be co-administrated with another therapeutic, such as an anti-depressant, an anti-psychotic, a benzodiazepine drug, or a combination thereof. Where a dosage regimen comprises multiple administrations, the effective amount of the carbohydrate transporter or carbohydrate metabolic enzyme molecule administered to the subject can comprise the total amount of gene product administered over the entire dosage regimen.

The carbohydrate transporter or carbohydrate metabolic enzyme molecules of the invention can be administered to a subject by any means suitable for delivering the carbohydrate transporter or carbohydrate metabolic enzyme molecules to cells of the subject, such as ileum cell or cecum cells. For example, carbohydrate transporter or carbohydrate metabolic enzyme molecules can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with autism or an ASD by any means that produces contact of the active ingredient with the agent's site of action in the body of an animal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. (1985), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use.

Lyophilized forms are also included. Pharmaceutical compositions of the present invention are characterized as being at least sterile and pyrogen-free. These pharmaceutical formulations include formulations for human and veterinary use.

Pharmaceutical formulations of the invention can comprise a carbohydrate transporter or carbohydrate metabolic enzyme molecule (e.g., 0.1 to 90% by weight), or a physiologically acceptable salt thereof, mixed with a pharmaceutically-acceptable carrier. The pharmaceutical formulations of the invention can also comprise the carbohydrate transporter or carbohydrate metabolic enzyme molecules of the invention which are encapsulated by liposomes and a pharmaceutically-acceptable carrier. Useful pharmaceutically-acceptable carriers are water, buffered water, normal saline, 0.4% saline, 0.3% glycine, or hyaluronic acid.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, or magnesium carbonate.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, or magnesium carbonate. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, or sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Nucleic acids, peptides, or polypeptides of the invention, when administered orally, can be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix, Pharm Res. 13: 1760-1764, 1996; Samanen, J. Pharm. Pharmacol. 48: 119-135, 1996; U.S. Pat. No. 5,391,377, describing lipid compositions for oral delivery of therapeutic agents (for example, liposomal delivery). In one embodiment, the carbohydrate transporter molecule (e.g., GLUT2 or SGLT1) or carbohydrate metabolic enzyme molecule (e.g., SI, MGAM, or LCT) can be delivered to the alimentary canal or intestine of the subject via oral administration that is can withstand digestion and degradation.

For oral administration, the therapeutic compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active agent. For buccal administration the therapeutic compositions can take the form of tablets or lozenges formulated in a conventional manner. For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflate or can be formulated containing a powder mix of the therapeutic agents and a suitable powder base such as lactose or starch.

The therapeutic compositions can be formulated for parenteral administration by injection, e.g., by bolus injection or continuous infusion. Formulations for injection can be presented in unit dosage form, e.g., in ampoules or in multidose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Suitable enteral administration routes for the present methods include oral, rectal, or intranasal delivery. Suitable parenteral administration routes include intravascular administration (e.g. intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. For example, the carbohydrate transporter or carbohydrate metabolic enzyme molecules of the invention can be administered by injection, infusion, or oral delivery.

In addition to the formulations described previously, the therapeutic compositions can also be formulated as a depot preparation. Such long acting formulations can be administered by implantation (for example subcutaneously or intramuscularly) or by intramuscular injection. For example, the therapeutic compositions can be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents can be used to facilitate permeation. Transmucosal administration can be through nasal sprays or using suppositories. For topical administration, the compositions of the invention are formulated into ointments, salves, gels, or creams as generally known in the art. A wash solution can be used locally to treat an injury or inflammation to accelerate healing. For oral administration, the therapeutic compositions are formulated into conventional oral administration forms such as capsules, tablets, and tonics.

A composition of the present invention can also be formulated as a sustained and/or timed release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the present invention.

In the present methods, the carbohydrate transporter or carbohydrate metabolic enzyme molecules can be administered to the subject either as RNA, in conjunction with a delivery reagent, or as a nucleic acid (e.g., a recombinant plasmid or viral vector) comprising sequences which expresses the gene product. Suitable delivery reagents for administration of the carbohydrate transporter or carbohydrate metabolic enzyme molecules include the Mirus Transit TKO lipophilic reagent; lipofectin; lipofectamine; cellfectin; or polycations (e.g., polylysine), or liposomes.

The dosage administered can be a therapeutically effective amount of the composition sufficient to result in amelioration of symptoms of autism or an autism spectrum disorder in a subject, and can vary depending upon known factors such as the pharmacodynamic characteristics of the active ingredient and its mode and route of administration; age, sex, health and weight of the recipient; nature and extent of symptoms; kind of concurrent treatment, frequency of treatment and the effect desired. For example, an effective enzyme unit of amount of SI, MGAM, and/or LCT can be administered to a subject in need thereof. The enzyme unit (U) is a unit for the amount of a particular enzyme. One U is defined as the amount of the enzyme that catalyzes the conversion of 1 micro mole of substrate per minute. In one embodiment, the therapeutically effective amount of the administered carbohydrate enzyme (e.g., SI, MGAM, or LCT) is at least about 1 U, at least about 10 U, at least about 20 U, at least about 25 U, at least about 50 U, at least about 100 U, at least about 150 U, at least about 200 U, at least about 250 U, at least about 300 U, at least about 350 U, at least about 400 U, at least about 450 U, at least about 500 U, at least about 550 U, at least about 600 U, at least about 650 U, at least about 700 U, at least about 750 U, at least about 800 U, at least about 850 U, at least about 900 U, at least about 950 U, at least about 1000 U, at least about 1250 U, at least about 1500 U, at least about 1750 U, at least about 2000 U, at least about 2250 U, at least about 2500 U, at least about 2750 U, at least about 3000 U, at least about 3250 U, at least about 3500 U, at least about 4000 U, at least about 4500 U, at least about 5000 U, at least about 5500 U, at least about 6000 U, at least about 6500 U, at least about 7000 U, at least about 7500 U, at least about 8000 U, at least about 8500 U, at least about 9000 U, at least about 9250 U, at least about 9500 U, or at least about 10,000 U.

In some embodiments, the effective amount of the administered carboydrate transporter molecule (e.g., GLUT2 or SGLT1) is at least about 0.01 µg/kg body weight, at least about 0.025 µg/kg body weight, at least about 0.05 µg/kg body weight, at least about 0.075 µg/kg body weight, at least about 0.1 µg/kg body weight, at least about 0.25 µg/kg body weight, at least about 0.5 µg/kg body weight, at least about 0.75 µg/kg body weight, at least about 1 µg/kg body weight, at least about 5 µg/kg body weight, at least about 10 µg/kg body weight, at least about 25 µg/kg body weight, at least about 50 µg/kg body weight, at least about 75 µg/kg body weight, at least about 100 µg/kg body weight, at least about 150 µg/kg body weight, at least about 200 µg/kg body weight, at least about 250 µg/kg body weight, at least about 300 µg/kg body weight, at least about 350 µg/kg body weight, at least about 400 µg/kg body weight, at least about 450 µg/kg body weight, at least about 500 µg/kg body weight, at least about 550 µg/kg body weight, at least about 600 µg/kg body weight, at least about 650 µg/kg body weight, at least about 700 µg/kg body weight, at least about 750 µg/kg body weight, at least about 800 µg/kg body weight, at least about 850 µg/kg body weight, at least about 900 µg/kg body weight, at least about 950 µg/kg body weight, or at least about 1000 µg/kg body weight.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

A therapeutically effective dose of carbohydrate transporter or carbohydrate metabolic enzyme molecules can depend upon a number of factors known to those or ordinary skill in the art. The dose(s) of the carbohydrate transporter or carbohydrate metabolic enzyme molecules can vary, for example, depending upon the identity, size, and condition of the subject or sample being treated, further depending upon the route by which the composition is to be administered, if applicable, and the effect which the practitioner desires the carbohydrate transporter or carbohydrate metabolic enzyme molecules to have upon the nucleic acid or polypeptide of the invention. These amounts can be readily determined by a skilled artisan.

Pharmaceutical Composition and Therapy

The invention provides methods for treating or preventing autism or an autism spectrum disorder in a subject. In one embodiment, the method can comprise administering to the subject a functional (e.g., wild-type) carbohydrate transporter molecule (e.g., GLUT2 or SGLT1) or carbohydrate metabolic enzyme molecule (e.g., SI, MGAM, or LCT), which can be a polypeptide or a nucleic acid.

Various approaches can be carried out to restore the carbohydrate transporter or carbohydrate metabolic enzyme activity or function in a subject, such as those carrying an altered gene locus comprising a carbohydrate transporter gene (e.g., GLUT2 or SGLT1) or a carbohydrate metabolic enzyme gene (e.g., SI, MGAM, or LCT). Supplying wild-type function of the carbohydrate transporter or carbohydrate metabolic enzyme to such subjects can suppress phenotypic expression of autism or an autism spectrum disorders in a pathological cell or organism. Increasing carbohydrate transporter or carbohydrate metabolic enzyme activity can be accomplished through gene or protein therapy as discussed later herein.

A nucleic acid encoding a carbohydrate transporter or carbohydrate metabolic enzyme or a functional part thereof can be introduced into the cells of a subject in one embodiment of the invention. The wild-type carbohydrate transporter gene or carbohydrate metabolic enzyme gene (or a functional part thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extra-chromosomal. Integration can occur randomly or at precisely defined sites, such as through homologous recombination. For example, a functional copy of the carbohydrate transporter gene or a carbohydrate metabolic enzyme gene can be inserted in replacement of an altered version in a cell, through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

Gene Therapy and Protein Replacement Methods

Delivery of nucleic acids into viable cells can be effected ex vivo, in situ, or in vivo by use of vectors, and more particularly viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpes viruses including HSV and EBV (Margolskee, 1992; Johnson et al., 1992; Fink et al., 1992; Breakfield and Geller, 1987; Freese et al., 1990), and retroviruses of avian (Biandyo-padhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Non-limiting examples of in vivo gene transfer techniques include transfection with viral (typically retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; and U.S. Application Publication Nos. 2002/0077313 and 2002/00069, which are all hereby incorporated by reference in their entireties. For additional reviews of gene therapy technology, see Friedmann, Science, 244:1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2):108-15; Herweijer et al., Gene Ther. 2007 January; 14(2):99-107; Eliyahu et al., Molecules, 2005 Jan. 31; 10(1): 34-64; and Altaras et al., Adv Biochem Eng Biotechnol. 2005; 99:193-260, all of which are hereby incorporated by reference in their entireties.

Protein replacement therapy can increase the amount of protein by exogenously introducing wild-type or biologically functional protein by way of infusion. A replacement polypeptide can be synthesized according to known chemical techniques or can be produced and purified via known molecular biological techniques. Protein replacement therapy has been developed for various disorders. For example, a wild-type protein can be purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

A polypeptide encoded by a carbohydrate transporter gene (e.g., GLUT2 or SGLT1) or a carbohydrate metabolic enzyme gene (for example, SI, MGAM, or LCT) can also be delivered in a controlled release system. For example, the polypeptide can be administered using intravenous infusion, an implantable osmotic pump, a transdermal patch, liposomes, or other modes of administration. In one embodiment, a pump can be used (see is Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

These methods described herein are by no means all-inclusive, and further methods to suit the specific application is understood by the ordinary skilled artisan. Moreover, the effective amount of the compositions can be further approximated through analogy to compounds known to exert the desired effect.

\* \* \*

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Identification of Carbohydrate Transporters and Carbohydrate Metabolic Enzymes as Biomarkers in a Subset of Autism Spectrum Disorders (ASD)

Gastrointestinal disturbances complicate clinical management in some children with autism. Reports of ileo-colonic lymphoid nodular hyperplasia and deficiencies in disaccharidase enzymatic activity led to the survey of intestinal gene expression and microflora in children with autism and gastrointestinal disease (AUT-GI) or gastrointestinal disease alone (Control-GI). In AUT-GI subjects, ileal transcripts for the disaccharidases sucrase isomaltase, maltase glucoamylase, and lactase, and the monosaccharide transporters, sodium-dependent glucose co-transporter, and glucose transporter 2 were significantly decreased. Alterations in intestinal carbohydrates as a result of these deficiencies would have a distinct impact on the composition of AUT-GI intestinal microbiota. Bacterial 16S rRNA gene pyrosequencing analysis of biopsy material from ileum and cecum revealed decreased Bacteroidetes, increased Firmicute/Bacteroidete ratios, higher cumulative levels of Firmicutes and Proteobacteria, and increased Betaproteobacteria in AUT-GI as compared with Control-GI biopsies. These results indicate a complex dependence between intestinal gene expression and bacterial community structure that contributes to gastrointestinal dysfunction in AUT-GI children.

Deficiencies in intestinal disaccharidase and/or glucoamylase activity are reported in over half of autistic children with gastrointestinal disturbances (AUT-GI) (Horvath et al., 1999). To determine whether functional deficits reflect decreased levels of mRNA encoding these enzymes transcript levels were examined for three primary brush border disaccharidases (sucrase isomaltase [SI], maltase glucoamylase [MGAM], and lactase [LCT]) in ileal biopsies of AUT-GI and Control-GI children by real time PCR. Levels of mRNA for all three enzymes were decreased in AUT-GI: SI (FIG. 16A: Mann-Whitney, p=0.001), MGAM (FIG. 16B: Mann-Whitney, p=0.003) and LCT (FIG. 16C: Mann-Whitney, p=0.032). Deficiencies in LCT mRNA in AUT-GI children were not attributable to disproportionate adult-type hypolactasia genotypes in the AUT-GI group relative to the Control-GI group (FIGS. 21A-21E and Methods). Within the ASD-GI group, 86.7% (SI), 80% (MGAM), and 80% (LCT) of children had transcript levels below the $25^{th}$ percentile of Control-GI children (Table 5A). Nearly all (14/15, or 93.3%) AUT-GI children had deficiencies in at least one disaccharidase enzyme; 80% had deficiencies in 2 or more enzymes; and 73.3% had deficiencies in all three enzymes (Table 5A). Tables 5A-C are summary tables for gene expression and bacterial assays. Increases or decreases in AUT-GI children in both gene expression and bacterial parameters were determined for each individual based on the levels of each parameter in the Control-GI group. The values for a given parameter in the AUT-GI children that exceeded the $75^{th}$ (arrow pointing up) percentile or were below the $25^{th}$ percentile (arrow pointing down) for the corresponding parameter in the Control-GI children were scored as an increase or decrease, respectively. Values that were also above the $90^{th}$ or below the $10^{th}$ percentiles of Control-GI children are indicated by double arrows.

TABLE 5A

Summary tables for gene expression and bacterial assays.

| ASD Patient # | SI | MGAM | LCT | SGLT1 | GLUT2 | CDX2 | Villin | # Disaccharidases | # Transporters | Total |
|---|---|---|---|---|---|---|---|---|---|---|
| 1 | ⇓⇓ | ⇓⇓ | ⇓⇓ | ⇓⇓ | ⇓⇓ | ⇓ | n.c. | 3/3 | 2/2 | 5/5 |
| 2 | ⇓⇓ | ⇓⇓ | ⇓⇓ | ⇓⇓ | ⇓⇓ | ⇓⇓ | ⇓⇓ | 3/3 | 2/2 | 5/5 |
| 3 | ⇓⇓ | ⇓⇓ | ⇓⇓ | ⇓⇓ | ⇓⇓ | ⇓⇓ | ⇑⇑ | 3/3 | 2/2 | 5/5 |
| 4 | ⇓⇓ | ⇓⇓ | ⇓⇓ | ⇓⇓ | ⇓⇓ | n.c. | ⇑⇑ | 3/3 | 2/2 | 5/5 |
| 5 | ⇓⇓ | ⇓⇓ | ⇓⇓ | ⇓⇓ | ⇓⇓ | ⇓⇓ | ⇓⇓ | 3/3 | 2/2 | 5/5 |
| 6 | ⇓⇓ | n.c. | n.c. | n.c. | n.c. | n.c. | n.c. | 1/3 | 0/2 | 1/5 |
| 7 | n.c. | n.c. | ⇑⇑ | n.c. | n.c. | ⇑ | ⇑⇑ | 0/3 | 0/2 | 0/5 |
| 8 | ⇓⇓ | ⇓⇓ | ⇓ | ⇓⇓ | ⇓⇓ | n.c. | ⇑ | 3/3 | 2/2 | 5/5 |
| 9 | ⇓⇓ | ⇓⇓ | ⇓⇓ | ⇓⇓ | n.c. | n.c. | ⇑ | 3/3 | 1/2 | 4/5 |
| 10 | ⇓⇓ | ⇓⇓ | ⇓⇓ | ⇓⇓ | ⇓⇓ | n.c. | ⇑ | 3/3 | 212 | 5/5 |
| 11 | ⇓⇓ | ⇓⇓ | ⇓⇓ | ⇓⇓ | ⇓⇓ | n.c. | ⇓ | 3/3 | 2/2 | 5/5 |
| 12 | ⇓⇓ | ⇓⇓ | ⇓⇓ | ⇓⇓ | ⇓⇓ | n.c. | n.c. | 3/3 | 2/2 | 5/5 |
| 13 | ⇓⇓ | ⇓⇓ | ⇓⇓ | ⇓⇓ | ⇓⇓ | ⇓⇓ | ⇓⇓ | 3/3 | 2/2 | 5/5 |
| 14 | ⇓⇓ | ⇓⇓ | n.c. | n.c. | ⇓⇓ | n.c. | ⇑⇑ | 2/3 | 1/2 | 3/5 |
| 15 | n.c. | n.c. | ⇓⇓ | n.c. | n.c. | n.c. | n.c. | 1/3 | 0/2 | 1/5 |
| % below controls | 86.7% | 80.0% | 80.0% | 73.3% | 73.3% | 33.3% | 26.7% | Summary All 3 = 73.3% At least 2 = 80% At least 1 = 93.3% | Summary Both = 66.7% At least 1 = 80% | Summary All 5 = 66.7% At least 4 = 73.3% At least 3 = 80% At least 1 = 93.3% |

TABLE 5B

Summary tables for gene expression and bacterial assays.

| ASD Patient # | Bacteroidetes | | | | Firmicutes | | | | |
|---|---|---|---|---|---|---|---|---|---|
| | Bacteroidetes RT-Ileum | Bacteroidetes RT-Cecum | Bacteroidetes 454-Ileum | Bacteroidetes 454-Cecum | Firmicutes RT-Ileum | Firmicutes RT-Cecum | Firmicutes 454-Ileum | Firmicutes 454-Cecum | Clostridia 454-Ileum |
| 1 | ⇓ | ⇓⇓ | ⇓⇓ | ⇓⇓ | ⇑ | ⇑ | ⇑⇑ | ⇑⇑ | ⇑⇑ |
| 2 | ⇓⇓ | ⇓ | ⇓⇓ | ⇓⇓ | ⇑⇑ | ⇑⇑ | ⇓ | n.c. | ⇓ |
| 3 | ⇓⇓ | ⇓⇓ | ⇓ | ⇓⇓ | ⇑ | ⇑ | ⇑⇑ | ⇑ | ⇑⇑ |
| 4 | ⇓⇓ | ⇓ | ⇓⇓ | ⇓⇓ | ⇑⇑ | ⇑⇑ | ⇑⇑ | ⇑⇑ | ⇑⇑ |
| 5 | ⇓⇓ | ⇓ | ⇑ | n.c. | n.c. | n.c. | ⇓ | n.c. | ⇓ |
| 6 | ⇓ | n.c. | n.c. | ⇑ | ⇑ | ⇑⇑ | ⇑ | n.c. | ⇑⇑ |
| 7 | ⇓ | ⇓ | ⇓ | ⇓⇓ | n.c. | ⇑ | ⇑⇑ | ⇑⇑ | ⇑⇑ |
| 8 | ⇓⇓ | ⇓⇓ | ⇓⇓ | ⇓⇓ | n.c. | n.c. | n.c. | n.c. | n.c. |
| 9 | ⇓ | ⇓ | ⇓⇓ | ⇓⇓ | ⇑ | n.c. | ⇑⇑ | ⇑⇑ | ⇑⇑ |
| 10 | ⇓ | ⇓ | ⇓⇓ | ⇓⇓ | n.c. | n.c. | ⇑⇑ | ⇑⇑ | ⇑⇑ |
| 11 | ⇓⇓ | ⇓⇓ | ⇓⇓ | ⇓⇓ | ⇑⇑ | ⇑⇑ | n.c. | n.c. | ⇑ |
| 12 | ⇓ | ⇓ | n.c. | n.c. | n.c. | n.c. | n.c. | n.c. | n.c. |
| 13 | ⇓⇓ | ⇓ | ⇓ | ⇓⇓ | n.c. | ⇑ | ⇑⇑ | ⇑⇑ | ⇑⇑ |
| 14 | ⇓ | n.c. | ⇓ | n.c. | n.c. | n.c. | ⇑⇑ | n.c. | ⇑⇑ |
| 15 | ⇓⇓ | ⇓ | ⇓ | ⇓⇓ | ⇓⇓ | ⇓⇓ | ⇓⇓ | ⇓⇓ | ⇓⇓ |
| % below or above controls | 100% | 86.7% | 80.0% | 73.3% | 46.7% | 53.3% | 60.0% | 46.7% | 66.7% |

TABLE 5B-continued

Summary tables for gene expression and bacterial assays.

Firmicutes | Proteobacteria

| ASD Patient # | Clostridia 454-Cecum | Lach. + Rumino. 454-Ileum | Lach. + Rumino. 454-Cecum | Proteobacteria 454-Ileum | Proteobacteria 454-Cecum | Beta-Proteobacteria 454-Ileum | Beta-Proteobacteria 454-Cecum | Sutterella-RT & 454 (Ileum & Cecum) |
|---|---|---|---|---|---|---|---|---|
| 1 | ↑↑ | ↑↑ | ↑↑ | n.c. | n.c. | ↑↑ | ↑↑ | ↑↑ |
| 2 | n.c. | ⇩ | n.c. | ↑↑ | ↑↑ | ↑↑ | ↑↑ | n.c. |
| 3 | ↑↑ | ↑↑ | ↑↑ | n.c. | n.c. | ↑↑ | ↑↑ | ↑↑ |
| 4 | ↑↑ | ↑↑ | ↑↑ | n.c. | n.c. | ↑ | n.c. | n.c. |
| 5 | n.c. | ⇩ | n.c. | n.c. | ↑ | ↑↑ | ↑↑ | ↑↑ |
| 6 | n.c. | ↑↑ | n.c. | ⇩⇩ | ⇩ | ⇩ | ⇩⇩ | n.c. |
| 7 | ↑↑ | ↑↑ | ↑↑ | n.c. | n.c. | n.c. | ↑ | ↑↑ |
| 8 | n.c. | n.c. | n.c. | ↑↑ | ↑↑ | ⇩ | n.c. | n.c. |
| 9 | ↑↑ | ↑↑ | ↑↑ | n.c. | n.c. | n.c. | ↑↑ | n.c. |
| 10 | ↑↑ | ↑↑ | ↑↑ | n.c. | n.c. | ↑↑ | ↑↑ | ↑↑ |
| 11 | n.c. | n.c. | n.c. | ↑↑ | ↑↑ | ↑↑ | ↑↑ | ↑↑ |
| 12 | n.c. | n.c. | n.c. | n.c. | n.c. | ↑↑ | ↑↑ | ↑↑ |
| 13 | ↑↑ | ↑↑ | ↑↑ | n.c. | ↑↑ | n.c. | ↑↑ | n.c. |
| 14 | ↑ | ↑↑ | ↑↑ | n.c. | n.c. | n.c. | n.c. | n.c. |
| 15 | ⇩⇩ | ⇩⇩ | ⇩⇩ | ↑↑ | ↑↑ | n.c. | ⇩⇩ | n.c. |
| % below or above controls | 53.3% | 60% | 53.3% | 26.7% | 40.0% | 53.3% | 68.7% | 46.7% |

TABLE 5C

Summary tables for gene expression and bacterial assays.

| ASD Patient # | Firm./Bacteroid. Ratio—RT Ileum | Firm./Bacteroid. Ratio—RT Cecum | Firm./Bacteroid. Ratio—454 Ileum | Firm./Bacteroid. Ratio—454 Cecum | Clostridiales/Bacteroidales Ratio—454 Ileum | Clostridiales/Bacteroidales Ratio—454 Cecum | Firm. + Proteobac. Ratio—454 Ileum | Firm. + Proteobac. Ratio—454 Ileum |
|---|---|---|---|---|---|---|---|---|
| 1 | ↑↑ | ↑↑ | ↑↑ | ↑↑ | ↑↑ | ↑↑ | ↑↑ | ↑↑ |
| 2 | ↑↑ | ↑↑ | ↑↑ | ↑ | ↑↑ | ↑ | ↑↑ | ↑↑ |
| 3 | ↑↑ | ↑↑ | ↑ | ↑↑ | ↑↑ | ↑↑ | ↑ | ↑↑ |
| 4 | ↑↑ | ↑↑ | ↑↑ | ↑↑ | ↑↑ | ↑↑ | ↑↑ | ↑↑ |
| 5 | ↑↑ | n.c. | ⇩ | n.c. | ⇩ | n.c. | ⇩ | n.c. |
| 6 | ↑↑ | ↑↑ | n.c. | n.c. | ↑ | n.c. | n.c. | ⇩ |
| 7 | ↑↑ | ↑ | ↑↑ | ↑↑ | ↑↑ | ↑↑ | ↑ | ↑↑ |
| 8 | ↑↑ | ↑ | ↑↑ | ↑↑ | ↑↑ | ↑↑ | ↑↑ | ↑↑ |
| 9 | ↑↑ | n.c. | ↑↑ | ↑↑ | ↑↑ | ↑↑ | ↑↑ | ↑↑ |
| 10 | ↑ | n.c. | ↑↑ | ↑↑ | ↑↑ | ↑↑ | ↑↑ | ↑↑ |
| 11 | ↑↑ | ↑↑ | ↑ | ↑ | ↑ | ↑↑ | ↑↑ | ↑↑ |
| 12 | ↑↑ | n.c. | n.c. | n.c. | n.c. | n.c. | n.c. | n.c. |
| 13 | ↑↑ | ↑↑ | ↑↑ | ↑↑ | ↑↑ | ↑↑ | ↑ | ↑↑ |
| 14 | ↑ | n.c. | ↑↑ | n.c. | ↑↑ | n.c. | ↑ | n.c. |
| 15 | ↑↑ | ⇩ | ⇩ | ⇩⇩ | ⇩ | ⇩⇩ | ↑↑ | ↑↑ |
| % above controls | 100% | 60% | 73.3% | 66.7% | 80.0% | 66.7% | 80% | 73.3% |

Two hexose transporters, SGLT1 and GLUT2, mediate transport of monosaccharides in the intestine. SGLT1, located on the luminal membrane of enterocytes, is responsible for the active transport of glucose and galactose from the intestinal lumen into enterocytes. GLUT2 transports glucose, galactose and fructose across the basolateral membrane into the circulation and can also translocate to the apical membrane (Kellett et al., 2008). Real-time PCR revealed a decrease in SGLT1 mRNA (FIG. 16D: Mann-Whitney, p=0.008) and GLUT2 mRNA (FIG. 16E: Mann-Whitney, p=0.010) in AUT-GI children. For SGLT1, 73.3% of AUT-GI children had transcript levels below the 25th percentile of Control-GI children; 73.3% of AUT-GI children had GLUT2 transcript levels below the $25^{th}$ percentile of Control-GI children (Table 5A). Deficiencies were found in at least one hexose transporter in 80% of AUT-GI children; 66.7% had deficiencies in both transporters. In total, 66.7% of AUT-GI children had mRNA deficiencies in all 5 molecules involved in carbohydrate digestion and transport (Table 5A). Expression levels were correlated (Bonferroni-adjusted Spearman rank order correlations) in the AUT-GI group for all gene combinations except LCT and GLUT2, for which only a trend was observed. In the Control-GI group, significance was limited to correlations of SI-MGAM, MGAM-SGLT1, and LCT-SGLT1 (Table 2).

(Khurana and George, 2008) were measured. Ileal villin mRNA levels were not decreased in AUT-GI children (Mann-Whitney, p=0.307) (FIG. 16F). Normalization of SI, MGAM, LCT, SGLT1 and GLUT2 to villin mRNA did not correct AUT-GI deficits in gene expression for these transcripts (FIGS. 22A-22E).

CDX2, a member of the caudal-related homeobox transcription factor family, regulates expression of SI, LCT, GLUT2, SGLT1 and villin (Suh and Traber, 1996; Troelsen et al., 1997; Uesaka et al., 2004; Balakrishnan et al., 2008; and Yamamichi et al., 2009). Real-time PCR experiments demonstrated lower levels of CDX2 mRNA in some AUT-GI subjects as compared with controls, but group differences were not significant (FIG. 16G: Mann-Whitney, p=0.192). Only 33.3% of AUT-GI patients had CDX2 mRNA levels below the $25^{th}$ percentile of the Control-GI group (FIG. 23A). However, 86.7% of AUT-GI children had CDX2 levels below the $50^{th}$ percentile of Control-GI children. Only one AUT-GI child (patient 7) had CDX2 levels above the $75^{th}$ percentile of Control-GI children. This child was the only subject who did not show signs of deficiencies in any disaccharidases or transporters (Table 5A). In the AUT-GI group, expression of CDX2 was correlated with that of SI, MGAM, LCT, SGLT1, GLUT2, and villin (Bonferroni-adjusted Spearman rank order correlations; Table 2). Among Control-GI subjects, the

TABLE 2

Spearman correlations between ileal gene expression and bacterial abundance variables.

|  | Group | SI | MGAM | LCT | SGLT1 | GLUT2 | Villin | CDX2 |
|---|---|---|---|---|---|---|---|---|
| SI | AUT | 1 | 0.89*** | 0.59* | 0.88** | 0.76** | 0.24 | 0.59* |
|  | Control | 1 | 0.93* | 0.54 | 0.68† | 0.75† | 0.57 | 0.68† |
| MGAM | AUT | — | 1 | 0.56* | 0.86** | 0.75** | 0.31 | 0.63* |
|  | Control | — | 1 | 0.75† | 0.82* | 0.64 | 0.71† | 0.82* |
| LCT | AUT | — | — | 1 | 0.62* | 0.52† | 0.58* | 0.65* |
|  | Control | — | — | 1 | 0.86* | 0.57 | 0.82* | 0.86* |
| SGLT1 | AUT | — | — | — | 1 | 0.71** | 0.34 | 0.54* |
|  | Control | — | — | — | 1 | 0.64 | 0.96* | 1.00* |
| GLUT2 | AUT | — | — | — | — | 1 | 0.51† | 0.69** |
|  | Control | — | — | — | — | 1 | 0.54 | 0.64 |
| Villin | AUT | — | — | — | — | — | 1 | 0.60* |
|  | Control | — | — | — | — | — | 1 | 0.96* |
| CDX2 | AUT | — | — | — | — | — | — | 1 |
|  | Control | — | — | — | — | — | — | 1 |
| Bacteroidetes Ileum | AUT | 0.33 | 0.10 | 0.31 | 0.52†$^a$ | 0.07 | 0.02 | −0.01 |
|  | Control | −0.29 | −0.29 | −0.32 | −0.18 | −0.75†$^a$ | 0.00 | −0.18 |
| Bacteroidetes Cecum | AUT | 0.18 | 0.06 | 0.23 | 0.33 | 0.05 | 0.12 | 0.10 |
|  | Control | −0.93* | −1.00* | −0.75† | −0.82* | −0.64 | −0.71† | −0.82* |
| Firmicutes Ileum | AUT | −0.61*$^a$ | −0.55*$^a$ | −0.00 | 0.12 | 0.23 | 0.64* | 0.48†$^a$ |
|  | Control | 0.43 | 0.36 | 0.18 | 0.32 | 0.61 | 0.14 | 0.32 |
| Firmicutes Cecum | AUT | −0.06 | 0.05 | −0.05 | 0.04 | 0.15 | 0.58* | 0.14 |
|  | Control | 0.86* | 0.86* | 0.68† | 0.89* | 0.86* | 0.79† | 0.89* |
| Firm./Bacteroid. Ileum | AUT | −0.72**$^a$ | −0.65*$^a$ | −0.61*$^a$ | −0.65*$^a$ | −0.55*$^a$ | 0.36 | −0.58*$^a$ |
|  | Control | 0.43 | 0.36 | 0.18 | 0.32 | 0.61 | 0.14 | 0.32 |
| Firm./Bacteroid. Cecum | AUT | −0.51†$^a$ | −0.08 | −0.11 | −0.23 | 0.00 | 0.42 | 0.06 |
|  | Control | 0.86* | 0.86* | 0.68† | 0.89* | 0.86* | 0.79† | 0.89* |
| Betaproteo. Ileum | AUT | −0.63* | −0.60* | −0.56* | −0.44† | −0.60* | −0.45† | −0.70** |
|  | Control | −0.75† | −0.82* | −0.54 | −0.61 | −0.57 | −0.39 | −0.61 |
| Betaproteo. Cecum | AUT | −0.56* | −0.59* | −0.64* | −0.51† | −0.61* | −0.61* | −0.85** |
|  | Control | −0.43 | −0.43 | 0.14 | −0.00 | 0.14 | 0.14 | −0.00 |

Spearman correlations are shown for the AUT-GI group alone (AUT) and the Control-GI group alone (Control).
* = p < 0.05,
** = p < 0.01,
*** = p < 0.001,
**** = p < 0.0001,
† = p < 0.1 (trend)
$^a$ = values obtained from bacteria-specific real-time PCR To determine whether reductions in disaccharidase and transporter transcript levels reflected loss of or damage to intestinal epithelial cells, mRNA levels associated with a tissue-specific marker restricted to these cells, villin expression of CDX2 was correlated only with that of MGAM, LCT, SGLT1, and villin (Table 2).

To determine whether deficient carbohydrate digestion and absorption influenced the composition of intestinal microflora, ileal and cecal biopsies from AUT-GI and Control-GI children were analyzed by bacterial 16S rRNA gene pyrosequencing (See also Methods and FIGS. 23A-23D). Bacteroidetes and Firmicutes were the most prevalent taxa present in the ileal and cecal tissues of AUT-GI children, with the exception of the ileal samples of patients 2, 15, and 19 and cecal samples of patient 15, wherein levels of Proteobacteria exceeded those of Firmicutes and/or Bacteroidetes (FIGS. 17A-B and FIGS. 24A-B). Other phyla identified at lower levels included Verrucomicrobia, Actinobacteria, Fusobacteria, Lentisphaerae, TM7, and Cyanobacteria, as well as unclassified bacterial sequences (FIGS. 17A-B and FIGS. 24A-24D). The abundance of Bacteroidetes was lower in AUT-GI ileal (FIG. 17C: Mann-Whitney, p=0.012) and cecal samples (FIG. 17D: Mann-Whitney, p=0.008) as compared with the abundance of Bacteroidetes in Control-GI samples. Real-time PCR using Bacteroidete-specific primers confirmed decreases in Bacteroidetes in AUT-GI ilea (FIG. 17E: Mann-Whitney, p=0.003) and ceca (FIG. 17F: Mann-Whitney, p=0.022), with levels below the $25^{th}$ percentile of Control-GI children in 100% of AUT-GI ilea and 86.7% of AUT-GI ceca (Table 5B). Family-level analysis of Bacteroidete diversity from pyrosequencing reads indicateed that losses among members of the family Bacteroidaceae in AUT-GI patient samples contributed substantially to overall decreases in Bacteroidete levels in ilea (FIG. 17G) and ceca (FIG. 17H). OTU (Operational Taxonomic Unit) analysis of Bacteroidete sequences indicated that deficiencies in Bacteroidete sequences in AUT-GI subjects were attributable to cumulative losses of 12 predominant phylotypes of Bacteroidetes, rather than loss of any one specific phylotype (FIGS. 25A-25E and Methods).

Figure 26:
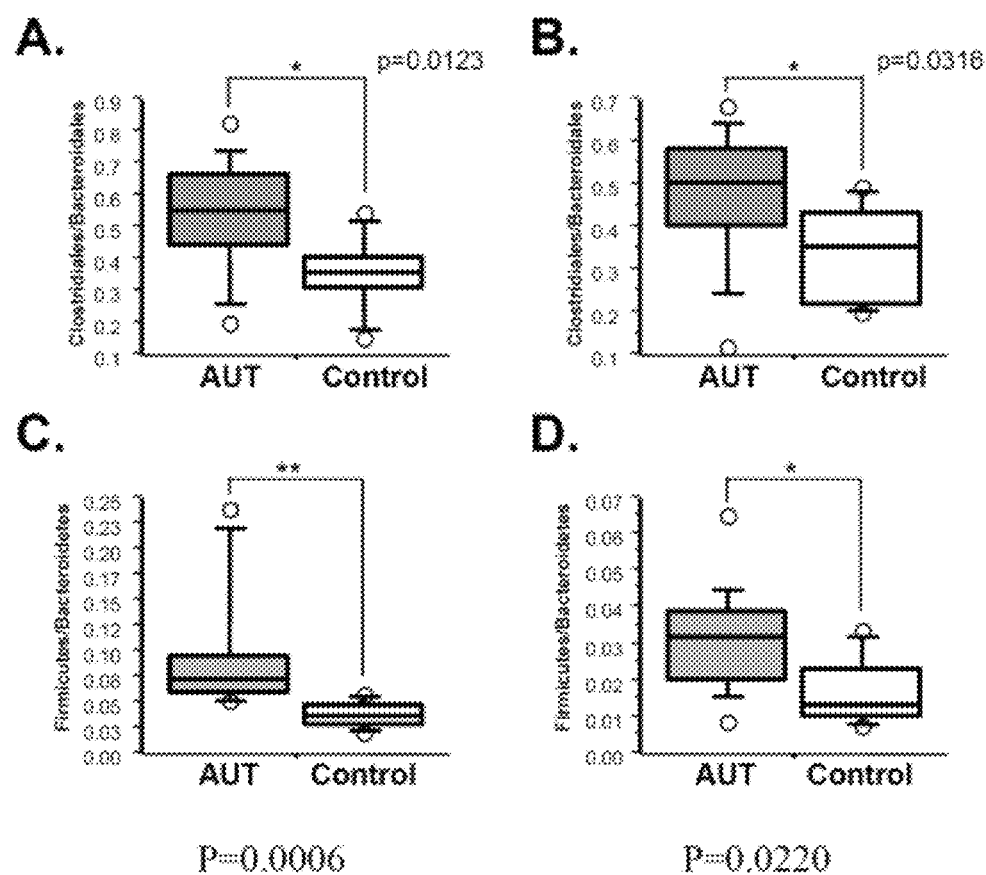
FIG. 26 shows graphs depicting order-level analysis. of Firmicute/Bacteroidete ratio and confirmation by real-time PCR.

Analysis of pyrosequencing reads revealed an increase in Firmicute/Bacteroidete ratios in AUT-GI ilea (FIG. 18A: Mann-Whitney, p=0.026) and ceca (FIG. 18B: Mann-Whitney, v0.032). An increase was also observed at the order level for Clostridiales/Bacteroidales ratios in ilea (FIG. 26A: Mann-Whitney, p=0.012) and ceca (FIG. 26B: Mann-Whitney, v0.032). Real-time PCR using Firmicute- and Bacteroidete-specific primers confirmed these increases in Firmicute/Bacteroidete ratios in AUT-GI ilea (FIG. 26C: Mann-Whitney, v0.0006) and ceca (FIG. 26D: Mann-Whitney, p=0.022). Firmicute/Bacteroidete ratios were above the $75^{th}$ percentile of Control-GI values in 100% of AUT-GI ilea and 60% of AUT-GI ceca (Table 5C). Order-level analysis of pyrosequencing reads indicated trends toward increased Clostridiales in AUT-GI ilea (FIG. 27E: Mann-Whitney, p=0.072) and ceca (FIG. 27F: Mann-Whitney, p=0.098). Family-level analysis revealed that increased Clostridiales levels in AUT-GI patient samples were largely attributable to increases in members of the families Lachnospiraceae and Ruminococcaceae (FIGS. 18C-18F). Cumulative levels of Lachnospiraceae and Ruminococcaceae above the $75^{th}$ percentile of the corresponding levels in Control-GI samples were found in 60% of AUT-GI ileal and 53.3% of AUT-GI cecal samples (FIGS. 18E-18F and Table 5B). Genus-level analysis indicated that members of the genus *Faecalibacterium* within the family Ruminococcaceae contributed to the overall trend toward increased *Clostridia* levels (FIGS. 28A-B). Within Lachnospiraceae, members of the genus Lachnopsiraceae Incertae Sedis, Unclassified Lachnospiraceae, and to a lesser extent *Bryantella* (cecum only) contributed to the overall trend toward increased *Clostridia* in ASD-GI patients (FIGS. 28A-B).

Figure 19E:
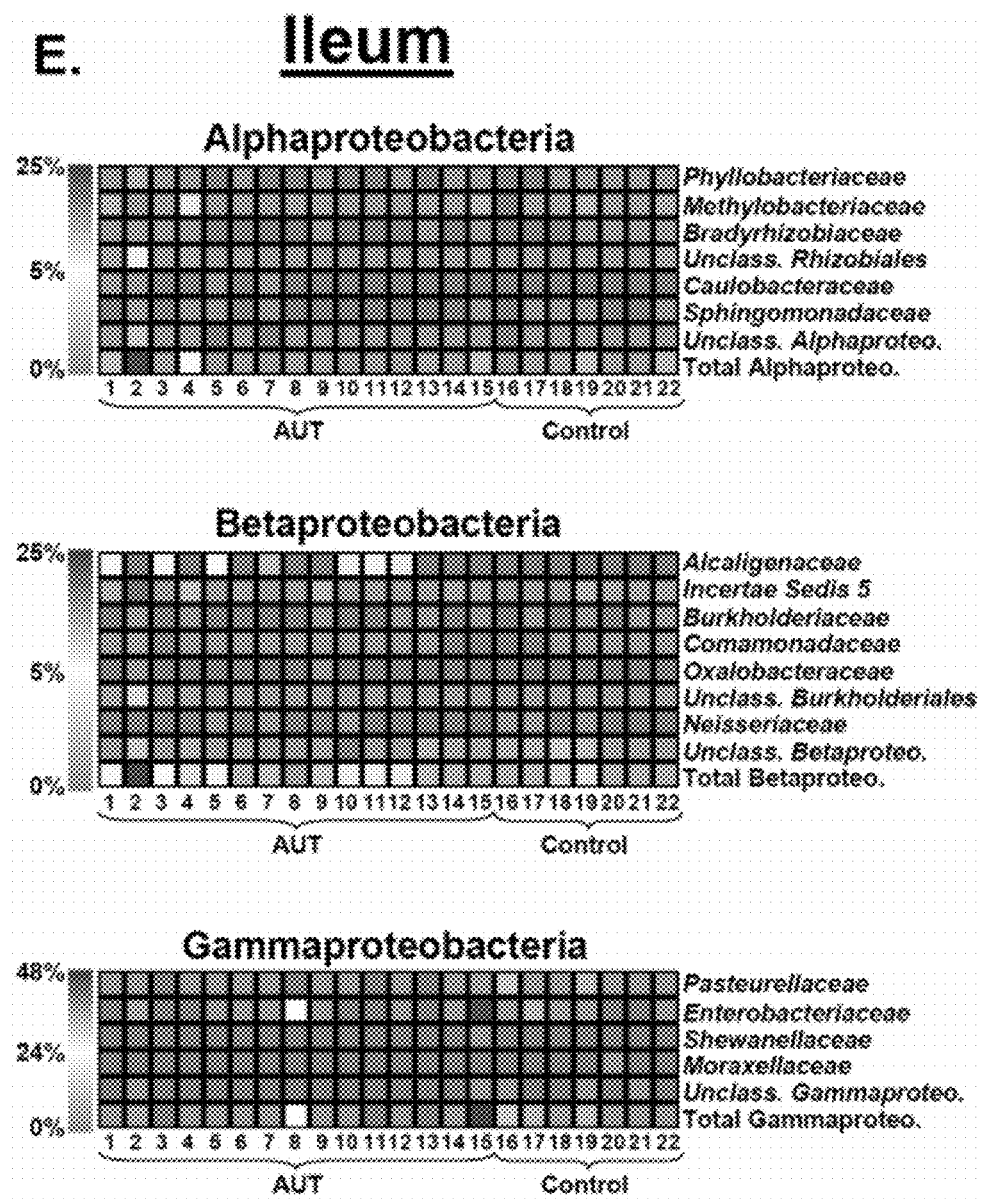
Figure 22:
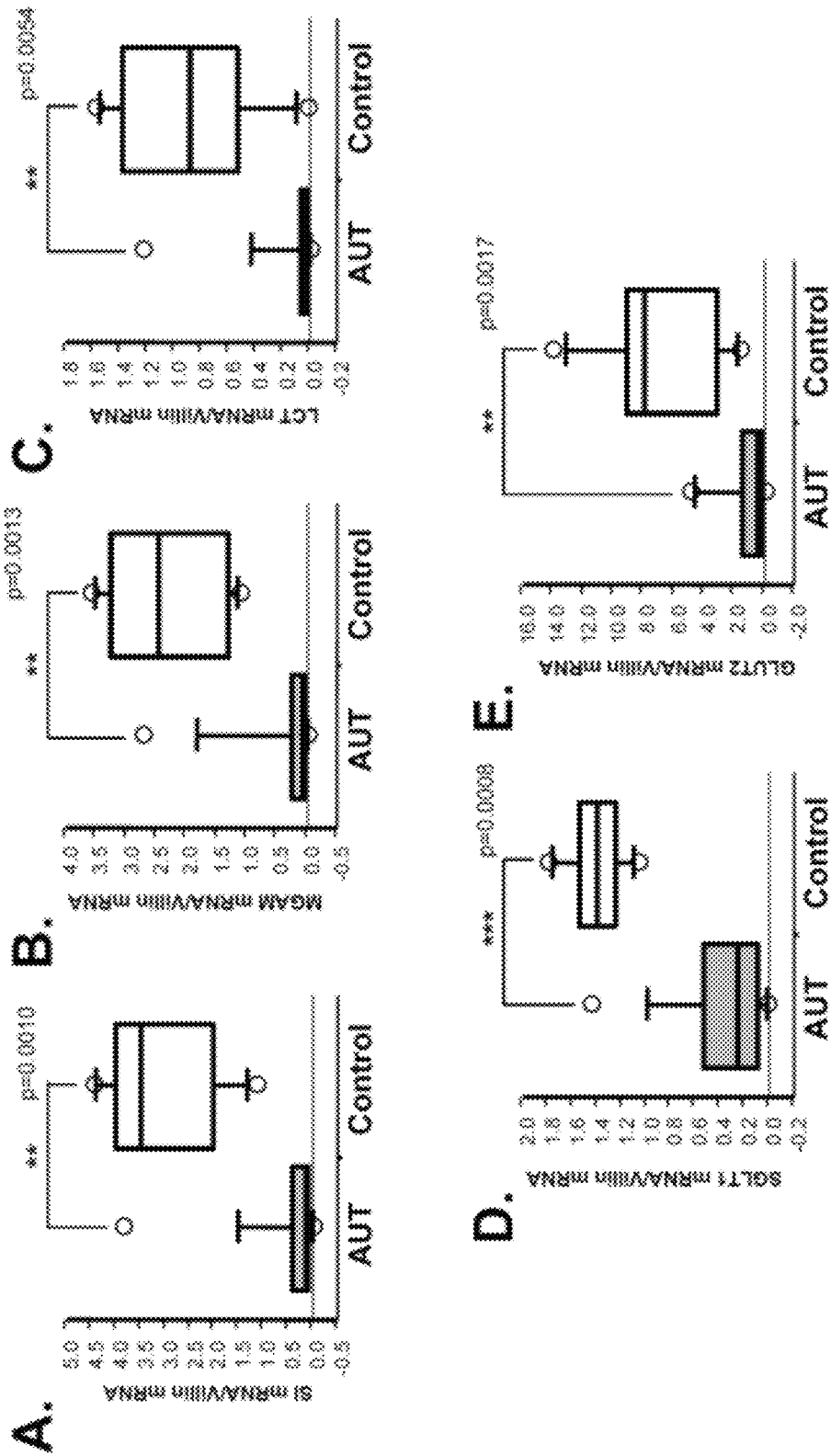
FIG. 22 shows graphs depicting Villin normalization and CDX2 expression stratified by total disaccharidase and transporter deficiencies. Disaccharidase or transporter mRNA/villin mRNA ratio for SI (FIG. 22A; Mann-Whitney, p=0.001), MGAM (FIG. 22B; Mann-Whitney, p=0.001), LCT (FIG. 22C; Mann-Whitney, p=0.005), SGLT1 (FIG. 22D; Mann-Whitney, p=0.0008), and GLUT2 (FIG. 22E; Mann-Whitney, p=0.002). *,p<0.05, ,p<0.01, *,p<0.001;†, p<0.1 (trend).

The cumulative level of Firmicutes and Proteobacteria was higher in AUT-GI group in both ileal (FIG. 18G: Mann-Whitney, p=0.015) and cecal samples (FIG. 18H: Mann-Whitney, p=0.007) (FIGS. 18I-J); however, neither Firmicute nor Proteobacteria levels showed significant differences on their own (FIGS. 19A-19B and FIGS. 27A-27D). Levels of Betaproteobacteria tended to be higher in the ilea of AUT-GI patients (FIG. 19C: Mann-Whitney, p=0.072); significantly higher levels of Betaproteobacteria were found in AUT-GI ceca (FIG. 19D: Mann-Whitney, p=0.038). Levels of Betaproteobacteria were above the $75^{th}$ percentile of Control-GI children in 53.3% of AUT-GI ilea and 66.7% of AUT-GI ceca (Table 5B). Family-level analysis revealed that members of the families Alcaligenaceae and Incertae Sedis 5 (patient 2 only) contributed substantively to the observed increases in Beta-Proteobacteria in ilea (FIG. 19E) and ceca (FIG. 19F). Alcaligenaceae sequences were detected in 46.7% of AUT-GI children and none of the Control-GI children. Overtly elevated levels of Proteobacteria in AUT-GI ilea and ceca reflected increased Alpha- (families Methylo-bacteriaceae and Unclassified Rhizobiales) and Betaproteobacteria (family Incertae Sedis 5) for patient #2 and increased Gammaproteobacteria (family Enterobacteriaceae) for patients #8 and #15 (FIGS. 19E-19F). Levels of Alpha-, Delta-, Gamma-, and Epsilonproteobacteria were not significantly different between AUT-GI and Control-GI samples.

The relationships between ileal and cecal microflora and levels of disaccharidases, transporters, villin, and CDX2 were assessed (Table 2). In the AUT-GI group, significant inverse Spearman correlations were found for ileal Firmicutes vs. SI and MGAM; the ileal Firmicute/Bacteroidete ratio vs. SI, MGAM, LCT, SGLT1, GLUT2, and CDX2; and ileal and cecal Betaproteobacteria vs. SI, MGAM, LCT, GLUT2, and CDX2. In the Control-GI group significant inverse Spearman correlations were found for cecal Bacteroidetes vs. SI, MGAM, SGLT1, and CDX2; as well as ileal Betaproteobacteria vs. MGAM. Positive Spearman correlations were also found in the Control-GI group: cecal Firmicutes vs. SI, MGAM, SGLT1, GLUT2, and CDX2; and cecal Firmicute/Bacteroidete ratio vs. SI, MGAM, SGLT1, GLUT2, and CDX2 (Table 2). These results indicate a complex dependence between carbohydrate metabolizing and transporting genes and the composition of the intestinal microbiome (See FIG. 20A-20C).

Discussion

ASD are brain disorders defined using behavioral criteria; however, many affected individuals also have substantial GI morbidity. A previous report on GI disturbances in ASD found low activities of at least one disaccharidase or glucoamylase in duodenum in 58% of children examined (21 of 36) (Horvath et al., 1999). As described herein, 93.3% of AUT-GI children had decreased mRNA levels for at least one of the three disaccharidases (SI, MGAM, or LCT). In addition, decreased levels of mRNA were found for two important hexose transporters, SGLT1 and GLUT2. Transcripts for the enterocyte marker, villin, were not deficient in AUT-GI ilea; thus these deficiencies are unlikely to be due to a general loss of enterocytes. However, defects in enterocyte maturational or migration along the crypt-villus axis can compromise ranscriptional regulation of ileal enzymes and transporters (Hodin et al., 1995). The expression of CDX2, a master transcriptional regulator in the intestine, was correlated with expression of disaccharidases and transporters in AUT-GI children. Therefore, CDX2 could play a role in the observed expression deficits for these genes. Whatever the mechanism, reduced capacity for digestion and transport of carbohydrates can have profound effects. Within the intestine malabsorbed monosaccharides can lead to osmotic diarrhea; non-absorbed sugars can also serve as substrates for intestinal microflora that produce fatty acids and gases (methane, hydrogen, and carbon dioxide), promoting additional GI symptoms such as bloating and flatulence. The deficiency of even a single gene in this important pathway can result in severe GI disease, as occurs with Glucose-galactose malabsorption syndrome caused by SGLT1 deficiency, Fanconi-Bickel syndrome resulting from GLUT2 mutations, sucrase-isomaltase deficiency, and congenital lactase deficiency. Without being bound by theory, a potential link between neurological dysfunction and malabsorption in childhood autism has been indicated (Goodwin et al., 1971). Extra-intestinal manifestations of GI disease, including neurologic presentation, are described in patients with inflammatory bowel disease and celiac disease (Bushara 2005; Lossos et al., 1995; Gupta et al., 2005). An association between language regression and GI symptoms has been reported in ASD, supporting a link between GI disease and behavioral outcomes (Valicenti-McDermott et al., 2008). Outside the intestine, the major role of dietary carbohydrates is to serve as the primary source of cellular energy throughout the body. Following digestion, nearly all ingested carbohydrates are converted to glucose, which serves a central role in metabolism and cellular homeostasis. The brain, of all organs, is quantitatively the most energy-demanding, accounting for 50% of total body glucose utilization (Owen et al., 1967). Abnormalities in glucose metabolism and homeostasis have been documented in ASD: recovery of blood glucose levels was delayed in ASD children following insulin-induced hypoglycemia (Maher et al., 1975). Brain glucose metabolism is decreased in ASD by positron emission tomography (Toal et al., 2005; Haznedar et al., 2000; Haznedar et al., 2006). Without being bound by theory, a reduced capacity to digest carbohydrates and absorb glucose due to deficient expression of disaccharidases and hexose transporters explains these previous observations in ASD.

Changes in diet can influence composition of intestinal microflora; thus, without being bound by theory carbohydrate malabsorption can have similar effects in AUT-GI subjects. 16S rRNA pyrosequencing revealed multicomponent dysbiosis in AUT-GI children including decreased levels of Bacteroidetes, an increase in the Firmicute/Bacteroidete ratio, increased cumulative levels of Firmicutes and Proteobacteria, and an increase in the class Betaproteobacteria. Bacteroidetes are implicated in mediating maturational and functional processes in the intestine as well as immune modulation. Monocolonization of mice with the prototypic gut symbiont, *Bacteroides thetaiotaomicron*, reverses the maturational defect in ileal epithelial glycan fucosylation that occurs in germ-free mice and regulates the expression of host genes, including SGLT-1 and LCT, that participate in key intestinal functions (i.e., nutrient absorption, metabolism, epithelial barrier function, and intestinal maturation) (Hooper et al., 2001).

A direct role for Bacteroidetes in carbohydrate metabolism is also evident. *B. thetaiotaomicron* encodes in its genome an expansive number of genes dedicated to polysaccharide acquisition and processing, including 236 glycoside hydrolases and 15 polysaccharide lyases (Flint et al., 2008). Thus, deficient digestion and absorption of di- and monosaccharides in the small intestine can alter the milieu of growth substrates in the ileum and cecum. As such, the growth advantages that Bacteroidetes enjoy in the healthy intestine as a result of their expansive capacity to thrive on polysaccharides can be compromised in AUT-GI children as bacterial species better suited for growth on undigested and unabsorbed carbohydrates flourish. Furthermore, polysaccharide A (PSA), a single molecule from another Bacteroidete member, *Bacteroides fragilis*, protects germ-free mice from *Helicobacter hepaticus*- and chemically-induced colitis by correcting defects in T-cell development, suppressing production of IL-17 and TNF-alpha, and inducing IL-10 (Mazmanian et al., 2008). These reports highlight the multiple roles Bacteroidete members play in the maintenance of intestinal homeostasis, including maturation of epithelium; regulation of intestinal gene expression, including carbohydrate metabolizing genes and transporters; metabolism of polysaccharides in the colon; and development of a competent immune system. Thus, deficient levels of Bacteroidetes in the muco-epithelium of AUT-GI children can directly compromise carbohydrate metabolism and trigger inflammatory pathways.

Mice that are genetically obese (ob/ob) have 50% fewer Bacteroidetes. A lower abundance of Bacteroidetes is reported in stool samples from obese individuals (Ley et al., 2005; Ley et al., 2006). Using Bacteroidete-specific real-time PCR, dramatic decreases were found in the ilea (~50% lower abundance) as well as significantly lower levels in the ceca (~25% lower abundance) of AUT-GI compared to Control-GI children. In ob/ob mice, diet-induced obese mice, and in obese humans, the decrease in Bacteroidetes is accompanied by an increase in Firmicutes (Turnbaugh et al., 2008; Ley et al., 2005; Ley et al., 2006). The increased Firmicute/Bacteroidete ratio in obesity increases the capacity to harvest energy from the diet (Turnbaugh et al., 2006). As discussed herein, the trend toward increased Firmicutes and the significant decrease in Bacteriodetes led to a significant increase in the Firmicute/Bacteroidete ratio in ilea and ceca of AUT-GI compared to Control-GI children. The trend toward increased Firmicutes was largely attributable to Clostridia members; based on pyrosequencing result, members of Ruminococcaceae and Lachnospiraceae were the major contributors.

Several members of Ruminococcaceae and Lachnospiraceae are known butyrate producers and can thus influence short-chain fatty acid (SCFA) levels (Louis et al., 2010). SCFA influence colonic pH and *Bacteroides* sp. are relatively sensitive to acidic pH (Duncan et al., 2009). Three reports indicated differences in *Clostridia* species in stool samples from ASD-GI as compared to control children, including greater abundance of *Clostridium* clusters I, II, XI and *C. bolteae* (Finegold et al, 2002; Song et al., 2004; Parracho et al., 2005). Although only a trend was observed for increased Firmicutes in AUT-GI children, the cumulative levels of Firmicutes and Proteobacteria were significantly higher. Three AUT-GI patients had extremely high levels of Alpha- and Beta-, or Gammaproteobacteria. In addition, the AUT-GI group had elevated levels of Betaproteobacteria compared to the Control-GI group, reflecting the presence of Alcaligenaceae members in the ilea and ceca of 46.7% of AUT-GI children. Alcaligenaceae sequences were not detected in tissues from Control-GI children.

Conclusions:

Metabolic interactions between intestinal symbionts and the human host are only beginning to be understood. Increasing evidence shows that gastrointestinal disease and dysbiosis exert system-wide effects on normal host physiology. As discussed herein, GI disease in autism has a molecular profile distinct from GI disease in normally-developing children. AUT-GI children have deficiencies in disaccharidase and hexose transporter gene expression that likely promote malabsorption and multicomponent, compositional dysbiosis. Although the extra-intestinal effects these changes can elicit remain speculative, the identification of specific molecular and microbial signatures that define gastrointestinal pathophysiology in AUT-GI children sets the stage for further research aimed at defining the epidemiology, diagnosis and informed treatment of GI symptoms in autism.

Materials and Methods:

Patient samples. Patient biopsies were collected as part of a study to assess the frequency of measles virus transcripts in ilea and ceca of children with autistic disorder and gastrointestinal complaints (AUT-GI, n=15) and children with gastrointestinal complaints without brain disorder (Control-GI, n=7). This cohort has been previously described in detail (Hornig et al., 2008). The present study restricted to male, Caucasian children from the original cohort between 3 and 5 years of age to control for confounding effects of gender, race and age on intestinal gene expression and bacterial microbiota. The age at biopsy was similar for AUT-GI and Control-GI subjects (median, in years [interquartile range, IQR]: AUT-GI, 4.5 (1.2); Control-GI, 3.98 (0.9); Mann-Whitney, p=0.504] (See Table 3).

TABLE 3

Patient information Table.

| Patient # | Group | Age (yrs.) | LCT (13910:22018) |
|---|---|---|---|
| 215 | 1 | ASD | 4.35 | C/T:G/A |
| 478 | 2 | ASD | 5.94 | T/T:A/A |
| 513 | 3 | ASD | 4.66 | T/T:A/A |
| 530 | 4 | ASD | 5.46 | C/T:G/A |
| 554 | 5 | ASD | 4.01 | T/T:A/A |
| 562 | 6 | ASD | 3.80 | C/T:G/A |
| 566 | 7 | ASD | 3.49 | T/T:A/A |
| 581 | 8 | ASD | 4.29 | T/T:A/A |
| 589 | 9 | ASD | 5.62 | C/C:G/G* |
| 648 | 10 | ASD | 4.71 | C/T:G/A |
| 678 | 11 | ASD | 5.28 | T/T:A/A |
| 686 | 12 | ASD | 5.03 | C/T:G/A |
| 688 | 13 | ASD | 4.00 | C/C:G/G* |
| 733 | 14 | ASD | 4.53 | T/T:A/A |
| 800 | 15 | ASD | 3.51 | C/C:G/G* |
| 667 | 16 | Control | 3.98 | T/T:A/A |
| 755 | 17 | Control | 5.06 | T/T:A/A |
| 760 | 18 | Control | 3.89 | C/T:G/A |
| 796 | 19 | Control | 5.48 | C/T:G/A |
| 797 | 20 | Control | 3.98 | C/T:G/A |
| 814 | 21 | Control | 3.95 | C/C:G/G* |
| 842 | 22 | Control | 4.12 | T/T:A/A |

RNA and DNA extraction. RNA and DNA were extracted sequentially from individual ileal and cecal biopsies (total of 176 biopsies: 88 ileal and 88 cecal biopsies; 4 biopsies per patient per region; 15 AUT-GI patients and 7 Control-GI patients) in TRIzol using standard protocols. RNA and DNA concentrations and integrity were determined using a Nanodrop ND-1000 Spectrophotometer (Nanodrop Technologies, Wilmington, Del.) and Bioanalyzer (Agilent Technologies, Foster City, Calif.) and stored at −80° C.

Quantitative Real-Time PCR of human mRNA. Intron/exon spanning, gene-specific PCR primers and probes for sucrase isomaltase, maltase glucoamylase, lactase, SGLT1, GLUT2, Villin, and CDX2, with GAPDH and Beta-actin as dual housekeeping gene controls were designed for real-time PCR using Primer Express 1.0 software (Applied Biosystems, Foster City, Calif.). Taqman probes were labeled with the reporter FAM (6-carboxyfluorescein) and the quencher BBQ (Blackberry) (TIB MolBiol). PCR standards for determining copy numbers of target transcripts were generated from amplicons cloned into the vector pGEM-T easy (Promega Corporation, Madison, Wis.). Linearized plasmids were quantitated by UV spectroscopy and 10-fold serial dilutions (ranging from $5 \times 10^5$ to $5 \times 10^0$ copies) were created in water containing yeast tRNA (1 ng/μl). Unpooled RNA from individual ileal biopsies were used for real time PCR assays; each individual biopsy was assayed in duplicate. cDNA was synthesized using Taqman reverse transcription reagents (Applied Biosystems) from 2 μg unpooled RNA per 100 μl reaction. Each 25-μl amplification reaction contained 10 μl template cDNA, 12.5 μl Taqman Universal PCR Master Mix (Applied Biosystems), 300 nM gene-specific primers and 200 nM gene-specific probe (Table 2). The thermal cycling profile using a ABI StepOnePlus Real-time PCR System (Applied Biosystems) consisted of: Stage 1, one cycle at 50° C. for 2 min; Stage 2, 1 cycle at 95° C. for 10 min; Stage 3, 45 cycles at 95° C. for 15 s and 60° C. for 1 min (1 min 30 s for LCT). GAPDH and B-actin mRNA were amplified in duplicate reactions by real-time PCR from the same reverse transcription reaction as was performed for the gene of interest. The mean concentration of GAPDH or Beta-actin in each sample was used to control for integrity of input RNA and to normalize values of target gene expression to those of the housekeeping gene expression. The final results shown were expressed as the mean copy number from replicate biopsies per patient, relative to values obtained for GAPDH mRNA. Beta-actin normalization gave similar results to GAPDH normalization for all assays. Due to insufficient or poor quality RNA, only 3 of the 4 biopsies were included for 3 patients (Patient #s 4, 7, 10) and only 2 of the 4 biopsies were included for 1 patient (Patient #2). Thus, 83 of the original 88 ileal biopsies were used in real-time PCR experiments.

Lactase genotyping. Genomic DNA from AUT-GI (n=15) and Control-GI (n=7) patients was subjected to previously-described PCR-restriction fragment length polymorphism (PCR-RFLP) analysis for the C/T-13910 and G/A-22018 polymorphisms associated with Adult-type Hypolactasia with minor modifications (Buning et al., 2003). Genotyping primers for C/T-13910 and G/A-22018 polymorphisms are as follows: C/T-13910 For (5'-GGATGCACTGC TGTGAT-GAG-3'[SEQ ID NO: 20]), C/T-13910Rev (5'-CCCACT-GACCTATCCTCGTG-3' [SEQ ID NO: 21]), G/A-22018 For (5'-AACAGGCACGTGGAGGAGTT-3' [SEQ ID NO: 22]), and G/A-22018Rev (5'-CCCACCTCAGCCTCTTGAGT-3' [SEQ ID NO: 23]). Each 50-μl amplification reaction contained 500 ng genomic DNA, 400 nM forward and reverse primers, and 25 μl High Fidelity PCR master mix. Thermal cycling consisted of 1 cycle at 94° C. for 4 min followed by 40 cycles at 94° C. for 1 min, 60° C. for 1 min, and 72° C. for 1 min. PCR reactions for C/T-13910 were directly digested with the restriction enzyme BsmFI at 65° C. for 5 hrs. PCR reactions for G/A-22018 were resolved on 1% agarose gels followed by gel extraction of the prominent 448 bp amplicon. Gel extracted G/A-22018 amplicons were then digested with the restriction enzyme HhaI at 37° C. for 5 hrs. Restriction digests of C/T-13910 and G/A-22018 were resolved on 1.5% ethidium-stained agarose gels for genotyping analysis. BsmFI digestion of the C/T-13910 amplicons generates two fragments (351 bp and 97 bp) for the hypolactasia genotype (C/C), four fragments (351 bp, 253 bp, 98 bp, and 97 bp) for the heterozygous genotype (C/T), and three fragments (253 bp, 98 bp, and 97 bp) for the normal homozygous allele (T/T). HhaI digestion of the G/A-22018 amplicons generates two fragments (284 bp and 184 bp) for the hypolactasia genotype (G/G), three fragments (448 bp, 284 bp, and 184 bp) for the heterozygous genotype (G/A), and a single fragment (448 bp) for the normal homozygous allele (A/A).

PCR amplification of bacterial 16S rRNA gene and bar-coded 454 pyrosequencing of intestinal microbiota. For DNA samples from 88 ileal biopsies (4 biopsies per patient; 15 AUT-GI patients, 7 Control-GI patients) and 88 cecal biopsies from the same patients, PCR was carried out using bacterial 16S rRNA gene-specific (V2-region), barcoded primers as previously described (Hamady et al., 2008). Composite primers were as follows: (For) 5'-GCCTTGCCAGCCCGCTCAGTCAGAGTTTGATCCTG GCTCAG-3'[SEQ ID NO: 24], (Rev) 5'-GCCTCCCTCGCGCCATCAGNNNNNNNNCATGCTGC CTCCCGTAGGAGT-3' [SEQ ID NO: 25]. Underlined sequences in the Forward and Reverse primers represent the 454 Life Sciences@ primer B and primer A, respectively. Bold sequences in the forward and reverse primers represent the broadly-conserved bacterial primer 27F and 338R, respectively. NNNNNNNN represents the eight-base barcode, which was unique for each patient. PCR reactions consisted of 8 µl 2.5×5 PRIME HotMaster Mix (5 PRIME Inc., Gaithersburg, Md.), 6 µl of 4 µM forward and reverse primer mix, and 200 ng DNA in a 20-µl reaction volume. Thermal cycling consisted of one cycle at 95° C. for 2 min; and 30 cycles at 95° C. for 20 seconds, 52° C. for 20 seconds, and 65° C. for 1 min. Each of 4 biopsies per patient was amplified in triplicate, with a single, distinct barcode applied per patient. Ileal and cecal biopsies were assayed separately. Triplicate reactions of individual biopsies were combined, and PCR products were purified using Ampure magnetic purification beads (Beckman Coulter Genomics, Danvers, Mass.) and quantified with the Quanti-iT PicoGreen dsDNA Assay Kit (Invitrogen, Carlsbad, Calif.) and Nanodrop ND-1000 Spectrophotometer (Nanodrop Technologies, Wilmington, Del.). Equimolar ratios were combined to create two master DNA pools, one for ileum and one for cecum, with a final concentration of 25 ng/µl. Master pools were sent for unidirectional pyrosequencing with primer A at 454 Life Sciences (Branford, Conn.) on a GS FLX sequencer.

Real-time PCR of Bacteroidete and Firmicute 16S rRNA genes. Primer sequences used for real-time PCR are listed in Table 4.

TABLE 4

Real-time PCR primers and probes used for gene expression and bacterial quantitative analysis.

| Name | SEQ ID NO. | Primers and Probe | | Amplicon size (bp) |
|---|---|---|---|---|
| SI | 26 | For: | 5'-TCTTCATGAGTTTTATGAGGATACGAAC-3' | 150 |
| | 27 | Rev: | 5'-TTTGCACCAGATTCATAATCATACC-3' | |
| | 28 | Probe: | 5'-CAGATACTGTGAGTGCCTACATCCCTGATGCTATT-3' | |
| MGAM | 29 | For: | 5'-TACCTTGATGCATAAGGCCCA-3' | 150 |
| | 30 | Rev: | 5'-GGCATTACGCTCCAGGACA-3' | |
| | 31 | Probe: | 5'-CGTCACTGTTGTGCGGCCTCTGC-3' | |
| LCT | 32 | For: | 5'-CAGGAATCAAGAGCGTCACAACT-3' | 180 |
| | 33 | Rev: | 5'-AAATCGACCGTGTCCTGGG-3' | |
| | 34 | Probe: | 5'-TCCTGCTAGAACCACCCATATCTGCGCT-3' | |
| SGLT1 | 35 | For: | 5'-GCTCATGCCCAATGGACTG-3' | 125 |
| | 36 | Rev: | 5'-CGGACCTTGGCGTAGATGTC-3' | |
| | 37 | Probe: | 5'-ACAGCGCCAGCACCCTCTTCACC-3' | |
| Glut2 | 38 | For: | 5'-AGTTAGATGAGGAAGTCAAAGCAA-3' | 164 |
| | 39 | Rev: | 5'-TAGGCTGTCGGTAGCTGG-3' | |
| | 40 | Probe: | 5'-ACAAAGCTTGAAAAGACTCAGAGGATATGATGATGTC-3' | |
| Villin | 41 | For: | 5'-CATGCGCTGAACTTCATCAAA-3' | 120 |
| | 42 | Rev: | 5'-GGTTGGACGCTGTCCACTTC-3' | |
| | 43 | Probe: | 5'-CGGCCGTCTTTCAGCAGCTCTTCC-3' | |
| CDX2 | 44 | For: | 5'-GGCAGCCAAGTGAAAACCAG-3' | 112 |
| | 45 | Rev: | 5'-TCCGGATGGTGATGTAGCG-3' | |
| | 46 | Probe: | 5'-ACCACCAGCGGCTGGAGCTGG-3' | |
| β-Actin | 47 | For: | 5'-AGCCTCGCCTTTGCCGA-3' | 175 |
| | 48 | Rev: | 5'-CTGGTGCCTGGGGCG-3' | |
| | 49 | Probe: | 5'-CCGCCGCCCGTCCACACCCGCC | |
| GAPDH | 50 | For: | 5'-CCTGTTCGACAGTCAGCCG-3' | 100 |
| | 51 | Rev: | 5'-CGACCAAATCCGTTGACTCC-3' | |
| | 52 | Probe: | 5'-CGTCGCCAGCCAGAGCCACA-3' | |
| Bacteroidetes | 53 | For: | 5'-AACGCTAGCTACAGGCTT-3' | ~293 (Frank et al.) |
| | 54 | Rev: | 5'-CCAATGTGGGGGACCTTC-3' | |
| Firmicutes | 55 | For: | 5'-GGAGYATGTGGTTTAATTCGAAGCA-3' | ~126 (Guo et al.) |
| | 56 | Rev: | 5'-AGCTGACGACAACCATGCAC-3' | |
| Total Bacteria | 57 | For: | 5'-GTGCCAGCMGCCGCGGTAA-3' | ~295 (Frank et al.) |
| | 58 | Rev: | 5'-GACTACCAGGGTATCTAAT-3' | |

PCR standards for determining copy numbers of bacterial 16S rDNA were prepared from representative amplicons of the partial 16S rRNA genes of Bacteroidetes and Firmicutes and total Bacteria cloned into the vector PGEM-T easy (Promega). A representative amplicon with high homology to *Bacteroides Vulgatus* (Accession #: NC_009614) was used with Bacteroidete-specific primers. A representative amplicon with high homology to *Faecalibacterium prausnitzii* (Accession #: NZ_ABED02000023) was used with Firmicute-specific primers. A representative amplicon with high homology to *Bacteroides intestinalis* (Accession #:

NZ_ABJL02000007) 16S rRNA gene was used with total Bacteria primers. Cloned sequences were classified using the RDP Seqmatch tool and confirmed by the Microbes BLAST database. Plasmids were linearized with the SphI restriction enzyme and ten-fold serial dilutions of plasmid standards were created ranging from $5\times10^7$ to $5\times10^0$ copies for Bacteroidetes, Firmicutes and total Bacteria. Amplification and detection of DNA by real-time PCR were performed with the ABI StepOnePlus Real-time PCR System (Applied Biosystems). Cycling parameters for Bacteroidetes and total Bacteria were as previously described (Frank et al., 2007), as were cycling parameters for Firmicutes (Guo et al., 2008). Each 25-μl amplification reaction mixture contained 50 ng DNA, 12.5 μl SYBR Green Master Mix (Applied Biosystems), and 300 nM bacteria-specific (Bacteroidete, Firmicute or total Bacteria) primers. DNA from each of 88 ileal biopsies (4 biopsies per patient) and 88 cecal biopsies (4 biopsies per patient) was assayed in duplicate. The final results were expressed as the mean number of Bacteroidete or Firmicute 16S rRNA gene copies normalized to 16S rRNA gene copies obtained using total Bacterial primers. Eight water/reagent controls were included for all amplifications. The average copy number for water/reagent controls (background) was subtracted from each ileal and cecal amplification prior to normalization. For the Bacteroidete assay all water controls contained undetectable levels of amplification. For the Firmicute assay average amplification signal from water samples were minimal, 12.03+/−15.0 copies.

Bioinformatic analysis of pyrosequencing reads. Pyrosequencing reads ranging from 235 to 300 base pairs in length (encompassing all sequences within the major peak obtained from pyrosequencing) were filtered for analysis. Low-quality sequences—i.e., those with average quality scores below 25—were removed based on previously described criteria (Huse et al., 2007; Hamady et al., 2008). Additionally, reads with any ambiguous characters were omitted from analysis. Sequences were then binned according to barcode, followed by removal of primer and barcode sequences. Taxonomic classifications of bacterial 16S rRNA sequences were obtained using the RDP Classifier with a minimum 80% bootstrap confidence estimate. To normalize data for differences in total sequences obtained per patient, phylotype abundance was expressed as a percentage of total bacterial sequence reads per patient at all taxonomic levels.

Statistical analysis. Data were not normally distributed, based on Kolmogorov-Smirnov test and evaluation of skewness and kurtosis; thus, the non-parametric Mann-Whitney U test was performed using StatView (Windows version 5.0.1; SAS Institute, Cary, N.C.). The comparative results of gene expression and bacteria levels were visualized as box-and-whisker plots showing: the median and the interquartile (midspread) range (boxes containing 50% of all values), the whiskers (representing the $25^{th}$ and $75^{th}$ percentiles) and the extreme data points (open circles). Associations between different variables were assessed by Spearman rank correlation test. Chi-squared test was used to evaluate between-group genotypes for adult-type hypolactasia. Kruskal-Wallis one-way analysis of variance was employed to assess significance of LCT mRNA expression levels split by genotype and group. Significance was accepted at $p<0.05$.

Genetically determined lactase non-persistence is not responsible for deficient lactase mRNA in AUT-GI. Although it is beyond the scope of this study to evaluate all possible mutations in carbohydrate genes that can affect expression, deficient LCT mRNA is not a result of the common adult-type hypolactasia genotype. LCT mRNA levels can be affected by two single nucleotide polymorphisms that determine adult-type hypolactasia; therefore, we genotyped these children using PCR-RFLP analysis (FIG. 21A). The homozygous, hypolactasia variant alleles were found in 20% (3 out of 15) of AUT-GI children and 14.3% (1 out of 7) of Control-GI children (chi-squared test, p=0.896) (FIG. 21B). LCT mRNA expression was significantly lower in individuals with the homozygous hypolactasia genotype compared to all other genotypes (FIG. 21C: Mann-Whitney, p=0.033). Comparison of LCT mRNA expression across genotype and group failed to reach significance (FIG. 21D: Kruskal-Wallis, p=0.097). Comparison of mRNA expression in subjects carrying at least one copy of the normal allele confirmed a significant decrease in LCT mRNA in AUT-GI relative to Control-GI subjects, independent of the individuals with the homozygous hypolactasia genotype (FIG.21E: Mann-Whitney, p=0.025). In summary, although the data support the notion that LCT genotype affects gene expression, deficient LCT mRNA in AUT-GI was not attributable to disproportionate hypolactasia genotypes between the AUT-GI and Control-GI groups.

Barcoded 16S rRNA gene pyrosequencing. A total of 525, 519 sequencing reads (representing 85% of the initial number of sequencing reads) remained after filtering based on read length, removing low-quality sequences and combining duplicate pyrosequencing runs (271,043 reads for ilea; 254,476 reads for ceca). Binning of sequences by barcode revealed similar numbers of 16S rRNA gene sequence reads per patient (average # sequences per patient+/−STD for ilea=12,320+/−1220; average # sequences per patient+/−STD for ceca=11,567+/−1589). There was not a significant difference between the AUT-GI and Control-GI groups in terms of the number of reads per patient. In order to assess whether sufficient sampling was achieved in the total pyrosequencing data set for all AUT-GI and Control-GI subjects, OTUs (Operational Taxonomic Units) were defined at a threshold of 97% identity, split by data for ileum and cecum, and rarefaction analysis was carried out (FIGS. 23A-23B). Rarefaction curves showed a tendency toward reaching plateau for all subjects; however failure to reach plateau means that additional sampling would be required to achieve complete coverage of all OTUs present in ileal and cecal biopsies. Investigation of diversity in AUT-GI and Control-GI patients was carried out using the Shannon Diversity Index calculated from OTU data for each subject. Rarefaction analysis revealed that all Shannon Diversity estimates had reached stable values (FIGS. 23C-23D). While Shannon Diversity estimates varied widely between individuals, there was not an apparent overall difference (loss or gain of diversity) between the AUT-GI and Control-GI groups in ileal (FIG. 23C) or cecal (FIG. 23D) biopsies.

OTU Analysis of Bacteroidetes. In order to determine whether the decreased abundance of Bacteroidete members was attributable to the loss of specific Bacteroidete phylotypes, the distribution of Bacteroidete OTUs (defined using a threshold of 97% identity or greater, 3% distance) was investigated. The number of Bacteroidete OTUs per patient ranged from 23 to 102 for ileal samples and 10 to 130 for cecal samples. Interestingly, no single OTU was significantly over or underrepresented between AUT-GI and Control-GI children and many OTUs contained single sequences. Thus, it was determined whether, the decrease in OTUs could be attributed to overall losses of the most prevalent Bacteroidete phylotypes. In both ileal and cecal samples, 12 OTUs accounted for the majority of Bacteroidete sequences (FIGS. 25A-25B). The cumulative levels of these 12 OTUs were significantly lower in AUT-GI compared to Control-GI children in both the ileum (FIG. 25C: Mann-Whitney, p=0.008)

and cecum (FIG. 25D: Mann-Whitney, p=0.008). Representative sequences from each of these 12 OTUs were classified using Green Genes Blast (greengenes.lbl.gov) and microbial blast alignment (NCBI) (FIG. 25E). The majority of sequences were members of the family Bacteroidaceae (OTUs 3, 5, 6, 7, and 19), except in the case of patient 20, where Prevotellaceae were the dominant phylotype. These results indicate that the loss of Bacteroidetes in AUT-GI children is primarily attributable to overall decreases in the dominant phylotypes of Bacteroidetes.

REFERENCES

1. Abrams G D, Bauer H, Sprinz H. Influence of the normal flora on mucosal morphology and cellular renewal in the ileum. A comparison of germ-free and conventional mice. Lab Invest 1963; 12:355-64.
2. Abt M C, Artis D. The intestinal microbiota in health and disease: the influence of microbial products on immune cell homeostasis. Curr Opin Gastroenterol 2009; 25:496-502.
3. Agarwal S, Mayer L. Pathogenesis and treatment of gastrointestinal disease in antibody deficiency syndromes. J Allergy Clin Immunol 2009; 124:658-64.
4. Agarwal S, Mayer L. Gastrointestinal manifestations in primary immune disorders. Inflamm Bowel Dis 2010; 16:703-11.
5. Alberti A, Pirrone P, Elia M, Waring R H, Romano C. Sulphation deficit in "low-functioning" autistic children: a pilot study. Biol Psychiatry 1999; 46:420-4.
6. Alper C M, Bluestone C D, Buchman C, et al. Recent advances in otitis media. 3. Middle ear physiology and pathophysiology. Ann Otol Rhinol Laryngol Suppl 2002; 188:26-35.
7. Ashwood P, Wills S, Van de Water J. The immune response in autism: a new frontier for autism research. J Leukoc Biol 2006; 80:1-15.
8. Backhed F, Ding H, Wang T, et al. The gut microbiota as an environmental factor that regulates fat storage. Proc Natl Acad Sci USA 2004; 101:15718-23.
9. Backhed F, Ley R E, Sonnenburg J L, Peterson D A, Gordon J I. Host-bacterial mutualism in the human intestine. Science 2005; 307:1915-20.
10. Beck P L, Xavier R, Wong J, et al. Paradoxical roles of different nitric oxide synthase isoforms in colonic injury. Am J Physiol Gastrointest Liver Physiol 2004; 286:G137-47.
11. Born P. Carbohydrate malabsorption in patients with non-specific abdominal complaints. World J Gastroenterol 2007; 13:5687-91.
12. Bover L C, Cardo-Vila M, Kuniyasu A, et al. A previously unrecognized protein-protein interaction between TWEAK and CD163: potential biological implications. J Immunol 2007; 178:8183-94.
13. Brockmann K. The expanding phenotype of GLUT1-deficiency syndrome. Brain Dev 2009; 31:545-52.
14. Brown A M, Ransom B R. Astrocyte glycogen and brain energy metabolism. Glia 2007; 55:1263-71.
15. Buie T, Campbell D B, Fuchs G J, 3rd, et al. Evaluation, diagnosis, and treatment of gastrointestinal disorders in individuals with ASDs: a consensus report. Pediatrics 2010; 125 Suppl 1:S1-18.
16. Buning C, Ockenga J, Kruger S, et al. The C/C(−13910) and G/G(−22018) genotypes for adult-type hypolactasia are not associated with inflammatory bowel disease. Scand J Gastroenterol 2003; 38:538-42.
17. Burkly L C, Michaelson J S, Hahm K, Jakubowski A, Zheng T S. TWEAKing tissue remodeling by a multifunctional cytokine: role of TWEAK/Fn14 pathway in health and disease. Cytokine 2007; 40:1-16.
18. Bushara K O. Neurologic presentation of celiac disease. Gastroenterology 2005; 128:S92-7.
19. Collins S M, Bercik P. The relationship between intestinal microbiota and the central nervous system in normal gastrointestinal function and disease. Gastroenterology 2009; 136:2003-14.
20. Corbett B A, Kantor A B, Schulman H, et al. A proteomic study of serum from children with autism showing differential expression of apolipoproteins and complement proteins. Mol Psychiatry 2007; 12:292-306.
21. D'Eufemia P, Celli M, Finocchiaro R, et al. Abnormal intestinal permeability in children with autism. Acta Paediatr 1996; 85:1076-9.
22. Dawson G. Recent advances in research on early detection, causes, biology, and treatment of autism spectrum disorders. Curr Opin Neurol 2010; 23:95-6.
23. Dohi T, Borodovsky A, Wu P, et al. TWEAK/Fn14 pathway: a nonredundant role in intestinal damage in mice through a TWEAK/intestinal epithelial cell axis. Gastroenterology 2009; 136:912-23.
24. Duncan S H, Louis P, Thomson J M, Flint H J. The role of pH in determining the species composition of the human colonic microbiota. Environ Microbiol 2009; 11:2112-22.
25. Dyer J, Daly K, Salmon K S, et al. Intestinal glucose sensing and regulation of intestinal glucose absorption. Biochem Soc Trans 2007; 35:1191-4.
26. Enstrom A M, Onore C E, Van de Water J A, Ashwood P. Differential monocyte responses to TLR ligands in children with autism spectrum disorders. Brain Behav Immun 2010; 24:64-71.
27. Fabriek B O, van Bruggen R, Deng D M, et al. The macrophage scavenger receptor CD163 functions as an innate immune sensor for bacteria. Blood 2009; 113:887-92.
28. Fehm H L, Kern W, Peters A. The selfish brain: competition for energy resources. Prog Brain Res 2006; 153:129-40.
29. Filkova M, Haluzik M, Gay S, Senolt L. The role of resistin as a regulator of inflammation: Implications for various human pathologies. Clin Immunol 2009; 133:157-70.
30. Finegold S M, Molitoris D, Song Y, et al. Gastrointestinal microflora studies in late-onset autism. Clin Infect Dis 2002; 35:S6-S16.
31. Flint H J, Bayer E A, Rincon M T, Lamed R, White B A. Polysaccharide utilization by gut bacteria: potential for new insights from genomic analysis. Nat Rev Microbiol 2008; 6:121-31.
32. Fraser D A, Laust A K, Nelson E L, Tenner A J. C1q differentially modulates phagocytosis and cytokine responses during ingestion of apoptotic cells by human monocytes, macrophages, and dendritic cells. J Immunol 2009; 183:6175-85.
33. Fullwood A, Drossman D A. The relationship of psychiatric illness with gastrointestinal disease. Annu Rev Med 1995; 46:483-96.
34. Furlano R I, Anthony A, Day R, et al. Colonic CD8 and gamma delta T-cell infiltration with epithelial damage in children with autism. J Pediatr 2001; 138:366-72.
35. Goodwin M S, Cowen M A, Goodwin T C. Malabsorption and cerebral dysfunction: a multivariate and comparative study of autistic children. J Autism Child Schizophr 1971; 1:48-62.

36. Gupta G, Gelfand J M, Lewis J D. Increased risk for demyelinating diseases in patients with inflammatory bowel disease. Gastroenterology 2005; 129:819-26.

37. Gupta S, Rimland B, Shilling P D. Pentoxifylline: brief review and rationale for its possible use in the treatment of autism. J Child Neurol 1996; 11:501-4.

38. Haznedar M M, Nussbaum M S, Metzger M, Salamander A, Spiegel-Cohen J, Hollander E. Anterior cingulated gyros volume and glucose metabolism in autistic disorder. Am J Psychiatry 1997; 154:1047-50.

39. Hodgson S, Ioannidis A S. Genetic testing in other GI diseases. Best Pact Res Clin Gastroenterol 2009; 23:245-56.

40. Hodin R A, Chamberlain S M, Ming S. Pattern of rat intestinal brush-border enzyme gene expression changes with epithelial growth state. Am J Physiol 1995; 269:C385-91.

41. Hooper L V, Wong M H, Thelon A, Hansson L, Falk P G, Gordon J I. Molecular analysis of commensally host-microbial relationships in the intestine. Science 2001; 291: 881-4.

42. Horvath K, Papadimitriou J C, Ralston A, Trachtenberg C, Tilden J T. Gastrointestinal abnormalities in children with autistic disorder. J Pediatr 1999; 135:559-63.

43. Irbil C W, Handel H G, Zheng Y, Dunes J A, Starr M G. Mechanisms of ileal adaptation for glucose absorption after proximal-based small bowel resection. J Gastrointest Surge 2008; 12:1854-64; discussion 64-5.

44. Ishigame H, Kakuta S, Nagai T, et al. Differential-roles of interleukin-17A and -17F in host defense against mucoepithelial bacterial infection and allergic responses. Immunity 2009; 30:108-19.

45. Jacobs D M, Gaudier E, van Duynhoven J, Vaughan E E. Non-digestible food ingredients, colonic microbiota and the impact on gut health and immunity: a role for metabolomics. Curr Drug Metab 2009; 10:41-54.

46. Johansson L, Linner A, Sunden-Cullberg J, et al. Neutrophil-derived hyperresistinemia in severe acute streptococcal infections. J Immunol 2009; 183:4047-54.

47. Jyonouchi H, Geng L, Ruby A, Zimmerman-Bier B. Dysregulated innate immune responses in young children with autism spectrum disorders: their relationship to gastrointestinal symptoms and dietary intervention. Neuropsychobiology 2005; 51:77-85.

48. Kalhan S C, Kilic I. Carbohydrate as nutrient in the infant and child: range of acceptable intake. Eur J Clin Nutr 1999; 53 Suppl 1:S94-100.

49. Kellett G L, Brot-Laroche E, Mace O J, Leturque A. Sugar absorption in the intestine: the role of GLUT2. Annu Rev Nutr 2008; 28:35-54.

50. Knivsberg A M, Reichelt K L, Hoien T, Nodland M. A randomised, controlled study of dietary intervention in autistic syndromes. Nutr Neurosci 2002; 5:251-61.

51. Kubes P, McCafferty D M. Nitric oxide and intestinal inflammation. Am J Med 2000; 109:150-8.

52. Lapointe T K, O'Connor P M, Buret A G. The role of epithelial malfunction in the pathogenesis of enteropathogenic E. coli-induced diarrhea. Lab Invest 2009; 89:964-70.

53. Le Gall M, Tobin V, Stolarczyk E, Dalet V, Leturque A, Brot-Laroche E. Sugar sensing by enterocytes combines polarity, membrane bound detectors and sugar metabolism. J Cell Physiol 2007; 213:834-43.

54. Leturque A, Brot-Laroche E, Le Gall M. GLUT2 mutations, translocation, and receptor function in diet sugar managing. Am J Physiol Endocrinol Metab 2009; 296: E985-92.

55. Lossos A, River Y, Eliakim A, Steiner I. Neurologic aspects of inflammatory bowel disease. Neurology 1995; 45:416-21.

56. Lu J H, Teh B K, Wang L, et al. The classical and regulatory functions of C1q in immunity and autoimmunity. Cell Mol Immunol 2008; 5:9-21.

57. Lupp C, Robertson M L, Wickham M E, et al. Host-mediated inflammation disrupts the intestinal microbiota and promotes the overgrowth of Enterobacteriaceae. Cell Host Microbe 2007; 2:204.

58. Lupp C, Robertson M L, Wickham M E, et al. Host-mediated inflammation disrupts the intestinal microbiota and promotes the overgrowth of Enterobacteriaceae. Cell Host Microbe 2007; 2:119-29.

59. Maher K R, Harper J F, Macleay A, King M G. Peculiarities in the endocrine response to insulin stress in early infantile autism. J Nery Ment Dis 1975; 161:180-4.

60. Mariat D, Firmesse O, Levenez F, et al. The Firm icutes/Bacteroidetes ratio of the human microbiota changes with age. BMC Microbiol 2009; 9:123.

61. Mazmanian S K, Round J L, Kasper D L. A microbial symbiosis factor prevents intestinal inflammatory disease. Nature 2008; 453:620-5.

62. McNay E C, Gold P E. Food for thought: fluctuations in brain extracellular glucose provide insight into the mechanisms of memory modulation. Behav Cogn Neurosci Rev 2002; 1:264-80.

63. McNay E C, McCarty R C, Gold P E. Fluctuations in brain glucose concentration during behavioral testing: dissociations between brain areas and between brain and blood. Neurobiol Learn Mem 2001; 75:325-37.

64. Melis D, Parenti G, Della Casa R, et al. Brain damage in glycogen storage disease type I. J Pediatr 2004; 144:637-42.

65. Montassir H, Maegaki Y, Ogura K, et al. Associated factors in neonatal hypoglycemic brain injury. Brain Dev 2009; 31:649-56.

66. Nehlig A. Cerebral energy metabolism, glucose transport and blood flow: changes with maturation and adaptation to hypoglycaemia. Diabetes Metab 1997; 23:18-29.

67. Nichols B L, Avery S E, Karnsakul W, et al. Congenital maltase-glucoamylase deficiency associated with lactase and sucrase deficiencies. J Pediatr Gastroenterol Nutr 2002; 35:573-9.

68. Nichols B L, Nichols V N, Putman M, et al. Contribution of villous atrophy to reduced intestinal maltase in infants with malnutrition. J Pediatr Gastroenterol Nutr 2000; 30:494-502.

69. Nichols B L, Quezada-Calvillo R, Robayo-Torres C C, et al. Mucosal maltase-glucoamylase plays a crucial role in starch digestion and prandial glucose homeostasis of mice. J Nutr 2009; 139:684-90.

70. Onofre G, Kolackova M, Jankovicova K, Krejsek J. Scavenger receptor CD163 and its biological functions. Acta Medica (Hradec Kralove) 2009; 52:57-61.

71. Parracho H M, Bingham M O, Gibson G R, McCartney A L. Differences between the gut microflora of children with autistic spectrum disorders and that of healthy children. J Med Microbiol 2005; 54:987-91.

72. Pascual J M, Wang D, Hinton V, et al. Brain glucose supply and the syndrome of infantile neuroglycopenia. Arch Neurol 2007; 64:507-13.

73. Pascual J M, Wang D, Lecumberri B, et al. GLUT1 deficiency and other glucose transporter diseases. Eur J Endocrinol 2004; 150:627-33.

74. Penders J, Stobberingh E E, van den Brandt P A, Thijs C. The role of the intestinal microbiota in the development of atopic disorders. Allergy 2007; 62:1223-36.
75. Penders J, Thijs C, Vink C, et al. Factors influencing the composition of the intestinal microbiota in early infancy. Pediatrics 2006; 118:511-21.
76. Pfannkuche H, Gabel G. Glucose, epithelium, and enteric nervous system: dialogue in the dark. J Anim Physiol Anim Nutr (Berl) 2009; 93:277-86.
77. Rautava S, Walker W A. Commensal bacteria and epithelial cross talk in the developing intestine. Curr Gastroenterol Rep 2007; 9:385-92.
78. Sandler R H, Finegold S M, Bolte E R, et al. Short-term benefit from oral vancomycin treatment of regressive-onset autism. J Child Neurol 2000; 15:429-35.
79. Scheepers A, Joost H G, Schurmann A. The glucose transporter families SGLT and GLUT: molecular basis of normal and aberrant function. JPEN J Parenter Enteral Nutr 2004; 28:364-71.
80. Schulzke J D, Troger H, Amasheh M. Disorders of intestinal secretion and absorption. Best Pract Res Clin Gastroenterol 2009; 23:395-406.
81. Seiderer J, Elben I, Diegelmann J, et al. Role of the novel Th17 cytokine IL-17F in inflammatory bowel disease (IBD): upregulated colonic IL-17F expression in active Crohn's disease and analysis of the IL17F p.His161Arg polymorphism in IBD. Inflamm Bowel Dis 2008; 14:437-45.
82. Sekirov I, Finlay B B. The role of the intestinal microbiota in enteric infection. J Physiol 2009; 587:4159-67.
83. Song Y, Liu C, Finegold S M. Real-time PCR quantitation of clostridia in feces of autistic children. Appl Environ Microbiol 2004; 70:6459-65.
84. Sonnenburg E D, Sonnenburg J L, Manchester J K, Hansen E E, Chiang H C, Gordon J I. A hybrid two-component system protein of a prominent human gut symbiont couples glycan sensing in vivo to carbohydrate metabolism. Proc Natl Acad Sci USA 2006; 103:8834-9.
85. Stecher B, Hardt W D. The role of microbiota in infectious disease. Trends Microbiol 2008; 16:107-14.
86. Swallow D M. Genetic influences on carbohydrate digestion. Nutr Res Rev 2003; 16:37-43.
87. Takahashi T. Pathophysiological significance of neuronal nitric oxide synthase in the gastrointestinal tract. J Gastroenterol 2003; 38:421-30.
88. Tammali R, Reddy A B, Ramana K V, Petrash J M, Srivastava S K. Aldose reductase deficiency in mice prevents azoxymethane-induced colonic preneoplastic aberrant crypt foci formation. Carcinogenesis 2009; 30:799-807.
89. Torrente F, Anthony A, Heuschkel R B, Thomson M A, Ashwood P, Murch S H. Focal-enhanced gastritis in regressive autism with features distinct from Crohn's and Helicobacter pylori gastritis. Am J Gastroenterol 2004; 99:598-605.
90. Torrente F, Ashwood P, Day R, et al. Small intestinal enteropathy with epithelial IgG and complement deposition in children with regressive autism. Mol Psychiatry 2002; 7:375-82, 34.
91. Turnbaugh P J, Ley R E, Mahowald M A, Magrini V, Mardis E R, Gordon J I. An obesity-associated gut microbiome with increased capacity for energy harvest. Nature 2006; 444:1027-31.
92. Ullner P M, Di Nardo A, Goldman J E, et al. Murine Glut-1 transporter haploinsufficiency: postnatal deceleration of brain weight and reactive astrocytosis. Neurobiol Dis 2009; 36:60-9.
93. Valicenti-McDermott M D, McVicar K, Cohen H J, Wershil B K, Shinnar S. Gastrointestinal symptoms in children with an autism spectrum disorder and language regression. Pediatr Neurol 2008; 39:392-8.
94. Van Citters G W, Lin H C. Ileal brake: neuropeptidergic control of intestinal transit. Curr Gastroenterol Rep 2006; 8:367-73.
95. Wakefield A J, Ashwood P, Limb K, Anthony A. The significance of ileo-colonic lymphoid nodular hyperplasia in children with autistic spectrum disorder. Eur J Gastroenterol Hepatol 2005; 17:827-36.
96. Wakefield A J, Puleston J M, Montgomery S M, Anthony A, O'Leary J J, Murch S H. Review article: the concept of entero-colonic encephalopathy, autism and opioid receptor ligands. Aliment Pharmacol Ther 2002; 16:663-74.
97. Warren R P, Odell J D, Warren W L, et al. Brief report: immunoglobulin A deficiency in a subset of autistic subjects. J Autism Dev Disord 1997; 27:187-92.
98. Wells S M, Buford M C, Migliaccio C T, Holian A. Elevated asymmetric dimethylarginine alters lung function and induces collagen deposition in mice. Am J Respir Cell Mol Biol 2009; 40:179-88.
99. Wong J M, de Souza R, Kendall C W, Emam A, Jenkins D J. Colonic health: fermentation and short chain fatty acids. J Clin Gastroenterol 2006; 40:235-43.
100. Wong J M, Jenkins D J. Carbohydrate digestibility and metabolic effects. J Nutr 2007; 137:2539S-46S.
101. Wright E M, Hirayama B A, Loo D F. ActiVe sugar transport in health and disease. J Intern Med 2007; 261:32-43.
102. Yap I K, Angley M, Veselkov K A, Holmes E, Lindon J C, Nicholson J K. Urinary metabolic phenotyping differentiates children with autism, from their unaffected siblings and age-matched controls. J Proteome Res 2010.
103. Yu L C, Flynn A N, Turner J R, Buret A G. SGLT-1-mediated glucose uptake protects intestinal epithelial cells against LPS-induced apoptosis and barrier defects: a novel cellular rescue mechanism? FASEB J 2005; 19:1822-35.
104. Zhao Y, Fung C, Shin D, et al. Neuronal glucose transporter isoform 3 deficient mice demonstrate features of autism spectrum disorders. Mol Psychiatry 2010; 15:286-99.
105. Zijlmans W C, van Kempen A A, Serlie M J, Sauerwein H P. Glucose metabolism in children: influence of age, fasting, and infectious diseases. Metabolism 2009; 58:1356-65.

Example 2

Intestinal Inflammation, Impaired Carbohydrate Metabolism and Transport, and Microbial Dysbiosis In Autism The objective of this study was to survey host gene expression and microflora in intestinal biopsies from children with autistic disorder and gastrointestinal complaints (AUT-GI) vs children with gastrointestinal complaints alone (Control-GI).

This example herein describes a rapid and specific PCR-based assay for diagnostic detection of *Sutterella* species in biological samples. It is a PCR-based detection scheme utilizing new genomic 16S rRNA sequences to allow rapid, sensitive, and specific species identification from gut samples.

Overview

Methods. Transcription profiling was pursued by cDNA microarray using RNA extracted from ileal biopsies (4 per patient) of 15 male AUT-GI and 7 age-matched, male Control-GI patients. Pathway analysis was performed using Ingenuity Pathway Analysis and GO Ontology. Changes in gene expression were confirmed by quantitative real-time PCR. Intestinal microbiota were investigated in ileal and cecal biopsies from AUT-GI and Control-GI children using amplicon-based, bar-coded pyrosequencing of the V2 region of bacterial 16S rDNA. Taxonomic classification of 525,519 bacterial sequences was accomplished using the Ribosomal Database Project classifier tool. Differences in microbiota between the two groups were further evaluated and confirmed using Bacteroidete-, Firmicute-, and Sutterella-specific real-time PCR.

Results. Microarray and pathway analysis revealed significant changes in genes involved in carbohydrate metabolism and transport and inflammation in ileal biopsies from AUT-GI as compared to Control-GI subjects. Real-time PCR confirmed significant decreases in the AUT-GI group in the primary brush border disaccharidases, sucrase isomaltase ($p=0.0013$), maltase glucoamylase ($p=0.0027$), and lactase ($p=0.0316$) as well as in two enterocyte hexose transporters, sodium glucose co-transporter 1 ($p=0.0082$) and glucose transporter 2 ($p=0.0101$). In contrast, increases were confirmed for inflammation-related genes in AUT-GI subjects: complement component 1, q subcomponent, A chain ($p=0.0022$), resistin ($p=0.0316$), CD163 ($p=0.0150$), tumor necrosis factor-like weak inducer of apoptosis ($p=0.015$), and interleukin 17F ($p=0.0220$). No significant group differences were observed for the enterocyte-specific marker, villin. In conjunction with changes in intestinal gene expression, bacterial content differed between the AUT-GI and Control-GI groups: pyrosequencing and real-time PCR revealed lower levels of Bacteroidetes (ileum: 50% reduction, $p=0.0027$; cecum: 25% reduction, $p=0.0220$, and higher Firmicute/Bacteroidete ratios in AUT-GI children (ileum: $p=0.0006$; cecum: $p=0.0220$). High levels of Sutterella species were found in 47% of AUT-GI biopsies (7/15), whereas Sutterella was not detected in any Control-GI biopsies (0/7; ileum: $p=0.0220$; cecum: $p=0.0368$).

Conclusions. A syndrome in autistic children is described wherein gastrointestinal dysfunction is associated with altered gene expression reflecting intestinal inflammation, impaired carbohydrate metabolism and transport, and dysbiosis. These findings provide insights into pathogenesis and allow for new strategies for therapeutic intervention.

In this study, high levels of Sutterella sp. were found in ileal and cecal biopsies from children with autism spectrum disorders (ASD) and gastrointestinal disease, while Sutterella sp. were undetectable in control children with gastrointestinal disease. Little is known about the epidemiology and pathogenesis of Sutterella sp. and their role in infectious diseases of humans and animals. Current methods for detecting Sutterella sp. are costly, labor intensive, and non-specific requiring isolation and anaerobic culture of the bacteria or generation, screening, sequencing, and sequence analysis of hundreds to thousands of bacterial 16S rRNA gene sequences from bacterial libraries or pyrosequencing analysis of hundreds of thousands of sequences. These methods can be costly, lack specificity, ease of execution, and are not strictly quantitative.

A rapid and specific PCR-based assay is described for the diagnostic identification, quantification, and phylogenetic analysis of Sutterella sp. in biological samples based on the variable sequence (V6-V8 region) of the 16S rRNA gene of Sutterella sp.

Study Background

An association between autistic spectrum disorder (ASD) and gastrointestinal (GI) immunopathology is supported by reports of a higher incidence of GI complaints, ileo-colonic lymphoid nodular hyperplasia, and enterocolitis in children with autism. In this study, intestinal bacteria were assessed in ileal (4 biopsies per patient) and cecal (4 biopsies per patient) biopsies from male ASD children (aged 3-5 years) with gastrointestinal symptoms (ASD-GI; n=15) and normally developing age-matched, male controls with gastrointestinal symptoms (Control-GI; n=7) by 454 pyrosequencing of the V2 region of the bacterial 16S rRNA gene. Taxonomic classification of 525,519 bacterial sequences was performed using the Ribosomal Database Project classifier tool. Genus-level analysis of pyrosequencing reads revealed a significant increase in Sutterella sp. The average confidence estimate of all genus-level Sutterella sequences identified using the RDP Classifier was high (99.1%) with the majority of sequences at 100% confidence.

Comparison of ASD-GI and Control-GI patients revealed significant increases in Sutterella sp. In the ileum (FIG. 8A: Mann-Whitney U, $p=0.022$) and cecum (FIG. 8B: Mann-Whitney U, v0.0368). Sutterella sp. sequences were completely absent from all Control-GI samples (% of total bacteria=0). Individual analysis of ASD-GI patients revealed that 7 out of 15 ASD-GI patients (46.7%) had high levels of Sutterella sp. sequences in both the ileum and cecum (FIG. 8C and FIG. 8D). By patient, ileal Sutterella sp. sequence abundance ranged from 1.7 to 6.7% of total bacterial reads (FIG. 8C). Similarly, in the Cecum Sutterella sp. sequence abundance ranged from 1.9 to 7.0% of total bacterial reads for the same patients (FIG. 8D). Sutterella sp. Sequences represented the majority of sequences present in the class Beta-proteobacteria in these select ASD-GI patients. In the Ileum of these ASD-GI patients, Sutterella sp. sequences accounted for 75.6% to 97.8% of all Beta-proteobacteria sequences (FIG. 8E). In the cecum, Sutterella sp. sequences accounted for 92.7% to 98.2% of all Beta-proteobacteria sequences (FIG. 8F). The results of this costly, time consuming, non-specific pyrosequencing analysis prompted the design of a Sutterella sp.-specific PCR assay to confirm, quantitate, and determine taxonomy of Sutterella sp. in the same samples analyzed by pyrosequencing.

Methods

Primer and Probe Design: Sutterella sp.-specific 16S rRNA gene PCR primers and probe were designed against the 16S sequence for Sutterella wadsworthensis (Genbank Accession #L37785) and Sutterella clone LW53 (Genbank Accession #AY976224) using Primer Express 1.0 software (Applied Biosystems, Foster City, Calif.). Genus specificity of candidate primers was evaluated using the RDP Probe Match tool. While several potential primer pairs were identified, only one pair showed high specificity for Sutterella sp. In PCR assays. These primers are designated here as SuttFor and SuttRev (Sequences of primers and probe are shown in Table 1).

TABLE 1

Sutterella sp.-specific primers and probes for classical and
real-time PCR assays and pan-bacterial primers used for normalization.

| SEQ ID NO. | Primers and Probe | | Amplicon size (bp) |
|---|---|---|---|
| 11 | SuttFor: | 5'-CGCGAAAAACCTTACCTAGCC-3' | ~260 |
| 12 | SuttRev: | 5'-GACGTGTGAGGCCCTAGCC-3' | |
| 13 | SuttProbe1: | 5'-CACAGGTGCTGCATGGCTGTCGT-3' | |
| 14 | SuttProbe2: | 5'-CCG CAAGGGAATCTGGACACAGGT-3' | |
| 15 | 515For: | 5'-GTGCCAGCMGCCGCGGTAA-3' | ~295 (Frank et al.) |
| 16 | 805Rev: | 5'-GACTACCAGGGTATCTAAT-3' | |

Evaluation of good quality sequences that were >1200 bases in the RDP database revealed a total of 248 Sutterella sequences at the time of analysis. SuttFor and SuttRev_primers showed high exclusivity for the genus Sutterella. Approximately 90% of RDP matches for SuttFor were in the genus Sutterella and 100% of matches for the reverse primer were Sutterella sequences. The SuttFor primer sequence matched exactly with approximately 91% (225/248 Sutterella sequences) of all Sutterella sequences, while the SuttRev primer matched exactly with approximately 81% (200/248 Sutterella sequences) of all Sutterella sequences. The SuttProbe1 (SEQ ID NO: 13) used for real-time PCR had low exclusivity but high coverage of Sutterella sequences (100%). An additional probe (SEQ ID NO: 143) with high exclusivity, but low coverage of Sutterella sequences (58.8%) was also designed and can be used when sequence information is available for Sutterella sp. in biological samples.

Figure 1:
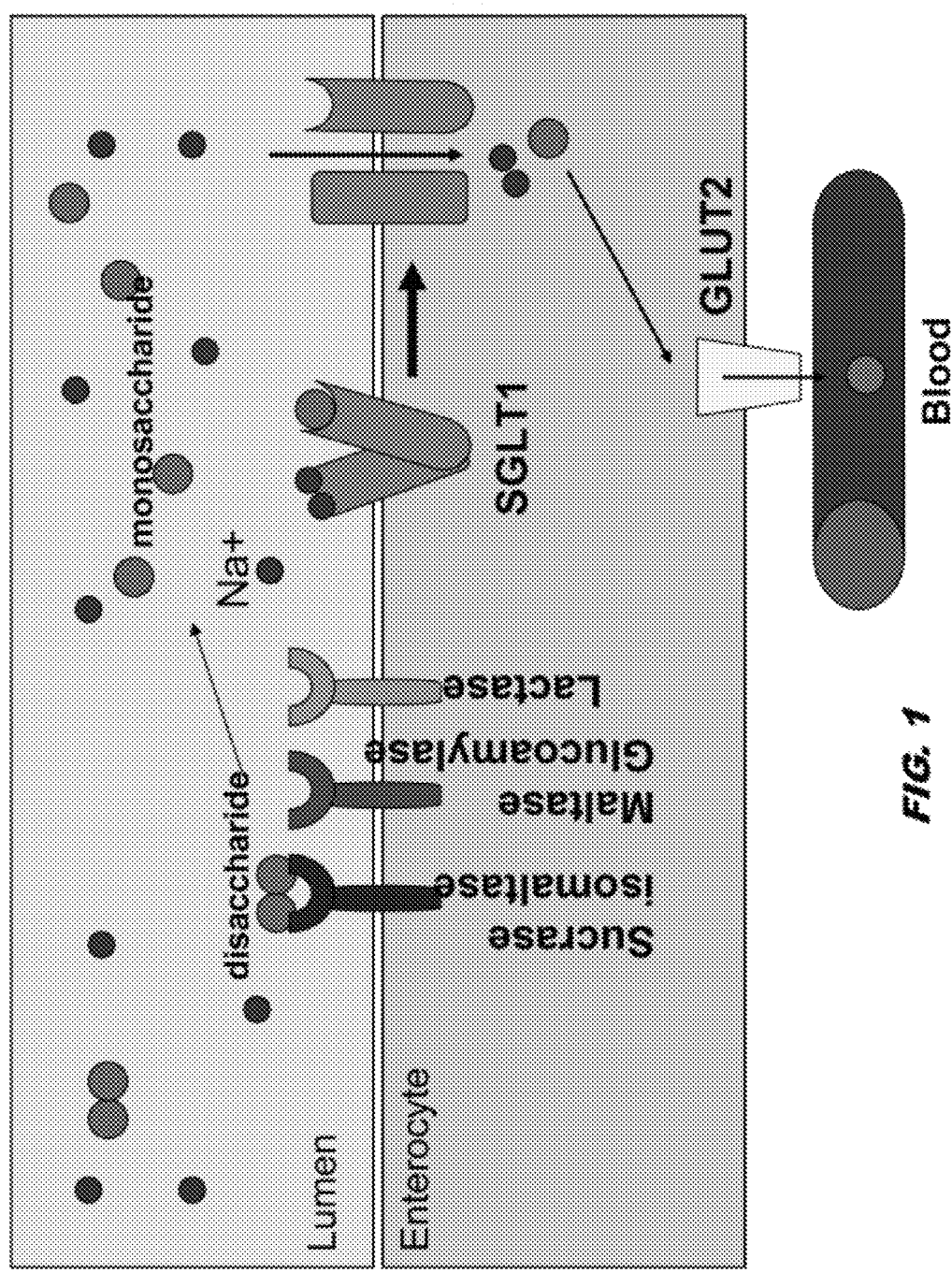
FIG. 1 is a schematic depicting carbohydrate metabolizing enzymes (e.g., sucrase isomaltase, maltase glucoamylase, and lactase) and carbohydrate transporter proteins (e.g., GLUT2 and SGLT1) involved in carbohydrate metabolism, uptake, and absorption in the enterocytes of the ileum.
Figure 2:
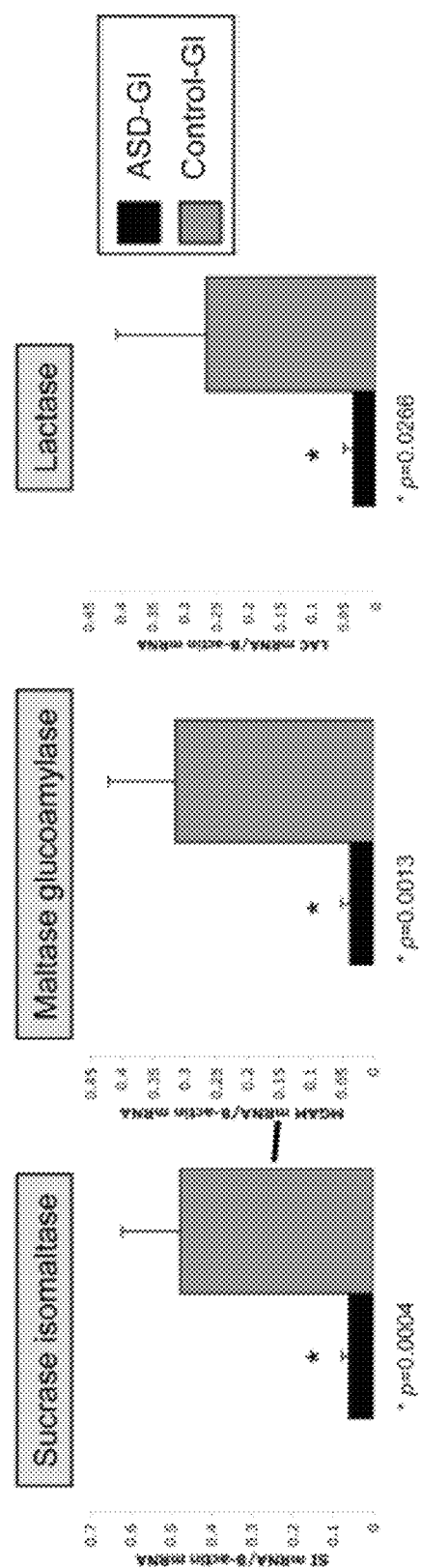
FIG. 2 shows bar graphs depicting that carbohydrate metabolizing enzyme mRNAs are reduced in the ileum of ASD subjects. Graphs are shown for sucrase isomaltase (left), maltase glucoamylase (center), and lactase (right).
Figure 3:
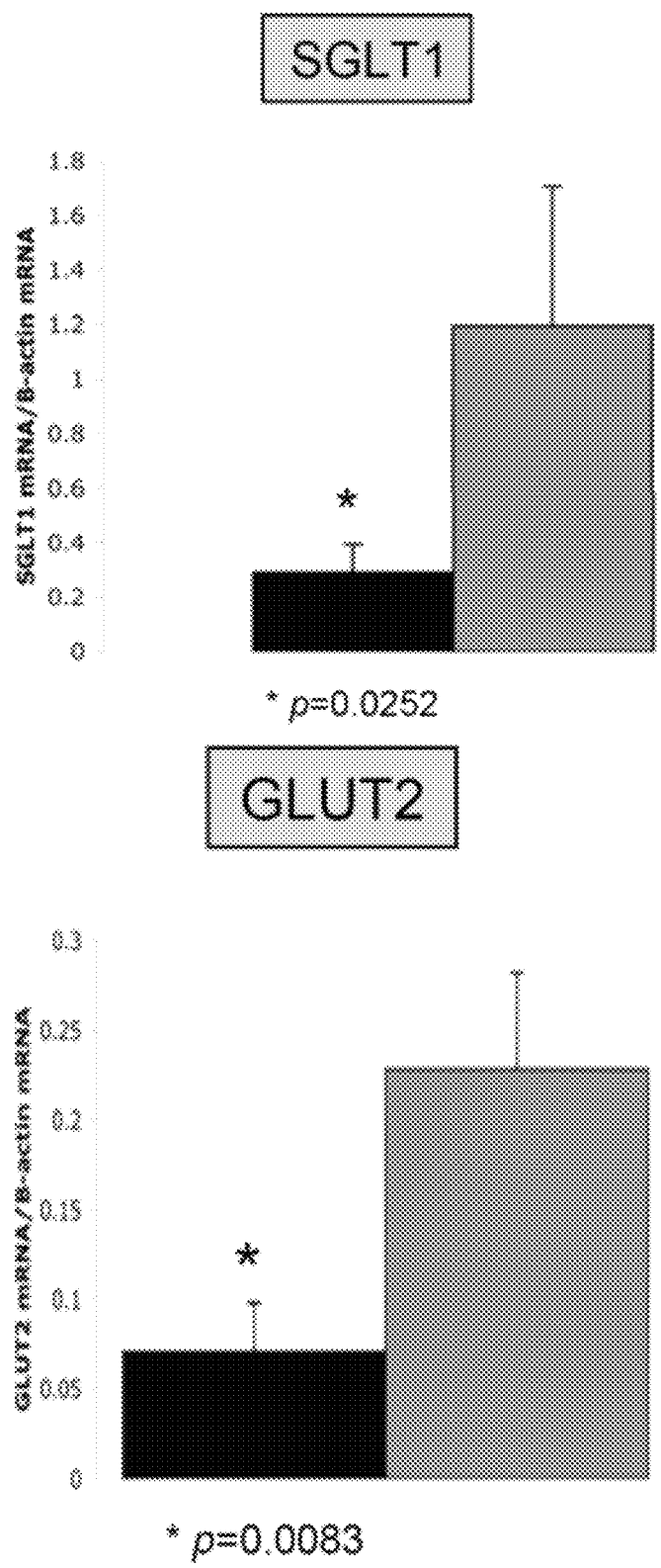
FIG. 3 shows bar graphs depicting that carbohydrate transporter mRNAs are reduced in the ileum of ASD subjects. Graphs are shown for SGLT1 (Top) and GLUT2 (Bottom).
Figure 4:
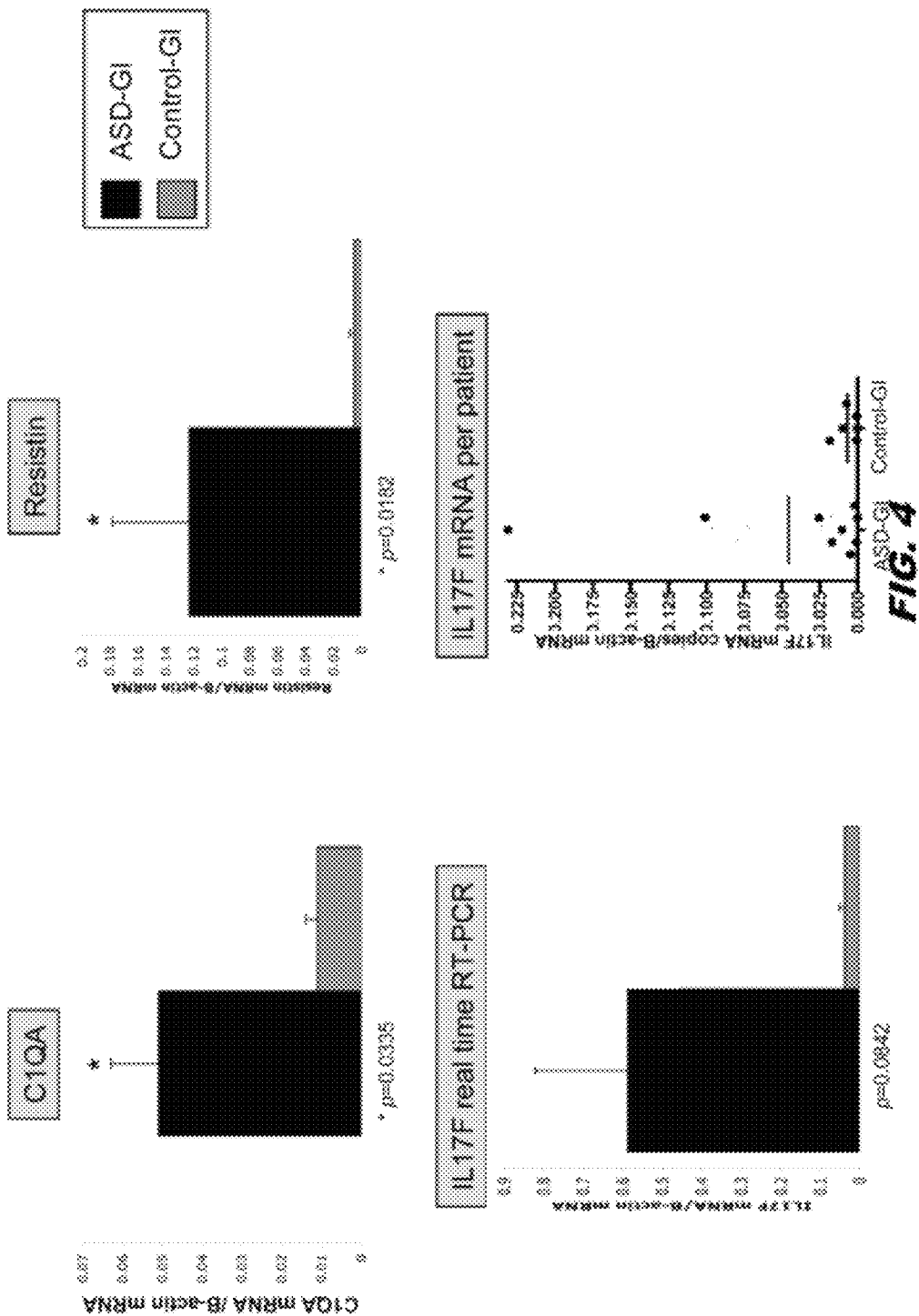
FIG. 4 shows graphs depicting that mRNA for ileal inflammatory markers are increased in the ileum of ASD subjects. Graphs are shown for C1QA (Top Left), Resistin (Top Right), and IL17F (Bottom Left and Right).
Figure 5:
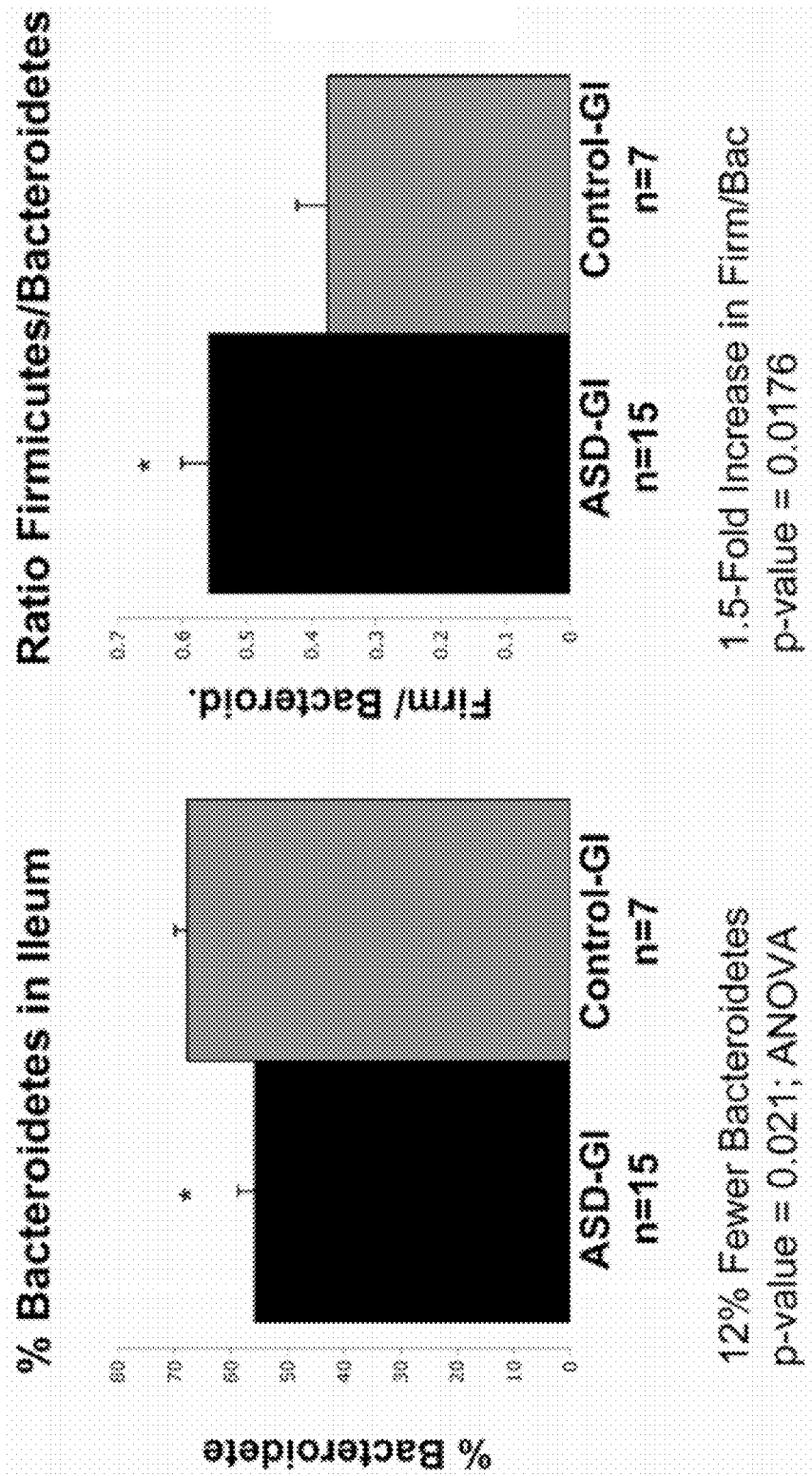
FIG. 5 shows bar graphs depicting the differences in bacteria phylum found in the ileum of ASD subjects. Changes at the phylum level were observed. Bar graphs show a decrease in Bacteroidetes (left) and increase in Firmicute/Bacteroidete ratios in ileum of AUT-GI children.
Figure 6:
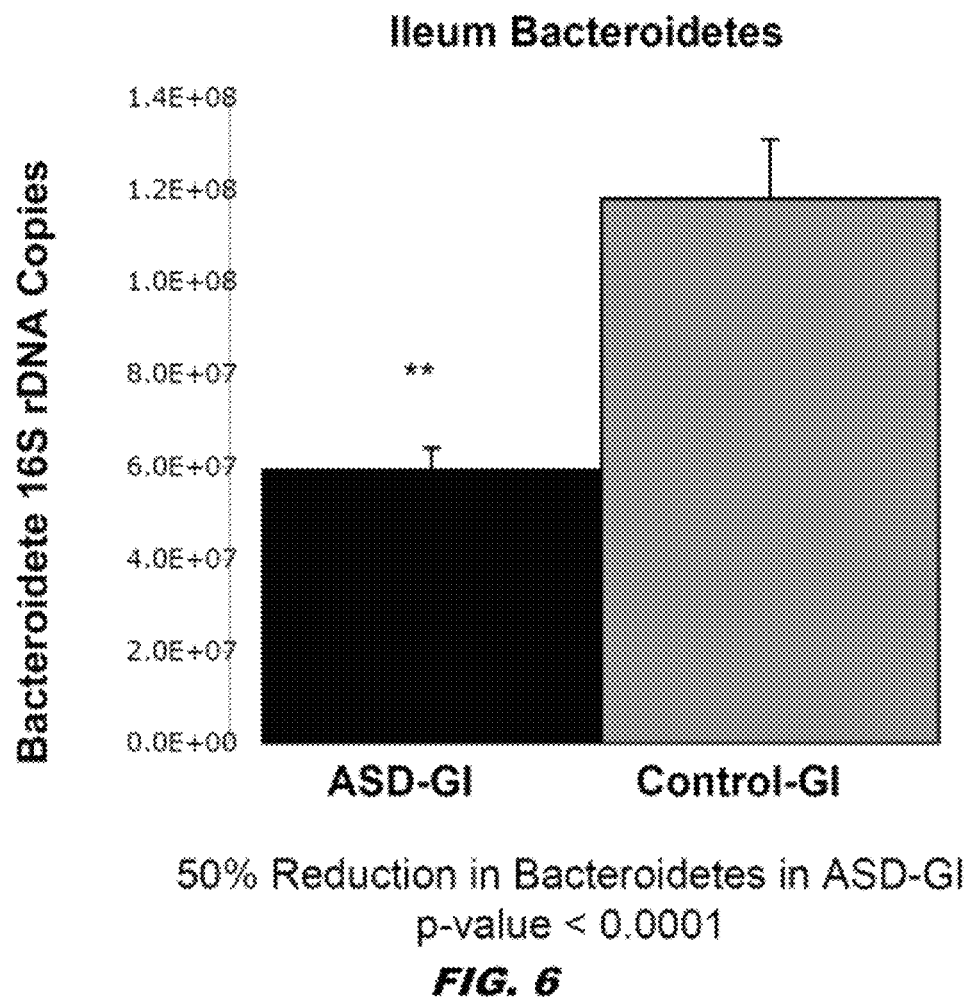
FIG. 6 is a bar graph depicting the copy number of bacteroidetes found in the ileum of ASD subjects. Real-time PCR confirmed a decrease in Bacteroidete. Bacteroidete 16S rDNA copies (Normalized to Total Bacterial 16S rDNA).
Figure 7:
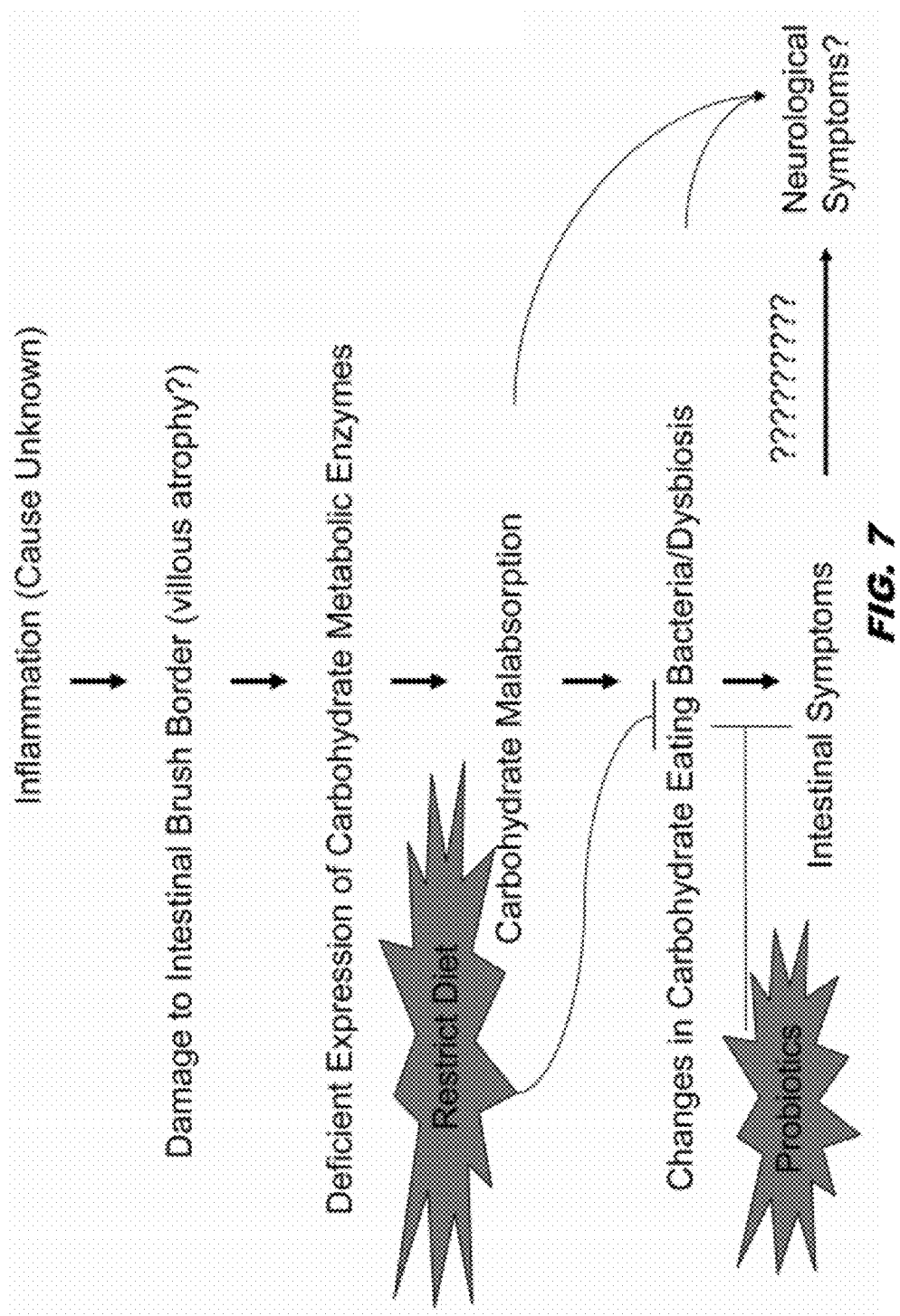
FIG. 7 is a schematic summarizing the interplay between expression levels of carbohydrate metabolic enzymes (e.g., sucrase isomaltase, maltase glucoamylase, and lactase), carbohydrate transporters (e.g., GLUT2 and SGLT1) and the population of bacteria in the ileum of ASD subjects.
Figure 9:
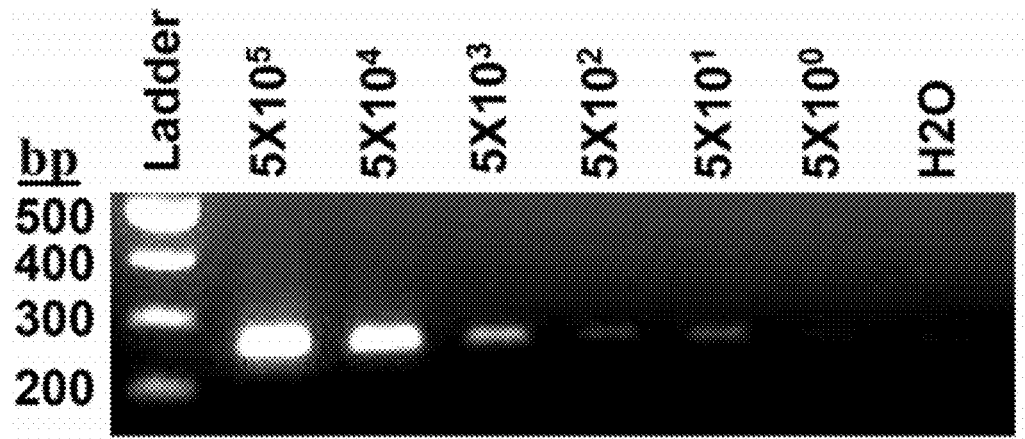
FIG. 9 is a photograph of an agarose gel showing the results of classical PCR experiments for the detection of *Sutterella*. *Sutterella*-specific 16S rRNA gene (V6-V8) PCR amplification of 10-fold dilutions of *Sutterella* plasmid DNA standards spiked into ileal DNA from a *Sutterella*-negative Control-GI patient. Note linear amplification down to $5 \times 10^2$ copies and an endpoint detection limit of $5 \times 10^1$ copies

Classical PCR. The SuttFor and SuttRev primers amplify a 260 bp region between variable regions 6, 7 and 8 (V6-V8) of the 16S rRNA of Sutterella. Classical PCR for detection of Sutterella was carried out in 25 ul reactions consisting of 25 ng genomic DNA, 300 nm each SuttFor and SuttRev primers, 2 ul dNTP mix (10 mM; Applied Biosystems), 2.5 ul of 10× PCR Buffer (Qiagen), 5 U of HotStarTaq DNA polymerase (Qiagen), and 5 ul Q-solution (Qiagen). Cycling parameters consisted of an initial denaturation step at 950 C for 15 min, followed by 30 cycles of 940 C for 1 min, 600 C for 1 min, and 720 C for 1 min and a final extension at 720 C for 5 min. Amplified products were run on a 1.5% agarose gel, extracted from the gel and either sent for direct PCR product sequencing using SuttFor and SuttRev primers or cloned into PGEM-T easy cloning vector for construction of bacterial libraries followed by sequencing using vector primers. Specificity of the assay was confirmed through direct sequence analysis of PCR products and clone sequences using the RDP Seqmatch and Classifier tools. All PCR products and clones were classified as Sutterella by RDP. In order to test linearity and sensitivity of the assay, the Sutterella clone used for real-time PCR standards was tested by classical PCR using the same conditions as all intestinal DNA. Ten fold dilutions of the Sutterella clone ranging from 5×10⁵ to 5×10⁰ were amplified by classical PCR alone as well as spiked into ileal DNA from a Sutterella negative patient. Both in the presence and absence of background ileal DNA, the Classical PCR was linear in the range of 5×10⁵ to 5×10² copies and had an end-point detection limit of 5×10¹ copies (FIG. 9).

Figure 10A:
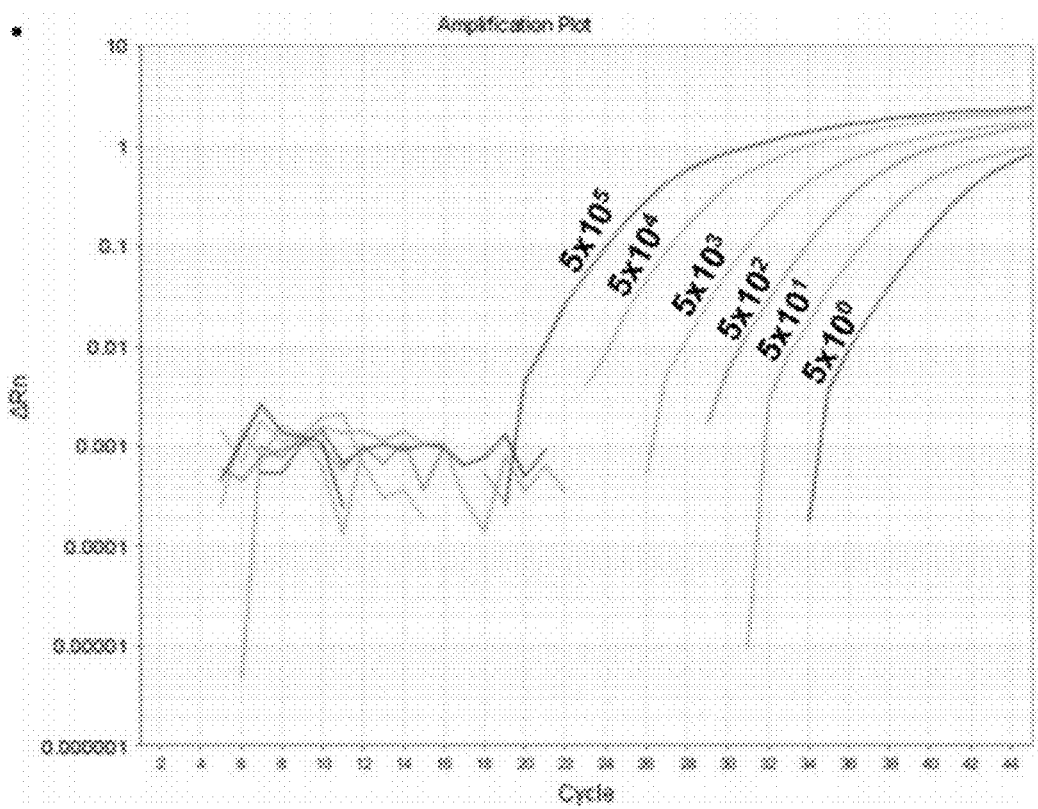
FIG. 10A is an amplification plot of *Sutterella* sp. through cycles of Real-time PCR experiments. The figure depicts Real-time PCR amplification plot of 10-fold serial dilutions of *Sutterella* plasmid DNA standards.
Figure 10B:
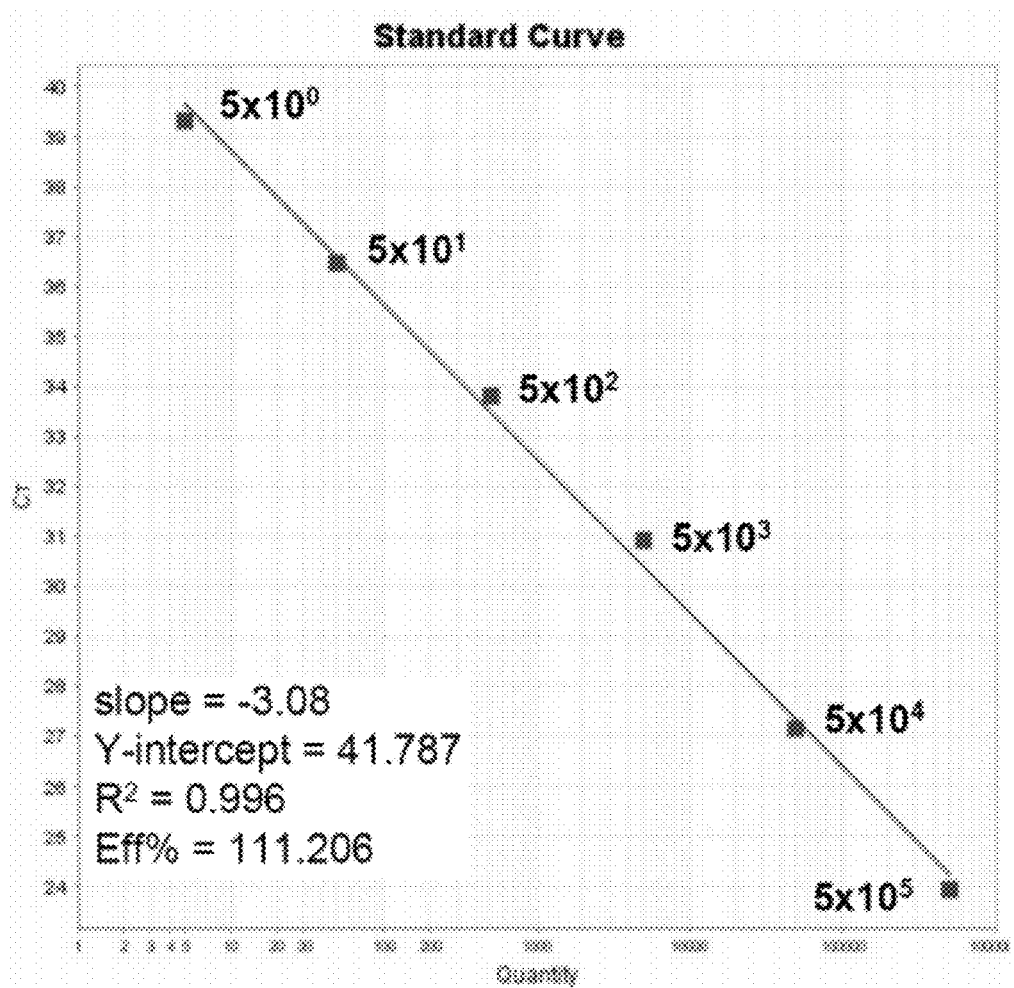
FIG. 10B is a standard curve graph showing the copy number of *Sutterella* sp. from Real-time PCR experiments.

Quantitative Real-time PCR. PCR standards for determining copy numbers of bacterial 16S rDNA were prepared from representative clones of the partial 16S rDNA of Sutterella obtained using the Classical PCR assay. Cloned sequences were classified using the RDP Seqmatch tool and confirmed by the Microbes BLAST database. Plasmids were linearized with the SphI restriction enzyme and ten fold serial dilutions of plasmid standards were created ranging from 500,000 to 5 copies for Sutterella (FIG. 10A and FIG. 10B). Amplification and detection of DNA by real-time PCR were performed with the ABI StepOnePlus Real-time PCR System (Applied Biosystems). For Sutterella sp.-specific real-time PCR, each 25 ul reaction contained 50 ng DNA, 12.5 ul Taqman universal master mix (ABI), 300 nm each of SuttFor and SuttRev primers, and 200 nm SuttProbe1 (Reporter=FAM, Quencher=BBQ). The standard curve had sensitivity down to 5 copies of plasmid, with a slope of −3.08, y-intercept of 41.787, and with an R2 value of 0.996 (FIG. 10A and FIG. 10B). DNA from each of 88 ileal biopsies and 88 cecal biopsies was assayed in duplicate. The final results were expressed as the mean number of copies normalized to 16S rRNA copies obtained using Pan-bacterial primers (Table 1: primers 515For and 805Rev) in a SYBR Green Real-time PCR assay (see Ref. 6 for more information). While normalization to total bacteria is not necessary, we have implemented its use in this study to control for variation in input DNA. Eight water/reagent controls were included for all amplifications. The average copy number for water controls (background) was subtracted from each ileal and cecal amplification prior to normalization. Where background copy number values exceeded amplification values in ileal and cecal samples, copy number was set to a value of 0. Average amplification signal from water samples with the Sutterella assay were very low (125.8+/−40 copies) compared to amplification in Sutterella positive samples (all ranging between 50,000 and 1,000,000 copies). Average copy numbers for all ileum and cecum Sutterella-negative amplifications was 26.6+/−21.0 copies (all were lower than the background controls).

Taxonomic Classification of Sutterella sp. Sequence alignments using sequences obtained by direct sequencing of Sutterella sp. from the classical PCR assay and phylogenetic analyses were conducted using MEGA4 software. Primer sequences were trimmed from the sequences obtained by direct sequencing of amplicons. Classification was confirmed using the RDP classifier and seqmatch tools. Sutterella sequences obtained from ileal and cecal biopsies were aligned with sequences from the 11 known isolates of Sutterella sp. found in the RDP database. Sequences from known Sutterella sp. isolates were trimmed to the length of the sequences obtained from ileal and cecal biopsies. Phylogenetic trees were constructed according to the neighbour-joining method, rooted to the outgroup Burkholderia pseudoma-

*Ilei*, and the stability of the groupings was estimated by bootstrap analysis (1000 replications) using MEGA4.

Results

Figure 11:
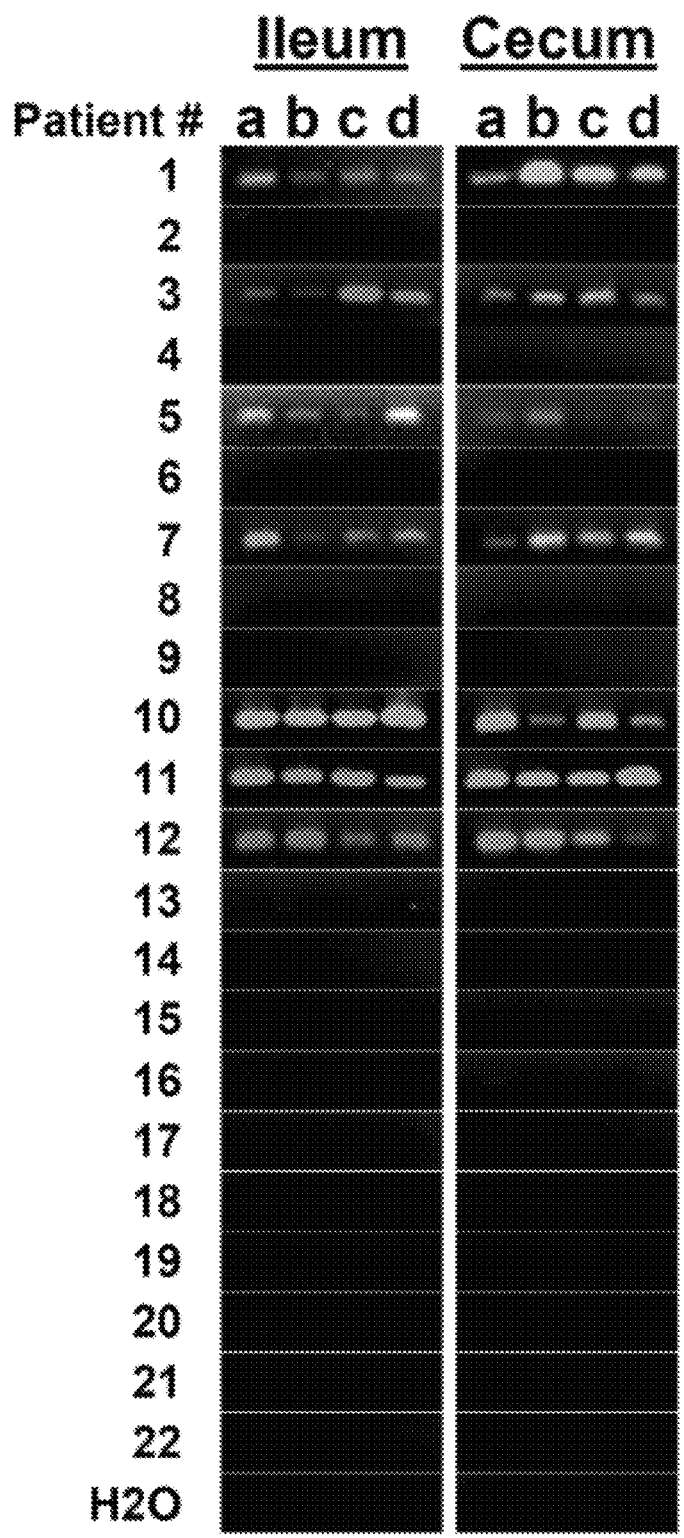
FIG. 11 is a photograph of an agarose gel showing the results of *Sutterella* detection in the ileum and cecum of patients using the V6-V8 *Sutterella* sp.-specific PCR.

Implementation of *Sutterella* sp.-specific Classical PCR for Detection. Classical PCR analysis of *Sutterella* sp. using DNA from all 88 ileal and 88 cecal biopsies showed that the same individuals identified as having high levels of *Sutterella* by V2 pyrosequencing were also positive by the V6-V8 *Sutterella* sp.-specific PCR. Additionally, all 4 biopsies per region in all 7 *Sutterella*-positive patients showed *Sutterella* amplicons, while no amplicons were observed in any Control-GI patients or ASD-GI patients that lacked *Sutterella* sequences in V2 pyrosequencing experiments (FIG. 11). All patients amplicons were confirmed to represent *Sutterella* by direct sequencing of PCR products and cloning of individual amplicons to create bacterial libraries followed by sequencing of 50 individual clones.

Implementation of *Sutterella* sp.-specific Real-time PCR for Quantification. Real-time PCR analysis using the same V6-V8 primers and a high coverage Taqman probe (SuttProbel), revealed significant increases in *Sutterella* in ASD-GI compared to Control-GI patients for both the ileum (FIG. 12A: Mann-Whitney U, p=0.0368) and cecum (FIG. 12B: Mann-Whitney U, p=0.0368). *Sutterella* copy numbers were quite high in both the ileum and cecum (in the range of $10^4$ to $10^5$ copies) of *Sutterella*-positive patients (FIG. 12C and FIG. 12D). The distribution of *Sutterella* abundance by patient and the copy number revealed by V2 pyrosequencing and V6-V8 real-time PCR, respectively, were in striking concordance (Compare ileum FIG. 8C with FIG. 12C and compare cecum FIG. 8D with FIG. 12D). There was 100% congruence between V2 region 454 pyrosequencing and both classical and real-time PCR using the V6-V8 region *Sutterella* sp.-specific primers.

Figure 13:
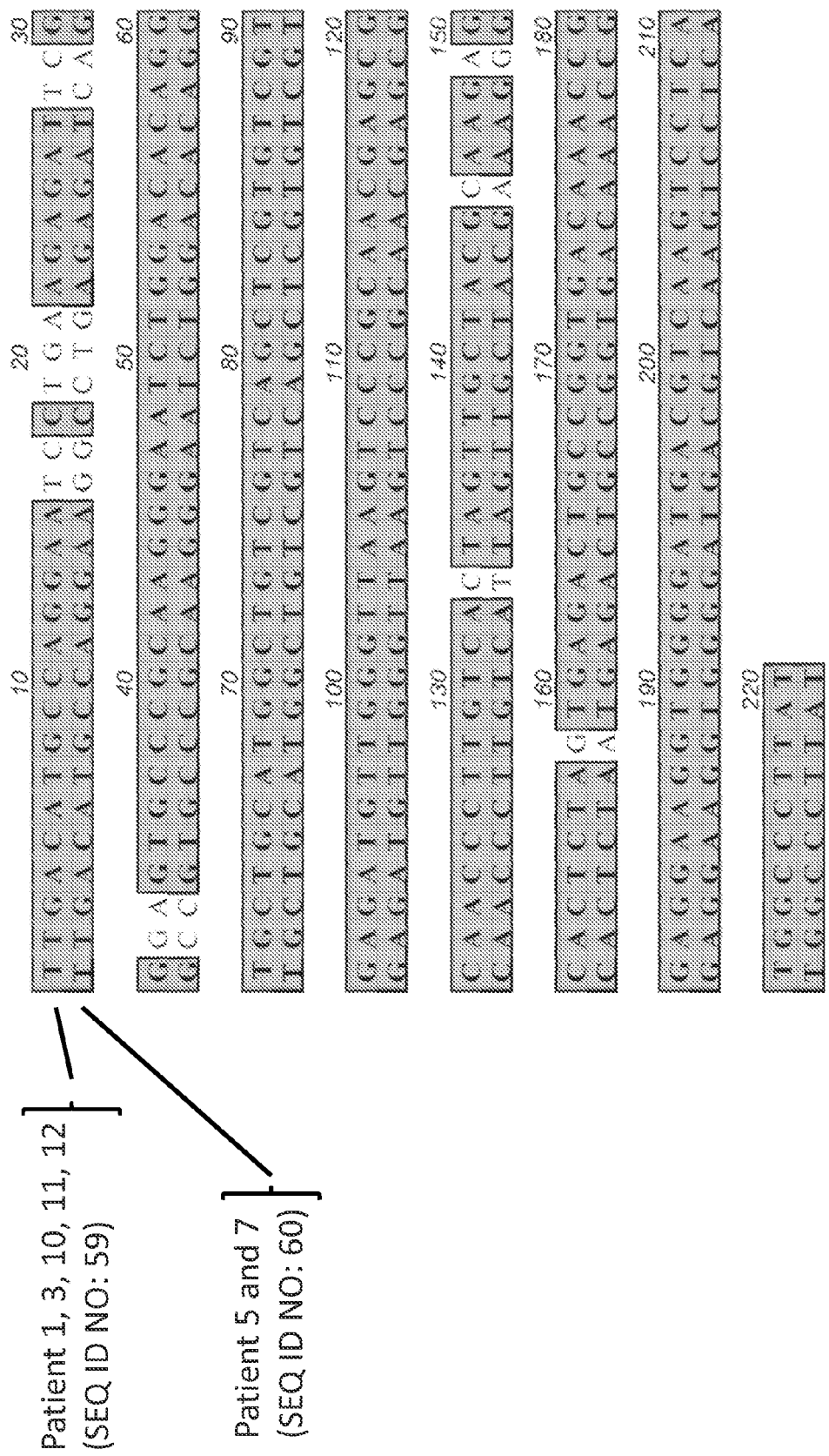
FIG. 13 is a sequence alignment for the V6-V8 region of *Sutterella* sp. obtained from biological samples of Autism patients 1, 3, 10, 11, and 12 (SEQ ID NO: 59), and Autism patients 5 and 7 (SEQ ID NO: 60).
Figure 14:
FIG. 14 depicts *Sutterella* sp. sequence clustering from the Operational Taxonomic Unit (OTU) analysis of V2 pyrosequencing reads.
Figure 15A:
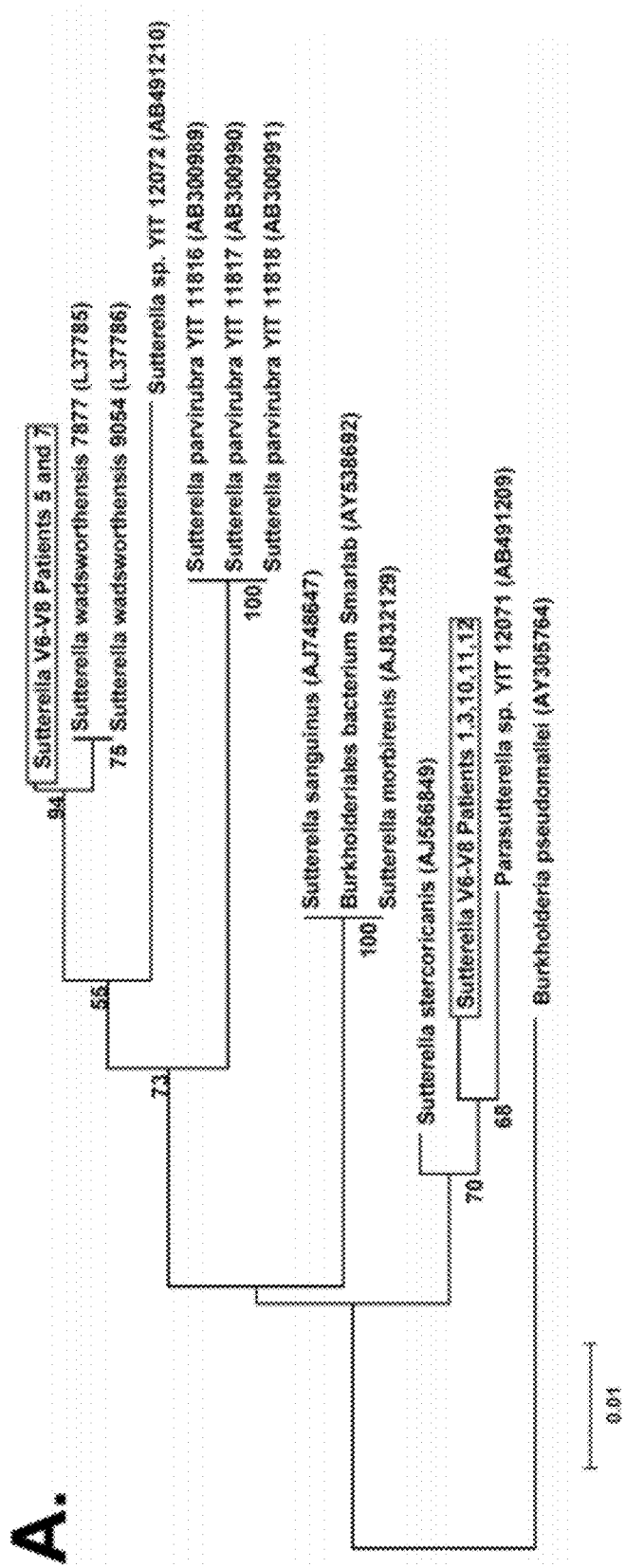
FIG. 15A is a schematic depicting *Sutterella* sp. treeing analysis of the V6-V8 sequences.
Figure 15B:
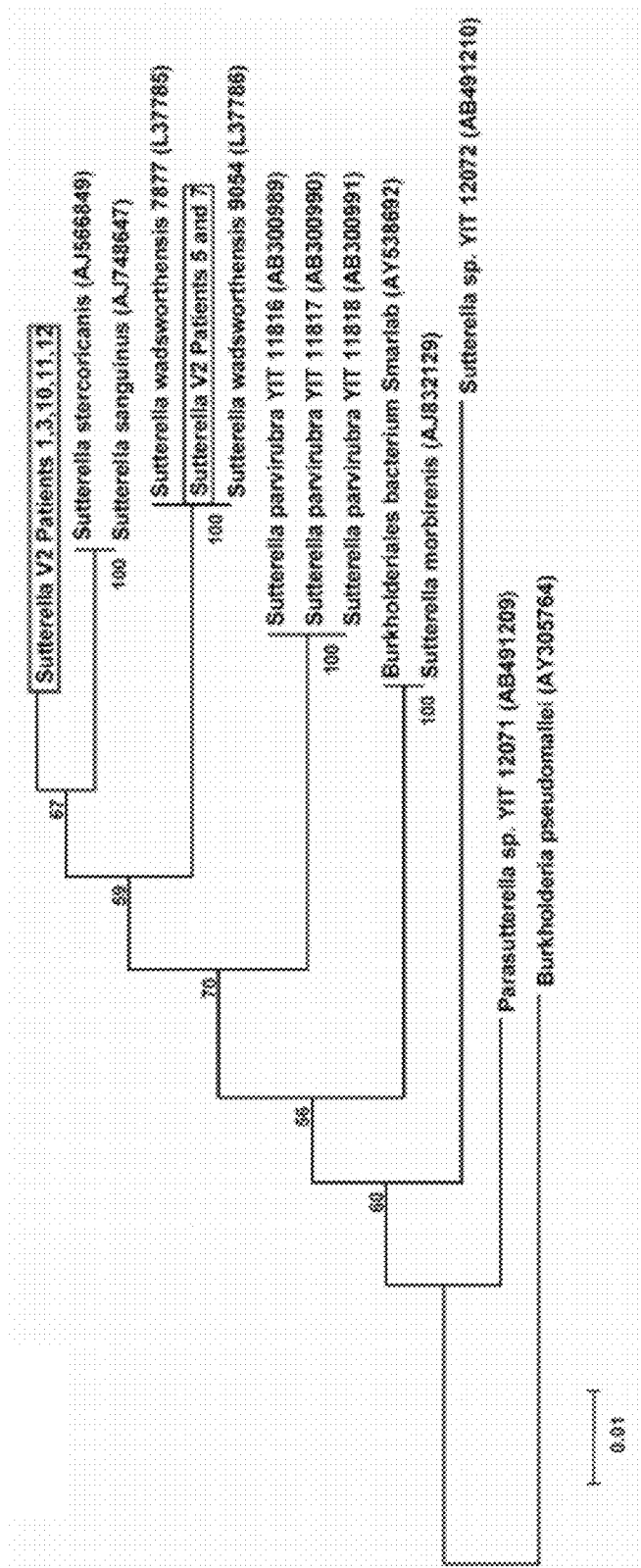
FIG. 15B is a schematic depicting *Sutterella* sp. treeing analysis of the V2 sequence.

Implementation of *Sutterella* sp.-specific Classical PCR for Taxonomic Classification. Sequences obtained from direct cloning and clone libraries of the V6-V8 regions of each patient were aligned following removal of primer sequences. This analysis revealed that the consensus sequence obtained in ileal biopsies matched exactly with sequences in cecal biopsies from the same patient. Furthermore, alignment of sequences revealed that patients 1, 3, 10, 11, and 12 had the exact same sequence for the V6-V8 region, while patients 5 and 7 had a distinct, but identical sequence (FIG. 13). These findings are in agreement with OTU analysis of V2 pyrosequencing reads in which patients 1, 3, 10, 11, and 12 clustered together with OTU 11 containing the majority of *Sutterella* sequences and patient 5 and 7 clustered together with OTU 38 containing the majority *Sutterella* sequences (FIG. 14). Treeing analysis of the V6-V8 sequences revealed that *Sutterella* sp. found in patients 1,3, 10, 11, and 12 were phylogenetically most closely associated with the isolates *Sutterella stercoricanis* (supported by a bootstrap resampling value of 70%) and *Parasutterella* sp. (supported by a bootstrap resampling value of 68%). In contrast, treeing analysis revealed that *Sutterella* sp. sequences found in patients 5 and 7 were most closely associated with the isolate *Sutterella wadsworthensis* (supported by a bootstrap resampling value of 94%) (FIG. 15A). These findings were consistent with treeing analysis obtained from V2 sequences obtained from pyrosequencing analysis in which V2 *Sutterella* sequences from patients 1,3, 10, 11, and 12 were most closely associated with the isolates *Sutterella stercoricanis* and *Sutterella sanguinus* (supported by a bootstrap resampling value of 67%) while the V2 *Sutterella* sequences from patients 5 and 7 were most closely associated with the isolates of *Sutterella wadsworthensis* (supported by a bootstrap resampling value of 100%) (FIG. 15B). Thus, sequences from patients 5 and 7 clustered with *Sutterella wadsworthensis* isolates using both the V2 pyrosequencing reads and the V6-V8 sequences obtained from this assay. In contrast, sequences from patients 1, 3, 10, 11, and 12 clustered with *Sutterella stercoricanis* using both the V2 pyrosequencing reads and the V6-V8 sequence obtained from this assay. However, there was some divergence between the V2 and V6-V8 regions in determining relationships to other isolates (i.e. relatedness to *Sutterella sanguinus* from the V2 sequences and relatedness to *Parasutterella* sp. from the V6-V8 sequences).

REFERENCES

A1.) Wexler H M, Reeves D, Summanen P H, Molitoris E, McTeague M, Duncan J, Wilson K H, Finegold S M. 1996. *Sutterella wadsworthensis* gen. nov., sp. nov., bile-resistant microaerophilic *Campylobacter gracilis*-like clinical isolates. Int J Syst Bacteriol, 46(1): 252-258.

A2.) Mangin I, Bonnet R, Seksik P, Rigottier-Gois L, Sutren M, Bouhnik Y, Neut C, Collins M D, Colombel J F, Marteau P, Dore J. 2004. Molecular inventory of faecal microflora in patients with Crohn's disease. FEMS Microbiol Ecol, 50(1): 25-36.

A3.) Gophna U, Sommerfeld K, Gophna S, Doolittle W F, Veldhuyzen van Zanten S J. 2006. Differences between tissue-associated intestinal microfloras of patients with Crohn's disease and ulcerative colitis. J Clin Microbiol, 44(11): 4136-4141.

A4.) Greetham H L, Collins M D, Gibson G R, Giffard C, Falsen E, Lawson P A. 2004. *Sutterella stercoricanis* sp. nov., isolated from canine faeces. Int J Syst Evol Microbiol. 54: 1581-1584.

A5.) J Scupham A, Patton T G, Bent E, Bayles D O. 2008. Comparison of the cecal microbiota of domestic and wild turkeys. Microb Ecol. 56: 322-331.

A6.) Frank D N, St Amand A L, Feldman R A, Boedeker E C, Harpaz N, Pace N R. 2007. Molecular-phylogenetic characterization of microbial community imbalances in human inflammatory bowel diseases. Proc Nati Acad Sci USA. 104: 13780-13785.

King A, Downes J, Nord C E, Phillips I; European Study Group. 1999. Antimicrobial susceptibility of non-Bacteroides fragilis group anaerobic Gram-negative bacilli in Europe. Clin Microbiol Infect. 5: 404-416.

Goldstein E J, Citron D M. 2009. Activity of a novel carbapenem, doripenem, against anaerobic pathogens. Diagn Microbiol Infect Dis. 63: 447-454.

Wexler H M, Molitoris D, St John S, Vu A, Read E K, Finegold S M. 2002. In vitro activities of faropenem against 579 strains of anaerobic bacteria. Antimicrob Agents Chemother. 46: 3669-3675.

Wexler H M, Molitoris D, Finegold S M. 2000. In vitro activities of MK-826 (L-749,345) against 363 strains of anaerobic bacteria. Antimicrob Agents Chemother. 44: 2222-2224.

Molitoris E, Wexler H M, Finegold S M. 1997. Sources and antimicrobial susceptibilities of Campylobacter gracilis and *Sutterella* wadsworthensis. Clin Infect Dis. Suppl 2: S264-265.

Wexler H M, Molitoris E, Molitoris D, Finegold S M. 1996. In vitro activities of trovafloxacin against 557 strains of anaerobic bacteria. Antimicrob Agents Chemother. 40: 2232-2235.

Example 3

Impaired Carbohydrate Digestion and Transport and Mucosal Dysbiosis

Gastrointestinal disturbances are commonly reported in children with autism, complicate clinical management, and can contribute to behavioral impairment. Reports of deficiencies in disaccharidase enzymatic activity and of beneficial responses to probiotic and dietary therapies led to the survey gene expression and the mucoepithelial microbiota in intestinal biopsies from children with autism and gastrointestinal disease and children with gastrointestinal disease alone. Ileal transcripts encoding disaccharidases and hexose transporters were deficient in children with autism, indicating impairment of the primary pathway for carbohydrate digestion and transport in enterocytes. Deficient expression of these enzymes and transporters was associated with expression of the intestinal transcription factor, CDX2. Metagenomic analysis of intestinal bacteria revealed compositional dysbiosis manifest as decreases in Bacteroidetes, increases in the ratio of Firmicutes to Bacteroidetes, and increases in Betaproteobacteria. Expression levels of disaccharidases and transporters were associated with the abundance of affected bacterial phylotypes. These results indicate a relationship between human intestinal gene expression and bacterial community structure and provide insights into the pathophysiology of gastrointestinal disturbances in children with autism.

Autism spectrum disorders (ASD) are defined by impairments in verbal and non-verbal communication, social interactions, and repetitive and stereotyped behaviors. In addition to these core deficits, the prevalence of gastrointestinal (GI) symptoms ranges widely in individuals with ASD, from 9 to 91% in different study populations [1]. Macroscopic and histological observations in ASD include findings of ileocolonic lymphoid nodular hyperplasia, enterocolitis, gastritis and esophagitis [2,3,4,5,6,7]. Associated changes in intestinal inflammatory parameters include higher densities of lymphocyte populations, aberrant cytokine profiles, and deposition of immunoglobulin (IgG) and complement C1q on the basolateral enterocyte membrane [5,8,9,10,11,12]. Reported functional disturbances include increased intestinal permeability [13], deficient enzymatic activity of disaccharidases [7], increased secretin-induced pancreatico-biliary secretion [7], and abnormal *Clostridia taxa* [14,15,16]. Some children placed on exclusion diets or treated with the antibiotic vancomycin are reported to improve in cognitive and social function [17,18]. Furthermore, a strong correlation between GI symptoms and autism severity was found [19].

The intestinal mucoepithelial layer must maximize nutritional uptake of dietary components while maintaining a barrier to toxins and infectious agents. Although some aspects of these functions are host-encoded, others are acquired through symbiotic relationships with microbial flora. Dietary carbohydrates enter the intestine as monosaccharides (glucose, fructose, and galactose), disaccharides (lactose, sucrose, maltose), or complex polysaccharides. Following digestion with salivary and pancreatic amylases, carbohydrates are further digested by disaccharidases expressed by absorptive enterocytes in the brush border of the small intestine and transported as monosaccharides across the intestinal epithelium. Although humans lack the glycoside hydrolases and polysaccharide lyases necessary for cleavage of glycosidic linkages present in plant cell wall polysaccharides, oligosaccharides, storage polysaccharides, and resistant starches, intestinal bacteria encoding these enzymes expand the capacity to extract energy from dietary polysaccharides [20,21]. As an end product of polysaccharide fermentation, bacteria produce short-chain fatty acids (butyrate, acetate, and propionate) that serve as energy substrates for colonocytes, modulate colonic pH, regulate colonic cell proliferation and differentiation, and contribute to hepatic gluconeogenesis and cholesterol synthesis [22,23]. Intestinal microbes also mediate postnatal development of the gut mucoepithelial layer, provide resistance to potential pathogens, regulate development of intraepithelial lymphocytes and Peyer's patches, influence cytokine production and serum immunoglobulin levels, promote systemic lymphoid organogenesis, and influence brain development and behavior [24,25,26].

Although bacteria have been examined in fecal material from children with autism, no study to date has reported analyses of microbiota adherent to their intestinal mucoepithelium. Furthermore, there are no reports wherein intestinal gene expression in children with autism has been correlated with alterations in intestinal microbiota. GI dysfunction is commonly reported in children with autism; however, it remains unclear how or whether GI dysfunction in children with autism differs from GI dysfunction found in typically developing children. Expression of human genes involved in carbohydrate digestion and transport was investigated along with bacterial community composition in intestinal biopsies from children with autistic disorder and GI disease (AUT-GI) compared to children with GI disease alone (Control-GI). Results from gene expression assays and metagenomic analysis of over half a million bacterial 16S rRNA gene sequences revealed decreased mRNA expression for human disaccharidases and hexose transporters and compositional dysbiosis in children in the AUT-GI group compared to those in the Control-GI group. Results described herein show the complex relationship between human intestinal gene expression and bacterial community structure, and provide insights into the molecular mechanisms underlying the pathophysiology of gastrointestinal disturbances in children with autism.

Results

Patient Characteristics

All AUT-GI and Control-GI children evaluated were male (Table 6A). Mean onset age for autism in AUT-GI was 13.4+/−5.4 months. Median age at biopsy was similar for AUT-GI and Control-GI children [median age in years (interquartile range, IQR), AUT-GI, 4.5 (1.3); and Control-GI, 4.0 (1.1)]. Median number of medications used and the IQR for number of medications used per subject were identical in AUT-GI and Control-GI children. Food allergies (FA) were commonly reported in both AUT-GI (67%) and Control-GI (71%) subjects. The majority of children with FA had reported milk-related allergy (90% for AUT-GI and 100% for Control-GI) and/or wheat-related allergy (80% for AUT-GI and 80% for Control-GI). Beneficial effects of dietary intervention on GI disturbances were reported for all AUT-GI and Control-GI subjects with FA. Comorbid conditions were reported in 67% of AUT-GI children and 100% of Control-GI children. The most commonly reported comorbid conditions were atopic manifestations (asthma, atopic dermatitis, and allergic rhinitis). Atopic manifestations were more common in Control-GI children (100%) than AUT-GI children (53%) (Table 6A). The frequency of individual atopic manifestations was higher in Control-GI children. The largest difference in frequency was for asthma, which was only reported in 20% of AUT-GI children compared to 71% of Control-GI children (Table 6A). Established intestinal disorders were only reported in a few subjects: two AUT-GI subjects (13%: 1 with IBD, 1 with Celiac disease) and one Control-GI subject (14%: IBD). For detailed information related to medication use, food allergy and comorbid conditions in individual AUT- GI and Control-GI children see Table 7. The prevalence of specific GI symptoms was similar in AUT-GI and Control-GI children (Table 6B). The most frequently reported GI symptoms in both groups were diarrhea (AUT-GI, 80%; Conrol-GI, 71%) and changes in stool frequency (AUT-GI, 87%; Control-GI, 71%) and consistency (AUT-GI, 80%; Control-GI, 86%). Mucus in stool was more frequent in Control-GI (86%) compared to AUT-GI (40%) children; bloating was more frequent in AUT-GI (60%) compared to Control-GI (29%) children. Regression (loss of language and/or other skills following acquisition) is reported in 20% to 40% of individuals with autism, and some studies indicate higher rates of GI symptoms in ASD subjects with regression than those without regression [27]. 87% of the AUT-GI subjects had behavioral regression (Table 8).

TABLE 6A, B

Summary of patient characteristics.

| Subject Characteristic | Subcategory | AUT-GI (n = 15) | Control-GI (n = 7) |
|---|---|---|---|
| Autism onset age in months, mean ± SD | AUT-GI subjects | 13.4 ± 5.4 | — |
| Gender | All subjects | All male | All male |
| Ethnicity, n (%) | Caucasian | 14 (93) | 6 (86) |
| | Hispanic | 1 (7) | 0 (0) |
| | African-American | 0 (0) | 1 (14) |
| Age at biopsy in years, median (IQR) [range] | All subjects | 4.5 (1.3) [3.5-5.9] | 4.0 (1.1) [3.9-5.5] |
| Medications-number per subject[a], median (IQR) [range] | All subjects | 5 (7) [1-21] | 5 (7) [0-8] |
| Food allergies, n (% of subjects) | All subjects | 10 (67) | 5 (71) |
| Milk-related allergy[b], n (% of subjects with food allergy) | Subjects reporting any food allergy | 9 (90) | 5 (100) |
| Wheat-related allergy[c], n (% of subjects with food allergy) | Subjects reporting any food allergy | 8 (80) | 4 (80) |

TABLE 6A, B-continued

Summary of patient characteristics.

| Subject Characteristic | Subcategory | AUT-GI (n = 15) | Control-GI (n = 7) |
|---|---|---|---|
| Diet improvement of GI problems, n (% of subjects with food allergy) | Subjects reporting any food allergy | 10 (100) | 5 (100) |
| Current comorbid conditions-number per subject, median (IQR) [range] | All subjects | 1 (1.75) [0-5] | 2 (2.75) [1-6] |
| Comorbid atopic disease manifestations[d], n (% of subjects) | All subjects | 8 (53) | 7 (100) |
| Asthma, n (% of subjects) | All subjects | 3 (20) | 5 (71) |
| Atopic dermatitis, n (% of subjects) | All subjects | 4 (27) | 4 (57) |
| Allergic rhinitis, n (% of subjects) | All subjects | 4 (27) | 3 (43) |

[a]Number of prescription drugs and alternative agents taken regularly, per subject
[b]Allergy to milk, casein, lactose or dairy
[c]Allergy to wheat or gluten
[d]Asthma, Allergic rhinitis, or Atopic dermatitis

TABLE 6B

Summary of patients' GI symptoms.

| GI Symptoms | AUT-GI, n (%) | Control-GI, n (%) |
|---|---|---|
| Diarrhea | 12 (80) | 5 (71) |
| Diarrhea w/ Vomiting | 2 (13) | 2 (29) |
| Vomiting | 2 (13) | 1 (14) |
| Bloating | 9 (60) | 2 (29) |
| Δ Stool Frequency | 13 (87) | 5 (71) |
| Δ Stool Consistency | 12 (80) | 6 (86) |
| Mucus in Stool | 6 (40) | 6 (86) |
| Blood in Stool | 2 (13) | 1 (14) |
| Pain | 8 (53) | 5 (71) |
| Weight Loss | 3 (20) | 0 (0) |
| Fever | 1 (7) | 0 (0) |

TABLE 7

Reported comorbid conditions, food allergies, and medication use by patient

| Patient # | Group | Current Comorbid Conditions | Food Allergy Reported | Medications |
|---|---|---|---|---|
| 1 | AUT-GI | asthma, atopic dermatitis, celiac disease, movement disorder, myopathy | milk, gluten, eggs, peanuts, tree nuts, soy, corn, peas | Vitamin B1, B2, B3, B6, B9, B12, C, E; Ca, Zn, Fish oil, Omega-3-fatty acids, Probiotic, Ibuprofen, Lanzoprazole, Montelukast sodium, Levalbuterol inhaler, Albuterol inhaler |
| 2 | AUT-GI | allergic rhinitis | milk, gluten, eggs | Vitamin C; MVM, Ca/Mg supplement, Omeprazole |
| 3 | AUT-GI | IBD | Milk, gluten, dyes | Vitamin B12, C; MVM, Ca/Mg supplement, Zn, flaxseed oil, antifungal herbal agent, digestive enzymes |
| 4 | AUT-GI | allergic rhinitis, asthma, atopic dermatitis, migraine | casein, gluten | Vitamin A, C, Methyl-B12, Folinic acid; MVM, Ca/Mg supplement, Zn, Mb, Fish oil, Omega-3-fatty acids, SAMe, Inositol, Selenomethionine, Trimethylglycine, 5-methyl-tetrahydrofolate, Transdermal glutathione, MgSO4 cream, Zn soy |

TABLE 7-continued

Reported comorbid conditions, food allergies, and medication use by patient

| Patient # | Group | Current Comorbid Conditions | Food Allergy Reported | Medications |
|---|---|---|---|---|
| | | | | cream, DMAE, DMPS, Alpha lipoic acid, Montelukast sodium |
| 5 | AUT-GI | atopic dermatitis | lactose | MVM |
| 6 | AUT-GI | allergic rhinitis, frequent URI, epilepsy | gluten, corn, soy | Vitamin D; Ca, Zn, Mg, P, Flaxseed oil, Probiotic, Artichoke extract, Sarsaparilla extract, Wasabi powder, Lipase, Amylase, Protease |
| 7 | AUT-GI | allergic rhinitis, frequent otitis media | milk, gluten, sweet potatoes, oranges, berries | Folinic acid; MVM, Ca/Mg supplement, Trimethylglycine, Lipase, Amylase, Protease, Cellulase, Lactase |
| 8 | AUT-GI | none | none reported | Vitamin B complex, L-carnitine, Lipase, Amylase, Protease, Diphenhydramine, Acetaminophen, Ibuprofen, Melatonin, Sertraline, Valproic acid |
| 9 | AUT-GI | none | none reported | MVM, Ca |
| 10 | AUT-GI | none | none reported | Omeprazole |
| 11 | AUT-GI | atopic dermatitis | cow's milk, goat's milk, barley, carrots, bananas, cantelope, coffee, cranberry, lamb, lettuce | Flaxseed oil, Coenzyme Q10, Cell signal enhancers (CSE-14, 15), Probiotic, Lipase |
| 12 | AUT-GI | Epstein-Barr virus infection | dairy, wheat, salicylates, Phenols | Methyl-B12, DMSA, Amphoterecin B |
| 13 | AUT-GI | asthma | dairy, wheat, yeast | Vitamin B12; Ca/Mg supplement, Zn, Probiotic, Clonidine, Secretin |
| 14 | AUT-GI | none | none reported | MVM, F |
| 15 | AUT-GI | none | none reported | Lipase, Amylase, Protease, Milk of magnesia, Lansoprazole |
| 16 | Control-GI | allergic rhinitis, asthma, atopic dermatitis, frequent sinusitis | none reported | MVM, Montelukast sodium, Fluticasone propionate, Lansoprazole, Amoxicillin |
| 17 | Control-GI | atopic dermatitis | none reported | Ca citrate, Mg/amino acid complex, Hydroxyzine, Budesonide, Prednisolone, Montelukast sodium, Levalbuterol inhaler, Tacrolimus |
| 18 | Control-GI | asthma | dairy, peanuts | Ibuprofen |
| 19 | Control-GI | asthma, atopic dermatitis, IBD, dysphagia, microcytic anemia, pancreatic insufficiency | milk, wheat, eggs, oats, salmon, soy, peanut, tree nut, chicken, turkey, beef, broccoli, cabbage, lentils, legumes | Lipase, Amylase, Protease, Diphenhydramine, Cetirizine hydrochloride, Omeprazole, Budesonide, Montelukast sodium, Levalbuterol inhaler |
| 20 | Control-GI | allergic rhinitis, asthma, atopic dermatitis | dairy, gluten, eggs, soy, citrus | Vitamin B12, Fish oil, Milk thistle, DMSA, Allithiamine |
| 21 | Control-GI | asthma | dairy, wheat, eggs, fruit | Probiotic |

TABLE 7-continued

Reported comorbid conditions, food allergies, and medication use by patient

| Patient # | Group | Current Comorbid Conditions | Food Allergy Reported | Medications |
|---|---|---|---|---|
| 22 | Control-GI | allergic rhinitis, vitiligo | dairy, wheat, eggs, peanuts, beef | none reported |

IBD—Inflammatory Bowel Disease;
URI—Upper respiratory tract infection;
MVM—multivitamin with minerals;
SAMe—S-adenosylmethionine;
DMAE—dimethylaminoethanol;
DMPS—2,3-Dimercapto-1-propanesulfonic acid;
DMSA—Dimercaptosuccinic acid

TABLE 8

Reported behavioral regression in AUT-GI children.

| PHENOTYPIC CHARACTERISTICS | | AUT/GI cases (n = 15) n (%) |
|---|---|---|
| ANY REPORTED LOSS (ADI-R or CDI) | | 13 (87) |
| ADI-R LOSS ITEMS | Language loss | 11 (73) |
| | Other skill loss (with or without language loss) | 12 (80) |
| | Other skill loss without language loss | 2 (13) |
| CPEA REGRESSION CATEGORY | Word loss regression | 12 (80) |
| | Non-word loss regression | 1 (7) |
| | No regression | 2 (13) |

Legend:
ADI-R, Autism Diagnostic Interview-Revised;
CDI, MacArthur Communicative Development Inventory;
CPEA, Collaborative Program for Excellence in Autism.

Deficient Ileal mRNA Expression of Disaccharidases and Hexose Transporters in AUT-GI Children Transcript levels were examined for three primary brush border disaccharidases (sucrase isomaltase [SI], maltase glucoamylase [MGAM], and lactase [LCT]) in ileal biopsies of AUT-GI and Control-GI children by real time PCR. Levels of mRNA for all three enzymes were decreased in AUT-GI children: SI (FIG. 16A: Mann-Whitney, p=0.001), MGAM (FIG. 16B: Mann-Whitney, p=0.003) and LCT (FIG. 16C: Mann-Whitney, p=0.032). Within the AUT-GI group, 86.7%, 80%, and 80% of children had deficient transcript levels (defined as below the $25^{th}$ percentile of values obtained for Control-GI children and at least two-fold below Control-GI mean values) for SI, MGAM, and LCT, respectively (Table 9A and Table 10). Nearly all (14/15, or 93.3%) AUT-GI children had deficiencies in at least one disaccharidase enzyme; 80% had deficiencies in 2 or more enzymes; 73.3% had deficiencies in all three enzymes (Table 9A). Deficiencies in LCT mRNA in AUT-GI children were not attributable to disproportionate adult-type hypolactasia genotypes in the AUT-GI group relative to the Control-GI group (FIG. 36A-D).

TABLE 9

Patient summary tables for gene expression and bacterial assays.

A

| AUT-GI Patient # | Disaccharidases | | | Transporters | | | | # Deficiencies (Disaccharidases) | # Deficiencies (Transporters) | Total Deficiencies (Disacch. + Transport.) |
|---|---|---|---|---|---|---|---|---|---|---|
| | SI | MGAM | LCT | SGLT1 | GLUT2 | CDX2 | Villin | | | |
| 1 | ⇓⇓ | ⇓⇓ | ⇓⇓ | ⇓⇓ | ⇓⇓ | ⇓ | n.c. | 3/3 | 2/2 | 5/5 |
| 2 | ⇓⇓ | ⇓⇓ | ⇓⇓ | ⇓⇓ | ⇓⇓ | ⇓⇓ | ⇓⇓ | 3/3 | 2/2 | 5/5 |
| 3 | ⇓⇓ | ⇓⇓ | ⇓⇓ | ⇓⇓ | ⇓⇓ | ⇓⇓ | ⇑⇑ | 3/3 | 2/2 | 5/5 |
| 4 | ⇓⇓ | ⇓⇓ | ⇓⇓ | ⇓⇓ | ⇓⇓ | n.c. | ⇑⇑ | 3/3 | 2/2 | 5/5 |
| 5 | ⇓⇓ | ⇓⇓ | ⇓⇓ | ⇓⇓ | ⇓⇓ | ⇓⇓ | ⇓⇓ | 3/3 | 2/2 | 5/5 |
| 6 | ⇓⇓ | n.c. | n.c. | n.c. | n.c. | n.c. | n.c. | 1/3 | 0/2 | 1/5 |
| 7 | n.c. | n.c. | ⇑⇑ | n.c. | n.c. | ⇑ | ⇑⇑ | 0/3 | 0/2 | 0/5 |
| 8 | ⇓⇓ | ⇓⇓ | ⇓ | ⇓⇓ | ⇓⇓ | n.c. | ⇑ | 3/3 | 2/2 | 5/5 |
| 9 | ⇓⇓ | ⇓⇓ | ⇓⇓ | ⇓⇓ | n.c. | n.c. | ⇑ | 3/3 | 1/2 | 4/5 |

TABLE 9-continued

Patient summary tables for gene expression and bacterial assays.

| | | | | | | | | | | |
|---|---|---|---|---|---|---|---|---|---|---|
| 10 | ⇩⇩ | ⇩⇩ | ⇩⇩ | ⇩⇩ | ⇩⇩ | n.c. | ⇧ | 3/3 | 2/2 | 5/5 |
| 11 | ⇩⇩ | ⇩⇩ | ⇩⇩ | ⇩⇩ | ⇩⇩ | n.c. | ⇩ | 3/3 | 2/2 | 5/5 |
| 12 | ⇩⇩ | ⇩⇩ | ⇩⇩ | ⇩⇩ | ⇩⇩ | n.c. | n.c. | 3/3 | 2/2 | 5/5 |
| 13 | ⇩⇩ | ⇩⇩ | ⇩⇩ | ⇩⇩ | ⇩⇩ | ⇩⇩ | ⇩⇩ | 3/3 | 2/2 | 5/5 |
| 14 | ⇩⇩ | ⇩⇩ | n.c. | n.c. | ⇩⇩ | n.c. | ⇧⇧ | 2/3 | 1/2 | 3/5 |
| 15 | n.c. | n.c. | ⇩⇩ | n.c. | n.c. | n.c. | n.c. | 1/3 | 0/2 | 1/5 |
| % below controls | 86.7% | 80.0% | 80.0% | 73.3% | 73.3% | 33.3% | 26.7% | Summary All 3 = 73.3% At least 2 = 80.0% At least 1 = 93.3% | Summary Both = 66.7% At least 1 = 80.0% | Summary All 5 = 66.7% At least 4 = 73.3% At least 3 = 80.0% At least 1 = 93.3% |

B

| AUT-GI Patient # | Bacteroidetes RT-Ileum | Bacteroidetes RT-Cecum | Bacteroidetes 454-Ileum | Bacteroidetes 454-Cecum | Firmicutes RT-Ileum | Firmicutes RT-Cecum | Firmicutes 454-Ileum | Firmicutes 454-Cecum | Clostridia 454-Ileum |
|---|---|---|---|---|---|---|---|---|---|
| 1 | ⇩ | ⇩⇩ | ⇩⇩ | ⇩⇩ | ⇧ | ⇧ | ⇧⇧ | ⇧⇧ | ⇧⇧ |
| 2 | ⇩⇩ | ⇩ | ⇩⇩ | ⇩⇩ | ⇧⇧ | ⇧⇧ | ⇩ | n.c. | ⇩ |
| 3 | ⇩⇩ | ⇩ | ⇩ | ⇩⇩ | ⇧ | ⇧⇧ | ⇧⇧ | ⇧ | ⇧⇧ |
| 4 | ⇩⇩ | ⇩ | ⇩⇩ | ⇩⇩ | ⇧⇧ | ⇧⇧ | ⇧⇧ | ⇧⇧ | ⇧⇧ |
| 5 | ⇩⇩ | ⇩ | ⇧ | n.c. | n.c. | n.c. | ⇩ | n.c. | ⇩ |
| 6 | ⇩ | n.c. | n.c. | ⇧ | ⇧ | ⇧⇧ | ⇧ | n.c. | ⇧⇧ |
| 7 | ⇩ | ⇩ | ⇩ | ⇩⇩ | n.c. | ⇧ | ⇧⇧ | ⇧⇧ | ⇧⇧ |
| 8 | ⇩⇩ | ⇩⇩ | ⇩⇩ | ⇩⇩ | n.c. | n.c. | n.c. | n.c. | n.c. |
| 9 | ⇩ | ⇩ | ⇩⇩ | ⇩⇩ | ⇧ | n.c. | ⇧⇧ | ⇧⇧ | ⇧⇧ |
| 10 | ⇩ | ⇩ | ⇩⇩ | ⇩⇩ | n.c. | n.c. | ⇧⇧ | ⇧⇧ | ⇧⇧ |
| 11 | ⇩⇩ | ⇩⇩ | ⇩⇩ | ⇩⇩ | ⇧⇧ | ⇧⇧ | n.c. | n.c. | ⇧ |
| 12 | ⇩ | ⇩ | n.c. | n.c. | n.c. | n.c. | n.c. | n.c. | n.c. |
| 13 | ⇩⇩ | ⇩ | ⇩ | ⇩⇩ | n.c. | ⇧ | ⇧⇧ | ⇧⇧ | ⇧⇧ |
| 14 | ⇩ | n.c. | ⇩ | n.c. | n.c. | n.c. | ⇧⇧ | n.c. | ⇧⇧ |
| 15 | ⇩⇩ | ⇩ | ⇩⇩ | ⇩⇩ | ⇩⇩ | ⇩⇩ | ⇩⇩ | ⇩⇩ | ⇩⇩ |
| % below[a] or above[b] controls | 100%[a] | 86.7%[a] | 80.0%[a] | 73.3%[a] | 46.7%[b] | 53.3%[b] | 60.0%[b] | 46.7%[b] | 66.7%[a] |

TABLE 9-continued

Patient summary tables for gene expression and bacterial assays.

| AUT-GI Patient # | Clostridia 454-Cecum | Firmicutes Lach. + Rumino. 454-Ileum | Lach. + Rumino. 454-Cecum | Proteobacteria 454-Ileum | Probacteria Proteobacteria 454-Cecum | Beta-Proteobacteria 454-Ileum | Beta-Proteobacteria 454-Cecum | Alcaligenaceae 454-Ileum & Cecum |
|---|---|---|---|---|---|---|---|---|
| 1 | ⇧⇧ | ⇧⇧ | ⇧⇧ | n.c. | n.c. | ⇧⇧ | ⇧⇧ | ⇧⇧ |
| 2 | n.c. | ⇩ | n.c. | ⇧⇧ | ⇧⇧ | ⇧⇧ | ⇧⇧ | n.c. |
| 3 | ⇧⇧ | ⇧⇧ | ⇧⇧ | n.c. | n.c. | ⇧⇧ | ⇧⇧ | ⇧⇧ |
| 4 | ⇧⇧ | ⇧⇧ | ⇧⇧ | n.c. | n.c. | ⇧ | n.c. | n.c. |
| 5 | n.c. | ⇩ | n.c. | n.c. | ⇧ | ⇧⇧ | ⇧⇧ | ⇧⇧ |
| 6 | n.c. | ⇧⇧ | n.c. | ⇩⇩ | ⇩ | ⇩ | ⇩⇩ | n.c. |
| 7 | ⇧⇧ | ⇧⇧ | ⇧⇧ | n.c. | n.c. | n.c. | ⇧ | ⇧⇧ |
| 8 | n.c. | n.c. | n.c. | ⇧⇧ | ⇧⇧ | ⇩ | n.c. | n.c. |
| 9 | ⇧⇧ | ⇧⇧ | ⇧⇧ | n.c. | n.c. | n.c. | ⇧⇧ | n.c. |
| 10 | ⇧⇧ | ⇧⇧ | ⇧⇧ | n.c. | n.c. | ⇧⇧ | ⇧⇧ | ⇧⇧ |
| 11 | n.c. | n.c. | n.c. | ⇧⇧ | ⇧⇧ | ⇧⇧ | ⇧⇧ | ⇧⇧ |
| 12 | n.c. | n.c. | n.c. | n.c. | n.c. | ⇧⇧ | ⇧⇧ | ⇧⇧ |
| 13 | ⇧⇧ | ⇧⇧ | ⇧⇧ | n.c. | ⇧⇧ | n.c. | ⇧⇧ | n.c. |
| 14 | ⇧ | ⇧⇧ | ⇧⇧ | n.c. | n.c. | n.c. | n.c. | n.c. |
| 15 | ⇩⇩ | ⇩⇩ | ⇩⇩ | ⇧⇧ | ⇧⇧ | n.c. | ⇩⇩ | n.c. |
| % below[a] or above[b] controls | 53.3%[b] | 60.0%[a] | 53.3%[b] | 26.7%[b] | 40.0%[b] | 53.3%[a] | 66.7%[a] | 46.7%[a] |

C

| AUT-GI Patient # | Firm./Bacteroid. Ratio-RT Ileum | Firm./Bacteroid. Ratio-RT Cecum | Firm./Bacteroid. Ratio-454 Ileum | Firm./Bacteroid. Ratio-454 Cecum | Clostridiales/ Bacteroidales Ratio-454 Ileum | Clostridiales/ Bacteroidales Ratio-454 Cecum | Firm. + Proteobac. Ratio-454 Ileum | Firm. + Proteobac. Ratio-454 Ileum |
|---|---|---|---|---|---|---|---|---|
| 1 | ⇧⇧ | ⇧⇧ | ⇧⇧ | ⇧⇧ | ⇧⇧ | ⇧⇧ | ⇧⇧ | ⇧⇧ |
| 2 | ⇧⇧ | ⇧⇧ | ⇧⇧ | ⇧ | ⇧⇧ | ⇧ | ⇧⇧ | ⇧⇧ |
| 3 | ⇧⇧ | ⇧⇧ | ⇧ | ⇧⇧ | ⇧⇧ | ⇧⇧ | ⇧ | ⇧⇧ |
| 4 | ⇧⇧ | ⇧⇧ | ⇧⇧ | ⇧⇧ | ⇧⇧ | ⇧⇧ | ⇧⇧ | ⇧⇧ |
| 5 | ⇧⇧ | n.c. | ⇩ | n.c. | ⇩ | n.c. | ⇩ | n.c. |
| 6 | ⇧⇧ | ⇧⇧ | n.c. | n.c. | ⇧ | n.c. | n.c. | ⇩ |
| 7 | ⇧⇧ | ⇧ | ⇧⇧ | ⇧⇧ | ⇧⇧ | ⇧⇧ | ⇧ | ⇧⇧ |
| 8 | ⇧⇧ | ⇧ | ⇧⇧ | ⇧⇧ | ⇧⇧ | ⇧⇧ | ⇧⇧ | ⇧⇧ |
| 9 | ⇧⇧ | n.c. | ⇧⇧ | ⇧⇧ | ⇧⇧ | ⇧⇧ | ⇧⇧ | ⇧⇧ |
| 10 | ⇧ | n.c. | ⇧⇧ | ⇧⇧ | ⇧⇧ | ⇧⇧ | ⇧⇧ | ⇧⇧ |
| 11 | ⇧⇧ | ⇧⇧ | ⇧ | ⇧ | ⇧ | ⇧⇧ | ⇧⇧ | ⇧⇧ |
| 12 | ⇧⇧ | n.c. | n.c. | n.c. | n.c. | n.c. | n.c. | n.c. |
| 13 | ⇧⇧ | ⇧⇧ | ⇧⇧ | ⇧⇧ | ⇧⇧ | ⇧⇧ | ⇧ | ⇧⇧ |
| 14 | ⇧ | n.c. | ⇧⇧ | ⇧⇧ | ⇧⇧ | ⇧⇧ | ⇧ | n.c. |
| 15 | ⇧⇧ | ⇩ | ⇩ | ⇩⇩ | ⇩ | ⇩⇩ | ⇧⇧ | ⇧⇧ |
| % above controls | 100% | 60% | 73.3% | 66.7% | 80.0% | 66.7% | 80% | 73.3% |

TABLE 9-continued

Patient summary tables for gene expression and bacterial assays.

(A-C) Legend:
Increases or decreases in AUT-GI children in both gene expression (A) and bacterial parameters (B and C) were determined for each individual based on the levels of each parameter in the Control-GI group.
(A) The gene expression levels in the AUT-GI children that exceeded the 75$^{th}$ percentile of Control-GI values and were at least 2-fold increased relative to the Control-GI mean (arrow pointing up) or below the 25$^{th}$ percentile of Control-GI values and at least 2-fold decreased relative to the Control-GI mean (arrow pointing down) were scored as an increase or decrease, respectively.
(B and C) Bacterial parameters in AUT-GI children that exceeded the 75$^{th}$ percentile of Control-GI values (arrows pointing up) or were below the 25$^{th}$ percentile of Control-GI values (arrows pointing down) were scored as an increase or decrease, respectively.
Values above the 90$^{th}$ or below the 10$^{th}$ percentiles of Control-GI children are indicated by double arrows.
Results are shown for data obtained by real-time PCR (RT), where performed, and pyrosequencing (454).
(n.c. = no change relative to defined cut-off values for Control-GI children).

TABLE 10

Fold-change in gene expression in AUT-GI children.

| Patient # | Si Fold Change | MGAM Fold Change | LCT Fold Change | SGLT1 Fold Change | GLUT2 Fold Change | CDX2 Fold Change | Villin Fold Change |
|---|---|---|---|---|---|---|---|
| 1 | 0.0273 | 0.0323 | 0.0083 | 0.1739 | 0.0037 | 0.3676 | 0.9095* |
| 2 | 0.0021 | 0.0004 | 0.0003 | 0.0028 | 0.0017 | 0.0209 | 0.0366 |
| 3 | 0.0135 | 0.0089 | 0.0396 | 0.0307 | 0.0275 | 0.0678 | 3.6382 |
| 4 | 0.0173 | 0.0111 | 0.0266 | 0.0954 | 0.0098 | 0.7851* | 4.7288 |
| 5 | 0.0202 | 0.0051 | 0.0074 | 0.0366 | 0.0014 | 0.2209 | 0.1294 |
| 6 | 0.2689 | 0.8365* | 1.2090* | 0.6701* | 0.7206* | 0.9873* | 0.9374* |
| 7 | 0.5089* | 0.4707 | 2.7187 | 1.0126* | 1.1281* | 1.9536* | 5.9871 |
| 8 | 0.0373 | 0.0321 | 0.0782 | 0.0368 | 0.0540 | 1.1297* | 1.5669* |
| 9 | 0.0556 | 0.0285 | 0.0026 | 0.1062 | 1.4925* | 0.6623* | 1.5851* |
| 10 | 0.0670 | 0.0962 | 0.0277 | 0.1432 | 0.0911 | 0.6832* | 1.6667* |
| 11 | 0.0663 | 0.0670 | 0.0353 | 0.2053 | 0.0758 | 0.3985 | 0.5064* |
| 12 | 0.1249 | 0.0275 | 0.0546 | 0.1859 | 0.0520 | 0.4089 | 0.9127* |
| 13 | 0.0908 | 0.0498 | 0.0004 | 0.1037 | 0.0381 | 0.1399 | 0.1662 |
| 14 | 0.2115 | 0.1669 | 0.5035* | 1.3283* | 0.1628 | 0.6335* | 3.9841 |
| 15 | 1.3133* | 1.2678* | 0.0365 | 1.0009* | 0.8145* | 0.8627* | 0.9506* |

Legend:
Fold-change values were calculated realtive to the mean expression level obtained for all Control-GI children for each gene.
Expression levels for individual patients that were at least 2-fold increased (>2) or decreased (<0.5) relative to the Control-GI mean (grey*) are highlighted in gray, and dark gray, respectively.

Two hexose transporters, sodium-dependent glucose cotransporter (SGLT1) and glucose transporter 2 (GLUT2), mediate transport of monosaccharides in the intestine. SGLT1, located on the luminal membrane of enterocytes, is responsible for the active transport of glucose and galactose from the intestinal lumen into enterocytes. GLUT2 transports glucose, galactose and fructose across the basolateral membrane into the circulation and can also translocate to the apical membrane [28]. Real-time PCR revealed a decrease in ileal SGLT1 mRNA (FIG. 16D: Mann-Whitney, p=0.008) and GLUT2 mRNA (FIG. 16E: Mann-Whitney, p=0.010) in AUT-GI children. For SGLT1, 73.3% of AUT-GI children had deficient transcript levels; 73.3% of AUT-GI children had deficient GLUT2 transcript levels relative to Control-GI children (Table 9A). Deficiencies were found in at least one hexose transporter in 80% of AUT-GI children; 66.7% had deficiencies in both transporters.

In total, 93.3% (14/15) of AUT-GI children had mRNA deficiencies in at least one of the 5 genes involved in carbohydrate digestion or transport; 66.7% (10/15) had mRNA deficiencies in all 5 genes (Table 9A).

To determine whether reductions in disaccharidase and transporter transcript levels reflected loss of or damage to intestinal epithelial cells, mRNA levels associated with a tissue-specific marker restricted to these cells, villin [29,30] was measured. Ileal villin mRNA levels were not decreased in AUT-GI children (Mann-Whitney, p=0.307) (FIG. 16F). Normalization of SI, MGAM, LCT, SGLT1 and GLUT2 to villin mRNA levels did not correct deficits (FIG. 22A-E).

The transcription factor, caudal type homeobox 2 (CDX2), regulates expression of SI, LCT, GLUT2, and SGLT1 [31,32, 33,34]. Real-time PCR experiments demonstrated lower levels of CDX2 mRNA in some AUT-GI subjects versus controls; however, group differences were not significant (FIG.

16G: Mann-Whitney, p=0.192). Although only 33.3% of AUT-GI patients had deficient CDX2 mRNA levels (Table 9A), 86.7% of AUT-GI children had CDX2 levels below the 50$^{th}$ percentile of Control-GI children and 46.7% of AUT-GI children had at least a two-fold decrease in CDX2 expression relative to the Control-GI mean. Only one AUT-GI child (patient #7) had CDX2 levels above the 75$^{th}$ percentile of Control-GI children and a near 2-fold (1.95-fold) increase in CDX2 expression (Table 9A and Table 10). This child was the only AUT-GI subject who did not show signs of deficiencies in disaccharidases or transporters.

AUT-GI children with deficiencies in all five disaccharidases and tranporters had significantly lower levels of CDX2 mRNA compared to AUT-GI children with fewer than five deficiencies (FIG. 33: Mann-Whitney, p=0.037). However, only a trend toward decreased CDX2 levels was found when comparing AUT-GI children with deficiencies in all five disaccharidases and transporters and Control-GI children (FIG. 33: Mann-Whitney, p=0.064).

Multiple linear regression analysis was conducted to determine whether diagnostic status (AUT-GI or Control-GI), CDX2 mRNA expression, or villin mRNA expression (predictor variables) was associated with mRNA expression levels of individual disaccharidases (SI, MGAM, LCT) or transporters (SGLT1, GLUT2) (Table 11). In each of the five models, where the expression of SI, MGAM, LCT, SGLT1, or GLUT2 served as outcome variables, CDX2 contributed significantly to the model. As the level of CDX2 increased by one unit of standard deviation, there was a concomitant approximate one unit increase in log-transformed disaccharidase and transporter transcript levels (ranging from 0.78 for SGLT1 to 1.30 for LCT). None of the interaction terms between CDX2 and status were significant, indicating that the magnitude of the effect of CDX2 on log-transformed enzyme and transporter levels was the same for AUT-GI and Control-GI children. For SGLT1 and GLUT2 expression, CDX2 was the sole significant predictor variable in the model. Status and CDX2 were significant predictors of SI, MGAM, and LCT expression, indicateing that additional factors associated with status must also contribute to expression levels for these enzymes. Villin was not a significant predictor of the expression levels of any of the five genes after adjusting for CDX2.

TABLE 11

Multiple linear regression analysis examining CDX2 and villin as predictors of disaccharidase and transporter mRNA expression among AUT-GI and Control-GI children.

| Outcome Variable | $F_{3,18}$ (p-value) | Adjusted $R^2$ | Predictor Variables: Coefficient Estimate | | |
|---|---|---|---|---|---|
| | | | Status | CDX2$^{STDev}$ | Villin$^{STDev}$ |
| SI | 10.35 (0.0003)*** | 0.57 | −1.83* | 0.93* | −0.19 |
| MGAM | 8.78 (0.0008)*** | 0.53 | −2.10* | 1.15* | −0.20 |
| LCT | 10.87 (0.0003)*** | 0.59 | −2.25* | 1.30* | 0.65 |

TABLE 11-continued

Multiple linear regression analysis examining CDX2 and villin as predictors of disaccharidase and transporter mRNA expression among AUT-GI and Control-GI children.

| Outcome Variable | $F_{3,18}$ (p-value) | Adjusted $R^2$ | Predictor Variables: Coefficient Estimate | | |
|---|---|---|---|---|---|
| | | | Status | CDX2$^{STDev}$ | Villin$^{STDev}$ |
| SGLT1 | 6.88 (0.0030)** | 0.46 | −1.36† | 0.78* | 0.12 |
| GLUT2 | 6.06 (0.0050)** | 0.42 | −1.90† | 1.06* | 0.03 |

$^{STDev}$Change in log-transformed outcome variable levels per unit standard deviation increase in predictor variable
*p < 0.05;
**p < 0.01;
***p < 0.001;
†p < 0.1 (trend)

Mucosal Dysbiosis in AUT-GI Children

To determine whether deficient carbohydrate digestion and absorption influenced the composition of intestinal microflora, ileal and cecal biopsies from AUT-GI and Control-GI children were analyzed by bacterial 16S rRNA gene pyrosquencing. The use of biopsies rather than fecal material allowed us to assess the mucoepithelia-associated microbiota, as these likely establish more intimate interactions with the human intestinal epithelium and immune cells [35]. A total of 525,519 bacterial sequences were subjected to OTU (Operational Taxonomic Unit; defined at 97% identity) analysis and classified with RDP (Ribosomal Database Project). Rarefaction analysis of OTUs did not indicate a loss or gain of overall diversity based on Shannon Diversity estimates in AUT-GI compared to Control-GI children (See FIG. 23A-D).

Classification of pyrosequencing reads revealed that Bacteroidetes and Firmicutes were the most prevalent taxa in ileal and cecal tissues of AUT-GI and Control-GI children, followed by Proteobacteria (FIG. 17A, B). Other phyla identified at lower levels included Verrucomicrobia, Actinobacteria, Fusobacteria, Lentisphaerae, and TM7, as well as "unclassified bacteria" (sequences that could not be assigned at the phylum-level) (FIG. 17A, B). The abundance of Bacteroidetes was lower in AUT-GI ileal (FIG. 17C: Mann-Whitney, p=0.012) and cecal biopsies (FIG. 17D: Mann-Whitney, p=0.008) as compared with the abundance of Bacteroidetes in Control-GI biopsies. Real-time PCR using Bacteroidete-specific primers confirmed decreases in Bacteroidetes in AUT-GI ilea (FIG. 17E: Mann-Whitney, p=0.003; Table 12: 50% average reduction in Bacteroidete 16S rDNA copies; range, 24.36% to 76.28% decrease) and ceca (FIG. 17F: Mann-Whitney, p=0.022; Table 12: 29% average reduction in 13 of 15 patients with reduced Bacteroidetes; range, 7.22% to 56.54% decrease), with levels below the 25$^{th}$ percentile of Control-GI children in 100% of AUT-GI ilea and 86.7% of AUT-GI ceca (Table 9B). OTU analysis of Bacteroidete sequences indicateed that deficiencies in Bacteroidete sequences in AUT-GI subjects were attributable to cumulative losses of 12 predominant phylotypes of Bacteroidetes, rather than loss of any one specific phylotype (FIG. 25A-E).

TABLE 12

Percent change in bacterial levels in AUT-GI children.

| Patient # | Bacteroidetes RT—Ileum % Change | Bacteroidetes RT—Cecum % Change | Bacteroidetes 454—Ileum % Difference | Bacteroidetes 454—Cecum % Difference | Firmicutes RT—Ileum % Change | Firmicutes RT—Cecum % Change | Firmicutes 454—Ileum % Difference | Firmicutes 454—Cecum % Difference |
|---|---|---|---|---|---|---|---|---|
| 1 | −38.45 | −45.21 | −12.97 | −8.04 | 22.53 | 39.63 | 12.22 | 8.24 |
| 2 | −76.28 | −32.49 | −41.41 | −18.38 | 57.67 | 96.65 | −6.97 | 1.43 |

TABLE 12-continued

Percent change in bacterial levels in AUT-GI children.

| | | | | | | | | |
|---|---|---|---|---|---|---|---|---|
| 3 | −54.81 | −27.47 | −9.17 | −13.61 | 26.31 | 86.51 | 6.54 | 7.84 |
| 4 | −61.97 | −16.71 | −18.16 | −11.57 | 132.28 | 77.63 | 17.25 | 13.88 |
| 5 | −48.68 | −22.27 | 5.65 | 3.02 | 5.58 | −3.18 | −5.16 | −5.10 |
| 6 | −38.60 | 0.94 | 0.80 | 4.77 | 19.05 | 131.95 | 5.23 | −0.68 |
| 7 | −38.80 | −14.12 | −4.85 | −12.24 | −2.18 | 48.42 | 10.23 | 14.63 |
| 8 | −53.67 | −50.41 | −20.58 | −21.64 | −13.25 | 2.35 | 3.26 | 3.41 |
| 9 | −41.25 | −17.14 | −12.58 | −10.11 | 24.21 | 22.06 | 16.30 | 8.73 |
| 10 | −40.14 | −9.41 | −10.88 | −12.04 | −13.93 | 18.59 | 13.69 | 12.11 |
| 11 | −70.52 | −55.54 | −13.25 | −16.26 | 45.33 | 83.50 | 3.06 | 3.85 |
| 12 | −35.81 | −7.22 | −0.12 | −4.52 | 17.67 | 30.06 | 2.06 | 3.13 |
| 13 | −47.99 | −40.26 | −6.34 | −20.96 | 14.14 | 49.60 | 8.90 | 10.92 |
| 14 | −24.36 | 13.00 | −7.63 | −3.02 | 8.86 | 15.44 | 12.74 | 5.19 |
| 15 | −75.62 | −34.87 | −29.30 | −14.41 | −60.76 | −62.03 | −14.79 | −16.49 |

| Patient # | Clostridia 454—Ileum % Difference | Clostridia 454—Cecum % Difference | Lach. + Rumino. 454—Ileum % Difference | Lach. + Rumino. 454—Cecum % Difference | Proteo- bacteria 454—Ileum % Difference | Proteo- bacteria 454—Cecum % Difference | Beta- Proteoabact. 454—Ileum % Difference | Beta- Proteoabact. 454—Cecum % Difference |
|---|---|---|---|---|---|---|---|---|
| 1 | 13.33 | 8.84 | 14.51 | 9.92 | 1.52 | 0.82 | 4.36 | 3.00 |
| 2 | −6.26 | 1.56 | −6.60 | 1.87 | 47.77 | 16.23 | 24.82 | 7.16 |
| 3 | 7.34 | 8.11 | 5.45 | 6.39 | −0.57 | 1.95 | 3.10 | 3.12 |
| 4 | 17.72 | 14.20 | 18.72 | 15.29 | 1.90 | −1.27 | 1.55 | 0.02 |
| 5 | −4.24 | −4.49 | −3.18 | −3.61 | −0.02 | 2.72 | 4.46 | 3.99 |
| 6 | 6.14 | 0.06 | 5.81 | 0.35 | −5.00 | −2.99 | −0.66 | −0.78 |
| 7 | 10.91 | 15.17 | 12.31 | 16.49 | −4.34 | −1.26 | 0.17 | 0.89 |
| 8 | 3.04 | 2.34 | 3.97 | 3.24 | 18.40 | 19.27 | −1.35 | −0.42 |
| 9 | 17.34 | 9.46 | 17.21 | 9.35 | −3.27 | 1.85 | 0.54 | 2.69 |
| 10 | 14.97 | 12.78 | 15.52 | 13.44 | −1.98 | 0.73 | 2.43 | 2.79 |
| 11 | 3.91 | 4.30 | 3.85 | 4.18 | 8.05 | 10.52 | 5.55 | 6.16 |
| 12 | 2.73 | 3.56 | 2.05 | 2.15 | −1.82 | 1.25 | 2.34 | 2.90 |
| 13 | 9.86 | 11.17 | 10.47 | 11.74 | −3.60 | 8.33 | 0.06 | 4.70 |
| 14 | 13.66 | 6.03 | 15.60 | 7.61 | −4.09 | −1.09 | −0.58 | −0.15 |
| 15 | −15.60 | −16.02 | −14.36 | −14.15 | 44.83 | 31.90 | −0.43 | −0.79 |

| Patient # | Firm./ Bacteroid. Ratio RT—Ileum % Change | Firm./ Bacteroid. Ratio RT—Cecum % Change | Firm./ Bacteroid. Ratio 454—Ileum % Change | Firm./ Bacteroid. Ratio 454—Cocum % Change | Clostrid./ Bacteroid. Ratio 454—Ileum % Change | Clostrid./ Bacteroid. Ratio 454—Cecum % Change | Firm. + Proteobact. 454—Ileum % Change | Firm. + Proteobact. 454—Cecum % Change |
|---|---|---|---|---|---|---|---|---|
| 1 | 85.85 | 130.48 | 80.63 | 48.14 | 89.92 | 52.85 | 13.73 | 9.06 |
| 2 | 520.47 | 163.47 | 81.04 | 39.53 | 83.47 | 39.47 | 40.79 | 17.66 |
| 3 | 160.98 | 132.59 | 43.00 | 60.37 | 47.41 | 62.46 | 5.97 | 9.79 |
| 4 | 470.19 | 92.89 | 126.70 | 84.43 | 133.22 | 87.82 | 19.15 | 12.62 |
| 5 | 92.09 | 12.65 | −28.53 | −26.23 | −26.69 | −25.13 | −5.18 | −2.38 |
| 6 | 81.61 | 107.84 | 17.08 | −10.99 | 21.09 | −8.72 | 0.24 | −3.67 |
| 7 | 49.24 | 56.32 | 48.85 | 90.21 | 53.38 | 94.97 | 5.89 | 13.37 |
| 8 | 74.81 | 86.66 | 59.00 | 60.28 | 57.63 | 53.77 | 21.65 | 22.68 |
| 9 | 97.40 | 33.24 | 99.17 | 55.50 | 107.51 | 59.77 | 13.04 | 10.59 |
| 10 | 34.24 | 18.40 | 81.88 | 77.16 | 90.50 | 82.97 | 11.91 | 12.84 |
| 11 | 360.23 | 281.88 | 36.65 | 46.99 | 40.77 | 49.43 | 11.11 | 14.37 |
| 12 | 71.17 | 26.80 | 6.13 | 18.04 | 8.99 | 20.18 | 0.24 | 4.39 |
| 13 | 104.90 | 126.51 | 46.68 | 101.59 | 55.16 | 107.58 | 5.30 | 19.25 |
| 14 | 34.37 | −7.59 | 66.89 | 24.23 | 74.34 | 28.28 | 8.65 | 4.09 |
| 15 | 50.31 | −47.27 | −30.42 | −62.02 | −43.09 | −63.48 | 30.04 | 15.41 |

Legend: Percent change values were calculated for real-time PCR and ratio data relative to the mean levels obtained for all Control-GI children for each bacterial variable. Percent difference values were calculated for pyrosequencing data by subtracting the mean percent abundance of Control-GI children from the percent abundance of each AUT-GI patient for each variable.

Analysis of pyrosequencing reads revealed a significant increase in Firmicute/Bacteroidete ratios in AUT-GI ilea (FIG. 18A: Mann-Whitney, p=0.026) and ceca (FIG. 18B: Mann-Whitney, p=0.032). An increase was also observed at the order level for Clostridiales/Bacteroidales ratios in ilea (FIG. 26A: Mann-Whitney, p=0.012) and ceca (FIG. 26B: Mann-Whitney, p=0.032). Real-time PCR using Firmicute- and Bacteroidete-specific primers confirmed increases in Firmicute/Bacteroidete ratios in AUT-GI ilea (FIG. 30C: Mann-Whitney, p=0.0006) and ceca (FIG. 30D: Mann-Whitney, p=0.022). Based on real-time PCR results, Firmicute/Bacteroidete ratios were above the 75$^{th}$ percentile of Control-GI values in 100% of AUT-GI ilea and 60% of AUT-GI ceca (Table 9C).

The cumulative level of Firmicutes and Proteobacteria was significantly higher in the AUT-GI group in both ileal (FIG. 18G: Mann-Whitney, p=0.015) and cecal (FIG. 18H: Mann-Whitney, p=0.007) biopsies; however, neither Firmicute nor Proteobacteria levels showed significant differences on their own (FIG. 27A-D and FIG. 19A, B). These results indicate that the observed decrease in Bacteroidetes in AUT-GI children is accompanied by an increase in Firmicutes (Ileal biopsies—Patients 1, 3, 4, 6, 7, 9, 10, 13, and 14; Cecal biopsies—Patients 1, 3, 4, 7, 9, 10, and 13), or Proteobacteria (Ileal biopsies—Patients 2, 8, 11 and 15; Cecal biopsies—Patients 2, 5, 8, 11, 13, and 15), or both (Cecal biopsies—Patient 13) (Table 9B and FIG. 34A-B).

Figure 27:
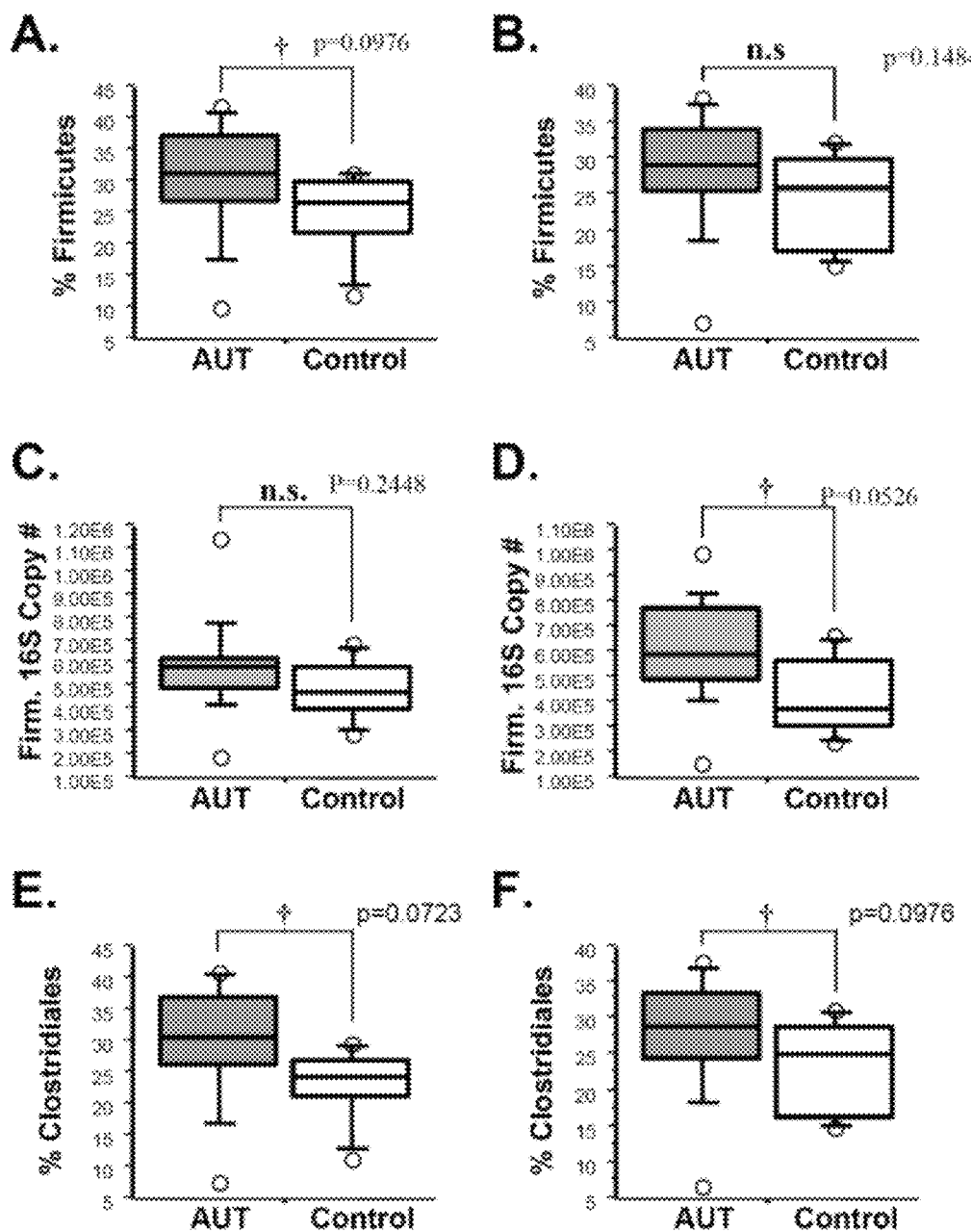
FIG. 27 shows graphs of the abundance of Firmicutes assayed by pyrosequencing and real-time PCR.
Figure 28A:
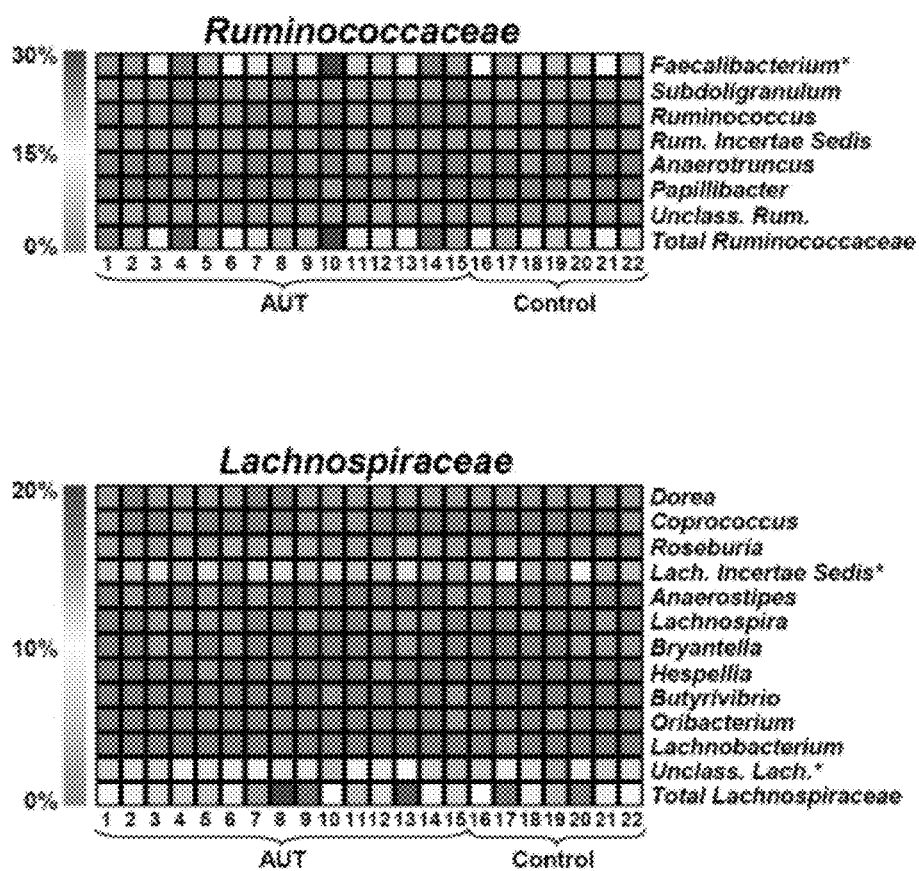

Within the *Firmicute phyla*, order-level analysis of pyrosequencing reads indicated trends toward increases in Clostridiales in AUT-GI ilea (FIG. 27E: Mann-Whitney, p=0.072) and ceca (FIG. 27F: Mann-Whitney, p=0.098). Family-level analysis revealed that increased Clostridiales levels in AUT-GI patient samples were largely attributable to increases in Lachnospiraceae and Ruminococcaceae (FIG. 18C-F). Cumulative levels of Lachnospiraceae and Ruminococcaceae above the 75$^{th}$ percentile of the corresponding levels in Control-GI samples were found in 60% of AUT-GI ileal and 53.3% of AUT-GI cecal samples (Table 9B). Genus-level analysis indicated that members of the genus *Faecalibacterium* within the family Ruminococcaceae contributed to the overall trend toward increased *Clostridia* levels (FIG. 28A-B). Within Lachnospiraceae, members of the genus Lachnopsiraceae Incertae Sedis, Unclassified Lachnospiraceae, and to a lesser extent *Bryantella* (cecum only), contributed to the overall trend toward increased *Clostridia* (FIG. 28A-B).

Within the *Proteobacteria phyla*, levels of Betaproteobacteria tended to be higher in the ilea of AUT-GI patients (FIG. 19C: Mann-Whitney, p=0.072); significantly higher levels of Betaproteobacteria were found in AUT-GI ceca (FIG. 19D: Mann-Whitney, p=0.038). Levels of Betaproteobacteria were above the 75$^{th}$ percentile of Control-GI children in 53.3% of AUT-GI ilea and 66.7% of AUT-GI ceca (Table 9B). Family-level analysis revealed that members of the families Alcaligenaceae (patients #1, 3, 5, 7, 10, 11, and 12) and Incertae Sedis 5 (patient #2 only) contributed to the increases in Betaproteobacteria in ilea (FIG. 19E) and ceca (FIG. 19F). Alcaligenaceae sequences were detected in 46.7% of AUT-GI children and none of the Control-GI children. Elevated levels of Proteobacteria in AUT-GI ilea and ceca reflected increased Alpha-(families Methylobacteriaceae and Unclassified Rhizobiales) and Betaproteobacteria (family Incertae Sedis 5) for patient #2 and increased Gammaproteobacteria (family Enterobacteriaceae) for patients #8 and #15 (FIG. 19E-F). Levels of Alpha-, Delta-, Gamma-, and Epsilonproteobacteria were not significantly different between AUT-GI and Control-GI samples.

The use of probiotics, proton-pump inhibitors, or antibiotics has been shown to impact the intestinal microbiome [36, 37,38]. Analysis of the potential effects of these agents in this cohort revealed only one potential confounding effect: a correlation between the ratio of Firmicutes to Bacteroidetes in the cecum obtained by real-time PCR in AUT-GI children who had taken probiotics (Table 13A). No effect of proton-pump inhibitors was observed for any of the significant variables assessed in this study (Table 13B). Only one patient, a control (Control-GI patient #16), had taken an antibiotic (amoxicillin) in the three months prior to biopsy (See Table 13C).

TABLE 13A

Evaluation of confounding effects attributed to the use of probiotics (Pb).

| Variable | AUT(−Pb) vs. Control(−Pb)$^a$, p-value$^{MW}$, [effect in AUT(−Pb)] | AUT(−Pb) vs. AUT(+Pb)$^b$, p-value$^{MW}$, [effect in AUT(+Pb)] |
|---|---|---|
| SI | 0.007**, [decreased] | 0.602, [no change] |
| MGAM | 0.007**, [decreased] | 0.240, [no change] |
| LCT | 0.012*, [decreased] | 0.695, [no change] |
| SGLT1 | 0.021*, [decreased] | 0.433, [no change] |
| GLUT2 | 0.021*, [decreased] | 0.794, [no change] |
| Bacteroidetes IL(RT) | 0.009**, [decreased] | 0.602, [no change] |
| Bacteroidetes CEC(RT) | 0.056†, [decreased] | 0.192, [no change] |
| Bacteroidetes IL(454) | 0.035*, [decreased] | 0.602, [no change] |
| Bacteroidetes CEC(454) | 0.009**, [decreased] | 0.999, [no change] |
| Firm./Bacteroid. Ratio IL(RT) | 0.004**, [increased] | 0.361, [no change] |
| Firm./Bacteroid. Ratio CEC(RT) | 0.159, [no change] | 0.037*, [increased] |
| Firm./Bacteroid. Ratio IL(454) | 0.070†, [increased] | 0.514, [no change] |
| Firm./Bacteroid. Ratio CEC(454) | 0.056†, [increased] | 0.896, [no change] |
| Clostridiales/Bacteroidales IL(454) | 0.044*, [increased] | 0.695, [no change] |
| Clostridiales/Bacteroidales CEC(454) | 0.070†, [increased] | 0.896, [no change] |
| Beta-proteobacteria CEC(454) | 0.108, [not significant] | 0.361, [no change] |

$^a$AUT(−Pb), n = 11; Control (−Pb), n = 6
$^b$AUT(−Pb), n = 11; AUT(+Pb), n = 4
$^{MW}$Mann-Whitney test

TABLE 13B

Evaluation of confounding effects attributed to use of proton-pump inhibitors (PPI).

| Variable | AUT(−PPI) vs. Control(−PPI)$^a$, p-value$^{MW}$, [effect in AUT(−PPI)] | AUT(−PPI) vs. AUT(+PPI)$^b$, p-value$^{MW}$, [effect in AUT(+PPI)] |
|---|---|---|
| SI | 0.003**, [decreased] | 0.794, [no change] |
| MGAM | 0.006**, [decreased] | 0.695, [no change] |
| LCT | 0.234, [no change] | 0.192, [no change] |
| SGLT1 | 0.036*, [decreased] | 0.896, [no chane] |
| GLUT2 | 0.036*, [decreased] | 0.602, [no change] |
| Bacteroidetes IL(RT) | 0.002**, [decreased] | 0.433, [no change] |
| Bacteroidetes CEC(RT) | 0.011*, [decreased] | 0.433, [no change] |
| Bacteroidetes IL(454) | 0.036*, [decreased] | 0.050†, [decreased] |
| Bacteroidetes CEC(454) | 0.036*, [decreased] | 0.514, [no change] |
| Firm./Bacteroid. Ratio IL(RT) | 0.004**, [increased] | 0.602, [no change] |
| Firm./Bacteroid. Ratio CEC(RT) | 0.011*, [increased] | 0.896, [no change] |
| Firm./Bacteroid. Ratio IL(454) | 0.027*, [increased] | 0.514, [no change] |
| Firm./Bacteroid. Ratio CEC(454) | 0.036*, [increased] | 0.514, [no change] |
| Clostridiales/Bacteroidales IL(454) | 0.015*, [increased] | 0.514, [no change] |
| Clostridiales/Bacteroidales CEC(454) | 0.036*, [increased] | 0.514, [no change] |
| Beta-proteobacteria CEC(454) | 0.047*, [increased] | 0.794, [no change] |

$^a$AUT(−PPI), n = 11; Control(−PPI), n = 5
$^b$AUT(−PPI), n = 11; AUT(+PPI), n = 4
$^{MW}$Mann-Whitney test

TABLE 13C

Evaluation of confounding effects attributed to the use of antibiotics.

| Variable | Including Antibiotic User (Ab) AUT (−Ab) vs. Control (+Ab and −Ab)[a], p-value[MW], [effect in AUT(−Ab)] | Excluding Antibiotic User (Ab) AUT (−Ab) vs. Control (−Ab)[b], p-value[MW], [effect in AUT(−Ab)] |
|---|---|---|
| SI | 0.001**, [decreased] | 0.003**, [decreased] |
| MGAM | 0.003**, [decreased] | 0.010**, [decreased] |
| LCT | 0.032*, [decreased] | 0.062†, [decreased] |
| SGLT1 | 0.008**, [decreased] | 0.020*, [decreased] |
| GLUT2 | 0.010*, [decreased] | 0.024*, [decreased] |
| Bacteroidetes IL (RT) | 0.003**, [decreased] | 0.0005***, [decreased] |
| Bacteroidetes CEC (RT) | 0.022*, [decreased] | 0.002**, [decreased] |
| Bacteroidetes IL (454) | 0.012*, [decreased] | 0.005**, [decreased] |
| Bacteroidetes CEC (454) | 0.008**, [decreased] | 0.008**, [decreased] |
| Firm./Bacteroid. Ratio IL (RT) | 0.0006***, [increased] | 0.001**, [increased] |
| Firm./Bacteroid. Ratio CEC (RT) | 0.022*, [increased] | 0.008**, [increased] |
| Firm./Bacteroid. Ratio IL (454) | 0.026*, [increased] | 0.013*, [increased] |
| Firm./Bacteroid. Ratio CEC (454) | 0.032*, [increased] | 0.029*, [increased] |
| Clostridiales/ Bacteroidales IL (454) | 0.012*, [increased] | 0.008**, [increased] |
| Clostridiales/ Bacteroidales CEC (454) | 0.032*, [increased] | 0.024*, [increased] |
| Beta-proteobacteria | 0.038*, [increased] | 0.120, [no change] |
| CEC (454) | | |

[a]AUT(−Ab), n = 15; Control(+Ab and −Ab), n = 7
[b]AUT(−Ab), n = 15; Control(−Ab), n = 6
[MW]Mann-Whitney test Disaccharidase and Transporter mRNA Levels as Predictors of Bacterial Abundance Multiple linear regression analysis was conducted to determine whether diagnostic status (AUT-GI or Control-GI) and mRNA expression of disaccharidases (SI, MGAM and LCT) and transporters (SGLT1 and GLUT2) (predictor variables) were associated with bacterial levels as outcome variables (Table 14). For Bacteroidetes, SGLT1 (ileum and cecum) and SI (cecum only) were significant predictors. In both the ileum and cecum, Bacteroidete levels increased as SGLT1 transcript levels increased. In the cecum, Bacteroidete levels significantly decreased as the levels of SI increased (a similar marginal effect was observed in ileum). Bacteroidete levels were lower among AUT-GI children compared to Control-GI children even after adjusting for the expression of all disaccharidases and transporters.

TABLE 14

Multiple linear regression analysis examining disaccharidases and transporters as predictors of bacterial levels among AUT-GI and Control-GI children.

| Outcome Variable | F-statistic (p-value) | Adjusted $R^2$ | Main Effects: Coefficient Estimate | | | | | Interaction Terms with Status (Coefficient[STDev]) |
|---|---|---|---|---|---|---|---|---|
| | | | Status | SI[STDev] | MGAM[STDev] | LCT[STDev] | SGLT1[STDev] | GLUT2[STDev] | |
| Bacteroidetes, Ileum—RT | 5.52[a] (0.003)** | 0.56 | −0.86*** | −0.54† | 0.05 | −0.02 | 0.35* | 0.05 | none |
| Bacteroidetes, Cecum—RT | 2.61[a] (0.062)† | 0.31 | −0.36* | −0.60* | 0.27 | −0.08 | 0.29* | 0.08 | none |
| Firmicutes, Ileum—RT | 2.50[b] (0.068)† | 0.33 | 0.40 | −0.57† | 0.44 | −0.01 | 0.10 | 0.10 | MGAM (−0.52)* |
| Firmicutes, Cecum—RT | 6.98[c] (0.001)** | 0.69 | 1.29*** | −0.99** | 0.86** | 0.18† | 0.06 | 0.40* | MGAM (−0.50)*. GLUT2 (−0.46)* |
| Firm./Bac., Ileum—RT | 3.43[b] (0.024)* | 0.45 | 1.43** | −0.19 | 0.19 | 0.04 | −0.27 | 0.48† | GLUT2 (−0.61)* |
| Firm./Bac., Cecum—RT | 5.13[b] (0.005)** | 0.58 | 1.47*** | 0.27 | 0.21 | 0.19 | −0.22 | −0.02 | SI (−0.93)** |
| Proteobacteria, Ileum—454 | 2.47[b] (0.071)† | 0.33 | −1.05 | 2.76** | −2.31* | 0.01 | −0.79† | −0.59† | MGAM (1.21)† |
| Proteobacteria, Cecum—454 | 5.41[b] (0.004)** | 0.59 | −1.21 | 3.34*** | −3.56*** | −0.03 | −0.68† | −0.38 | MGAM (1.59)** |
| BetaProteobacteria, Ileum—454 | 1.14[a] (0.385) | 0.04 | −0.14 | 0.61 | −0.87 | 0.05 | −0.26 | −0.16 | none |
| BetaProteobacteria, Cecum—454 | 5.64[a] (0.003)** | 0.57 | −0.16 | 1.43* | −2.07** | 0.27 | −0.44 | 0.08 | none |

[a]on 6 and 15 degrees of freedom
[b]on 7 and 14 degrees of freedom
[c]on 8 and 13 degrees of freedom
[STDev]Change in log-transformed outcome variable levels per unit standard deviation increase in predictor variable (main effect variables or interaction terms)
*p < 0.05;
**p < 0.01;
***p < 0.001;
†p < 0.1 (trend)

Finnicute levels significantly decreased as SI levels increased in cecum. Cecal Firmicute levels were increased as the levels of MGAM and GLUT2 increased. The levels of Firmicutes in the cecum were higher in AUT-GI compared to Control-GI children after adjusting for the expression of disaccharidases and transporters. Significant interaction was found between status and MGAM and GLUT2 levels in the Firmicute models. Whereas higher levels of MGAM and GLUT2 were associated with higher levels of Firmicutes among Control-GI children, the effects of MGAM and GLUT2 on Firmicutes was not present in AUT-GI children.

Disaccharidases and transporter levels were not significant predictors of the ratios of Firmicutes to Bacteroidetes in ileum or cecum. However, the interaction terms with GLUT2 in the ileum and SI in the cecum were significant.

Proteobacteria abundance significantly increased as the levels of SI increased, but decreased as MGAM increased for both ileum and cecum. However, the interaction terms with MGAM in both ileum and cecum were significant, indicating that the magnitude of decline is significantly smaller among AUT-GI children. Betaproteobacteria abundance was positively associated with SI and inversely associated with MGAM only in cecum; none of the interactions were significant. In addition, Proteobacteria and Betaproteobacteria abundance were not significantly different between AUT-GI and Control-GI children after adjusting for the expression of all disaccharidases and transporters. Overall, these results indicate that expression levels of disaccharidases and transporters are associated with the abundance of Bacteroidetes, Firmicutes, and Betaproteobacteria in the mucoepithelium.

The levels of Betaproteobacteria in the ileum and cecum were higher in AUT-GI children with deficiencies in all 5 disaccharidases and transporters versus AUT-GI children with fewer than 5 disaccharidase and transporter deficiencies (FIG. 35A-B). Levels of CDX2 were lower in AUT-GI children with levels of Betaproteobacteria above the $75^{th}$ percentile of Control-GI children compared to AUT-GI children with levels of Betaproteobacteria below the $75^{th}$ percentile of Control-GI children (FIG. 35C-D). These results indicate a potential link between increased levels of Betaproteobacteria, reduced levels of CDX2 expression, and overall deficiencies in disaccharidases and transporters.

Timing of GI Disturbances Relative to Onset of Autism is Associated with Changes in Clostridiales Members In this cohort, the onset of GI symptoms was reported to occur before or at the same time as the development of autism in 67% of AUT-GI children. As a sub-analysis, it was determined whether the timing of GI onset relative to autism onset was associated with gene expression and bacterial variables.

Patients were stratified based on whether the first episode of GI symptoms occurred before or at the same time (within the same month) as the onset of autism (AUT-GI-Before or Same group) or whether the first episode of GI symptoms occurred after the onset of autism (AUT-GI-After group). The timing of GI onset was not associated with levels of disaccharidase, hexose transporter or CDX2 transcripts, Bacteroidetes, Proteobacteria or Beta-proteobacteria (data not shown). However, a significant effect was observed for the levels of Clostridiales and cumulative levels of Lachnospiraceae and Ruminococcaceae in both the ileum and cecum (FIG. 31A-D). Whereas only a trend toward increased Clostridiales and cumulative levels of Lachnospiraceae and Ruminococcaceae were observed when comparing all AUT-GI and Control-GI children (FIG. 27E-F and FIG. 18C-D), stratification based on timing of GI onset revealed a significant increase in these variables in both the ileum and cecum of the AUT-GI-Before or Same group relative to all Control-GI children (FIG. 31A: Clostridiales-ileum, Mann-Whitney, p=0.015; FIG. 31B: Clostridiales-cecum, Mann-Whitney, p=0.019; FIG. 31C: Lach.+Rum.-ileum, Mann-Whitney, p=0.015; FIG. 31D: Lach.+Rum.-cecum, Mann-Whitney, p=0.01 1). Furthermore, the levels of Clostridiales and cumulative levels of Lachnospiraceae and Ruminococcaceae were significantly higher in the AUT-GI-Before or Same group relative to the AUT-GI-After group (FIG. 31A: Clostridiales-ileum, Mann-Whitney, p=0.028; FIG. 31B: Clostridiales-cecum, Mann-Whitney, p=0.037; FIG. 31C: Lach.+Rum.-ileum, Mann-Whitney, p=0.028; FIG. 31D: Lach.+Rum.-cecum, Mann-Whitney, p=0.020); the AUT-GI-After group was not significantly different from the Control-GI group. As expected, the AUT-GI-After group had a significantly older age at first onset of GI symptoms [median age in months, (interquartile range, IQR)=36, (22.5)] compared to the AUT-GI-Before or Same group [median age in months, (interquartile range, IQR)=1, (12)] (FIG. 31E: Mann-Whitney, p=0.007), and was also higher than the Control-GI group [median age in months, (interquartile range, IQR)=1, (14)] (FIG. 31E: Mann-Whitney, p=0.027). The age at first GI onset was not significantly different between the AUT-GI-Before or Same group and the Control-GI group (FIG. 31E: Mann-Whitney, p=0.757). Thus, the increased levels of Clostridiales in the AUT-GI-Before or Same group as compared to the Control-GI group were not influenced by differences in age of onset of GI symptoms between these two groups. These results indicate that the timing of onset of GI symptoms relative to onset of autism or the age at first GI onset can be associated with increases in Clostridiales.

Associations Between Gene Expression, Bacterial Abundance, and Food Allergies and Other Comorbid Atopic Manifestations A National Survey of Children's Health performed under the auspices of the Centers for Disease Control reported that parents of autistic children reported more allergy symptoms than control children, and FA were the most prevalent complaint [39]. Parental reports of FA in the cohort were reported with similar frequency in AUT-GI (67%) and Control-GI (71%) children. Milk-related (MA) and wheat-related (WA) allergies were the most commonly reported allergies in both groups (Table 6 and Table 7). To determine whether FA was associated with gene expression or bacterial levels, patients in the AUT-GI group and Control-GI group were stratified based on reports of any FA (Table 15A), MA (Table 15B), or WA (Table 15C).

Stratification by any FA revealed a significant effect for levels of GLUT2, ileal and cecal Firmicutes, ileal and cecal ratios of Firmicutes to Bacteroidetes, and cecal Betaproteobacteria (Table 15A). No effect was observed for the levels of Bacteroidetes, which were significantly reduced in AUT-GI children independent of FA status.

Stratification by MA status revealed even more significant effects (Table 15B). Significant effects were observed for MGAM, GLUT2, and CDX2 expression, as well as ileal and cecal ratios of Firmicutes to Bacteroidetes, and ileal and cecal Beta-proteobacteria. Additional trends were observed for SI expression and ileal and cecal Firmicutes. No effect was observed for the levels of Bacteroidetes, which were significantly reduced in AUT-GI children independent of MA status.

Stratification by WA status was associated with a significant effect only for cecal levels of Firmicutes, though this effect was highly significant [AUT (+WA) vs. AUT (−WA): Mann-Whitney, p-value=0.008], and the cecal ratio of Firmicutes to Bacteroidetes (Table 15C).

These results indicate that changes in the expression of some disaccharidases and transporters and CDX2, as well as changes in the abundance of some bacterial phylotypes, are significantly associated with reported FA, especially MA. Whereas the levels of Firmicutes, the ratio of Firmicutes to Bacteroidetes, and levels of Betaproteobacteria were increased in AUT-GI children with FA, the levels of Bacteroidetes were not significantly different. This indicates that the levels of Bacteroidetes were significantly decreased in AUT-GI children, independent of FA status.

Atopic disease manifestations (AD: asthma, allergic rhinitis, or atopic dermatitis) were the most commonly reported comorbid conditions in both AUT-GI and Control-GI children. The frequency of AD tended to be higher in the Control-GI group (100%) than in the AUT-GI group (53%) (Table 6: Fisher's Exact Test, 2-sided p=0.051). In the combined group (all AUT-GI and Control-GI patients), 86.7% of children with reported FA had at least one reported AD; only 28.6% of children without reported food allergy had one or more AD (Fisher's Exact Test, 2-sided p=0.014). As AD was associated with reported FA, it was determined whether AD manifestation was also associated with changes in disaccharidases and transporters or bacterial parameters. Stratification of subjects by AD status revealed that cecal Firmicutes and the cecal ratio of Firmicutes to Bacteroidetes were higher in AUT-GI children with AD compared to Control-GI children with AD [Table 15D: AUT(+AD) vs. Control(+AD); Firmicutes CECRT, Mann-Whitney, p=0.015; Firm./Bacteroid. Ratio CECRT, Mann-Whitney, p=0.002] and AUT-GI children without AD [Table 15D: AUT(-AD) vs. AUT(+AD); Firmicutes CEC(RT), Mann-Whitney, p=0.049; Firm./Bacteroid. Ratio CEC(RT), Mann-Whitney, p=0.049].

TABLE 15A

Association of food allergies (FA) with host gene expression and bacterial phylotypes in AUT-GI children.

| Variable | AUT(+FA) vs. Control(+FA)[a], p-value[MW], [effect in AUT(+FA)] | AUT(-FA) vs. AUT(+FA)[b], p-value[MW], [effect in AUT(+FA)] |
|---|---|---|
| GLUT2 | 0.014*, [decreased] | 0.037*, [decreased] |
| Bacteroidetes IL(RT) | 0.002**, [decreased] | 0.806, [no change] |
| Bacteroidetes CEC(RT) | 0.005**, [decreased] | 0.713, [no change] |
| Bacteroidetes IL(454) | 0.037*, [decreased] | 0.221, [no change] |
| Bacteroidetes CEC(454) | 0.050*, [decreased] | 0.713, [no change] |
| Firmicutes IL(RT) | 0.221, [no change] | 0.037*, [increased] |
| Firmicutes CEC(RT) | 0.037*, [increased] | 0.010*, [increased] |
| Firm./Bacteroid. Ratio IL(RT) | 0.003**, [increased] | 0.037*, [increased] |
| Firm./Bacteroid. Ratio CEC(RT) | 0.005**, [increased] | 0.020*, [increased] |
| Beta-proteobacteria IL(454) | 0.050†, [increased] | 0.066†, [increased] |
| Beta-proteobacteria CEC(454) | 0.028*, [increased] | 0.037*, [increased] |

[a]AUT(+FA), n = 10; Control(+FA), n = 5
[b]AUT(-FA), n = 5; AUT(+FA), n = 10
[MW]Mann-Whitney test

TABLE 15B

Association of milk allergies (MA) with host gene expression and bacterial phylotypes in AUT-GI children.

| Variable | AUT(+MA) vs. Control(+MA)[a], p-value[MW], [effect in AUT(+MA)] | AUT(-MA) vs. AUT(+MA)[b], p-value[MW], [effect in AUT(+MA)] |
|---|---|---|
| SI | 0.006**, [decreased] | 0.099†, [decreased] |
| MGAM | 0.006**, [decreased] | 0.045*, [decreased] |

TABLE 15B-continued

Association of milk allergies (MA) with host gene expression and bacterial phylotypes in AUT-GI children.

| Variable | AUT(+MA) vs. Control(+MA)[a], p-value[MW], [effect in AUT(+MA)] | AUT(-MA) vs. AUT(+MA)[b], p-value[MW], [effect in AUT(+MA)] |
|---|---|---|
| GLUT2 | 0.009**, [decreased] | 0.013*, [decreased] |
| CDX2 | 0.072†, [decreased] | 0.034*, [decreased] |
| Bacteroidetes IL(RT) | 0.003**, [decreased] | 0.480, [no change] |
| Bacteroidetes CEC(RT) | 0.003**, [decreased] | 0.289, [no change] |
| Bacteroidetes IL(454) | 0.028*, [decreased] | 0.637, [no change] |
| Bacteroidetes CEC(454) | 0.020*, [decreased] | 0.637, [no change] |
| Firmicutes IL(RT) | 0.205, [no change] | 0.059†, [increased] |
| Firmicutes CEC(RT) | 0.053†, [increased] | 0.099†, [increased] |
| Firm./Bacteroid. Ratio IL(RT) | 0.004**, [increased] | 0.034*, [increased] |
| Firm./Bacteroid. Ratio CEC(RT) | 0.006**, [increased] | 0.045*, [increased] |
| Beta-proteobacteria IL(454) | 0.020*, [increased] | 0.013*, [increased] |
| Beta-proteobacteria CEC(454) | 0.009**, [increased] | 0.007**, [increased] |

[a]AUT(+MA), n = 9; Control(+MA), n = 5
[b]AUT(-MA), n = 6; AUT(+MA), n = 9
[MW]Mann-Whitney test

TABLE 15C

Association of wheat allergies (WA) with host gene expression and bacterial phylotypes in AUT-GI children.

| Variable | AUT(+WA) vs. Control(+WA)[a], p-value[MW], [effect in AUT(+WA)] | AUT(-WA) vs. AUT(+WA)[b], p-value[MW], [effect in AUT(+WA)] |
|---|---|---|
| Bacteroidetes IL(RT) | 0.007**, [decreased] | 0.643, [no change] |
| Bacteroidetes CEC(RT) | 0.017*, [decreased] | 0.643, [no change] |
| Bacteroidetes IL(454) | 0.017*, [decreased] | 0.488, [no change] |
| Bacteroidetes CEC(454) | 0.089†, [decreased] | 0.908, [no change] |
| Firmicutes IL(RT) | 0.174, [no change] | 0.083†, [increased] |
| Firmicutes CEC(RT) | 0.089†, [increased] | 0.008*, [increased] |
| Firm./Bacteroid. Ratio IL(RT) | 0.011*, [increased] | 0.203, [no change] |
| Firm./Bacteroid. Ratio CEC(RT) | 0.011*, [increased] | 0.049*, [increased] |
| Beta-proteobacteria IL(454) | 0.089†, [increased] | 0.643, [no change] |
| Beta-proteobacteria CEC(454) | 0.042*, [increased] | 0.418, [no change] |

[a]AUT(+WA), n = 8; Control(+WA), n = 4
[b]AUT(-WA), n = 7; AUT(+WA), n = 8
[MW]Mann-Whitney test

TABLE 15D

Association of atopic disease (AD) status with host gene expression and bacterial phylotypes in AUT-GI children.

| Variable | AUT(+AD) vs. Control(+AD)[a], p-value[MW], [effect in AUT(+AD)] | AUT(-AD) vs. AUT(+AD)[b], p-value[MW], [effect in AUT(+AD)] |
|---|---|---|
| Bacteroidetes IL(RT) | 0.008**, [decreased] | 0.563, [no change] |
| Bacteroidetes CEC(RT) | 0.028*, [decreased] | 0.418, [no change] |
| Bacteroidetes IL(454) | 0.049*, [decreased] | 0.643, [no change] |
| Bacteroidetes CEC(454) | 0.064†, [decreased] | 0.908, [no change] |
| Firmicutes IL(RT) | 0.064†, [increased] | 0.133, [no change] |
| Firmicutes CEC(RT) | 0.015*, [increased] | 0.049*, [increased] |
| Firm./Bacteroid. Ratio IL(RT) | 0.002**, [increased] | 0.064†, [increased] |

TABLE 15D-continued

Association of atopic disease (AD) status with host gene expression and bacterial phylotypes in AUT-GI children.

| Variable | AUT(+AD) vs. Control(+AD)[a], p-value[MW], [effect in AUT(+AD)] | AUT(−AD) vs. AUT(+AD)[b], p-value[MW], [effect in AUT(+AD)] |
| --- | --- | --- |
| Firm./Bacteroid. Ratio CEC(RT) | 0.006**, [increased] | 0.049*, [increased] |
| Beta-proteobacteria IL(454) | 0.049*, [increased] | 0.203, [no change] |
| Beta-proteobacteria CEC(454) | 0.028*, [increased] | 0.133, [no change] |

[a]AUT(+AD), n = 8; Control(+AD), n = 7
[b]AUT(−AD), n = 7; AUT(+AD), n = 8
[MW]Mann-Whitney test Discussion Although the major deficits in ASD are social and cognitive, many affected individuals with ASD also have substantial GI morbidity. Findings in this study that can shed light on GI morbidity in ASD include the observations that: (1) levels of transcripts for disaccharidases and hexose transporters are reduced in AUT-GI children; (2) AUT-GI children have microbial dysbiosis in the mucoepithelium; and (3) dysbiosis is associated with deficiencies in host disacharidase and hexose transporter mRNA expression. Without being bound by theory, deficiencies in disaccharidases and hexose transporters alter the milieu of carbohydrates in the distal small intestine (ileum) and proximal large intestine (cecum), resulting in the supply of additional growth substrates for bacteria. These changes manifest in significant and specific compositional changes in the microbiota of AUT-GI children (see FIG. 32, FIG. 20).

A previous report on GI disturbances in ASD found low activities of at least one disaccharidase or glucoamylase in duodenum in 58% of children [7]. In this study, 93.3% of AUT-GI children had decreased mRNA levels for at least one of the three disaccharidases (SI, MGAM, or LCT). In addition, decreased levels of mRNA were found for two important hexose transporters, SGLT1 and GLUT2. Congenital defects in these enzymes and transporters are extremely rare [40,41], and even the common variant for adult-type hypolactasia was not responsible for reduced LCT expression in AUT-GI children in this cohort. It is unlikely, therefore, that the combined deficiency of disaccharidases (maldigestion) and transporters (malabsorption) are indicative of a primary malabsorption resulting from multiple congenital or acquired defects in each of these genes: Transcripts for the enterocyte marker, villin, were not reduced in AUT-GI ilea and did not predict the expression levels of any of the disaccharidases or transporters in multiple regression models. This indicates that a general loss of enterocytes is unlikely. Without being bound by theory, defects in the maturational status of enterocytes or enterocyte migration along crypt-villus axis can contribute to deficits in disaccharidase and transporter expression [42].

The ileal expression of CDX2, a master transcriptional regulator in the intestine, was a significant predictor of mRNA expression of all five disaccharidases and transporters in AUT-GI and Control-GI children based on linear regression models. However, as ASD status remained a significant predictor of disaccharidase mRNA expression even after adjusting for CDX2 and villin, additional factors must also contribute. One factor is diet. Dietary intake of carbohydrates can regulate the mRNA expression of disaccharidases and hexose transporters in mice and rats [43,44,45]. ASD children exhibit feeding selectivity and aberrant nutrient consumption [46,47,48,49,50,51,52]. However, of the four studies reporting carbohydrate intake, none found differences in total carbohydrate intake in ASD children [47,48,49,50]. Furthermore, one study found no association between dietary intake of macronutrients (i.e., carbohydrates, proteins, or fats) and GI symptoms [47]. Unfortunately, dietary diaries for the period immediately preceding biopsy were not available for the children evaluated in this study; hence, the extent to which dietary intake affected intestinal gene expression could not be determined.

Hormonal and growth factor regulation of some disaccharidases and hexose transporters have been reported in in vitro studies and in animals [53,54]. Inflammatory cytokines can regulate SI gene expression in human intestinal epithelial cells in vitro [55]. Thus, immunological or hormonal imbalances reported in ASD children [5,8,9,10,11,12,56,57,58] can also contribute to expression deficits. Additionally, intestinal microbes can influence the expression of disaccharidases and transporters [59] through the influence of pathogen-associated molecular patterns (PAMPs) and butyrate (a byproduct of bacterial fermentation) on CDX2 expression and activity [60,61,62,63]. In this regard, the observation that CDX2 was decreased in AUT-GI children with increased levels of Betaproteobacteria can be important.

Whatever the underlying mechanisms, reduced capacity for digestion and transport of carbohydrates can have profound effects. Within the intestine, malabsorbed carbohydrates can lead to osmotic diarrhea [64]; non-absorbed sugars can also serve as substrates for intestinal microflora that produce fatty acids and gases (methane, hydrogen, and carbon dioxide), promoting additional GI symptoms such as bloating and flatulence [65]. The deficiency of even a single gene in this important pathway can result in severe GI disease, as occurs with glucose-galactose malabsorption syndrome caused by SGLT1 deficiency, Fanconi-Bickel syndrome resulting from GLUT2 mutations, sucrase-isomaltase deficiency, and congenital lactase deficiency [40,41].

Changes in the type and quantity of dietary carbohydrates can influence composition and function of intestinal microflora [66,67,68]; thus, we reasoned that carbohydrate maldigestion and malabsorption, resulting from deficient expression of disaccharidases and hexose transporters, might have similar effects in AUT-GI subjects. Pyrosequencing analysis of mucoepithelial bacteria revealed significant multicomponent dysbiosis in AUT-GI children, including decreased levels of Bacteroidetes, an increase in the Firmicute/Bacteroidete ratio, increased cumulative levels of Firmicutes and Proteobacteria, and an increase in levels of bacteria in the class Betaproteobacteria.

A recent pyrosequencing study reported an increase in Bacteroidetes in fecal samples of ASD subjects [69]. Although these findings can appear to be incongruent with those reported here, the data were obtained using biopsies rather than free fecal material. Others have reported differences in the composition of fecal versus mucosal microflora [35,70,71,72]. Only about 50% of cells in feces are viable, with dead and injured cells making up the remaining fractions [73]. The loss of Bacteroidetes from the mucoepithelium as a result of death, injury, or competition for binding in the mucosal space can result in increased wash out of Bacteroidete cells into the fecal stream. Thus, higher levels of Bacteroidetes in feces could be indicative of an inability to thrive in the mucosal microbiome rather than an indication that Bacteroidetes are found at higher levels in the microbiome.

The trend toward increased Firmicutes was largely attributable to *Clostridia* with Ruminococcaceae and Lachnospiraceae as major contributors. Several Ruminococcaceae and Lachnospiraceae are known butyrate producers and can thus influence short-chain fatty acid (SCFA) levels [74]. SCFA influence colonic pH, and some *Bacteroides* sp. are sensitive to acidic pH [75]. Three previous reports indicated differences in *Clostridia* species in children with ASD, including greater abundance of *Clostridium* clusters I, II, XI and C. bolteae [14,15,16]. Stratification of AUT-GI children based on the timing of GI symptom development relative to autism onset revealed that the levels of Clostridiales and cumulative levels of Lachnospiraceae and Ruminococcaceae were significantly higher in AUT-GI children for whom GI symptoms developed before or at the same time as the onset of autism symptoms compared to AUT-GI children for whom GI symptoms developed after the onset of autism and compared to Control-GI children. However, we cannot discern whether changes in Clonstridiales members occurred before the onset of autism in this subgroup. We can only conclude that increased levels of Clostridiales members in biopsies taken after the development of both GI symptoms and autism are associated with the timing of GI onset relative to autism onset in this cohort. Although the reason for this association remains unclear, this finding can indicate that the timing of GI onset relative to autism is an important variable to consider in the design of future prospective studies investigating the microbiota of children with autism.

Although we found only a trend for increased Firmicutes in AUT-GI children, the cumulative levels of Firmicutes and Proteobacteria were significantly higher. These results indicate that in some patients the decrease in Bacteroidetes is associated with an increase in Firmicutes, whereas in others increases in Proteobacteria are associated with a reduced abundance of Bacteroidetes. Three AUT-GI patients had high levels of Alpha-, Beta-, or Gammaproteobacteria. In addition, the AUT-GI group had elevated levels of Betaproteobacteria compared to the Control-GI group, primarily reflecting the presence of Alcaligenaceae. Alcaligenaceae sequences were not detected in any tissues from Control-GI children.

Deficient digestion and absorption of di- and monosaccharides in the small intestine can alter the balance of growth substrates, eliminating the growth advantages that Bacteroidetes enjoy in the healthy intestine and enabling competitive growth of bacterial phylotypes better suited for growth on undigested and unabsorbed carbohydrates. In support of this hypothesis, multiple linear regression models demonstrated that levels of ileal SGLT1 and Si mRNA were associated with levels of Bacteroidetes in ileum and cecum, or cecum alone, respectively. Levels of ileal SI, MGAM and GLUT2 mRNA were associated with levels of cecal Firmicutes, although the magnitude of the effects of MGAM and GLUT2 differed between AUT-GI and Control-GI children. Significant associations were also observed between levels of SI and MGAM mRNA and of Proteobacteria in ileum and cecum, and of Betaproteobacteria in cecum. Although deficiencies in disaccharidase and transporter expression appear to at least partially contribute to these alterations in the AUT-GI microbiota, diagnostic status remained a significant predictor of Bacteroidete and cecal Firmicute abundance even after adjusting for gene expression.

Metabolic interactions between intestinal microflora and their hosts are only beginning to be understood. Nonetheless, there is already abundant evidence that microflora can have system-wide effects [76,77,78,79,80,81,82,83] and influence immune responses, brain development and behavior [24,25, 26,84,85]. We acknowledge that this is a small study comprising 22 subjects. The small sample size evaluated in this study is a limitation arising from the difficulty in obtaining biopsies from young children undergoing invasive endoscopic examination. Without being bound by theory, the data show that at least some children with autism have a distinct intestinal profile that is linked to deficient expression of disaccharidases and hexose transporters, potentially promoting maldigestion, malabsorption and multicomponent, compositional dysbiosis. Although the underlying cause of these changes and the extra-intestinal effects these changes can elicit remain speculative, the identification of specific molecular and microbial signatures that define GI pathophysiology in AUT-GI children sets the stage for further research aimed at defining the epidemiology, diagnosis and informed treatment of GI symptoms in autism.

Materials and Methods

All samples were analyzed anonymously. Samples assessed in this example were restricted to those derived from male children from the original cohort between 3 and 5 years of age to control for confounding effects of gender and age on intestinal gene expression and the microbiota. This subset comprised 15 AUT-GI (Patient #1-15) and 7 Control-GI (Patient #16-22) patients.

Clinical Procedures: Specific clinical procedures for defining neuropsychiatric and regression status in this cohort have been previously described [86]. Briefly, neuropsychiatric status was established for all subjects using Diagnostic and Statistical Manual-Fourth Edition, Text Revision (DSM-IV-TR) diagnostic criteria. Only cases meeting full DSM-IV-TR criteria for Autistic Disorder (AUT) were included for further analysis. DSM-IV-TR diagnosis of AUT was confirmed by certified raters using the Autism Diagnostic Interview-Revised (ADI-R). Regression status was determined based on ADI-R and Shortened CPEA Regression Interview. Control-GI children were evaluated in the same manner as cases to exclude subjects with any developmental disturbances, including ASD. Age of AUT onset was determined by an ADI-R certified interviewer. Questions posed to parents in standardized data collection forms regarding GI symptoms were based on previous work [27]. Symptoms were only reported if the child had experienced the specific GI symptoms, including food allergies, for 3 consecutive months. History of medication use, presence of comorbid conditions, age at first GI episode, and presence and type of food allergies were also acquired through parental questionnaires.

RNA and DNA extraction: All biopsies were snap frozen at collection and stored at -80° C. until extraction. RNA and DNA were extracted sequentially from individual ileal and cecal biopsies [total of 176 biopsies from 15 AUT-GI patients and 7 Control-GI patients: 8 biopsies per patient (4 each from ileum and cecum), yielding 88 ileal and 88 cecal biopsies] in TRIzol (Invitrogen) using standard protocols. RNA from half of the biopsies (2 ileal and 2 cecal biopsies per AUT-GI or Control-GI patient) was derived from residual extracts from the original study completed in 2008 [86]. RNA from the other half of the biopsies (the remaining 2 ileal and 2 cecal biopsies per AUT-GI or Control-GI patient) was newly extracted from stored biopsies (stored undisturbed at −80° C.) at the inception of the current study in 2008. The interphase and organic phase fractions were stored at −80° C., following RNA extraction, for subsequent DNA extraction. All extractions were stored in aliquots at −80° C. to avoid repeated freeze thawing of samples. RNA and DNA concentrations, purity and integrity were determined for all residual extracts and newly extracted biopsies just prior to cDNA synthesis for mRNA expression studies and just prior to PCR of newly extracted DNA using a Nanodrop ND-1000 Spectrophotometer (Nanodrop Technologies) and Bioanalyzer (Agilent Technologies).

Quantitative Real-Time PCR of human mRNA: Intron/exon spanning, gene-specific PCR primers and probes (Table 16) for SI, MGAM, LCT, SGLT1, GLUT2, villin, and CDX2, with GAPDH and β-actin as dual housekeeping gene controls were designed for real-time PCR using Primer Express 1.0 software (Applied Biosystems). Taqman probes were labeled with the reporter FAM (6-carboxyfluorescein) and the quencher BBQ (Blackberry) (TIB MolBiol). Assays were designed and implemented as previously described [87,88, 89]. Levels of mRNA expression for each gene and in each AUT-GI individual were considered significantly increased or decreased if they were above the $75^{th}$ percentile or below the $25^{th}$ percentile, respectively, of gene expression obtained for all Control-GI children and were at least 2-fold increased or decreased from the Control-GI mean (Table 9 and Table 10).

Barcoded pyrosequencing of intestinal microbiota: PCR was carried out using bacterial 16S rRNA gene-specific (V2-region), barcoded primers as previously described [91]. Barcoded 16S rRNA genes were amplified from DNA samples from the 88 ileal biopsies and 88 cecal biopsies. Amplicons were sequenced at 454 Life Sciences on a GS FLX sequencer.

Quantitative Real-time PCR of Bacteroidete and Firmicute 16S rRNA genes: Primer sequences and PCR conditions used for bacterial real-time PCR assays to quantify Bacteroidetes, Firmicutes, and total Bacterial 16S rRNA genes have been previously described [92,93]; primer sequences are listed in Table 16. Copy numbers of Bacteroidetes, Firmicutes, or Firmicute to Bacteroidete ratios that were above the $75^{th}$ percentile or below the $25^{th}$ percentile of Control-GI children were scored as an increase or decrease, respectively (Table 9). Percent changes in bacterial parameters for individuals in the

TABLE 16

Real-time PCR primers and probes used for gene expression and bacterial quantitative analysis.

| Name | SEQ ID | Primers and Probe | Amplicion size (bp) |
|---|---|---|---|
| SI | 26 | For: 5'-TCTTCATGAGTTTTATGAGGATACGAAC-3' | 150 |
|  | 27 | Rev: 5'-TTTGCACCAGATTCATAATCATACC-3' |  |
|  | 27 | Probe: 5'-CAGATACTGTGAGTGCCTACATCCCTGATGCTATT-3' |  |
| MGAM | 29 | For: 5'-TACCTTGATGCATAAGGCCCA-3' | 150 |
|  | 30 | Rev: 5'-GGCATTACGCTCCAGGACA-3' |  |
|  | 31 | Probe: 5'-CGTCACTGTTGTGCGGCCTCTGC-3' |  |
| LCT | 32 | For: 5'-CAGGAATCAAGAGCGTCACAACT-3' | 180 |
|  | 33 | Rev: 5'-AAATCGACCGTGTCCTGGG-3' |  |
|  | 34 | Probe: 5'-TCCTGCTAGAACCACCCATATCTGCGCT-3' |  |
| SGLT1 | 35 | For: 5'-GCTCATGCCCAATGGACTG-3' | 125 |
|  | 36 | Rev: 5'-CGGACCTTGGCGTAGATGTC-3' |  |
|  | 37 | Probe: 5'-ACAGCGCCAGCACCCTCTTCACC-3' |  |
| Glut2 | 38 | For: 5'-AGTTAGATGAGGAAGTCAAAGCAA-3' | 164 |
|  | 39 | Rev: 5'-TAGGCTGTCGGTAGCTGG-3' |  |
|  | 40 | Probe: 5'-ACAAAGCTTGAAAAGACTCAGAGGATATGATGATGTC-3' |  |
| Villin | 41 | For: 5'-CATGCGCTGAACTTCATCAAA-3' | 120 |
|  | 42 | Rev: 5'-GGTTGGACGCTGTCCACTTC-3' |  |
|  | 43 | Probe: 5'-CGGCCGTCTTTCAGCAGCTCTTCC-3' |  |
| CDX2 | 44 | For: 5'-GGCAGCCAAGTGAAAACCAG-3' | 112 |
|  | 45 | Rev: 5'-TCCGGATGGTGATGTAGCG-3' |  |
|  | 46 | Probe: 5'-ACCACCAGCGGCTGGAGCTGG-3' |  |
| β-Actin | 47 | For: 5'-AGCCTCGCCTTTGCCGA-3' | 175 |
|  | 48 | Rev: 5'-CTGGTGCCTGGGGCG-3' |  |
|  | 49 | Probe: 5'-CCGCCGCCCGTCCACACCCGCC |  |
| GAPDH | 50 | For: 5'-CCTGTTCGACAGTCAGCCG-3' | 100 |
|  | 51 | Rev: 5'-CGACCAAATCCGTTGACTCC-3' |  |
|  | 52 | Probe: 5'-CGTCGCCAGCCGAGCCACA-3' |  |
| Bacteroidetes | 53 | For: 5'-AACGCTAGCTACAGGCTT-3' | ~293 |
|  | 54 | Rev: 5'-CCAATGTGGGGGACCTTC-3' |  |
| Firmicules | 55 | For: 5'-GGAGYATGTGGTTTAATTCGAAGCA-3' | ~126 |
|  | 56 | Rev: 5'-AGCTGACGACAACCATGCAC-3' |  |
| Total Bacteria | 57 | For: 5'-GTGCCAGCMGCCGCGGTAA-3' | ~295 |
|  | 58 | Rev: 5'-GACTACCAGGGTATCTAAT-3' |  |

Lactase genotyping: Genomic DNA from AUT-GI and Control-GI patients was subjected to previously-described, PCR-restriction fragment length polymorphism (PCR-RFLP) analysis for the C/T-13910 and G/A-22018 polymorphisms associated with adult-type hypolactasia with minor modifications [90]. For details, see FIG. 21B-E.

AUT-GI group were determined based on the mean levels in Control-GI children (Table 12).

Bioinformatic analysis of pyrosequencing reads: Pyrosequencing reads ranging from 235 to 300 base pairs in length (encompassing all sequences within the major peak obtained from pyrosequencing) were filtered for analysis. Low-quality sequences—i.e., those with average quality scores below 25—were removed based on previously described criteria [91,94]. Additionally, reads with any ambiguous characters were omitted from analysis. Sequences were then binned according to barcode, followed by removal of primer and barcode sequences. Taxonomic classifications of bacterial 16S rRNA sequences were obtained using the RDP classifier tool with a minimum 80% bootstrap confidence estimate. To normalize data for differences in total sequences obtained per patient, phylotype abundance was expressed as a percentage of total bacterial sequence reads per patient at all taxonomic levels. Taxonomy note: the RDP classifier binned all of the limited number of sequences obtained for the phylum Cyanobacteria into the chloroplast-derived genus *Streptophyta*. Heatmaps were constructed with MeV (Version 4.5.0), using abundance data from pyrosequencing reads. Heatmap scales were made linear where possible, with the upper limit reflecting the highest abundance recorded for any taxa in a given heatmap (red), the lower limit reflecting sequences above 0% abundance (green), and the midpoint limit (white) set to the true midpoint between 0% and the upper limit. In some instances, the midpoint limit was adjusted to highlight salient differences between the AUT-GI and Control-GI groups. Gray cells in all heatmaps reflect the complete absence of sequences detected for a given taxa in a given patient.

OTU-based analysis was carried out in MOTHUR (version 1.8.0) [95]. Filtered sequences generated from 454 pyrosequencing were aligned to the greengenes reference alignment (greengenes.lbl.gov), using the Needleman-Wunsch algorithm with the "align.seqs" function (ksize=9). Pairwise genetic distances among the aligned sequences were calculated using the "dist.seqs" function (calc=onegap, countends=T). Sequences were assigned to OTUs (97% identity) using nearest neighbor clustering. Rarefaction curves to assess coverage and diversity (Shannon Diversity Index) were constructed in MOTHUR. For OTU analysis of Bacteroidete sequences, phylum level classification in RDP was used to subselect all Bacteroidete sequences, followed by OTU assignment at 97% identity. Representative sequences (defined as the sequence with the minimum distance to all other sequences in the OTU) from each OTU were obtained using the get.oturep command in MOTHUR. Representative sequences were classified using the nearest species match from Greengenes Blast (greengenes.lbl.gov) and NCBI BLAST alignment. OTU abundance by patient was expressed as percent relative abundance, determined by dividing the number of reads for an OTU in a given patient sample by the total number of bacterial reads obtained through pyrosequencing for that sample.

Statistical analysis: Most of the data were not normally distributed, based on Kolmogorov-Smirnov test and evaluation of skewness and kurtosis; thus, the non-parametric Mann-Whitney U test was performed to evaluate differences between groups using StatView (Windows version 5.0.1; SAS Institute). The comparative results of gene expression and bacteria 16S rRNA gene levels were visualized as box-and-whisker plots showing: the median and the interquartile (midspread) range (boxes containing 50% of all values), the whiskers (representing the $25^{th}$ and $75^{th}$ percentiles) and the extreme data points (open circles). Chi-squared test was used to evaluate between-group genotypes for adult-type hypolactasia as well as differences in the frequency of atopic disease between groups. Kruskal-Wallis one-way analysis of variance was employed to assess significance of LCT mRNA expression levels split by genotype and group. To evaluate the effects of CDX2 and/or villin on enzyme and transporter levels and the effects of levels of enzymes and transporters on bacterial levels, multiple linear regression analyses were conducted. For details on multiple linear regression analyses see Table 11, and Table 14. Significance was accepted for all analyses at $p<0.05$.

Supporting Results

Genetically determined lactase non-persistence is not responsible for deficient lactase mRNA in AUT-GI children (FIG. 21): Although it is beyond the scope of this study to evaluate all possible mutations in carbohydrate genes that can affect expression, it was confirmed that deficient LCT mRNA in AUT-GI children is not a result of the common adult-type hypolactasia genotype. LCT mRNA levels can be affected by two single nucleotide polymorphisms that determine adult-type hypolactasia; therefore, these children were genotyped using PCR-RFLP analysis. The homozygous, hypolactasia variant alleles were found in 20% (3 out of 15) of AUT-GI children and 14.3% (1 out of 7) of Control-GI children. Genotype proportions were not significantly different between the two groups (chi-squared test, p=0.896) (FIG. 21B). LCT mRNA expression was significantly lower in individuals with the homozygous hypolactasia genotype compared to all other genotypes (FIG. 21C: Mann-Whitney, p=0.033). Comparison of LCT mRNA expression across genotype and group failed to reach significance (FIG. 21D: Kruskal-Wallis, p=0.097). Comparison of mRNA expression in subjects carrying at least one copy of the normal allele confirmed a significant decrease in LCT mRNA in AUT-GI relative to Control-GI subjects, independent of the individuals with the homozygous hypolactasia genotype (FIG. 21E: Mann-Whitney, p=0.025). In summary, although the data support the notion that LCT genotype affects gene expression, deficient LCT mRNA in AUT-GI was not attributable to disproportionate hypolactasia genotypes between the AUT-GI and Control-GI groups.

Barcoded 16S rRNA gene pyrosequencing (FIG. 23): A total of 525,519 sequencing reads (representing 85% of the initial number of sequencing reads) remained after filtering based on read length, removing low-quality sequences and combining duplicate pyrosequencing runs (271,043 reads for ilea; 254,476 reads for ceca). Binning of sequences by barcode revealed similar numbers of 16S rRNA gene sequence reads per patient (average # sequences per patient+/−STD for ilea=12,320+/−1220; average # sequences per patient+/−STD for ceca=11,567+/−1589). There was not a significant difference between the AUT-GI and Control-GI groups in terms of the number of reads per patient. In order to assess whether sufficient sampling was achieved in the total pyrosequencing data set for all AUT-GI and Control-GI subjects, OTUs (Operational Taxonomic Units) were defined at a threshold of 97% identity, split by data for ileum and cecum, and rarefaction analysis was carried out (FIG. 23A-B). Rarefaction curves showed a tendency toward reaching plateau for all subjects; however failure to reach plateau indicates that additional sampling would be required to achieve complete coverage of all OTUs present in ileal and cecal biopsies. Investigation of diversity in AUT-GI and Control-GI patients was carried out using the Shannon Diversity Index calculated from OTU data for each subject. Rarefaction analysis revealed that all Shannon Diversity estimates had reached stable values (FIG. 23C-D). While Shannon Diversity estimates varied widely between individuals, there was not an apparent overall difference (loss or gain of diversity) between the AUT-GI and Control-GI groups in ileal (FIG. 23C) or cecal (FIG. 23D) biopsies.

OTU Analysis of Bacteroidetes (FIG. 25): In order to determine whether the decreased abundance of Bacteroidete members was attributable to the loss of specific Bacteroidete phylotypes, the distribution of Bacteroidete OTUs (defined using a threshold of 97% identity or greater; 3% distance) were investigated. The number of Bacteroidete OTUs per patient ranged from 23 to 102 for ileal samples and 10 to 130 for cecal samples. Interestingly, no single OTU was significantly over or underrepresented between AUT-GI and Control-GI children and many OTUs contained single sequences. Furthermore, high inter-subject variability in the distribution and abundance of individual Bacteroidete phylotypes was observed, as has been previously described [B1]. Thus, it was determined whether the decrease in Bacteroidete abundance in AUT-GI children could be attributed to overall losses of the most prevalent Bacteroidete phylotypes. In both ileal and cecal samples, 12 OTUs accounted for the majority of Bacteroidete sequences (FIG. 25A-B). The cumulative levels of these 12 OTUs were significantly lower in AUT-GI compared to Control-GI children in both the ileum (FIG. 25C: Mann-Whitney, p=0.008) and cecum (FIG. 25D: Mann-Whitney, p=0.008). Representative sequences from each of these 12 OTUs were classified using Greengenes Blast and microbial blast alignment (NCBI) (FIG. 25E). The majority of sequences were members of the family Bacteroidaceae (OTUs 1, 3, 5, 6, 7, and 19), except in the case of patient 20, where Prevotellaceae were the dominant phylotype (OTU #21). These results indicate that the loss of Bacteroidetes in AUT-GI children is primarily attributable to overall decreases in the dominant phylotypes of Bacteroidetes in individual patients Evaluation of confounding effects of probiotic, proton-pump inhibitor and antibiotic use: The use of probiotics (Pb), proton-pump inhibitors (PPI), and antibiotics are reported to exert effects on the composition of the intestinal microbiota [B2, B3]. As some patients in both the AUT-GI and Control-GI groups had taken these medications, we sought to determine whether potential confounding effects of these medications on the findings could be excluded. Probiotics had been used by both AUT-GI (n=4; 27%) and Control-GI (n=1; 14%) children. If probiotics use determined the outcome of gene expression and bacterial variables, then the significant effect for a given variable should not be present when comparing individuals that had not taken probiotics in the AUT-GI and Control-GI groups [Table 13A: AUT(−Pb) vs. Control(−Pb)]. For each of the 16 variables, except the ratio of Firmicutes to Bacteroidetes in the cecum (RT) and Betaproteobacteria in the cecum (454), either a significant result or trend was observed between the AUT(-Pb) and Control(-Pb) groups. If the cecal ratio of Firmicutes to Bacteroidetes and Betaproteobacteria are affected by probiotic use, then a difference in the levels of these bacterial parameters should be evident when comparing AUT-GI probiotic non-users vs. AUT-GI probiotic users [Table S5A: AUT(−Pb) vs. AUT(+Pb)]. There was not a significant difference in Betaproteobacteria levels between these groups; however, the ratio of Firmicutes to Bacteroidetes in the cecum, determined by real-time PCR, was significantly higher in the AUT(+Pb) group compared to the AUT(−Pb) group (Table 13A: Mann-Whitney, p=0.037). Thus an effect mediated by probiotics on this variable cannot be excluded. This effect, however, was not apparent in the corresponding ratio of Firmicutes to Bacteroidetes in the cecum, determined by pyrosequencing.

The use of proton-pump inhibitors (PPI: Lanzoprazole or Omeprazole) was similarly examined. PPI had been used by both AUT-GI (n=4; 27%) and Control-GI (n=2; 29%) children. A significant difference was found for all variables, except LCT, when comparing AUT(−PPI) children with Control(−PPI) children [Table S5B: AUT(−PPI) vs. Control(−PPI)]. Thus a potential effect of PPI use should only be considered for LCT. As LCT levels were not significantly different between AUT(−PPI) and AUT(+PPI) children, it is unlikely that PPIs exerted any major effect on LCT expression. A trend toward an effect in the levels of Bacteroidetes in the ileum, determined by pyrosequencing, was evident between AUT(−PPI) and AUT(+PPI) children; however, a significant effect was observed between AUT(−PPI) and Control(−PPI) children. This indicates that this potential effect was not a major determinant of the difference in ileal Bacteroidetes between AUT-GI and Control-GI children. Only one patient (AUT-GI patient #1) had used both probiotics and proton-pump inhibitors, thus an additive effect was not evaluated. Grouping of patients based on whether they had taken either probiotics or proton-pump inhibitors did not reveal any significant effects in the 16 variables.

Only one individual had taken an antibiotic (amoxicillin) in this cohort (Control-GI patient #16). This patient had high levels of mRNA expression for all disaccharidases and transporters, within the range of other Control-GI children and at least above the $90^{th}$ percentile of all AUT-GI children. Thus, exclusion of this patient from the analysis had a negative effect on significance values obtained for gene expression assays (Table 13C). These results indicate that antibiotic use had no effect on disaccharidase and hexose transporter levels in this patient. In contrast, Control-GI patient #16 consistently had the lowest levels of Bacteroidetes (representing the low-range outlier) compared to all other Control-GI children in pyrosequencing and real-time PCR assays. Thus, exclusion of this patient from analysis of bacterial phylotypes generally improved the significance of results obtained for Bacteroidetes, ratios of Firmicutes to Bacteroidetes, and ratios of Clostridiales to Bacteroidales. Levels of Beta-proteobacteria in the cecum for this patient were near the median value of all other Control-GI children. Thus, it is likely that antibiotic use in this patient had some effect on Bacteroidete levels, but no effect on Betaproteobacteria or gene expression for disaccharidases and transporters. As the effect of antibiotic use in this patient did not affect all variables and exclusion of this patient did not affect the interpretation of results, this patient was not excluded from the overall analysis.

REFERENCES FOR SUPPORTING RESULTS

B1. Eckburg P B, Bik E M, Bernstein C N, Purdom E, Dethlefsen L, et al. (2005) Diversity of the human intestinal microbial flora. Science 308: 1635-1638.

B2. Reid G, Younes J A, Van der Mei H C, Gloor G B, Knight R, et al. (2011) Microbiota restoration: natural and supplemented recovery of human microbial communities. Nat Rev Microbiol 9: 27-38.

B3. Lombardo L, Foti M, Ruggia O, Chiecchio A (2010) Increased incidence of small intestinal bacterial overgrowth during proton pump inhibitor therapy. Clin Gastroenterol Hepatol 8: 504-508.

Supporting Methods

Quantitative Real-Time PCR of human mRNA: PCR standards for determining copy numbers of target transcripts were generated from amplicons of SI, MGAM, LCT, SGLT1, GLUT2, Villin, CDX2, GAPDH, and Beta-actin cloned into the vector pGEM-T easy (Promega Corporation). Linearized plasmids were quantitated using a Nanodrop ND-1000 Spectrophotometer, and 10-fold serial dilutions (ranging from $5 \times 10^5$ to $5 \times 10^0$ copies) were created in water containing yeast tRNA (1 ng/µl). Unpooled RNA from individual ileal biopsies were used for real time PCR assays; each individual biopsy was assayed in duplicate. cDNA was synthesized using Taqman reverse transcription reagents (Applied Biosystems) from 2 μg unpooled RNA per 100 μl reaction. Each 25-μl amplification reaction contained 10 μl template cDNA, 12.5 μl Taqman Universal PCR Master Mix (Applied Biosystems), 300 nM gene-specific primers and 200 nM gene-specific probe (Table 16). The thermal cycling profile using a ABI StepOnePlus Real-time PCR System (Applied Biosystems) consisted of: Stage 1, one cycle at 50° C. for 2 min; Stage 2, 1 cycle at 95° C. for 10 min; Stage 3, 45 cycles at 95° C. for 15 s and 60° C. for 1 min (1 min 30 s for LCT). GAPDH and B-actin mRNA were amplified in duplicate reactions by real-time PCR from the same reverse transcription reactions as were used for the genes of interest. The mean concentration of GAPDH or Beta-actin in each sample was used to control for integrity of input RNA and to normalize values of target gene expression to those of the housekeeping gene expression. GAPDH and Beta-actin have been shown to be the most stable reference genes in small bowel and colonic biopsies from healthy patients and pediatric patients with inflammatory bowel disease [C1]. The final results shown were expressed as the mean copy number from replicate biopsies per patient, relative to values obtained for GAPDH mRNA. Beta-actin normalization gave similar results to GAPDH normalization for all assays (data not shown). Due to insufficient or poor quality RNA (OD 260/280 ratio <1.7, or RNA integrity number <7.0), only 3 of the 4 biopsies were included for 3 patients (Patient #s 4, 7, 10) and only 2 of the 4 biopsies were included for 1 patient (Patient # 2). Thus, 83 of the original 88 ileal biopsies were used in real-time PCR experiments.

Lactase genotyping: Genotyping primers for the LCT C/T-13910 and G/A-22018 polymorphisms are as follows: C/T-13910For (5'-GGATGCACTGCTGTGATGAG-3' [SEQ ID NO: 20]), C/T-13910Rev (5'-CCCACTGACCTATC-CTCGTG-3' [SEQ ID NO: 21]), G/A-22018For (5'-AACAG-GCACGTGGAGGAGTT-3' [SEQ ID NO: 22]), and G/A-22018Rev (5'-CCCACCTCAGCCTCTTGAGT-3' [SEQ ID NO: 23]). Each 50-μl amplification reaction contained 500 ng genomic DNA, 400 nM forward and reverse primers, and 25 μl High Fidelity PCR master mix (Roche). Thermal cycling consisted of 1 cycle at 94° C. for 4 min followed by 40 cycles at 94° C. for 1 min, 60° C. for 1 min, and 72° C. for 1 min. PCR reactions for C/T-13910 were directly digested with the restriction enzyme BsmFI at 65° C. for 5 hrs. PCR reactions for G/A-22018 were resolved on 1% agarose gels followed by gel extraction of the prominent 448bp amplicon. Gel extracted G/A-22018 amplicons were then digested with the restriction enzyme HhaI at 37° C. for 5 hrs. Restriction digests of C/T-13910 and G/A-22018 were resolved on 1.5% ethidium-stained agarose gels for genotyping analysis. BsmFI digestion of the C/T-13910 amplicons generates two fragments (351bp and 97bp) for the hypolactasia genotype (C/C), four fragments (351bp, 253bp, 98bp, and 97bp) for the heterozygous genotype (C/T), and three fragments (253bp, 98bp, and 97bp) for the normal homozygous allele (T/T). HhaI digestion of the G/A-22018 amplicons generates two fragments (284bp and 184bp) for the hypolactasia genotype (G/G), three fragments (448bp, 284bp, and 184bp) for the heterozygous genotype (G/A), and a single fragment (448bp) for the normal homozygous allele (A/A).

Barcoded pyrosequencing of intestinal microbiota: Composite primers used for pyrosequencing analysis were as follows: (For) 5'-GCCTTGCCAGCCCGCTCAGTCAGAGTTTGATCCTGG CTCAG-3' [SEQ ID NO: 24], (Rev) 5'-GCCTCCCTCGCGCCATCAGNNNNNNNNCATGCTGC CTCCCGTAGGAGT-3' [SEQ ID NO: 25]. Underlined sequences in the Forward and Reverse primers represent the 454 Life Sciences@ primer B and primer A, respectively. Bold sequences in the forward and reverse primers represent the broadly-conserved bacterial primer 27F and 338R, respectively. NNNNNNNN represents the eight-base barcode, which was unique for each patient. PCR reactions consisted of 8 μl 2.5× 5 PRIME HotMaster Mix (5 PRIME Inc), 6 μl of 4 μM forward and reverse primer mix, and 200 ng DNA in a 20-μl reaction volume. Thermal cycling consisted of one cycle at 95° C. for 2 min; and 30 cycles at 95° C. for 20 seconds, 52° C. for 20 seconds, and 65° C. for 1 min. Each of 4 biopsies per patient was amplified in triplicate, with a single, distinct barcode applied per patient. Ileal and cecal biopsies were assayed separately. Reagent controls were included (negative controls) to control for any background contamination. Triplicate reactions of individual biopsies and reagent controls were combined, and PCR products were purified using Ampure magnetic purification beads (Beckman Coulter Genomics) and quantified with the Quanti-iT PicoGreen dsDNA Assay Kit (Invitrogen) and Nanodrop ND-1000 Spectrophotometer (Nanodrop Technologies). Equimolar ratios were combined to create two master DNA pools, one for ileum and one for cecum, with a final concentration of 25 ng/μl. Master pools were sent for unidirectional pyrosequencing with primer A at 454 Life Sciences on a GS FLX sequencer. Each master pool was sequenced in duplicate on different days to control for variability in the sequencing reactions. Sequences obtained from duplicate runs were combined for the final analysis. No sequences were obtained from reagent controls, indicating that no background contamination was present.

Quantitative Real-time PCR of Bacteroidete and Firmicute 16S rRNA genes: PCR standards for determining copy numbers of bacterial 16S rDNA were prepared from representative amplicons of the partial 16S rRNA genes of Bacteroidetes, Firmicutes and total Bacteria cloned into the vector PGEM-T easy (Promega). A representative amplicon with high sequence similarity to *Bacteroides Vulgatus* (Accession #: NC_009614) was used with Bacteroidete-specific primers. A representative amplicon with high sequence similarity to *Faecalibacterium prausnitzii* (Accession #: NZ_A-BED02000023) was used with Firmicute-specific primers. A representative amplicon with high sequence similarity to *Bacteroides intestinalis*. (Accession #: NZ ABJL02000007) 16S rRNA gene was used with total Bacteria primers (primers 515F and 805R). Cloned sequences were classified using the Ribosomal Database Project (RDP, release 10) Seqmatch tool and confirmed by the Microbes BLAST database. Plasmids were linearized with the SphI restriction enzyme, quantitated, and ten-fold serial dilutions of plasmid standards were created ranging from $5\times10^7$ to $5\times10^0$ copies for Bacteroidetes, Firmicutes and total Bacteria. Amplification and detection of DNA by real-time PCR were performed with the ABI StepOnePlus Real-time PCR System (Applied Biosystems). Cycling parameters for Bacteroidetes and total Bacteria were as previously described [C2], as were cycling parameters for Firmicutes [C3]. Each 25-μl amplification reaction mixture contained 50 ng DNA, 12.5 μl SYBR Green Master Mix (Applied Biosystems), and 300 nM bacteria-specific (Bacteroidete, Firmicute or total Bacteria) primers. DNA from each of 88 ileal biopsies (4 biopsies per patient) and 88 cecal biopsies (4 biopsies per patient) was assayed in duplicate. The final results were expressed as the mean number of Bacteroidete or Firmicute 16S rRNA gene copies normalized to 16S rRNA gene copies obtained using total Bacterial primers. Eight water/reagent controls were included for all amplifications. The average copy number for water/reagent controls (background) was subtracted from each ileal and cecal amplification prior to normalization. For the Bacteroidete assay all water controls contained undetectable levels of amplification. For the Firmicute assay average amplification signal from water samples were minimal, 12.03+/−15.0 copies.

Statistical analysis: To evaluate the effects of CDX2 and/or villin on enzyme and transporter levels and the effects of levels of enzymes and transporters on bacterial levels, multiple linear regression analyses were conducted. For assessing the affects of CDX2 and villin on disaccharidase and transporter expression levels, disaccharidase and transporter levels were log-transformed to stabilize the variance. Using each log-transformed disaccharidase and transporter mRNA expression level as an outcome, three models were fitted: first with CDX2 only as independent variable; second with CDX2 and status (dummy coded; AUT-GI=1 vs. Control-GI=0); and third with CDX2, status, and the interaction term between CDX2 and status. The interaction term allowed us to evaluate whether the effect of CDX2 on disaccharidases and transporters was similar for AUT-GI and Control-GI children. The same models were fitted after adding villin and the interaction term between villin and status. The coefficient estimates in Table 11 represent change in log-transformed disaccharidase or transporter mRNA levels per unit standard deviation increase in CDX2 and villin mRNA levels.

To delineate the effects of disaccharidases and transporters on bacterial levels in ileal and cecal biopsies, bacterial 16S rRNA gene quantities (obtained from real-time PCR for Bacteroidetes and Firmicutes) or abundance (obtained from 454 pyrosequencing data for Proteobacteria and Betaproteobacteria) were log-transformed to stabilize variance. For each of the log-transformed bacterial levels, enzyme levels were first fitted simultaneously as the main effects (SI, MGAM, LCT, SGLT1, and GLUT2) to evaluate the effects of enzymes on a given bacterial taxa. Status was added to the model to determine whether there was a residual difference in bacterial levels between AUT-GI and Control-GI children after adjusting for the levels of disaccharidases and transporters. It was further examined whether the effect of disaccharidases or transporters on bacterial levels was the same depending on the status by examining two-way interaction terms between status and each disaccharidase and transporter. The final model was derived by including all the main effect terms and selectively including two-way interaction terms using the backward elimination method starting from all possible two-way interaction terms with status and the individual disaccharidases and transporters. The coefficient estimates in Table 14 represent change in log-transformed bacterial levels per unit standard deviation increase in disaccharidase or transporter levels. The statistical package R (version 2.7.0) was used for regression analysis.

SUPPORTING METHODS REFERENCES

C1. Zilbauer M, Jenke A, Wenzel G, Goedde D, Postberg J, et al. (2010) Intestinal alpha-defensin expression in pediatric inflammatory bowel disease. Inflamm Bowel Dis. In press.
C2. Frank D N, St Amand A L, Feldman R A, Boedeker E C, Harpaz N, et al. (2007) Molecular-phylogenetic characterization of microbial community imbalances in human inflammatory bowel diseases. Proc Natl Acad Sci USA 104: 13780-13785.
C3. Guo X, Xia X, Tang R, Zhou J, Zhao H, et al. (2008) Development of a real-time PCR method for Firmicutes and Bacteroidetes in faeces and its application to quantify intestinal population of obese and lean pigs. Lett Appl Microbiol 47: 367-373.

REFERENCES FOR EXAMPLE

1. Buie T, Campbell D B, Fuchs G J, 3rd, Furuta G T, Levy J, et al. (2010) Evaluation, diagnosis, and treatment of gastrointestinal disorders in individuals with ASDs: a consensus report. Pediatrics 125 Suppl 1: S1-18.
2. White J F (2003) Intestinal pathophysiology in autism. Exp Biol Med (Maywood) 228: 639-649.
3. Wakefield A J, Anthony A, Murch S H, Thomson M, Montgomery S M, et al. (2000) Enterocolitis in children with developmental disorders. Am J Gastroenterol 95: 2285-2295
4. Wakefield A J, Ashwood P, Limb K, Anthony A (2005) The significance of ileo-colonic lymphoid nodular hyperplasia in children with autistic spectrum disorder. Eur J Gastroenterol Hepatol 17: 827-836.
5. Furlano R I, Anthony A, Day R, Brown A, McGarvey L, et al. (2001) Colonic CD8 and gamma delta T-cell infiltration with epithelial damage in children with autism. .1 Pediatr 138: 366-372.
6. Torrente F, Ashwood P, Day R, Machado N, Furlano R I, et al. (2002) Small intestinal enteropathy with epithelial IgG and complement deposition in children with regressive autism. Mol Psychiatry 7: 375-382, 334.
7. Horvath K, Papadimitriou J C, Rabsztyn A, Drachenberg C, Tildon J T (1999) Gastrointestinal abnormalities in children with autistic disorder. J Pediatr 135: 559-563.
8. Ashwood P, Wills S, Van de Water J (2006) The immune response in autism: a new frontier for autism research. J Leukoc Biol 80: 1-15.
9. Ashwood P, Anthony A, Torrente F, Wakefield A J (2004) Spontaneous mucosal lymphocyte cytokine profiles in children with autism and gastrointestinal symptoms: mucosal immune activation and reduced counter regulatory interleukin-10. J Clin Immunol 24: 664-673.
10. Ashwood P, Anthony A, Pellicer A A, Torrente F, Walker-Smith J A, et al. (2003) Intestinal lymphocyte populations in children with regressive autism: evidence for extensive mucosal immunopathology. J Clin Immunol 23: 504-517.
11. Enstrom A M, Onore C E, Van de Water J A, Ashwood P (2010) Differential monocyte responses to TLR ligands in children with autism spectrum disorders. Brain Behav Immun 24: 64-71.
12. Jyonouchi H, Geng L, Ruby A, Zimmerman-Bier B (2005) Dysregulated innate immune responses in young children with autism spectrum disorders: their relationship to gastrointestinal symptoms and dietary intervention. Neuropsychobiology 51: 77-85.
13. D'Eufemia P, Celli M, Finocchiaro R, Pacifico L, Viozzi L, et al. (1996) Abnormal intestinal permeability in children with autism. Acta Paediatr 85: 1076-1079.
14. Finegold S M, Molitoris D, Song Y, Liu C, Vaisanen M L, et al. (2002) Gastrointestinal microflora studies in late-onset autism. Clin Infect Dis 35: S6-S16.
15. Song Y, Liu C, Finegold S M (2004) Real-time PCR quantitation of clostridia in feces of autistic children. Appl Environ Microbiol 70: 6459-6465.
16. Parracho E N, Bingham M O, Gibson G R, McCartney A L (2005) Differences between the gut microflora of children with autistic spectrum disorders and that of healthy children. J Med Microbiol 54: 987-991.
17. Knivsberg A M, Reichelt K L, Hoien T, Nodland M (2002) A randomised, controlled study of dietary intervention in autistic syndromes. Nutr Neurosci 5: 251-261.

18. Sandler R H, Finegold S M, Bolte E R, Buchanan C P, Maxwell A P, et al. (2000) Short-term benefit from oral vancomycin treatment of regressive-onset autism. J Child Neurol 15: 429-435.
19. Adams J B, Johansen L J, Powell L D, Quig D, Rubin R A (2011) Gastrointestinal flora and gastrointestinal status in children with autism--comparisons to typical children and correlation with autism severity. BMC Gastroenterol 11: 22.
20. Sonnenburg E D, Sonnenburg J L, Manchester J K, Hansen E E, Chiang H C, et al. (2006) A hybrid two-component system protein of a prominent human gut symbiont couples glycan sensing in vivo to carbohydrate metabolism. Proc Natl Acad Sci USA 103: 8834-8839.
21. Flint H J, Bayer E A, Rincon M T, Lamed R, White B A (2008) Polysaccharide utilization by gut bacteria: potential for new insights from genomic analysis. Nat Rev Microbiol 6: 121-131.
22. Wong J M, Jenkins D J (2007) Carbohydrate digestibility and metabolic effects. J Nutr 137: 2539S-2546S.
23. Jacobs D M, Gaudier E, van DuynhOven J, Vaughan E E (2009) Non-digestible food ingredients, colonic microbiota and the impact on gut health and immunity: a role for metabolomics. Curr Drug Metab 10: 41-54.
24. O'Hara A M, Shanahan F (2006) The gut flora as a forgotten organ. EMBO Rep 7: 688-693.
25. Macpherson A J, Harris N L (2004) Interactions between commensal intestinal bacteria and the immune system. Nat Rev Immunol 4: 478-485.
26. Heijtz R D, Wang S, Anuar F, Qian Y, Bjorkholm B, et al. (2011) Normal gut microbiota modulates brain development and behavior. Proc Natl Acad Sci USA. 108: 3047-3052.
27. Richler J, Luyster R, Risi S, Hsu W L, Dawson G, et al. (2006) Is there a 'regressive phenotype' of Autism Spectrum Disorder associated with the measles-mumps-rubella vaccine? A CPEA Study. J Autism Dev Disord 36: 299-316.
28. Kellett G L, Brot-Laroche E, Mace O J, Leturque A (2008) Sugar absorption in the intestine: the role of GLUT2. Annu Rev Nutr 28: 35-54.
29. Khurana S, George SP (2008) Regulation of cell structure and function by actin-binding proteins: villin's perspective. FEBS Lett 582: 2128-2139.
30. Arijs I, De Hertogh G, Lemaire K, Quintens R, Van Lommel L, et al. (2009) Mucosal gene expression of antimicrobial peptides in inflammatory bowel disease before and after first infliximab treatment. PLoS One 4: e7984.
31. Suh E, Traber P G (1996) An intestine-specific homeobox gene regulates proliferation and differentiation. Mol Cell Biol 16: 619-625.
32. Troelsen J T, Mitchelmore C, Spodsberg N, Jensen A M, Noren O, et al. (1997) Regulation of lactase-phlorizin hydrolase gene expression by the caudal-related homoeodomain protein Cdx-2. Biochem J 322 (Pt 3): 833-838.
33. Uesaka T, Kageyama N, Watanabe H (2004) Identifying target genes regulated downstream of Cdx2 by microarray analysis. J Mol Biol 337: 647-660.
34. Balakrishnan A, Stearns A T, Rhoads D B, Ashley S W, Tavakkolizadeh A (2008) Defining the transcriptional regulation of the intestinal sodium-glucose cotransporter using RNA-interference mediated gene silencing. Surgery 144: 168-173.
35. Zoetendal E G, von Wright A, Vilpponen-Salmela T, Ben-Amor K, Akkermans AD, et al. (2002) Mucosa-associated bacteria in the human gastrointestinal tract are uniformly distributed along the colon and differ from the community recovered from feces. Appl Environ Microbiol 68: 3401-3407.
36. Rauch M, Lynch S V (2010) Probiotic manipulation of the gastrointestinal microbiota. Gut Microbes 1: 335-338.
37. Vesper B J, Jawdi A, Altman K W, Haines G K, 3rd, Tao L, et al. (2009) The effect of proton pump inhibitors on the human microbiota. Curr Drug Metab 10: 84-89.
38. Dethlefsen L, Huse S, Sogin M L, Reiman D A (2008) The pervasive effects of an antibiotic on the human gut microbiota, as revealed by deep 16S rRNA sequencing. PLoS Biol 6: e280.
39. Gurney J G, McPheeters M L, Davis M M (2006) Parental report of health conditions and health care use among children with and without autism: National Survey of Children's Health. Arch Pediatr Adolesc Med 160: 825-830.
40. Scheepers A, Joost H G, Schurmann A (2004) The glucose transporter families SGLT and GLUT: molecular basis of normal and aberrant function. JPEN J Parenter Enteral Nutr 28: 364-371.
41. Swallow D M (2003) Genetic influences on carbohydrate digestion. Nutr Res Rev 16: 37-43.
42. Hodin R A, Chamberlain S M, Meng S (1995) Pattern of rat intestinal brush-border enzyme gene expression changes with epithelial growth state. Am J Physiol 269: C385-391.
43. Kishi K, Tanaka T, Igawa M, Takase S, Goda T (1999) Sucrase-isomaltase and hexose transporter gene expressions are coordinately enhanced by dietary fructose in rat jejunum. J Nutr 129: 953-956.
44. Tanaka T, Suzuki A, Kuranuki S, Mochizuki K, Suruga K, et al. (2008) Higher expression of jejunal LPH gene in rats fed the high-carbohydrate/low-fat diet compared with those fed the low-carbohydrate/high-fat diet is associated with in vitro binding of Cdx-2 in nuclear proteins to its promoter regions. Life Sci 83: 122-127.
45. Mochizuki K, Honma K, Shimada M, Goda T (2010) The regulation of jejunal induction of the maltase-glucoamylase gene by a high-starch/low-fat diet in mice. Mol Nutr Food Res 54: 1445-1451.
46. Bandini L G, Anderson S E, Curtin C, Cermak S, Evans E W, et al. (2010) Food selectivity in children with autism spectrum disorders and typically developing children. J Pediatr 157: 259-264.
47. Levy S E, Souders M C, Ittenbach R F, Giarelli E, Mulberg A E, et al. (2007) Relationship of dietary intake to gastrointestinal symptoms in children with autistic spectrum disorders. Biol Psychiatry 61: 492-497.
48. Herndon A C, DiGuiseppi C, Johnson S L, Leiferman J, Reynolds A (2009) Does nutritional intake differ between children with autism spectrum disorders and children with typical development? J Autism Dev Disord 39: 212-222.
49. Emond A, Emmett P, Steer C, Golding J (2010) Feeding symptoms, dietary patterns, and growth in young children with autism spectrum disorders. Pediatrics 126: e337-342.
50. Shearer T R, Larson K, Neuschwander J, Gedney B (1982) Minerals in the hair and nutrient intake of autistic children. J Autism Dev Disord 12: 25-34.
51. Raiten D J, Massaro T (1986) Perspectives on the nutritional ecology of autistic children. J Autism Dev Disord 16: 133-143.
52. Schreck K A, Williams K, Smith A F (2004) A comparison of eating behaviors between children with and without autism. J Autism Dev Disord 34: 433-438.
53. Matosin-Matekalo M, Mesonero J E, Delezay O, Poiree J C, Ilundain A A, et al. (1998) Thyroid hormone regulation 53. of the Na+/glucose cotransporter SGLT1 in Caco-2 cells. Biochem J 334 (Pt 3): 633-640.
54. Emvo E N, Raul F, Koch B, Neuville P, Foltzer-Jourdainne C (1996) Sucrase-isomaltase gene expression in suckling rat intestine: hormonal, dietary, and growth factor control. J Pediatr Gastroenterol Nutr 23: 262-269.
55. Ziambaras T, Rubin D C, Perlmutter D H (1996) Regulation of sucrase-isomaltase gene expression in human intestinal epithelial cells by inflammatory cytokines. J Biol Chem 271: 1237-1242.
56. Suzuki K, Hashimoto K, Iwata Y, Nakamura K, Tsujii M, et al. (2007) Decreased serum levels of epidermal growth factor in adult subjects with high-functioning autism. Biol Psychiatry 62: 267-269.
57. Iseri E, Guney E, Ceylan MF, Yucel A, Aral A, et al. (2010) Increased Serum Levels of Epidermal Growth Factor in Children with Autism. J Autism Dev Disord.
58. Curin J M, Terzic J, Petkovic Z B, Zekan L, Terzic I M, et al. (2003) Lower cortisol and higher ACTH levels in individuals with autism. J Autism Dev Disord 33: 443-448.
59. Hooper L V, Wong M H, Thelin A, Hansson L, Falk P G, et al. (2001) Molecular analysis of commensal host-microbial relationships in the intestine. Science 291: 881-884.
60. Barros R, Marcos N, Reis C A, De Luca A, David L, et al. (2009) CDX2 expression is induced by Helicobacter pylori in AGS cells. Scand J Gastroenterol 44: 124-125.
61. Ikeda H, Sasaki M, Ishikawa A, Sato Y, Harada K, et al. (2007) Interaction of Toll-like receptors with bacterial components induces expression of CDX2 and MUC2 in rat biliary epithelium in vivo and in culture. Lab Invest 87: 559-571.
62. Nguyen H T, Dalmasso G, Powell K R, Yan Y, Bhatt S, et al. (2009) Pathogenic bacteria induce colonic PepT1 expression: an implication in host defense response. Gastroenterology 137: 1435-1447 e1431-1432.
63. Dalmasso G, Nguyen H T, Yan Y, Charrier-Hisamuddin L, Sitaraman S V, et al. (2008) Butyrate transcriptionally enhances peptide transporter PepT1 expression and activity. PLoS One 3: e2476.
64. Hammer H F, Santa Ana C A, Schiller L R, Fordtran J S (1989) Studies of osmotic diarrhea induced in normal subjects by ingestion of polyethylene glycol and lactulose. J Clin Invest 84: 1056-1062.
65. Robayo-Torres C C, Quezada-Calvillo R, Nichols B L (2006) Disaccharide digestion: clinical and molecular aspects. Clin Gastroenterol Hepatol 4: 276-287.
66. Flint H J, Duncan S H, Scott K P, Louis P (2007) Interactions and competition within the microbial community of the human colon: links between diet and health. Environ Microbiol 9: 1101-1111.
67. O'Keefe S J (2008) Nutrition and colonic health: the critical role of the microbiota. Curr Opin Gastroenterol 24: 51-58.
68. Sonnenburg E D, Zheng H, Joglekar P, Higginbottom S K, Firbank S J, et al. (2010) Specificity of polysaccharide use in intestinal bacteroides species determines diet-induced microbiota alterations. Cell 141: 1241-1252.
69. Finegold S M, Dowd S E, Gontcharova V, Liu C, Henley K E, et al. (2010) Pyrosequencing study of fecal microflora of autistic and control children. Anaerobe 16: 444-453.
70. Gillevet P, Sikaroodi M, Keshavarzian A, Mutlu E A (2010) Quantitative assessment of the human gut microbiome using multitag pyrosequencing. Chem Biodivers 7: 1065-1075.
71. Marteau P, Pochart P, Dore J, Bera-Maillet C, Bernalier A, et al. (2001) Comparative study of bacterial groups within the human cecal and fecal microbiota. Appl Environ Microbiol 67: 4939-4942.
72. Momozawa Y, Deffontaine V, Louis E, Medrano J F (2011) Characterization of Bacteria in Biopsies of Colon and Stools by High Throughput Sequencing of the V2 Region of Bacterial 16S rRNA Gene in Human. PLoS One 6: e16952.
73. Ben-Amor K, Heilig H, Smidt H, Vaughan E E, Abee T, et al. (2005) Genetic diversity of viable, injured, and dead fecal bacteria assessed by fluorescence-activated cell sorting and 16S rRNA gene analysis. Appl Environ Microbiol 71: 4679-4689.
74. Louis P, Young P, Holtrop G, Flint H J (2010) Diversity of human colonic butyrate-producing bacteria revealed by analysis of the butyryl-CoA:acetate CoA-transferase gene. Environ Microbiol 12: 304-314.
75. Duncan S H, Louis P, Thomson J M, Flint E U (2009) The role of pH in determining the species composition of the human colonic microbiota. Environ Microbiol 11: 2112-2122.
76. Ley R E, Turnbaugh P J, Klein S, Gordon J I (2006) Microbial ecology: human gut microbes associated with obesity. Nature 444: 1022-1023.
77. Ley R E, Backhed F, Turnbaugh P, Lozupone C A, Knight R D, et al. (2005) Obesity alters gut microbial ecology. Proc Natl Acad Sci USA 102: 11070-11075.
78. Collins S M, Bercik P (2009) The relationship between intestinal microbiota and the central nervous system in normal gastrointestinal function and disease. Gastroenterology 136: 2003-2014.
79. Gupta G, Gelfand J M, Lewis J D (2005) Increased risk for demyelinating diseases in patients with inflammatory bowel disease. Gastroenterology 129: 819-826.
80. Fullwood A, Drossman D A (1995) The relationship of psychiatric illness with gastrointestinal disease. Annu Rev Med 46: 483-496.
81. Lossos A, River Y, Eliakim A, Steiner I (1995) Neurologic aspects of inflammatory bowel disease. Neurology 45: 416-421.
82. Bushara K O (2005) Neurologic presentation of celiac disease. Gastroenterology 128: S92-97.
83. Turnbaugh P J, Ley R E, Mahowald M A, Magrini V, Mardis E R, et al. (2006) An obesity-associated gut microbiome with increased capacity for energy harvest. Nature 444: 1027-1031.
84. Sudo N, Sawamura S, Tanaka K, Aiba Y, Kubo C, et al. (1997) The requirement of intestinal bacterial flora for the development of an IgE production system fully susceptible to oral tolerance induction. J Immunol 159: 1739-1745.
85. Sudo N, Chida Y, Aiba Y, Sonoda J, Oyama N, et al. (2004) Postnatal microbial colonization programs the hypothalamic-pituitary-adrenal system for stress response in mice. J Physiol 558: 263-275.
86. Hornig M, Briese T, Buie T, Bauman M L, Lauwers G, et al. (2008) Lack of association between measles virus vaccine and autism with enteropathy: a case-control study. PLoS One 3: e3140.
87. Williams B L, Yaddanapudi K, Hornig M, Lipkin W I (2007) Spatiotemporal analysis of purkinje cell degeneration relative to parasagittal expression domains in a model of neonatal viral infection. J Virol 81: 2675-2687.
88. Williams B L, Yaddanapudi K, Kirk C M, Soman A, Hornig M, et al. (2006) Metallothioneins and zinc dysregulation contribute to neurodevelopmental damage in a model of perinatal viral infection. Brain Pathol 16: 1-14.

89. Williams B L, Lipkin W I (2006) Endoplasmic reticulum stress and neurodegeneration in rats neonatally infected with borna disease virus. J Virol 80: 8613-8626.
90. Buning C, Ockenga J, Kruger S, Jurga J, Baier P, et al. (2003) The C/C(-13910) and G/G(-22018) genotypes for adult-type hypolactasia are not associated with inflammatory bowel disease. Scand J Gastroenterol 38: 538-542.
91. Hamady M, Walker J J, Harris J K, Gold N J, Knight R (2008) Error-correcting barcoded primers for pyrosequencing hundreds of samples in multiplex. Nat Methods 5: 235-237.
92. Frank D N, St Amand A L, Feldman R A, Boedeker E C, Harpaz N, et al. (2007) Molecular-phylogenetic characterization of microbial community imbalances in human inflammatory bowel diseases. Proc Natl Acad Sci USA 104: 13780-13785.
93. Guo X, Xia X, Tang R, Zhou J, Zhao H, et al. (2008) Development of a real-time PCR method for Firmicutes and Bacteroidetes in faeces and its application to quantify intestinal population of obese and lean pigs. Lett Appl Microbiol 47: 367-373.
94. Huse S M, Huber J A, Morrison H G, Sogin M L, Welch D M (2007) Accuracy and quality of massively parallel DNA pyrosequencing. Genome Biol 8: R143.
95. Schloss P D, Westcott S L, Ryabin T, Hall J R, Hartmann M, et al. (2009) Introducing mothur: open-source, platform-independent, community-supported software for describing and comparing microbial communities. Appl Environ Microbiol 75: 7537-7541.

Example 4

Application of *Sutterella*-SpecificPCR-based Methods for Detection, Quantitation, and Phylogenetic Characterization of *Sutterella* Species Abstract. Gastrointestinal disturbances are commonly reported in children with autism and can be associated with compositional changes in intestinal bacteria. In a previous report we surveyed intestinal microbiota in ileal and cecal biopsies from children with autism and gastrointestinal dysfunction (AUT-GI) and children with only gastrointestinal dysfunction (Control-GI). The results demonstrated the presence of members of the family Alcaligenaceae in some AUT-GI children, while no Control-GI children had Alcaligenaceae sequences. Here we demonstrate that increased levels of Alcaligenaceae in intestinal biopsies from AUT-GI children result from the presence of high levels of members of the genus *Sutterella*. We also report the first *Sutterella*-specific polymerase chain reaction assays for detecting, quantitating, and genotyping *Sutterella* species in biological and environmental samples. *Sutterella* 16S rRNA gene sequences were found in 12 of 23 AUT-GI children but in none of 9 Control-GI children. Phylogenetic analysis revealed a predominance of either the species *Sutterella wadsworthensis* or *Sutterella stercoricanis* in 11 of the individual *Sutterella*-positive AUT-GI patients; in one AUT-GI patient, *Sutterella*-sequences were obtained that could not be given a species level classification based on the 16S rRNA gene sequences of known *Sutterella* isolates. Western immunoblots revealed plasma IgG or IgM antibody reactivity to *Sutterella wadsworthensis* antigens in 11 AUT-GI patients, 8 of whom were also PCR-positive, indicating the presence of an immune response to *Sutterella* in some children.

Autism spectrum disorders affect approximately 1% of the population. Many children with autism have gastrointestinal (GI) disturbances that can complicate clinical management and contribute to behavioral problems. Understanding the molecular and microbial underpinnings of these GI issues is of paramount importance for elucidating pathogenesis, rendering diagnosis, and administering informed treatment. An association between high levels of intestinal, mucoepithelial-associated *Sutterella* species and GI disturbances in children with autism is described. These findings elevate this little-recognized bacterium to the forefront by demonstrating that *Sutterella* is a major component of the microbiota in over half of AUT-GI children and is absent in Control-GI children evaluated in this study. Furthermore, these findings bring into question the role *Sutterella* plays in the human microbiota in health and disease. With the *Sutterella*-specific molecular assays described herein, some of these questions are addressed.

Introduction

Autism spectrum disorders (ASD) are pervasive developmental disorders that depend on triadic presentation of social abnormalities, communication impairments, and stereotyped and repetitive behaviors for diagnosis (DSM-IV-TR criteria, American Psychiatric Association, 2000). Gastrointestinal (GI) symptoms are commonly reported in children with autism and can correlate with autism severity (D1, D2). Intestinal disturbances in autism have been associated with macroscopic and histological abnormalities, altered inflammatory parameters, and various functional disturbances (D3-9).

In a previous study, we showed that a complex interplay exists between human intestinal gene expression for disaccharidases and hexose transporters and compositional differences in the mucoepithelial microbiota of children with autism and gastrointestinal disease (AUT-GI children) compared to children with GI disease but typical neurological status (Control-GI children). Significant compositional changes in Bacteroidetes, Firmicute/Bacteroidete ratios, and Betaproteobacteria in AUT-GI intestinal biopsies were reported (D10). Although others have demonstrated changes in fecal bacteria of children with autism (D2, D11-15), the study differed from these by investigating mucoepithelial microbiota (D10). The GI microbiota plays an essential role in physiological homeostasis in the intestine and periphery, including maintaining resistance to infection, stimulating immunological development, and perhaps even influencing brain development and behavior (D16-19). Thus, disruption of the balanced communication between the microbiota and the human host could have profound effects on human health.

In the previous metagenomic study, sequences were found to correspond to members of the family Alcaligenaceae in the class Betaproteobacteria that were present in ileal and cecal biopsies from 46.7% (7/15) of AUT-GI children. Alcaligenaceae sequences were completely absent from biopsies of Control-GI children (D10). Members of the family Alcaligenaceae inhabit diverse habitats, ranging from humans and animals to soil (D20). Several members of Alcaligenaceae cause clinically relevant infections or are suspected opportunistic pathogens in humans and animals, including members of the genus *Bordetella* (the human respiratory pathogens, *B. pertussis* and *B. parapertussis*; the mammalian respiratory pathogen *B. bronchiseptica*; and the poultry respiratory pathogen, *B. avium*); a member of the genus *Alcaligenes* (the human opportunistic pathogen *A. faecalis*); members of the genus *Achromobacter* (the human opportunistic pathogens *A. xylosoxidans* and *A. piechaudii*), members of the genus *Oligella* (the potential opportunistic genitourinary species *O. urethralis* and *O. ureolytica*); a member of the genus *Taylorella* (the equine urogenital pathogen, *T. equigenitalis*); and a member of the genus *Pelistega* (the pigeon respiratory pathogen, *P. europaea*) (D20).

In some cases the pathogenic potential of Alcaligenaceae members is unclear. The genus *Sutterella* represents one such Alcaligenaceae member. Members of the genus *Sutterella* are anaerobic, bile-resistant, asaccharolytic, Gram-negative, short rods (D21). Members of the genus *Sutterella* have been isolated from human infections below the diaphragm (D22, D23). *Sutterella* 16S rRNA gene sequences have also been identified in intestinal biopsies and fecal samples from individuals with Crohn's disease and ulcerative colitis (D24, D25). Whether the presence of *Sutterella* species at sites of human infection and inflammation represents cause or consequence, or whether *Sutterella* is a normal part of the microbiota in some individuals, remains unclear. The dearth of knowledge concerning the epidemiology and pathogenic potential of *Sutterella* derives in part from the lack of specific assays to detect and characterize members of this genus.

Alcaligenaceae sequences identified were further characterized in AUT-GI children and describe PCR assays for detection, quantitation, and genotyping of *Sutterella* as well as serological assays for detection of immunological responses to *Sutterella*.

Results

High levels of *Sutterella* in a subset of AUT-GI patients identified by pyrosequencing: Previous pyrosequencing results (D10) demonstrated a high abundance of sequences from the family Alcaligenaceae in nearly half of AUT-GI children (Patients #1-15) and the absence of corresponding sequences in Control-GI children (Patients #16-22), and prompted a more detailed investigation of these taxa of bacteria. Genus level analysis of pyrosequencing reads revealed that all sequences of Alcaligenaceae found in AUT-GI patients' biopsies were classified as members of the genus *Sutterella*. The average confidence estimate of all genus level, RDP (Ribosomal Database Project)-classified *Sutterella*-sequences was high (99.1%), with the majority of sequences classified at 100% confidence.

Comparison of *Sutterella* abundance from pyrosequencing reads revealed significant increases in *Sutterella* in the ilea (FIG. 8A: Mann-Whitney, tied p-value=0.022) and ceca (FIG. 8B: Mann-Whitney, tied p-value=0.037) of AUT-GI children compared to Control-GI children. Individual analysis of AUT-GI patients revealed that 46.7% (7/15) of AUT-GI patients (Patients # 1, 3, 5, 7, 10, 11, 12) had high levels of *Sutterella* 16S rRNA gene sequences in both the ileum (FIG. 8C and Table 19) and cecum (FIGS. 8D and 36 and Table 19). *Sutterella*-sequences were absent from all Control-GI samples (Patients # 16-22). In those seven AUT-GI patients with *Sutterella*-sequences, ileal *Sutterella*-sequence abundance ranged from 1.7 to 6.7% of total bacterial reads (FIG. 8C and Table 19). For the same patients, cecal *Sutterella*-sequence abundance ranged from 2.0 to 7.0% of total bacterial reads (FIGS. 8D and 36 and Table 19).

TABLE 19

Summary of total bacteria, Betaproteobacteria, and *Sutterella* sequences obtained by 16S rRNA gene (V2-region) pyrosequencing from ileal and cecal biopsies of AUT-GI and Control-GI children.

| Patient # | AUT/Control | # of Total Bacteria Reads-Ileum | # of Total Bacteria Reads-Cecum | # of Betaproteobacteria Reads-Ileum |
|---|---|---|---|---|
| 1 | AUT-GI | 11,881 | 13,032 | 706 |
| 2 | AUT-GI | 13,734 | 7,647 | 3627 |
| 3 | AUT-GI | 11,434 | 10,147 | 536 |
| 4 | AUT-GI | 12,756 | 11,779 | 400 |
| 5 | AUT-GI | 10,708 | 10,502 | 647 |
| 6 | AUT-GI | 14,739 | 11,075 | 137 |
| 7 | AUT-GI | 11,941 | 11,246 | 209 |
| 8 | AUT-GI | 11,348 | 11,754 | 27 |
| 9 | AUT-GI | 12,320 | 10,661 | 262 |
| 10 | AUT-GI | 12,483 | 12,295 | 501 |
| 11 | AUT-GI | 11,211 | 12,436 | 800 |
| 12 | AUT-GI | 11,055 | 11,103 | 434 |
| 13 | AUT-GI | 10,420 | 10,670 | 171 |
| 14 | AUT-GI | 12,217 | 11,012 | 123 |
| 15 | AUT-GI | 12,002 | 12,561 | 138 |
| 16 | Control-GI | 13,758 | 13,630 | 129 |
| 17 | Control-GI | 12,246 | 14,956 | 147 |
| 18 | Control-GI | 11,888 | 14,330 | 315 |
| 19 | Control-GI | 11,290 | 10,136 | 377 |
| 20 | Control-GI | 14,844 | 11,794 | 134 |
| 21 | Control-GI | 13,308 | 11,567 | 145 |
| 22 | Control-GI | 13,460 | 10,143 | 131 |

| Patient # | # of Betaproteobacteria Reads-Cecum | # of *Sutterella* Reads-Ileum | *Sutterlla*-Ileum (% of Total Bacteria) | *Sutterella*-Ileum (% of Betaproteobacteria) |
|---|---|---|---|---|
| 1 | 535 | 534 | 4.5 | 75.6 |
| 2 | 632 | 0 | 0 | 0 |
| 3 | 428 | 503 | 4.4 | 93.8 |
| 4 | 132 | 0 | 0 | 0 |
| 5 | 535 | 581 | 5.4 | 89.8 |
| 6 | 36 | 0 | 0 | 0 |
| 7 | 224 | 201 | 1.7 | 96.2 |
| 8 | 80 | 0 | 0 | 0 |
| 9 | 404 | 0 | 0 | 0 |
| 10 | 478 | 490 | 3.9 | 97.8 |
| 11 | 903 | 747 | 6.7 | 93.4 |
| 12 | 444 | 408 | 3.7 | 94.0 |
| 13 | 619 | 0 | 0 | 0 |
| 14 | 105 | 0 | 0 | 0 |
| 15 | 39 | 0 | 0 | 0 |
| 16 | 136 | 0 | 0 | 0 |
| 17 | 116 | 0 | 0 | 0 |
| 18 | 404 | 0 | 0 | 0 |
| 19 | 151 | 0 | 0 | 0 |
| 20 | 58 | 0 | 0 | 0 |
| 21 | 34 | 0 | 0 | 0 |
| 22 | 85 | 0 | 0 | 0 |

| Patient # | # of *Sutterella* Reads-Cecum | *Sutterella*-Cecum (% of Total Bacteria) | *Sutterella*-Cecum (% of Betaproteobacteria) |
|---|---|---|---|
| 1 | 520 | 4.0 | 97.2 |
| 2 | 0 | 0 | 0 |
| 3 | 403 | 4.0 | 94.2 |
| 4 | 0 | 0 | 0 |
| 5 | 498 | 4.7 | 93.1 |
| 6 | 0 | 0 | 0 |
| 7 | 220 | 2.0 | 98.2 |
| 8 | 0 | 0 | 0 |
| 9 | 0 | 0 | 0 |
| 10 | 459 | 3.7 | 96.0 |
| 11 | 870 | 7.0 | 96.3 |
| 12 | 409 | 3.7 | 92.1 |
| 13 | 0 | 0 | 0 |
| 14 | 0 | 0 | 0 |
| 15 | 0 | 0 | 0 |
| 16 | 0 | 0 | 0 |
| 17 | 0 | 0 | 0 |
| 18 | 0 | 0 | 0 |
| 19 | 0 | 0 | 0 |
| 20 | 0 | 0 | 0 |
| 21 | 0 | 0 | 0 |
| 22 | 0 | 0 | 0 |

To put the levels of *Sutterella* in these patients into perspective, the abundance of all ileal and cecal genus level classifications were ranked from pyrosequencing results. In the ileum, *Sutterella*-sequences represented the 4$^{th}$ most abundant genera for patient #1, the 6$^{th}$ most abundant genera for patient #3, the 5$^{th}$ most abundant genera for patient #5, the 5$^{th}$ most abundant genera for patient #7, the 3$^{rd}$ most abundant genera for patient #10, the 8$^{th}$ most abundant genera for patient #11, and the 5$^{th}$ most abundant genera for patient #12 (FIG. 44 and FIG. 45). Similar rankings were obtained in the cecum of these patients.

*Sutterella*-sequences represented the majority of sequences present in the class Betaproteobacteria in these seven AUT-GI patients. In ileal biopsies from the seven AUT-GI patients with *Sutterella*-sequences, *Sutterella*-sequences accounted for 75.6% to 97.8% of all Betaproteobacteria sequences (FIG. 8E and Table 19). In cecal biopsies, *Sutterella*-sequences accounted for 92.1% to 98.2% of all Betaproteobacteria sequences (FIG. 8F and Table 19).

OTU and sequence analysis of *Sutterella*-sequences in AUT-GI children: OTU (Operational Taxonomic Unit) analysis of V2 pyrosequencing reads in ileum (FIG. 46A) and cecum (FIG. 46B) revealed that sequences from patients #1, 3, 10, 11, and 12 clustered together with OTU 2 containing the majority of *Sutterella*-sequences, and patients #5 and 7 clustered together with OTU 1 containing the majority of *Sutterella*-sequences. OTU 2 accounted for 87% and 84% for patient #1, 85% and 87% for patient #3, 66% and 66% for patient #10, 87% and 85% for patient #11, and 81% and 81% for patient #12 of all *Sutterella*-sequences obtained by pyrosequencing of the 16S rRNA gene in ileum and cecum, respectively (FIG. 37). OTU 1 accounted for 88% and 86% for patient #5 and 88% and 83% for patient #7 of all *Sutterella* sequences obtained by pyrosequencing of the V2 region of the 16S rRNA gene in ileum and cecum, respectively (FIG. 37). Subdominant OTUs can represent true phylotypes, but could also arise from PCR or sequencing artifacts. The analysis was focused on those OTUs containing the majority of *Sutterella*-sequences, namely OTU 1 and OTU 2.

The representative sequences from OTU 1 and OTU 2 were aligned and used for phylogenetic analysis (FIG. 47. The representative sequence from OTU 1 was phylogenetically most closely related to the species *S. wadsworthensis*; the representative sequence from OTU 2 was most closely related to *S. stercoricanis*. Although some branches in the tree are clearly differentiated by high bootstrap values, others are differentiated poorly by low bootstrap values. Furthermore, members of the genus *Comamonas* and *Burkholderia* were grouped with members of the genus *Sutterella*. This indicates that sequences from the V2 region alone can be insufficient for accurate species level phylogenetic analysis of *Sutterella*-sequences.

Confirmation and quantitation of *Sutterella*-sequences using new PCR assays: To independently verify V2 pyrosequencing results for *Sutterella, Sutterella*-specific PCR assays were designed that could be used in both conventional and real-time PCR, using primers that amplify a 260bp region spanning the V6 to V8 regions of the 16S rRNA gene (SuttFor and SuttRev primers) (FIG. 38, FIG. 9, FIG. 10A-B). Conventional PCR analysis using DNA from each of 4 ileal and 4 cecal biopsies per patient showed that the same individuals identified as having high levels of *Sutterella* by V2 pyrosequencing (Patients #1, 3, 5, 7, 10, 11, 12) were also positive by the novel V6-V8 *Sutterella*-specific PCR (FIG. 39A). All 4 biopsies from ileum and cecum, in all seven *Sutterella*-positive patients, showed *Sutterella* products. A single 260 by product was observed in positive amplifications, and non-specific products were never observed. No products were observed in any Control-GI patients that were evaluated by pyrosequencing (Patients #16-22), the AUT-GI patients that were negative for *Sutterella* sequences by V2 pyrosequencing (Patients #2, 4, 6, 8, 9, 13, 14, 15), or water/reagent controls (FIG. 39A). Furthermore, the positive control (DNA from a cultured *S. wadsworthensis* isolate) was positive by PCR. In addition to those patients evaluated by pyrosequencing, ileal and cecal biopsies were assessed from eight additional male AUT-GI (Patients #23a-30a) and two additional male Control-GI (Patients #31a and 32a) children using the V6-V8 *Sutterella* PCR. Of these additional samples, 5 of the 8 AUT-GI patients were positive for *Sutterella* in ileal and cecal biopsies (Patients #24a, 25a, 27a, 28a, and 29a). All biopsies from the two additional Control-GI patients were PCR-negative (Patients #31a and 32a). In summary, whereas 12 of 23 (52%) AUT-GI children were PCR-positive for *Sutterella*, 0 of the 9 Control-GI children were PCR-positive for *Sutterella*.

In addition, the broadly conserved, pan-bacterial primer 515For was used in combination with the SuttRev primer in conventional PCR assays (FIG. 39B). These primers amplify a 715 by region of the 16S rRNA gene from conserved region 4 (C4) to variable region 8 (V8) (see FIG. 38A). Results of the C4-V8 amplification were identical to the V6-V8 assay. All products were confirmed to represent *Sutterella* by sequencing of V6-V8 and C4-V8 products. These results indicate that the SuttRev primer is sufficient to confer specificity for *Sutterella* amplification.

In addition, *Sutterella* 16S rRNA gene sequences were quantified in biopsies from AUT-GI and Control-GI patients using real-time PCR (FIG. 10A-B). Real-time PCR analysis using the SuttFor and SuttRev (V6-V8) primers and a high coverage Taqman probe revealed similar results to conventional PCR assays. By real-time PCR, *Sutterella* was detected in patients #1, 3, 5, 7, 10, 11, 12, 24a, 25a, 27a, 28a, and 29a (FIG. 40), consistent with both pyrosequencing and conventional PCR results. *Sutterella* was undetectable in all Control-GI and *Sutterella*-negative AUT-GI patients' samples. Mean *Sutterella* copy numbers were high in both the ileum and cecum [in the range of $10^3$ to $10^5$ copies] of *Sutterella*-positive patients.

Phylogenetic analysis of *Sutterella*-sequences obtained by novel PCR assays: The predominant *Sutterella*-sequence from the ileum and cecum of each patient was determined following alignment of all V6-V8 sequences obtained by library cloning of products. This analysis revealed that the predominant sequences obtained in ileal biopsies were identical to the predominant sequences in cecal biopsies from each individual patient. Thus, a single predominant sequence was further assessed for each patient.

Phylogenetic analysis of the predominant V6-V8 sequences obtained by PCR revealed that the dominant *Sutterella* species found in patients #1, 3, 10, 11, 12, 24a, 27a, and 29a were most closely associated with the isolates *S. stercoricanis* and *Parasutterella secunda*; the dominant V6-V8 *Sutterella*-sequences found in patients #5, 7, and 25a were most closely associated with isolates of *S. wadsworthensis* (FIG. 48). Sequences from patient #28a were most closely associated with *Sutterella* sp. YIT 12072. Thus, sequences from patients #5 and 7. grouped with *S. wadsworthensis* isolates using both the V2 pyrosequencing reads and the V6-V8 sequences obtained by PCR, while sequences from patients #1, 3, 10, 11, and 12 grouped with *S. stercoricanis* using both the V2 pyrosequencing reads and the V6-V8 sequences obtained by PCR. However, as was the case from phylogenetic analysis of V2 pyrosequencing, bootstrap values were low at many branches, indicateing that neither the V2 nor V6-V8 regions provide sufficient information for accurate species level differentiation. Furthermore, members of the genus *Sutterella* did not all group together based on the V6-V8 region sequences, with *Parasutterella secunda, S. stercoricanis, S. sanguinus*, and *S. morbirenis* being more closely associated with other Alcaligenaceae and Burkholderiales members.

480 sequences (40 sequences per patient; 20 ileal sequences and 20 cecal sequences) obtained from clone libraries of C4-V8 products were analyzed from the 12 *Sutterella*-positive patients (FIG. 41). No sequences were obtained from any genus other than *Sutterella* from any cloned PCR products. The majority or all of the C4-V8 sequences from patients #1, 3, 10, 11, 12, 24a, 27a, and 29a were most closely matched with *S. stercoricanis*, the majority or all of the C4-V8 sequences obtained from patients #5, 7, and 25a matched most closely with *S. wadsworthensis*, and all sequences obtained from patient #28a matched most closely with *Sutterella* sp. YIT 12072. It was evident from this analysis that although one species predominated in each patient, mixed populations were detected in many patients. Most individuals with mixed populations harbored sequences of *S. wadsworthensis* and *S. stercorcanis*. Patient #24a had species matches for *S. stercoricanis, S. wadsworthensis*, and *S. parvirubra*.

To determine the accuracy of the C4-V8 region for confirmation of species level classification, the predominant C4-V8 16S rRNA gene sequences obtained from the ileum and cecum of each patient were analyzed. Similar to the results obtained with the V6-V8 region, this analysis revealed that the predominant *Sutterella* 16S rRNA gene sequences identified in ileal biopsies were identical to the predominant *Sutterella*-sequences in cecal biopsies for each of the individual patients. Thus, a single predominant sequence was further assessed for each patient.

Alignment of the predominant C4-V8 sequence from each patient revealed that patients #1 and 24a had identical predominant sequences, but that these were distinct from all other patients; patients #3, 10, 11, 12, 27a, and 29a had identical sequences, distinct from all other patients; patients #5, 7, and 25a had identical sequences that were distinct from all other patients; and patient #28a had a unique sequence (FIG. 49).

Comparison of percent sequence similarity between these groups (Table 17) revealed 99.9% similarity between sequences of patients #1 and 24a and those of patients #3, 10, 11, 12, 27a, and 29a. This value is above the cut-off value of 97% similarity, commonly applied for bacterial species definition (D26), indicateing that the predominant sequences from these two groups are likely the same species.

TABLE 17

Sequence similarity between 16S rRNA gene (C4-V8 region) of *Sutterella* from AUT-GI children and *Sutterella* isolates.

| % Similarity | Patients 1, 24a | Patients 3, 10, 11, 12, 27a, 29a | Patients 5, 7, 25a | Patient 28a | *Sutterella stercoricanis* (AJ566849) | *Sunerella wadsworthensis* (GU585669) | *Sutterella parvirubra* (AB300989) | *Sutterella sanguinus* (AJ748647) | *Sutterella* sp. YIT 12072 (AB491210) |
|---|---|---|---|---|---|---|---|---|---|
| Patients 1, 24a | — | 99.9% | 94.8% | 93.8% | 98.5% | 94.8% | 95.4% | 96.3% | 93.2% |
| Patients 3, 10, 11, 12, 27a, 29a | | — | 94.7% | 93.6% | 98.4% | 94.7% | 95.4% | 96.4% | 93.3% |
| Patients 5, 7, 25a | | | — | 92.8% | 94.7% | 100% | 96.6% | 93.6% | 92.9% |
| Patient 28a | | | | — | 93.0% | 92.8% | 93.6% | 92.0% | 95.3% |
| *Sutterella stercoricanis* (AJ566849) | | | | | — | 94.7% | 94.7% | 96.6% | 93.2% |
| *Sutterella wadsworthensis* (GU585669) | | | | | | — | 96.6% | 93.6% | 92.9% |
| *Sutterella parvirubra* (AB300989) | | | | | | | — | 95.0% | 92.6% |
| *Sutterella sanguinus* (AJ748647) | | | | | | | | — | 92.2% |
| *Sutterella* sp. YIT 12072 (AB491210) | | | | | | | | | — |

Highest sequence similarities are shown in bold.

The predominant sequences from patients #1 and 24a and patients #3, 10, 11, 12, 27a, and 29a had the highest percent similarity to the isolate *S. stercorcanis* (98.5% similarity and 98.4% similarity, respectively) (Table 17). The percent similarity of sequences from patients #1, 24a, 3, 10, 11, 12, 27a, and 29a were below 97% compared to the other *Sutterella* isolates, indicateing that the predominant species in these patients is likely *S. stercorcanis*. In addition, the 16S rRNA gene sequence from patients #1 and 24a shared 100% similarity with 16S rRNA gene sequences from uncultured bacteria in genbank, such as those derived from intestinal biopsies from an ulcerative colitis patient (i.e., Accession FJ512128) (D27) and mucosal biopsies from the intestinal pouch of a familial adenomatous polyposis patient (i.e., Accession GQ159316). Similarly, the sequences from patients #3, 10, 11, 12, 27a, and 29a shared 100% similarity with 16S rRNA gene sequences from uncultured bacteria in genbank, including sequences derived from intestinal biopsies from a patient with ulcerative colitis (i.e., Accession 512152) (D27) and fecal samples from bovines (i.e., Accession FJ682648) (D28).

Sequences from patients #5, 7, and 25a had 100% sequence similarity to *S. wadsworthensis* and below 97% sequence similarity to all other *Sutterella* isolates (Table 17). Thus, the predominant sequences from patients #5, 7, and 25a are likely *S. wadsworthensis*. The sequence from patients #5, 7, and 25a also shared 100% sequence similarity to 16S rRNA sequences in genbank, such as those derived from intestinal biopsies from an ulcerative colitis patient (i.e., Accession FJ509042) (D27).

The unique sequence found in patient #28a matched most closely with the isolate, *Sutterella* sp. YIT 12072; however, the percent similarity was only 95.3% (Table 17). Thus, based on sequence analysis alone, *Sutterella*-sequences from patient #28a cannot be classified as *Sutterella* sp. YIT 12072 or any of the other known isolates. Despite the closest association of sequences from patient #28a with the sequence of the isolate *Sutterella* sp. YIT 12072, the 16S rRNA gene sequence from patient #28a shared 100% similarity with 16S rRNA gene sequences from uncultured bacteria in genbank that were derived from intestinal biopsies from a Crohn's disease'patient (i.e., Accession FJ503635) (D27), human skin popliteal fossa swab (i.e., Accession HM305996), and feces from a 95-year old woman (i.e., Accession EF401376) (D29). Thus, the 16S rRNA gene sequences from patient #28a and identical genbank sequences likely represent an uncharacterized species of *Sutterella*.

Phylogenetic analysis of the predominant sequences obtained from patient biopsies using the C4-V8 PCR assay revealed high bootstrap values at most branches and good grouping of members of the genus *Sutterella* from other Alcaligenaceae family members and other Burkholderiales order members (FIG. 42). Thus, sequences obtained by C4-V8 PCR can be used for accurate species level classification of *Sutterella*-sequences. This tree demonstrates that sequences from patients #1, 24a, 3, 10, 11, 12, 27a, and 29a grouped most closely with *S. stercoricanis* (supported by a bootstrap resampling value of 92%); sequences from patients #5, 7, and 25a grouped most closely with *S. wadsworthensis* (supported by a bootstrap resampling value of 99%); and sequences from patient #28a grouped most closely with the isolate *Sutterella* sp. YIT 12072 (supported by a bootstrap resampling value of 97%) but formed a distinct phylogenetic lineage.

AUT-GI plasma antibodies bind to *S. wadsworthensis* proteins: It was also determined whether systemic antibody responses to *Sutterella* were present in this cohort. The antigens used for western blot analysis were whole protein lysates from cultured *S. wadsworthensis* containing a wide range of proteins, as observed on Coommassie-stained SDS-polyacrylamide gels. Individual patient's plasma was assessed for IgG (FIG. 43A) and IgM (FIG. 43B) antibody immunoreactivity against the bacterial antigens. Immunoreactive bands were visible for 11 out of 23 (48%) AUT-GI patients. In ten AUT-GI children the immunoreactive antibodies were IgG (FIG. 43A); one (patient #26a) had IgM antibodies (FIG. 43B). In contrast, only 1 of the 9 (11%) Control-GI patients (patient #21) had weak immunoreactivity to 84-kDa and 41-kDa *Sutterella* proteins. A total of 11 distinct immunoreactive protein bands were identified, based on size (104-, 89-, 84-, 62-, 56-, 50-, 48-, 44-, 41-, 30-, and 27-kDa). AUT-GI patients #1 and #5 (both positive by PCR) had the most immunoreactive protein bands with four protein bands in common (89-, 62-, 56-, and 41-kDa). The 89-kDa band was detected by IgG or IgM antibodies in seven AUT-GI patients. The 56-, 41-, and 30-kDa bands were detected by IgG antibodies in each of three patients. The other bands (104-, 84-, 62-, 50-, 48-, and 44-kDa) were less frequent.

Of the 12 AUT-GI patients that were PCR-positive for *Sutterella*, 8 (66.7%) had plasma IgG antibodies against *S. wadsworthensis* proteins (patients #1, 3, 5, 7, 10, 11, 24a, and 25a). Three AUT-GI patients (patients #4, 23a, and 26a) had IgG or IgM antibodies against *S. wadsworthensis* proteins, but were PCR-negative. In total, 15 out of 23 (65.2%) AUT-GI children had evidence of *Sutterella* either by PCR or serology (Table 18).

TABLE 18

Summary of PCR assays and western immunoblot analysis.

| Patient | AUT/Control | PCR | IgG | MW of Bands | IgM | MW of Bands | Any Ig Positive | Any Positive |
|---|---|---|---|---|---|---|---|---|
| 1 | AUT-GI | + | ++ | 89, 62, 56, 41 | − | − | Yes | Yes |
| 2 | AUT-GI | − | − | − | − | − | No | No |
| 3 | AUT-GI | + | + | 30 | − | − | Yes | Yes |
| 4 | AUT-GI | − | ++ | 89 | − | − | Yes | Yes |
| 5 | AUT-GI | + | ++ | 89, 62, 56, 48, 44, 41 | − | − | Yes | Yes |
| 6 | AUT-GI | − | − | − | − | − | No | No |
| 7 | AUT-GI | + | ++ | 50, 44 | − | − | Yes | Yes |
| 8 | AUT-GI | − | − | − | − | − | No | No |
| 9 | AUT-GI | − | − | − | − | − | No | No |
| 10 | AUT-GI | + | ++ | 30 | − | − | Yes | Yes |
| 11 | AUT-GI | + | + | 89, 48 | − | − | Yes | Yes |
| 12 | AUT-GI | + | − | − | − | − | No | Yes |
| 13 | AUT-GI | − | − | − | − | − | No | No |
| 14 | AUT-GI | − | − | − | − | − | No | No |
| 15 | AUT-GI | − | − | − | − | − | No | No |
| 23a | AUT-GI | − | ++ | 104, 30, 27 | − | − | Yes | Yes |
| 24a | AUT-GI | + | + | 89 | − | − | Yes | Yes |
| 25a | AUT-GI | + | ++ | 89, 56 | − | − | Yes | Yes |
| 26a | AUT-GI | − | − | − | ++ | 89 | Yes | Yes |
| 27a | AUT-GI | + | − | − | − | − | No | Yes |
| 28a | AUT-GI | + | − | − | − | − | No | Yes |
| 29a | AUT-GI | + | − | − | − | − | No | Yes |
| 30a | AUT-GI | − | − | − | − | − | No | No |
| 16 | Control-GI | − | − | − | − | − | No | No |
| 17 | Control-GI | − | − | − | − | − | No | No |
| 18 | Control-GI | − | − | − | − | − | No | No |
| 19 | Control-GI | − | − | − | − | − | No | No |
| 20 | Control-GI | − | − | − | − | − | No | No |
| 21 | Control-GI | − | + | 84, 41 | − | − | Yes | Yes |
| 22 | Control-GI | − | − | − | − | − | No | No |
| 31a | Control-GI | − | − | − | − | − | No | No |

TABLE 18-continued

Summary of PCR assays and western immunoblot analysis.

| Patient | AUT/Control | PCR | IgG | MW of Bands | IgM | MW of Bands | Any Ig Positive | Any Positive |
|---|---|---|---|---|---|---|---|---|
| 32a | Control-GI | – | – | – | – | – | No | No |
|  | % AUT-GI+ | 52% | 43% | – | 4% | – | 48% | 65% |
|  | % Control-GI+ | 0% | 11% | – | 0% | – | 11% | 11% |

Discussion

Detection by pyrosequencing of Alcaligenaceae sequences in AUT-GI children (10) was previously reported. More focused analysis revealed that this finding reflects the presence of *Sutterella* species. Whereas 12 of 23 AUT-GI patients (52%) were PCR-positive both in ileum and cecum, 0 of 9 Control-GI children'were PCR-positive for *Sutterella*. *Sutterella* abundance in the seven *Sutterella*-positive AUT-GI patients, assessed by pyrosequencing, ranged from 1 to 7% of total bacterial sequences. Novel real-time PCR assays confirmed high copy numbers of *Sutterella* species in DNA from ileal and cecal biopsies of *Sutterella*-positive patients, with averages ranging from $10^3$ to $10^5$ *Sutterella* 16S rRNA gene copies amplified from only 25 ng of total genomic biopsy DNA.

OTU analysis of V2-region pyrosequencing reads indicated that only two OTUs accounted for the majority of *Sutterella*-sequences in the seven AUT-GI patients that were *Sutterella*-positive by pyrosequencing. Sequencing of PCR products from V6-V8 and C4-V8 *Sutterella*-specific PCR assays corroborated this finding. The analysis also indicates that C4-V8 *Sutterella* products can be accurately classified at the species level. Classification with RDP and phylogenetic analysis of *Sutterella*-sequences obtained from C4-V8 *Sutterella*-specific PCR indicated that the predominant sequences obtained from patients #1, 3, 10, II, 12, 24a, 27a, and 29a were most closely related to the isolate *S. stercoricanis*, supported by a sequence similarity of over 98%. The predominant C4-V8 sequences obtained from patients #5, 7, and 25a were most closely related to the isolate *S. wadsworthensis*, supported by a sequence similarity of 100%. The results indicate that these two species of *Sutterella* are the dominant phylotypes present at high levels in the intestines of AUT-GI children in this cohort. Of the known isolates, the predominant C4-V8 sequence obtained from patient #28a was most closely related to *Sutterella* sp. YIT 12072. However, the low sequence similarity (95.3%) between sequences from patient #28a and *Sutterella* sp. YIT 12072 indicates that these are not likely to be the same species. Sequences from patient #28a did have 100% sequence similarity with uncultured *Sutterella*-sequences in genbank, indicating that this undefined species has been detected previously in human samples using non-specific techniques.

*Sutterella* species have been isolated from human and animal feces (D30-D32) and have also been isolated from human infections below the diaphragm; most often from patients with appendicitis, peritonitis or rectal or perirectal abscesses (D22, D23). *Sutterella*-sequences have been identified in fecal samples and intestinal biopsies from individuals with Crohn's disease and ulcerative colitis but also from apparently healthy adults (D24, D25, D27, D33). Without being bound by theory, *Sutterella* species can contribute to inflammation and infection or are simply normal inhabitants of the human microbiota in some individuals. Even if the latter is the case, the results demonstrate that *Sutterella* is a major component of the mucoepithelial microbiota in some children, accounting for up to 7% of all bacteria. Relative to all other bacterial genera identified in biopsies, *Sutterella* ranged from the $3^{rd}$ to $8^{th}$ most abundant genera in the patients assessed by pyrosequencing. Only the most abundant Bacteroidete and Firmicute genera outnumbered *Sutterella*-sequences. This result is remarkable given that *Sutterella* is not reported as a major component of the microbiota (D34).

Loss of commensals in the intestine can affect immune responses and disrupt colonization resistance to potentially pathogenic bacteria (D17, D19). A significant loss of commensals, namely members of the Bacteroidete phyla, were found in AUT-GI biopsies (D10). Thus, the loss of Bacteroidetes in AUT-GI children could facilitate the growth of opportunistic pathogens. Whether *Sutterella* is pathogenic in AUT-GI children cannot be determined from current data. However, the observation that some AUT-GI children have antibodies that react with *S. wadsworthensis* proteins is generally consistent with infection. We detected either IgG or IgM antibodies against *S. wadsworthensis* proteins in approximately 48% (11/23) of AUT-GI children. Only one Control-GI child had very weak IgG immunoreactivity against *S. wadsworthensis* proteins. Of the 12 patients that were positive for *Sutterella* by PCR, 8 (66.7%) demonstrated plasma IgG antibodies against *S. wadsworthensis* proteins. In total, 65.2% (15 out of 23) of AUT-GI children were either positive by PCR assays or had immunoglobulin reactivity to *S. wadsworthensis* proteins. Three AUT-GI patients were negative by PCR but had IgG or IgM antibodies against *S. wadsworthensis* proteins. Without being bound by theory, *Sutterella* species can also be present in other regions of the small or large intestine or elsewhere in the body of these three patients, explaining the presence of *Sutterella*-specific antibodies without detection of the agent by PCR. Alternatively, IgG antibodies can persist long after antigenic exposure; thus, the presence of IgG antibodies can indicate past exposure in some children. The IgM immunoreactivity of patient #26a indicates recent or current exposure to *Sutterella* antigen in this patient. It is well recognized that the use of different strains and species as antigen leads to variations in the immunoreactive profile of immunogenic proteins (D35). Several *Sutterella*-positive patients in this study had *S. stercoricanis* as the dominant *Sutterella* species.

The nature of intestinal damage in autism has not been fully defined. Abnormalities in intestinal permeability in children with autism have been reported in two studies (D8, D9). In Crohn's disease, a condition associated with increased intestinal permeability, a generalized enhancement of antimicrobial IgG to many members of the intestinal microbiota is reported (D36). A defective epithelial barrier could lead to enhanced contact between many members of the microbiota and antigen-presenting cells in the lamina propria. If this turns out to be the case in autism, then antibodies against *Sutterella* proteins can reflect inter-individual, compositional variation in the microbiota, rather than an indication of *Sutterella* infection.

In conclusion, *Sutterella* 16S rRNA gene sequences were identified in mucoepithelial biopsies from AUT-GI children using non-specific, pan-microbial pyrosequencing. New *Sut-* terella-specific PCR assays were designed and applied that confirmed high levels of *Sutterella* species in over half of AUT-GI children and the complete absence of *Sutterella* in Control-GI children tested in this study. The *Sutterella*-specific molecular assays reported in this study will enable more directed studies to detect, quantify, and classify this poorly understood bacterium in biological and environmental samples. With such specific techniques, the following can be understood: the epidemiology of this bacterium and its associations with human infections and inflammatory diseases; the role *Sutterella* plays in the microbiota, and the extent to which *Sutterella* can contribute to the pathogenesis of GI disturbances in children with autism.

Materials and Methods

Clinical samples: Clinical procedures for this study population are previously described (D10, D37). The Institutional Review Board (IRB) at Columbia University Medical Center reviewed and approved the use of de-identified residual ileal and cecal samples, obtained as described in an earlier publication (D37), and waived the need for patient consent for these analyses, as all samples were analyzed anonymously. Patients assessed by pyrosequencing were restricted to male children between 3 to 5 years of age to control for confounding effects of gender and age on the microbiota (D10). This subset comprised 15 AUT-GI (patients #1-15) and 7 Control-GI (patients #16-22) children. For assessment of *Sutterella*-sequences in ileal and cecal biopsies, we also included 8 additional male AUT-GI children (patients #23a-30a: 6 children between 6 and 7 years of age, and 2 children between 8 and 10 years of age) and 2 additional male Control-GI children (patients #31a and 32a: 1 child between 6 and 7 years of age and 1 child between 8 and 10 years of age) from the initial cohort (D37).

Bacterial Culture: *S. wadsworthensis* was obtained from American Type Culture Collection (ATCC, # 51579). The isolate was grown in chopped meat broth in Hungate capped tubes (Anaerobe Systems, Morgan Hill, Calif.), supplemented with sodium formate and fumaric acid at a final concentration of 0.3% each. Inoculated cultures were incubated at 37° C. and growth was monitored at 0, 6, 12, 24, and 48 hours using a *Sutterella*-specific real-time PCR assay (see below).

DNA extraction: DNA was extracted from individual ileal and cecal biopsies (total of 256 biopsies: 128 ileal biopsies and 128 cecal biopsies; 8 biopsies per patient [4 from ileum and 4 from cecum]; 23 AUT-GI patients and 9 Control-GI patients) and bacterial cultures of *S. wadsworthensis* in TRIzol (Invitrogen, Carlsbad, Calif.) using standard protocols. DNA concentrations and integrity were determined using a Nanodrop ND-1000 Spectrophotometer (Nanodrop Technologies, Wilmington, Del.) and Bioanalyzer (Agilent Technologies, Foster City, Calif.) and stored at −80° C.

Pyrosequencing: Barcoded pyrosequencing of the bacterial V2 region of the 16S rRNA gene and analyses are previously described for ileal and cecal biopsies from AUT-GI patients #1-15 and Control-GI patients #16-22 (D10). The pan-bacterial barcoded V2 primers, designated V2For and V2Rev, amplify a region of the 16S rRNA gene from nucleotide position 27 to 338 (D38) (FIG. 38).

*Sutterella*-specific PCR assay design: *Sutterella*-specific 16S rRNA PCR primers were designed against the 16S rRNA gene sequence for *S. wadsworthensis* (Accession L37785) using Primer Express 1.0 software (Applied Biosystems, Foster City, Calif.). Genus specificity of candidate primers was evaluated using the RDP (Ribosomal Database Project) probe match tool. Several potential primer pairs were identified but only one pair showed high specificity for *Sutterella*. These primers are designated here as SuttFor (nucleotide position 936-956 of *S. wadsworthensis*: Accession L37785) and SuttRev (nucleotide position 1177-1195 of *S. wadsworthensis*: Accession L37785) [Table 20]. SuttFor and SuttRev primers amplify a 260 base pair (bp) region between variable regions 6, 7 and 8 (V6-V8) of the 16S rRNA gene of *Sutterella* (FIG. 38).

TABLE 20

Primers and probes used for conventional PCR or real-time PCR amplification and quantitation of *Sutterella* species.

| Name | Primers and Probe (5'-3') | | Nucleotide Position* | Amplicon size (bp) | SEQ ID NO: |
|---|---|---|---|---|---|
| *Sutterella* (V6-V8) | SuttFor: | CGCGAAAAACCTTACCTAGCC | 936-956 | ~260 | 11 |
| | SuttRev: | GACGTGTGAGGCCCTAGCC | 1177-1195 | | 12 |
| | SuttProbe: | FAM-CACAGGTGCTGCATGGCTGTCGT-NFQ | 1011-1033 | | 13 |
| *Sutterella* (C4-V8) | 515For: | GTGCCAGCMGCCGCGGTAA | 482-500 | ~715 | 65 |
| | SuttRev: | GACGTGTGAGGCCCTAGCC | 1177-1195 | | 66 |
| Total Bacteria | 515For: | GTGCCAGCMGCCGCGGTAA | 482-500 | ~292 | 15 |
| | 805Rev: | GACTACCAGGGTATCTAAT | 754-772 | | 16 |

*Nucleotide position relative to the 16S rRNA gene of *Sutterella wadsworthensis* (Accession # L37785)

Conventional PCR Assays: Conventional PCR for detection of *Sutterella* was carried out in 25 µl reactions consisting of 25 ng of biopsy DNA or 25 pg of genomic DNA from cultured *S. wadsworthensis* (ATCC, # 51579: positive control), 300 nm each SuttFor and SuttRev primers (for V6-V8 amplification) or 515For and SuttRev (for C4-V8 amplification), 2 µl dNTP Mix (10 mM; Applied Biosystems, Foster City, Calif.), 2.5 µl of 10×PCR Buffer (Qiagen, Valencia, Calif.), 5 U of HotStarTaq DNA polymerase (Qiagen), and 5 µl Q-solution (Qiagen). Cycling parameters consisted of an initial denaturation step at 95° C. for 15 min, followed by 30 cycles of 94° C. for 1 min, 60° C. for 1 min, 72° C. for 1 min, and a final extension at 72° C. for 5 min. The amplified product was detected by electrophoresis on a 1.5% agarose gel stained with ethidium bromide. To confirm specificity of PCR amplification, V6-V8 products were gel-extracted and sent for direct sequencing with SuttFor and SuttRev primers. Additionally, V6-V8 and C4-V8 products were subcloned into the vector PGEM-T easy (Promega, Madison, Wis.) and bacterial libraries were created. One hundred and twenty V6-V8 plasmid clones were sequenced. A total of 480 C4-V8 colonies were sequenced and analyzed (40 sequences from each of the 12 PCR-positive patients; 20 sequences from ileal and 20 sequences from cecal biopsies). All V6-V8 and C4-V8 plasmid clones were found to contain *Sutterella*-sequences using the RDP classifier tool with a minimum 80% bootstrap confidence estimate. The closest sequence match to *Sutterella* isolates was determined using the RDP seqmatch tool. Sequences from each individual patient were aligned using MacVector, and a consensus sequence was determined from the predominant *Sutterella* species in each patient.

Quantitative Real-time PCR Assay: PCR standards for determining copy numbers of bacterial 16S rRNA genes were prepared from products of the partial 16S rRNA gene (V6-V8 region) of *S. wadsworthensis* (Accession GU585669). A representative product with high sequence similarity to *Bacteroides intestinalis* (Accession NZ_ABJL02000007) 16S rRNA gene was used with broadly conserved total bacteria primers (D10, D39). Products were cloned into the vector PGEM-T easy (Promega) and ten-fold serial dilutions of linearized plasmid standards were created ranging from $5 \times 10^5$ to $5 \times 10^0$ copies. Amplification and detection of DNA by real-time PCR were performed with the ABI StepOne Plus Real-time PCR system (Applied Biosystems). Linearity and sensitivity of plasmid standards were tested with SuttFor and SuttRev primers and the SuttProbe. Amplification plots of plasmid standards indicated sensitivity of detection down to 5 copies of plasmid (FIG. 10A), and standard curves generated from plasmid dilutions had correlation coefficients of 0.996 (FIG. 10B).

Bioinformatics analysis: Operational taxonomic unit (OTU)-based analysis of pyrosequencing data was carried out in MOTHUR (version 1.8.0) and as previously described (D10, D40).

Phylogenetic analysis of *Sutterella* sequences: Phylogenetic analyses were conducted in MEGA4 (D41). Sequence alignments were based on representative sequences from OTU 1 and OTU 2, obtained from pyrosequencing analysis of the V2 region of the 16S rRNA gene, as well as sequences of *Sutterella* from the V6-V8 (SuttFor and Sutt Rev amplifications) conventional PCR assay, and the predominant sequences obtained from clone libraries of the C4-V8 (515For and SuttRev amplifications) conventional PCR assay. Primer sequences were trimmed from the sequences. Classification was confirmed using the RDP classifier and seqmatch tools. *Sutterella* sequences obtained from ileal and cecal biopsies were aligned with sequences from 8 isolates of *Sutterella* found in the RDP database and sequences from 14 additional related species (members of the family Alcaligenaceae and order Burkholderiales). Sequences from *Sutterella* isolates and related species were trimmed to the length of the sequences obtained from ileal and cecal biopsies of AUT-GI patients. Phylogenetic trees were constructed according to the neighbour-joining method with evolutionary distances determined using the Jukes-Cantor method (D42, D43). Trees were rooted to the outgroup *Escherichia coli* (Accession X80725). The stability of the groupings was estimated by bootstrap analysis (1000 replications) using MEGA4. The percentages of 16S rRNA gene sequence similarity were determined for *Sutterella* C4-V8 products and *Sutterella* isolates using the EzTaxon server 2.1 (D44).

Western Immunoblots: Soluble proteins of cultured *S. wadsworthensis* (ATCC, #51579) were extracted and used as antigen in immunoblot assays. *S. wadsworthensis* antigens were separated by SDS-PAGE and transferred to nitrocellulose membranes. Membranes were blocked, incubated with each patent's plasma (diluted 1:100 in blocking solution), probed with secondary antibodies [either peroxidase-conjugated goat anti-human IgG (Fc$_\gamma$ fragment-specific; Jackson ImmunoResearch, West Grove, Pa.) or peroxidase-conjugated goat anti-human IgM (Fc$_{5\mu}$ fragment-specific; Jackson ImmunoResearch)], and developed with ECL Plus Western blot detection system (Amersham Biosciences, Arlington Heights, Ill.).

Supplemental Materials and Methods

Pyrosequencing: 16S rRNA genes were amplified using V2-region specific, barcoded primers (E1) and products were sequenced at 454 Life Sciences on a GS FLX sequencer as previously described (E2). A total of 525,519 16S rRNA gene (V2 region) sequencing reads remained after filtering based on read length, removing low-quality sequences and sequences with ambiguous characters, and combining duplicate pyrosequencing runs (271,043 reads for ilea; 254,476 reads for ceca). Binning of sequences by barcode revealed similar numbers of 16S rRNA gene sequence reads per patient (average # sequences per patient +/− standard deviation [SD], ilea: 12,320+/−1220; ceca: 11,567+/−1589) (see Table 19). Taxonomic classifications of bacterial 16S rRNA gene sequences were obtained using the Ribosomal Database Project (RDP), Release 10, classifier tool with a minimum 80% bootstrap confidence estimate. To normalize data for differences in the total number of sequences obtained per patient, the abundance of sequences corresponding to members of the genus *Sutterella* and all other genera were expressed as a percentage of total bacterial sequence reads. The abundance of *Sutterella* was also expressed as a percentage of total class Betaproteobacteria sequence reads per patient (see Table 19).

Operational taxonomic unit (OTU) analysis: For OTU analysis of *Sutterella* sequences, genus level classification from RDP was used to subselect all *Sutterella*-sequences. *Sutterella*-sequences generated from 454 pyrosequencing were aligned to the greengenes reference alignment using the Needleman-Wunsch algorithm with the "align.seqs" function (ksize=9). Pairwise genetic distances among the aligned sequences were calculated using the "dist.seqs" function (calc=onegap, countends=T). Sequences were assigned to OTUs (defined at 97% sequence similarity) using average neighbor clustering. Representative sequences (the sequence which is the minimum distance to all other sequences in an OTU) from OTU 1 and OTU 2 were obtained using the get.oturep command in MOTHUR. OTU abundance by patient was expressed as percent relative abundance, determined by dividing the number of reads for an OTU in a given patient by the total number of bacterial reads obtained by pyrosequencing for that patient. Heatmaps were constructed using MeV (Version 4.5.0) using OTU abundance data from pyrosequencing reads. Heatmaps were drawn using Pearson's correlation as the similarity metric and complete linkage clustering. The upper limit approximately reflects the highest abundance recorded for any taxa in the heatmap (6%; red), and the lower limit reflects sequences above 0% abundance (0%; green); the midpoint limit (1%; white) is adjusted to highlight salient differences between the AUT-GI and Control-GI groups. Gray cells in the heatmaps represent instances wherein no sequences were detected for a given taxa in a given patient.

*Sutterella*-specific PCR primers and probe bioinformatics: Evaluation of good quality sequences greater than or equal to 1200 nucleotides in length revealed a total of 724 *Sutterella*-sequences in the RDP database at the time of most recent analysis (RDP Release 10, Update 27: Aug. 9, 2011). SuttFor and SuttRev primers showed high exclusivity for the genus *Sutterella*. Approximately 90% (692/768 bacterial 16S sequence matches) of all SuttFor matches and 98% (674/688 bacterial 16S sequence matches) of all SuttRev matches were specific to the genus *Sutterella*. The SuttFor primer sequence matched exactly with approximately 96% (692/724 *Sutter*- ella 16S sequences) of all *Sutterella*-sequences, while the SuttRev primer matched exactly with approximately 93% (674/724 *Sutterella* 16S sequences) of all *Sutterella* sequences in the RDP database. The SuttProbe (nucleotide position 1011-1033 of S. wadsworthens is: Accession L37785) (Table 20) used for real-time PCR had low exclusivity but high coverage of *Sutterella*-sequences (99%). The SuttProbe was labeled with the reporter FAM (6-carboxyfluorescein) and the nonfluorescent quencher BBQ (Blackberry) (TIB MolBiol, Berlin, Germany).

*Sutterella* V6-V8 PCR sensitivity, linearity, and end-point detection: To determine V6-V8 assay sensitivity, *Sutterella* plasmid standards (see quantitative real-time PCR methods) were tested by conventional PCR using the same conditions as for the biopsy DNA. Ten-fold dilutions of the *Sutterella* clone ranging from $5 \times 10^5$ to $5 \times 10^0$ were spiked into ileal DNA (25 ng) from a *Sutterella*-negative patient. We previously demonstrated that the ileal DNA from this *Sutterella*-negative patient contains 16S rRNA genes from a broad range of bacterial phylotypes dominated by Bacteroidetes, Firmicutes and Proteobacteria, but does not contain any *Sutterella* 16S rRNA sequences (2). The conventional V6-V8 PCR was linear in the range of $5 \times 10^5$ to $5 \times 10^2$ copies and had an end-point detection limit of $5 \times 10^1$ copies in the presence of background ileal DNA (FIG. 9).

Quantitative Real-time PCR Assay Details: For *Sutterella*-specific real-time PCR on biopsy material, each 25 μl reaction contained 25 ng biopsy DNA, 12.5 μl Taqman universal master mix (ABI), 300 nm each of SuttFor and SuttRev primers, and 200 nm SuttProbe. The cycling protocol for *Sutterella* amplification consisted of denaturation at 95° C. (10 min) followed by 45 cycles of 95° C. (15 sec) and 60° C. (1 min). For total bacteria real-time PCR, each 25 μl of amplification reaction mixture contained 25 ng DNA, 12.5 μl SYBR Green Master Mix (Applied Biosystems), and 300 nM each of the pan-bacterial primers (515For and 805Rev: Table 20). The cycling protocol for total bacteria consisted of denaturation at 95° C. (10 min) followed by 45 cycles of 95° C. (15 sec), 56° C. (15 sec), and 60° C. (1 min). DNA from each of 128 ileal (4 biopsies per patient) and 128 cecal biopsies (4 biopsies per patient) was assayed in duplicate. The final results were expressed as the mean number of *Sutterella* 16S rRNA gene copies normalized to the average 16S rRNA gene copies obtained using total bacterial primers. Eight water/reagent controls were included for all amplifications and the average copy number for water/reagent controls (background) was subtracted from each ileal and cecal amplification prior to normalization.

Western Immunoblots (Detailed Protocol): Anaerobic cultures of *S. wadsworthensis* (ATCC, #51579) were pelleted by centrifugation at 5000×g for 10 minutes and stored at −80° C. Protein lysates were prepared from *S. wadsworthensis* bacterial pellets using B-PER Solution (Thermo Scientific, Rockford, Ill.) supplemented with DNase I (2 μl/ml B-PER), lysozyme (2 μm! B-PER), and protease inhibitor cocktail and incubated for 10 minutes at room temperature. The lysate was centrifuged at 15,000×g for 5 minutes to remove insoluble proteins. The protein concentration of the soluble fraction was determined using the BCA protein assay kit (Pierce Biotechnology; Rockford, Ill.). Protein lysates (200 μg) in sample buffer (10 mM Tris-Hcl, pH 7.5; 10 mM EDTA, 20% v/v glycerol; 1% w/v SDS; 0.005% w/v bromophenol blue; 100 mM dithiothreitol; 1% v/v beta-mercaptoethanol) were boiled for 5 min and size-fractionated by 10% SDS-PAGE using a single large well on each gel to achieve uniform separation of proteins. Proteins were transferred to nitrocellulose membranes using the iBlot Gel Transfer System (Invitrogen). Membranes were blocked in 5% nonfat milk powder in TTBS (20 mM Tris-Hcl, pH 7.6; 137 mM NaCl; 0.3% Tween 20) for 1 hour at room temperature. Blocked membranes were transferred to a Mini-Protean II MultiScreen apparatus (BioRad, Hercules, Calif.). Plasma from each individual patient was diluted 1:100 in blocking solution (650 μl) and loaded onto the membrane in the individual chambers of the Mini-Protean II MultiScreen apparatus and incubated overnight at 4° C. Membranes were then removed from the apparatus and washed three times with TTBS for 10 minutes each wash. Secondary antibodies, either peroxidase-conjugated goat anti-human IgG ($Fc_\gamma$ fragment-specific; Jackson ImmunoResearch, West Grove, Pa.) or peroxidase-conjugated goat anti-human IgM ($Fc_{5\mu}$ fragment-specific; Jackson ImmunoResearch) were diluted 1:50,000 in blocking solution and incubated with the membranes for one hour at room temperature, followed by three washes with TTBS for 10 minutes each wash. Membranes were developed using ECL Plus Western blot detection system (Amersham Biosciences, Arlington Heights, Ill.) and scanned for chemiluminescence using a Typhoon Trio imager (GE Healthcare Life Sciences, Piscataway, N.J.). Western blots were performed three times to confirm reproducibility of results. Secondary antibody alone controls were included for all immunoblots to control for nonspecific binding. Background adjustments using ImageQuant (Molecular Dynamics) were applied equally to all immunoblots.

REFERENCES

D1. Buie, T., D. B. Campbell, G. J. Fuchs, 3rd, G. T. Furuta, J. Levy, J. Vandewater, A. H. Whitaker, D. Atkins, M. L. Bauman, A. L. Beaudet, E. G. Carr, M. D. Gershon, S. L. Hyman, P. Jirapinyo, H. Jyonouchi, K. Kooros, R. Kushak, P. Levitt, S. E. Levy, J. D. Lewis, K. F. Murray, M. R. Natowicz, A. Sabra, B. K. Wershil, S. C. Weston, L. Zeltzer, and H. Winter. 2010. Evaluation, diagnosis, and treatment of gastrointestinal disorders in individuals with ASDs: a consensus report. Pediatrics 125 Suppl 1:S1-18.

D2. Adams, J. B., L. J. Johansen, L. D. Powell, D. Quig, and R. A. Rubin. 2011. Gastrointestinal flora and gastrointestinal status in children with autism—comparisons to typical children and correlation with autism severity. BMC Gastroenterol 11:22.

D3. White, J. F. 2003. Intestinal pathophysiology in autism. Exp Biol Med (Maywood) 228:639-49.

D4. Horvath, K., J. C. Papadimitriou, A. Rabsztyn, C. Drachenberg, and J. T. Tildon. 1999. Gastrointestinal abnormalities in children with autistic disorder. J Pediatr 135:559-63.

D5. Ashwood, P., S. Wills, and J. Van de Water. 2006. The immune response in autism: a new frontier for autism research. J Leukoc Biol 80:1-15.

D6. Enstrom, A. M., C. E. Onore, J. A. Van de Water, and P. Ashwood. 2010. Differential monocyte responses to TLR ligands in children with autism spectrum disorders. Brain Behav Immun 24:64-71.

D7. Jyonouchi, H., L. Geng, A. Ruby, and B. Zimmerman-Bier. 2005. Dysregulated innate immune responses in young children with autism spectrum disorders: their relationship to gastrointestinal symptoms and dietary intervention. Neuropsychobiology 51:77-85.

D8. D'Eufemia, P., M. Celli, R. Finocchiaro, L. Pacifico, L. Viozzi, M. Zaccagnini, E. Cardi, and O. Giardini. 1996. Abnormal intestinal permeability in children with autism. Acta Paediatr 85:1076-9.

D9. de Magistris, L., V. Familiari, A. Pascotto, A. Sapone, A. Frolli, P. Iardino, M. Carteni, M. De Rosa, R. Francavilla, G. Riegler, R. Militerni, and C. Bravaccio. 2010. Alterations of the intestinal barrier in patients with autism spectrum disorders and in their first-degree relatives. J Pediatr Gastroenterol Nutr 51:418-24.

D10. Williams, B. L., M. Hornig, T. Buie, M. L. Bauman, M. Cho Paik, I. Wick, A. Bennett, O. Jabado, D. L. Hirschberg, and W. I. Lipkin. 2011. Impaired carbohydrate digestion and transport and mucosal dysbiosis in the intestines of children with autism and gastrointestinal disturbances. PLoS One 6:e24585.

D11. Finegold, S. M., D. Molitoris, Y. Song, C. Liu, M. L. Vaisanen, E. Bolte, M. McTeague, R. Sandler, H. Wexler, E. M. Marlowe, M. D. Collins, P. A. Lawson, P. Summanen, M. Baysallar, T. J. Tomzynski, E. Read, E. Johnson, R. Rolfe, P. Nasir, H. Shah, D. A. Haake, P. Manning, and A. Kaul. 2002. Gastrointestinal microflora studies in late-onset autism. Clin Infect Dis 35:S6-S16.

D12. Song, Y., C. Liu, and S. M. Finegold. 2004. Real-time PCR quantitation of clostridia in feces of autistic children. Appl Environ Microbiol 70:6459-65.

D13. Parracho, H. M., M. O. Bingham, G. R. Gibson, and A. L. McCartney. 2005. Differences between the gut microflora of children with autistic spectrum disorders and that of healthy children. J Med Microbiol 54:987-91.

D14. Wang, L., C. T. Christophersen, M. J. Sorich, J. P. Gerber, M. T. Angley, and M. A. Conlon. 2011. Low Relative Abundances of the Mucolytic Bacterium Akkermansia muciniphila and Bifidobacterium spp. in Feces of Children with Autism. Appl Environ Microbiol 77:6718-21.

D15. Finegold, S. M., S. E. Dowd, V. Gontcharova, C. Liu, K. E. Henley, R. D. Wolcott, E. Youn, P. H. Summanen, D. Granpeesheh, D. Dixon, M. Liu, D. R. Molitoris, and J. A. Green, 3rd. 2010. Pyrosequencing study of fecal microflora of autistic and control children. Anaerobe 16:444-53.

D16. O'Hara, A. M., and F. Shanahan. 2006. The gut flora as a forgotten organ. EMBO Rep 7:688-93.

D17. Macpherson, A. J., and N. L. Harris. 2004. Interactions between commensal intestinal bacteria and the immune system. Nat Rev Immunol 4:478-85.

D18. Heijtz, R. D., S. Wang, F. Anuar, Y. Qian, B. Bjorkholm, A. Samuelsson, M. L. Hibberd, H. Forssberg, and S. Pettersson. 2011. Normal gut microbiota modulates brain development and behavior. Proc Natl Acad Sci USA 108:3047-52.

D19. Vollaard, E. J., and H. A. Clasener. 1994. Colonization resistance. Antimicrob Agents Chemother 38:409-14.

D20. Busse, H.-J., and G. Auling. 2005. Family III. Alcaligenaceae in Bergey's Manual of Systematic Bacteriology Volume 2: The Proteobacteria, Part C. Springer-Verlag, New York.

D21. Wexler, H. M. 2005. Genus VIII. *Sutterella* in Bergey's Manual of Systematic Bacteriology Volume 2: The Proteobacteria, Part C. Springer-Verlag, New York.

D22. Wexler, H. M., D. Reeves, P. H. Summanen, E. Molitoris, M. McTeague, J. Duncan, K. H. Wilson, and S. M. Finegold. 1996. *Sutterella wadsworthensis* gen. nov., sp. nov., bile-resistant microaerophilic *Campylobacter gracilis*-like clinical isolates. Int J Syst Bacteriol 46:252-8.

D23. Molitoris, E., H. M. Wexler, and S. M. Finegold. 1997. Sources and antimicrobial susceptibilities of *Campylobacter gracilis* and *Sutterella wadsworthensis*. Clin Infect Dis 25 Suppl 2:S264-5.

D24. Mangin, I., R. Bonnet, P. Seksik, L. Rigottier-Gois, M. Sutren, Y. Bouhnik, C. Neut, M. D. Collins, J. F. Colombel, P. Marteau, and J. Dore. 2004. Molecular inventory of faecal microflora in patients with Crohn's disease. FEMS Microbiol Ecol 50:25-36.

D25. Gophna, U., K. Sommerfeld, S. Gophna, W. F. Doolittle, and S. J. Veldhuyzen van Zanten. 2006. Differences between tissue-associated intestinal microfloras of patients with Crohn's disease and ulcerative colitis. J Clin Microbiol 44:4136-41.

D26. Stackebrandt, E., and B. M. Goebel. 1994. A place for DNA-DNA reassociation and 16S ribosomal-RNA sequence analysis in the present species definition in bacteriology. Int J Syst Bacteriol 44:846-849.

D27. Walker, A. W., J. D. Sanderson, C. Churcher, G. C. Parkes, B. N. Hudspith, N. Rayment, J. Brostoff, J. Parkhill, G. Dougan, and L. Petrovska. 2011. High-throughput clone library analysis of the mucosa-associated microbiota reveals dysbiosis and differences between inflamed and non-inflamed regions of the intestine in inflammatory bowel disease. BMC Microbiol 11:7.

D28. Durso, L. M., G. P. Harhay, T. P. Smith, J. L. Bono, T. Z. Desantis, D. M. Harhay, G. L. Andersen, J. E. Keen, W. W. Laegreid, and M. L. Clawson. 2010. Animal-to-animal variation in fecal microbial diversity among beef cattle. Appl Environ Microbiol 76:4858-62.

D29. Li, M., B. Wang, M. Zhang, M. Rantalainen, S. Wang, H. Zhou, Y. Zhang, J. Shen, X. Pang, H. Wei, Y. Chen, H. Lu, J. Zuo, M. Su, Y. Qiu, W. Jia, C. Xiao, L. M. Smith, S. Yang, E. Holmes, H. Tang, G. Zhao, J. K. Nicholson, L. Li, and L. Zhao. 2008. Symbiotic gut microbes modulate human metabolic phenotypes. Proc Natl Acad Sci USA 105:2117-22.

D30. Engberg, J., S. L. On, C. S. Harrington, and P. Gerner-Smidt. 2000. Prevalence of Campylobacter, Arcobacter, Helicobacter, and *Sutterella* spp. in human fecal samples as estimated by a reevaluation of isolation methods for Campylobacters. J Clin Microbiol 38:286-91.

D31. Sakon, H., F. Nagai, M. Morotomi, and R. Tanaka. 2008. *Sutterella parvirubra* sp. nov. and *Megamonas funiformis* sp. nov., isolated from human faeces. Int J Syst Evol Microbiol 58:970-5.

D32. Greetham, H. L., M. D. Collins, G. R. Gibson, C. Giffard, E. Falsen, and P. A. Lawson. 2004. *Sutterella stercoricanis* sp. nov., isolated from canine faeces. Int J Syst Evol Microbiol 54:1581-4.

D33. Hong, P. Y., J. A. Croix, E. Greenberg, H. R. Gaskins, and R. I. Mackie. 2011. Pyrosequencing-based analysis of the mucosal microbiota in healthy individuals reveals ubiquitous bacterial groups and micro-heterogeneity. PLoS One 6:e25042.

D34. Arumugam, M., J. Raes, E. Pelletier, D. Le Paslier, T. Yamada, D. R. Mende, G. R. Fernandes, J. Tap, T. Bruls, J. M. Batto, M. Bertalan, N. Borruel, F. Casellas, L. Fernandez, L. Gautier, T. Hansen, M. Hattori, T. Hayashi, M. Kleerebezem, K. Kurokawa, M. Leclerc, F. Levenez, C. Manichanh, H. B. Nielsen, T. Nielsen, N. Pons, J. Poulain, J. Qin, T. Sicheritz-Ponten, S. Tims, D. Torrents, E. Ugarte, E. G. Zoetendal, J. Wang, F. Guarner, O. Pedersen, W. M. de Vos, S. Brunak, J. Dore, M. Antolin, F. Artiguenave, H. M. Blottiere, M. Almeida, C. Brechot, C. Cara, C. Chervaux, A. Cultrone, C. Delorme, G. Denariaz, R. Dervyn, K. U. Foerstner, C. Friss, M. van de Guchte, E. Guedon, F. Haimet, W. Huber, J. van Hylckama-Vlieg, A. Jamet, C. Juste, G. Kaci, J. Knol, O. Lakhdari, S. Layec, K. Le Roux, E. Maguin, A. Merieux, R. Melo Minardi, C. M'Rini, J. Muller, R. Oozeer, J. Parkhill, P. Renault, M. Rescigno, N. Sanchez, S. Sunagawa, A. Torrejon, K. Turner, G. Vandemeulebrouck, E. Varela, Y. Winogradsky, G. Zeller, J.

Weissenbach, S. D. Ehrlich, and P. Bork. 2011. Enterotypes of the human gut microbiome. Nature 473:174-80.

D35. Mavin, S., S. McDonagh, R. Evans, R. M. Milner, J. M. Chatterton, and D. O. Ho-Yen. 2011. Interpretation criteria in Western blot diagnosis of Lyme borreliosis. Br J Biomed Sci 68:5-10.

D36. Adams, R. J., S. P. Heazlewood, K. S. Gilshenan, M. O'Brien, M. A. McGuckin, and T. H. Florin. 2008. IgG antibodies against common gut bacteria are more diagnostic for Crohn's disease than IgG against mannan or flagellin. Am J Gastroenterol 103:386-96.

D37. Hornig, M., T. Briese, T. Buie, M. L. Bauman, G. Lauwers, U. Siemetzki, K. Hummel, P. A. Rota, W. J. Bellini, J. J. O'Leary, O. Sheils, E. Alden, L. Pickering, and W. I. Lipkin. 2008. Lack of association between measles virus vaccine and autism with enteropathy: a case-control study. PLoS One 3:e3140.

D38. Hamady, M., J. J. Walker, J. K. Harris, N. J. Gold, and R. Knight. 2008. Error-correcting barcoded primers for pyrosequencing hundreds of samples in multiplex. Nat Methods 5:235-7.

D39. Frank, D. N., A. L. St Amand, R. A. Feldman, E. C. Boedeker, N. Harpaz, and N. R. Pace. 2007. Molecular-phylogenetic characterization of microbial community imbalances in human inflammatory bowel diseases. Proc Natl Acad Sci USA 104:13780-5.

D40. Schloss, P. D., S. L. Westcott, T. Ryabin, J. R. Hall, M. Hartmann, E. B. Hollister, R. A. Lesniewski, B. B. Oakley, D. H. Parks, C. J. Robinson, J. W. Sahl, B. Stres, G. G. Thallinger, D. J. Van Horn, and C. F. Weber. 2009. Introducing mothur: open-source, platform-independent, community-supported software for describing and comparing microbial communities. Appl Environ Microbiol 75:7537-41.

D41. Tamura, K., J. Dudley, M. Nei, and S. Kumar. 2007. MEGA4: Molecular Evolutionary Genetics Analysis (MEGA) software version 4.0. Mol Biol Evol 24:1596-9.

D42. Saitou, N., and M. Nei. 1987. The neighbor-joining method: a new method for reconstructing phylogenetic trees. Mol Biol Evol 4:406-25.

D43. Jukes, T., and C. Cantor. 1969. Evolution of Protein Molecules. Academic Press, New York.

D44. Chun, J., J. H. Lee, Y. Jung, M. Kim, S. Kim, B. K. Kim, and Y. W. Lim. 2007. EzTaxon: a web-based tool for the identification of prokaryotes based on 16S ribosomal RNA gene sequences. Int J Syst Evol Microbiol 57:2259-61.

Supp. References

E1. Hamady, M., J. J. Walker, J. K. Harris, N. J. Gold, and R. Knight. 2008. Error-correcting barcoded primers for pyrosequencing hundreds of samples in multiplex. Nat Methods 5:235-7.

E2. Williams, B. L., M. Hornig, T. Buie, M. L. Bauman, M. Cho Paik, I. Wick, A. Bennett, O. Jabado, D. L. Hirschberg, and W. I. Lipkin. 2011. Impaired carbohydrate digestion and transport and mucosal dysbiosis in the intestines of children with autism and gastrointestinal disturbances. PLoS One 6:e24585

---

What is claimed is:

1. A method of detecting a *Sutterella* sp. in a sample, the method comprising:
   (a) selecting a *Sutterella* sp.-specific primer pair, wherein the primer pair comprises a primer comprising CGCGAAAAACCTTACSYAGCC (residues 31 to 51 of SEQ ID NO: 17), or a primer comprising GACGTGTGARGCCCYAGCC (residues 23 to 41 of SEQ ID NO: 18), or a combination thereof, wherein S is a G nucleotide or a C nucleotide, wherein Y is a C nucleotide or T nucleotide, and wherein R is an A nucleotide or G nucleotide;
   (b) contacting a nucleic acid from the sample with the *Sutterella* sp.-specific primer pair in a reaction mixture under conditions that promote amplification of at least one polynucleotide amplicon, wherein the primer pair will prime a polymerase reaction only when the nucleic acid of a *Sutterella* sp. is present;
   (c) amplifying the at least one polynucleotide amplicon by a polymerase chain reaction; and
   (d) detecting the at least one polynucleotide amplicon, wherein the detection of an amplicon of a selected, known length is indicative of the sample containing the nucleic acid of a *Sutterella* sp.

2. The method of claim 1, wherein the sample comprises intestinal tissue, feces, blood, skin, or a combination thereof.

3. The method of claim 1, wherein the primer pair comprises SEQ ID NO: 11.

4. The method of claim 1, wherein the primer pair comprises SEQ ID NO: 12.

5. The method of claim 1, wherein the detecting further comprises contacting the at least one polynucleotide amplicon with a probe having SEQ ID NO: 19, wherein Y is a C nucleotide or T nucleotide, wherein R is an A nucleotide or G nucleotide, wherein W is an A nucleotide or T nucleotide, and wherein H is an A nucleotide or T nucleotide or C nucleotide.

6. The method of claim 1, wherein the primer pair comprises SEQ ID NO: 17, wherein S is a G nucleotide or a C nucleotide, wherein Y is a C nucleotide or T nucleotide, wherein R is an A nucleotide or G nucleotide, wherein B is a T nucleotide, C nucleotide or G nucleotide, wherein V is an A nucleotide, G nucleotide or C nucleotide, wherein D is an A nucleotide, G nucleotide or T nucleotide, and wherein K is a G nucleotide or a T nucleotide.

7. The method of claim 1, wherein the primer pair comprises SEQ ID NO: 18, wherein R is an A nucleotide or G nucleotide, and wherein Y is a C nucleotide or T nucleotide.

8. The method of claim 1, wherein the detecting further comprises contacting the at least one polynucleotide amplicon with a probe having SEQ ID NO: 13.

9. The method of claim 1, wherein the detecting further comprises contacting the at least one polynucleotide amplicon with a probe having SEQ ID NO: 14.

* * * * *

SEQUENCE LISTING

```
<160> NUMBER OF SEQ ID NOS: 66

<210> SEQ ID NO 1
<211> LENGTH: 524
<212> TYPE: PRT
<213> ORGANISM: Homo sapiens

<400> SEQUENCE: 1

Met Thr Glu Asp Lys Val Thr Gly Thr Leu Val Phe Thr Val Ile Thr
1               5                   10                  15

Ala Val Leu Gly Ser Phe Gln Phe Gly Tyr Asp Ile Gly Val Ile Asn
            20                  25                  30

Ala Pro Gln Gln Val Ile Ile Ser His Tyr Arg His Val Leu Gly Val
        35                  40                  45

Pro Leu Asp Asp Arg Lys Ala Ile Asn Asn Tyr Val Ile Asn Ser Thr
    50                  55                  60

Asp Glu Leu Pro Thr Ile Ser Tyr Ser Met Asn Pro Lys Pro Thr Pro
65                  70                  75                  80

Trp Ala Glu Glu Glu Thr Val Ala Ala Ala Gln Leu Ile Thr Met Leu
                85                  90                  95

Trp Ser Leu Ser Val Ser Ser Phe Ala Val Gly Gly Met Thr Ala Ser
            100                 105                 110

Phe Phe Gly Gly Trp Leu Gly Asp Thr Leu Gly Arg Ile Lys Ala Met
        115                 120                 125

Leu Val Ala Asn Ile Leu Ser Leu Val Gly Ala Leu Leu Met Gly Phe
    130                 135                 140

Ser Lys Leu Gly Pro Ser His Ile Leu Ile Ile Ala Gly Arg Ser Ile
145                 150                 155                 160

Ser Gly Leu Tyr Cys Gly Leu Ile Ser Gly Leu Val Pro Met Tyr Ile
                165                 170                 175
```

Gly Glu Ile Ala Pro Thr Ala Leu Arg Gly Ala Leu Gly Thr Phe His
            180                 185                 190

Gln Leu Ala Ile Val Thr Gly Ile Leu Ile Ser Gln Ile Ile Gly Leu
        195                 200                 205

Glu Phe Ile Leu Gly Asn Tyr Asp Leu Trp His Ile Leu Leu Gly Leu
    210                 215                 220

Ser Gly Val Arg Ala Ile Leu Gln Ser Leu Leu Leu Phe Phe Cys Pro
225                 230                 235                 240

Glu Ser Pro Arg Tyr Leu Tyr Ile Lys Leu Asp Glu Val Lys Ala
                245                 250                 255

Lys Gln Ser Leu Lys Arg Leu Arg Gly Tyr Asp Asp Val Thr Lys Asp
            260                 265                 270

Ile Asn Glu Met Arg Lys Glu Arg Glu Ala Ser Ser Glu Gln Lys
        275                 280                 285

Val Ser Ile Ile Gln Leu Phe Thr Asn Ser Ser Tyr Arg Gln Pro Ile
    290                 295                 300

Leu Val Ala Leu Met Leu His Val Ala Gln Gln Phe Ser Gly Ile Asn
305                 310                 315                 320

Gly Ile Phe Tyr Tyr Ser Thr Ser Ile Phe Gln Thr Ala Gly Ile Ser
                325                 330                 335

Lys Pro Val Tyr Ala Thr Ile Gly Val Gly Ala Val Asn Met Val Phe
            340                 345                 350

Thr Ala Val Ser Val Phe Leu Val Glu Lys Ala Gly Arg Arg Ser Leu
        355                 360                 365

Phe Leu Ile Gly Met Ser Gly Met Phe Val Cys Ala Ile Phe Met Ser
    370                 375                 380

Val Gly Leu Val Leu Leu Asn Lys Phe Ser Trp Met Ser Tyr Val Ser
385                 390                 395                 400

Met Ile Ala Ile Phe Leu Phe Val Ser Phe Phe Glu Ile Gly Pro Gly
                405                 410                 415

Pro Ile Pro Trp Phe Met Val Ala Glu Phe Phe Ser Gln Gly Pro Arg
            420                 425                 430

Pro Ala Ala Leu Ala Ile Ala Ala Phe Ser Asn Trp Thr Cys Asn Phe
        435                 440                 445

Ile Val Ala Leu Cys Phe Gln Tyr Ile Ala Asp Phe Cys Gly Pro Tyr
    450                 455                 460

Val Phe Phe Leu Phe Ala Gly Val Leu Leu Ala Phe Thr Leu Phe Thr
465                 470                 475                 480

Phe Phe Lys Val Pro Glu Thr Lys Gly Lys Ser Phe Glu Glu Ile Ala
                485                 490                 495

Ala Glu Phe Gln Lys Lys Ser Gly Ser Ala His Arg Pro Lys Ala Ala
            500                 505                 510

Val Glu Met Lys Phe Leu Gly Ala Thr Glu Thr Val
        515                 520

<210> SEQ ID NO 2
<211> LENGTH: 3439
<212> TYPE: DNA
<213> ORGANISM: Homo sapiens

<400> SEQUENCE: 2
tctggtttgt aacttatgcc taagggacct gctcccattt tctttcctag tggaacaaag    60
gtattgaagc cacaggttgc tgaggcaaag cacttattga ttagattccc atcaatattc   120

```
agctgccgct gagaagatta gacttggact ctcaggtctg ggtagcccaa ctcctccctc    180
tccttgctcc tcctcctgca atgcataact aggcctaggc agagctgcga ataaacaggc    240
aggagctagt caggtgcatg tgccacactc acacaagacc tggaattgac aggactccca    300
actagtacaa tgacagaaga taaggtcact gggaccctgg ttttcactgt catcactgct    360
gtgctgggtt ccttccagtt tggatatgac attggtgtga tcaatgcacc tcaacaggta    420
ataatatctc actatagaca tgttttgggt gttccactgg atgaccgaaa agctatcaac    480
aactatgtta tcaacagtac agatgaactg cccacaatct catactcaat gaacccaaaa    540
ccaacccctt gggctgagga agagactgtg gcagctgctc aactaatcac catgctctgg    600
tccctgtctg tatccagctt tgcagttggt ggaatgactg catcattctt tggtgggtgg    660
cttgggggaca cacttggaag aatcaaagcc atgttagtag caaacattct gtcattagtt    720
ggagctctct tgatggggtt ttcaaaattg ggaccatctc atatacttat aattgctgga    780
agaagcatat caggactata ttgtgggcta atttcaggcc tggttcctat gtatatcggt    840
gaaattgctc caaccgctct caggggagca cttggcactt tcatcagct  ggccatcgtc    900
acgggcattc ttattagtca gattattggt cttgaattta tcttgggcaa ttatgatctg    960
tggcacatcc tgcttggcct gtctggtgtg cgagccatcc ttcagtctct gctactcttt   1020
ttctgtccag aaagccccag ataccttttac atcaagttag atgaggaagt caaagcaaaa   1080
caaagcttga aaagactcag aggatatgat gatgtcacca agatattaa tgaaatgaga   1140
aaagaaagag aagaagcatc gagtgagcag aaagtctcta taattcagct cttcaccaat   1200
tccagctacc gacagcctat tctagtggca ctgatgctgc atgtggctca gcaatttttcc   1260
ggaatcaatg gcattttta ctactcaacc agcattttc agacggctgg tatcagcaaa   1320
cctgtttatg caaccattgg agttggcgct gtaaacatgg ttttcactgc tgtctctgta   1380
ttccttgtgg agaaggcagg gcgacgttct ctctttctaa ttggaatgag tgggatgttt   1440
gtttgtgcca tcttcatgtc agtgggactt gtgctgctga ataagttctc ttggatgagt   1500
tatgtgagca tgatagccat cttcctcttt gtcagcttct ttgaaattgg gccaggcccg   1560
atccctggt tcatggtggc tgagtttttc agtcaaggac cacgtcctgc tgctttagca   1620
atagctgcat tcagcaattg gacctgcaat ttcattgtag ctctgtgttt ccagtacatt   1680
gcggacttct gtggacctta tgtgttttc ctctttgctg gagtgctcct ggcctttacc   1740
ctgttcacat tttttaaagt tccagaaacc aaaggaaagt cttttgagga aattgctgca   1800
gaattccaaa agaagagtgg ctcagcccac aggccaaaag ctgctgtaga atgaaaattc   1860
ctaggagcta cagagactgt gtaaaaaaaa aaccctgctt tttgacatga acagaaacaa   1920
taagggaacc gtctgttttt aaatgatgat tccttgagca ttttatatcc acatctttaa   1980
gtattgtttt atttttatgt gctctcatca gaaatgtcat caaatattac caaaaagta    2040
ttttttttaag ttagagaata tatttttgat ggtaagactg taattaagta aaccaaaaag   2100
gctagtttat tttgttacac taaagggcag gtggttctaa tattttttagc tctgttcttt   2160
ataacaaggt tcttctaaaa ttgaagagat ttcaacatat catttttttta acacataact   2220
agaaacctga ggatgcaaca aatatttata tatttgaata tcattaaatt ggaattttct   2280
tacccatata tcttatgtta aaggagatat ggctagtggc aataagttcc atgttaaaat   2340
agacaactct tccattttatt gcactcagct ttttcttga gtactagaat ttgtatttttg   2400
cttaaaattt tactttttgtt ctgtattttc atgtggaatg gattatagag tatactaaaa   2460
aatgtctata gagaaaaact ttcattttttg gtaggcttat caaaatcttt cagcactcag   2520
```

```
aaaagaaaac catttagtt cctttattta atggccaaat ggttttttgca agatttaaca    2580 ctaaaaaggt ttcacctgat catatagcgt gggttatcag ttaacattaa catctattat    2640
aaaaccatgt tgattccctt ctggtacaat cctttgagtt atagtttgct ttgctttta    2700 attgaggaca gcctggtttt cacatacact caaacaatca tgagtcagac atttggtata    2760
ttacctcaaa ttcctaataa gtttgatcaa atctaatgta agaaaatttg aagtaaagga    2820
ttgatcactt tgttaaaaat attttctgaa ttattatgtc tcaaaataag ttgaaaaggt    2880
agggtttgag gattcctgag tgtgggcttc tgaaacttca taaatgttca gcttcagact    2940
tttatcaaaa tccctatta atttcctgg aaagactgat tgttttatgg tgtgttccta    3000
acataaaata atcgtctcct ttgacatttc cttctttgtc ttagctgtat acagattcta    3060
gccaaactat tctatggcca ttactaacac gcattgtaca ctatctatct gcctttacct    3120
acataggcaa attggaaata cacagatgat taaacagact ttagcttaca gtcaattta    3180 caattatgga aatatagttc tgatgggtcc caaaagctta gcagggtgct aacgtatctc    3240
taggctgttt tctccaccaa ctggagcact gatcaatcct tcttatgttt gctttaatgt    3300
gtattgaaga aaagcacttt ttaaaaagta ctctttaaga gtgaaataat taaaaccac    3360 tgaacatttg ctttgttttc taaagttgtt cacatatatg taatttagca gtccaaagaa    3420
caagaaattg tttcttttc                                                 3439

<210> SEQ ID NO 3
<211> LENGTH: 664
<212> TYPE: PRT
<213> ORGANISM: Homo sapiens

<400> SEQUENCE: 3

Met Asp Ser Ser Thr Trp Ser Pro Lys Thr Thr Ala Val Thr Arg Pro
1               5                   10                  15

Val Glu Thr His Glu Leu Ile Arg Asn Ala Ala Asp Ile Ser Ile Ile
            20                  25                  30

Val Ile Tyr Phe Val Val Met Ala Val Gly Leu Trp Ala Met Phe
        35                  40                  45

Ser Thr Asn Arg Gly Thr Val Gly Gly Phe Phe Leu Ala Gly Arg Ser
    50                  55                  60

Met Val Trp Trp Pro Ile Gly Ala Ser Leu Phe Ala Ser Asn Ile Gly
65                  70                  75                  80

Ser Gly His Phe Val Gly Leu Ala Gly Thr Gly Ala Ala Ser Gly Ile
                85                  90                  95

Ala Ile Gly Gly Phe Glu Trp Asn Ala Leu Val Leu Val Val Leu
            100                 105                 110

Gly Trp Leu Phe Val Pro Ile Tyr Ile Lys Ala Gly Val Val Thr Met
        115                 120                 125

Pro Glu Tyr Leu Arg Lys Arg Phe Gly Gly Gln Arg Ile Gln Val Tyr
    130                 135                 140

Leu Ser Leu Leu Ser Leu Leu Tyr Ile Phe Thr Lys Ile Ser Ala
145                 150                 155                 160

Asp Ile Phe Ser Gly Ala Ile Phe Ile Asn Leu Ala Leu Gly Leu Asn
                165                 170                 175

Leu Tyr Leu Ala Ile Phe Leu Leu Ala Ile Thr Ala Leu Tyr Thr
            180                 185                 190

Ile Thr Gly Gly Leu Ala Ala Val Ile Tyr Thr Asp Thr Leu Gln Thr
        195                 200                 205
```

Val Ile Met Leu Val Gly Ser Leu Ile Leu Thr Gly Phe Ala Phe His
210                 215                 220

Glu Val Gly Gly Tyr Asp Ala Phe Met Glu Lys Tyr Met Lys Ala Ile
225                 230                 235                 240

Pro Thr Ile Val Ser Asp Gly Asn Thr Thr Phe Gln Glu Lys Cys Tyr
            245                 250                 255

Thr Pro Arg Ala Asp Ser Phe His Ile Phe Arg Asp Pro Leu Thr Gly
            260                 265                 270

Asp Leu Pro Trp Pro Gly Phe Ile Phe Gly Met Ser Ile Leu Thr Leu
        275                 280                 285

Trp Tyr Trp Cys Thr Asp Gln Val Ile Val Gln Arg Cys Leu Ser Ala
        290                 295                 300

Lys Asn Met Ser His Val Lys Gly Gly Cys Ile Leu Cys Gly Tyr Leu
305                 310                 315                 320

Lys Leu Met Pro Met Phe Ile Met Val Met Pro Gly Met Ile Ser Arg
                325                 330                 335

Ile Leu Tyr Thr Glu Lys Ile Ala Cys Val Val Pro Ser Glu Cys Glu
            340                 345                 350

Lys Tyr Cys Gly Thr Lys Val Gly Cys Thr Asn Ile Ala Tyr Pro Thr
            355                 360                 365

Leu Val Val Glu Leu Met Pro Asn Gly Leu Arg Gly Leu Met Leu Ser
370                 375                 380

Val Met Leu Ala Ser Leu Met Ser Ser Leu Thr Ser Ile Phe Asn Ser
385                 390                 395                 400

Ala Ser Thr Leu Phe Thr Met Asp Ile Tyr Ala Lys Val Arg Lys Arg
                405                 410                 415

Ala Ser Glu Lys Glu Leu Met Ile Ala Gly Arg Leu Phe Ile Leu Val
            420                 425                 430

Leu Ile Gly Ile Ser Ile Ala Trp Val Pro Ile Val Gln Ser Ala Gln
            435                 440                 445

Ser Gly Gln Leu Phe Asp Tyr Ile Gln Ser Ile Thr Ser Tyr Leu Gly
        450                 455                 460

Pro Pro Ile Ala Ala Val Phe Leu Leu Ala Ile Phe Trp Lys Arg Val
465                 470                 475                 480

Asn Glu Pro Gly Ala Phe Trp Gly Leu Ile Leu Gly Leu Leu Ile Gly
                485                 490                 495

Ile Ser Arg Met Ile Thr Glu Phe Ala Tyr Gly Thr Gly Ser Cys Met
            500                 505                 510

Glu Pro Ser Asn Cys Pro Thr Ile Cys Gly Val His Tyr Leu Tyr Tyr
        515                 520                 525

Phe Ala Ile Ile Leu Phe Ala Ile Ser Phe Ile Thr Ile Val Val Ile
        530                 535                 540

Ser Leu Leu Thr Lys Pro Ile Pro Asp Val His Leu Tyr Arg Leu Cys
545                 550                 555                 560

Trp Ser Leu Arg Asn Ser Lys Glu Glu Arg Ile Asp Leu Asp Ala Glu
                565                 570                 575

Glu Glu Asn Ile Gln Glu Gly Pro Lys Glu Thr Ile Glu Ile Glu Thr
            580                 585                 590

Gln Val Pro Glu Lys Lys Lys Gly Ile Phe Arg Arg Ala Tyr Asp Leu
        595                 600                 605

Phe Cys Gly Leu Glu Gln His Gly Ala Pro Lys Met Thr Glu Glu Glu
610                 615                 620

```
Glu Lys Ala Met Lys Met Lys Met Thr Asp Thr Ser Glu Lys Pro Leu
625                 630                 635                 640

Trp Arg Thr Val Leu Asn Val Asn Gly Ile Ile Leu Val Thr Val Ala
                645                 650                 655

Val Phe Cys His Ala Tyr Phe Ala
            660
```

<210> SEQ ID NO 4
<211> LENGTH: 5061
<212> TYPE: DNA
<213> ORGANISM: Homo sapiens

<400> SEQUENCE: 4

| | |
|---|---|
| ccccattcgc aggacagctc ttacctgccg ggccgccgcc ccagccaaca gctcagccgg | 60 |
| gtgctccttc ctgggctcca cgcccggagc tgcttcctga cggtgcagcc gcaaggcatc | 120 |
| gcagggcccc cgcgctactg ccctgctccc tcaaagtccc aggtcccctc ccctggtgct | 180 |
| gatcattaac caggaggccg tataaggagc tagcggccct ggcgagaggg aaggacgcaa | 240 |
| cgctgccacc atggacagta gcacctggag ccccaagacc accgcggtca cccggcctgt | 300 |
| tgagacccac gagctcattc gcaatgcagc cgatatctcc atcatcgtta tctacttcgt | 360 |
| ggtagtgatg gccgtcggac tgtgggctat gttttccacc aatcgtggga ctgttggagg | 420 |
| cttcttcctg gcaggccgaa gtatggtgtg gtggccgatt ggagcctccc tctttgctag | 480 |
| taacattgga agtggccact tgtggggct ggccgggact ggggcagctt caggcatcgc | 540 |
| cattggaggc tttgaatgga atgccctggt tttggtggtt gtgctgggct ggctgtttgt | 600 |
| ccccatctat attaaggctg gggtggtgac aatgccagag tacctgagga gcggtttgg | 660 |
| aggccagcgg atccaggtct acctttccct tctgtccctg ctgctctaca ttttcaccaa | 720 |
| gatctcggca gacatcttct cggggccat attcatcaat ctggccttag gcctgaatct | 780 |
| gtatttagcc atctttctct tattggcaat cactgcccct tacacaatta caggggcct | 840 |
| ggcggcggtg atttacacgg acaccttgca gacggtgatc atgctggtgg ggtctttaat | 900 |
| cctgactggg tttgcttttc acgaagtggg aggctatgac gccttcatgg aaaagtacat | 960 |
| gaaagccatt ccaaccatag tgtctgatgg caacaccacc tttcaggaaa aatgctacac | 1020 |
| tccaagggcc gactccttcc acatcttccg agatcccctc acgggagacc tcccatggcc | 1080 |
| tgggttcatc tttgggatgt ccatccttac cttgtggtac tggtgcacag tcaggtcat | 1140 |
| tgtgcagcgc tgcctctcag ccaagaatat gtctcacgtg aagggtggct gcatcctgtg | 1200 |
| tgggtatcta aagctgatgc ccatgttcat catggtgatg ccaggaatga tcagccgcat | 1260 |
| tctgtacaca gaaaaaattg cctgtgtcgt cccttcagaa tgtgagaaat attgcggtac | 1320 |
| caaggttggc tgtaccaaca tcgcctatcc aaccttagtg gtggagctca tgcccaatgg | 1380 |
| actgcgaggc ctgatgctat cagtcatgct ggcctccctc atgagctccc tgacctccat | 1440 |
| cttcaacagc gccagcaccc tcttcaccat ggacatctac gccaaggtcc gcaagagagc | 1500 |
| atctgagaaa gagctcatga ttgccggaag gttgtttatc ctggtgctga ttggcatcag | 1560 |
| catcgcctgg gtgcccattg tgcagtcagc acaaagtggg caactcttcg attacatcca | 1620 |
| gtccatcacc agttacttgg gaccacccat gcggctgtc ttcctgcttg ctattttctg | 1680 |
| gaagagagtc aatgagccag gagccttttg gggactgatc ctaggacttc tgattgggat | 1740 |
| ttcacgtatg attactgagt ttgcttatgg aaccgggagc tgcatggagc cagcaactg | 1800 |
| tcccacgatt atctgtgggg tgcactactt gtactttgcc attatcctct tcgccatttc | 1860 |

```
tttcatcacc atcgtggtca tctccctcct caccaaaccc attccggatg tgcatctcta    1920
ccgtctgtgt tggagcctgc gcaacagcaa agaggagcgt attgacctgg atgcggaaga    1980
ggagaacatc caagaaggcc ctaaggagac cattgaaata gaaacacaag ttcctgagaa    2040
gaaaaaagga atcttcagga gagcctatga cctattttgt gggctagagc agcacggtgc    2100
acccaagatg actgaggaag aggagaaagc catgaagatg aagatgacgg acacctctga    2160
gaagcctttg tggaggacag tgttgaacgt caatggcatc atcctggtga ccgtggctgt    2220
cttttgccat gcatattttg cctgagtcct acctttttgct gtagatttac catggctgga    2280
ctcttactca ccttccttta gtctcgtcct gtggtgttga agggaaatca gccagttgta    2340
aattttgccc aggtggataa atgtgtacat gtgtaattat aggctagctg aagaaaaacc    2400
attagtttgc tgttaattta tgcatttgaa gccagtgtga tacagccatc tgtacctact    2460
ggagctgcag aagggaagtc cactcagtca catccagaaa aaggcagact aagaatcaga    2520
agccatgtga ttgatgtctg acgtgagtct gtctcaggta gattccgggt gtcagtgtgg    2580
tttataatcc ttgaatattg ttttagaaac tttggtctcc ctggttcctg ccactttcc     2640 tgtccgtcct cctccccatt ttttttttaa aagaaagctg ttttcccctc atcatatccc    2700
tcttgagttt tgcctggact ttccctctca gtgtgtcaa tcaggtaaac tgaggaatgc     2760
atggaagctg aggatggagc ttgatgggct ccctgtcctg ggtgtttgct ctctgaagtg    2820
gaggcctgag gaaggtagta cttccacaaa agggagggac ccgggcccca gcctcaagct    2880
agtgggggag gcagatagcc tgaatccagg ggattttctg ggcttcttaa aatgtccatt    2940
gtgagttccc cgtgtttggg attccactca ttttggcatt cacagtgcct ggaatgtctt    3000
agattttcag caatgcgtgt tgaataaatg aatgacatag gcatttattt ttaaatcttt    3060
gcttgctttt tacatgagcc tggcccttag ttaaccttt cttgtggcta cacaaagtat     3120
gctcactggt tactaatgac ttgggatgca tttgtcaaac tgattatatt agttttctag    3180
ggatgccata acaaagtagc acagaccaga tggctcaagc agcagacatt tattttctca    3240
cagttctaga ggctagaagt tggaggccaa gatgtcagca gggttggttt cttctgaggc    3300
ctctctcctt ggttgcagat ggtcatatct cactctgtct tccgtggcct tccttttgtc    3360
tgtgtcctaa atctactctt ctgataagga catcagtcat attggaatag gacccaccct    3420
aatgtcttca ttttaatcac ctctttaaag cccctacctc caaatacagt cacactgtga    3480
gaaactgagg gttaggaagt cagcaagtga gtcttgaaga gatactaaac aaacccacaa    3540
cacagataaa gtatgcattt tggagatttc caagccagag tctcccgtga aaaaggtaaa    3600
cggaagcagt tattgtgcag caaaaggaaa aagaattaca aactgaacgt atgtaggtga    3660
ggcaaggcag ggtagggcag ggcctttggg taggctgatc agagggtttt tcaacaataa    3720
atcaatggga atgcatttgt tgctcccagg accctggcac cttgactctg gtactatagc    3780
atgtcagcaa atacaagcaa agcccaacac tctgatttgc atttatgcca atctaaacta    3840
tccggtgttt agtttgattt tttgagtgca ggttcattca aggaccaggt tcccttgtgc    3900
tcagggtgaa gtagaaccag aaaacatcgt tatccattcc cagaagtttt ggaagagcct    3960
tggtagaaaa gcagaagctg ctttgaccgt gaaaatattt gactcctatc agttttggt     4020 caggagaaga tatccaccta gaccaacctg aggagaaggc tcagagtaca gatataccc     4080 gagcaacgtg atcaatgtcc ttgaaccttc attttcatc tgaaacagaa gacataaatg     4140
cctggctcac agatttaaat gttatacatt gacagcattt atcagtataa catttattta    4200
aataagtagg tgctcaatag gtgttggtct tctaacttgt ctacatccca tccccattcc    4260
```

-continued

```
agggtcttca gaattgaagg agagatgttg tatcactgtt agaaggctgc tttgggacat    4320
tctgcagcag ggaggaggga ctgtcaaccc ctacaccatg accaccaagt tcctcacctt    4380
ggctgagtcc ctaaaactct ctgaacctca ggttcctcca agcataatgc agacttcaca    4440
gagctgttgt aaagattagg tgaggtcaat tgatactgct taaaaggccc ggtccgtaga    4500
aaatgcccaa taaacattac tgctttcccc ctcaccctac tgcctgaaaa aatattacac    4560
ctgtgagact gactttgaga accagtgtgg gtggggagtt gtgcatataa actatttaat    4620
gagtaccaaa cacaaaagtc aagcttgtaa aatatcaggc cttgcccag aaagacaaat     4680 accacatgat ctcactgata tgtagaatct taaaaagtca aactcagaag cagagagtag    4740
aatgatggtt atcaagggct gggggaggga gggactgggg agatgttggt caaatgatac    4800
aaaggtttag ttaggtggaa taagttcaga aaatcaattg tacaatgtat caattatagt    4860
taatagcaat ataacatata cttgaaaatt gctgagagta gtgtgagtgt tctaccacaa    4920
aaaaatatgt gcagtaatag atgttaatta ccttaattta gtcatttcac aatatgtaca    4980
tatataaaaa tatgttgtat gccatgagta tatataatta ttatttgtga atttaaaaaa    5040
taaaaataat ttccaaaaaa a                                               5061
```

<210> SEQ ID NO 5
<211> LENGTH: 1827
<212> TYPE: PRT
<213> ORGANISM: Homo sapiens

<400> SEQUENCE: 5

```
Met Ala Arg Lys Lys Phe Ser Gly Leu Glu Ile Ser Leu Ile Val Leu
1               5                   10                  15

Phe Val Ile Val Thr Ile Ile Ala Ile Ala Leu Ile Val Val Leu Ala
                20                  25                  30

Thr Lys Thr Pro Ala Val Asp Glu Ile Ser Asp Ser Thr Ser Thr Pro
            35                  40                  45

Ala Thr Thr Arg Val Thr Thr Asn Pro Ser Asp Ser Gly Lys Cys Pro
        50                  55                  60

Asn Val Leu Asn Asp Pro Val Asn Val Arg Ile Asn Cys Ile Pro Glu
65                  70                  75                  80

Gln Phe Pro Thr Glu Gly Ile Cys Ala Gln Arg Gly Cys Cys Trp Arg
                85                  90                  95

Pro Trp Asn Asp Ser Leu Ile Pro Trp Cys Phe Phe Val Asp Asn His
                100                 105                 110

Gly Tyr Asn Val Gln Asp Met Thr Thr Thr Ser Ile Gly Val Glu Ala
            115                 120                 125

Lys Leu Asn Arg Ile Pro Ser Pro Thr Leu Phe Gly Asn Asp Ile Asn
        130                 135                 140

Ser Val Leu Phe Thr Thr Gln Asn Gln Thr Pro Asn Arg Phe Arg Phe
145                 150                 155                 160

Lys Ile Thr Asp Pro Asn Asn Arg Arg Tyr Glu Val Pro His Gln Tyr
                165                 170                 175

Val Lys Glu Phe Thr Gly Pro Thr Val Ser Asp Thr Leu Tyr Asp Val
            180                 185                 190

Lys Val Ala Gln Asn Pro Phe Ser Ile Gln Val Ile Arg Lys Ser Asn
        195                 200                 205

Gly Lys Thr Leu Phe Asp Thr Ser Ile Gly Pro Leu Val Tyr Ser Asp
    210                 215                 220
```

-continued

Gln Tyr Leu Gln Ile Ser Thr Arg Leu Pro Ser Asp Tyr Ile Tyr Gly
225                 230                 235                 240

Ile Gly Glu Gln Val His Lys Arg Phe Arg His Asp Leu Ser Trp Lys
            245                 250                 255

Thr Trp Pro Ile Phe Thr Arg Asp Gln Leu Pro Gly Asp Asn Asn Asn
            260                 265                 270

Asn Leu Tyr Gly His Gln Thr Phe Phe Met Cys Ile Glu Asp Thr Ser
            275                 280                 285

Gly Lys Ser Phe Gly Val Phe Leu Met Asn Ser Asn Ala Met Glu Ile
            290                 295                 300

Phe Ile Gln Pro Thr Pro Ile Val Thr Tyr Arg Val Thr Gly Gly Ile
305                 310                 315                 320

Leu Asp Phe Tyr Ile Leu Leu Gly Asp Thr Pro Glu Gln Val Val Gln
                325                 330                 335

Gln Tyr Gln Gln Leu Val Gly Leu Pro Ala Met Pro Ala Tyr Trp Asn
            340                 345                 350

Leu Gly Phe Gln Leu Ser Arg Trp Asn Tyr Lys Ser Leu Asp Val Val
            355                 360                 365

Lys Glu Val Val Arg Arg Asn Arg Glu Ala Gly Ile Pro Phe Asp Thr
370                 375                 380

Gln Val Thr Asp Ile Asp Tyr Met Glu Asp Lys Lys Asp Phe Thr Tyr
385                 390                 395                 400

Asp Gln Val Ala Phe Asn Gly Leu Pro Gln Phe Val Gln Asp Leu His
                405                 410                 415

Asp His Gly Gln Lys Tyr Val Ile Ile Leu Asp Pro Ala Ile Ser Ile
            420                 425                 430

Gly Arg Arg Ala Asn Gly Thr Thr Tyr Ala Thr Tyr Glu Arg Gly Asn
            435                 440                 445

Thr Gln His Val Trp Ile Asn Glu Ser Asp Gly Ser Thr Pro Ile Ile
            450                 455                 460

Gly Glu Val Trp Pro Gly Leu Thr Val Tyr Pro Asp Phe Thr Asn Pro
465                 470                 475                 480

Asn Cys Ile Asp Trp Trp Ala Asn Glu Cys Ser Ile Phe His Gln Glu
                485                 490                 495

Val Gln Tyr Asp Gly Leu Trp Ile Asp Met Asn Glu Val Ser Ser Phe
            500                 505                 510

Ile Gln Gly Ser Thr Lys Gly Cys Asn Val Asn Lys Leu Asn Tyr Pro
            515                 520                 525

Pro Phe Thr Pro Asp Ile Leu Asp Lys Leu Met Tyr Ser Lys Thr Ile
            530                 535                 540

Cys Met Asp Ala Val Gln Asn Trp Gly Lys Gln Tyr Asp Val His Ser
545                 550                 555                 560

Leu Tyr Gly Tyr Ser Met Ala Ile Ala Thr Glu Gln Ala Val Gln Lys
                565                 570                 575

Val Phe Pro Asn Lys Arg Ser Phe Ile Leu Thr Arg Ser Thr Phe Ala
            580                 585                 590

Gly Ser Gly Arg His Ala Ala His Trp Leu Gly Asp Asn Thr Ala Ser
            595                 600                 605

Trp Glu Gln Met Glu Trp Ser Ile Thr Gly Met Leu Glu Phe Ser Leu
            610                 615                 620

Phe Gly Ile Pro Leu Val Gly Ala Asp Ile Cys Gly Phe Val Ala Glu
625                 630                 635                 640

Thr Thr Glu Glu Leu Cys Arg Arg Trp Met Gln Leu Gly Ala Phe Tyr

-continued

```
                645                 650                 655
Pro Phe Ser Arg Asn His Asn Ser Asp Gly Tyr Glu His Gln Asp Pro
            660                 665                 670
Ala Phe Phe Gly Gln Asn Ser Leu Leu Val Lys Ser Ser Arg Gln Tyr
        675                 680                 685
Leu Thr Ile Arg Tyr Thr Leu Leu Pro Phe Leu Tyr Thr Leu Phe Tyr
    690                 695                 700
Lys Ala His Val Phe Gly Glu Thr Val Ala Arg Pro Val Leu His Glu
705                 710                 715                 720
Phe Tyr Glu Asp Thr Asn Ser Trp Ile Glu Asp Thr Glu Phe Leu Trp
                725                 730                 735
Gly Pro Ala Leu Leu Ile Thr Pro Val Leu Lys Gln Gly Ala Asp Thr
            740                 745                 750
Val Ser Ala Tyr Ile Pro Asp Ala Ile Trp Tyr Asp Tyr Glu Ser Gly
        755                 760                 765
Ala Lys Arg Pro Trp Arg Lys Gln Arg Val Asp Met Tyr Leu Pro Ala
    770                 775                 780
Asp Lys Ile Gly Leu His Leu Arg Gly Gly Tyr Ile Ile Pro Ile Gln
785                 790                 795                 800
Glu Pro Asp Val Thr Thr Ala Ser Arg Lys Asn Pro Leu Gly Leu
                805                 810                 815
Ile Val Ala Leu Gly Glu Asn Asn Thr Ala Lys Gly Asp Phe Phe Trp
            820                 825                 830
Asp Asp Gly Glu Thr Lys Asp Thr Ile Gln Asn Gly Asn Tyr Ile Leu
        835                 840                 845
Tyr Thr Phe Ser Val Ser Asn Asn Thr Leu Asp Ile Val Cys Thr His
    850                 855                 860
Ser Ser Tyr Gln Glu Gly Thr Thr Leu Ala Phe Gln Thr Val Lys Ile
865                 870                 875                 880
Leu Gly Leu Thr Asp Ser Val Thr Glu Val Arg Val Ala Glu Asn Asn
                885                 890                 895
Gln Pro Met Asn Ala His Ser Asn Phe Thr Tyr Asp Ala Ser Asn Gln
            900                 905                 910
Val Leu Leu Ile Ala Asp Leu Lys Leu Asn Leu Gly Arg Asn Phe Ser
        915                 920                 925
Val Gln Trp Asn Gln Ile Phe Ser Glu Asn Arg Phe Asn Cys Tyr
    930                 935                 940
Pro Asp Ala Asp Leu Ala Thr Glu Gln Lys Cys Thr Gln Arg Gly Cys
945                 950                 955                 960
Val Trp Arg Thr Gly Ser Ser Leu Ser Lys Ala Pro Glu Cys Tyr Phe
                965                 970                 975
Pro Arg Gln Asp Asn Ser Tyr Ser Val Asn Ser Ala Arg Tyr Ser Ser
            980                 985                 990
Met Gly Ile Thr Ala Asp Leu Gln Leu Asn Thr Ala Asn Ala Arg Ile
        995                 1000                1005
Lys Leu Pro Ser Asp Pro Ile Ser Thr Leu Arg Val Glu Val Lys
    1010                1015                1020
Tyr His Lys Asn Asp Met Leu Gln Phe Lys Ile Tyr Asp Pro Gln
    1025                1030                1035
Lys Lys Arg Tyr Glu Val Pro Val Pro Leu Asn Ile Pro Thr Thr
    1040                1045                1050
Pro Ile Ser Thr Tyr Glu Asp Arg Leu Tyr Asp Val Glu Ile Lys
    1055                1060                1065
```

-continued

```
Glu Asn Pro Phe Gly Ile Gln Ile Arg Arg Arg Ser Ser Gly Arg
    1070            1075                1080

Val Ile Trp Asp Ser Trp Leu Pro Gly Phe Ala Phe Asn Asp Gln
    1085            1090                1095

Phe Ile Gln Ile Ser Thr Arg Leu Pro Ser Glu Tyr Ile Tyr Gly
    1100            1105                1110

Phe Gly Glu Val Glu His Thr Ala Phe Lys Arg Asp Leu Asn Trp
    1115            1120                1125

Asn Thr Trp Gly Met Phe Thr Arg Asp Gln Pro Pro Gly Tyr Lys
    1130            1135                1140

Leu Asn Ser Tyr Gly Phe His Pro Tyr Tyr Met Ala Leu Glu Glu
    1145            1150                1155

Glu Gly Asn Ala His Gly Val Phe Leu Leu Asn Ser Asn Ala Met
    1160            1165                1170

Asp Val Thr Phe Gln Pro Thr Pro Ala Leu Thr Tyr Arg Thr Val
    1175            1180                1185

Gly Gly Ile Leu Asp Phe Tyr Met Phe Leu Gly Pro Thr Pro Glu
    1190            1195                1200

Val Ala Thr Lys Gln Tyr His Glu Val Ile Gly His Pro Val Met
    1205            1210                1215

Pro Ala Tyr Trp Ala Leu Gly Phe Gln Leu Cys Arg Tyr Gly Tyr
    1220            1225                1230

Ala Asn Thr Ser Glu Val Arg Glu Leu Tyr Asp Ala Met Val Ala
    1235            1240                1245

Ala Asn Ile Pro Tyr Asp Val Gln Tyr Thr Asp Ile Asp Tyr Met
    1250            1255                1260

Glu Arg Gln Leu Asp Phe Thr Ile Gly Glu Ala Phe Gln Asp Leu
    1265            1270                1275

Pro Gln Phe Val Asp Lys Ile Arg Gly Glu Gly Met Arg Tyr Ile
    1280            1285                1290

Ile Ile Leu Asp Pro Ala Ile Ser Gly Asn Glu Thr Lys Thr Tyr
    1295            1300                1305

Pro Ala Phe Glu Arg Gly Gln Gln Asn Asp Val Phe Val Lys Trp
    1310            1315                1320

Pro Asn Thr Asn Asp Ile Cys Trp Ala Lys Val Trp Pro Asp Leu
    1325            1330                1335

Pro Asn Ile Thr Ile Asp Lys Thr Leu Thr Glu Asp Glu Ala Val
    1340            1345                1350

Asn Ala Ser Arg Ala His Val Ala Phe Pro Asp Phe Phe Arg Thr
    1355            1360                1365

Ser Thr Ala Glu Trp Trp Ala Arg Glu Ile Val Asp Phe Tyr Asn
    1370            1375                1380

Glu Lys Met Lys Phe Asp Gly Leu Trp Ile Asp Met Asn Glu Pro
    1385            1390                1395

Ser Ser Phe Val Asn Gly Thr Thr Thr Asn Gln Cys Arg Asn Asp
    1400            1405                1410

Glu Leu Asn Tyr Pro Pro Tyr Phe Pro Glu Leu Thr Lys Arg Thr
    1415            1420                1425

Asp Gly Leu His Phe Arg Thr Ile Cys Met Glu Ala Glu Gln Ile
    1430            1435                1440

Leu Ser Asp Gly Thr Ser Val Leu His Tyr Asp Val His Asn Leu
    1445            1450                1455
```

```
Tyr Gly Trp Ser Gln Met Lys Pro Thr His Asp Ala Leu Gln Lys
    1460            1465                1470
Thr Thr Gly Lys Arg Gly Ile Val Ile Ser Arg Ser Thr Tyr Pro
    1475            1480                1485
Thr Ser Gly Arg Trp Gly Gly His Trp Leu Gly Asp Asn Tyr Ala
    1490            1495                1500
Arg Trp Asp Asn Met Asp Lys Ser Ile Ile Gly Met Met Glu Phe
    1505            1510                1515
Ser Leu Phe Gly Met Ser Tyr Thr Gly Ala Asp Ile Cys Gly Phe
    1520            1525                1530
Phe Asn Asn Ser Glu Tyr His Leu Cys Thr Arg Trp Met Gln Leu
    1535            1540                1545
Gly Ala Phe Tyr Pro Tyr Ser Arg Asn His Asn Ile Ala Asn Thr
    1550            1555                1560
Arg Arg Gln Asp Pro Ala Ser Trp Asn Glu Thr Phe Ala Glu Met
    1565            1570                1575
Ser Arg Asn Ile Leu Asn Ile Arg Tyr Thr Leu Leu Pro Tyr Phe
    1580            1585                1590
Tyr Thr Gln Met His Glu Ile His Ala Asn Gly Gly Thr Val Ile
    1595            1600                1605
Arg Pro Leu Leu His Glu Phe Phe Asp Glu Lys Pro Thr Trp Asp
    1610            1615                1620
Ile Phe Lys Gln Phe Leu Trp Gly Pro Ala Phe Met Val Thr Pro
    1625            1630                1635
Val Leu Glu Pro Tyr Val Gln Thr Val Asn Ala Tyr Val Pro Asn
    1640            1645                1650
Ala Arg Trp Phe Asp Tyr His Thr Gly Lys Asp Ile Gly Val Arg
    1655            1660                1665
Gly Gln Phe Gln Thr Phe Asn Ala Ser Tyr Asp Thr Ile Asn Leu
    1670            1675                1680
His Val Arg Gly Gly His Ile Leu Pro Cys Gln Glu Pro Ala Gln
    1685            1690                1695
Asn Thr Phe Tyr Ser Arg Gln Lys His Met Lys Leu Ile Val Ala
    1700            1705                1710
Ala Asp Asp Asn Gln Met Ala Gln Gly Ser Leu Phe Trp Asp Asp
    1715            1720                1725
Gly Glu Ser Ile Asp Thr Tyr Glu Arg Asp Leu Tyr Leu Ser Val
    1730            1735                1740
Gln Phe Asn Leu Asn Gln Thr Thr Leu Thr Ser Thr Ile Leu Lys
    1745            1750                1755
Arg Gly Tyr Ile Asn Lys Ser Glu Thr Arg Leu Gly Ser Leu His
    1760            1765                1770
Val Trp Gly Lys Gly Thr Thr Pro Val Asn Ala Val Thr Leu Thr
    1775            1780                1785
Tyr Asn Gly Asn Lys Asn Ser Leu Pro Phe Asn Glu Asp Thr Thr
    1790            1795                1800
Asn Met Ile Leu Arg Ile Asp Leu Thr Thr His Asn Val Thr Leu
    1805            1810                1815
Glu Glu Pro Ile Glu Ile Asn Trp Ser
    1820            1825

<210> SEQ ID NO 6
<211> LENGTH: 6023
<212> TYPE: DNA
```

<213> ORGANISM: Homo sapiens

<400> SEQUENCE: 6

| | | | | | |
|---|---|---|---|---|---|
| ttattttggc | agccttatcc | aagtctggta | caacatagca | aagagaacag | gctatgaaat | 60 |
| aagatggcaa | gaaagaaatt | tagtggattg | gaaatctctc | tgattgtcct | ttttgtcata | 120 |
| gttactataa | tagctattgc | cttaattgtt | gttttagcaa | ctaagacacc | tgctgttgat | 180 |
| gaaattagtg | attctacttc | aactccagct | actactcgtg | tgactacaaa | tccttctgat | 240 |
| tcaggaaaat | gtccaaatgt | gttaaatgat | cctgtcaatg | tgagaataaa | ctgcattcca | 300 |
| gaacaattcc | caacagaggg | aatttgtgca | cagagaggct | gctgctggag | gccgtggaat | 360 |
| gactctctta | ttccttggtg | cttcttcgtt | gataatcatg | gttataacgt | tcaagacatg | 420 |
| acaacaacaa | gtattggagt | tgaagccaaa | ttaaacagga | taccttcacc | tacactattt | 480 |
| ggaaatgaca | tcaacagtgt | tctcttcaca | actcaaaatc | agacacccaa | tcgtttccgg | 540 |
| ttcaagatta | ctgatccaaa | taatagaaga | tatgaagttc | ctcatcagta | tgtaaaagag | 600 |
| tttactggac | ccacagtttc | tgatacgttg | tatgatgtga | aggttgccca | aaacccattt | 660 |
| agcatccaag | ttattaggaa | aagcaacggt | aaaactttgt | ttgacaccag | cattggtccc | 720 |
| ttagtgtact | ctgaccagta | cttacagatc | tcaacccgtc | ttccaagtga | ttatatttat | 780 |
| ggtattggag | aacaagttca | taagagattt | cgtcatgatt | tatcctggaa | acatggcca | 840 |
| atttttactc | gagaccaact | tcctggtgat | aataataata | atttatacgg | ccatcaaaca | 900 |
| ttctttatgt | gtattgaaga | tacatctgga | aagtcattcg | gtgttttttt | aatgaatagc | 960 |
| aatgcaatgg | agatttttat | ccagcctact | ccaatagtaa | catatagagt | taccggtggc | 1020 |
| attctggatt | tttacatcct | tctaggagat | acaccagaac | aagtagttca | acagtatcaa | 1080 |
| cagcttgttg | gactaccagc | aatgccagca | tattggaatc | ttggattcca | actaagtcgc | 1140 |
| tggaattata | agtcactaga | tgtagtgaaa | gaagtggtaa | ggagaaaccg | ggaagctggc | 1200 |
| ataccatttg | atacacaggt | cactgatatt | gactacatgg | aagacaagaa | agactttact | 1260 |
| tatgatcaag | ttgcgtttaa | cggactccct | caatttgtgc | aagatttgca | tgaccatgga | 1320 |
| cagaaatatg | tcatcatctt | ggaccctgca | atttccatag | gtcgacgtgc | caatggaaca | 1380 |
| acatatgcaa | cctatgagag | gggaaacaca | caacatgtgt | ggataaatga | gtcagatgga | 1440 |
| agtacaccaa | ttattggaga | ggtatggcca | ggattaacag | tataccctga | tttcactaac | 1500 |
| ccaaactgca | ttgattggtg | ggcaaatgaa | tgcagtattt | tccatcaaga | agtgcaatat | 1560 |
| gatggacttt | ggattgacat | gaatgaagtt | tccagcttta | ttcaaggttc | aacaaaagga | 1620 |
| tgtaatgtaa | acaaattgaa | ttatccaccg | tttactcctg | atattcttga | caaactcatg | 1680 |
| tattccaaaa | caatttgcat | ggatgctgtg | cagaactggg | gtaaacagta | tgatgttcat | 1740 |
| agcctctatg | gatacagcat | ggctatagcc | acagagcaag | ctgtacaaaa | agttttttcct | 1800 |
| aataagagaa | gcttcattct | tacccgctca | acatttgctg | gatctggaag | acatgctgcg | 1860 |
| cattggttag | gagacaatac | tgcttcatgg | gaacaaatgg | aatggtctat | aactggaatg | 1920 |
| ctggagttca | gtttgtttgg | aataccttttg | gttggagcag | acatctgtgg | atttgtggct | 1980 |
| gaaaccacag | aagaactttg | cagaagatgg | atgcaacttg | ggcattttta | tccatttttcc | 2040 |
| agaaaccata | attctgacgg | atatgaacat | caggatcctg | catttttttgg | gcagaattca | 2100 |
| cttttggtta | aatcatcaag | gcagtattta | actattcgct | acaccttatt | acccttcctc | 2160 |
| tacactctgt | tttataaagc | ccatgtgttt | ggagaaacag | tagcaagacc | agttcttcat | 2220 |
| gagttttatg | aggatacgaa | cagctggatt | gaggacactg | agttttttgtg | gggccctgca | 2280 |

```
ttacttatta ctcctgttct aaaacaggga gcagatactg tgagtgccta catccctgat    2340
gctatttggt atgattatga atctggtgca aaaaggccat ggaggaaaca acgggttgat    2400
atgtatcttc cagcagacaa aataggatta catcttagag gaggttatat catccccatt    2460
caagaaccag atgtaacaac aacagcaagc cgtaagaatc ctctaggact tatagtcgca    2520
ttaggtgaaa acaacacagc caaaggagac tttttctggg atgatggaga aactaaagat    2580
acaatacaaa atggcaacta catattatat acattttcag tttctaataa cacattagat    2640
attgtgtgca cacattcatc atatcaggaa ggaactacct tagcatttca gactgtaaaa    2700
atccttgggt tgacagacag tgttacagaa gttagagtgg cggaaaataa tcaaccaatg    2760
aacgctcatt ccaatttcac ttatgatgct tctaaccagg ttctcctaat tgcagatctc    2820
aaacttaatc ttggaagaaa ctttagtgtt caatggaatc aaattttctc agaaaatgaa    2880
agatttaatt gttatccaga tgcagatttg gcaactgaac aaaagtgcac acaacgtggc    2940
tgtgtatgga gaacgggttc ttctctatcc aaagcacctg agtgttactt tcccagacaa    3000
gataactctt attcagtcaa ctcagctcgc tattcatcca tgggtataac agctgacctc    3060
caactaaata ctgcaaatgc cagaataaag ttaccttctg accccatctc aactcttcgt    3120
gtggaggtga aatatcacaa aaatgatatg ttgcagttta agatttatga tccccaaaag    3180
aagagatatg aagtaccagt accgttaaac attccaacca ccccaataag tacttatgaa    3240
gacagacttt atgatgtgga aatcaaggaa aatccttttg gcatccagat tcgacggaga    3300
agcagtggaa gagtcatttg ggattcttgg ctgcctggat ttgcttttaa tgaccagttc    3360
attcaaatat cgactcgcct gccatcagaa tatatatatg gttttgggga agtggaacat    3420
acagcattta gcgagatct gaactggaat acttggggaa tgttcacaag agaccaaccc    3480
cctggttaca aacttaattc ctatggattt catccctatt acatggctct ggaagaggag    3540
ggcaatgctc atggtgtttt cttactcaac agcaatgcaa tggatgttac attccagcca    3600
actcctgctc taacttaccg tacagttgga gggatcttgg atttttatat gttttttggc    3660
ccaactccag aagttgcaac aaagcaatac catgaagtaa ttggccatcc agtcatgcca    3720
gcttattggg ctttgggatt ccaattatgt cgttatggat atgcaaatac ttcagaggtt    3780
cgggaattat atgacgctat ggtggctgct aacatcccct atgatgttca gtacacagac    3840
attgactaca tggaaaggca gctagacttt acaattggtg aagcattcca ggaccttcct    3900
cagtttgttg acaaaataag aggagaagga atgagataca ttattatcct ggatccagca    3960
atttcaggaa atgaaacaaa gacttaccct gcatttgaaa aggacagca gaatgatgtc    4020 tttgtcaaat ggccaaacac caatgacatt tgttgggcaa aggtttggcc agatttgccc    4080
aacataacaa tagataaaac tctaacggaa gatgaagctg ttaatgcttc cagagctcat    4140
gtagctttcc cagatttctt caggacttcc acagcagagt ggtgggccag agaaattgtg    4200
gacttttaca atgaaaagat gaagtttgat ggttgtgga ttgatatgaa tgagccatca    4260
agttttgtaa atggaacaac tactaatcaa tgcagaaatg acgaactaaa ttatccacct    4320
tatttcccag aactcacaaa aagaactgat ggattacatt tcagaacaat ttgcatggaa    4380
gctgagcaga ttcttagtga tggaacatca gtttgcatt acgatgttca caatctctat    4440
ggatggtcac agatgaaacc tactcatgat gcattgcaga agacaactgg aaaaagaggg    4500
attgtaattt ctcgttccac gtatcctact agtggacgat ggggaggaca ctggcttgga    4560
gacaactatg cacgatggga caacatggac aaatcaatca ttggtatgat ggaatttagt    4620
```

```
ctgtttggaa tgtcatatac tggagcagac atctgtggtt ttttcaacaa ctcagaatat    4680
catctctgta cccgctggat gcaacttgga gcatttatc catactcaag gaatcacaac    4740
attgcaaata ctagaagaca agatcccgct tcctggaatg aaacttttgc tgaaatgtca    4800
aggaatattc taaatattag atacacctta ttgccctatt tttacacaca aatgcatgaa    4860
attcatgcta atggtggcac tgttatccga ccccttttgc atgagttctt tgatgaaaaa    4920
ccaacctggg atatattcaa gcagttctta tggggtccag catttatggt tacccccagta   4980 ctggaacctt atgttcaaac tgtaaatgcc tacgtcccca atgctcggtg gtttgactac    5040
catacaggca agatattgg cgtcagagga caatttcaaa catttaatgc ttcttatgac    5100
acaataaacc tacatgtccg tggtggtcac atcctaccat gtcaagagcc agctcaaaac    5160
acattttaca gtcgacaaaa acacatgaag ctcattgttg ctgcagatga taatcagatg    5220
gcacagggtt ctctgttttg ggatgatgga gagagtatag acacctatga aagagaccta    5280
tatttatctg tacaatttaa tttaaaccag accaccttaa caagcactat attgaagaga    5340
ggttacataa ataaaagtga aacgaggctt ggatcccttc atgtatgggg gaaaggaact    5400
actcctgtca atgcagttac tctaacgtat aacggaaata aaaattcgct tccttttaat    5460
gaagacacta ccaacatgat attacgtatt gatctgacca cacacaatgt tactctagaa    5520
gaaccaatag aaatcaactg gtcatgaaga tcaccatcaa ttttagttgt caatgggaaa    5580
aaacaccagg atttaagttt cacagcactt acaattttcc ctcttcactt ggttcttgta    5640
ctctacaaaa tatagctttc ataacatcga aaagttattt tgtagcgtac atcaatgata    5700
atgctaattt tattatagta atgtgacttg gattcaattt taaggcatat ttaacaaaat    5760
ttgaatagcc ctatttatcc ttgttaagta tcagctacaa ttgtaaacta gttactaaac    5820
atgtatgtaa atagctaaga tataatttaa acgtgatttt taaattaaat aaaattttta    5880
tgtaattata tatactatat ttttctcaat gtttagcaga tttaagatat gtaacaacaa    5940
ttatttgaag atttaattac ttcttagtat gtgcatttaa ttagaaaaag agaataaaaa    6000
atgtaagtgt aaaaaaaaaa aaa                                          6023
```

<210> SEQ ID NO 7
<211> LENGTH: 1857
<212> TYPE: PRT
<213> ORGANISM: Homo sapiens

<400> SEQUENCE: 7

```
Met Ala Arg Lys Lys Leu Lys Lys Phe Thr Thr Leu Glu Ile Val Leu
1               5                   10                  15

Ser Val Leu Leu Leu Val Leu Phe Ile Ile Ser Ile Val Leu Ile Val
                20                  25                  30

Leu Leu Ala Lys Glu Ser Leu Lys Ser Thr Ala Pro Asp Pro Gly Thr
            35                  40                  45

Thr Gly Thr Pro Asp Pro Gly Thr Thr Gly Thr Pro Asp Pro Gly Thr
        50                  55                  60

Thr Gly Thr Thr His Ala Arg Thr Thr Gly Pro Pro Asp Pro Gly Thr
65                  70                  75                  80

Thr Gly Thr Thr Pro Val Ser Ala Glu Cys Pro Val Val Asn Glu Leu
                85                  90                  95

Glu Arg Ile Asn Cys Ile Pro Asp Gln Pro Pro Thr Lys Ala Thr Cys
                100                 105                 110

Asp Gln Arg Gly Cys Cys Trp Asn Pro Gln Gly Ala Val Ser Val Pro
            115                 120                 125
```

-continued

```
Trp Cys Tyr Tyr Ser Lys Asn His Ser Tyr His Val Glu Gly Asn Leu
            130                 135                 140
Val Asn Thr Asn Ala Gly Phe Thr Ala Arg Leu Lys Asn Leu Pro Ser
145                 150                 155                 160
Ser Pro Val Phe Gly Ser Asn Val Asp Asn Val Leu Leu Thr Ala Glu
                165                 170                 175
Tyr Gln Thr Ser Asn Arg Phe His Phe Lys Leu Thr Asp Gln Thr Asn
            180                 185                 190
Asn Arg Phe Glu Val Pro His Glu His Val Gln Ser Phe Ser Gly Asn
            195                 200                 205
Ala Ala Ala Ser Leu Thr Tyr Gln Val Glu Ile Ser Arg Gln Pro Phe
        210                 215                 220
Ser Ile Lys Val Thr Arg Arg Ser Asn Asn Arg Val Leu Phe Asp Ser
225                 230                 235                 240
Ser Ile Gly Pro Leu Leu Phe Ala Asp Gln Phe Leu Gln Leu Ser Thr
                245                 250                 255
Arg Leu Pro Ser Thr Asn Val Tyr Gly Leu Gly Glu His Val His Gln
            260                 265                 270
Gln Tyr Arg His Asp Met Asn Trp Lys Thr Trp Pro Ile Phe Asn Arg
        275                 280                 285
Asp Thr Thr Pro Asn Gly Asn Gly Thr Asn Leu Tyr Gly Ala Gln Thr
        290                 295                 300
Phe Phe Leu Cys Leu Glu Asp Ala Ser Gly Leu Ser Phe Gly Val Phe
305                 310                 315                 320
Leu Met Asn Ser Asn Ala Met Glu Val Val Leu Gln Pro Ala Pro Ala
                325                 330                 335
Ile Thr Tyr Arg Thr Ile Gly Gly Ile Leu Asp Phe Tyr Val Phe Leu
            340                 345                 350
Gly Asn Thr Pro Glu Gln Val Val Gln Glu Tyr Leu Glu Leu Ile Gly
            355                 360                 365
Arg Pro Ala Leu Pro Ser Tyr Trp Ala Leu Gly Phe His Leu Ser Arg
        370                 375                 380
Tyr Glu Tyr Gly Thr Leu Asp Asn Met Arg Glu Val Val Glu Arg Asn
385                 390                 395                 400
Arg Ala Ala Gln Leu Pro Tyr Asp Val Gln His Ala Asp Ile Asp Tyr
                405                 410                 415
Met Asp Glu Arg Arg Asp Phe Thr Tyr Asp Ser Val Asp Phe Lys Gly
            420                 425                 430
Phe Pro Glu Phe Val Asn Glu Leu His Asn Asn Gly Gln Lys Leu Val
        435                 440                 445
Ile Ile Val Asp Pro Ala Ile Ser Asn Asn Ser Ser Ser Ser Lys Pro
        450                 455                 460
Tyr Gly Pro Tyr Asp Arg Gly Ser Asp Met Lys Ile Trp Val Asn Ser
465                 470                 475                 480
Ser Asp Gly Val Thr Pro Leu Ile Gly Glu Val Trp Pro Gly Gln Thr
                485                 490                 495
Val Phe Pro Asp Tyr Thr Asn Pro Asn Cys Ala Val Trp Trp Thr Lys
            500                 505                 510
Glu Phe Glu Leu Phe His Asn Gln Val Glu Phe Asp Gly Ile Trp Ile
        515                 520                 525
Asp Met Asn Glu Val Ser Asn Phe Val Asp Gly Ser Val Ser Gly Cys
530                 535                 540
```

```
Ser Thr Asn Asn Leu Asn Pro Pro Phe Thr Pro Arg Ile Leu Asp
545                 550                 555                 560

Gly Tyr Leu Phe Cys Lys Thr Leu Cys Met Asp Ala Val Gln His Trp
            565                 570                 575

Gly Lys Gln Tyr Asp Ile His Asn Leu Tyr Gly Tyr Ser Met Ala Val
                580                 585                 590

Ala Thr Ala Glu Ala Ala Lys Thr Val Phe Pro Asn Lys Arg Ser Phe
            595                 600                 605

Ile Leu Thr Arg Ser Thr Phe Ala Gly Ser Gly Lys Phe Ala Ala His
            610                 615                 620

Trp Leu Gly Asp Asn Thr Ala Thr Trp Asp Asp Leu Arg Trp Ser Ile
625                 630                 635                 640

Pro Gly Val Leu Glu Phe Asn Leu Phe Gly Ile Pro Met Val Gly Pro
                645                 650                 655

Asp Ile Cys Gly Phe Ala Leu Asp Thr Pro Glu Glu Leu Cys Arg Arg
                660                 665                 670

Trp Met Gln Leu Gly Ala Phe Tyr Pro Phe Ser Arg Asn His Asn Gly
            675                 680                 685

Gln Gly Tyr Lys Asp Gln Asp Pro Ala Ser Phe Gly Ala Asp Ser Leu
            690                 695                 700

Leu Leu Asn Ser Ser Arg His Tyr Leu Asn Ile Arg Tyr Thr Leu Leu
705                 710                 715                 720

Pro Tyr Leu Tyr Thr Leu Phe Phe Arg Ala His Ser Arg Gly Asp Thr
                725                 730                 735

Val Ala Arg Pro Leu Leu His Glu Phe Tyr Glu Asp Asn Ser Thr Trp
            740                 745                 750

Asp Val His Gln Gln Phe Leu Trp Gly Pro Gly Leu Leu Ile Thr Pro
            755                 760                 765

Val Leu Asp Glu Gly Ala Glu Lys Val Met Ala Tyr Val Pro Asp Ala
770                 775                 780

Val Trp Tyr Asp Tyr Glu Thr Gly Ser Gln Val Arg Trp Arg Lys Gln
785                 790                 795                 800

Lys Val Glu Met Glu Leu Pro Gly Asp Lys Ile Gly Leu His Leu Arg
                805                 810                 815

Gly Gly Tyr Ile Phe Pro Thr Gln Gln Pro Asn Thr Thr Thr Leu Ala
            820                 825                 830

Ser Arg Lys Asn Pro Leu Gly Leu Ile Ile Ala Leu Asp Glu Asn Lys
            835                 840                 845

Glu Ala Lys Gly Glu Leu Phe Trp Asp Asn Gly Glu Thr Lys Asp Thr
850                 855                 860

Val Ala Asn Lys Val Tyr Leu Leu Cys Glu Phe Ser Val Thr Gln Asn
865                 870                 875                 880

Arg Leu Glu Val Asn Ile Ser Gln Ser Thr Tyr Lys Asp Pro Asn Asn
                885                 890                 895

Leu Ala Phe Asn Glu Ile Lys Ile Leu Gly Thr Glu Glu Pro Ser Asn
            900                 905                 910

Val Thr Val Lys His Asn Gly Val Pro Ser Gln Thr Ser Pro Thr Val
            915                 920                 925

Thr Tyr Asp Ser Asn Leu Lys Val Ala Ile Ile Thr Asp Ile Asp Leu
            930                 935                 940

Leu Leu Gly Glu Ala Tyr Thr Val Glu Trp Ser Ile Lys Ile Arg Asp
945                 950                 955                 960

Glu Glu Lys Ile Asp Cys Tyr Pro Asp Glu Asn Gly Ala Ser Ala Glu
```

-continued

```
                965                 970                 975
Asn Cys Thr Ala Arg Gly Cys Ile Trp Glu Ala Ser Asn Ser Ser Gly
                980                 985                 990
Val Pro Phe Cys Tyr Phe Val Asn Asp Leu Tyr Ser Val Ser Asp Val
                995                1000                1005
Gln Tyr Asn Ser His Gly Ala Thr Ala Asp Ile Ser Leu Lys Ser
       1010                1015                1020
Ser Val Tyr Ala Asn Ala Phe Pro Ser Thr Pro Val Asn Pro Leu
       1025                1030                1035
Arg Leu Asp Val Thr Tyr His Lys Asn Glu Met Leu Gln Phe Lys
       1040                1045                1050
Ile Tyr Asp Pro Asn Lys Asn Arg Tyr Glu Val Pro Val Pro Leu
       1055                1060                1065
Asn Ile Pro Ser Met Pro Ser Ser Thr Pro Glu Gly Gln Leu Tyr
       1070                1075                1080
Asp Val Leu Ile Lys Lys Asn Pro Phe Gly Ile Glu Ile Arg Arg
       1085                1090                1095
Lys Ser Thr Gly Thr Ile Ile Trp Asp Ser Gln Leu Leu Gly Phe
       1100                1105                1110
Thr Phe Ser Asp Met Phe Ile Arg Ile Ser Thr Arg Leu Pro Ser
       1115                1120                1125
Lys Tyr Leu Tyr Gly Phe Gly Glu Thr Glu His Arg Ser Tyr Arg
       1130                1135                1140
Arg Asp Leu Glu Trp His Thr Trp Gly Met Phe Ser Arg Asp Gln
       1145                1150                1155
Pro Pro Gly Tyr Lys Lys Asn Ser Tyr Gly Val His Pro Tyr Tyr
       1160                1165                1170
Met Gly Leu Glu Glu Asp Gly Ser Ala His Gly Val Leu Leu Leu
       1175                1180                1185
Asn Ser Asn Ala Met Asp Val Thr Phe Gln Pro Leu Pro Ala Leu
       1190                1195                1200
Thr Tyr Arg Thr Thr Gly Gly Val Leu Asp Phe Tyr Val Phe Leu
       1205                1210                1215
Gly Pro Thr Pro Glu Leu Val Thr Gln Gln Tyr Thr Glu Leu Ile
       1220                1225                1230
Gly Arg Pro Val Met Val Pro Tyr Trp Ser Leu Gly Phe Gln Leu
       1235                1240                1245
Cys Arg Tyr Gly Tyr Gln Asn Asp Ser Glu Ile Ala Ser Leu Tyr
       1250                1255                1260
Asp Glu Met Val Ala Ala Gln Ile Pro Tyr Asp Val Gln Tyr Ser
       1265                1270                1275
Asp Ile Asp Tyr Met Glu Arg Gln Leu Asp Phe Thr Leu Ser Pro
       1280                1285                1290
Lys Phe Ala Gly Phe Pro Ala Leu Ile Asn Arg Met Lys Ala Asp
       1295                1300                1305
Gly Met Arg Val Ile Leu Ile Leu Asp Pro Ala Ile Ser Gly Asn
       1310                1315                1320
Glu Thr Gln Pro Tyr Pro Ala Phe Thr Arg Gly Val Glu Asp Asp
       1325                1330                1335
Val Phe Ile Lys Tyr Pro Asn Asp Gly Asp Ile Val Trp Gly Lys
       1340                1345                1350
Val Trp Pro Asp Phe Pro Asp Val Val Val Asn Gly Ser Leu Asp
       1355                1360                1365
```

-continued

```
Trp Asp Ser Gln Val Glu Leu Tyr Arg Ala Tyr Val Ala Phe Pro
    1370                1375                1380

Asp Phe Phe Arg Asn Ser Thr Ala Lys Trp Trp Lys Arg Glu Ile
    1385                1390                1395

Glu Glu Leu Tyr Asn Asn Pro Gln Asn Pro Glu Arg Ser Leu Lys
    1400                1405                1410

Phe Asp Gly Met Trp Ile Asp Met Asn Glu Pro Ser Ser Phe Val
    1415                1420                1425

Asn Gly Ala Val Ser Pro Gly Cys Arg Asp Ala Ser Leu Asn His
    1430                1435                1440

Pro Pro Tyr Met Pro His Leu Glu Ser Arg Asp Arg Gly Leu Ser
    1445                1450                1455

Ser Lys Thr Leu Cys Met Glu Ser Gln Gln Ile Leu Pro Asp Gly
    1460                1465                1470

Ser Leu Val Gln His Tyr Asn Val His Asn Leu Tyr Gly Trp Ser
    1475                1480                1485

Gln Thr Arg Pro Thr Tyr Glu Ala Val Gln Glu Val Thr Gly Gln
    1490                1495                1500

Arg Gly Val Val Ile Thr Arg Ser Thr Phe Pro Ser Ser Gly Arg
    1505                1510                1515

Trp Ala Gly His Trp Leu Gly Asp Asn Thr Ala Ala Trp Asp Gln
    1520                1525                1530

Leu Lys Lys Ser Ile Ile Gly Met Met Glu Phe Ser Leu Phe Gly
    1535                1540                1545

Ile Ser Tyr Thr Gly Ala Asp Ile Cys Gly Phe Phe Gln Asp Ala
    1550                1555                1560

Glu Tyr Glu Met Cys Val Arg Trp Met Gln Leu Gly Ala Phe Tyr
    1565                1570                1575

Pro Phe Ser Arg Asn His Asn Thr Ile Gly Thr Arg Arg Gln Asp
    1580                1585                1590

Pro Val Ser Trp Asp Val Ala Phe Val Asn Ile Ser Arg Thr Val
    1595                1600                1605

Leu Gln Thr Arg Tyr Thr Leu Leu Pro Tyr Leu Tyr Thr Leu Met
    1610                1615                1620

His Lys Ala His Thr Glu Gly Val Thr Val Val Arg Pro Leu Leu
    1625                1630                1635

His Glu Phe Val Ser Asp Gln Val Thr Trp Asp Ile Asp Ser Gln
    1640                1645                1650

Phe Leu Leu Gly Pro Ala Phe Leu Val Ser Pro Val Leu Glu Arg
    1655                1660                1665

Asn Ala Arg Asn Val Thr Ala Tyr Phe Pro Arg Ala Arg Trp Tyr
    1670                1675                1680

Asp Tyr Tyr Thr Gly Val Asp Ile Asn Ala Arg Gly Glu Trp Lys
    1685                1690                1695

Thr Leu Pro Ala Pro Leu Asp His Ile Asn Leu His Val Arg Gly
    1700                1705                1710

Gly Tyr Ile Leu Pro Trp Gln Glu Pro Ala Leu Asn Thr His Leu
    1715                1720                1725

Ser Arg Gln Lys Phe Met Gly Phe Lys Ile Ala Leu Asp Asp Glu
    1730                1735                1740

Gly Thr Ala Gly Gly Trp Leu Phe Trp Asp Asp Gly Gln Ser Ile
    1745                1750                1755
```

| | | | | | | | | | | |
|---|---|---|---|---|---|---|---|---|---|---|
| Asp | Thr | Tyr | Gly | Lys | Gly | Leu | Tyr | Tyr | Leu | Ala | Ser | Phe | Ser | Ala |
| | 1760 | | | | 1765 | | | | 1770 | |

Ser Gln Asn Thr Met Gln Ser His Ile Ile Phe Asn Asn Tyr Ile
  1775            1780                1785

Thr Gly Thr Asn Pro Leu Lys Leu Gly Tyr Ile Glu Ile Trp Gly
  1790            1795                1800

Val Gly Ser Val Pro Val Thr Ser Val Ser Ile Ser Val Ser Gly
  1805            1810                1815

Met Val Ile Thr Pro Ser Phe Asn Asn Asp Pro Thr Thr Gln Val
  1820            1825                1830

Leu Ser Ile Asp Val Thr Asp Arg Asn Ile Ser Leu His Asn Phe
  1835            1840                1845

Thr Ser Leu Thr Trp Ile Ser Thr Leu
  1850            1855

<210> SEQ ID NO 8
<211> LENGTH: 6513
<212> TYPE: DNA
<213> ORGANISM: Homo sapiens

<400> SEQUENCE: 8

```
attgctaagc catccttcag acagagaggg agcggctgca agaggtaatg agagatggca      60
agaaagaagc tgaaaaaatt tactactttg gagattgtgc tcagtgttct tctgcttgtg     120
ttgtttatca tcagtattgt tctaattgtg cttttagcca aagagtcact gaaatcaaca     180
gccccagatc ctgggacaac tggtacccca gatcctggga caactggtac cccagatcct     240
ggaacaactg gtaccacaca tgctaggaca acgggtcccc cagatcctgg aacaactggt     300
accactcctg tttctgctga atgtccagtg gtaaatgaat tggaacgaat taattgcatc     360
cctgaccagc cgccaacaaa ggccacatgt gaccaacgtg gctgttgctg gaatcccccag    420
ggagctgtaa gtgttccctg gtgctactat tccaagaatc atagctacca tgtagagggc     480
aaccttgtca acacaaatgc aggattcaca gcccggttga aaaatctgcc ttcttcacca     540
gtgtttggaa gcaatgttga caatgttctt ctcacagcag aatatcagac atctaatcgt     600
ttccacttta agttgactga ccaaaccaat aacaggtttg aagtgcccca cgaacacgtg     660
cagtccttca gtggaaatgc tgctgcttct tgacctacc aagttgaaat ctccagacag      720
ccatttagca tcaaagtgac cagaagaagc aacaatcgtg ttttgtttga ctcgagcatt     780
gggccctac tgtttgctga ccagttcttg cagctctcca ctcgactgcc tagcactaac      840
gtgtatggcc tgggagagca tgtgcaccag cagtatcggc atgatatgaa ttggaagacc      900
tggcccatat ttaacagaga cacaactccc aatggaaacg gaactaattt gtatggtgcg     960
cagacattct tcttgtgcct tgaagatgct agtggattgt cctttggggt gtttctgatg    1020
aacagcaatg ccatggaggt tgtccttcag cctgcgccag ccatcactta ccgcaccatt    1080
gggggcattc tcgacttcta tgtgttcttg ggaaacactc agagcaagt tgttcaagaa     1140
tatctagagc tcattgggcg gccagccctt ccctcctact gggcgcttgg atttcacctc    1200
agtcgttacg aatatggaac cttagacaac atgaggggaag tcgtggagag aaatcgcgca    1260
gcacagctcc cttatgatgt tcagcatgct gatattgatt atatgatga gagaagggac    1320
ttcacttatg attcagtgga ttttaaaggc ttccctgaat tgtcaacga gttacacaat   1380
aatggacaga agcttgtcat cattgtggat ccagccatct ccaacaactc ttcctcaagt   1440
aaacctatg gcccatatga caggggttca gatatgaaga tatgggtgaa tagttcagat   1500
```

```
ggagtgactc cactcattgg ggaggtctgg cctggacaaa ctgtgtttcc tgattatacc    1560
aatcccaact gtgctgtttg gtggacaaag gaatttgagc ttttcacaa tcaagtagag     1620 tttgatggaa tctggattga tatgaatgaa gtctccaact ttgttgatgg ttcggtctca    1680
ggatgttcca caaacaacct aaataatccc ccattcactc ccagaatcct ggatgggtac    1740
ctgttctgca agactctctg tatggatgca gtgcagcact ggggcaagca gtatgacatt    1800
cacaatctgt atggctactc catggcggtc gccacagcag aagctgccaa gactgtgttc    1860
cctaataaga gaagcttcat tctgacccgt tctacctttg cgggctctgg caagtttgca    1920
gcacattggt taggagacaa cactgccacc tgggatgacc tgagatggtc catccctggc    1980
gtgcttgagt tcaaccttt tggcatccca atggtgggtc ctgacatatg tggctttgct    2040
ttggacaccc ctgaggagct ctgtaggcgg tggatgcagt tgggtgcatt ttatccgttt    2100
tctagaaatc acaatggcca aggctacaag gaccaggatc ctgcctcctt tggagctgac    2160
tccctgctgt tgaattcctc caggcactac cttaacatcc gctatactct attgccctac    2220
ctatacaccc tcttcttccg tgctcacagc cgagggggaca cggtgccagg ccccttttg    2280 catgagttct acgaggacaa cagcacttgg gatgtgcacc aacagttctt atggggggcccc  2340 ggcctcctca tcactccagt tctggatgaa ggtgcagaga aagtgatggc atatgtgcct    2400
gatgctgtct ggtatgacta cgagactggg agccaagtga gatggaggaa gcaaaaagtc    2460
gagatggaac ttcctggaga caaaattgga cttcccttc gaggaggcta catcttcccc     2520
acacagcagc caaatacaac cactctggcc agtcgaaaga accctcttgg tcttatcatt    2580
gccctagatg agaacaaaga agcaaaagga gaacttttct gggataatgg ggaaacgaag    2640
gatactgtgg ccaataaagt gtatcttta tgtgagtttt ctgtcactca aaaccgcttg     2700
gaggtgaata tttcacaatc aacctacaag gaccccaata ttttagcatt taatgagatt    2760
aaaattcttg ggacggagga acctagcaat gttacagtga acacaatgg tgtcccaagt    2820 cagacttctc ctacagtcac ttatgattct aacctgaagg ttgccattat cacagatatt    2880
gatcttctcc tgggagaagc atacacagtg gaatggagca taaagataag ggatgaagaa    2940
aaaatagact gttaccctga tgagaatggt gcttctgccg aaaactgcac tgcccgtggc    3000
tgtatctggg aggcatccaa ttcttctgga gtccctttt gctattttgt caacgaccta    3060
tactctgtca gtgatgttca gtataattcc catggggcca cagctgacat ctccttaaag    3120
tcttccgttt atgccaatgc cttcccctcc acacccgtga accccttcg cctggatgtc    3180 acttaccata gaatgaaat gctgcagttc aagatttatg atcccaacaa gaatcggtat    3240
gaagttccag tccctctgaa catacccagc atgccatcca gcacccctga gggtcaactc    3300
tatgatgtgc tcattaagaa gaatccattt gggattgaaa ttcgccggaa gagtacaggc    3360
actataattt gggactctca gctccttggc tttaccttca gtgacatgtt tatccgcatc    3420
tccacccgcc ttccctccaa gtacctctat ggctttgggg aaactgagca caggtcctat    3480
aggagagact ggagtggca cacttggggg atgttctccc gagaccagcc cccagggtac    3540
aagaagaatt cctatggtgt ccaccctac tacatggggc tggaggagga cggcagtgcc    3600 catgagtgc cctgctgaa cagcaatgcc atggatgtga cgttccagcc cctgcctgcc    3660
ttgacatacc gcaccacagg gggagttctg gactttatg tgttcttggg gccgactcca    3720
gagcttgtca cccagcagta cactgagttg attggccggc ctgtgatggt accttactgg    3780 tctttgggggt tccagctgtg tcgctatggc taccagaatg actctgagat cgccagcttg    3840
tatgatgaga tggtggctgc ccagatccct tatgatgtgc agtactcaga catcgactac    3900
```

```
atggagcggc agctggactt caccctcagc cccaagtttg ctgggtttcc agctctgatc    3960
aatcgcatga aggctgatgg gatgcgggtc atcctcattc tggatccagc catttctggc    4020
aatgagacac agcctcatcc tgccttcact cggggcgtgg aggatgacgt cttcatcaaa    4080
tacccaaatg atggagacat tgtctgggga aggtctggc ctgattttcc tgatgttgtt    4140
gtgaatgggt ctctagactg gacagccaa gtggagctat atcgagctta tgtggccttc    4200
ccagactttt tccgtaattc aactgccaag tggtggaaga gggaaataga agaactatac    4260
aacaatccac agaatccaga gaggagcttg aagtttgatg gcatgtggat tgatatgaat    4320
gaaccatcaa gcttcgtgaa tggggcagtt tctccaggct gcagggacgc ctctctgaac    4380
caccctccct acatgccaca tttggagtcc agggacaggg gcctgagcag caagacccctt    4440
tgtatggaga gtcagcagat cctcccagac ggctccctgg tgcagcacta caacgtgcac    4500
aacctgtatg ggtggtccca gaccagaccc acatacgaag ccgtgcagga ggtgacggga    4560
cagcgagggg tcgtcatcac ccgctccaca tttccctctt ctggccgctg ggcaggacat    4620
tggctgggag acaacacggc cgcatgggat cagctgaaga agtctatcat ggcatgatg    4680
gagttcagcc tcttcggcat atcctatacg ggagcagata tctgtgggtt ctttcaagat    4740
gctgaatatg agatgtgtgt tcgctggatg cagctggggg ccttttaccc cttctcaaga    4800
aaccacaaca ccattgggac caggagacaa gaccctgtgt cctgggatgt tgcttttgtg    4860
aatatttcca gaactgtcct gcagaccaga tacaccctgt gccatatctc gtataccttg    4920
atgcataagg cccacacgga gggcgtcact gttgtgcggc ctctgctcca tgagttttgtg    4980
tcagaccagg tgacatggga catagacagt cagttcctgc tgggcccagc cttcctggtc    5040
agccctgtcc tggagcgtaa tgccagaaat gtcactgcat atttccctag agcccgctgg    5100
tatgattact acacgggtgt ggatattaat gcaagaggag agtggaagac cttgccagcc    5160
cctcttgacc acattaatct tcatgtccgt gggggctaca tcctgccctg gcaagagcct    5220
gcactgaaca cccacttaag ccgccagaaa ttcatgggct tcaaaattgc cttggatgat    5280
gaaggaactg ctgggggctg gctcttctgg gatgatgggc aaagcattga tacctatggg    5340
aaaggactct attacttggc cagcttttct gccagccaga atacgatgca aagccatata    5400
attttcaaca attacatcac tggtacaaat ccttttgaaac tgggctacat tgaaatctgg    5460
ggagtgggca gtgtccccgt taccagtgtc agcatctctg tgagtggcat ggtcataaca    5520
ccctccttca acaatgaccc cacgacacag gtattaagca tcgatgtgac tgacagaaac    5580
atcagcctac ataattttac ttcattgacg tggataagca ctctgtgaat ttttacagca    5640
agattctaac taactatgaa tgactttgaa actacttata cttcatactc ataaaaatta    5700
ttgtgtgttg ctaatttgtt catcccact attggtgaaa tatttctgtt aattttgtta    5760
tatgtttttt gtgtgaaccc taaaggttaa accttagccc tgtgggatag gcagttaggg    5820
aggtgtggaa aatctatgca ttaccttaat gtctctgtgt ggttagtatg gtagtgactg    5880
ttcatcatat gacatttact gaagatgaac tgggtccatg atgaagtgtg tgtatgtcca    5940
cgtttgtaat catagaatgg acccccattct tttgttaaat acacaagaga aagctttctg    6000
tgacagttcc aggtcttgaa gctaatcagc atctcaagaa agtatccaga aagaacatct    6060
gctagttggt tataggcggt gggaggaata atatacctaa ttggttatag gtgggggag    6120
catgataagc aaagaaaagg caaacacaag gaaagatcag atgaaacaga agatgatagt    6180
aaaagtgatc ctaagtaaga acataatgta aaattgtcag cagcctcatg gggaggaaaa    6240
```

-continued

```
aggaagagtc aactcacttg aagaagaggg tcttgagaaa tccttagcat aaagggctac    6300
tggtgagatt gagatctgag caggcaaagc tcaaaagaga gtttggaggt taaaaataat    6360
ttatttttgc agtagtgtgc tttgaaatgt gtaaatctta tttctaatgt atacaaccac    6420
atttcacata aaatatgca atttatatgc cagataaaaa taaaacaagt gaatttgcaa    6480
gtgaaaaaaa aaaaaaaaaa aaaaaaaaaa aaa                                 6513
```

<210> SEQ ID NO 9
<211> LENGTH: 1927
<212> TYPE: PRT
<213> ORGANISM: Homo sapiens

<400> SEQUENCE: 9

| Met | Glu | Leu | Ser | Trp | His | Val | Val | Phe | Ile | Ala | Leu | Leu | Ser | Phe |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Cys Trp Gly Ser Asp Trp Glu Ser Asp Arg Asn Phe Ile Ser Thr Ala
                20                  25                  30

Gly Pro Leu Thr Asn Asp Leu Leu His Asn Leu Ser Gly Leu Leu Gly
            35                  40                  45

Asp Gln Ser Ser Asn Phe Val Ala Gly Asp Lys Asp Met Tyr Val Cys
50                  55                  60

His Gln Pro Leu Pro Thr Phe Leu Pro Glu Tyr Phe Ser Ser Leu His
65                  70                  75                  80

Ala Ser Gln Ile Thr His Tyr Lys Val Phe Leu Ser Trp Ala Gln Leu
                85                  90                  95

Leu Pro Ala Gly Ser Thr Gln Asn Pro Asp Glu Lys Thr Val Gln Cys
            100                 105                 110

Tyr Arg Arg Leu Leu Lys Ala Leu Lys Thr Ala Arg Leu Gln Pro Met
        115                 120                 125

Val Ile Leu His His Gln Thr Leu Pro Ala Ser Thr Leu Arg Arg Thr
130                 135                 140

Glu Ala Phe Ala Asp Leu Phe Ala Asp Tyr Ala Thr Phe Ala Phe His
145                 150                 155                 160

Ser Phe Gly Asp Leu Val Gly Ile Trp Phe Thr Phe Ser Asp Leu Glu
                165                 170                 175

Glu Val Ile Lys Glu Leu Pro His Gln Glu Ser Arg Ala Ser Gln Leu
            180                 185                 190

Gln Thr Leu Ser Asp Ala His Arg Lys Ala Tyr Glu Ile Tyr His Glu
        195                 200                 205

Ser Tyr Ala Phe Gln Gly Gly Lys Leu Ser Val Leu Arg Ala Glu
210                 215                 220

Asp Ile Pro Glu Leu Leu Glu Pro Pro Ile Ser Ala Leu Ala Gln
225                 230                 235                 240

Asp Thr Val Asp Phe Leu Ser Leu Asp Leu Ser Tyr Glu Cys Gln Asn
                245                 250                 255

Glu Ala Ser Leu Arg Gln Lys Leu Ser Lys Leu Gln Thr Ile Glu Pro
            260                 265                 270

Lys Val Lys Val Phe Ile Phe Asn Leu Lys Leu Pro Asp Cys Pro Ser
        275                 280                 285

Thr Met Lys Asn Pro Ala Ser Leu Leu Phe Ser Phe Glu Ala Ile
                290                 295                 300

Asn Lys Asp Gln Val Leu Thr Ile Gly Phe Asp Ile Asn Glu Phe Leu
305                 310                 315                 320

Ser Cys Ser Ser Ser Ser Lys Lys Ser Met Ser Cys Ser Leu Thr Gly

```
                    325                 330                 335
        Ser Leu Ala Leu Gln Pro Asp Gln Gln Asp His Glu Thr Thr Asp
                        340                 345                 350
        Ser Ser Pro Ala Ser Ala Tyr Gln Arg Ile Trp Glu Ala Phe Ala Asn
                    355                 360                 365
        Gln Ser Arg Ala Glu Arg Asp Ala Phe Leu Gln Asp Thr Phe Pro Glu
                    370                 375                 380
        Gly Phe Leu Trp Gly Ala Ser Thr Gly Ala Phe Asn Val Glu Gly Gly
        385                 390                 395                 400
        Trp Ala Glu Gly Gly Arg Gly Val Ser Ile Trp Asp Pro Arg Arg Pro
                        405                 410                 415
        Leu Asn Thr Thr Glu Gly Gln Ala Thr Leu Glu Val Ala Ser Asp Ser
                    420                 425                 430
        Tyr His Lys Val Ala Ser Asp Val Ala Leu Leu Cys Gly Leu Arg Ala
                    435                 440                 445
        Gln Val Tyr Lys Phe Ser Ile Ser Trp Ser Arg Ile Phe Pro Met Gly
                    450                 455                 460
        His Gly Ser Ser Pro Ser Leu Pro Gly Val Ala Tyr Tyr Asn Lys Leu
        465                 470                 475                 480
        Ile Asp Arg Leu Gln Asp Ala Gly Ile Glu Pro Met Ala Thr Leu Phe
                        485                 490                 495
        His Trp Asp Leu Pro Gln Ala Leu Gln Asp His Gly Gly Trp Gln Asn
                    500                 505                 510
        Glu Ser Val Val Asp Ala Phe Leu Asp Tyr Ala Ala Phe Cys Phe Ser
                    515                 520                 525
        Thr Phe Gly Asp Arg Val Lys Leu Trp Val Thr Phe His Glu Pro Trp
                    530                 535                 540
        Val Met Ser Tyr Ala Gly Tyr Gly Thr Gly Gln His Pro Pro Gly Ile
        545                 550                 555                 560
        Ser Asp Pro Gly Val Ala Ser Phe Lys Val Ala His Leu Val Leu Lys
                        565                 570                 575
        Ala His Ala Arg Thr Trp His His Tyr Asn Ser His Arg Pro Gln
                    580                 585                 590
        Gln Gln Gly His Val Gly Ile Val Leu Asn Ser Asp Trp Ala Glu Pro
                    595                 600                 605
        Leu Ser Pro Glu Arg Pro Glu Asp Leu Arg Ala Ser Glu Arg Phe Leu
                    610                 615                 620
        His Phe Met Leu Gly Trp Phe Ala His Pro Val Phe Val Asp Gly Asp
        625                 630                 635                 640
        Tyr Pro Ala Thr Leu Arg Thr Gln Ile Gln Gln Met Asn Arg Gln Cys
                        645                 650                 655
        Ser His Pro Val Ala Gln Leu Pro Glu Phe Thr Glu Ala Glu Lys Gln
                    660                 665                 670
        Leu Leu Lys Gly Ser Ala Asp Phe Leu Gly Leu Ser His Tyr Thr Ser
                    675                 680                 685
        Arg Leu Ile Ser Asn Ala Pro Gln Asn Thr Cys Ile Pro Ser Tyr Asp
                    690                 695                 700
        Thr Ile Gly Gly Phe Ser Gln His Val Asn His Val Trp Pro Gln Thr
        705                 710                 715                 720
        Ser Ser Ser Trp Ile Arg Val Val Pro Trp Gly Ile Arg Arg Leu Leu
                        725                 730                 735
        Gln Phe Val Ser Leu Glu Tyr Thr Arg Gly Lys Val Pro Ile Tyr Leu
                    740                 745                 750
```

```
Ala Gly Asn Gly Met Pro Ile Gly Glu Ser Glu Asn Leu Phe Asp Asp
            755                 760                 765

Ser Leu Arg Val Asp Tyr Phe Asn Gln Tyr Ile Asn Glu Val Leu Lys
    770                 775                 780

Ala Ile Lys Glu Asp Ser Val Asp Val Arg Ser Tyr Ile Ala Arg Ser
785                 790                 795                 800

Leu Ile Asp Gly Phe Glu Gly Pro Ser Gly Tyr Ser Gln Arg Phe Gly
                805                 810                 815

Leu His His Val Asn Phe Ser Asp Ser Ser Lys Ser Arg Thr Pro Arg
                820                 825                 830

Lys Ser Ala Tyr Phe Phe Thr Ser Ile Ile Glu Lys Asn Gly Phe Leu
                835                 840                 845

Thr Lys Gly Ala Lys Arg Leu Leu Pro Pro Asn Thr Val Asn Leu Pro
    850                 855                 860

Ser Lys Val Arg Ala Phe Thr Phe Pro Ser Glu Val Pro Ser Lys Ala
865                 870                 875                 880

Lys Val Val Trp Glu Lys Phe Ser Ser Gln Pro Lys Phe Glu Arg Asp
                885                 890                 895

Leu Phe Tyr His Gly Thr Phe Arg Asp Asp Phe Leu Trp Gly Val Ser
                900                 905                 910

Ser Ser Ala Tyr Gln Ile Glu Gly Ala Trp Asp Ala Asp Gly Lys Gly
                915                 920                 925

Pro Ser Ile Trp Asp Asn Phe Thr His Thr Pro Gly Ser Asn Val Lys
    930                 935                 940

Asp Asn Ala Thr Gly Asp Ile Ala Cys Asp Ser Tyr His Gln Leu Asp
945                 950                 955                 960

Ala Asp Leu Asn Met Leu Arg Ala Leu Lys Val Lys Ala Tyr Arg Phe
                965                 970                 975

Ser Ile Ser Trp Ser Arg Ile Phe Pro Thr Gly Arg Asn Ser Ser Ile
                980                 985                 990

Asn Ser His Gly Val Asp Tyr Tyr Asn Arg Leu Ile Asn Gly Leu Val
            995                 1000                1005

Ala Ser Asn Ile Phe Pro Met Val Thr Leu Phe His Trp Asp Leu
    1010                1015                1020

Pro Gln Ala Leu Gln Asp Ile Gly Gly Trp Glu Asn Pro Ala Leu
    1025                1030                1035

Ile Asp Leu Phe Asp Ser Tyr Ala Asp Phe Cys Phe Gln Thr Phe
    1040                1045                1050

Gly Asp Arg Val Lys Phe Trp Met Thr Phe Asn Glu Pro Met Tyr
    1055                1060                1065

Leu Ala Trp Leu Gly Tyr Gly Ser Gly Glu Phe Pro Pro Gly Val
    1070                1075                1080

Lys Asp Pro Gly Trp Ala Pro Tyr Arg Ile Ala His Ala Val Ile
    1085                1090                1095

Lys Ala His Ala Arg Val Tyr His Thr Tyr Asp Glu Lys Tyr Arg
    1100                1105                1110

Gln Glu Gln Lys Gly Val Ile Ser Leu Ser Leu Ser Thr His Trp
    1115                1120                1125

Ala Glu Pro Lys Ser Pro Gly Val Pro Arg Asp Val Glu Ala Ala
    1130                1135                1140

Asp Arg Met Leu Gln Phe Ser Leu Gly Trp Phe Ala His Pro Ile
    1145                1150                1155
```

```
Phe Arg Asn Gly Asp Tyr Pro Asp Thr Met Lys Trp Lys Val Gly
1160                     1165                1170

Asn Arg Ser Glu Leu Gln His Leu Ala Thr Ser Arg Leu Pro Ser
1175                     1180                1185

Phe Thr Glu Glu Glu Lys Arg Phe Ile Arg Ala Thr Ala Asp Val
1190                     1195                1200

Phe Cys Leu Asn Thr Tyr Tyr Ser Arg Ile Val Gln His Lys Thr
1205                     1210                1215

Pro Arg Leu Asn Pro Pro Ser Tyr Glu Asp Gln Glu Met Ala
1220                     1225                1230

Glu Glu Glu Asp Pro Ser Trp Pro Ser Thr Ala Met Asn Arg Ala
1235                     1240                1245

Ala Pro Trp Gly Thr Arg Arg Leu Leu Asn Trp Ile Lys Glu Glu
1250                     1255                1260

Tyr Gly Asp Ile Pro Ile Tyr Ile Thr Glu Asn Gly Val Gly Leu
1265                     1270                1275

Thr Asn Pro Asn Thr Glu Asp Thr Asp Arg Ile Phe Tyr His Lys
1280                     1285                1290

Thr Tyr Ile Asn Glu Ala Leu Lys Ala Tyr Arg Leu Asp Gly Ile
1295                     1300                1305

Asp Leu Arg Gly Tyr Val Ala Trp Ser Leu Met Asp Asn Phe Glu
1310                     1315                1320

Trp Leu Asn Gly Tyr Thr Val Lys Phe Gly Leu Tyr His Val Asp
1325                     1330                1335

Phe Asn Asn Thr Asn Arg Pro Arg Thr Ala Arg Ala Ser Ala Arg
1340                     1345                1350

Tyr Tyr Thr Glu Val Ile Thr Asn Asn Gly Met Pro Leu Ala Arg
1355                     1360                1365

Glu Asp Glu Phe Leu Tyr Gly Arg Phe Pro Glu Gly Phe Ile Trp
1370                     1375                1380

Ser Ala Ala Ser Ala Ala Tyr Gln Ile Glu Gly Ala Trp Arg Ala
1385                     1390                1395

Asp Gly Lys Gly Leu Ser Ile Trp Asp Thr Phe Ser His Thr Pro
1400                     1405                1410

Leu Arg Val Glu Asn Asp Ala Ile Gly Asp Val Ala Cys Asp Ser
1415                     1420                1425

Tyr His Lys Ile Ala Glu Asp Leu Val Thr Leu Gln Asn Leu Gly
1430                     1435                1440

Val Ser His Tyr Arg Phe Ser Ile Ser Trp Ser Arg Ile Leu Pro
1445                     1450                1455

Asp Gly Thr Thr Arg Tyr Ile Asn Glu Ala Gly Leu Asn Tyr Tyr
1460                     1465                1470

Val Arg Leu Ile Asp Thr Leu Leu Ala Ala Ser Ile Gln Pro Gln
1475                     1480                1485

Val Thr Ile Tyr His Trp Asp Leu Pro Gln Thr Leu Gln Asp Val
1490                     1495                1500

Gly Gly Trp Glu Asn Glu Thr Ile Val Gln Arg Phe Lys Glu Tyr
1505                     1510                1515

Ala Asp Val Leu Phe Gln Arg Leu Gly Asp Lys Val Lys Phe Trp
1520                     1525                1530

Ile Thr Leu Asn Glu Pro Phe Val Ile Ala Tyr Gln Gly Tyr Gly
1535                     1540                1545

Tyr Gly Thr Ala Ala Pro Gly Val Ser Asn Arg Pro Gly Thr Ala
```

-continued

```
               1550                1555                1560
Pro Tyr Ile Val Gly His Asn Leu Ile Lys Ala His Ala Glu Ala
   1565                1570                1575
Trp His Leu Tyr Asn Asp Val Tyr Arg Ala Ser Gln Gly Gly Val
   1580                1585                1590
Ile Ser Ile Thr Ile Ser Ser Asp Trp Ala Glu Pro Arg Asp Pro
   1595                1600                1605
Ser Asn Gln Glu Asp Val Glu Ala Ala Arg Arg Tyr Val Gln Phe
   1610                1615                1620
Met Gly Gly Trp Phe Ala His Pro Ile Phe Lys Asn Gly Asp Tyr
   1625                1630                1635
Asn Glu Val Met Lys Thr Arg Ile Arg Asp Arg Ser Leu Ala Ala
   1640                1645                1650
Gly Leu Asn Lys Ser Arg Leu Pro Glu Phe Thr Glu Ser Glu Lys
   1655                1660                1665
Arg Arg Ile Asn Gly Thr Tyr Asp Phe Phe Gly Phe Asn His Tyr
   1670                1675                1680
Thr Thr Val Leu Ala Tyr Asn Leu Asn Tyr Ala Thr Ala Ile Ser
   1685                1690                1695
Ser Phe Asp Ala Asp Arg Gly Val Ala Ser Ile Ala Asp Arg Ser
   1700                1705                1710
Trp Pro Asp Ser Gly Ser Phe Trp Leu Lys Met Thr Pro Phe Gly
   1715                1720                1725
Phe Arg Arg Ile Leu Asn Trp Leu Lys Glu Glu Tyr Asn Asp Pro
   1730                1735                1740
Pro Ile Tyr Val Thr Glu Asn Gly Val Ser Gln Arg Glu Glu Thr
   1745                1750                1755
Asp Leu Asn Asp Thr Ala Arg Ile Tyr Tyr Leu Arg Thr Tyr Ile
   1760                1765                1770
Asn Glu Ala Leu Lys Ala Val Gln Asp Lys Val Asp Leu Arg Gly
   1775                1780                1785
Tyr Thr Val Trp Ser Ala Met Asp Asn Phe Glu Trp Ala Thr Gly
   1790                1795                1800
Phe Ser Glu Arg Phe Gly Leu His Phe Val Asn Tyr Ser Asp Pro
   1805                1810                1815
Ser Leu Pro Arg Ile Pro Lys Ala Ser Ala Lys Phe Tyr Ala Ser
   1820                1825                1830
Val Val Arg Cys Asn Gly Phe Pro Asp Pro Ala Thr Gly Pro His
   1835                1840                1845
Ala Cys Leu His Gln Pro Asp Ala Gly Pro Thr Ile Ser Pro Val
   1850                1855                1860
Arg Gln Glu Glu Val Gln Phe Leu Gly Leu Met Leu Gly Thr Thr
   1865                1870                1875
Glu Ala Gln Thr Ala Leu Tyr Val Leu Phe Ser Leu Val Leu Leu
   1880                1885                1890
Gly Val Cys Gly Leu Ala Phe Leu Ser Tyr Lys Tyr Cys Lys Arg
   1895                1900                1905
Ser Lys Gln Gly Lys Thr Gln Arg Ser Gln Gln Glu Leu Ser Pro
   1910                1915                1920
Val Ser Ser Phe
   1925

<210> SEQ ID NO 10
```

<211> LENGTH: 6274
<212> TYPE: DNA
<213> ORGANISM: Homo sapiens

<400> SEQUENCE: 10

| | | | | | |
|---|---|---|---|---|---|
| gttcctagaa | aatggagctg | tcttggcatg | tagtctttat | tgccctgcta | agttttcat | 60 |
| gctggggtc | agactgggag | tctgatagaa | atttcatttc | caccgctggt | cctctaacca | 120 |
| atgacttgct | gcacaacctg | agtggtctcc | tgggagacca | gagttctaac | tttgtagcag | 180 |
| gggacaaaga | catgtatgtt | tgtcaccagc | cactgcccac | tttcctgcca | gaatacttca | 240 |
| gcagtctcca | tgccagtcag | atcacccatt | ataaggtatt | tctgtcatgg | gcacagctcc | 300 |
| tcccagcagg | aagcacccag | aatccagacg | agaaaacagt | gcagtgctac | cggcgactcc | 360 |
| tcaaggccct | caagactgca | cggcttcagc | ccatggtcat | cctgcaccac | cagaccctcc | 420 |
| ctgccagcac | cctccggaga | accgaagcct | ttgctgacct | cttcgccgac | tatgccacat | 480 |
| tcgccttcca | ctccttcggg | gacctagttg | ggatctggtt | caccttcagt | gacttggagg | 540 |
| aagtgatcaa | ggagcttccc | caccaggaat | caagagcgtc | acaactccag | accctcagtg | 600 |
| atgcccacag | aaaagcctat | gagatttacc | acgaaagcta | tgcttttcag | ggcggaaaac | 660 |
| tctctgttgt | cctgcgagct | gaagatatcc | cggagctcct | gctagaacca | cccatatctg | 720 |
| cgcttgccca | ggacacggtc | gatttcctct | ctcttgattt | gtcttatgaa | tgccaaaatg | 780 |
| aggcaagtct | gcggcagaag | ctgagtaaat | tgcagaccat | tgagccaaaa | gtgaaagttt | 840 |
| tcatcttcaa | cctaaaactc | ccagactgcc | cctccaccat | gaagaaccca | gccagtctgc | 900 |
| tcttcagcct | ttttgaagcc | ataaataaag | accaagtgct | caccattggg | tttgatatta | 960 |
| atgagtttct | gagttgttca | tcaagttcca | agaaaagcat | gtcttgttct | ctgactggca | 1020 |
| gcctggccct | tcagcctgac | cagcagcagg | accacgagac | cacggactcc | tctcctgcct | 1080 |
| ctgcctatca | gagaatctgg | gaagcatttg | ccaatcagtc | cagggcggaa | agggatgcct | 1140 |
| tcctgcagga | tactttccct | gaaggcttcc | tctggggtgc | ctccacagga | gcctttaacg | 1200 |
| tggaaggagg | ctgggccgag | ggtgggagag | ggtgagcat | ctgggatcca | cgcaggcccc | 1260 |
| tgaacaccac | tgagggccaa | gcgacgctgg | aggtggccag | cgacagttac | acaaggtag | 1320 |
| cctctgacgt | cgccctgctt | tgcggcctcc | gggctcaggt | gtacaagttc | tccatctcct | 1380 |
| ggtcccggat | cttccccatg | gggcacggga | gcagccccag | cctcccaggc | gttgcctact | 1440 |
| acaacaagct | gattgacagg | ctacaggatg | cgggcatcga | gcccatggcc | acgctgttcc | 1500 |
| actgggacct | gcctcaggcc | ctgcaggatc | atggtggatg | gcagaatgag | agcgtggtgg | 1560 |
| atgccttcct | ggactatgcg | gccttctgct | tctccacatt | tggggaccgt | gtgaagctgt | 1620 |
| gggtgacctt | ccatgagccg | tgggtgatga | gctacgcagg | ctatggcacc | ggccagcacc | 1680 |
| ctcccggcat | ctctgaccca | ggagtggcct | cttttaaggt | ggctcacttg | gtcctcaagg | 1740 |
| ctcatgccag | aacttggcac | cactacaaca | gccatcatcg | cccacagcag | caggggcacg | 1800 |
| tgggcattgt | gctgaactca | gactgggcag | aaccctgtc | tccagagagg | cctgaggacc | 1860 |
| tgagagcctc | tgagcgcttc | ttgcacttca | tgctgggctg | gtttgcacac | cccgtctttg | 1920 |
| tggatggaga | ctaccagccc | accctgagga | cccagatcca | acagatgaac | agacagtgct | 1980 |
| cccatcctgt | ggctcaactc | cccgagttca | cagaggcaga | gaagcagctc | ctgaaaggct | 2040 |
| ctgctgattt | tctgggtctg | tcgcattaca | cctcccgcct | catcagcaac | gcccacacaaa | 2100 |
| acacctgcat | ccctagctat | gataccattg | gaggcttctc | ccaacacgtg | aaccatgtgt | 2160 |
| ggccccagac | ctcatcctct | tggattcgtg | tggtgccctg | ggggataagg | aggctgttgc | 2220 |

```
agtttgtatc cctggaatac acaagaggaa aagttccaat ataccttgcc gggaatggca    2280
tgcccatagg ggaaagtgaa aatctctttg atgattcctt aagagtagac tacttcaatc    2340
aatatatcaa tgaggtgctc aaggctatca aggaagactc tgtggatgtt cgttcctaca    2400
ttgctcgttc cctcattgat ggcttcgaag gcccttctgg ttacagccag cggtttggcc    2460
tgcaccacgt caacttcagc gacagcagca agtcaaggac tcccaggaaa tctgcctact    2520
ttttcactag catcatagaa aagaacggtt tcctcaccaa gggggcaaaa agactgctac    2580
cacctaatac agtaaacctc ccctccaaag tcagagcctt cacttttcca tctgaggtgc    2640
cctccaaggc taaagtcgtt tgggaaaagt tctccagcca acccaagttc gaaagagatt    2700
tgttctacca cgggacgttt cgggatgact ttctgtgggg cgtgtcctct tccgcttatc    2760
agattgaagg cgcgtgggat gccgatggca aggcccccag catctgggat aactttaccc    2820
acacaccagg gagcaatgtg aaagacaatg ccactggaga catcgcctgt gacagctatc    2880
accagctgga tgccgatctg aatatgctcc gagctttgaa ggtgaaggcc taccgcttct    2940
ctatctcctg gtctcggatt ttcccaactg ggagaaacag ctctatcaac agtcatgggg    3000
ttgattatta caacaggctg atcaatggct tggtggcaag caacatcttt ccatggtga    3060 cattgttcca ttgggacctg ccccaggccc tccaggatat cggaggctgg gagaatcctg    3120
ccttgattga cttgtttgac agctacgcag acttttgttt ccagaccttt ggtgatagag    3180
tcaagttttg gatgactttt aatgagccca tgtacctggc atggctaggt tatggctcag    3240
gggaatttcc cccaggggtg aaggaccag gctgggcacc atataggata gcccacgccg    3300
tcatcaaagc ccatgccaga gtctatcaca cgtacgatga gaaatacagg caggagcaga    3360 aggggggtcat ctcgctgagc ctcagtacac actgggcaga gcccaagtca ccaggggtcc    3420
ccagagatgt ggaagccgct gaccgaatgc tgcagttctc cctgggctgg tttgctcacc    3480 ccattttag aaacggagac tatcctgaca ccatgaagtg gaaagtgggg aacaggagtg    3540
aactgcagca cttagccacc tcccgcctgc caagcttcac tgaggaagag aagaggttca    3600
tcagggcgac ggccgacgtc ttctgcctca acacgtacta ctccagaatc gtgcagcaca    3660
aaacacccag gctaaaccca ccctcctacg aagacgacca ggagatggct gaggaggagg    3720 accccttcgtg gccttccacg gcaatgaaca gagctgcgcc ctgggggacg cgaaggctgc    3780
tgaactggat caaggaagag tatggtgaca tccccattta catcaccgaa aacggagtgg    3840
ggctgaccaa tccgaacacg gaggatactg ataggatatt ttaccacaaa acctacatca    3900
atgaggcttt gaaagcctac aggctcgatg gtatagacct tcgagggtat gtcgcctggt    3960
ctctgatgga caactttgag tggctaaatg gctacacggt caagtttgga ctgtaccatg    4020
ttgatttcaa caacacgaac aggcctcgca cagcaagagc ctcgccagg tactacacag    4080 aggtcattac caacaacggc atgccactgg ccagggagga tgagtttctg tacggacggt    4140
ttcctgaggg cttcatctgg agtgcagctt ctgctgcata tcagattgaa ggtgcgtgga    4200
gagcagatgg caaaggactc agcatttggg acacgttttc tcacacacca ctgagggttg    4260
agaacgatgc cattggagac gtggcctgtg acagttatca caagattgct gaggatctgg    4320
tcaccctgca gaacctgggc gtgtcccact accgtttttc catctcctgg tctcgcatcc    4380
tccctgatgg aaccaccagg tacatcaatg aagcgggcct gaactactac gtgaggctca    4440
tcgatacact gctggccgcc agcatccagc cccaggtgac catttaccac tgggacctac    4500
cacagacgct ccaagatgta ggaggctggg agaatgagac catcgtgcag cggtttaagg    4560
```

```
agtatgcaga tgtgctcttc cagaggctgg gagacaaggt gaagttttgg atcacgctga    4620
atgagccctt tgtcattgct taccagggct atggctacgg aacagcagct ccaggagtct    4680
ccaataggcc tggcactgcc ccctacattg ttggccacaa tctaataaag gctcatgctg    4740
aggcctggca tctgtacaac gatgtgtacc gcgccagtca aggtggcgtg atttccatca    4800
ccatcagcag tgactgggct gaacccagag atccctctaa ccaggaggat gtggaggcag    4860
ccaggagata tgttcagttc atgggaggct ggtttgcaca tcctattttc aagaatggag    4920
attacaatga ggtgatgaag acgcggatcc gtgacaggag cttggctgca ggcctcaaca    4980
agtctcggct gccagaattt acagagagtg agaagaggag gatcaacggc acctatgact    5040
tttttgggtt caatcactac accactgtcc tcgcctacaa cctcaactat gccactgcca    5100
tctcttcttt tgatgcagac agaggagttg cttccatcgc agatcgctcg tggccagact    5160
ctggctcctt ctggctgaag atgacgcctt ttggcttcag gaggatcctg aactggttaa    5220
aggaggaata caatgaccct ccaatttatg tcacagagaa tggagtgtcc cagcgggaag    5280
aaacagacct caatgacact gcaaggatct actaccttcg gacttacatc aatgaggccc    5340
tcaaagctgt gcaggacaag gtggaccttc gaggatacac agtttggagt gcgatggaca    5400
attttgagtg ggccacaggc ttttcagaga gatttggtct gcattttgtg aactacagtg    5460
acccttctct gccaaggatc cccaaagcat cagcgaagtt ctacgcctct gtggtccgat    5520
gcaatggctt ccctgacccc gctacagggc ctcacgcttg tctccaccag ccagatgctg    5580
gacccaccat cagccccgtg agacaggagg aggtgcagtt cctggggcta atgctcggca    5640
ccacagaagc acagacagct ttgtacgttc tcttttctct tgtgcttctt ggagtctgtg    5700
gcttggcatt tctgtcatac aagtactgca agcgctctaa gcaagggaaa acacaacgaa    5760
gccaacagga attgagcccg gtgtcttcat tctgatgagt taccacctca agttctatga    5820
agcaggccta gtttcttcat ctatgtttac cggccaccaa acaccttagg gtcttagact    5880
ctgctgatac tggacttctc cataaagtcc tgctgcaccg ttagagatga ctttaatctt    5940
gaatgatttc gacttgctga gtaaaatgga aatatctcca tcttgctcca gtatcagagt    6000
tcatttgggc atttgagaag caagtagctc ttgcggaaac gtgtagatac tggtctagtg    6060
ggtctgtgaa ccacttaatt gaacttaaca gggctgtttt aagtttcaga gttgttaagg    6120
gttgttaagg gagcaaaaac cgtaaaaatc cttcctataa gaagaaatca actccattgc    6180
atagactgca atatcatctc ctgcccttct gcaagctctc cctagcttca catcttgtgt    6240
tttccagaaa ataaaaacag cagactgtcc tttc                                6274
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcgaaaaac cttacctagc c                                              21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gacgtgtgag gccctagcc                                                    19

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cacaggtgct gcatggctgt cgt                                               23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ccgcaaggga atctggacac aggt                                              24

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgccagcmg ccgcggtaa                                                    19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gactaccagg gtatctaat                                                    19

<210> SEQ ID NO 17
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cggtggatga tgtggattaa ttcgaygcaa cgcgaaaaac cttacsyagc cttgacatgy        60
crrgaabbyb bvdkrr                                                       76

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 18
ccctctgttc cgaccattgt atgacgtgtg argcccyagc crtaagggcc atgaggactt      60

<210> SEQ ID NO 19
<211> LENGTH: 100
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gtrcccghaa grgaryyygr rcacaggtgc tgcatggctg tcgtcagctc gtgtcgtgrg      60
atrtyrrgtt argtcccgca rcragcgcaa ccctygwcay                          100

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatgcactg ctgtgatgag                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cccactgacc tatcctcgtg                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aacaggcacg tggaggagtt                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccacctcag cctcttgagt                                                 20

<210> SEQ ID NO 24
<211> LENGTH: 41
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 24
gccttgccag cccgctcagt cagagtttga tcctggctca g                          41

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(27)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 25
gcctccctcg cgccatcagn nnnnnnncat gctgcctccc gtaggagt                   48

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcttcatgag ttttatgagg atacgaac                                         28

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tttgcaccag attcataatc atacc                                            25

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cagatactgt gagtgcctac atccctgatg ctatt                                 35

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
taccttgatg cataaggccc a                                                21
```

```
<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggcattacgc tccaggaca                                               19

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
cgtcactgtt gtgcggcctc tgc                                          23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caggaatcaa gagcgtcaca act                                          23

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaatcgaccg tgtcctggg                                               19

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tcctgctaga accacccata tctgcgct                                     28

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctcatgccc aatggactg                                               19
```

```
<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cggaccttgg cgtagatgtc                                               20

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
acagcgccag caccctcttc acc                                           23

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agttagatga ggaagtcaaa gcaa                                          24

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
taggctgtcg gtagctgg                                                 18

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
acaaagcttg aaaagactca gaggatatga tgatgtc                            37

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
catgcgctga acttcatcaa a                                             21

<210> SEQ ID NO 42
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggttggacgc tgtccacttc                                              20

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
cggccgtctt tcagcagctc ttcc                                         24

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggcagccaag tgaaaaccag                                              20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tccggatggt gatgtagcg                                               19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
accaccagcg gctggagctg g                                            21

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agcctcgcct ttgccga                                                 17

<210> SEQ ID NO 48
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctggtgcctg gggcg                                                       15

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ccgccgcccg tccacacccg cc                                               22

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cctgttcgac agtcagccg                                                   19

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgaccaaatc cgttgactcc                                                  20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
cgtcgccagc cgagccaca                                                   19

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aacgctagct acaggctt                                                    18

<210> SEQ ID NO 54
<211> LENGTH: 18
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 54
ccaatgtggg ggaccttc                                                 18

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ggagyatgtg gtttaattcg aagca                                         25

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
agctgacgac aaccatgcac                                               20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gtgccagcmg ccgcggtaa                                                19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
gactaccagg gtatctaat                                                19

<210> SEQ ID NO 59
<211> LENGTH: 220
<212> TYPE: DNA
<213> ORGANISM: Sutterella sp.

<400> SEQUENCE: 59
ttgacatgcc aggaatcctg aagagattcg ggagtgcccg caagggaatc tggacacagg    60
tgctgcatgg ctgtcgtcag ctcgtgtcgt gagatgttgg gttaagtccc gcaacgagcg   120 caaccctttgt cactagttgc tacgcaagag cactctagtg agactgccgg tgacaaaccg   180
gaggaaggtg gggatgacgt caagtcctca tggcccttat                         220

<210> SEQ ID NO 60

```
<211> LENGTH: 220
<212> TYPE: DNA
<213> ORGANISM: Sutterella sp.

<400> SEQUENCE: 60
ttgacatgcc aggaaggcct gagagatcag gccgtgcccg caagggaatc tggacacagg      60
tgctgcatgg ctgtcgtcag ctcgtgtcgt gagatgttgg gttaagtccc gcaacgagcg     120
caaccttgt cattagttgc tacgaaaggg cactctaatg agactgccgg tgacaaaccg      180
gaggaaggtg gggatgacgt caagtcctca tggcccttat                           220

<210> SEQ ID NO 61
<211> LENGTH: 676
<212> TYPE: DNA
<213> ORGANISM: Sutterlla sp.

<400> SEQUENCE: 61
tacgtagggt gcaagcgtta atcggaatta ctgggcgtaa agcgtgcgca ggcggttctg      60
taagacagat gtgaaatccc cgggctcaac ctgggaattg catttgtgac tgcaggacta     120
gagttcatca gagggggtg gaattccaag tgtagcagtg aaatgcgtag atatttggaa      180
gaacaccaat ggcgaaggca gccccctggg atgcgactga cgctcatgca cgaaagcgtg     240
gggagcaaac aggattagat accctggtag tccacgccct aaacgatgtc tactggttgt     300
tggggtttat taaccttggt aacgaagcta acgcgtgaag tagaccgcct ggggagtacg     360
gtcgcaagat taaaactcaa aggaattgac ggggacccgc acaagcggtg gatgatgtgg     420
attaattcga tgcaacgcga aaaaccttac ctagccttga catgccagga atcctgaaga     480
gattcgggag tgcccgcaag ggaatctgga cacaggtgct gcatggctgt cgtcagctcg     540
tgtcgtgaga tgttgggtta agtcccgcaa cgagcgcaac ccttgtcact agttgctacg     600
caagagcact ctagtgagac tgccggtgac aaaccggagg aaggtgggga tgacgtcaag     660
tcctcatggc ccttat                                                    676

<210> SEQ ID NO 62
<211> LENGTH: 676
<212> TYPE: DNA
<213> ORGANISM: Sutterlla sp.

<400> SEQUENCE: 62
tacgtagggt gcaagcgtta atcggaatta ctgggcgtaa agcgtgcgca ggcggttctg      60
taagacagat gtgaaatccc cgggctcaac ctgggaattg catttgtgac tgcaggacta     120
gagttcatca gagggggtg gaattccaag tgtagcagtg aaatgcgtag atatttggaa      180
gaacaccaat ggcgaaggca gccccctggg atgcgactga cgctcatgca cgaaagcgtg     240
gggagcaaac aggattagat accctggtag tccacgccct aaacgatgtc tactggttgt     300
tggggttttt taaccttggt aacgaagcta acgcgtgaag tagaccgcct ggggagtacg     360
gtcgcaagat taaaactcaa aggaattgac ggggacccgc acaagcggtg gatgatgtgg     420
attaattcga tgcaacgcga aaaaccttac ctagccttga catgccagga atcctgaaga     480
gattcgggag tgcccgcaag ggaatctgga cacaggtgct gcatggctgt cgtcagctcg     540
tgtcgtgaga tgttgggtta agtcccgcaa cgagcgcaac ccttgtcact agttgctacg     600
caagagcact ctagtgagac tgccggtgac aaaccggagg aaggtgggga tgacgtcaag     660
tcctcatggc ccttat                                                    676
```

<210> SEQ ID NO 63
<211> LENGTH: 676
<212> TYPE: DNA
<213> ORGANISM: Sutterlla sp.

<400> SEQUENCE: 63

```
tacgtagggt gcaagcgtta atcggaatta ctgggcgtaa agcgtgcgca ggcggttctg    60
taagatagat gtgaaatccc cgggctcaac ctgggaattg catatatgac tgcaggactt   120
gagtttgtca gaggagggtg gaattccacg tgtagcagtg aaatgcgtag atatgtggaa   180
gaacaccgat ggcgaaggca gccctctggg acatgactga cgctcatgca cgaaagcgtg   240
gggagcaaac aggattagat accctggtag tccacgccct aaacgatgtc tactagttgt   300
tggggacgat agtccttggt aacgcagcta acgcgtgaag tagaccgcct ggggagtacg   360
gtcgcaagat taaaactcaa aggaattgac ggggacccgc acaagcggtg gatgatgtgg   420
attaattcga tgcaacgcga aaaaccttac ctagccttga catgccagga aggcctgaga   480
gatcaggccg tgcccgcaag ggaatctgga cacaggtgct gcatggctgt cgtcagctcg   540
tgtcgtgaga tgttgggtta agtcccgcaa cgagcgcaac ccttgtcatt agttgctacg   600
aaagggcact ctaatgagac tgccggtgac aaaccggagg aaggtgggga tgacgtcaag   660
tcctcatggc ccttat                                                   676
```

<210> SEQ ID NO 64
<211> LENGTH: 678
<212> TYPE: DNA
<213> ORGANISM: Sutterlla sp.

<400> SEQUENCE: 64

```
tacgtagggt gcgagcgtta atcggaatta ctgggcgtaa agcgtgcgca ggcggttggg    60
taagacagat gtgaaatccc cgggcttaac ctgggaactg catttgtgac tgtccgactg   120
gagtatgtca gaggggggtg gaattccaag tgtagcagtg aaatgcgtag atatttggaa   180
gaacaccgat ggcgaaggca gccccctggg gcaaaactga cgctcatgca cgaaagcgtg   240
gggagcaaac aggattagat accctggtag tccacgccct aaacgatgtc tactggttgt   300
tgagggtaa aaccttcagt aacgaagcta acgcgtgaag tagaccgcct ggggagtacg    360
gtcgcaagat taaaactcaa aggaattgac ggggacccgc acaagcggtg gatgatgtgg   420
attaattcga tgcaacgcga aaaaccttac ctagccttga catgtcagga acgctccgga   480
gatgggcgg tgcccgcaag ggaacctgag cacaggtgct gcatggctgt cgtcagctcg    540
tgtcgtgaga tgttgggtta agtcccgcaa cgagcgcaac ccttgtcact agttgctacg   600
taacagagca ctctagtgag actgccggtg acaaaccgga ggaaggtggg gatgatgtca   660
agtcctcatg gcccttat                                                 678
```

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 65

```
gtgccagcmg ccgcggtaa                                                 19
```

<210> SEQ ID NO 66
<211> LENGTH: 19

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gacgtgtgag gccctagcc                                                    19
```